United States Patent
Jacobs et al.

(10) Patent No.: US 9,447,449 B2
(45) Date of Patent: Sep. 20, 2016

(54) RECOMBINANT MYCOBACTERIOPHAGES FOR DELIVERY OF NUCLEIC ACIDS OF INTEREST INTO MYCOBACTERIA

(71) Applicants: Albert Einstein College of Medicine of Yeshiva University, Bronx, NY (US); University of Pittsburgh—Of the Commonwealth System of Higher Education, Pittsburgh, PA (US)

(72) Inventors: William R. Jacobs, Pelham, NY (US); Graham F. Hatfull, Pittsburgh, PA (US)

(73) Assignees: Albert Einstein College of Medicine, Inc., Bronx, NY (US); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/352,761

(22) PCT Filed: Oct. 19, 2012

(86) PCT No.: PCT/US2012/061059
§ 371 (c)(1),
(2) Date: Apr. 18, 2014

(87) PCT Pub. No.: WO2013/059616
PCT Pub. Date: Apr. 25, 2013

(65) Prior Publication Data
US 2014/0370495 A1  Dec. 18, 2014

Related U.S. Application Data

(60) Provisional application No. 61/550,094, filed on Oct. 21, 2011.

(51) Int. Cl.
| | |
|---|---|
| *C12N 7/00* | (2006.01) |
| *C12Q 1/18* | (2006.01) |
| *C12N 15/74* | (2006.01) |
| *C07K 14/005* | (2006.01) |

(52) U.S. Cl.
CPC ............... *C12Q 1/18* (2013.01); *C07K 14/005* (2013.01); *C12N 7/00* (2013.01); *C12N 15/74* (2013.01); *C12N 2795/00021* (2013.01); *C12N 2795/00022* (2013.01); *C12N 2795/00031* (2013.01); *C12N 2795/00043* (2013.01); *C12N 2795/00051* (2013.01); *G01N 2333/035* (2013.01); *G01N 2333/35* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 5,968,733 A | 10/1999 | Bloom et al. | |
| 5,972,700 A * | 10/1999 | Jacobs et al. | 435/320.1 |
| 6,004,771 A | 12/1999 | Thornton | |
| 6,225,066 B1 | 5/2001 | Jacobs et al. | |
| 7,919,234 B2 | 4/2011 | Mulvey et al. | |
| 2009/0047658 A1* | 2/2009 | Mulvey | C12Q 1/689 435/5 |

OTHER PUBLICATIONS

PCT International Search Report and Written Opinion, dated Dec. 21, 2012 in connection with PCT International Application No. PCT/2012/061059, 12 pages.
Rybniker et al., entitled "Insights into the function of the WhiB-like protein of mycobacteriophage TM4—a transcription inhibitor of WhiB2," Mol Microbiol, Aug. 2010, vol. 77, No. 3, pp. 642-657.
Ferraira et al., entitled "Mycobacterium phage Pixie, complete genome," GenBank Direct Submission Accession No. JF937104, May 11, 2011, 39 pages.
Hatfull, entitled "Mycobacteriophages: Genes and Genomes," Ann Rev Microbiol, vol. 64, pp. 331-356, (2010).

* cited by examiner

*Primary Examiner* — Nicole Kinsey White
(74) *Attorney, Agent, or Firm* — Amster, Rothstein & Ebenstein LLP

(57) ABSTRACT

Methods are provided for detecting mycobacteria in a sample, including clinical samples. Methods are also provided for determining susceptibility of mycobacterial strains to known or potential antibiotic agents, as are kits therefor. Recombinant mycobacteriophages are also provided comprising heterologous nucleic acids of interest.

14 Claims, 14 Drawing Sheets

RECOMBINANT MYCOBACTERIOPHAGES FOR DELIVERY OF NUCLEIC ACIDS OF INTEREST INTO MYCOBACTERIA

CROSS-REFERENCE TO RELATED APPLICATIONS

This application is a U.S. national stage entry under 35 U.S.C. §371 of PCT International Patent Application No. PCT/US2012/61059, filed Oct. 19, 2012, which claims priority of U.S. Provisional Application No. 61/550,094, filed Oct. 21, 2011, the contents of each of which are incorporated herein by reference into the subject application.

STATEMENT OF GOVERNMENT SUPPORT

This invention was made with government support under grant numbers GM093901, CFAR AI051519 and 4R37 AI026170-23 awarded by the National Institutes of Health. The government has certain rights in the invention.

BACKGROUND OF THE INVENTION

Throughout this application various publications are referred to in square brackets by number. Full citations for these references may be found at the end of the specification. The disclosures of each of these publications, and also the disclosures of the patents and patent application publications recited herein, are hereby incorporated by reference in their entirety into the subject application to more fully describe the art to which the subject invention pertains.

There is an urgent need for improved assays for both diagnosis of tuberculosis (TB) and drug susceptibility testing (DST) that are accurate, rapid and inexpensive [1]. The most important advances will be assays that can be applied at the point of care in the developing world. Recent advances in nucleic acid amplification approaches ("genotypic assays"), especially the Xpert MTB/RIF assay, are important contributions to the rapid initial diagnosis of pulmonary TB. However, Xpert MTB/RIF detects only rifampicin resistance (RifR) and relies on the fact that almost all clinical RifR identified to date is due to any of three specific point mutations [2-7]. Other clinical drug resistance phenotypes have more varied genetic underpinnings (e.g., hundreds of different mutations can lead to isoniazid resistance [8]) and are therefore refractory to diagnosis via sequence-specific approaches.

In South Africa both multidrug resistant tuberculosis (MDR-TB) and extensively drug resistant tuberculosis (XDR-TB) strains are endemic; MDR-TB and XDR-TB together account for as much as 20% of all TB cases, and contribute significantly to mortality among hospitalized patients [9, 10]. Since both MDR-TB and XDR-TB are resistant to rifampicin, Xpert MTB/RIF cannot distinguish between them. Thus, because of the limitations of currently available diagnostic tests, patients with MDR-TB and XDR-TB are often put on inappropriate therapy for weeks or even months until drug susceptibility testing results become available.

Phenotypic assays, in contrast, recognize the organismal response of bacteria to antibiotics without limitation to any particular antibiotic, allele or mechanism. Culture remains the gold standard for phenotypic assays, but a classical culture identification of M. tuberculosis takes 4 to 8 weeks. Newer approaches, such as microscopic-observation drug-susceptibility (MODS), have shortened the time needed for phenotypic assays to between 1 and 2 weeks [11].

Fluorophages are a type of "reporter-phage" that inject their DNA specifically into mycobacteria [12]. Fluorescence is produced by expression of a fluorescent protein, such as Green Fluorescent Protein (GFP), gene cloned into the phage. Bacterial physiology required for growth and division is similar to that required to produce fluorescence, but the appearance of fluorescent signal after phage infection takes substantially less time than any assay requiring multiple cycles of cell growth and division. Moreover, the drugs which inhibit host gene expression likewise inhibit fluorescence. Since the proof of principle demonstration in 1993 [13], mycobacterial reporter phages have remained a potentially elegant solution to the problem of TB diagnosis. In laboratory cultures, including cultures derived from clinical isolates, reporter phages detect mycobacterial cells, and allow assays of DST in appreciably less time than culture alone [13-18]. However, existing reporter phages are unable to identify mycobacteria directly in clinical specimens, which limits their use.

The present invention address the need for improved mycobacterium phages for delivering nucleic acids of interest, including those encoding reporter proteins, into mycobacteria, and also addresses the need to identify mycobacteria directly in clinical specimens without costly equipment.

SUMMARY OF THE INVENTION

An isolated recombinant mycobacteriophage is provided comprising a vector backbone into which (a) heterologous mycobacteriophage promoter nucleic acid and (b) a heterologous nucleic acid encoding a protein of interest are integrated, and wherein (a) is upstream of (b), and wherein the vector backbone is derived from a mycobacteriophage TM4 and wherein the recombinant mycobacteriophage is conditionally propagating.

Also provided is an isolated recombinant mycobacteriophage comprising a vector into which (a) heterologous $P_{Left}$ lytic promoter of mycobacteriophage L5 and (b) a heterologous nucleic acid encoding a reporter protein are integrated, and wherein (a) is upstream of (b).

The invention also provides a method of detecting a mycobacterium in a sample comprising:
a) contacting the sample with the isolated recombinant mycobacteriophage described herein under conditions permitting the mycobacteriophage to infect a mycobacterium present in the sample and the protein of interest to be expressed in the mycobacterium; and
b) detecting the protein of interest in the mycobacterium in the sample, thereby detecting the mycobacterium in the sample.

The invention further provides a method of determining if a mycobacterium is susceptible to a candidate agent comprising:
a) contacting a sample comprising the mycobacterium with the isolated recombinant mycobacteriophage described herein in (i) the absence of the candidate agent and (ii) in the presence of the candidate agent, under conditions permitting the mycobacteriophage to infect a mycobacterium present in the sample and the protein of interest to be expressed in the mycobacterium;
b) detecting the protein of interest in the mycobacterium in the sample in (i) and (ii); and
c) comparing the amount of the protein of interest detected in the presence of the candidate agent and the absence of the candidate agent, wherein a decrease in amount of the protein of interest in the presence of the candidate agent compared to in the absence of the candidate agent indicates that the mycobacterium is susceptible to the candidate agent.

The invention additionally provides a method of identifying a candidate agent as effective in treating an infection caused by a strain of mycobacterium, the method comprising culturing a mycobacterium with the isolated recombinant mycobacteriophage described herein in (a) the absence of the candidate agent under conditions permitting the mycobacteriophage to infect a mycobacterium present in the sample and the protein of interest to be expressed in the mycobacterium, and (b) the presence of the candidate agent under conditions permitting the mycobacteriophage to infect a mycobacterium present in the sample and the protein of interest to be expressed in the mycobacterium, and detecting the protein of interest in the mycobacterium in the sample in (a) and in (b), and comparing the amount of the protein of interest detected in the presence of the candidate agent and the absence of the candidate agent, wherein a decrease in the amount of the protein of interest in the presence of the candidate agent compared to in the absence of the candidate agent indicates the agent as effective to treat an infection caused by the strain of mycobacterium.

Also provided is a method for producing recombinant mycobacteriophages comprising:

a) introducing a vector into a mycobacterium so as to form a lysogen, which vector comprises (i) a mycobacteriophage promoter nucleic acid and (ii) a heterologous nucleic acid encoding a protein of interest, and wherein (i) is upstream of (ii), and integrated into a vector backbone derived from a mycobacteriophage TM4 and is temperature-sensitive conditionally propagating;

b) maintaining the lysogen at a temperature that permits the lysogen to replicate into a plurality of lysogens; and then c) maintaining the plurality of lysogens at a temperature that effects induction in the plurality of lysogens, so as thereby to produce recombinant mycobacteriophages comprising (i) and (ii).

Also provided is a method of preparing a sputum sample for reporter phage infection comprising: a) mixing the sputum sample with diluted dithiothreitol in phosphate buffer; b) vortexing the resultant product; c) allowing the product resulting from b) to rest; d) centrifuging the product resulting from c); e) decanting the supernatant; f) mixing remainder with a diluted sodium hydroxide solution; g) vortexing the product resulting from f); h) allowing the product resulting from g) to rest; i) adding phosphate buffer saline and centrifuging the resulting product; j) re-suspending resultant pellet in a mycobacterium-supporting broth.

Additional objects of the invention will be apparent from the description which follows.

DETAILED DESCRIPTION OF THE INVENTION

Figure 1A:
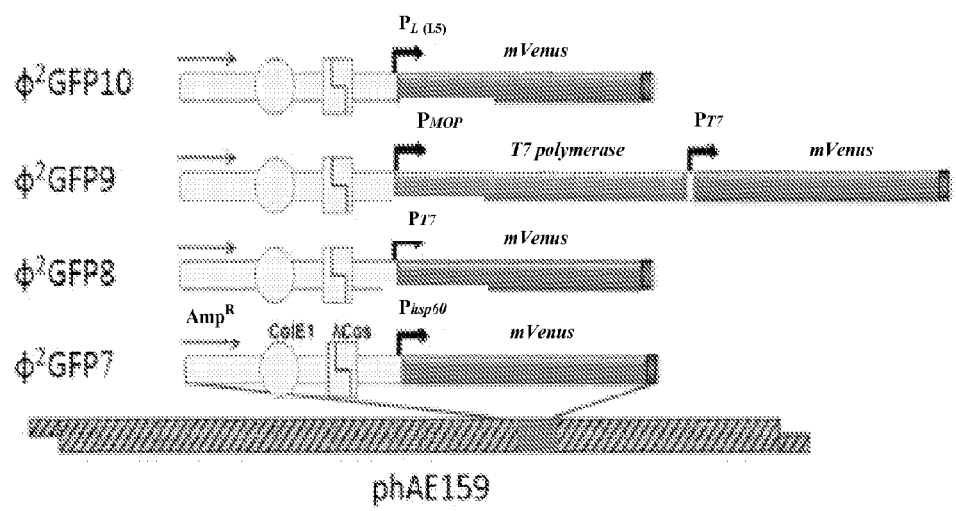
FIG. 1A-1D. Generation of improved fluorophage. A) Schematic representation of various fluorophages constructed in the present study. B) Comparison of fluorescence obtained from hsp60-driven mVenus fluorophage $\phi^2$GFP7 and episomal plasmid pYUB1378 expressing mVenus from same promoter. C) Flow cytometric comparison of fluorophages in M. smegmatis. D) Time lapse microscopy of mVenus expression in mycobacteria after infection with fluorophage $\phi^2$GFP10.

As used herein, a "heterologous" nucleic acid, with regard to its presence in a phage or vector backbone, refers to nucleic acid that is not naturally present in the phage or vector backbone, respectively.

As used herein, a "mycobacteriophage" is a phage capable of infecting one or more mycobacteria. A "recombinant" mycobacteriophage is one containing, in its genome, a heterologous nucleic acid. An "isolated" recombinant mycobacteriophage is one that is not naturally occurring.

As used herein, the term "expression," with regard to a nucleic acid, refers to the process by which a nucleotide sequence undergoes successful transcription and, for polypeptides or proteins, translation.

As used herein, the term "promoter" refers to a minimal nucleotide sequence sufficient to direct transcription. In an embodiment of the invention described herein, the mycobacteriophage promoter controls expression of the protein of interest.

Sambrook, Molecular Cloning: A Laboratory Manual (Third Edition), Cold Spring Harbor Laboratory Press (CSH Press), 2001 (ISBN-10: 0879695773; ISBN-13: 978-0879695774), the contents of which are hereby incorporated by reference in their entirety provides an overview of molecular biology techniques that can be employed herein.

This invention provides an isolated recombinant mycobacteriophage comprising a vector backbone into which (a) heterologous mycobacteriophage promoter nucleic acid and (b) a heterologous nucleic acid encoding a protein of interest are integrated, and wherein (a) is upstream of (b), and wherein the vector backbone is derived from a mycobacteriophage TM4 and wherein the recombinant mycobacteriophage is conditionally propagating.

This invention also provides isolated recombinant mycobacteriophage comprising a vector into which (a) heterologous $P_{Left}$ lytic promoter of mycobacteriophage L5 and (b) a heterologous nucleic acid encoding a reporter protein are integrated, and wherein (a) is upstream of (b). In the recombinant mycobacteriophage, the vector backbone can advantageously be derived from a mycobacteriophage TM4. In a preferred embodiment, mutations, deletions or insertions are used so as to obtain a recombinant mycobacteriophage that is conditionally propagating.

In either case, the conditional propagation property of the recombinant mycobacteriophage permits it to be introduced into specific cells without killing them, e.g. for reporting purposes. By changing the relevant condition, for example temperature, the phage can be induced to propagate, e.g. for production purposes. Novel temperature-sensitive TM4 mutants have been identified, and critical residues therefore are disclosed herein. Thus, TM4 (and derivatives thereof) are therefore useful for vector backbones for the present isolated recombinant mycobacteriophages. A recombinant phage having the property of "conditionally propagating" as used herein means that the phage replicates only under certain conditions. In preferred embodiments, the relevant condition is temperature (herein designated by "temperature-sensitive" or a grammatical equivalent thereof). In a preferred embodiment of the invention, the conditionally propagating recombinant phage is a phage which replicates at 30° C., but fails to replicate (and/or lyse its host cell) at 37° C. In an embodiment, the conditionally propagating recombinant mycobacteriophage is based on a TM4 phage, GenBank: AF068845, and in non-limiting examples is a point mutant, a deletion mutant, an insertion mutant, or a combination of point mutation(s) and deletion(s) and/or insertion(s).

As used herein, the term "vector backbone" refers to a nucleic acid molecule capable of transporting one or more other nucleic acid(s) to which it has been linked. As used herein, vector backbone "derived from TM4" is vector that comprises one or more nucleic acid sequences identical to a portion of a TM4 genome sequence but the complete sequence of which is not identical to a TM4 genome sequence. Such a vector backbone may be made, in non-limiting examples, by way of one or more of a mutation, insertion and/or deletion of a TM4 genome sequence, or by one or more subsequent mutation(s), insertion(s) and/or deletion(s) of a mutated, deleted and or inserted TM4 genome sequence. Accordingly, a vector backbone derived from a TM4 as used herein includes both directly derived from TM4, and one derived from one which in turn is derived from TM4, and so forth (e.g., in a non-limiting example, derived from phAE159). In embodiments of the isolated recombinant mycobacteriophages described herein, the vector backbone comprises a TM4 genomic sequence having a deletion in a non-essential area thereof (i.e., not essential for replication) permitting insertion of heterologous DNA. In an embodiment, there is a 5.5 kbp to 6.5 kbp deletion of non-essential DNA of the TM4 genomic sequence, and in one embodiment a 5.8 kbp deletion. This permits insertion of a large amount of heterologous nucleic acids, for example up to 10 kbp, without loss of performance. Such heterologous nucleic acids can comprise any protein of interest, as well as expression-controlling nucleic acids such as promoters and other related entities. In a specific embodiment, the vector backbone does not comprise a portion having the sequence of residues 33,877 through 39,722 of the TM4 genome. In embodiments the vector backbone does not comprise TM4 gene 49.

Various mutations of TM4 genome that contribute to temperature sensitivity/conditional propagation have been identified herein. These are used to advantageously effect conditionally propagation recombinant mycobacteriophages. In an embodiment, the isolated recombinant mycobacteriophages described herein comprise a vector backbone which does not comprise a portion having the sequence of TM4 gene 49 through the first sixteen codons of gene 64 of the TM4 genome. In an embodiment, the vector backbone of the isolated recombinant mycobacteriophages described herein does not comprise a portion having the sequence of the last twelve codons of gene 48 of the TM4 genome. In an embodiment, the vector backbone of the isolated recombinant mycobacteriophages described herein does not encode a proline at a residue equivalent to residue 220 of gene product gp48 of the TM4 genome. In an embodiment, the vector backbone encodes a serine at a residue equivalent to residue 220 of gene product gp48 of the TM4 genome. In an embodiment, the vector backbone does not encode an alanine at a residue equivalent to residue 131 of gene product gp66 of the TM4 genome. In an embodiment, the vector backbone encodes a threonine at a residue equivalent to residue 131 of gene product gp66 of the TM4 genome. In an embodiment, the vector backbone does not encode an arginine at a residue equivalent to residue 116 of gene product gp20 of the TM4 genome. In an embodiment, the vector backbone encodes a cysteine at a residue equivalent to residue 116 of gene product gp20 of the TM4 genome.

The vector phAE159 is a useful vector having a high cloning capacity and is derived from the temperature sensitive ph101 vector which in turn is derived from TM4. As such, phAE159 is useful as a vector backbone of the invention. In a preferred embodiment, the vector backbone is a phAE159 vector. In an embodiment, the phAE159 vector backbone comprises the sequence set forth in SEQ ID NO:1. In a preferred embodiment employing the phAE159 vector, the mycobacteriophage promoter nucleic acid is cloned into a PacI site of the phAE159 vector. In another embodiment, the vector backbone is a ph101 vector. Phages derived from TM4 which are useful as embodiments of the vector backbone in the present invention include, in non-limiting examples, those set forth in Genbank Accession No. JF937104 (SEQ ID NO:4); JF704106 (SEQ ID NO:5); JF704105 (SEQ ID NO:6); HM152764 (SEQ ID NO:7); and HM152767 (SEQ ID NO:8).

Insertion sites of the heterologous mycobacteriophage promoter nucleic acid, $P_{Left}$ lytic promoter, and the heterologous nucleic acid encoding a protein of interest, may be within any non-essential region of the vector backbone. In a preferred embodiment the insertions are within the sequence that results from a deletion of a ~6 kb region encompassing genes encoding gp48-64 from the temperature-sensitive mutant of TM4 known as ph101, in the site of the deletion.

The heterologous mycobacteriophage promoter nucleic acid and heterologous nucleic acid encoding a protein of interest/reporter protein can be integrated into such vector backbones in the isolated recombinant mycobacteriophages of the invention.

In an embodiment, the mycobacteriophage promoter nucleic acid is a mycobacteriophage L5 promoter. In a preferred embodiment, the mycobacteriophage promoter nucleic acid is a $P_{Left}$ lytic promoter of mycobacteriophage L5. In another embodiment, the mycobacteriophage promoter nucleic acid is a T7 promoter and the isolated recombinant phage further comprises a nucleic acid encoding a T7 polymerase. In an embodiment the L5 promoter has the following sequence:

L5 promoter sequence:
(SEQ ID NO: 3)
CGATGATAAGCGGTCAAACATGAGAATTCGCGGCCGCATAATACGACTC

ACTATAGGGATCTTAATTAAGGCGCCTCATGTTCTTTCCTGCGTTATCC

CCTGATTCTGTGGATAACCGTATTACCGCCTTTGAGTGAGCTGATACCG

CTCGCCGCAGCCGAACGACCGAGCGCAGCGAGTCAGTGAGCGAGGAAGC

GGAAGAGCGCCCAATACGCAAACCGCCTCTCCCAGATCTGATATCGCTA

GAGGAAACAGCTATGACCATGATTACGCCAAGCTTGCATGCCTGCAGCT

AGGGCACCAATTTGCGATTAGGGCTTGACAGCCACCCGGCCAGTAGTGC

ATTCTTGTGTCACCGCAGCAGCAAGGCGGTAGGCGGATCCGAGAGGATC

GTGCCGGTGCCGGTGAAAATCCGGCGGCAAGATTCTCCGGTTTGACAGC

CACCCGGTTATCGGGTAAGCTGCAAGCATCACCAACTTGGACGGGAAAG

GGAGATCGCATATG

A "protein of interest" as used herein, includes peptides, polypeptides and proteins. In a preferred embodiment, the protein of interest is a protein. In a preferred embodiment, the protein is a reporter protein. A "reporter protein" as used herein is any detectable protein that can be encoded by a nucleic acid in a mycobacteriophage. Many reporter proteins are known in the art, and the selection of which reporter protein to use can be made on usability considerations and expected conditions. In a preferred embodiment for recombinant phages to be used in visual assays, the reporter protein is a fluorescent protein. In a further preferred embodiment, the fluorescent protein is a green or yellow fluorescent protein. In a further preferred embodiment, the fluorescent protein is green fluorescent protein derived from A. victoria. In a preferred embodiment, the yellow fluorescent protein is Venus monomeric fluorescent protein (see Nagai et al., Nat Biotechnol. 2002 January; 20(1):87-90, the content of which is hereby incorporated by reference in its entirety). In an embodiment, the Venus fluorescent protein comprises SEQ ID NO:2. In an embodiment the yellow fluorescent protein has an excitation peak of 514 nm and an emission peak is 527 nm. In other embodiments, the yellow fluorescent protein is Citrine or Ypet. Other fluorescent proteins that may be used include those described in U.S. Pat. No. 8,034,614 (the content of which is hereby incorporated by reference in its entirety).

Other fluorescent proteins that may be used as reporter proteins are set forth below in Table 1:

| Protein | Excitation Maximum (nm) | Emission Maximum (nm) | Molar Extinction Coefficient | Quantum Yield | in vivo Structure |
|---|---|---|---|---|---|
| GFP (wt) | 395/475 | 509 | 21,000 | 0.77 | Monomer* |
| EGFP | 484 | 507 | 56,000 | 0.60 | Monomer* |
| Emerald | 487 | 509 | 57,500 | 0.68 | Monomer* |
| Superfolder GFP | 485 | 510 | 83,300 | 0.65 | Monomer* |
| Azami Green | 492 | 505 | 55,000 | 0.74 | Monomer |
| mWasabi | 493 | 509 | 70,000 | 0.80 | Monomer |
| TagGFP | 482 | 505 | 58,200 | 0.59 | Monomer* |
| TurboGFP | 482 | 502 | 70,000 | 0.53 | Dimer |
| AcGFP | 480 | 505 | 50,000 | 0.55 | Monomer* |
| ZsGreen | 493 | 505 | 43,000 | 0.91 | Tetramer |
| T-Sapphire | 399 | 511 | 44,000 | 0.60 | Monomer* |
| EBFP | 383 | 445 | 29,000 | 0.31 | Monomer* |
| EBFP2 | 383 | 448 | 32,000 | 0.56 | Monomer* |
| Azurite | 384 | 450 | 26,200 | 0.55 | Monomer* |
| mTagBFP | 399 | 456 | 52,000 | 0.63 | Monomer |
| ECFP | 439 | 476 | 32,500 | 0.40 | Monomer* |

-continued

| Protein | Excitation Maximum (nm) | Emission Maximum (nm) | Molar Extinction Coefficient | Quantum Yield | in vivo Structure |
|---|---|---|---|---|---|
| mECFP | 433 | 475 | 32,500 | 0.40 | Monomer |
| Cerulean | 433 | 475 | 43,000 | 0.62 | Monomer* |
| CyPet | 435 | 477 | 35,000 | 0.51 | Monomer* |
| AmCyan1 | 458 | 489 | 44,000 | 0.24 | Tetramer |
| Midori-Ishi Cyan | 472 | 495 | 27,300 | 0.90 | Dimer |
| TagCFP | 458 | 480 | 37,000 | 0.57 | Monomer |
| mTFP1 (Teal) | 462 | 492 | 64,000 | 0.85 | Monomer |
| EYFP | 514 | 527 | 83,400 | 0.61 | Monomer* |
| Topaz | 514 | 527 | 94,500 | 0.60 | Monomer* |
| Venus | 515 | 528 | 92,200 | 0.57 | Monomer* |
| mCitrine | 516 | 529 | 77,000 | 0.76 | Monomer |
| YPet | 517 | 530 | 104,000 | 0.77 | Monomer* |
| TagYFP | 508 | 524 | 64,000 | 0.60 | Monomer |
| PhiYFP | 525 | 537 | 124,000 | 0.39 | Monomer* |
| ZsYellow1 | 529 | 539 | 20,200 | 0.42 | Tetramer |
| mBanana | 540 | 553 | 6,000 | 0.7 | Monomer |
| Kusabira Orange | 548 | 559 | 51,600 | 0.60 | Monomer |
| Kusabira Orange2 | 551 | 565 | 63,800 | 0.62 | Monomer |
| mOrange | 548 | 562 | 71,000 | 0.69 | Monomer |
| mOrange2 | 549 | 565 | 58,000 | 0.60 | Monomer |
| dTomato | 554 | 581 | 69,000 | 0.69 | Dimer |
| dTomato-Tandem | 554 | 581 | 138,000 | 0.69 | Monomer |
| TagRFP | 555 | 584 | 100,000 | 0.48 | Monomer |
| TagRFP-T | 555 | 584 | 81,000 | 0.41 | Monomer |
| DsRed | 558 | 583 | 75,000 | 0.79 | Tetramer |
| DsRed2 | 563 | 582 | 43,800 | 0.55 | Tetramer |
| DsRed-Express (T1) | 555 | 584 | 38,000 | 0.51 | Tetramer |
| DsRed-Monomer | 556 | 586 | 35,000 | 0.10 | Monomer |
| mTangerine | 568 | 585 | 38,000 | 0.30 | Monomer |
| mRuby | 558 | 605 | 112,000 | 0.35 | Monomer |
| mApple | 568 | 592 | 75,000 | 0.49 | Monomer |
| mStrawberry | 574 | 596 | 90,000 | 0.29 | Monomer |
| AsRed2 | 576 | 592 | 56,200 | 0.05 | Tetramer |
| mRFP1 | 584 | 607 | 50,000 | 0.25 | Monomer |
| JRed | 584 | 610 | 44,000 | 0.20 | Dimer |
| mCherry | 587 | 610 | 72,000 | 0.22 | Monomer |
| HcRed1 | 588 | 618 | 20,000 | 0.015 | Dimer |
| mRaspberry | 598 | 625 | 86,000 | 0.15 | Monomer |
| dKeima-Tandem | 440 | 620 | 28,800 | 0.24 | Monomer |
| HcRed-Tandem | 590 | 637 | 160,000 | 0.04 | Monomer |
| mPlum | 590 | 649 | 41,000 | 0.10 | Monomer |
| AQ143 | 595 | 655 | 90,000 | 0.04 | Tetramer |

In other embodiments, the reporter protein is a β-galactosidase encoded by a LacZ, a maltose binding protein, or a chloramphenicol acetyltransferase.

A protein of interest also includes an antigen, a peptide anti-inflammatory agent, an enzyme, a lymphokine, and a peptide antibiotic.

In an embodiment, the mycobacteriophage is a temperature-sensitive conditionally propagating mutant. In a preferred embodiment, the recombinant mycobacteriophage does not propagate in a mycobacteria at 37° C. In a preferred embodiment, the recombinant mycobacteriophage propagates in a mycobacteria at 30° C.

In an embodiment, the mycobacteria is *M. smegmatis*. In an embodiment, the mycobacteria is *M. tuberculosis*. In embodiments, the mycobacteria is *M. bovis*, *M. bovis*-BCG, *M. avium*, *M. phlei*, *M. fortuitum*, *M. lufu*, *M. paratuberculosis*, *M. habana*, *M. scrofulaceum* or *M. intracellulare*.

Other useful elements, commonly known in the art, may also be included in the genome of the recombinant mycobacteriophages of the invention. For example, the recombinant genome may further comprise one of, more than one of, or all of (1) an antibiotic resistance gene, (2) a ColE1 sequence and (3) a λ Cos sequence upstream of (a). A preferred antibiotic resistance gene is an ampicillin resistance gene. The recombinant mycobacteriophages and vectors of the invention can optionally comprise a mycobacteriophage integration sequence. The recombinant mycobacteriophages and vectors of the invention can optionally comprise an *E. coli* cosmid sequence.

Methods employing the isolated recombinant mycobacteriophages of the invention are also within the scope of the invention. Methods for determining the presence of particular strains of mycobacteria in a sample, for example therapy-resistant strains, as well as determining susceptibility of a strain to a treatment, are particularly advantageous uses of the recombinant mycobacteriophages described herein.

Thus, in one aspect of the invention a method is provided of detecting a mycobacterium in a sample comprising:

a) contacting the sample with an isolated recombinant mycobacteriophage of as described herein conditions permitting the mycobacteriophage to infect a mycobacterium present in the sample and the protein of interest to be expressed in the mycobacterium; and b) detecting the protein of interest in the mycobacterium in the sample, thereby detecting the mycobacterium in the sample.

The sample may be treated to promote infection of the mycobacteria present by the mycobacteriophage. Non-limiting suitable protocols are set forth in the specification. The protein of interest is in such methods is preferably a readily-detected reporter protein. The fluorophages made of the recombinant mycobacteriophages herein are especially useful for their high expression of visually detectable fluorescence. Thus, the presence of the targeted mycobacterium in a sample infected by the recombinant mycobacteriophages would be indicated by the presence of fluorescence, under suitable illumination, which can be readily ascertained, e.g. by standard microscopy or flow cytometry, avoiding the need for more complex and/or expensive detection strategies. Sputum samples are a preferred sample, they are easily obtained and treated. The detection of *M. tuberculosis* in a sputum sample is readily effected by the present method, especially if the reporter protein is a visually-detectable fluorescent protein, such as a suitable yellow fluorescent protein.

The same advantageous aspects conferred by the recombinant mycobacteriophages of the invention can be utilized to determine efficacy of treatments against mycobacteria. As such, one aspect of the invention is a method of determining if a mycobacterium is susceptible to a candidate agent comprising:

a) contacting a sample comprising the mycobacterium with an isolated recombinant mycobacteriophage as described herein in (i) the absence of the candidate agent and (ii) in the presence of the candidate agent, under conditions permitting the mycobacteriophage to infect a mycobacterium present in the sample and the protein of interest to be expressed in the mycobacterium;

b) detecting the protein of interest in the mycobacterium in the sample in (i) and (ii); and c) comparing the amount of the protein of interest detected in the presence of the candidate agent and the absence of the candidate agent, wherein a decrease in amount of the protein of interest in the presence of the candidate agent compared to in the absence of the candidate agent indicates that the mycobacterium is susceptible to the candidate agent.

In non-limiting embodiments, the candidate agent may be a known antibiotic or may be a suspected antibiotic, the efficacy of which is to be determined. Any other treatment method can be assayed for efficacy in the same manner.

Also within the scope of the invention is a method of identifying a candidate agent as effective in treating an infection caused by a strain of mycobacterium, the method comprising culturing a mycobacterium with an isolated recombinant mycobacteriophage as described herein in (a) the absence of the candidate agent under conditions permitting the mycobacteriophage to infect a mycobacterium present in the sample and the protein of interest to be expressed in the mycobacterium, and (b) the presence of the candidate agent under conditions permitting the mycobacteriophage to infect a mycobacterium present in the sample and the protein of interest to be expressed in the mycobacterium, and detecting the protein of interest in the mycobacterium in the sample in (a) and in (b), and comparing the amount of the protein of interest detected in the presence of the candidate agent and the absence of the candidate agent, wherein a decrease in the amount of the protein of interest in the presence of the candidate agent compared to in the absence of the candidate agent indicates the agent as effective to treat an infection caused by the strain of mycobacterium. In non-limiting embodiments, the candidate agent may be a known antibiotic or may be a suspected antibiotic, the efficacy of which is to be determined. The method may be used to identify a therapy for a mycobacterial infection otherwise resistant to treatment by other methods.

In an embodiment of the methods employing candidate agents, the candidate agent is an antibiotic. In an embodiment the candidate agent is an organic molecule of 2000 Da or less. In an embodiment the candidate agent is an organic molecule of 1500 Da or less In an embodiment of the methods described hereinabove, the mycobacteria are *Mycobacterium tuberculosis*. In an embodiment of the methods, the mycobacteria are *Mycobacterium bovis* or *Mycobacterium smegmatis*. In embodiments, the mycobacteria is *M. bovis*-BCG, *M. avium, M. phlei, M. fortuitum, M. lufu, M. paratuberculosis, M. habana, M. scrofulaceum* or *M. intracellulare.*

In embodiments the *Mycobacterium tuberculosis* is MDR-TB and XDR-TB. In embodiments the mycobacteria is resistant to, or is suspected of being resistant to kanamycin, isoniazid and/or rifampicin. In embodiments, the treatment/therapy can be an aminoglycosides (e.g., amikacin), a polypeptide (e.g., capreomycin, viomycin, enviomycin), a fluoroquinolone, (e.g., ciprofloxacin, levofloxacin, moxifloxacin), and/or a thioamide (e.g. ethionamide).

The conditions of the methods are chosen so as to reflect the conditionally propagating nature of the recombinant mycobacteriophage. In an embodiment, the conditions comprise culturing the sample with the isolated recombinant mycobacteriophage substantially at 36° C. to 38° C. In an embodiment, the conditions comprise culturing the sample with the isolated recombinant mycobacteriophage at 37° C. In an embodiment, the conditions comprise culturing the sample for infection with the mycobacteriophage at a temperature not below 31° C.

In a preferred embodiment, the methods further comprise processing the sample with a concentration of NaOH of 1% to 2% prior to culturing the mycobacterium therein for infection with the isolated recombinant mycobacteriophage.

In embodiments of the methods, suitable proteins of interest are as described hereinabove, but any protein of interest may be used. In an embodiment, the protein of interest is a fluorescent protein and the fluorescence of the fluorescent protein is detected. Preferably, the fluorescence is detected/quantified visually using a microscope or flow cytometry apparatus.

In all of the inventions described herein, the sample may be a sputum sample obtained from a mammal, including from a human. The human may be known to have tuberculosis, be at risk of tuberculosis, or be suspected as having tuberculosis.

Kits are also provided for the detecting of a mycobacterium in a sample comprising the described recombinant mycobacteriophages, packaging therefor, and written instructions for use thereof.

The recombinant mycobacteriophages of the present invention can be made in multiple ways. Background art for the concept of producing reporter mycobacteriophages is discussed in U.S. Pat. No. 6,300,061, and shuttle phasmids are discussed in U.S. Pat. No. 5,750,384, both of which patents are incorporated by reference in their entirety. With regard to the present recombinant mycobacteriophages, one method of production is described in the Experimental section hereinbelow. An additional method for producing recombinant mycobacteriophages comprises:

a) introducing a vector into a mycobacterium so as to form a lysogen, which vector comprises (i) a mycobacteriophage promoter nucleic acid and (ii) a heterologous nucleic acid encoding a protein of interest, and wherein (i) is upstream of (ii), and integrated into a vector backbone derived from a mycobacteriophage TM4 and which is temperature-sensitive conditionally propagating;
b) maintaining the lysogen at a temperature that permits the lysogen to replicate into a plurality of lysogens; and then
c) maintaining the plurality of lysogens at a temperature that effects induction in the plurality of lysogens, so as thereby to produce recombinant mycobacteriophages comprising (i) and (ii).

In embodiments of this method of production the vector backbone derived from a mycobacteriophage TM4 comprises a mutation and/or a deletion relative to TM4, in one of, more than one of, or all of (i) a gp48 gene, (ii) a gp66 gene and (iii) a gp20 gene of TM4, which mutation(s) and/or a deletion(s) confer temperature-sensitivity of phage propagation. In embodiments, the vector backbone derived from a mycobacteriophage TM4 comprises a mutation and/or a deletion relative to TM4 that confers temperature-sensitivity of repression, and mutation and/or a deletion relative to TM4 that confers conditional-sensitivity of a lysis function thereof. In an embodiment, the method further comprises recovering the recombinant mycobacteriophages produced by a means available in the art. One such way is to purify the recombinant mycobacteriophages on a CsCl gradient. In an embodiment of the methods of production, the plurality of lysogens is induced by subjecting the plurality to a temperature that releases repression and/or permits lysis. In an embodiment, the mycobacterium of the method of production is M. smegmatis. In an embodiment of the methods of production, the temperature-sensitivity results in replication of the mycobacteriophages in the mycobacterium at 30° C. but not at 37° C.

In an embodiment of the methods, the vector backbone of the isolated recombinant mycobacteriophage does not comprise TM4 gene 49. In an embodiment, the vector backbone comprises a TM4 genomic sequence having a 5.5 kbp to 6.5 kbp deletion of non-essential DNA thereof. In an embodiment, the vector backbone does not comprise a portion having the sequence of residues 33,877 through 39,722 of the TM4 genome. In an embodiment, the vector backbone:
(i) does not comprise a portion having the sequence of gene 49 through the first sixteen codons of gene 64 of the TM4 genome;
(ii) does not comprise a portion having the sequence of the last twelve codons of gene 48 of the TM4 genome;
(iii) does not encode a proline at a residue equivalent to residue 220 of gene product gp48 of the TM4 genome;
(iv) encodes a serine at a residue equivalent to residue 220 of gene product gp48 of the TM4 genome;
(v) does not encode an alanine at a residue equivalent to residue 131 of gene product gp66 of the TM4 genome;
(vi) encodes a threonine at a residue equivalent to residue 131 of gene product gp66 of the TM4 genome;
(vii) does not encode an arginine at a residue equivalent to residue 116 of gene product gp20 of the TM4 genome; and/or
(viii) encodes a cysteine at a residue equivalent to residue 116 of gene product gp20 of the TM4 genome.

In an embodiment, the vector backbone comprises the sequence set forth in Genbank Accession No. JF937104; JF704106; JF704105; HM152764; or HM152767. These backbones confer preferred temperature sensitivities/conditional propagation. In embodiments, the vector backbone is a phAE159 vector or a ph101 vector.

In the methods described, unless otherwise indicated, any mycobacteriophage promoter known in the art may be employed. In a preferred embodiment, the mycobacteriophage promoter nucleic acid is a $P_{Left}$ lytic promoter of mycobacteriophage L5.

Treatment of samples for analysis with fluorophages is known in the art (e.g. see [13]) and can be used with the methods described herein. However, a novel and preferred method for treating sputum samples for infection by the isolated recombinant mycobacteriophages of the invention is provided by this invention comprising: a) mixing the sputum sample with diluted dithiothreitol in phosphate buffer; b) vortexing the resultant product; c) allowing the product resulting from b) to rest; d) centrifuging the product resulting from c); e) decanting the supernatant; f) mixing remainder with a diluted sodium hydroxide solution; g) vortexing the product resulting from f); h) allowing the product resulting from g) to rest; i) adding phosphate buffer saline and centrifuging the resulting product; j) re-suspending resultant pellet in a mycobacterium-supporting broth.

In embodiments, the sputum sample is mixed with 30-70% diluted dithiothreitol. In a preferred embodiment, the sputum sample is mixed with 35-60% diluted dithiothreitol. In a most preferred embodiment, the sputum sample is mixed with 50% diluted dithiothreitol. In a further preferred embodiment, the sputum sample is mixed with an equal volume of the diluted dithiothreitol.

In embodiments, in step b) the product is vortexed at 2000-6000 rpm. In a preferred embodiment, the product is vortexed at 3500-5000 rpm. In a most preferred embodiment, the product is vortexed at 4000 rpm. In embodiments, in step b) the product is vortexed for 1-25 mins. In a preferred embodiment, the product is vortexed for 5-15 mins. In a most preferred embodiment, the product is vortexed for about 10 mins or for 10 mins.

In an embodiment, in step f) the remainder is mixed with 0.4-2.0% NaOH. In a preferred embodiment, the remainder is mixed with 0.8-1.6% NaOH. In a most preferred embodiment, the remainder is mixed with 1% NaOH.

In embodiments, in step g) the product is vortexed at 2000-6000 rpm. In a preferred embodiment, the product is vortexed at 3500-5000 rpm. In a most preferred embodiment, the product is vortexed at 4000 rpm.

In embodiments, in step g) the product is vortexed for 10-30 mins. In a preferred embodiment, the product is vortexed for 15-25 mins. In a most preferred embodiment the product is vortexed for about 20 mins or for 20 mins.

In one preferred embodiment, the method comprises: a) mixing the sputum sample with an equal volume of 50% diluted dithiothreitol in phosphate buffer; b) vortexing the resultant product; c) allowing the product resulting from b) to rest; d) centrifuging the product resulting from c) at 4000 RPM for about 10 minutes; e) decanting the supernatant; f) mixing remainder with 1% sodium hydroxide solution; g) vortexing the product resulting from f); h) allowing the product resulting from g) to rest; i) adding phosphate buffer saline and centrifuging the resultant at 4000 RPM for about 20 minutes; j) re-suspending resultant pellet in a suitable mycobacterium-supporting broth; k) adding reporter phage and incubating therewith at 37° C. One suitable broth well known in the art is Middlebrook 7H9 Broth (for example, available from BD, Franklin Lakes, N.J.).

In the inventions described herein, the mycobacteria may be M. tuberculosis, M. smegmatis, M. bovis, M. bovis-BCG, or any other known mycobacteria, including those described hereinabove.

The methods disclosed herein involving subjects can be used with any mammalian subject. Preferably, the mammal is a human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL RESULTS

Introduction

To date, the key limitations of reporter phages have been (a) their relatively poor reporter signals, which require a relatively long exposure time to discern fluorescent mycobacteria from cells displaying autofluorescence, and (b) the incompatibility of common sputum processing methods with phage infection. Herein a new unexpectedly high-intensity fluorophage is disclosed for rapid and inexpensive point-of-care diagnostic tool and as a tool for drug susceptibility testing of M. tuberculosis in clinical sputum samples. This high-intensity fluorophage for the first time allows direct optics-to-human microscopic observation of phage-encoded fluorescence of M. tuberculosis cells in sputum samples. The fluorophage permitted M. tuberculosis diagnosis made at 12 hr and drug susceptibility testing results were complete within 36 hr of sputum collection from TB patients.

Materials and Methods

Generation of high-intensity fluorophage: Vector pYUB1378 was generated by cloning the mVenus gene downstream of hsp60 promoter in pMV261 [19] (mVenus obtainable from IKEN Brain Science Institute, Saitama, JAPAN-Atsushi Miyawaki). (Venus is disclosed in Nagai T et al., Nat. Biotechnol. 2002 January; 20(1):87-90, A variant of yellow fluorescent protein with fast and efficient maturation for cell-biological applications). Vector pYUB1228 was generated for reporter phage construction by introducing a lambda cos site and a unique PacI site at the BspH1 site in pEXP 1-DEST (Invitrogen). The hsp60-mVenus cassette was cloned from pYUB1378 into pYUB1228 at BglII-NaeI sites to generate pYUB1167. Vector pYUB1361 encoding mVenus gene from T7 promoter was generated by replacing the hsp60 promoter with T7 promoter using BglII and NdeI sites. Plasmid pYUB1383 was generated by cloning T7 polymerase gene [20, 21] upstream of pYUB1361 at BglII site. The L5 promoter [22] was cloned in the forward orientation upstream of the mVenus gene between the BglII and NdeI site in plasmid pYUB1167 to generate pYUB1391. The plasmids pYUB1167, pYUB1361, pYUB1383 and pYUB1391 were cloned individually into phAE159 at a unique PacI site to obtain phasmids [23]. M. smegmatis mc2155 [24] was used to generate the reporter phage using the method described previously [13]. The phasmids harboring pYUB1167, PYUB1168, pYUB1361, pYUB1383, and pYUB1391 resulted in fluorophages $\phi^2$GFP7, $\phi^2$GFP8, $\phi^2$GFP9, and $\phi^2$GFP10, respectively (FIG. 1A). Individual plaques were picked and propagated at 30° C. to obtain high-titer fluorophages [23].

Infection of Mycobacterial strains with fluorophages: M. tuberculosis mc$^2$6230 was used as the drug-sensitive strain [25]. Drug-resistant mutants of M. tuberculosis mc$^2$6230 were isolated by selecting cells on 7H10 plates in the presence of various drugs at 5 times the MIC value [26, 27]. M. tuberculosis mc$^2$7201, mc$^2$7202 and mc27203 are the strains resistant to rifampicin, kanamycin, or both rifampicin and kanamycin respectively. Mycobacterial cells were grown to an OD600 nm of 0.8-1.0 in 7H9+OADC+0.05% Tween. Before infection, the cells were washed twice with MP buffer and re-suspended in 7H9+OADC to an OD600 nm of 1.0. 200 µl of fluorophage was added to 5 µl of cells. The samples were incubated for 12 hr at 37° C. The cells were visualized on a fluorescence microscope (Nikon Ti) using a DIC filter for bright field and a FITC filter for green fluorescence. Fluorescent bacilli after incubation with phage indicate the presence of mycobacteria. To determine relative fluorescence and the percentage of cells infected as a function of the multiplicity of infection (MOI), M. tuberculosis mc26230 cells were infected as described above with the appropriate phage dilution to obtain an MOI of 100, 10, 1, 0.1, 0.01, 0.001, 0.0001, and 0.00001. After infection, cells were acquired using flow cytometry and the data was analyzed using FlowJo 7.6.1.

When performing drug susceptibility testing (DST), antibiotics were added simultaneously with phage or pre-incubated as noted in the respective experiments. Antibiotics used for DST were kanamycin (4 µg/ml), rifampicin (2 µg/ml), isoniazid (0.4 µg/ml) and ofloxacin (10 µg/ml). 200 µl of fluorophage (MOI=100) was added to 5 µl of cells. After phage addition samples were incubated for 12 hr at 37° C. and either analyzed on FACS caliber to quantitate fluorescence per cell and to determine the percentage of fluorescent cells or on a fluorescence microscope. Some samples were fixed in 2% paraformaldehyde before assay and this did not appreciably change fluorescence. Absence of fluorescence in the presence of antibiotic and phage indicated a drug-sensitive sample. Fluorescence in the presence of antibiotic and phage indicated that the sample was resistant to that particular drug.

M. tuberculosis detection and DST in sputum samples: Anonymous, de-identified sputum samples were collected from smear-positive TB patients in Durban, South Africa prior to initiation of treatment. Samples were treated using a standard protocol, except that the concentration of NaOH was reduced to 0.625%. Samples were re-suspended in 500 µl of 7H9+OADC. 100 µl of sample was used for Ziehl Neelsen staining and 100 µl of sample was incubated with 500 µl of phage in the presence or absence of antibiotic. After incubation for 12 hr at 37° C., the samples were fixed in 2% paraformaldehyde for 3 hr. The samples were then centrifuged, re-suspended in 10 µl of MP buffer, and analyzed by fluorescence microscopy.

Results

Figure 1B:
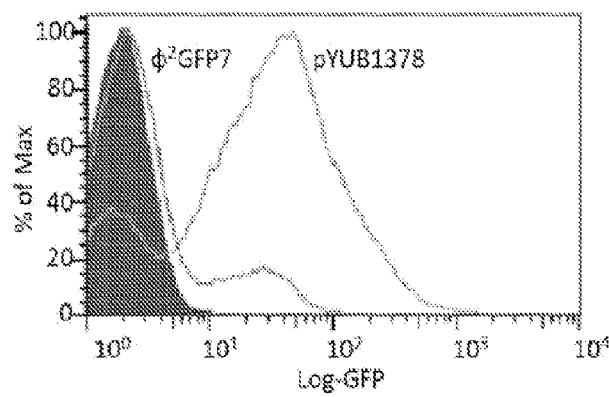
Figure 7:
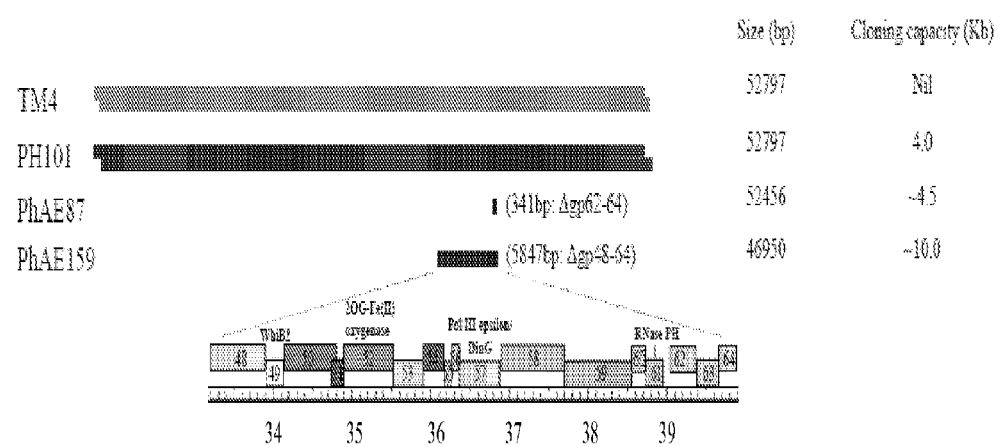
FIG. 7. The vector backbone, phAE159, for the new phage was generated by the deletion of a ~6 kb region encompassing genes gp48-64 [29] from the temperature-sensitive mutant of TM4 known as ph101.

Development of high-intensity fluorophage: The first generation fluorophages provided an important proof-of-principle for the use of phage-mediated delivery of fluorescent reporter genes as a diagnostic tool for detecting M. tuberculosis and assessing drug susceptibilities [17, 28]. However, they were of limited fluorescence and could not be used with clinical samples. To address the main shortfall of that approach, which is poor signal to background ratio, two complementary strategies were investigated, although it was not clear whether they would be successful: 1) a new the vector backbone was engineered to increase cloning capacity, and 2) promoters originating from bacteriophages were used to enhance the expression of reporter genes. The new vector backbone, phAE159, was generated by the deletion of a ~6 kb region encompassing genes gp48-64 [29] from the temperature-sensitive mutant of TM4 known as ph101 (FIG. 7, [30]). Similar to parent ph101 and phAE87 [31], shuttle phasmid phAE159 propagates as a phage at 30° C., but at 37° C. will inject its DNA without propagating. The phAE159 can accommodate ~10 Kb of recombinant DNA without compromising its ability to form phage particles. First, the monomeric fluorescent protein mVenus [32] was cloned under the hsp60 promoter [19] to generate φ²GFP7 (FIG. 1A). However, the fluorescence intensity obtained from φ²GFP7 was similar to previous reporter phage phAE87::hsp60-EGFP [28] and was at least 10-fold lower than cells harboring the multi-copy plasmid pYUB1378 (FIG. 1B).

Figure 1C:
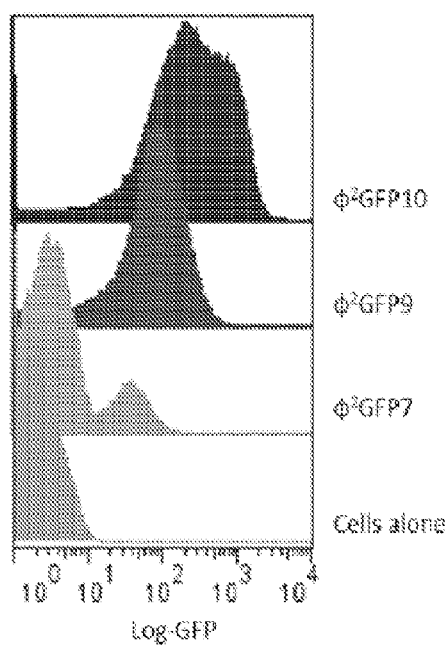
Figure 1D:
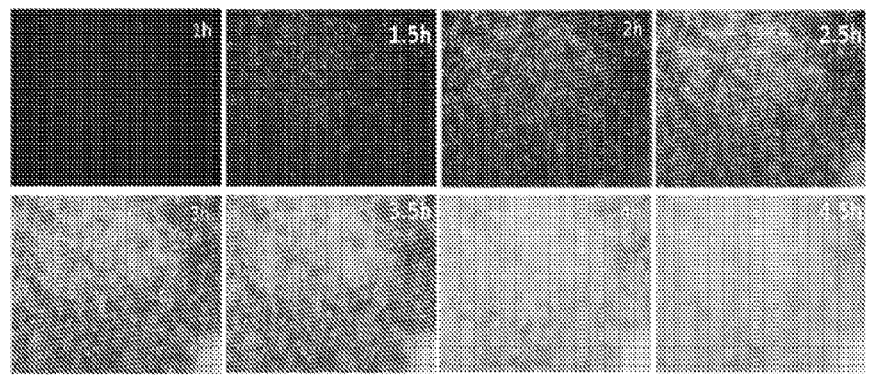

The enhanced cloning capacity of phAE159 was used to evaluate various chromosomal promoters from *M. tuberculosis* and *M. smegmatis* for their potential improvement of reporter expression. No promoters were found that increased the reporter signal to a level appreciably higher than hsp60 promoter in the phage (data not shown). It was investigated whether phage promoters might be better suited for high expression from mycobacteriophages, since phages have evolved to express large quantities of their structural and lytic proteins in short periods of time. First tested was the late promoter of *E. coli* T7 phage, which has been extensively used on episomal plasmids for the overexpression of recombinant proteins in *E. coli* [33, 34]. Fluorophage φ²GFP8 was generated by cloning the T7 phage promoter upstream of mVenus (FIG. 1A). The T7 promoter functions only with its cognate RNA polymerase [21, 33], therefore no fluorescence signal was observed when φ²GFP8 infected *M. smegmatis* strain (mc2155) lacking T7 polymerase. In contrast, infection of a *M. smegmatis* strain expressing T7 polymerase (mc24517) with φ²GFP8 resulted in a high level of fluorescence. Fluorescent cells were detected as early as 2 hr after infection. The population of fluorescent cells increased with time, and more than 90% of the cells were fluorescent after 12 hr of infection with φ²GFP8. Following the above results, the T7 polymerase gene was cloned upstream of the T7 promoter in φ²GFP8 to generate φ²GFP9. φ²GFP9 overcame the requirement of a strain to endogenously express T7 polymerase and strong fluorescent signal was obtained when φ₂GFP9 infected the wild type *M. smegmatis* strain (mc²155) (FIG. 1C). Based on these results another reporter phage, φ²GFP10, was generated using $P_{Left}$ lytic promoter of mycobacteriophage L5 [35]. This strong phage promoter requires only the mycobacterial host RNA polymerase. The comparison of these two phage promoters with hsp60 promoter shows that the fluorescence obtained from φ2GFP10 was almost 100-fold greater than that from cells infected with φ2GFP7 and was marginally better than φ2GFP9 under similar conditions (FIG. 1C). Fluorescent cells were observed after 1 hr of infection with φ2GFP10 and the fluorescence signal increased over time. More than 90% of the cells were fluorescent after 4 and one half hr and resulted in the saturation of the fluorescent detector (FIG. 1D).

Figure 2A:
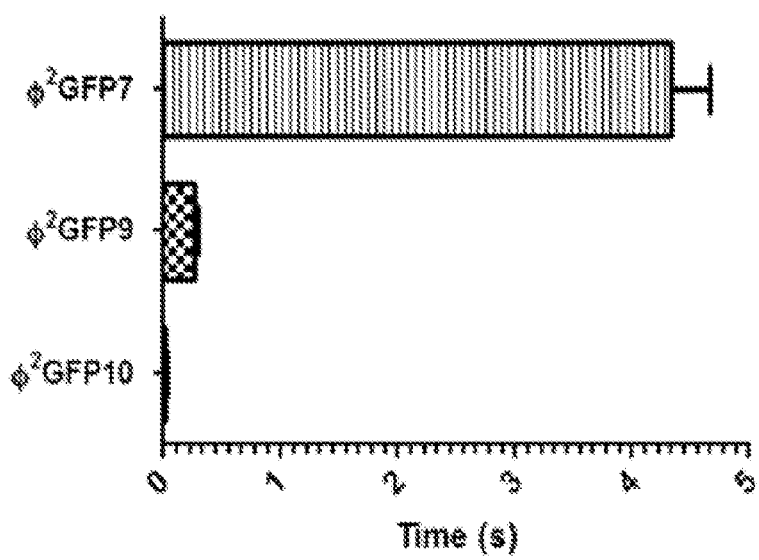
FIG. 2A-2B. Comparison of fluorophages in M. tuberculosis. A) Determination of exposure time to capture a fluorescent image with a similar fluorescent intensity (arbitrary level) by a Nikon Ti microscope after infection of M. tuberculosis mc26230 with the indicated fluorophages. B) Flow cytometric determination of fluorescent intensity obtained after infection of M. tuberculosis mc$^2$6230 with $\phi^2$GFP7 and $\phi^2$GFP10.
Figure 2B:
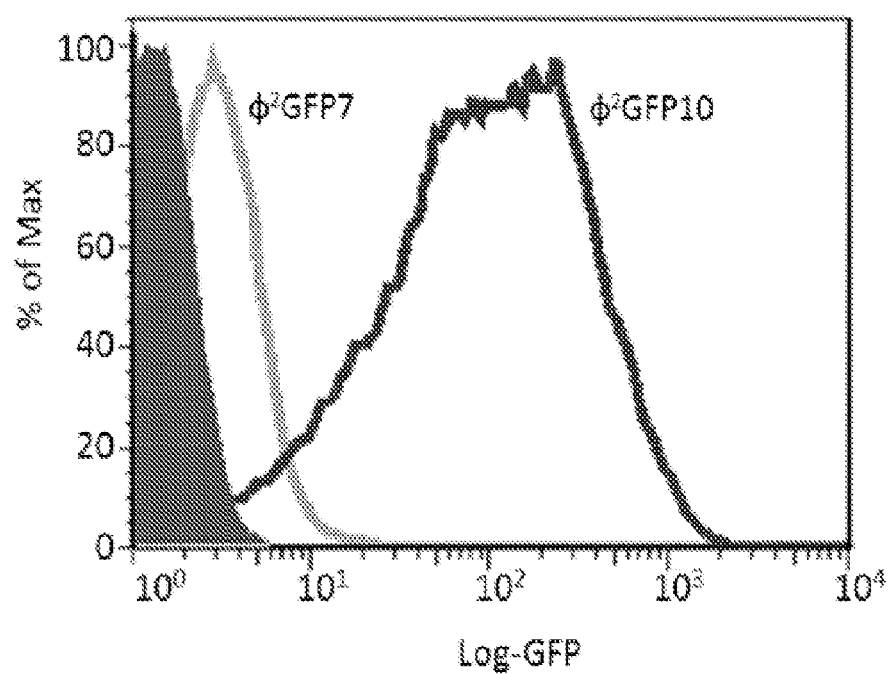
Figure 8:
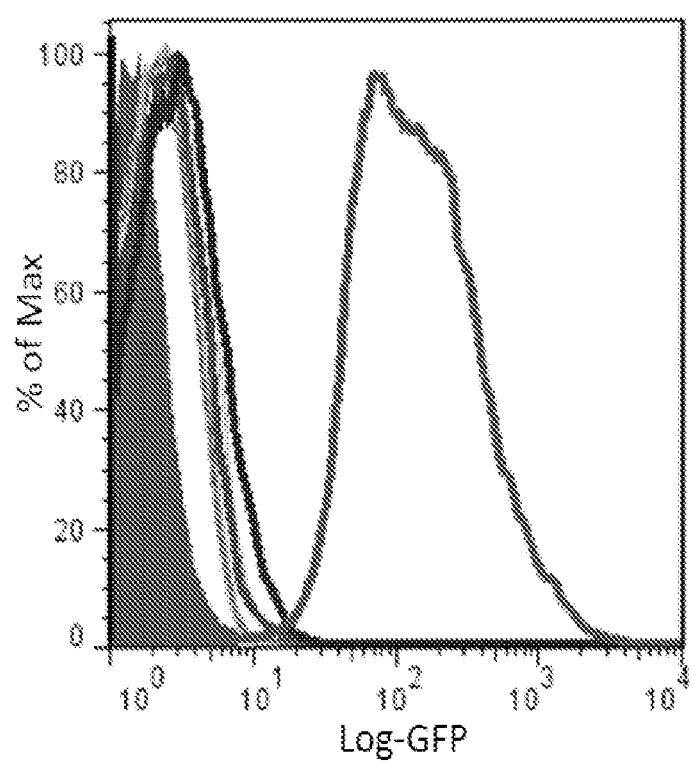
FIG. 8. Kinetics of accumulation of fluorescence protein in M. tuberculosis after infection with $\phi^2$GFP10. The M. tuberculosis cells were incubated with $\phi^2$GFP7. The samples were fixed at 12, 24, 36 and 48 hr with 2% paraformaldehyde and analyzed by flow cytometry. M. tuberculosis cells incubated with $\phi^2$GFP10 and fixed after 12 h were used as a positive control. All the infections were performed at a MOI of 100.

Comparison of fluorophages in *M. tuberculosis*: The attenuated *M. tuberculosis* strain mc²6230 [25] was infected with the reporter phages described in the previous section. Individual bacilli were fluorescent in all cases, but displayed a wide range of fluorescence intensity. *M. tuberculosis* cells infected with φ²GFP10 required an average exposure time of 15-20 ms to record an image, and φ²GFP9 required an average time of 100-300 ms. Significantly, both φ²GFP9- and φ²GFP10-infected cells could be visualized easily through the microscope eye-piece. By contrast, mc²6230 cells infected with φ²GFP7 were not identifiable with optics alone (eyes on the microscope eyepiece with no intervening camera and image processing), and required an average exposure time of 4-5 sec to boost the signal of cells to a similar level (FIG. 2A). Flow cytometry data paralleled microscopy results and showed that mc²6230 infected with φ²GFP10 fluoresced at approximately a 100-fold greater intensity than mc²6230 infected with φ²GFP7 (FIG. 2B). The fluorescence intensity did not increase significantly after prolonged incubation of φ2GFP7 with mc²6230 and significant differences were also observed after 48 hr of φ²GFP7 and φ²GFP10 infected *M. tuberculosis* mc²6230 cells (FIG. 8). Overall, the $P_{Left}$ promoter of L5 mycobacteriophage in φ²GFP10 was found to drive the strongest reporter expression from the phage.

Figure 3A:
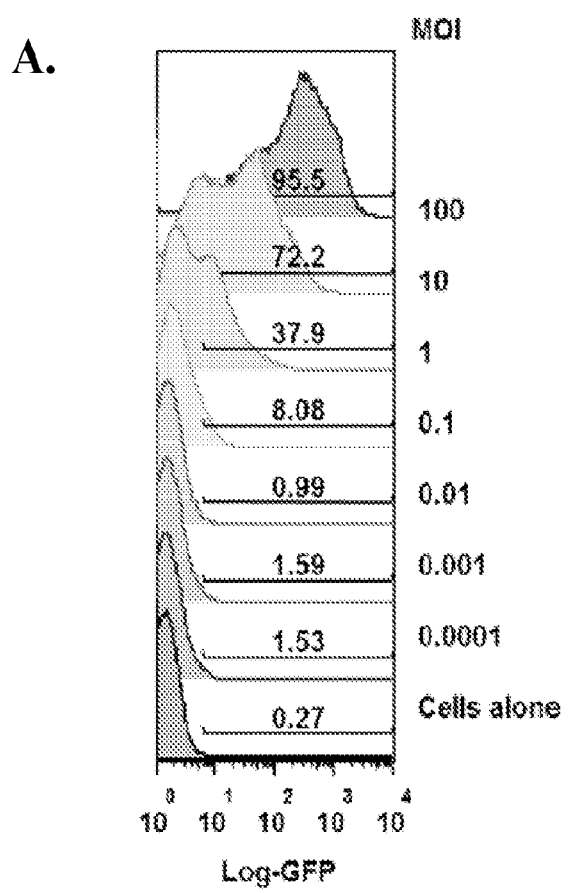
FIG. 3A-3B. Efficiency of detection of M. tuberculosis using fluorophage. M. tuberculosis mc26230 cells were infected with $\phi^2$GFP10 at different multiplicities of infection (MOI). Percent fluorescent cells was determined using flow cytometry. B) Mean Fluorescent Intensity (MFI) of M. tuberculosis mc$^2$6230 cells infected with $\phi^2$GFP10 at different MOI was determined using FlowJo analysis.
Figure 3B:
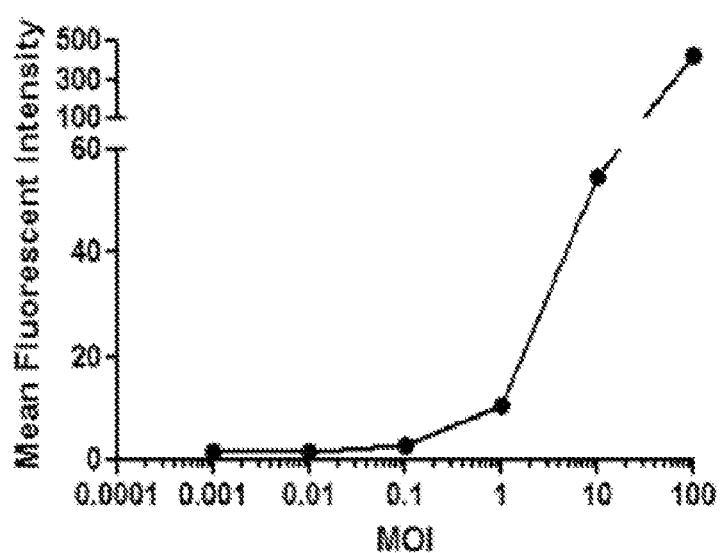

Next, the relationship of MOI to signal was determined. The proportion of fluorescent cells in a given sample increased with increasing MOI of φ²GFP10 (FIG. 3A). At MOIs of 1, 10, and 100, approximately 38%, 72%, and 95.5% of the cells, respectively, were fluorescent (FIG. 3A). The Mean Fluorescent Intensity (MFI) signal per cell also increased as a function of MOI (FIG. 3B). The increase in this ratio implies that a single mycobacterial cell can be incited to express product from more than one reporter phage. *M. smegmatis* or *M. tuberculosis* cells infected with other fluorophages φ²GFP7, φ²GFP9) also resulted in increased MFI with increased MOI (data not shown) suggesting that the new vector backbone supports multiple infections from the same phage. Based on the results, an MOI of 100 was used in subsequent experiments.

Figure 4A:
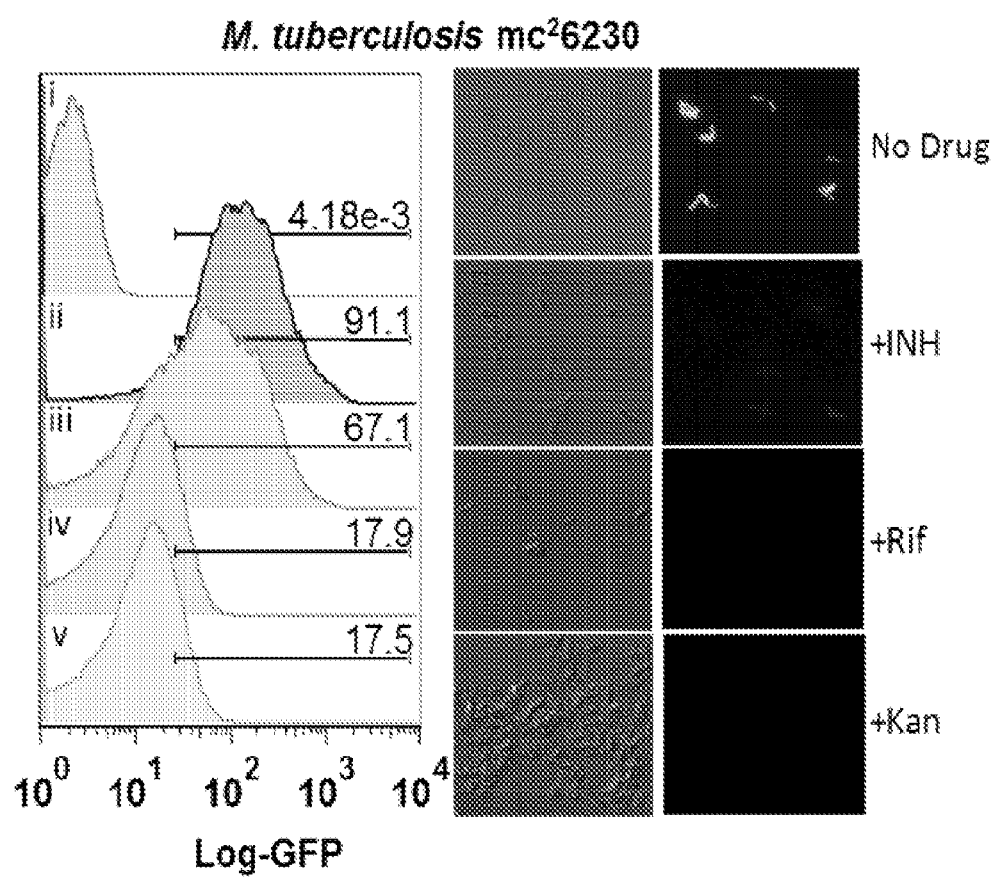
FIG. 4A-4D. Drug susceptibility test for M. tuberculosis strains using fluorophage $\phi^2$GFP10. Drug-sensitive M. tuberculosis mc$^2$6230 (A); Rifampicin-resistant M. tuberculosis mc$^2$7201 (B); Kanamycin-resistant M. tuberculosis mc$^2$7202 (C). Rifampicin- and Kanamycin-resistant M. tuberculosis mc$^2$7203 (D) were incubated with $\phi^2$GFP10 and the indicated antibiotics simultaneously, incubated for 12 hr, and then examined by microscopy and flow cytometry. Failure to fluoresce in the presence of antibiotic indicates sensitivity, and a fluorescence signal in the presence of a specific antibiotic indicates resistance to that antibiotic.
Figure 9:
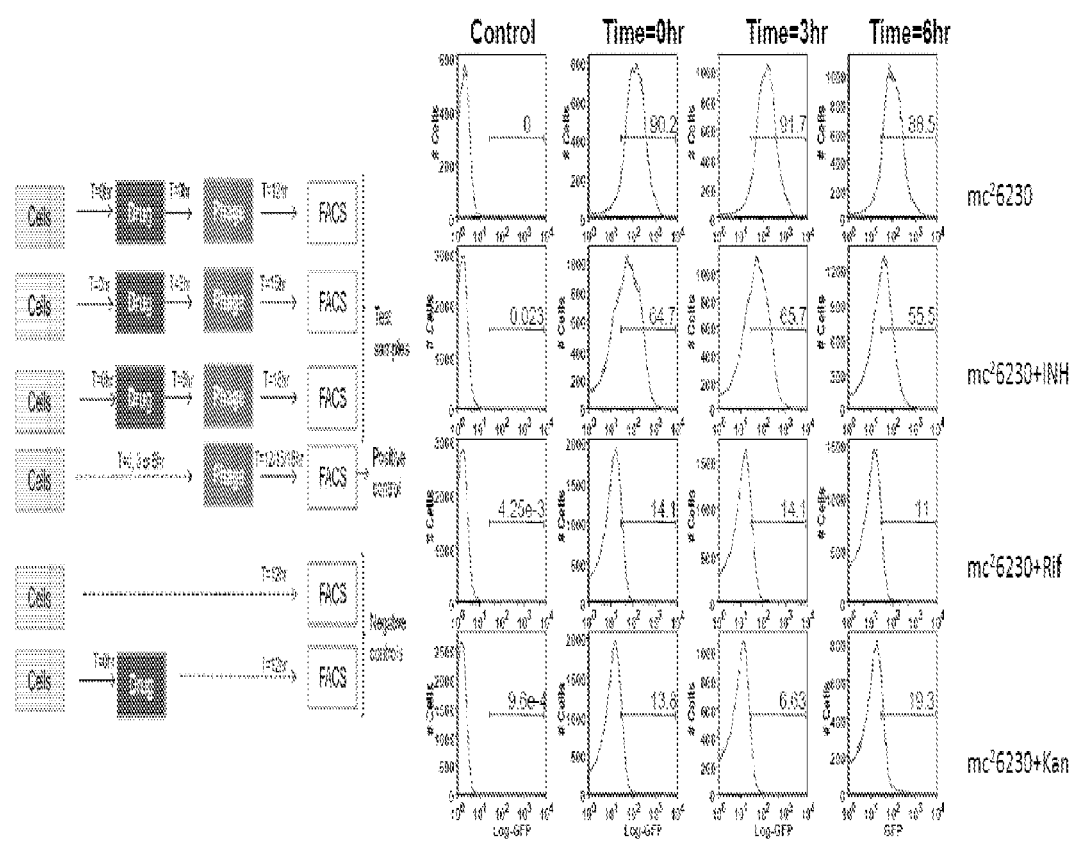
FIG. 9. Drug susceptibility test for M. tuberculosis strains using fluorophage $\phi^2$GFP10. Drug sensitive M. tuberculosis mc$^2$6230 was incubated with the indicated antibiotics. Phage $\phi^2$GFP10 was added either at the time of drug exposure or 3 h and 6 h after drug treatment and percent fluorescent population was determined for each case after 12 h of incubation at 37° C. The schematic representation of the experiment is shown at left. The percent fluorescent population was determined in each case by flow cytometry. Failure to fluoresce in the presence of antibiotic indicates sensitivity and the percent fluorescent population does not significantly decrease by longer incubation in presence of Rifampicin and Kanamycin. The six hour pre-incubation is not sufficient to determine drug sensitivity to isoniazid and ofloxacin.
Figures 10A, 10B:
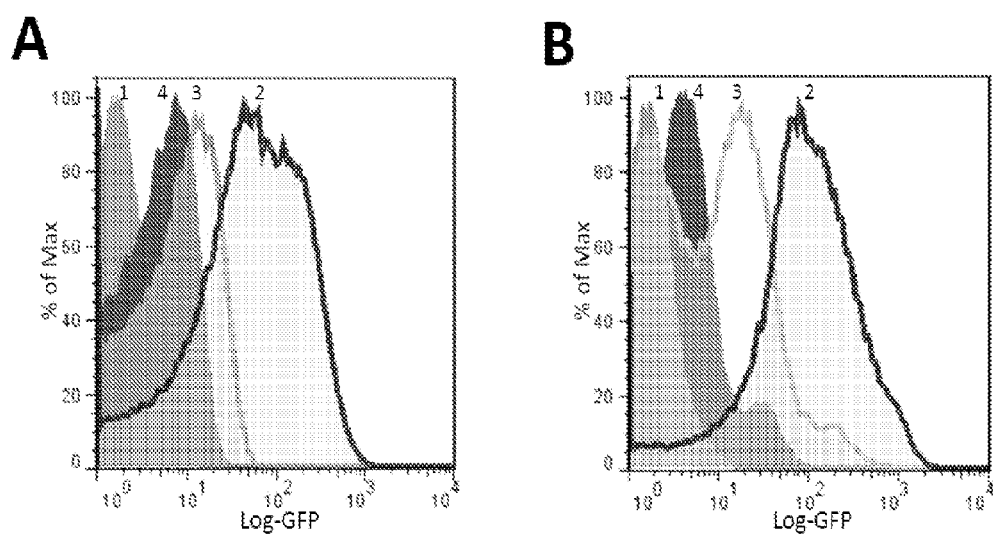
FIG. 10A-10B. *M. tuberculosis* drug susceptibility test for ofloxacin and isoniazid using fluorophage φ²GFP10. Drug sensitive *M. tuberculosis* mc²6230 was incubated with ofloxacin or isoniazid. Phage φ²GFP10 was added after 18 and 24 h after pre-treatment with (A) ofloxacin and (B) isoniazid. Results indicate that 18 h of pre-treatment is sufficient to determine drug susceptibility for both the antibiotics

Phenotypic drug susceptibility testing using fluorophage φ²GFP10. Reporter phage have previously been shown to allow the assay of drug sensitivity in laboratory cultures. The reporter signal is unchanged by antibiotic in a genetically resistant strain but in a sensitive strain the reporter signal is greatly attenuated by the antibiotic [18]. Drug-susceptible *M. tuberculosis* mc²6230 was incubated with antibiotics, and phage φ²GFP10 was added either simultaneously (i.e., at time t=0), or after 3 hr or 6 hr preincubation with antibiotic. The proportion of fluorescent population was determined in each case 12 hr after φ²GFP10 addition. In the absence of drug treatment, approximately 90% of *M. tuberculosis* cells were positive for fluorescence after incubation with φ²GFP10 by both flow cytometry and microscopy (FIG. 4A). When rifampicin or kanamycin were added to cells along with φ²GFP10 (time t=0), fluorescence of the *M. tuberculosis* cells diminished by approximately 85%, as analyzed by flow cytometry. The remaining 10-15% of cells were just above the cut-off level on the FACS plot and were not detected by fluorescence microscopy (FIG. 4A). Longer pre-incubation with these drugs (t=3 hr and t=6 hr) did not significantly alter the results indicating that both the drug and the phage can be added simultaneously at the time of assay (FIG. 9). In contrast, isoniazid-inhibition of fluorescence was sensitive to the time of addition. When isoniazid was added simultaneously with the phage (t=0), fluorescent cells were detected by both flow cytometry and microscopy, although MFI was lower than the untreated control (FIG. 4A). Isoniazid pre-treatment for 18 hr prior to phage addition increased the difference between treated and non-treated samples. Ofloxacin behaved similarly to isoniazid, in that an 18 hr pretreatment with antibiotic increased the signal differences in DST (FIG. 10).

Figure 4B:
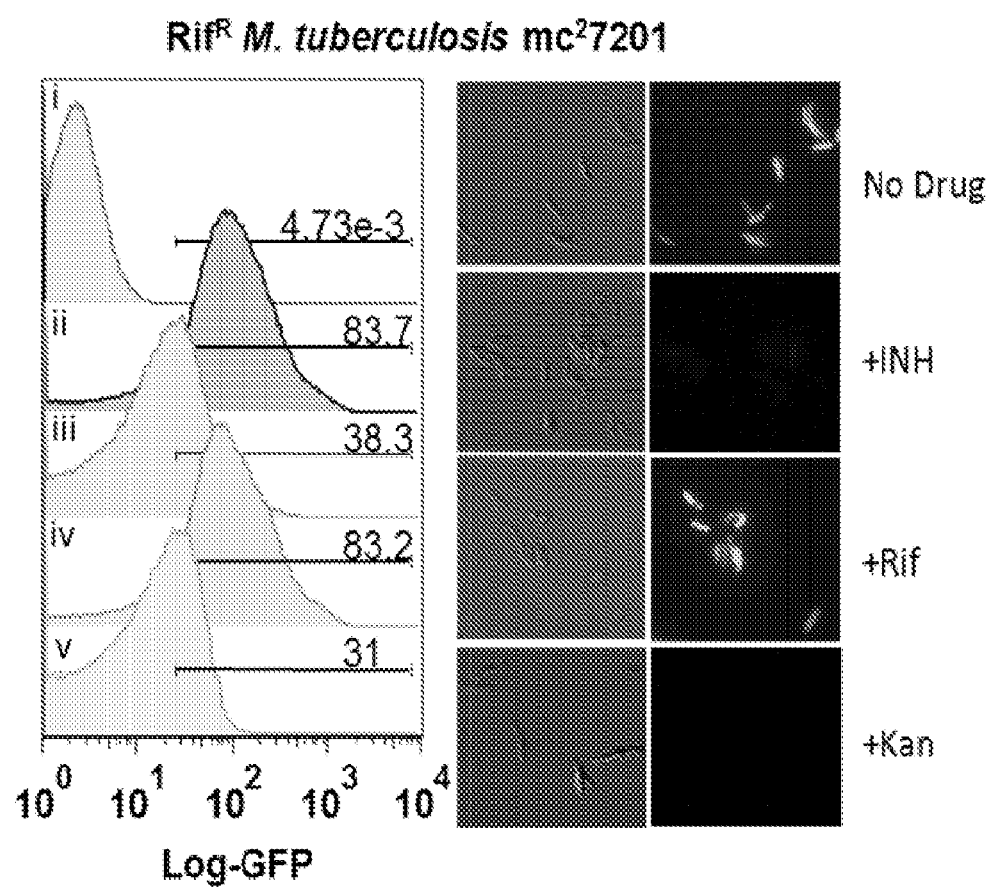
Figure 4C:
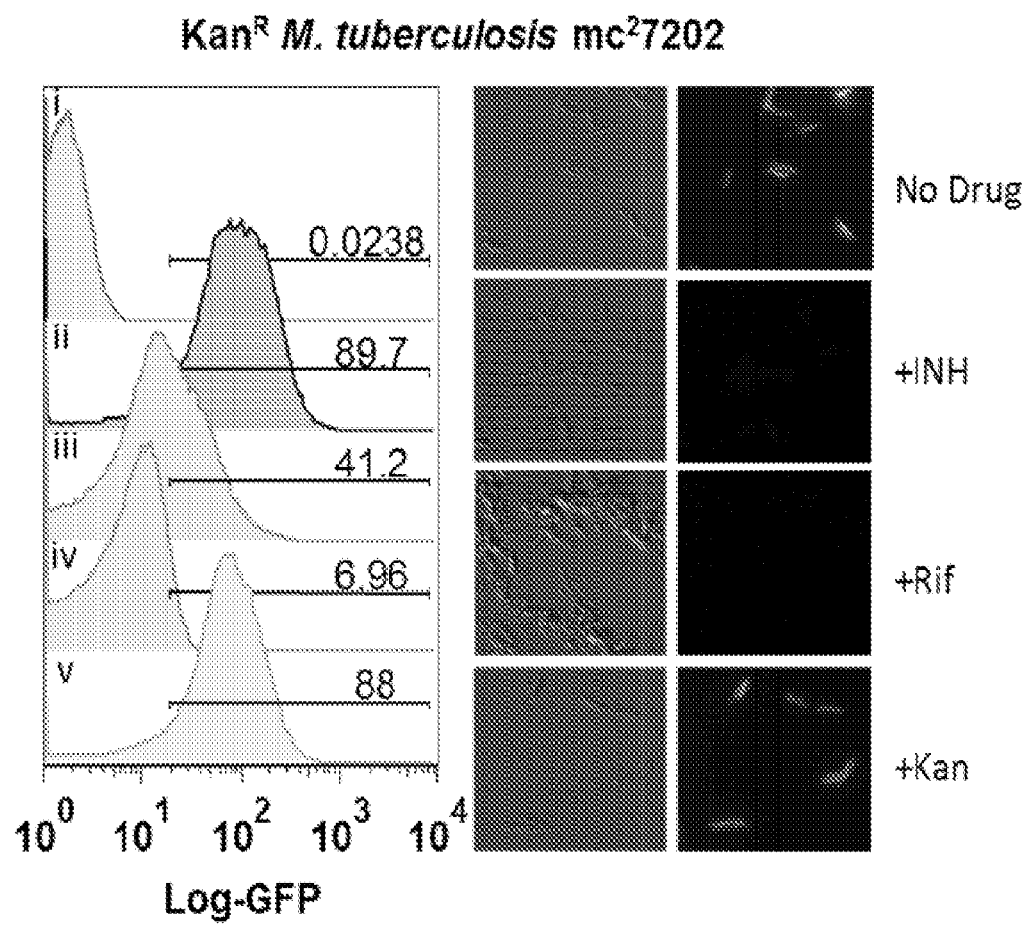
Figure 4D:
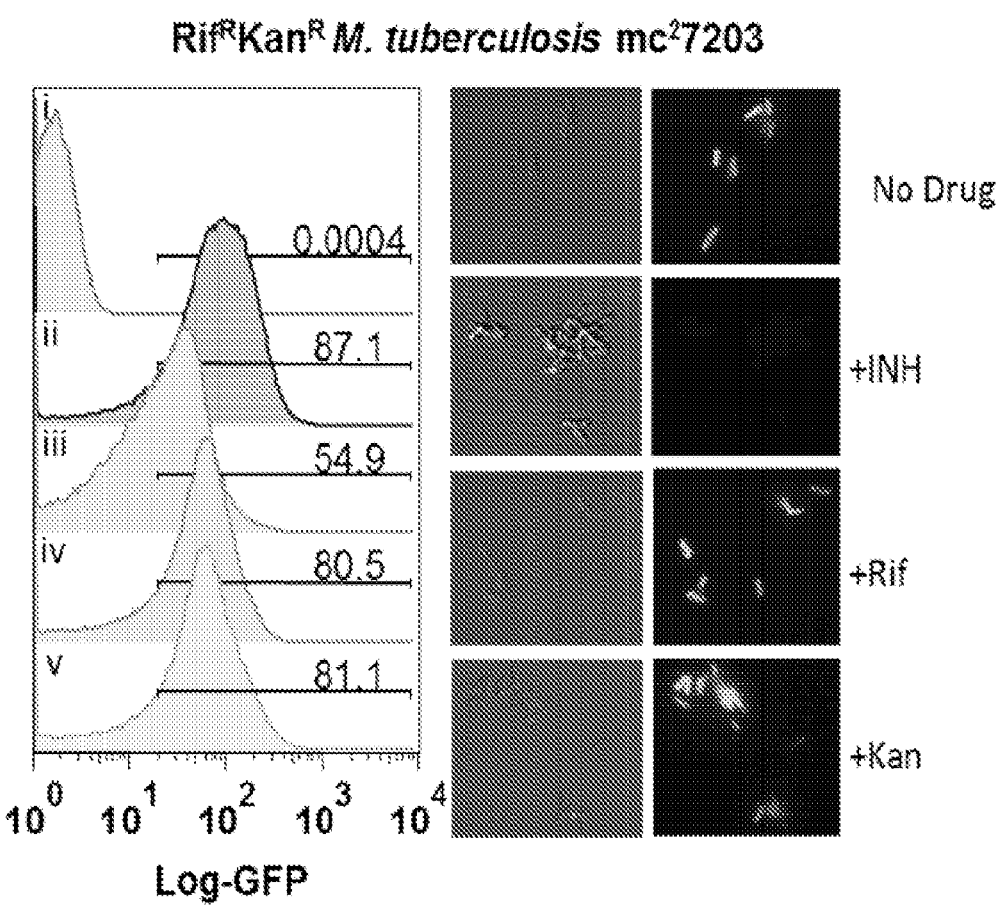

The fluorescence pattern of the rifampicin-resistant strain mc²7201 after infection with φ²GFP10 was similar in the presence and absence of rifampicin. Rifampicin resistance did not change the result of treatment with kanamycin (FIG. 4B). Conversely, for kanamycin-resistant *M. tuberculosis*, mc²7202 fluorescence decreased in the presence of rifampicin, but not in the presence of kanamycin (FIG. 4C). Fluorescence results consistently agreed with CFU plating (data not shown). *M. tuberculosis* mc²7203 is doubly-resistant to kanamycin and rifampicin and its fluorescence intensity did not change in the presence of either antibiotic (FIG. 4D). These results show that φ²GFP10 distinguishes *M. tuberculosis* strains that are resistant to a single drug from those strains that are resistant to multiple drugs.

Figure 5:
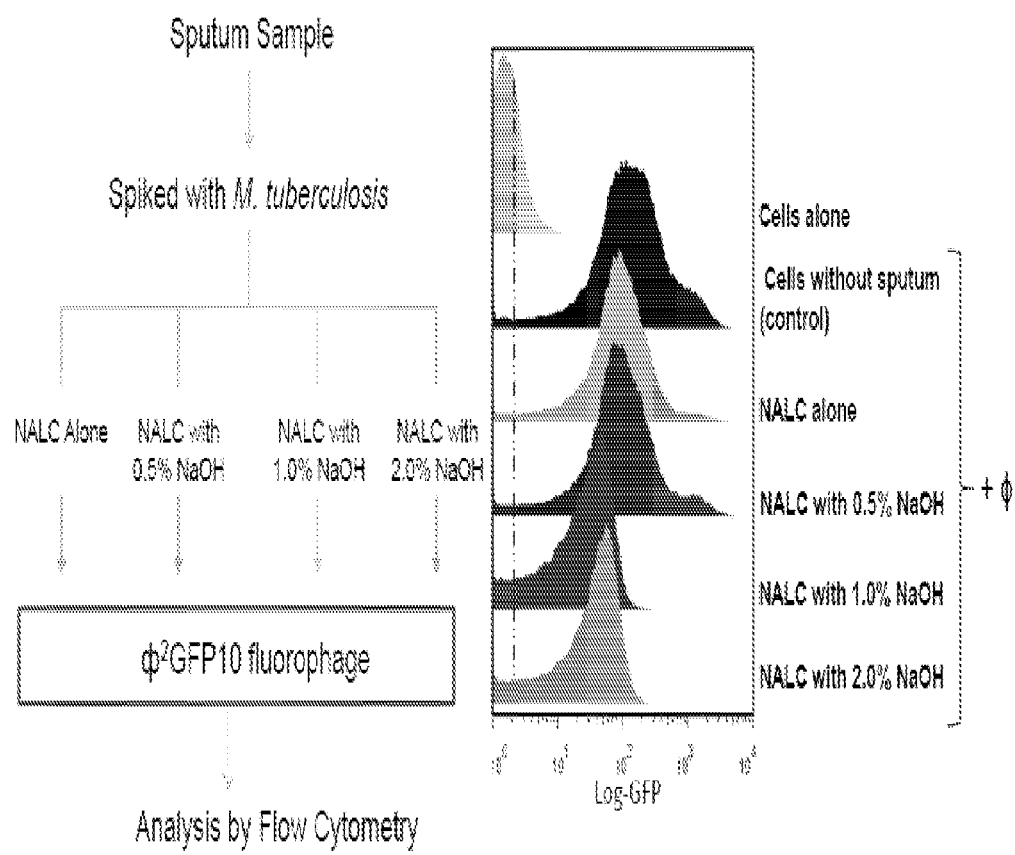
FIG. 5. Detection of M. tuberculosis in spiked sputum samples. Laboratory-cultured cells of M. tuberculosis mc$^2$6230 cells were added to sputum samples to a final concentration of $10^4$ cells per ml. The sample was decontaminated with N-acetyl-L-cysteine (NALC) alone, or with NALC and NaOH, and then incubated with $\phi^2$GFP10 for 12 hr at 37° C. before analysis by flow cytometry.

Detection of *M. tuberculosis* cells in spiked sputum samples with φ²GFP10. The high signal per cell encouraged us to proceed with reconstruction experiments in which defined laboratory grown log phase mycobacteria were spiked into human sputum. A pool of sputum from healthy volunteers was spiked with $10^4$ *M. tuberculosis* cells per ml, processed with NALC and NaOH, and incubated for 12 hr with φ²GFP10. A fluorescent signal was readily observed if and only if *M. tuberculosis* cells were present. Processing with NALC alone or with NALC with 0.5% NaOH did not decrease the reporter signal (FIG. 5). However, fluorescence intensity/cell decreased 10-fold when samples were processed with a higher concentration of NaOH (1-2%) prior to phage incubation (FIG. 5). Treatment with 0.5% NaOH was sufficient to eliminate outgrowth of non-mycobacterial species during the assay period (data not shown). These data show that with φ²GFP10, 90% of *M. tuberculosis* cells were detected in the spiked sputum samples (FIG. 5).

Figure 6:
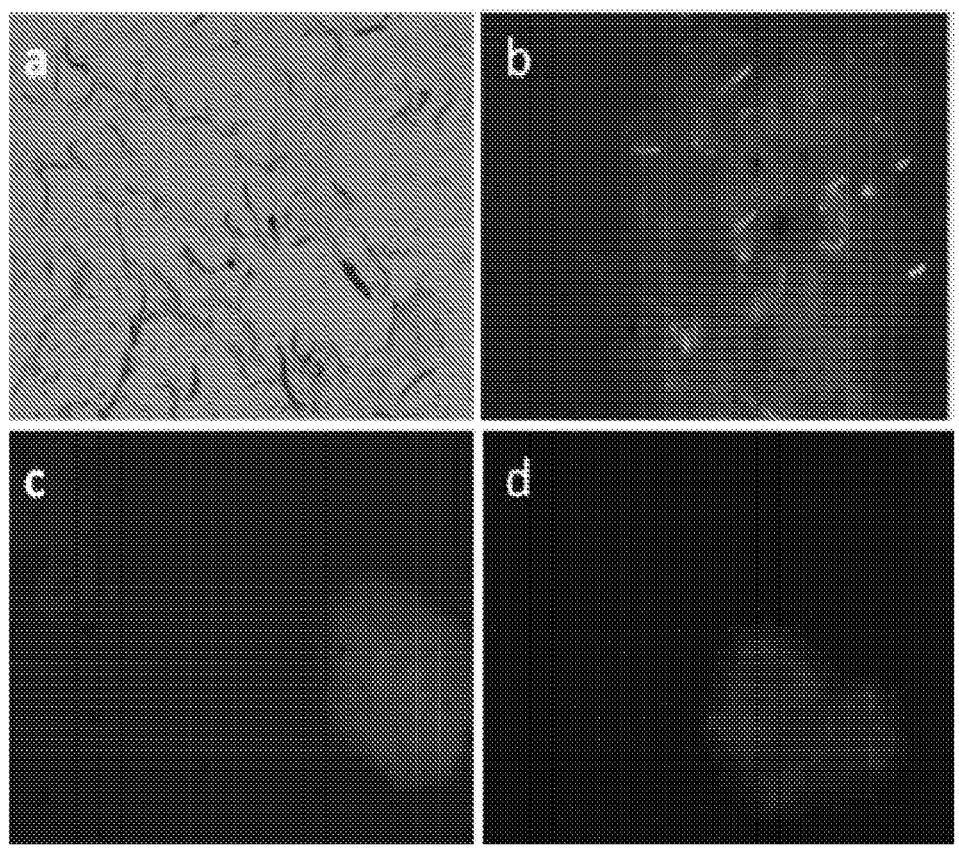
FIG. 6A-6D. Diagnosis and DST of M. tuberculosis in primary clinical samples from active TB patients. Sputum samples were collected from TB patients and analyzed for the presence of M. tuberculosis using (A) Ziehl-Neelsen staining, or (B) $\phi^2$GFP10. The DST for (C) rifampicin and (D) kanamycin was performed on the same sample using $\phi^2$GFP10. The DST results, available within 14 hr from the time of sputum collection with $\phi^2$GFP10 showed that the patient was infected with a drug sensitive M. tuberculosis and were in corroboration with the DST results of agar proportion method available after three weeks.

Detection of *M. tuberculosis* cells in clinical samples: Considering the differences in metabolism, as reflected in the transcriptome of laboratory-grown *M. tuberculosis* compared to the expression thought to occur in patient sputum samples [36], it was not certain that φ²GFP10 would be able to detect bacilli in clinical specimens. Clinical sputums also have variable amounts of background fluorescence which make further demands on signal strength. Sputum samples with smear-positive TB were obtained from patients in Durban, South Africa. These were processed using the procedure detailed above in the spiking experiments, and incubated with fluorophage for 12 hr at 37° C. Fluorescent bacilli were readily detected by fluorescence microscopy (FIG. 6). The total time from sputum collection to detection was approximately 14 hr.

DST of the clinical *M. tuberculosis* was determined for kanamycin and rifampicin in parallel as shown in FIG. 6. Results obtained after 14 hr by fluorophage indicated that the strains were sensitive to both of the drugs and were in 100% agreement with the results of DST determined using the agar proportion method, which were available only after 3 weeks.

Treatment of Clinical Specimen: An improved protocol for preparing decontaminating and liquefying clinical sputum specimens prior to phage infection has been determined. This non-limiting protocol describes the steps for processing the suspected or known Tuberculosis (TB) clinical sputum sample in order to allow for reporter phage infection and direct visualization of *Mycobacterium tuberculosis*. The advanced protocol allows sufficient liquefaction for processing in a clinical flow cytometer and decontaminates the specimen without inhibiting reporter phage infection.
1. Add equal volume 50% diluted Dithiothreitol in phosphate buffer (Sputuolysin) to sputum sample;
2. Vortex×30 secs.-1 minute;
3. If sample still mucoid, add another equal volume of 50% diluted Dithiothreitol in phosphate buffer;
4. Let sit for 10 minutes;
5. Centrifuge at 4000 RPM×10 minutes;
6. Decant supernatant;
7. Add 5 ml 1% sodium hydroxide solution;
8. Vortex×30 secs.;
9. Let sit for 15 minutes;
10. Add PBS to make up volume to 10 ml;
11. Centrifuge at 4000 RPM×20 minutes;
12. Re-suspend pellet in 250 μl 7H9;
13. Transfer 100 microliters to microcentrifuge tube;
14. Add 200 microliters of reporter phage, e.g. fluorophage;
15. Place in 37° C. incubator overnight
16. Conduct analysis of sample to detect *Mycobacterium tuberculosis* using, for example, either fluorescent microscopy or flow cytometry.

Discussion

A high-intensity fluorophage, φ²GFP10 with a mycobacteriophage L5 promoter driving a GFP derivative, yielded 100-fold more per-cell signal than previously described GFP reporter phage [28]; it also allowed real-time visualization using standard fluorescence microscopy of individual *M. tuberculosis* bacilli in primary clinical sputum samples. It is speculated that the phage promoter works so well because phages have been selected during evolution to achieve the maximum level of gene expression in the shortest amount of time. For example, mycobacteriophage D29 yields 120 new phages from a single infected cell of *M. tuberculosis* in 3 hr; the doubling time of *M. tuberculosis* itself is approximately 24 hr [37]. The new reporter phage vector, based on mycobacteriophage TM4, is also deleted for TM4 gp49 a gene that may inhibit bacteriophage superinfection [38]. Deletion of gp49 might be responsible for the enhanced the per cell signal at greater MOI (FIG. 3). Unlike all previous reporter phage φ²GFP10 illuminated *M. tuberculosis* directly from clinical sputum samples without prior culture. The immediate assay of clinical samples has not been possible with any previous reporter phage because the background fluorescence was too large compared to the weaker signal from the reporter phage.

DST by φ²GFP10 has advantages over both nucleic acid tests, such as MTB/RIF, and culture assays. Nucleic acid tests are dependent upon the foreknowledge of a specified candidate sequence leading to drug resistance. DST by culture is not limited to known genotypes but does requires 4-8 weeks for classical culture and 1-2 weeks for MODS [39]. The reporter phage φ²GFP10 yielded DST results from primary clinical samples within 36 hr. Rifampicin and kanamycin (which block transcription and translation, respectively) inhibited reporter gene expression in sensitive cells when drug and phage were added concurrently at time zero and gave antibiotic susceptibility results in 12 hr. The strongest differential signal for isoniazid and ofloxacin (which block mycolic acid biosynthesis and DNA replication, respectively) required pretreatment of bacilli for 18 hr prior to phage addition and the DST results were obtained 36 hr after drug addition to the bacteria. Isoniazid and ofloxacin disrupt mycolic acid metabolism and DNA replication respectively. Since φ²GFP10 assesses the transcription and translation ability of the cells, we reason that the inhibition of transcription and translation are later and secondary effects of these drugs. All four drugs displayed similar kinetics of killing, as measured by CFU, and in all cases a drop in CFU was observed only after 48 hr of antibiotic treatment. Thus φ²GFP10 detects the inhibition of essential metabolic processes prior to the inhibition becoming irreversible. Thus φ²GFP10 gives an extremely rapid but absolutely predictive DST.

Two results with φ²GFP10 imply distinct metabolic subpopulations within log phase cultures of *M. tuberculosis:* 1) When isoniazid and phage were added together at time zero, the average fluorescence measured at 12 hr decreased by 64%, yet a subpopulation of cells retained maximal fluorescence (FIG. 4). 2) In experiments performed to determine the optimum MOI of infection the whole population shifted to a higher MFI with increasing MOI, yet the population spread of dynamic range of fluorescence intensity per cell, i.e. the variance around the MFI, did not change with increasing MOI (FIG. 3A: compare MOI 10 versus 100).

According to the persister model a metabolically less active subpopulation survives transient antibiotic exposure [40]. An alternative possibility is that a rapidly metabolizing subpopulation survives e.g. by inducing a drug efflux pump [41]. Further work will be required to learn if persisters are enriched in one or the other metabolic subpopulations identified by $\phi^2$GFP10 and to distinguish these alternative mechanisms for persistence in *M. tuberculosis*.

The fluorescence microscope and appropriate filters needed for DST with $\phi^2$GFP10 are already included in the recommended diagnostic equipment for laboratories in resource-poor settings. Reagents are inexpensive and could be renewed locally by growing fluorophage stocks. Fluorophages have potential as a point-of-care test for resource poor-settings, since *M. tuberculosis* diagnosis can be available within as little as 12 hr and complete DST completed within 36 hr.

To the best of applicants' knowledge, $\phi^2$GFP10 offers the most rapid assessment of metabolic inhibition by antimicrobials against *M. tuberculosis*. The disappearance of acid-fast bacteria in sputum, loss of CFU, and diminution of mycobacterial DNA detected through PCR are all expected to occur weeks or months after metabolic inhibition. The applications of $\phi^2$GFP10 extend beyond initial diagnosis. Treatment efficacy is currently followed by sputum conversion from positive to negative and is typically noted at two months. $\phi^2$GFP10 allows a much earlier indication of treatment efficacy or failure. Shortening the time to determine if initial treatment is working can improve the efficiency of follow up and of EBA (Early Bactericidal Activity) trials.

REFERENCES

1. Keeler, E., et al., *Reducing the global burden of tuberculosis: the contribution of improved diagnostics*. Nature, 2006. 444 Suppl 1: p. 49-57.
2. Banada, P. P., et al., *Containment of bioaerosol infection risk by the Xpert MTB/RIF assay and its applicability to point-of-care settings*. J Clin Microbiol, 2010. 48(10): p. 3551-7.
3. Blakemore, R., et al., *Evaluation of the analytical performance of the Xpert MTB/RIF assay*. J Clin Microbiol, 2010. 48(7): p. 2495-501.
4. Boehme, C. C., et al., *Rapid molecular detection of tuberculosis and rifampin resistance*. N Engl J Med, 2010. 363(11): p. 1005-15.
5. Helb, D., et al., *Rapid detection of Mycobacterium tuberculosis and rifampin resistance by use of on-demand, near-patient technology*. J Clin Microbiol, 2010. 48(1): p. 229-37.
6. Melzer, M., *An automated molecular test for Mycobacterium tuberculosis and resistance to rifampin (Xpert MTB/RIF) is sensitive and can be carried out in less than 2 h*. Evid Based Med, 2011. 16(1): p. 19.
7. Van Rie, A., et al., *Xpert((R)) MTB/RIF for point-of-care diagnosis of TB in high-HIV burden, resource-limited countries: hype or hope?* Expert Rev Mol Diagn, 2010. 10(7): p. 937-46.
8. Sandgren, A., et al., *Tuberculosis drug resistance mutation database*. PLoS Med, 2009. 6(2): p. e2.
9. Hassim, S., et al., *Detection of a substantial rate of multidrug-resistant tuberculosis in an HIV-infected population in South Africa by active monitoring of sputum samples*. Clin Infect Dis, 2010. 50(7): p. 1053-9.
10. Cohen, T., et al., *The prevalence and drug sensitivity of tuberculosis among patients dying in hospital in Kwa-Zulu-Natal, South Africa: a postmortem study*. PLoS Med, 2010. 7(6): p. e1000296.
11. Moore, D. A., et al., *Microscopic observation drug susceptibility assay, a rapid, reliable diagnostic test for multidrug-resistant tuberculosis suitable for use in resource-poor settings*. Journal of clinical microbiology, 2004. 42(10): p. 4432-7.
12. Jain, P., et al., *Reporter Phage and Breath Tests: Emerging Phenotypic Assays for Diagnosing Active Tuberculosis, Antibiotic Resistance, and Treatment Efficacy* J Infect Dis., In Press.
13. Jacobs, W. R., Jr., et al., *Rapid assessment of drug susceptibilities of Mycobacterium tuberculosis by means of luciferase reporter phages*. Science, 1993. 260(5109): p. 819-22.
14. Banaiee, N., et al., *Luciferase reporter mycobacteriophages for detection, identification, and antibiotic susceptibility testing of Mycobacterium tuberculosis in Mexico*. J Clin Microbiol, 2001. 39(11): p. 3883-8.
15. Banaiee, N., et al., *Rapid identification and susceptibility testing of Mycobacterium tuberculosis from MGIT cultures with luciferase reporter mycobacteriophages*. J Med Microbiol, 2003. 52(Pt 7): p. 557-61.
16. Pearson, R. E., et al., *Construction of D29 shuttle phasmids and luciferase reporter phages for detection of mycobacteria*. Gene, 1996. 183(1-2): p. 129-36.
17. Rondon, L., et al., *Evaluation of Fluoromycobacteriophages for detecting drug resistance in Mycobacterium tuberculosis*. Journal of clinical microbiology, 2011.
18. Riska, P. F., et al., *Rapid film-based determination of antibiotic susceptibilities of Mycobacterium tuberculosis strains by using a luciferase reporter phage and the Bronx Box*. J Clin Microbiol, 1999. 37(4): p. 1144-9.
19. Stover, C. K., et al., *New use of BCG for recombinant vaccines*. Nature, 1991. 351(6326): p. 456-60.
20. Davanloo, P., et al., *Cloning and expression of the gene for bacteriophage T7 RNA polymerase*. Proceedings of the National Academy of Sciences of the United States of America, 1984. 81(7): p. 2035-9.
21. Wang, F., et al., *Mycobacterium tuberculosis dihydrofolate reductase is not a target relevant to the antitubercular activity of isoniazid*. Antimicrobial agents and chemotherapy, 2010. 54(9): p. 3776-82.
22. Brown, K. L., et al., *Transcriptional silencing by the mycobacteriophage L5 repressor*. The EMBO journal, 1997. 16(19): p. 5914-21.
23. Bardarov, S., et al., *Specialized transduction: an efficient method for generating marked and unmarked targeted gene disruptions in Mycobacterium tuberculosis, M. bovis BCG and M. smegmatis*. Microbiology, 2002. 148(Pt 10): p. 3007-17.
24. Snapper, S. B., et al., *Isolation and characterization of efficient plasmid transformation mutants of Mycobacterium smegmatis*. Molecular microbiology, 1990. 4(11): p. 1911-9.
25. Sambandamurthy, V. K., et al., *Mycobacterium tuberculosis DeltaRD1 DeltapanCD: a safe and limited replicating mutant strain that protects immunocompetent and immunocompromised mice against experimental tuberculosis*. Vaccine, 2006. 24(37-39): p. 6309-20.
26. Maus, C. E., B. B. Plikaytis, and T. M. Shinnick, *Molecular analysis of cross-resistance to capreomycin, kanamycin, amikacin, and viomycin in Mycobacterium tuberculosis*. Antimicrobial agents and chemotherapy, 2005. 49(8): p. 3192-7.

27. Gumbo, T., et al., *Concentration-dependent Mycobacterium tuberculosis killing and prevention of resistance by rifampin.* Antimicrobial agents and chemotherapy, 2007. 51(11): p. 3781-8.
28. Piuri, M., W. R. Jacobs, Jr., and G. F. Hatfull, *Fluoromycobacteriophages for rapid, specific, and sensitive antibiotic susceptibility testing of Mycobacterium tuberculosis.* PLoS One, 2009. 4(3): p. e4870.
29. Ford, M. E., et al., *Mycobacteriophage TM4: genome structure and gene expression.* Tuber Lung Dis, 1998. 79(2): p. 63-73.
30. Carriere, C., et al., *Conditionally replicating luciferase reporter phages: improved sensitivity for rapid detection and assessment of drug susceptibility of Mycobacterium tuberculosis.* J Clin Microbiol, 1997. 35(12): p. 3232-9.
31. Bardarov, S., et al., *Conditionally replicating mycobacteriophages: a system for transposon delivery to Mycobacterium tuberculosis.* Proc Natl Acad Sci USA, 1997. 94(20): p. 10961-6.
32. Nagai, T., et al., *A variant of yellow fluorescent protein with fast and efficient maturation for cell-biological applications.* Nature biotechnology, 2002. 20(1): p. 87-90.
33. Studier, F. W., et al., *Use of T7 RNA polymerase to direct expression of cloned genes.* Methods in enzymology, 1990. 185: p. 60-89.
34. Golomb, M. and M. Chamberlin, *Characterization of T7-specific ribonucleic acid polymerase. IV. Resolution of the major in vitro transcripts by gel electrophoresis.* The Journal of biological chemistry, 1974. 249(9): p. 2858-63.
35. Nesbit, C. E., et al., *Transcriptional regulation of repressor synthesis in mycobacteriophage L5.* Molecular microbiology, 1995. 17(6): p. 1045-56.
36. Garton, N. J., et al., *Cytological and transcript analyses reveal fat and lazy persister-like bacilli in tuberculous sputum.* PLoS medicine, 2008. 5(4): p. e75.
37. David, H. L., S. Clavel, and F. Clement, *Adsorption and growth of the bacteriophage D29 in selected mycobacteria.* Annales de l'Institut Pasteur/Virologie. 131(2): p. 167-179, 181-184.
38. Rybniker, J., et al., *Insights into the function of the WhiB-like protein of mycobacteriophage TM4-a transcriptional inhibitor of WhiB2.* Mol Microbiol, 2010. 77(3): p. 642-57.
39. Ejigu, G. S., et al., *Microscopic-observation drug susceptibility assay provides rapid and reliable identification of MDR-TB.* The international journal of tuberculosis and lung disease: the official journal of the International Union against Tuberculosis and Lung Disease, 2008. 12(3): p. 332-7.
40. Balaban, N. Q., et al., *Bacterial persistence as a phenotypic switch.* Science, 2004. 305(5690): p. 1622-1625.
41. Alland, D., et al., *The Mycobacterium tuberculosis iniA gene is essential for activity of an efflux pump that confers drug tolerance to both isoniazid and ethambutol.* Molecular Microbiology, 2005. 55(6): p. 1829-1840.

What is claimed:

1. An isolated recombinant mycobacteriophage comprising a vector backbone into which (a) a heterologous mycobacteriophage promoter nucleic acid and (b) a heterologous nucleic acid encoding a protein of interest are integrated, and wherein (a) is upstream of (b) and operatively linked thereto, and wherein the vector backbone is derived from a mycobacteriophage TM4 and comprises a TM4 genomic sequence having a 5.5 kbp to 6.5 kbp deletion of non-essential DNA thereof, and wherein the recombinant mycobacteriophage is conditionally propagating.

2. The isolated recombinant mycobacteriophage of claim 1 wherein the heterologous mycobacteriophage promoter nucleic acid is a heterologous $P_{Left}$ lytic promoter of mycobacteriophage L5.

3. The isolated recombinant mycobacteriophage of claim 1, wherein the vector backbone does not comprise TM4 gene 49.

4. The isolated recombinant mycobacteriophage of claim 1, wherein the vector backbone derived from a mycobacteriophage TM4 does not comprise a portion having the sequence of residues 33,877 through 39,722 of the TM4 genome.

5. The isolated recombinant mycobacteriophage of claim 1, wherein the vector backbone comprises the nucleic acid sequence set forth in Genbank Accession No. JF937104 (SEQ ID NO:4); JF704106 (SEQ ID NO:5); JF704105 (SEQ ID NO:6); HM152764 (SEQ ID NO:7); or HM152767 (SEQ ID NO:8).

6. The isolated recombinant mycobacteriophage of claim 1, wherein the mycobacteriophage is a temperature-sensitive conditionally propagating mutant.

7. The isolated recombinant mycobacteriophage of claim 1, wherein the recombinant mycobacteriophage does not propagate in a mycobacteria at 37° C.

8. The isolated recombinant mycobacteriophage of claim 1, wherein the recombinant mycobacteriophage propagates in a mycobacteria at 30° C.

9. A method of detecting a mycobacterium in a sample comprising:
   a) acting the sample with the isolated recombinant mycobacteriophage of claim 1 under conditions permitting the mycobacteriophage to infect a mycobacterium present in the sample and the protein of interest to be expressed in the mycobacterium; and
   b) detecting the protein of interest in the mycobacterium in the sample, thereby detecting the mycobacterium in the sample.

10. A method of determining if a mycobacterium is susceptible to a candidate agent comprising:
   a) contacting a sample comprising the mycobacterium with the isolated recombinant mycobacteriophage of claim 1 in (i) the absence of the candidate agent and (ii) in the presence of the candidate agent, under conditions permitting the mycobacteriophage to infect a mycobacterium present in the sample and the protein of interest to be expressed in the mycobacterium;
   b) detecting the protein of interest in the mycobacterium in the sample in (i) and (ii); and
   c) comparing the amount of the protein of interest detected in the presence of the candidate agent and the absence of the candidate agent, wherein a decrease in amount of the protein of interest in the presence of the candidate agent compared to in the absence of the candidate agent indicates that the mycobacterium is susceptible to the candidate agent.

11. A method of identifying a candidate agent as effective in treating an infection caused by a strain of mycobacterium, the method comprising:
   culturing a mycobacterium with the isolated recombinant mycobacteriophage of claim 1 in (a) the absence of the candidate agent under conditions permitting the mycobacteriophage to infect a mycobacterium present in the sample and the protein of interest to be expressed in the mycobacterium, and (b) the presence of the candidate agent under conditions permitting the mycobacteriophage to infect a mycobacterium present in the sample and the protein of interest to be expressed in the mycobacterium, and
   detecting the protein of interest in the mycobacterium in the sample in (a) and in (b), and comparing the amount of the protein of interest detected in the presence of the candidate agent and the absence of the candidate agent, wherein a decrease in the amount of the protein of interest in the presence of the candidate agent compared to in the absence of the candidate agent indicates the agent as effective to treat an infection caused by the strain of mycobacterium.

12. The method of claim 10, wherein the candidate agent is an antibiotic.

13. The method of claim 9, wherein the mycobacteria is a *Mycobacterium tuberculosis*.

14. A kit for the detecting of a mycobacterium in a sample comprising the mycobacteriophage of claim 1, packaging therefor and written instructions for use thereof.

* * * * *

SEQUENCE LISTING

```
<160> NUMBER OF SEQ ID NOS: 8

<210> SEQ ID NO 1
<211> LENGTH: 50725
<212> TYPE: DNA
<213> ORGANISM: artificial sequence
<220> FEATURE:
<223> OTHER INFORMATION: deletion mutant to TM4 bacteriophage
<220> FEATURE:
<221> NAME/KEY: misc_feature
<222> LOCATION: (34574)..(34574)
<223> OTHER INFORMATION: n is a, c, g, or t

<400> SEQUENCE: 1
ctcgcggcat aggcagccct ctctcgccag cgttttttcc accagcaaac accggccggt      60
catcccggct acgtcgccac accaccagga ggcagacaca tggaccccga gctgatgcgc     120
gcccgcctcg atgcggtcgc cctcgcgatc cgcgccgccg agctgggcct gctggccgac     180
ggcaagacgg tgctcgactc ggcccgcgac attgccgcgt tcgtcgaggg ttgacatgcg     240
cgcccccgac atgctcagcg tgcagtgccc tggctgcgcc gcgccggtcg agtgcacgat     300
cacgaccgag ccggtggagc ccgagcccgg cgacacgcac gccaagatcc gcgtgcgcgc     360
ggtcgatctg cgcgagcggt tccgcgccca tctcgtcgag tgcactcgca cccccgaggc     420
tgtgctggcg gtggcttatg gcggttaagt ctgtcgccgc cgcggcggcc gacggcgacc     480
ggcgcgagct gctcgtcgcg atgcgcgccc gcgtggcgac cgcggttgaa gatcccgaga     540
cacctgcccg cgatctggct gccctgacgc ggcggctgtt ggagattgcc aacgagattg     600
cggcgattga cgctcaggcc gagcagggcg agggcagcgt cgccgccgcg gcagcgacgc     660
ccgatgaacc attcgacggc gacgcttagc gaggtcgcgc gccacgtcat tgcgccgcaa     720
ggcatcgtgt cgacggcctg gccgtcggtg cgcgcgacgt gtggcgcgat gggcctcggg     780
ttcgacctgt ggcaggacga cctcggcaag ctgatttgcg cgaagcgcga cgacggcctg     840
```

```
tacgcggccg acatgttcgc aatgtcgatc ccgcggcaga ccggcaagac gtacctgctc    900
ggcgcgctcg tgttcgcgct gtgcatcaag acgcctaaca cgacggtgat ctggacggcg    960
caccggaccc gcacggccgc agagactttc gcagcatgc agggcctcgc gaagcgcgac    1020
aagatcgccc cgcacatctt gaacgtgcac accggcaacg gcaaagaggc cgtgctgttt    1080
aagaacggct cgcgcatcct gttcggtgcc cgcgagcgcg ggttcggccg tgggttcgcc    1140
ggtgtcgacg tcctgatttt cgacgaggcg cagatcctca ccgagaacgc gatggacgac    1200
atggtgcccg cgacgaacgc ggcgcctaac ccgctgatcc tgctggccgg tacgccaccg    1260
aagccgacga accccggcga ggtgttcacg gtgatgcgcc tcgacgccct ggcgggcgac    1320
gtcgacgacg tcgggtacgt cgagatttcc gccgacgagg acgccgaccc cgacgaccgc    1380
tcgcagtggc gcaagatgaa tccgagctac ccgcaccgga cgtcggcccg agcgatcctg    1440
cgtatgcgta aagcgttggg cgatgagagc tttaagcgcg aggcgatggg catatggccc    1500
aaggtcagcg tgcaccagcc ggtcgtgaag tcggggcggt ggcacgacct gttcgacctc    1560
ggccccgagg acggcgaagc gcctaacgcc ctggcggtcg acatgtcgca cggcctggcg    1620
atttcggtcg gcgcgtgctg gctgatggac gacgacggcc gccacgtcga ggaggtgtgg    1680
gccggtaccg acaccgcggc ggcggtcgac tggatcgctg agcgggccgg gcggcgcatc    1740
ccggtgctga tcgacagcat gagcccggcg gcggcgctgg cgcccgagct gaaagcccgc    1800
aaggtcaagg tgaagctgac cggcgcggcc gatatggcga agggctgcgg cctgtttgag    1860 aacgcgtca cgccgacac gttgacgcat ggcgatcagc ccgcgctgaa tgacgccctc    1920
gctggcgccc gtaaacgccc gatccgcgac gcaggcggtt ggggctggga ccgccgcgac    1980
ccgacctgcg taatccatcc attagtggcc gtgacgctgg ccctgctcgg tgccgccgac    2040
ggccgccgtc gccgagctgg ccgcggtggc ggcgccatgt tcgtgtgaga gggggggcc    2100 gtgactgttc ctgttgacgt gatcgccgac gccccagcgg ccgacgtgga gttccccgag    2160
gactcgatga gccgcgagca gctcggcgcc ttggtcgccg acatgtggcg gctgcatatt    2220
tccgagcgtc agtggctcga ccggatttac gagtacacca aggggctgcg tgggcgcccc    2280
gaggtgcccg agggcgccag cgacgaagtc aaggaactgg cgaagctgtc ggtcaagaat    2340
gtgctttcgc tcgtgcgtga ttcgttcgcg cagaacttga gcgtggtcgg ctaccgcaac    2400
gccctggcga aagagaacga ccccgcctgg gagatgtggc agcgcaaccg catggacgcg    2460
cgccaggccg aggtgcaccg cccggcgctg acgtacggcg cctcgtatgt gacggtgacg    2520
ccgactgatg aggggccggt gttccgcacg cggtcgccgc ggcagatcct cgccgtgtac    2580
gccgacccgt cggtcgacgc ctggccgcag tacgccctcg aaacgtgggt cgcgcaaaag    2640
gatgcgaagc cgcaccggcg cggcgtgctg tacgacgaca cgtacatgta cgagcttgac    2700
ctcggcgagg ttgtgctcgg cgacgcgggc ggcgggcagg ccacgcagca gccggtgaac    2760
gtgcgcgagg tcaccgacgt gatcgagcac ggcgcgacgt cgagggcaa accgtttgc    2820 cccgttgtgc gtttcgtcaa cggccgcgac gccgacgaca tgatcgtcgg tgaggtcgcc    2880
ccgctgatcc tgctgcagca ggcgatcaac tcggtgaact tcgaccggct gatcgtgtcg    2940
cggttcggcg ccaacccgca gcgcgtgatc agcgggtgga ccggcagcaa ggccgaggtg    3000
ctcaaggcat ccgcgttgcg cgtgtggacg tttgaagatc ccgaggtgaa ggcgcaggcg    3060
ttcccgcccg cctcggtcga gccgtacaac ctgatccttg aggaaatgct gcagcacgtg    3120
gcgatggtcg cgcagatcag cccggctcag gtcaccggca agatgatcaa cgtatccgcg    3180
```

```
gaggccctcg cagccgcgga ggccaaccag cagcgcaagc tcgccgcgaa gcgtgaaagt    3240
ttcggcgagt catgggagca actgctgcgc ctggccgccg aaatggacga cgaccccgac    3300
acggccgccg actcgggcgc cgaggtgctg tggcgtgaca ccgaggcccg ctcgtttggc    3360
gcggtcgtcg acggcatcac caagctggcc tcggcgggca tcccgatcga gcacctgctg    3420
tcgatggtgc ccggcatgac gcagcagacg atccaagcga ttaaggactc gctgcgcggc    3480
ggcgaggtga atcgcttgt cgacaaactg ctgtcgaacg aaccggcgcc agtgcccccg    3540
ccgccgcccc aggcggctgc tcaggcgctc aacgagggcg gcgtgaatgg taacggcggc    3600
gcctgagttt cagggcgtcc tggccgagct gagcgggcgt gcgggtatcg ccgtcgaccg    3660
gctcgtgccc cggctgagcg gcctgaccga ggccgagggg ctgcggttca tcaccgacgc    3720
ctatccggcg ctgatcgacc cgtacctgtc ggcgtcgtcc aagctgacga cgcagtggta    3780
cgccgagcag cccgcccgcc agcaacccgc cggcaaaagt gccaacgcgc agctcgcagg    3840
cgatttccgc ggtggcccag caaacacgca gggcggcaag ctgtttgtgc cggaaccggc    3900
gccgctgccc gaccctgacc gcctgggtgc taacgcccgg tgggcgctgc tgcagaacga    3960
cccggtggtc gcgctgcaag gctcggcgac ccgcgcggtc atggactcgt cgcggcgcac    4020
ggtgctcgac aacgccaagc gcgagggcgt gcggtgggtg cgatacgcct cggtcacggc    4080
gtgcgggttc tgccgcatgc tcgcgacccg cggcgccgtg tacaagtcgg ccgacaccgc    4140
gctgcgttca cacgatcact gcgtgtgcct ggcggtgcca gaccgcaacg gctcgtatca    4200 gccgccgcgac tacgtgcagc agtgggagca ggattacctg caggcccgcc gcgacggcct    4260
cactacgccg caagagattt cgcgggcgat ggaggccgcg ggcgagcagc gcaccgcgac    4320
ccggcagtgg ctcaacgccg agaaggcgca ccagcgcaac gtaagcgact ggctcgacgc    4380
cgagttcgtc cacaacaacg ccgtcgacta ctggcagaac gtcgacgccg agctgggcaa    4440
ggcgttcgcc gagcccgcgc cgaaggccga gccgaccgcc gagcccgccg cgaaggccga    4500
gcccgcggag gccccgctcg accggctgct gcgcgaagcg aacgcagcaa tggaaacggg    4560
cgactacgac aaggccgaca agctgctcgc cgaggccgac aagctcgaac gcgcgcagca    4620
agccaaggcg gccaaggcgg ccaaggccga taaggacaag gcccggcgcc aagcggccga    4680
cgccgccaag caagacgagg tgctgaacct cgtcgagcag ggctgggaac cggccgaggc    4740
cgagtctcac gtgtacgcca agagtgtcga gtcgatccgg cgccgtgact tcatgtcgca    4800
ggcccgcggc gacggccaca acggcaagtc gttcgacgcg cttgtcggcg acgtgcacgc    4860
cgagatggcg gccgagcagt tctggaaggc cgaggcggcg acgaacggct acatgctcaa    4920
acgcaagtac gagggcaagg tcgacccgcg caagctgtgg acgatgaacg aggcggcggc    4980
ccgcaagtac atgtcggagg agatggccgc gtggttcgac cagcacgcca ggctcacgag    5040
ggcggcgctg cgcgagtcgg tgctcagcgg taaaggcaac tggcgcaacc cactaacggc    5100
ggatttcctg caatgagcga taacagcgag ctgatcgccg cacgcgacga ggggcgctcg    5160
gcgccggtcg gtgcagtcaa tccgtatgcg gggcagggca tcaaggcccg gctgtggcgc    5220
ctcgggtacc gcacgatgct gctcgacatg ctgaacaact cgcccgctgt gcgggcgtac    5280
ctgcaggcgc agcaatagat ttcacgccca acctgggcgg gtgagcgtgg acggccaacg    5340
cctaatcggc cggtgatgct gacgagctac ggagcaacta acatggcag aacaaactga    5400 gtcgaccacc gaaaccaccg aaggcaagcc cgccgaggac aactcgaccg agggcgccga    5460
cggcggccaa agcggtgacc agggcaagac tttcacacag gccgagcttg acaaggtgat    5520
cgagcagcgg ctcgcccgcg agcgggcgaa gttcggcgat tacgaccagc tcaaggctga    5580
```

```
cgccgccgag ctggcaaaga tccgcgacgg cgaaaagagc gagctgcaga aggcgctcga      5640
acgcgccgag caagccgaga agcgcgccga gcaagccgag ttcacttctc tgcgcagcaa      5700
ggtggcggcg gtcaagggcg tgcccgcgtc gtcgctgacc ggcaagaccg aggacgagct      5760
gaacgcctcg gccgacgagc tgatcgcctg gcgtgaccag aacaagccgc cgcaccacc      5820 gaagcgcaac cccgcgcaag gcggcggcgg cctcaagtcc ggtgccaccg gcaacggcaa      5880
caccaattcc gaccccaaag ctgccgcggc agaagcattg cgccgcttac cgcgcggggg      5940
ctgacaacag gtttccgcgc gaggaccgac ctcggcggga gaaggagaa agccaatcat      6000 ggctgacatt tcacgcgccg aggtcgcctc gctcatccaa gaggcttact cggacacgct      6060
gctggccgcg gccaagcagg gcagcaccgt cctgtctgcg ttccagaacg tgaacatggg      6120
caccaagacc acgcacctgc cggtgctggc gaccctgccc gaggccgatt gggtcggtga      6180
gtctgcgact gacccgaagg gcgtcaagcc caccagcaag gtgacgtggg ccaaccggac      6240
cctcgtcgcc gaggaaatcg ccgtcatcat cccggtgcac gagaacgtca tcgacgacgc      6300
gaccgtggcc gtgctgaccg aggtcgccga gctgggcggc caggcgatcg gcaagaagct      6360
cgaccaggcc gtcattttcg gcaccgacaa gcccgcctcg tgggtttccc cggcgctgat      6420
tccggccgcg gtgactgcgg gccaggccgt cgaggtcgtg ggcggcgtcg ccaacgagtc      6480
cgacattgtc ggcgcgacca accgggccgc gaaggcagtt gcgtcggccg ggtgggcacc      6540
tgacaccctg ctgtcgtccc tggcgctgcg ttacgaggtc gcgaacattc gcgacgcgaa      6600
cggcaacccg gtgttccgcg acgactcgtt cgccggtttc cgcaccttct tcaaccgtaa      6660
cggcgcatgg gacgccgacg cggcgatcga ggtgattgcc gacagctcgc gggtgaagat      6720
cggtgtccgt caggacatta cggtcaagtt cctcgaccag gccacccctcg gcaccggcga      6780 gaaccagatc aacctggccg agcgcgacat ggtcgccctg cggctcaagg cgcggttcgc      6840
ctacgtgctg ggtgtgagcg cgaccgctca gggcgccaac aagacgccgg tcgccgtcgt      6900
ggcaccggct gcctagtgcg ctatcgccac gccttgacgg gggcggttat cggggtgcgt      6960
gagggcaccc tgctggccgc cctcgtcgag ggcgacgaca actggacccg gtacggaggt      7020
gctagccatg acggagtgca aggcgctggc gacaagccag gacgtcaagc gggcgctgcg      7080
gcgggatctg acggaagcgg agcagacgga cctaagcgag ctgctcgccg aggcaacgga      7140
tctcgtcgtc gggtatctgc acccgtaccc ggtcccgaca ccaacaccgg ggccgatcaa      7200
gcgggtggtg cgtcaatgg tggccgcggt gctgacccgg ccgacgcaaa tcctgcctga      7260
gacacaatcc ctcaccgctg acgggttcgg cgtgacgttc acgcccggcg gtaactcgcc      7320
ggggccgtac ctgtcggctg cgctcaagca acggctgcgg ccgtaccgca ccggcatggt      7380
tgcggtcgaa atgggcagcg agcgttactg ctgatgttcc cgacaccgca caaggttgtg      7440
catgtcgacc gagtgaaggt cggcgagaac gcgatgggcc aggcgatcac cgagccgcgc      7500
acccgcaccc gctgggtgac gagtctgcgg ccgagggtga acgagagcgg cactgctgcc      7560
gccctggccg atcgcgtcat cactgagtac acgatggcga cccccgagag tgactggacg      7620
cacggcgacc aagtgaccga tgcgcggggg cgcaagttca aggtgcacgg cgacgtcgag      7680
gactacaacc tcgcccgtt cgggttcacg ccgggctatc gagtgacgtt gcggagggtg      7740
aacgatggcg cgcaaaccgc ttgacatgcc caactcggag caccgcaaga tccgcaagct      7800
gcccgaggtg caggccgagc tgcaacgcct ggcggccgag gtcgcccggc gcgcaggcgg      7860
aatcgccgac gcccccgacg gctacggcac cgaccttgag gtcggccgca ctcgtgcccg      7920
```

```
cgcgcacgtg tggccgaagt cgagtgcggc gatcaaggcc gaaatcaaga cggcgccgct      7980
tatgacgatc gccgcggagc aggggccgca acagtgactc tcgtgccctc tgtcggcccg      8040
ctggtggccg cgcgagccta tctgctcgac gagctggcgg cccgcgctaa cccgctgccg      8100
gtcggcgcca acccgcccga gggcgagccc agctcgtacg cgctgctgtc ccggccgggc      8160
agcgaccgcg acgtgtttct cggccacttc ctgatccgcg tgcgcgtttt cgacagcgac      8220
gtcgtgcgtt tggagcgcaa cgccgatctg ctgcacgcgc tgctgtgcgg ggccaaccac      8280
cgcaaggtgc acacgcccga gggcgacgtg tggatcaccg gcgcggcgca tcactacggc      8340
ccggccgacc tcgacgaccc cgacgtgccg ctgttcggca tgcaggccgc ggtgttctgg      8400
acgatcggcc tcaagcccgc ccgccgtagc taaccgccgg caaaaactcg agcacacccg      8460
ctgacctgcg gcggcgccca attccgcagc gattcaagca aacacaccac cacaccaggc      8520
aagtgtccct cgggccgacc ggctcgcggg tagttagttg cccgcgcggg caagttagga      8580
gagtaagcaa tggcagactc gcccgtcctc gaaaactcgt ggggcgacgt taccaaggtg      8640
ttcgcggcct cgccgtctga cctcgaaacc gttggcggcc tgtggtatgc gccgttcggc      8700
acgccgctgc cgaccgacgt cgacgagccg ctcgacgaca agttcaagaa cctgggcttt      8760
atctcggtcg agggcgtaac cgtcaagatc gacgaccaga ccaagccgat cgaggtttgg      8820
ggtggcgacg aaatcggtgc gctgcgcgac aagttcgcga tcgagtacag catgaagctg      8880
ttccaagtgc tgtcgcccga ggtgaacgcc gccattttcg gcgagggcaa cgtgctcacg      8940
tccgaggcca ccgcgatgca cggcgcccgc atgaaggtgc tcatcaacag caagctgccc      9000
aagcgttgct cgctggtgct cgactcggtg tacgaggaca agatgatccg ccaggtcgcg      9060
cagatcgcgc agaaggcggg cctggctgac ctcaagctgg tgcacaacga gccgatggca      9120
ttcgagccga cattcaaggt gctcaagggc actgacggca accacgtcgt gcagtacagc      9180
gacgacggcg tcatttccgt ctagctgaca cctcacagac cggcaccccg cgcgcttttcc     9240 tggtgggggc gcggggtgtc tcaccacatt cacaccaggg cacgccagga aacacaccag      9300
gaggttaaaa gctatggaaa tcaacgcgac tgacacggcc cccgaggtcg acgtcgtcga      9360
gcaccaggac gtcgacgagc cggtggcggc cgaggcgacc cccgaggcgg gcaagacgat      9420
cgccgaggag tgggccgacg agtacgacgc gggcgccgag ctgttctgcg ccacgttcga      9480
cgccgacgat ttcgaccccg agtacggcgt caacgagtac cccgacggca cgaccgtggc      9540
cgtcaagcgg tgcctgcgca agccgccgcc ggggtggatt cgccagcacg cgcacctgtc      9600
cgaccttgag cgcacgttcg cgctgatcga gaagcactgc agcgacaagg ctctcgacat      9660
tctcgacagc ctcgccgaga agccgtggaa tggtttcgtc gaggcgtggg gccgtgacgg      9720
cgggctgatc gagggaaaat ctcgcaggtc tgcgcggcgg taaggcaagt cgaggacgcg      9780
atccgccggg acatggttct ggcgggtcgc gctttcgacg acgggtcgct cgattgggac      9840
gacctttacg ctttcatttt cgcctcgccg ccgggcaccg cggtgttcca tgcgttcgag      9900
aagggctgga cgacaagcga ttacctgctc gcacacgtga tcgacgccct acggatcaac      9960
aactggcagc gcaccgaggg cgcgcataag aatccgccgc agggcgcacc cgacccgttc     10020
ccgcggccgg gcgacgacga cgacgagccg aagcgcgccg agggcgcggt gtcggccggt     10080
atcacggcgg cgaccaggac gacggtcggc aagttcatgg caatgcgcgc tgagcgcgaa     10140
aagcgttggc gcgaaaagca ccagcgagga gagggggggcg taaatgtcag aggccaagta     10200
ttacctgaca atcctccccg agactcgcga gcttgagtcg ggcatccgcg acgcgatgag     10260
ccgcgccgag cgcgggctca aggtcgcccc gaagttcgac acctcgggcg ctcagcgcgc     10320
```

```
aggccaggac gcgggcaagg gaatcagccg cggcgtcgat acggccgacc ccggtaaggg    10380
cctgggccgc aagctggccc gcaacctcgg cgacggttcg cgcgtcggca agcagtacgg    10440
ctcgcggctg tcggcgggca tcgacagcgc gctgtcggtc gccggtggca tggcgatcgc    10500
caaggttggc agcaagatca gcggggcgct cggctcggcg atgcgggccg ggttcggccg    10560
tctgacgcag atcgactcgg cgcagttcaa gctgaaatcg cttggcaatg aggccagcac    10620
ggtcgcctcg gtcatgcagg acgcgaccgc ggcggtgaag ggtacggcgt tcggcctcga    10680
cgcggctgcg accacggccg cctcggcggt ggccgccggt atcaagccgg gcgagcaact    10740
gaccaagtac ctgtcgctga ccgctgacac ggccgcgatc gccggtacga gcctcgacga    10800
aatgggctcg atcttcaaca aggtgcaggg ctcgggcaag gcgatgacgt tggagcttcg    10860
ccagctcgcc gaccgcggtc tgccgatctt ccaatggctg caggacgagt ttcacgtcag    10920
cggcgacgcg ctgcaggaca tggtcgcgca gggcgcggtc gactctgaga ctttccgccg    10980
ggtgatcgag aagaatatcg gcggcgccgc aaagggtatg ggcggcagtt tcgttggctc    11040
gatggcgaac atgaaggccg ctatgtcgcg gttcggcgcc gaggttatgg ggccgatctt    11100
taagggcgtg cagccgctcg cgaccgggct tatgggcgtg ttcgacaagc tgaccgccgc    11160
gatcaaggcg cctatgggca acgtgacgac tgtggtcgag cagtgggcca agggcatgtc    11220
ggacaagatg caggcgtggg ccgacggcga cggcatgaaa aaggtcattg acttttttcgg    11280 ccgcgtcggc gactcgatca aggctcttgc gaccggcggc gacagcggca agctcggcga    11340
gattgtccag tcgttcaaaa acattgggcc gtcactgcag acggccgggt cgtcgtttgc    11400
ggcgatcggc gccacgctgg ccgcgatcgg ccccgaggtg ctgtcgtcgg tgctcgtgcc    11460
cgcgctgcag ctcgccgccg gggcgctcaa gttcatggcc gacaatgcct cgtgggcggt    11520
gcctacgatc gtcggcctgc gtgtcgccct gttcgcgcac caggccgtgc tgactgcggt    11580
ggcgatcggc accaaggcgt acggcgtcgc gatggccgtg tggtcgggca tcacgaaggc    11640
cgcgaccgcc gcgcagtggc tattcaacgt cgcgctgacc gctaacccga tcgggctgat    11700
tatcgccgcg gtcgtcgggc tcgctgtcgc gatttgggcg ttttttcacga aaaccgaagt    11760 cggccgccaa ctgtggtcga agatttgggg cggcatcaag gccgctgtgc acgtgttcgt    11820
cgagtggttc aagaacacgg ccgtgccgtt catcaaggcc gcctgggaca tgatcgcggc    11880
gggggccatg tggttgtggc acaacgtcat cgagccggtg tgggagggca tcaagacggc    11940
gatcaagttc gccattgatt tcatcaaggc cgagattcaa gcctgggtgg cgatcttcca    12000
tttcatcgag gacgtgtggc gcggcctggt cgacacggcg catgcggtgt ggcagggcat    12060
cgtcgacaag ttcaccggcg tggtgaattt cgtcaaggag ctgcccggca agatcacctc    12120
ggccgctaag gcatgtggg acggcatcaa agacgcattc aagtcgatga tcaacagcct    12180
gatcgacatg tggaacgggc tggccgacaa gatgacgttc accgttcccg acattcccgg    12240
cgtgccccgg cgtggcgaga gcgtgcaccc gatcccgaat atcccgcgcc tggcgaccgg    12300
cggccggatc agcgggccgg gcaccggcac gagcgacagc atcctcgcgc gtatcgctaa    12360
cggcgagttc atcaccaacg ccgccgcgac ggccgcaat ctgccgctgc tgcaggcgat    12420
caactccggt gcgccgctgt gggagctgat tagggcgctg ccgaggttcg ctggcggcgg    12480
cctggccgcg ggcctggcgt ccgagcagaa cctacagccc aacagcatcc tgatttcgcg    12540
gctggtgtcc aagctgttcc gcagatcaa gacgattggc ggctggcggt cgcaggacgc    12600
ttaccccgat cacccgtcgg gccgggcgct cgacattatg atccccaact actcgtcgaa    12660
```

```
ggacggtgtt gcgctgggcg acagcgtgat gcagttcctt atgaagaacg ccgacgcgct    12720
cggcgtcgag tacacgatct ggcggcagac ctaccgcaac acctcggggc agtcgaacct    12780
catggaggac cgcggcagcg acacgcagaa ccacatggat cacgtgcacg tgacgtcgaa    12840
gggcggcaag ccgaagggcg cgtggacac cgcaccggcg ggcctgtctt tgccgtctgg    12900
cgtcaacgtg agcggcctcg acggcgtggg ggtgcctagt ggtggctcgt cggcgctcgg    12960
cagtgccacg tcggcgtctg gcggctcgta ccggcggcc accgacgacg agcttaaggc    13020
gtcgtcgggc aaggtcgaca cgcccgcac gtcgctgcgc aacgccgaca aggctatcga    13080
ggacaagcag tacgcgctcg acaaggcgaa gcgtgacctc gaaatcctca agggtaagaa    13140
gcacaccgcg gcgcagcttg aggacgccga gcaccgcgtg cagaaggccg agcgcgacct    13200
ggccgacgcg atcgagaagc gcggcaaggt caacgacaag ctgaccgacg ccgagcaggc    13260
cgacagcgat ctgcgcacca agggcaaggc caccaagggc aagtcgaaag acggcaaggg    13320
cggcggcctc gacggcagcg acctgggcaa gacgttcgtg tcgggcatgc tcgaaagcat    13380
tggcctcgac gggtcgctgt tctcgaatcc gtttgagtgg ccgacggtta agtcggcgct    13440
cgccggtgtg aactacctcg gcaacctgct gtcgggcaag ggccgcgacg gcgaggaggg    13500
caccaccgac agccccggcg ggttcgccgg tggagtcgct gacagcgtcg gcctgggctc    13560
gctgttcaag ggcctgggca gcccgatcga cgggcaggac gtcggctggt cgccgcagtc    13620
tggcagcccc gcgctggcac cgggtgagtt caacccggcc accgtcggcg gcggctcggt    13680
cgccgagggc gccgtcgacg ctatgtcggc gttcgtcccg agcgcggccc aggcggcgca    13740
gggcgatcag cctgcgcagg ttgacaactc gatcaacatt tcggggccgg tcggtatgga    13800
cccggtcgcg ctgcgctcgc agatccacag cgagcagaac gcccgcaccc gctccacggt    13860
tcggcgcgtc tagctaacgg ccggcagagcc gccgattcat gccttgagct gcggcggctc    13920
gtcgagccag ctaacaactt ctatctatgt gaggcggtga agcgcggtca tgtcttggat    13980
gcacgacgat ttctggctcg acccgcccaa gtatccgaat gactggcagg caacccggc    14040 gtaccccgag gagaatccgg cgcacccgca ctttcagcgg atgggcgcct ggcacgacct    14100
cggtaagaac ggcgagtacc tgcggtcgac ggcgaccaag tggtattact gccacccatc    14160
taacggcaag gtgtggcacc tcgccgggcc gggccgcggg cgtgagggcg tcgtgatggc    14220
gcgcgagctt gagggcgtca tgcagcccga tttcgagatc cgttggagtg agggcgctta    14280
cacgatcggc gccaagcccg agcgcgtcga ctataaaaag cggcgcatca acctgggcgt    14340
ggcgattcag cccaacctca acgcggagcg gatcgaggag cctaattcgt tctcgtaccg    14400
catgatcgag gactcgtggt ggtcgtcgtg gtctgagact gtgcccggtt tcctgggctc    14460
gttcacgcgc acgcatgggt tccgttggct gcgtgtgctg ctcggcgagg ccactaaggg    14520
cgcgctgtcg atcgacccga cgggcaacga caacaactcg gtgattcaca acatggcggt    14580
cgacgccgcc tggccgttct acgccaagcg cccgctcaag cgtgtgtgga aggtcaaccc    14640
ggccgacgtg tacgcgaagg gcaaggccga gggcgttatc gcgatcgcga accgcggcac    14700
gtgggagtcg tggccgaagt tcctggtgcg cgggtctggc gaggtgtgga ttcaggacgg    14760
catcgagggc cggatggtca agctgcccaa gctgtatgac accgacggct cgtacatgat    14820
ggtcgacacc gacccgacgg cgcgcacgat cacgaccgag aaagatccgg tcgacggcca    14880
gctctacaag tacctgcgca acagccaact gctcgacctg ctgctgcacg acgtgacggc    14940
tgcgcggcta ccggcgcagc ggcgcatccc cggtggtatc ggtttcgacg gcaagatccc    15000
gccgcgcacg gtggcgcaca tcaaggtgtc gcacaccaac ccgcagggct caatcacgtg    15060
```

```
catcatgccg cagtattacc ggatggcgtg gtcgtgacgg cgacgctgtt ggagccccg    15120
cggatcggcg tcaacggggc gcctgaccct gtgcgcgacc cgattgccgc gtacacctac    15180
ctcgacgcgc gccgcgaggt gatcgacgag gaggcccgcg cccggccgct cattcgcttg    15240
tgggacaagc aaatgcagta cataggcacg gtcgccgccg agaagtcggt cgacgccgag    15300
gagatgttgc acgacaccgg caccggcgac attgtgctgc gcggcgacga ctggctcgtc    15360
gagttcatgc gctcggacgt gcgcaaagac gaggatctgc acatcacgat cgacccgtac    15420
ccgcaccggc gtaactggcg gtggcggtgg aacgcgaagg tcactaacgt gcgcgtgaag    15480
cgcggcgagg atggtctgcg cacggtcacg cttgagtgct cgcacaatcg ggagcattgg    15540
aagcacatct atttcggcgc aacgcctttc agcccgccgg aggtgcagcc gattcgcgcc    15600
tggctgctgc cgggcaacac tcggaccatt atcgcgacaa cgggtttcat caacctggcg    15660
cgtaattaca acccgctgct ggcgttgccc acgcaggtga tgaatcccgg cgcgtggctc    15720
ggcgaggcca gcaatgtgct gaacctcaac ccgttaaatt ggcctgtcca aatgcaattc    15780
gtcaatccgg tgttcgacca gtcgcgcttt agcgtgatca tgtcgcgctg gctgacgcg    15840
cacagcgtca ccgaggcgat gctgaaagac gcgggctgca acgtgcgcgc gtacatgtgg    15900
ctgcccgagg acgaggacag cccgcacccc gagctggccg cgattatcgg tgagaaggcc    15960
gcccggccga ctcgcgcctg cattgtgctt gcggtggagg acaattcggg ccgcactggc    16020
tggtccggta cggccgccga cggtttcatg cagcttatcg gcgtcactgg cgacgacatg    16080
atccgcgagg tcgtcgggca gatcgacgac aagggccgga ttatcgaccc gataaccaag    16140
gcaacgcttt tcggcaagct gctgggcacc gccccgtcga tcccgagtgt ggtattccgc    16200
gacaccgagc actcgtcgat catcacggcc gagcactcga tgttccgtgc gaaggcccaa    16260
aaaatcctga caggcggaaa atcacccggc tgggttaacc aaactcagac cttcctgatc    16320
cgatatgcgt tgtcgcagtt ggctcaagtg gtgttcgcta ctgagcaacc cggcgccgag    16380
ggcttggaca acctctatca gggccaggcc gacgacacg tgatggcgtt catcgcgttc    16440
acagatccgt tgcgcgccat gcgttctgga ccgtacggct accttgagca tttcgagcag    16500
ggcagcgggt cggcgtacac ggtcagctcg gaatgactc tgcggcaagg gcattggaaa    16560
acgcgccctt accaggcgtt caaggtgcag gtgcgcaacg gcggcaacgc cgggacgctt    16620
tactacgatt tcgacctcgg cacgcgcgcc ctgttcgaga ttgaccgcat tatgcacgtc    16680
gaccaggtgt cggcgatcaa gctgcattac gacgagaaca cgcccaagac gttcgacctc    16740
gtgatcggcg acgacgccga gtctgagaat ccgctcgcct caattacccg caccgcgcag    16800
cactttggga gtgcgctggc gatgctattc ggatcggggg atttgttctg atgcaactgc    16860
cgaaactcac gccgcgcgag gagatggcgc cgcacgccca ggcgatgcac gacatagccg    16920
acgcgctgca gtacccggcc gacaacatgg ggcgccgcta cgacgttcgg tacctgatcc    16980
cggtgctggc gtttcacctg cgcgcgggcgg gctgcgtcat cgaccccgag cgggcgctaa    17040
tcaaaccgcg gcggctgccg ccctcgccgg gcgtcgtcga ggacgcgatc gagtgggtcg    17100
acgtcaacgc ccccaacact atcgacgacg agctggcggg ggcgacgctc gacgacctcg    17160
accggctgtc accggcggcc cgcgctgagc tggtgcgccg cctgggcggc gacggcgcga    17220
aagtggccga ggccgaggca gatacaccgc tcgacgagcg cacgccgtgg cgtgtcgaaa    17280
cgtcgatcca gttcgacgac gaccccgaca gctaacagcc ggcgaatccg ccaatcacac    17340
cgctgacctg cggtggcgct tctgcgtgcc gcaaggtcgg caaacaacga ataggagcga    17400
```

```
cctagtcatg gccgaaattc ccgcgaccgg cgacgccgtc aggctgtttc aaacgctgct   17460
gtcggcgacc tggtacggaa tcgtgcgcag caaggacgat cccggcggca tggccgcgac   17520
tatggaaatg atcgacgacg aggcggtcat caccaccgac gtgctgatcg gcccgaaggg   17580
tgacaagggc gacaacgccc cgctggtcga cctgcagtgg ccgccgcttg agcaggccgc   17640
cgacctcgaa ccgttgaagg cgagcctcgg cccgaccgac aagggcaagg cgtggtggat   17700
cgggacgctg gtctatgtct ggacgggcag caagttcgag gcggtgcgcc ccggcccggc   17760
cgggccgcca ggggccacac cgctcatcac ggcgtcggcc gaaacgatcc ccatgtcgga   17820
gcgcacgccc gagagcaaag acgaggtgat cccgtcgggc acttctcttg cgccgcacct   17880
gcatttccgg ctgctctcac cgcaaggccc gcgcgggccg tcgacgaaca ttctcgacgc   17940
ccccgactac gacaacacca aggcgcccga ggacgggcag accccggtgt ggtcgtcggt   18000
caagcaaaag tgggtgccgt cgagtttcgc gcacaagcac ccgcggctgt acagcgtgcc   18060
cgaggcggcg tttcagaact tcaccggcgt tgcccagcgg cacccgatcc tgacgtacat   18120
cgtcgaggcg caggattatg cgtggacgcc gtacgtcacc gggcacctca aggcggttgg   18180
catcgagttc gacgtcgacc cgctgacgat cggctgcgag gtgcgcctcg gcgacgcgac   18240
gaccggcgac ctggtcgccc gcgggtttgg caatatcgcg agctggacga acatttcgcc   18300
gcactactcg accagcgccg acccggccgc ggcggtggcg cccggcaacg gcgtggccgt   18360
cgtgcccgcc ggtcagaccg cgcagatcaa cgtcaacctc tacaacgacg gcatcctcgg   18420
cgcctacctg ttcaaccgga aaggcgcgca actgaccatc ctcaccattc gacaggggga   18480
ataaggctgt ggcataccaa aagtcatacc gcacggtcgt gccgcttgag ccgggcaccg   18540
accgcgacgt ggcgctgtgg cttgtgcgcg agtcgttcga gcgcaaggcc gagggcgacg   18600
ccctggtgct cgtcgagttc gcgcaccgcg acgtcgacgc cgccgatctg ccgccgaagg   18660
ccgagaagca actcggccgc ccgctaaccg atttcgagtt cgtcgagtac accggggtgg   18720
ggcgccgtgc cgaggcagta tgacagcagg cagctcgtcg tcgaccgcga cccgctgcgg   18780
cagctcatac ccgaccccgg caagctgccg aagctcgacc cgaaagtctt ttacgacggg   18840
ttaattcagg gcatcaagat gctgacgggc atcgacctgt cgtcgcccga ggcgctcgtc   18900
gcgagcatca tcgagctgct taaagacgcc gtcggcggcg cgctcgaccc tacgcagctt   18960
ctcgcgacgt tcggcaagat cctcggtttc gtcggcaccc cggcgagcat cgacgagctg   19020
gcggcgtggg cctcgacgaa cctgttcgga tggatcgacc ccggccgcct gccgatcatc   19080
ccggtgtcgc atatcgggca gatcatcacg agcctgctgc ctaacggcat gttcggaggc   19140
gcgcagtcga tcatcgaccc gaccgggcgg tggctcgtcg acgctgtcga gggcgcggcc   19200
cgcacggtcg ctaacggcac gttcaccgac ctgctgtcaa cggatctgat cagcgtcgcg   19260
ccgggccagg tgctcaacat cgtcggcaag gtgaagtgga gcggcctgac cgcctcgggc   19320
agcccgatcc agctcggcgt gaccgagtac agcgacgagc gcggcgagaa cctggccggg   19380
cgggctctgg ttgccacgcc tgcgggtcaa accggcacga ccggtggaa ggacgtcgcg   19440 ggcacttaca ccgtcccaca gggcgttaag gccgtgcggg cgcgtgtcag tgtgggcgcc   19500
gaggccaccg cgggcgacgt gtggttcaag gcgtggatg ccaaccgggg caactcgctg   19560
ctgccgatcg cgctcgtcga gaacctgtcg agtcggctgg cgagcctgct cggcgtcgac   19620
gtgtggcagt cgttccttga cgccgcgaag ggcgcgacgg gcggctcgat cagcgacatt   19680
atcaaccgca ttgtgcacct gggcgtcgac ggctcgttcg acgcctcgca gctcgtgaac   19740
gtgccgaata tcccaatggt gccgggtacg aaggtcggcg gcctcgccgg aaacatgctg   19800
```

```
caggactttg gcagtcacat cgacaacatt gtcaatcggc tgtccggcac ccgcgggtcg     19860
aatcaatctc tcgacgacgc cgacgcggcg ctgggcgccc tgcaagacac cgtgctgggc     19920
ctgagccagg acgtgcaaga cctcaagatc gaccaggctg gcacctcgac gtcgggcaag     19980
aggtaccgcg tcgacttcac aacgctgccc tcggggccgt tctccgcggc gccgttcgac     20040
ctcacgtatt ccggtgctgg ctcagggtat ttagagcttg ccggtagggc tcagtggcac     20100
aaggtgaacg acgcgaccg ctctgtgatc gccaggtaca ccgacggcac caacaccgac      20160
accgaaaccg atttccagtt cattcaggcc accgtcggct cgccaccgga cggcgccgcc     20220
gtgaactacg catgcgctcg gatgaacacc gccaagacga cgtttgtcta cgcgatgggc     20280
tttcgggccg ggttttcgg gctgcagttc cgagccgagc tgggctgcta cgtcaacggc       20340
gtccggtacg tgtttgtggc gaatgcgcct gcgacgtaca actacaacct cgccttgaag     20400
gcgggcgtgg gcggtaaccc gtaccgtttt caggtgctct cgggcacgac cgtggttatc     20460
gactacaccg acaccagccg cgttagtcag atcggcgcgg cgttccgcgg gtggggtttc     20520
cgctccgaca ccggcaacag cggtagcgat gcgcctgccc ctgcggtgtt cgtcggctgc     20580
gccgataacg ccccggtggg cgtgcagggc accacatttc gggcctatcg ttcgctgtcg     20640
agttctgtgt cgaaaccggc gggcaatgtg ccgctcccgg cgaacacgtt cgacaccgtc     20700
gactacatca gctcggactt gaagtggaat cccaccacta acgagataac ggttctcaag     20760
gccggtacct acctgtgctc gatgcgcctg caaggcgcgt cggccctcgg ctttggtaac     20820
ggcaagcggg tttacccgtt ctggttcgtg ggtggcgcag cgaaggcgat gggccacgac     20880
aaatatgcct tgaacctcaa cggtttcggt gccccggcgg cgtcattgga ggatgcgatc     20940
ggcggcgacc cgttcgtcta ttacgttccc gagggcggcg tcatccgggc aggggcgggc     21000
aacgccgcga atgccgcgat agctctcgtc ggcgacagcc ccgggctgtc aacatggctg     21060
accgtcgcca gggtgggcta atgccccgac ggctcaacgt atctcagcac atcactactc     21120
actaggagcg cgtaaatatg gcagacgtcg aaaacacggc cgacatggtt caggcggtca     21180
agcagcggct cggcgaggag ctttccgagg agcaggtgca cgccgtgctg gccgcgtgga     21240
acagcgtgcg ggcgcagggc gatccggtcg gcatggtgcg ccgcgacgag gagtcgggca     21300
aggtggcgca ccgcgtcgtc gtcgaggccg tcgagcagtg gcgcgtgagc ggggctgacg     21360
gcgaccagta caacgacctg cagccgacgc tgccctggcc ggtgctgttc gacccgcgct     21420
aatgccttgg acgccaacgc ccccggcggc ccggcgcagc agctacggct ggtcaactaa     21480 cccgccccg ctggcgcagc ccgcgccggt cgggccgggc tggttcgtgt cgctgcacga      21540
gccggccgct cgcgctgagta tcagcaccgg cgacgcccgc gtcgtcgtgc agaccgtggc     21600
ccaggcgcgc ggcatcagcg aggccgacgc ggcgctgctg gtgcacatga tcgggcaggc    21660
gtcgagcgtc agctcgtcga ccgcggcggc ggccgagcac gtgttcgccg acgccctggc     21720
cgcctcggcg agcgcggccc gcgccgacct ggtcgtggaa atcgtcgccg aggcgctcgg     21780
cgtcagcgcc accgacgcgc tgttcgcgct caagttgacc gcggcggcca gctcggcgag     21840
cgacgccgtg gcgaccaacg ctttcccggc gatggcccg ctaccgcaac agttcacggc      21900
cgcgggcaac tacacgtacg cgatcccgta ctggtgccga ttcatcgaca ttgtggtgct     21960
cggcggcggg ggcggcgggc aggcgtctgc ggcgctgttc aactacggtg cgcccggtga     22020
tcccggccag tatcaggccg tgacgctaga gcgcggcgtc gacattccgt gggcggtggc     22080
ggcgatcacc ggcaccgttg gcgacggcgg tagcgcgtgg ggcacgtacg gcgccatccc     22140
```

```
cggcggccct ggcggcaata cgacggcgac gttcactggc ggcggcacgc tcagcggccc   22200 aggcggggc ggcggtatcg ggtgggccac ccaagcgggc tctcgcggcc ccggcccgg     22260 caatttcacc tataacgggc agctctacgt cggcggtgga ctggcagacc agggcgccaa   22320 caaaccggc aagccgcctg gtggcgccgg atcaggtaac tctcccggcg ccggtggggc   22380
tggcccaggc gcacccggcg cagtgtggtt ccgcgcctat cagtgaggag tgcaacgaaa   22440
ttgaatcctg acgacgacta cacgttcgcg ctccggtacg agtggctgcc cgaccccggc   22500
gccgaccccg acgacccggc caactggcgc gaatggatca tgcccgccgc gaccctggcc   22560
caggccgagg gctggctcga cgcggtggcg caggcagata cccgcacgc ccgcgggttc    22620 gccatcgtct actcgcccaa ggtcacttgg cggccctggc cgcccgccga cgactgagcg   22680
catgctcgct ggccctgata acggccgagc gggtttcgta gcacgtgcgc ctcgcccgta   22740
gctaaccgcc ggcaaaaact cgagcacccc ctctcacctg cggatacctc gcgaaacggc   22800
gcgaggtcgg caaacactgg ataggagcac cgtggcagca acggacgcat tcaagctcgc   22860
gatcgccaac gcgatcggcg cgcaaggcgc actgatcagc ctgcactcgg ctgaccccgg   22920
caagaccgac gcgacggcca acgcgaccga aattagcggc gccggataca cgcgcaagct   22980
gaccgcgtgg ggcgccccgg tcatcgtgtc gggcggcgcc gacgacggca aggcccgcat   23040
caccggctcg acgcagcagt tcaacgtgcc cggcggcgtg ccgatcacgc actacgccgt   23100
gcgcaaggcc gacagcacat tcctgtacgg caagccgctg gcgcccggcg cgaccctcac   23160
cggcaacggt gtcatcgacg tcacgccgac acatacctac gacctgacct agctcgaaat   23220
ggtcggcgtc gagggcattt tcgcagcatt gtctgcggct gtggtgctcg gcgccctcgg   23280
gcactggctc tatgacgtgc tggcgcaccg gcgctacgac aacgacgagg atacgacac   23340 atgagtttca cccggttcct gcaggatgac ccgctgctca cccgcgagca agtgatggcc   23400
gagctgattc gggtcgccga cgagctgaac atgcccgaca agcgcggcgc ctgcgtcatt   23460
gcgggcatga cgatttcgca agaggtcggc gtaaaggaca acgacccgcc gttcgagcgg   23520
cggttctggt gcccggccaa ccgcgccgac cccgaatcgt tcaactaccc gcacgactcg   23580
gaatcgaacg acgccgctc ggtcggctac ttccagcagc agaagggcc taacggcgag    23640 ctgtggtggg gcacaacggc atccgagatg aacctgcaca gcgccgcgac gcagtttatg   23700
acgcggctca aggcggccgg atacaacgcg agcaacgccc aggcggcgaa cgactcggcg   23760
caggcgatcc agcggtcggg cgtcccgcag gcgtacaagc aatggtggga cgacattaac   23820
cgcctgtacg acaaggtgaa gggctcgggc ggtggcccgg cgcccgcgcc taagccgccg   23880
cagtcggggc cgtggaccgg cgacccggtg tggctggccg acgtgctgcg cgccgagggg   23940
ctgaacgtcg tcgagctgcc cggctggctc gaccgcgggc acggcgacat gggccgcttg   24000
tggggcgtgg tgtgccatca caccggcagc gataacaccc cgtcgagcga gattgcgttt   24060
cacccgtcgc tcggcctgtg ctcgcagatt cacctggcgc gcaacggaac tgtgacgctg   24120
tgcggtgtcg gcatcgcctg gcatgcgggc gtcgcagct atcccggcct gcccgaggac   24180
aacgccaacg cggtcactat cggcatcgag gcccaaaaca gcggcaccta tgacggcgca   24240
ccgcaccgga cgaattggcc tgacgcgcaa tacgacgcct atgtgaagtg ctgcgccgcg   24300
atctgccgcc gcctcggcgt gcgcgccgat cacgtgatca gtcacaagga atgggccggg   24360
cgcaagcaag gcaaatggga tccaggcgcc atcgacatga acatctttcg cgccgacgta   24420
cagcggcgca tcgacgccca tcaaccaaac ggagaggacg atttcatggc cgcactatca   24480
gccgacgagc agcgcgaggt gctgaacctg ctgcgcgtcc tggccgaccg gcggttcgtc   24540
```

```
agccgcagcc cgttccgcca ccttggcgag gggccgagcg aaactgtcgc cgggttcggg   24600
ctcaacaccg acggcctcaa tcacgcgcag tacacgattg agcttgcgcg cctgggcgac   24660
ccgacgcacc tcgccctgct gcgcgaggtc gccagcgccg agggtgactc gcgctatccc   24720
gaccggcagt acgacgccaa gctcgccaag cgcgtgctcg ccgaaatcga gggcgccgca   24780
acggcaccgg ccaagccgag cacgccgagc gccccgaccg agcccgcccc cgaggcgccc   24840
acgccgccgg tcaaggccgc gtgtgcgctg tctgcggccg ggtgcgtggt ggctggctcg   24900
acctcgggcg gtggctgcgc cctgtccacc gacggcaccg gcaagtgcgt tgtgaccgcc   24960
gcgaccgacg gcggggccgc ctgatggcct gggtcggttg gcagctcggc atgcaggggg   25020
agcaggtcaa ggtgatacag caaaagctga tcgccaagta ccagtgggtg cgtgaccgtt   25080
acccgcggct gacggccagc ggcgtctatg acgtgaacac gcaggccgcg atcgtcgagt   25140
ttcagttccg cgcagggctt cccgtcaccg gcatagctga ctatgcgacg caggttcggc   25200
tcggcgcggt ggccccggcg ccgccgccgc ggcagcgcat catggtgctg acgtttagcg   25260
gcacctcggc cgacatgtgg accggctatc cggccgacgt cgcgcgtgcg ctcgacccgt   25320
cgatcttcta ctggcagcca gtgtgctacg gccccaacgg catcccggcg atattcccga   25380
tgggttccag cgccaagagc ggcgaggtcg aggggctgcg gctgctcgac gagaaggcgc   25440
gcgatttcga ctacatcgtg cttatcggat actcgcaggg cgcgctgccc gcgtcgcggc   25500
tcatgcggcg catcctgtcg ggcgacctgc agcggttcaa gtccaagctg atcgccggtg   25560
tcacgttcgg caacccgatg cgcgagaagg ggcacacgtt ccccggcggc gccgaccccg   25620
gcgggcacgg cctcgacccg cagtgcctcg tgaatacgcc cgactggtgg cacgactacg   25680
ccgccaaggg cgacatttac accgtcggct cgggcagtaa cgacgagaag gccaacgccg   25740
acatgacgtt catttaccag ctcgtgcagg gcgacattct cggcatgatg ttcggcaccg   25800
gcaacccgct cgacattctc ggcctgctcg gcggcctcgg tggcggcctg ctcggcggcc   25860
tgggcggtgg cctgctcggt ggcggcaagg gtggcctgca gttgccgagc ggcctggtgc   25920
tccccggcgt ccagggcggc gcgctcaccg accaccagcg cggcctcgtc gaggcggtgc   25980
tggcgctgct cgctaacccg ttcgccgagg ttccggcggc ggtcaaggcg attgtgtccg   26040
gtgtcgggtt catcgccacc aacccgccga cggcgccgca catcgagtac cacattcgcg   26100
aggctgcgcc cggcgtgacg tatttccagc acgcgatcga ctacctgcgc caggtcggcg   26160
cgtccgtcgc cgctcgcgcg gcctgacccc gaggagtcaa ccccgatga tgtcgatttt   26220 ggatctgcgc tcgcgcgacg acgtgcgcg cttcattcac agcgtcgccc cggcgatcgc   26280
cgtgctgatg gtcagcatgg gcgtgctcga ccgcaacgtc gcaatgctcg gcgtggctgt   26340
cgtgctggct gtgttcaacg acaccctggc tcatatcaac tcgtccgatg cgttccgcaa   26400
gtggttctat ccggtgctga cgtcggctac cgcaatgctg atcgggctgg gcatggtgac   26460
cgacgagcag ctcacgccgt ggatcgcgat tatcaccatt ctgatcggcg gcggtgttgc   26520
ggctaagaat gcgctgcccg aggagtgcga ggccgacgac gacgagccgt caggcaagca   26580
cgcgacgaca tgacgccctt gcgggcggtg ccgggcatgc tggctcgtgc tgacaacgcc   26640
tcggcggcga agctggacgg catgcggggg atgccatgac gtaccgctac gtcgagaacc   26700
gggtgctgcg tttcgtgcag ctcgcgctgc tcgtcgacgc cgtcgtgcgc ggcgcgagct   26760
ggatcgcgac cccggcgagc ggcataccc cagcgatcgg cctggccgcc gaaggcaccg   26820
cagccatgtg ggtgtggggc gccgtattcg ccgtgtttgg catcttgggc ctgctcggcg   26880
```

```
agctgtggat gcacctcggc gagtctgagc atcgcgcgtg gccgtcattc ctggcgtacg    26940
ccgcgctgct gttcctgttc gccgggctgg ccctgtcggc ggtcaataac gtcatcacaa    27000
cgcacgcaac ggacgggttc agcgccccat acactttcgc ccttctcgcg ttgctgcatt    27060
gggtgttcgc gaggcggcgg aagcatgtcg gctgagctga tcgagaagct gccgcagcag    27120
tgggtcggca tcgtcgtcct ggtgctgttc gtcgtctacg tggccgggca gctcatcgag    27180
aaatccgagc gcgtcgcgaa gctgctgccc ctcggcgtgt ggtggcgcga gcgcaaccgg    27240
cgcaagtctg cggtcgaccc ggccgagctg acacgcgcgg tcgaggcggc ccggcatgcc    27300
tggtcgcgcg aggagaacgc cgcactggcg gcccttgaga gccgcgtcgc cgtgatcgcc    27360
gcgatttcgg agcaccaggc cctcaacatc aaagagctgc aagactcggt gcgggcgttc    27420
acggcgttct ctgtgtacga cgcgcgctgg caccaccgcg ccgacgtcgc cctggctgac    27480
tgcccgatgt gcgacctgcc cgaccacctc gattacttcg ctttcgagcg gctgtggcgc    27540
gaagatccgg ccgccgccgc gaggttgcct gtatgagcct cgctgaccgc ctcgggccgc    27600
tgacacgagc cccgatcggc tgcgcggtgt gccgctggta cgagggcctc gacgacaccg    27660
accggctggc gttcgactcg tgggtcaacg gcggcggcag tatctcgcag ctctggcgcg    27720
agtgctgcgc cgaccccgac aggccgctgc atatcagccg ccccccggttt tccgagtgca    27780
tcaaccaaca ccaccgcgga ggccctcgtg tcgctagctg accggctgag caccccggcg    27840
gtgcccgacg agaagtaccg cccgtcggtc gagttcgaca gccgcggcgc cacgatcgac    27900
accggcgcgg tcgagcagga gcccggccag ccgcccgagt acgccgagct gctgcgccag    27960
gtcggccgcg accccgagcg gttccggctc gtggcgatcg accgcgagaa gcactggcag    28020
gtgccttacc gcccgatcga gggcaccgac gagcgcggca agccgatcct cggcgagctg    28080
acgaccaagt ggctcgcctc gtactcgctg cgcgtcgaac ctatcgacca gggcggcaac    28140
gaccttgagg cgctgatcgc cgaggcccgc aagcgcccca cgatcgagcc cggccagctc    28200
ggctcgccgt attggttcgt ctttcagggc ggcgacctgc agctcggcaa cgcgcagccg    28260
gacggctcga ccgagcagat cgtcgagcgg ttcgtacagt cggtcgaggc cgccaaggct    28320
caactgcacg cctgggcacc cctcggtatc gcgggcgtgc agatcagcct gccgggcgac    28380
tgtttggaag gcgtcgtgtc gcagggcggg cgcaactcgt ggctgacgca ggaaacgatc    28440
gccgagcaga cccggctgct gcggcggctc atggtgtaca cgatcgacga gctggcggcg    28500
gcccccgagg tcaagctcga cgtcgtcggc ggcaaccacg acgacgctaa ccggcagtgg    28560
aacaccaagc ccggcgacaa ttgggcgacc gaggcggcga tcgccgtcga cgacgccctc    28620
aagctcaaca ccgccgcgta cgggcacgtc gaggtgcgca tccctgagtc atggtcggga    28680
cacatgaccg tgccggtcgg cgacaccgtc gtgaccgtga ttcacggcca ccagtggcgc    28740
aaagggcagg ccctcaagtg gtggagcgag caggcggtgc acaaccagcc gcccggcgct    28800
gcgcacgtgc tgcagcatgg gcactggcac accgcggcgt gggaagcgca cgccaccaag    28860
acgatcgtgt gctcgccgac gttcgactgc gggtcggact ggtaccgcga gcggcacggc    28920
gccgagtccc ggcgcggcgc cctcacgtat ctgctgcgcg gcggcgaggt ttcacgcctg    28980
agtgtcgtgt agctaaccgc cggcaaaaac tcgagcgcac ccgctaagct gcagcaatgc    29040
gctgcgcccg tccgaagtca gcaaacagcg cccctcggct cacgccgggg ggcgtttcgg    29100
cgtttctagg gcctgttgac gcgccaacag ttctgcgcct aagctgttgg ggtatcaaca    29160
ccccagcgga taggagcccg acatgacaac ggcattcgcc gacccgacga tcgaggacgg    29220
tatcgacatg gcccgaggca agcaggtgcg catcgacggc aaggtgcgca cgatcccggc    29280
```

```
cgacaaggtc gagcagtacg aggcgatggc aacccgcatc gacgccctgt tcccggcga   29340 ccgcgggcac gagcgccagg ccgcgctgaa agccgccgcg cgcttcatcc tcggcgacct   29400
gaccgtcagc ggcgccggtg acgacctcga tctcgcccgc cgggcgcagg aggaggccgc   29460
cgcagcggcc cgcgcggtcg ctatcctcgc gatcgagaac ggcgccagcg agcagggcac   29520
ggcccgcgag atgggcgtcg accggctgac cgtgcgcaag tggaacggca aggtcgaccg   29580
ggcatgagcg acgaggtgtg ggtgctcgac ttcgaggccg aggggccgga gccgggcgac   29640
tatgtcgggt atcagtcggt gcaccgcacg cgcgacggcg cgagtaaccg gctgctcgaa   29700
cgcctcgccg acgtcgacgt cgacgtggcc gaggtcgagg cgctcggcgg cgcccaggcc   29760
gacgacggca gctacgcggg cgagctggac gccgacggca tgacgatcag ctacggcgtg   29820
caccgcatgc cgatcgagga ctagcgtcac ccgcccggcc cgtagcaatc tgctacacga   29880
ggcgcccctg tcgattcgtc ggcgagggcg cttcgtgtt gacgggtcaa cagcccgcgg   29940
tgtactgttg aggcatcaac agcactacgg gataggagcc caaaatgacc acagcgacat   30000
ggactaaggc cgaggccaag gcgagcgacc gcgagtacgc ccgactggtc ggtatcgccc   30060
aggccgccag cgccgccgtc gacaccgccc acgagcgcgc cctgacggcc gccggggcga   30120
gcatgcagta cctcaacggc gggtaccgcc gcaagggcct gagcttcgac cgtggccgca   30180
ccgaggccac cctcgaccag gcccgcgcga tcgcctcggg caaggagcag tgccgagcc   30240 ggtacgccga cgtcgagcgc gccgccgagg ccgtcgcccg gtacgacgcc gcggtcgtcg   30300
agtaccgcga ggccaacgcc gcggcccgcg cctgggacga cgcgcattac cagggctggc   30360 ggcgctttt cctggtgccc ggcggccaca ttcacgagtc gaccgcctgc agctcgctgc   30420
gcatcacgac catgatcgtg tggctgcccg agctgtcggg tgaaaccgag gccgaggcgg   30480
tggccgagca cggcgccctg ctgtgcacca agtgcttccc gtcggcgccg gtcgagtgga   30540
ccgtcggcaa cgtcgacccc gacaagtgca acgggcgccc cgacatggac cgccgccgcg   30600
gccggtacgc gccgtgccgc gagtgcgggt acgtcggcca catcacgacg cacggcaacc   30660
tgcgcaagca caagcgcgag agcgcctgag agccaacgag aaacgccccc gaccggtcg   30720 caccggcggg ggcgttttcg tgcgcctgcg gggcgctcag ccgggcaggt gacccggctc   30780
gtcgggcagc accgtgtcgg gcgtgaccgt gtactgctcg cggtcgttga tcttcatgtc   30840
gacgaaataa ccgccgtacg tggtgcacga gacatagctg cgcccatagc agctcgtgcg   30900
cgtcggcacc tggtgcgccg gtgtccacac gctgcgcttg cgctcccagc tcccgtcggg   30960
ctgcaccggg ccgtcgcaga tcgtgcgccg ctggctgccc aggaatcccc acagcaccgt   31020
gtcgcagttg gggccgaggt caggatcggg ccgagcgtgc gccggggcgg cggccagcac   31080
ggcaccggcg ccgatggcac cggcgacggc gagtgttgcg gctgttttga atccgatcac   31140 gacgcaccc cgagcgccag gtgggcgccg cccgagaaca tcgagtcgtg caggatcagc   31200
tcggttgcct cggtgccggg cggcacgtcg aacgcgacgc gcgcctgaat cgcgttgcct   31260
gggttaatgt ctccggtcct gcaggtagta ccgcgatttt gacatttgca gcgcctctaa   31320
tatctcgcgc agcttgagcg gtctacccac taagtagcca agcactgcgg caaggctctt   31380
ggcggtgtcg tcgtctggca cctggtgtc ctgtctatta ggggcgggtc cgaaatcgcc   31440
cgtatggcgt gtcactttag tctaggtttc tggactaaac aataggcttg agcagcgatt   31500
atgagaaacg ctaatcgttc gcgcgtgcaa taagtcgcgc ccaatggtgc agattctgga   31560
caagtgggct atggtgacag ccatgacagc cccgcgacac gagctgcgat ggaatcccgg   31620
```

```
caaagtctca aaaacactgg cccgcctcgg tattcgtgac cgcaccgccc tggctaagcg    31680
cgtcagcatg cccaagagca cgatatacgc ggcgttcgac gccgactggt caggcgtagc    31740
aacgaccaac gtgttagcgc aggtcgcagg cgagttaggg gtgtccctgc tcgacctggt    31800
cgccgagccc gcaccgcgcc gaaaccagaa agtgcagaaa actgcaccgc gccggtcggt    31860
gcagaaaact gagcaattcg gcgcgacggt gctgctatga ccggcgcctt gctgacctat    31920
cccgtcgccg acgtcgcgcg acgtatcccc tgctccgagc ggtggctcac cgagcagatc    31980
cgcgccggtc gcatccccgg ccgcaaggtc ggtcgtcact ggcggatgac tgaggccgac    32040
atagaggccg ctctcgaatc gttccgcgtc gcccccgagt cgggtcgcaa gtctgtcgcc    32100
gccgagcgcc cgttcgcgct caccgccacc tcgcaacgcc ggattagggg ctgacgcaat    32160
gcaactcatg cgccacatcg aggagtgccg ccgcctgcag gcacagattg acgagctgac    32220
cgccgagctg cgcgtcgtca ccgacgagcg cgacgccgcg ctgcgcgagc gcgacgagct    32280
ggccgaccgc ctggccgtcg ccgaggccga caaggcgtgg gggcgcgagg agcaccggcg    32340
gctgcacaac ccgatgcccg acatggaccg ctgcggctga tcgccgccta aacgacacaa    32400
cccccgcacg aggcggggc tggccgacac aaccaaggga taggagccac ttgttatgcc    32460
gacacagagt ttagcgccag atcggcccgc agtgcctagc gccatgcggg cgtttgcgtc    32520
gaccccggcg ccgtggtgcg acgactgccg ctgcgtgcac gcccggccgt gcgaggcgca    32580
gcagcgcatc aaccgcgccc tcgacgccct cgggttcgcg ctgctcatcc tgacgtcgat    32640
cctgctcggg ctcgccgcgg gggcgctgac cctatgagcc tcaaggacat aacgctcacg    32700
cacgccgagc tgaacctcgc cgcgcacgtc gtcgacaccc acatgacaca gggcttcacg    32760
gcgcacggcg cggtggcctc ggcgattcgg gctgtcaact cgatgcgcaa ccacccggcc    32820
gcgtaccgcg gggtcgacct ggcgcagctc aagcaatctc agcgcagccc gcaccgcggg    32880
gcggggcggt tccgcgtcgc cgactgcgcc gactgccagc tcgacgacaa cacctgcccc    32940
ggccaccgga tttaggagct atcaccgcat gtctgaccta gtgattttcg acagctgca    33000 gcaaggcgag gagccgcgcg actacgtgcc cgcgttcgag cgggccgtgc tgtacgccat    33060
gcagttcaaa ccgatgtacg agggcaccgt gccgcaccgg gtgcgcgcca agcgccgcga    33120
gcgtaaccgc gtcgcccgcc gttctcgcaa gatcaaccgg aaagccatct agcgcaatga    33180
cttacgaccc aactaaccgc gagcaagaat ccaaggatcg ccgccgcatg cggatcgcgc    33240
agcgcaagcg cgaggcccgc tcggcgatgg ccgtcaagac gtacgtgctc gacgacgtcc    33300
tgcccggcct gccgccgatc cccgacaccg acgacgtgtg caaggcccct ggcatcaagg    33360
cccgcacgac gctgcacaac gtgctttacc gtcaccgtga cgaaatgatc gcgggcggat    33420
gggacgccgc cgcaggcaca ttcacgcgcg aggccgttgt gcggctgtgc ctgctgctgc    33480
gcgccaccac ctcgcgcaag gcggccgaag tcgccgaggc ggtcggcgcc cgcgatcgcg    33540
tgatcaagtt caacgccagc aaggtgccgc acattcggcg ctgccaggcg ttgatagaca    33600
aggcattcgg ccttgctgag cgcgtgcgcg acgaagatcc cgccgaggtg tggcacgacc    33660
tcaatcagat ggacgcctac acgctgcagg gcatcaccgt ggccctggcg gcgatggtcg    33720
acctcgactc ggcgaccggc ggtgtgacgc agtggcttag ctcgctgcc ccgtctaagc    33780 ggcaccccgg caagggcaac ggcggcgccg cgagcggttt ggcccggctg gtgccgacac    33840
ccgatgaggc gcaggcatc ccgctgggca agatcctgat caggcgcctt aattaagatc    33900
cctatagtga gtcgtattat gcggccgcga attctcatgt ttgaccgctt atcatcgata    33960
agctctgctt tttgttgact tccattgttc attccacgga caaaaacaga gaaaggaaac    34020
```

```
gacagaggcc aaaaagctcg ctttcagcac ctgtcgtttc ctttcttttc agagggtatt   34080
ttaaataaaa acattaagtt atgacgaaga agaacggaaa cgccttaaac cggaaaattt   34140
tcataaatag cgaaaacccg cgaggtcgcc gccccgtaac aaggcggatc gccggaaagg   34200
acccgcaaat gataataatt atcaattgca tactatcgac ggcactgctg ccagataaca   34260
ccaccgggga acattccat catgatggcc gtgcggacat aggaagccag ttcatccatc    34320
gctttcttgt ctgctgccat ttgctttgtg acatccagcg ccgcacattc agcagcgttt   34380
ttcagcgcgt tttcgatcaa cgtttcaatg ttggtatcaa caccaggttt aactttgaac   34440
ttatcggcac tgacggttac cttgttctgc gctggctcat cacgcaggat accaaggctg   34500
atgttgtaga tattggtcac cggctgaggg ttttcgattg ccgctgcgtg gatagcacca   34560
tttgcgatca ggcngtcctt gatgaatgac actccattgc gaataagttc gaaggagacg   34620
gtgtcacgaa tgcgctggtc cagctcggtc gattgccttt tgtgcagcag aggtatcaat   34680
ctcaacgcca aggctcatcg aagcgcaata ttgctgctca ccaaaacgcg tattgaccag   34740
gtgttcaacg gcaaatttct gcccttctga tgtcagaaag gcaaagtgat tttctttctg   34800
gtattcagtt gctgtgtgtc ggtttcagca aaaccaagct cgcgcaattc ggctgtgcag   34860
atttagaagg cagatcacca gacagcaacg gccaacggaa aacagcgcat acagaacatc   34920
cgtcgccgcg ccgacaacgt gataattttt atgacccatg atttatttcc ttttagacgt   34980
gagcctgtcg cacagcaaag ccgccgaaag ttcctcgacc gatgcccttg agagccttca   35040
acccagtcag ctccttccgg tgggcgcggg gcatgactat cgtcgccgca cttatgactg   35100
tcttctttat catgcaactc gtaggacagg tgccggcagc gctctgggtc atttcggcg    35160 aggaccctt tcgctggagc gcgacgatga tcggcctgtc gcttgcggta ttcggaatct    35220
tccacgccct cgctcaagcc ttcgtcactg gtcccgccac caaacgtttc ggcgagaagc    35280
aggccattat cgccggcatg gcggccgacg cgctgggcta cgtcttgctg gcgttcggtg   35340
gctttgttga ataaatcgaa cttttgctga gttgaaggat cagatcacgc atcttcccga   35400
caacgcagac cgttccgtgg caaagcaaaa gttcaaaatc accaactggt ccacctacaa   35460
caaagctctc atcaaccgtg gctccctcac tttctggctg gatgatgggg cgattcaggc   35520
ctggtatgag tcagcaacac cttcttcacg aggcagacct cagcgctagc ggagtgtata   35580
ctggcttact atgttggcac tgatgagggt gtcagtgaag tgcttcatgt ggcaggagaa   35640
aaaaggctgc accggtgcgt cagcagaata tgtgatacag gatatattcc gcttcctcgc   35700
tcactgactc gctacgctcg gtcgttcgac tgcggcgagc ggaaatggct tacgaacggg   35760
gcggagattt cctggaagat gccaggaaga tacttaacag ggaagtgaga gggccgcggc   35820
aaagccgttt ttccataggc tccgcccccc tgacaagcat cacgaaatct gacgctcaaa   35880
tcagtggtgg cgaaacccga caggactata agataccag gcgtttcccc ctggcggctc    35940
cctcgtgcgc tctcctgttc ctgccttttcg gtttaccggt gtcattccgc tgttatggcc   36000
gcgtttgtct cattccacgc ctgacactca gttccgggta ggcagttcgc tccaagctgg   36060
actgtatgca cgaaccccccc gttcagtccg accgctgcgc cttatccggt aactatcgtc   36120
ttgagtccaa cccggaaaga catgcaaaag caccactggc agcagccact ggtaattgat   36180
ttagaggagt tagtcttgaa gtcatgcgcc ggttaaggct aaactgaaag gacaagtttt   36240
ggtgactgcg ctcctccaag ccagttacct cggttcaaag agttggtagc tcagagaacc   36300
ttcgaaaaac cgccctgcaa ggcggttttt tcgttttcag agcaagagat tacgcgcaga   36360
```

```
ccaaaacgat ctcaagaaga tcatcttatt aaggggtctg acgctcagtg gaacgaaaac    36420
tcacgttaag ggattttggt catgagatta tcaaaaagga tcttcaccta gatccttta     36480 aattaaaaat gaagttttaa atcaatctaa agtatatatg agtaaacttg gtctgacagt    36540
taccaatgct taatcagtga ggcacctatc tcagcgatct gtctatttcg ttcatccata    36600
gttgcctgac tccccgtcgt gtagataact acgatacggg agggcttacc atctggcccc    36660
agtgctgcaa tgataccgcg agacccacgc tcaccggctc cagatttatc agcaataaac    36720
cagccagccg gaagggccga gcgcagaagt ggtcctgcaa ctttatccgc ctccatccag    36780
tctattaatt gttgccggga agctagagta agtagttcgc cagttaatag tttgcgcaac    36840
gttgttgcca ttgctgcagg catcgtggtg tcacgctcgt cgtttggtat ggcttcattc    36900
agctccggtt cccaacgatc aaggcgagtt acatgatccc ccatgttgtg caaaaaagcg    36960
gttagctcct tcggtcctcc gatcgttgtc agaagtaagt tggccgcagt gttatcactc    37020
atggttatgg cagcactgca taattctctt actgtcatgc catccgtaag atgcttttct    37080
gtgactggtg agtactcaac caagtcattc tgagaatagt gtatgcggcg accgagttgc    37140
tcttgcccgg cgtcaacacg ggataatacc gcgccacata gcagaacttt aaaagtgctc    37200
atcattggaa aacgttcttc ggggcgaaaa ctctcaagga tcttaccgct gttgagatcc    37260
agttcgatgt aacccactcg tgcacccaac tgatcttcag catctttac tttcaccagc     37320 gtttctgggt gagcaaaaac aggaaggcaa aatgccgcaa aaaagggaat aagggcgaca    37380
cggaaatgtt gaatactcat actcttcctt tttcaatatt attgaagcat ttatcagggt    37440
tattgtctca tgagcggata catatttgaa tgtatttaga aaataaaca aatagggggtt    37500 ccgcgcacat ttccccgaaa agtgccacct gacgtctaag aaaccattat tatcatgaca    37560
ttaacctata aaaataggcg tatcacgagg ccctttcgtc ttcaagaatt cgcggccgca    37620
attaaccctc actaaaggat cttaattaag gatcgcgaag gcgacgcagc gcgtgcagca    37680
gcggcagatc gggctgctga cgacgcagcg cgagattatc gacgaccagc tcgccgacgc    37740
ggtgcgcaag cgcaacgagg ccagcggcct gattgcgcag gctttgggca tgttgaacgc    37800
tcaacagtga gcactcggca tgaccgttat cgctgaatac atctaggcgc atagacatag    37860
cagcgtgcct caccacaact gccccggcga cgactgcggt cgttgcgagg cgcgcattgc    37920
ggcgatcgag tacgagcgcg aggtcgcgca cgacgattac ccgcagttct acgacggcac    37980
ctagagcccc gcgggcgctc gcgcgggaat ccacaacggg cgcaaatgat cacgaaggaa    38040
acacaggaac acatgagcaa cgattcgtac ggattcctcg caggcggcgg cccggcgtcg    38100
ggcaagttca aggcccacgg cgacaccgtc ggcggcccga tcgtcgtcga gccctcgcag    38160
cagcagcaga ccaacatgga caacaagccg ctgacctggg acgacggcag cccccgcatg    38220
cagctcgtcg tgaccgtgca gaccgatctg cgcgaccct cgatcgagga cgacgacggc     38280
aagcgccgcc tgttcgtcaa gggcgaaatg cggaaagccg tgcagcaggc cgtgatcgcg    38340
gccggggcca agggcctcga cgtcggcggc gagctgcacg tgacctacgt cggcgacggc    38400
gaaccggccc ggcccggcct gacagcgccg aagctgtaca gcgccaagta catcaagccg    38460
agcgccgctg cgctggcgac cgccggtggc ccggcaccga gcagcgacct gcccgagggc    38520 gtgaccccccg aggcgttcga ggcgctgcag aagctcggca tggtcaagta gcacaccgca    38580
tttcgaggcg ggccggtggc gtggttttgg gaccgtcacc ggcccgtttc atcaccaggg    38640
ataggagccc cgagaacatg atcaccgttt acacgaccgg acctgagtgc cacaagtgca    38700
acctgaccaa gcgcgccctc gacaaggcgg gcgtcgagta caccgaggtg cgcctcgacc    38760
```

```
aagatcccgc gctcgcagcc gatttcaagg ccaaagggca caagacgcg ccgatcgtgc    38820 gcgacgcgct caccgacaca atgtggtcgg atttccgcgg cgacctaatc aaggccgcga    38880
tcgcggctcg ggcggtggcc tgatggacgg cgagctggtc gccaaggtgc gcgacgcgat    38940
cgaggccgag ctgaaagcgc aagcatggtg cctgatcggc gtcgacgcc gggtcgactg    39000 cgtcgacggc gacattgaca cccacgcgat cgccgaggcc gctgtcgacg cgatcgaggg    39060
gcgatcgtga gccgcgagct gctggcgctg cacgaccgga tcaagtggca gcgcgccgac    39120
ggccgctgcg agtgtcaggg cgagtgcggc cggtcgcacc gtttcggcgg cgtgcactac    39180
cgctgcccga ataagcacgg caactccgcg gtgcatggcg cgacaaggt cgtgacgctg    39240 accgtgcgcc ccctcgacgg cgacgagcga aacctcgacg agcgcaacct catcgccatg    39300
tgccaggcgt gcgtgaagcg ccaccgcgcg aaatgcaagg ccgacgccga gcgtgaggcc    39360
gagcgccggg cgaccgaggc gcagcacgag tcgctgttcg agctacccga ggtcaccggc    39420
gcggccctga cgccgccctg actgccccg ccccaatgtc gcaccaggcc caacccgata    39480
gggacagaat gaatttcacg gagctgctcg actcgctcgg ctacatggag ggcgagcacc    39540
tgtcgctctg ccaccaggtg cccggccaca acttcatggc gaacgtgatc gagttcgacg    39600
accgcgccca agctaaggcg ctgcggtacg tcgacgactg cgacctgtgg ttcggcgtca    39660
acccgacccg gcgtcgcggc gccgacgaag gcggccgggg cacggccgag gacgtcaccc    39720
ggctggccgc ggtgtggtgc gacctcgacg tcaagccggg cgcgtgccgc gacctggcgc    39780
acgcctggca gatcatcgac gagctgagca tcctggtcgg ccagcggccg acggcggtcg    39840
tgatgagcgg gcacggcctg cagccgtatt gggagattga ggacggccag ctcgtgccgt    39900
gtgccgccga cgccgacgac ccgacgatgc aggccgccag cgaggagctg cgcgcggagg    39960
ccgccgcggt gctcaagcgg tggggccgcc tggccgtgat ggtcgccgag cgccagggcg    40020
ccaagatcga ccgcggcgtg tacgacctgg cgcgcgtgct gcgggtgccc ggctcgtaca    40080
accgcaaggg tgagccggtg ctcgtcacgt gtgaacgtgg cggcggtggc ccgctgtcga    40140
tcgaggagct gaccgagcgc ctcaacgagg cgggcgtgcg cgagcaggac ggcgaccggc    40200
gcaccgcgat gggcgaggtt gtgtcgaaac ccgacacctg gaacacgcc gcagctacgt    40260 gcgactattt cgccccgacg atcaaggcgt ggcgcgacga gcagatcacc gagcggcaca    40320
actggctggt gacgcaggcc gtgcggatca tgtgcgggct gcgcaacggc tgcctgactg    40380
aggagcagtt cgagcaggcc cgcaaggtcg tcaccgagcg gttcaaggcc gagtgcgccg    40440
cgaccaaccg ggcgatcccg ccgtgggaga tccccaacgc attcgcctgg gcgaccgatc    40500
acgcggcccg catgaccgac gccgagctgg cgagcgagat tggcgcgcac ctgcacctgt    40560
gggagaaggc cgagccccgc ccggtgaccc tcgcccccat gcagcccgag caaaccgccg    40620
gcaataccgc aactgtgcag ctcagcgaga taatccgcga gtcgacagct aacgtcacgc    40680
cgaccgatac cggcaacgcc gacctgctcg tcagggcgtg ctcggatcgg ctgcgctggt    40740
gccccgagtc gggcaagtgg ctggtgtgga aaggcacgcg gtggcagccg agccccgacg    40800
gcggcgaggc gatcatggcg gcgatcgagg tcgtgcagtc gatcaaggtc gaggacggcg    40860
acaaggccgg gggccagcac aaaatgcgca gcctgcagcg ccggtcgctc gacaacatgg    40920
tcgcgctcgc caagtgccgc cccggcatgc gcgtgagcct ggccgacctt gacgccgacc    40980
cgtacgcgct gaacacccg agcggtgtcg tcaacctcaa gacgggcgag ctgacccgc    41040 accgccccga gggctggcac accagggtga cgggcgccgg gtacgagcgc gacggcgcgg    41100
```

-continued

```
cgccgcggtg gtgggcgttc ctgcaccgca cgttcggcgg cgacaagtcg atggtcgagt    41160
acgtgcaacg gctggccggg tacgcggcga tcggcgaggt gacgcaccac gtgttgccgt    41220
tcctgttcgg cgccgggtcc aacggcaaga gcgtgctcat ggacgtgctc agcgcggtgc    41280
tgggcgacta cgccgatcac a gcgccgggca atttcctgct cgcgggccgg gagcggcacg    41340
aaacggagat agctcgcctg cacggcgccc ggctggtcgt gtgctcggag gtcaacgccg    41400
acagcaagtt cgacgaggcc aaggtcaagc tgctgaccgg cggcgacgtc ctgtcggggc    41460
ggttcatgcg gcaagacttc tttgatttcg tcccgtcgca ccttgttc ctaatgggca    41520 accaccagcc cgatgtgaag gctggcggca cctcattctt tcggcggttc cggctgatcc    41580
cgttcgagca catagtgccc gagcgcgagc gggtcgaggg actggcgcac cagctagtcg    41640
ccgaggaggg cgacgcgatc ctggcgtgga tcgccgacgg cgcccgccag gtgctcgacg    41700
gcggcatgcg ggagcccgcg agcgtgttgg cggctaccgc gcagtaccag gacgacacca    41760
ggaccggcgt cgcccgcttc ctcgacgagt gctgcacgat cggcgagggc gaggccgagg    41820
tcggggcggt gcaccagtgc tatatcgcgt gggccatcgc gcacggtgag ccgctcgtcg    41880
atacggccaa gttcgggcgc gagctgagcg ggaatcaggt cgcccgccgc cgcacggcga    41940
aggcccgcat ggcgaagctg acggttcacg tcgaccggct gccagcaaac ggtgacagca    42000
cctcacccta ccgtcacaac taccgtcacc ccggtgacag tgcaatgacg gatgagtgac    42060
ggacgtatcg acgtgttttc gcaggtagtg acggatatga cggatatgac ggactctcgc    42120
aacattgaaa ctaacatcaa cgcttttgtg tttggtgacc tgcggaaatg ctgcgcggca    42180
gtgctgggtg taaccgtag tgcaaaagtg ccgtcatacc gtcataccc c tggcctgcag    42240 caaacaccgc gccgcgcggt ggctcgccgt gtctctcgat tacctcgcgc gcaccggcga    42300
ggccccgaca ccgcacgcaa ctggatagga gacaggtgcc catgacaacc gacgacccgg    42360
tggtcgacga ggcgaagctc gccgcggctg acgctgtgct cgcgatgctg cccgccgacg    42420
cgcacgaggc gctgcgcgag gcgctgcacg cccgcgtgac gggtgaccgt aacggctcac    42480
ggcagttgcg tctgttcgtg ccgggccgcc cggcgccgca gggctcgaaa gacttcaagg    42540
gcttctctaa gacgggcaag gcgatcctca aggagtcgag cgacgccgtc gggccgtggc    42600
gcgagcgtgt ggccctggcc gcggcctcgg cgatcctggc cgaggggctg ccggtgctcg    42660
ccaaagagtt ctcgatcgcc gcgtcggtga cgttcgttat gcctcgcccg gccgggcgc    42720 cgaagcgcag cacgccgccc gccgtgaagc ggcccgacct cgacaagctg gcccgcgcga    42780
tcctcgacgg gctgaccgac gtcgtgtgga tcgacgacag ccaggtcgtc gatttgcact    42840
gccgcaaggt gctggccgag ctgacgcagc cgccgggcgc gcatatccgt atcgcgtcgc    42900
cgggctgggg cgacgaggcg ctcgcgaagg ctcaggccgc ggctcaggcc gcgatcgccg    42960
ctgccgccga ggcggtgctg tgaggcacta ccgcatcgag ctgctgatca agtcagacct    43020
gaccgaggag caggtcgccg agcgcgtcga gggccgtcct gggccggtgt tcggcggcca    43080
ggtcgtcgac gccgcggtgt acgaggtgac gcatttcgag gcgcggcgct cggaggtggt    43140
cgcgtgagca ggcaccggca agaggatcgg gtgttgcccg gcccgttcga cccgcggccg    43200
atcgtggcgt ggtcggagtc gatgggctgg acgcggctgg aatggatcgc cacgccgacc    43260
ccgtcgggcg ggcatctgtg gctttcggac gtttgccagc aagacccggc cgcggccgat    43320
ccgtgcagct caggcgacgc gctcgagttt ttgccggcgg ttagctgcgc ccggccgccc    43380
gagccgatcg tgacggttta cgacaaggac atgcgcaagc tcgccgggcc tgcgccgtgg    43440
agccaggtta ggagcgtttt cgaccatgcg tgagtgcgcg aactgcaagg gccgcagcga    43500
```

```
gctgacggtg tgctggccgt gcggcaaggc gatccgccgc cagctcgtcg gcacggccga    43560
ggagccgggc ctcgcgtggc tgatcgaccg gctgcaggag tcggcgtacg gcgaggcgaa    43620
gatcggccgc ctggcgccga aggtgtccgg tcagggcgag cggccgggcc tgccgttgaa    43680
cgcgaaagcg gccgagctgc tgcgcgacat tctgcgcgcg ctgcacaagt ggtccgaggg    43740
cgcgctgtgg cgcctgcccg ccgctgcgca ggccgcgatg atggccgaca atgtcccgcg    43800
gctgatggcc cgcgacgacg ccgcggagat cctgcgcgag ctgctgcggc tgcgcgccgc    43860
ggccgagcgg gcgatcgacc tgccgcccga tctgcagtac gtcggcacgt gcccgagcgt    43920
gttcgccgac ggcccgcgca agggcgaggc gtgcgctgtg ggcctgtatg tcgagcgggg    43980
cgagtcgacg gtgaactgcc gcggtgcaa gacgccgagc gtcgtcgagg atctgcagcg    44040
caccgcgctt gagcgggtcg acgacgagcc caagacggcc gccgacatgt tccggctgct    44100
gcggtggctc gggcgtgagg tgccgcggtc gtcgttctat gtgttggtgc gccgtgtccc    44160
ggctcgcatg tatctgcagc gcgacgggcg tcggaacatg ctgcagcagg agggctctca    44220
gccgctctac gcctacagcg acgtcgtgtc ggccattgac acgtgggagg ccgagcaggc    44280
ggcgcagcgg gccgctggga agggcaagcg gggccgccca cgcaaggcgt cgcccgcggc    44340
cgaggccaag cgcgacacgg tgggcgcagc gtgttgacag ctcaacagtg cgcgggtaac    44400
gtcgccggtg ttgaccaatc aacactcggg ataggagccc acgaaatgac cgaaatcaca    44460
gcaggtttgc gagttcaggt gttccgcagc tcgctcggcg actgcaccaa cggcggcgtg    44520
accagtaagg ccgacgtcgt gacgctgatc ggctacgccg accctcacag tggcgccctc    44580
aagccgctgc cgcgcatgtc gcaggtgttc gagcctgccg acgacgcccc ggcggtcgtc    44640
atggtgcgct cgaacctgcc cggcgccctg ccgcacctcg tgccgctgga cgccaagcag    44700
gcgggcgagt ggacgatgca cggcggcaac ctggccgggt cgagcgactc gcggttcggc    44760
gagctgatcg agaaggtgtt cgacggcccg cgctgcgtta gctcgctgcc ggtgcacgat    44820
cggatcgaga agtgaagcgc accaggacgg ttgcggcgcc cccacctgcg cgcagcccg    44880
aggtcgtcgt gcacggccgc acgcttgagc cgggcaccga ggtgtcgatc gcgggcgagc    44940
gcggccggtt ccgctacatg cgggcgacga cgacgagcgc gggccgcctg gtgctcgact    45000
tcattggcgg cccggccggg catgaggcgt ggcgctcgtt ttaccccgag cggattcgca    45060
cggttcaccg catcaacaaa acccgccgca acgcggcctg attcaagcga ggagacacaa    45120
acgatgcgca agtggatagc gggcaccgcg gtgccctgg tggtcgccct cggggctcag    45180
gtggccgccg gtgtcggcat tgtggtgggc ctcggccagg tgccgggcga cttgaacgat    45240
ctgcccgagc tgaccgacga ctgaccacca cgaaacgcga aacgccgcag gctgcaacgc    45300
ttgcggcgtt ttcgtgttga caggtcaaca ccacgcatgt ttaactgttg acagctcaac    45360
accgacaccg caagcgcggg gcaaccggcc ccgccccgag cccgaggagg gcctcatgca    45420
caacacccac gtttacggcg agtcggctgt tgagttcgcc gtcggccagc gggtcgcggt    45480
tcacccgatc accccgcagt tcatgcaggg cgaccgttac ggcgaggtcg tgctcgtcgg    45540
ccgcactcgc gtgtcggtga agctcgaccg atcgggtcgc acgctgcggt tctcgccgca    45600
gaacctcgcc cacatggccc gcgactagcg ggcctcgggc aggtaatcga acaatcgca    45660
acgggatagg agcccacgag atgaccaacc acatgacacc ggcgcaggcc cgcagaatcg    45720
cgaccgacct gctgcgcgag cacggcctga ccggctggtc tgtcacgttc gacaacgcgc    45780
gacgccgcgc cgggcagtgc agctaccgca cccggcagat cagcctgtcg aaaccgctta    45840
```

```
tggcgcagcg gtcctacgac gacaccatga tgacgattac gcacgagctt gcgcacgcgc   45900
tggtcggcgg caggcatggg cacgacgccg tgtgggccgc gaagcaccgc gagctgggcg   45960
gcaacggcaa acgtgcttc  gagcacttcg acagtcggc  gccgtggatc ggcacgtgcg   46020
ggcacggcaa gcagttcacc cgctaccgcg ccccgaagcg cctcgacggg tggcgctgcc   46080
gctgcgcccg cggtggctcg ccgatcacgt ggcagacccg cgcgcagcgc gccaccgagg   46140
cccgcgcggt cgcgcaggcg caggcccgca aggtgcccgc accggcggcg cggccgagg    46200 tgacccgcac gatcgtgtcg cgcccggtcg gccgcggcca gcagctcggg ctgttctgat   46260
gatgaccgac gcagagttcg ccgcccgcct cgacgaaatc gaggcggcgc gcgagcgcga   46320
gtatcaggag cacctggccg ccgagcgcgc caagggcaac cacattcgca agcgggccgg   46380
gcgcagcctg ggcaaccagt ggtacagcca ccagcaccgc gtgcagttca tcgagggtta   46440
cgtcgacccg ctgtcgcaga cgttgtgcgg cgccgacgca acgattttcg accagtcctg   46500
ggccgacacg cggtggccga agcaccgcgc cgaggtcacg tgccaggcgt gcatcgacgc   46560
ccgcctcgcc gacccaaaag cccgccgcta acccacctca caaccaccac aacgggatag   46620
gagcccctgc aatgtccaac cacaccacca cctcggaatc gtcgcccag  gaggccgcca   46680 cgcggttctt ttgggcctgg ctgatcgccg ccacggccgc ctcaatcctc gggaacgtca   46740
cgcacgcggt gctcggcgca gccagctcgc cgctgatcgc cgcggcggcg gccatcgtcc   46800
cgccggtcgt gctgctcggc gcgacgcacg gcgtgcacgc cctggtgcgc agccggatcg   46860
tcggcgccgc ctaccgcgcc gccctgacga tcgttgtcgc gcttgcggtg tgcgcgttcg   46920
tgctcagctt cgaggcgctg cgtgagctgg cgatcgtgca cgcgggcatg cggccgtcga   46980
tcgcgtggct gtggccgctg caatcgacc  tgagcatcac cggctcgacg gttgcgctgc   47040
tggcgctcac cgggcaggct cgcggcgcgc aggcgtacga agtcgagcac ctcgacgcgc   47100
acccgctgtc acccgtcgcg cctgtacacg tgtcggtgca caccagcgcg caggcggtcg   47160 cgcaggcgg  ggccgtcgac gttgctgagc ccgcaacgga tctgccggtc gaggcggccg   47220
agcggctgct cgacgccggg gtgacgcgca tcgaccgcgt gaaggtcgcc caggtgctcg   47280
ccgagcacgc cgagggcacg gccccgagca tgatcgcgcg caagctgagc gtcgggtaca   47340
gcaccgtggt gcgcatcctt gagcaccaca ctgcgcacgc tgcgcaggcg gatgcggagg   47400
tgggcgcgtg aacgtcgccg agcagtaccc ggcacgcaca gacggcaacg ggcgcacttg   47460
gtttcggccg gtgcgcccgc ccggcgtcga cgtgtcgcaa tggggctgga cgtcgcagcc   47520
cgagcaggct caccccgatt acggcctcgc cgaggtgcgc ccgctgccgg gcggtggcct   47580
ggcagtgctg ccgctggcgg ccccgattta cgagccggtc ggcgagcttg gccccgagtg   47640
ggtcgacgtc ggagcggtcg agcagtgctg agcgtcagc  ccggcatgaa cgtgccgaag   47700
caacgccgga agatcgagca gcgcctcgtc gaggccccga gcgaggccca tgcgcgttac   47760
ctgcggtggc tgctggcgca gttcgacgag agcctcgccc gcggcctgcc gcgcccggcg   47820
agcgagttcc tgccgatgta cgacgaggag ttcgacccgt agcaaaatgc cggcgagcag   47880
ccgatttgtg cgctgagctg cgcgtcgccg aaaagtcagc aaacgccctg aggcccgcga   47940
ggactcgggg cgtttgtgtt gacacctcaa caccccgcgg tgtagtgttg aggtatcaac   48000
agcacgacgg gataggagcc caaaatgtac aagatgatcg ttcaaatgta cggccgcacc   48060
gaggttaccg agcacgacac gatcgccgag gccgcgagc  gcctggtcac gatcgccgtt   48120
acgcagaact gccgtgtgac cggcgacaac gccaccggcg agttcatcct gcgcgaccgg   48180
gacggcaacg acgacccgcg cgtcacctgg acttacggcg cctaccggat cgaggaggtg   48240
```

```
gccgacgtgc gcaccgaggt gatcgtgaag gccgtcgaga acggctgggc cgtcaacgcg   48300 atgcgcccg  acttcattca ggccgcccgc ggcaacgtga ccgcgtacgt ggcgctcgac   48360
gccgacggcg gcctcgacac cgccgagctg tacgtcgggc ggcagatcgt cgcctcggcg   48420
tacgccagcg aggacgacgt cgagccgacc ccggcccgcg aggtcgtcgg caactggctg   48480
acgctggccg cctgaccggc gagcacgagg caccctgag  cccgcggtgg ctcggggggc   48540
gctttgtgtt gacacctcaa caggccgcgg tgtactgttg aggtatcaac agcacgaggg   48600
gataggagcc tacaatgtcg aacttcaccg ccgaggaccg cgtcgcgcag accattctcg   48660
accagatcgg tgtcggtacc ctgatgcgcc tgggcgcgca caaggtcgag cgttacctcg   48720
acgccgtcgc gtttcaggtc aagctggcgc tgcccggcca gacccgcggc cggatcatgc   48780
gctgcacgat cgacctcacc gcggccgacc tgtacaacgt caagatcggg ttcctgcagc   48840
gcaagacgct cgattgggtc gcccttgaga acgtcgaggg cgtcgacgtc gagggcatgg   48900
tcacgatcat gcggaagcac gcaaagctga tctgaacgcc agcgcgaagc gcccccgagc   48960
cgatagcggc cgggggcgtt ttcgtttgct gtgcacgcgg catgcacgca agcgcagagc   49020
gcgtcgcgca atttagactc ccgattgcag cagcacaact gtgcccaaaa cagcgcgcaa   49080
cccgcgcgag gctgcccaca cgcgcccggc cgaacatgcc agggcgcgtc tgactttcac   49140 gacgggggc  gccggtatgc acgtacgcct ggcgatcctc ggcaccgagg tgctgagcct   49200
gcacgtcggc cgcggcctgg tgctcgacgt cgacgccctg gccctcgacg acctcgacga   49260
ggacgacgac cccgagccct gccagctcgt cggcggcggc gcctcgcaca acttcgagcg   49320
cgaccccgac ccgctgagcg ccgacggcga ggtgccgtgg agcgaggccg atttcggatt   49380
cggccggtga ccggcgagcg cctgcggcgc cgcctcgaac tgcgccggtc gaacgccgcg   49440
cagccgcacc gcaaccgaca ccgcgaacgc cagaccgggc aggagcagct cgacgagcca   49500
tgccccgtcg acggccaccc ttgcccctgc gccgccgct  accgctgccg ctaagcaccg   49560
cgcatgcacg caggcgccga gcacaccgtg cgccctagcg tcgctcatgt gaccgccgtc   49620
gaggccctga cactggcaat agtgccgcta acgattctcg ttgcggccct tgctgcgtgg   49680
ctggtgaccc gcaaacgcaa ggccgcagcg catccgaccc cggtcgagcg cctcggcggc   49740
ggcatacaca actacccgcc cgactggtgg ctgggcgtcg atcgcccga  gtgggactga   49800 gaggagcgac atgctgcaga agatcctgac cggcgtcgct gccgcggtgg ccccggtgat   49860
cgcgaaggcc gtcgccgaga agctcgtcga ggtgctgccc gagctggccg acatcatcgt   49920
gacccggctc gctgagaagc tgcccgacgt cgctgccgcg gtggccgacc gcatcctggc   49980
gcacctgccc gacctgtcgg ccctcgacga cgaggcgatc aaggccctgc gtaccctgcc   50040
ggggctgggg gagcacatcg tgcaggccct actcgaccgc ctgccccact ggcccctcaa   50100
gttctaggag tacccccgca tggctactcg caccccgcgt gacgcattcg acgctgacac   50160
tgtcgagcag gtcgagcagg acgctgtcga gcaggccgct gagcagcctg ctgacgagtc   50220
aacagcacca gtcgagactg acggcaacgc cgcgcccgag cgcgcggttt acaagccgtt   50280
tgagtggtga gcgaaggtcg caacacagcg cgacgcgatc ggttccgtcg catcattcgc   50340
cgcgacgagc cagactgtca cgtttgcggc gagccaatcg actaccaggc cgaccacctc   50400
gacccgctgt cgttcacgat cgaccacata acgcccttgg ccttgggtgg cactgacacc   50460
ctcgacaaca ttggggcggc tcaccgcaag tgcaaccgcg acaagagcga caagccgccg   50520
agctggcggc cgggcgtcac tttcgtgacc gagcgcgagt ggtagcaaac cgcccggcga   50580
```

```
gcgagctcag caaacacgcc ctgacctgcg gttatgcagg ggagtcgagc cagcaaacgc    50640
ccgcggcgcc gatcgagcgc gtttgtgcag gtcagcgacc cctgggggg tgccccgcga    50700 acgatcgcgg cgcccctcgc ggcat                                          50725
```

<210> SEQ ID NO 2
<211> LENGTH: 239
<212> TYPE: PRT
<213> ORGANISM: artificial sequence
<220> FEATURE:
<223> OTHER INFORMATION: Yellow fluorescent protein based on jellyfish
      aqueora victoria GFP.

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 3
<211> LENGTH: 52797
<212> TYPE: DNA
<213> ORGANISM: TM4 phage

<400> SEQUENCE: 3

```
ctcgcggcat aggcagccct ctctcgccag cgttttttcc accagcaaac accggccggt     60
catcccggct acgtcgccac accaccagga ggcagacaca tggaccccga gctgatgcgc    120
gcccgcctcg atgcggtcgc cctcgcgatc cgcgccgccg agctgggcct gctggccgac    180
ggcaagacgg tgctcgactc ggcccgcgac attgccgcgt tcgtcgaggg ttgacatgcg    240
cgcccccgac atgctcagcg tgcagtgccc tggctgcgcc gcgccggtcg agtgcacgat    300
```

```
cacgaccgag ccggtggagc ccgagcccgg cgacacgcac gccaagatcc gcgtgcgcgc    360
ggtcgatctg cgcgagcggt tccgcgccca tctcgtcgag tgcactcgca cccccgaggc    420
tgtgctggcg gtggcttatg gcggttaagt ctgtcgccgc cgcggcggcc gacggcgacc    480
ggcgcgagct gctcgtcgcg atgcgcgccc gcgtggcgac cgcggttgaa gatcccgaga    540
cacctgcccg cgatctggct gccctgacgc ggcggctgtt ggagattgcc aacgagattg    600
cggcgattga cgctcaggcc gagcagggcg agggcagcgt cgccgccgcg gcagcgacgc    660
ccgatgaacc attcgacggc gacgcttagc gaggtcgcgc gccacgtcat tgcgccgcaa    720
ggcatcgtgt cgacggcctg gccgtcggtg cgcgcgacgt gtggcgcgat gggcctcggg    780
ttcgacctgt ggcaggacga cctcggcaag ctgatttgcg cgaagcgcga cgacggcctg    840
tacgcggccg acatgttcgc aatgtcgatc ccgcggcaga ccggcaagac gtacctgctc    900
ggcgcgctcg tgttcgcgct gtgcatcaag acgcctaaca cgacggtgat ctggacggcg    960
caccggaccc gcacggccgc agagactttc cgcagcatgc agggcctcgc gaagcgcgac   1020
aagatcgccc cgcacatctt gaacgtgcac accggcaacg gcaaagaggc cgtgctgttt   1080
aagaacggct cgcgcatcct gttcggtgcc cgcgagcgcg ggttcggccg tgggttcgcc   1140
ggtgtcgacg tcctgatttt cgacgaggcg cagatcctca ccgagaacgc gatggacgac   1200
atggtgcccg cgacgaacgc ggcgcctaac ccgctgatcc tgctggccgg tacgccaccg   1260
aagccgacgg accccggcga ggtgttcacg gtgatgcgcc tcgacgccct ggcgggcgac   1320
gtcgacgacg tcgggtacgt cgagatttcc gccgacgagg acgccgaccc cgacgaccgc   1380
tcgcagtggc gcaagatgaa tccgagctac ccgcaccgga cgtcggcccg agcgatcctg   1440
cgtatgcgta aagcgttggg cgatgagagc tttaagcgcg aggcgatggg catatggccc   1500
aaggtcagcg tgcaccagcc ggtcgtgaag tcggggcggt ggcacgacct gttcgacctc   1560
ggccccgagg acggcgaagc gcctaacgcc ctggcggtcg acatgtcgca cggcctggcg   1620
atttcggtcg gcgcgtgctg gctgatggac gacgacggcc gccacgtcga ggaggtgtgg   1680
gccggtaccg acaccgcggc ggcggtcgac tggatcgctg agcgggccgg gcggcgcatc   1740
ccggtgctga tcgacagcat gagcccgcg gcggcgctgg cgcccgagct gaaagcccgc   1800
aaggtcaagg tgaagctgac cggcgcggcc gatatggcga agggctgcgg cctgtttgag   1860
aacgcgtcga acgccgacac gttgacgcat ggcgatcagc ccgcgctgaa tgacgccctc   1920
gctggcgccc gtaaacgccc gatccgcgac gcaggcggtt ggggctggga ccgccgcgac   1980
ccgacctgcg taatccatcc attagtggcc gtgacgctgg ccctgctcgg tgccgccgac   2040
ggccgccgtc gccgagctgg ccgcggtggc ggcgccatgt tcgtgtgaga ggggggggcc   2100
gtgactgttc ctgttgacgt gatcgccgac gccccagcgg ccgacgtgga gttccccgag   2160
gactcgatga gccgcgagca gctcggcgcc ttggtcgccg acatgtggcg gctgcatatt   2220
tccgagcgtc agtggctcga ccggatttac gagtacacca aggggctgcg tgggcgcccc   2280
gaggtgcccg agggcgccag cgacgaagtc aaggaactgg cgaagctgtc ggtcaagaat   2340
gtgctttcgc tcgtgcgtga ttcgttcgcg cagaacttga gcgtggtcgg ctaccgcaac   2400
gccctggcga aagagaacga ccccgcctgg gagatgtggc agcgcaaccg catggacgcg   2460
cgccaggccg aggtgcaccg cccggcgctg acgtacggcg cctcgtatgt gacggtgacg   2520
ccgactgatg aggggccggt gttccgcacg cggtcgccgc ggcagatcct cgccgtgtac   2580
gccgacccgt cggtcgacgc ctggccgcag tacgccctcg aaacgtgggt cgcgcaaaag   2640
```

-continued

```
gatgcgaagc cgcaccggcg cggcgtgctg tacgacgaca cgtacatgta cgagcttgac    2700
ctcggcgagg ttgtgctcgg cgacgcgggc ggcgggcagg ccacgcagca gccggtgaac    2760
gtgcgcgagg tcaccgacgt gatcgagcac ggcgcgacgt tcgagggcaa acccgtttgc    2820
cccgttgtgc gtttcgtcaa cggccgcgac gccgacgaca tgatcgtcgg tgaggtcgcc    2880
ccgctgatcc tgctgcagca ggcgatcaac tcggtgaact tcgaccggct gatcgtgtcg    2940
cggttcggcg ccaacccgca gcgcgtgatc agcgggtgga ccggcagcaa ggccgaggtg    3000
ctcaaggcat ccgcgttgcg cgtgtggacg tttgaagatc ccgaggtgaa ggcgcaggcg    3060
ttcccgcccg cctcggtcga gccgtacaac ctgatccttg aggaaatgct gcagcacgtg    3120
gcgatggtcg cgcagatcag cccggctcag gtcaccggca agatgatcaa cgtatccgcg    3180
gaggccctcg cagccgcgga ggccaaccag cagcgcaagc tcgccgcgaa gcgtgaaagt    3240
ttcggcgagt catgggagca actgctgcgc ctggccgccg aaatggacga cgaccccgac    3300
acggccgccg actcgggcgc cgaggtgctg tggcgtgaca ccgaggcccg ctcgtttggc    3360
gcggtcgtcg acggcatcac caagctgccc tcggcgggca tcccgatcga gcacctgctg    3420
tcgatggtgc ccggcatgac gcagcagacg atccaagcga ttaaggactc gctgcgcggc    3480
ggcgaggtga atcgcttgt cgacaaactg ctgtcgaacg aaccggcgcc agtgcccccg    3540
ccgccgcccc aggcggctgc tcaggcgctc aacgagggcg gcgtgaatgg taacggcggc    3600
gcctgagttt cagggcgtcc tggccgagct gagcgggcgt gcgggtatcg ccgtcgaccg    3660
gctcgtgccc cggctgagcg gcctgaccga ggccgagggg ctgcggttca tcaccgacgc    3720
ctatccggcg ctgatcgacc cgtacctgtc ggcgtcgtcc aagctgacga cgcagtggta    3780
cgccgagcag cccgcccgcc agcaacccgc cggcaaaagt gccaacgcgc agctcgcagg    3840
cgatttccgc ggtggcccag caaacacgca gggcggcaag ctgtttgtgc cggaaccggc    3900
gccgctgccc gaccctgacc gctgggtgc taacgcccgg tgggcgctgc tgcagaacga    3960 cccgtggtc gcgctgcaag gctcggcgac ccgcgcggtc atggactcgt cgcggcgcac    4020
ggtgctcgac aacgccaagc gcgagggcgt gcggtgggtg cgatacgcct cggtcacggc    4080
gtgcgggttc tgccgcatgc tcgcgacccg cggcgccgtg tacaagtcgg ccgacaccgc    4140
gctgcgttca cacgatcact gcgtgtgcct ggcggtgcca gaccgcaacg gctcgtatca    4200
gccgcccgac tacgtgcagc agtgggagca ggattacctg caggcccgcc gcgacggcct    4260
cactacgccg caagagattt cgcgggcgat ggaggccgcg ggcgagcagc gcaccgcgac    4320
ccggcagtgg ctcaacgccg agaaggcgca ccagcgcaac gtaagcgact ggctcgacgc    4380
cgagttcgtc cacaacaacg ccgtcgacta ctggcagaac gtcgacgccg agctgggcaa    4440
ggcgttcgcc gagcccgcgc cgaaggccga gccgaccgcc gagcccgccg cgaaggccga    4500
gcccgcggag gcccgctcg accggctgct gcgcgaagcg aacgcagcaa tggaaacggg    4560
cgactacgac aaggccgaca gctgctcgc cgaggccgac aagctcgaac gcgcgcagca    4620
agccaaggcg gccaaggcgg ccaaggccga taaggacaag gcccggcgcc aagcggccga    4680
cgccgccaag caagacgagg tgctgaacct cgtcgagcag ggctgggaac cggccgaggc    4740
cgagtctcac gtgtacggca agagtgtcga gtcgatccgg cgccgtgact tcatgtcgca    4800
ggcccgcggc gacggccaca cggcaagtc gttcgacgcg cttgtcggcg acgtgcacgc    4860
cgagatggcg gccgagcagt tctggaaggc cgaggcggcg acgaacggct acatgctcaa    4920
acgcaagtac gagggcaagg tcgacccgcg caagctgtgg acgatgaacg aggcggcggc    4980
ccgcaagtac atgtcggagg agatggccgc gtggttcgac cagcacggca ggctcacgag    5040
```

```
ggcggcgctg cgcgagtcgg tgctcagcgg taaaggcaac tggcgcaacc cactaacggc    5100
ggatttcctg caatgagcga taacagcgag ctgatcgccg cacgcgacga ggggcgctcg    5160
gcgccggtcg gtgcagtcaa tccgtatgcg gggcagggca tcaaggcccg gctgtggcgc    5220
ctcgggtacc gcacgatgct gctcgacatg ctgaacaact cgcccgctgt gcgggcgtac    5280
ctgcaggcgc agcaatagat ttcacgccca acctgggcgg gtgagcgtgg acggccaacg    5340
cctaatcggc cggtgatgct gacgagctac ggagcaacta acatggcag aacaaactga     5400 gtcgaccacc gaaaccaccg aaggcaagcc cgccgaggac aactcgaccg agggcgccga    5460
cggcggccaa agcggtgacc agggcaagac tttcacacag gccgagcttg acaaggtgat    5520
cgagcagcgg ctcgcccgcg agcgggcgaa gttcggcgat tacgaccagc tcaaggctga    5580
cgccgccgag ctggcaaaga tccgcgacgg cgaaaagagc gagctgcaga aggcgctcga    5640
acgcgccgag caagccgaga agcgcgccga gcaagccgag ttcacttctc tgcgcagcaa    5700
ggtggcggcg tcaagggcg tgcccgcgtc gtcgctgacc ggcaagaccg aggacgagct     5760
gaacgcctcg gccgacgagc tgatcgcctg gcgtgaccag aacaagccgc ccgcaccacc    5820
gaagcgcaac cccgcgcaag gcggcggcgg cctcaagtcc ggtgccaccg gcaacggcaa    5880
caccaattcc gaccccaaag ctgccgcggc agaagcattg cgccgcttac gcgccggggg    5940
ctgacaacag gtttccgcgc gaggaccgac ctcggcggga gaaggagaa agccaatcat     6000 ggctgacatt tcacgcgccg aggtcgcctc gctcatccaa gaggcttact cggacacgct    6060
gctggccgcg gccaagcagg gcagcaccgt cctgtctgcg ttccagaacg tgaacatggg    6120
caccaagacc acgcacctgc cggtgctggc gaccctgccc gaggccgatt gggtcggtga    6180
gtctgcgact gacccgaagg gcgtcaagcc caccagcaag gtgacgtggg ccaaccggac    6240
cctcgtcgcc gaggaaatcg ccgtcatcat cccggtgcac gagaacgtca tcgacgacgc    6300
gaccgtggcc gtgctgaccg aggtcgccga gctgggcggc caggcgatcg gcaagaagct    6360
cgaccaggcc gtcatttttcg gcaccgacaa gcccgcctcg tgggtttccc cggcgctgat    6420
tccggccgcg gtgactgcgg gccaggccgt cgaggtcgtg ggcggcgtcg ccaacgagtc    6480
cgacattgtc ggcgcgacca accgggccgc gaaggcagtt gcgtcggccg ggtgggcacc    6540
tgacaccctg ctgtcgtccc tggcgctgcg ttacgaggtc gcgaacattc gcgacgcgaa    6600
cggcaacccg gtgttccgcg acgactcgtt cgccggtttc cgcaccttct tcaaccgtaa    6660
cggcgcatgg gacgccgacg cggcgatcga ggtgattgcc gacagctcgc gggtgaagat    6720
cggtgtccgt caggacatta cggtcaagtt cctcgaccag gccaccctcg gcaccggcga    6780
gaaccagatc aacctggccg agcgcgacat ggtcgccctg cggctcaagg cgcggttcgc    6840
ctacgtgctg ggtgtgagcg cgaccgctca gggcgccaac aagacgccgg tcgccgtcgt    6900
ggcaccggct gcctagtgcg ctatcgccac gccttgacgg gggcggttat cggggtgcgt    6960
gagggcaccc tgctgccgc cctcgtcgag ggcgacgaca actggacccg gtacggaggt     7020
gctagccatg acggagtgca aggcgctggc gacaagccag gacgtcaagc gggcgctgcg    7080
gcgggatctg acggaagcgg agcagacgga cctaagcgag ctgctcgccg aggcaacgga    7140
tctcgtcgtc gggtatctgc acccgtaccc ggtcccgaca ccaacaccgg ggccgatcaa    7200
gcgggtggtg gcgtcaatgg tggccgcggt gctgacccgg ccgacgcaaa tcctgcctga    7260
gacacaatcc ctcaccgctg acgggttcgg cgtgacgttc acgcccggcg gtaactcgcc    7320
ggggccgtac ctgtcggctg cgctcaagca acggctgcgg ccgtaccgca ccggcatggt    7380
```

```
tgcggtcgaa atgggcagcg agcgttactg ctgatgttcc cgacaccgca caaggttgtg   7440
catgtcgacc gagtgaaggt cggcgagaac gcgatgggcc aggcgatcac cgagccgcgc   7500
acccgcaccc gctgggtgac gagtctgcgg ccgagggtga acgagagcgg cactgctgcc   7560
gccctggccg atcgcgtcat cactgagtac acgatggcga ccccgagag tgactggacg    7620 cacggcgacc aagtgaccga tgcgcggggg cgcaagttca aggtgcacgg cgacgtcgag   7680
gactacaacc tcggcccgtt cgggttcacg ccgggctatc gagtgacgtt gcggagggtg   7740
aacgatggcg cgcaaaccgc ttgacatgcc caactcggag caccgcaaga tccgcaagct   7800
gcccgaggtg caggccgagc tgcaacgcct ggcggccgag gtcgcccggc gcgcaggcgg   7860
aatcgccgac gcccccgacg gctacggcac cgaccttgag gtcggccgca ctcgtgcccg   7920
cgcgcacgtg tggccgaagt cgagtgcggc gatcaaggcc gaaatcaaga cggcgccgct   7980
tatgacgatc gccgcggagc aggggccgca acagtgactc tcgtgccctc tgtcggcccg   8040
ctggtggccg cgcgagccta tctgctcgac gagctggcgg cccgcgctaa cccgctgccg   8100
gtcggcgcca cccgcccga gggcgagccc agctcgtacg cgctgctgtc ccggccgggc    8160
agcgaccgcg acgtgtttct cggccacttc ctgatccgcg tgcgcgtttt cgacagcgac   8220
gtcgtgcgtt tggagcgcaa cgccgatctg ctgcacgcgc tgctgtgcgg ggccaaccac   8280
cgcaaggtgc acacgcccga gggcgacgtg tggatcaccg gcgcggcgca tcactacggc   8340
ccggccgacc tcgacgaccc cgacgtgccg ctgttcggca tgcaggccgc ggtgttctgg   8400
acgatcggcc tcaagcccgc ccgccgtagc taaccgccgg caaaaactcg agcacacccg   8460
ctgacctgcg gcgcgcccca attccgcagc gattcaagca aacacaccac cacaccaggc   8520
aagtgtccct cgggccgacc ggctcgcggg tagttagttg cccgcgcggg caagttagga   8580
gagtaagcaa tggcagactc gcccgtcctc gaaaactcgt ggggcgacgt taccaaggtg   8640
ttcgcggcct cgccgtctga cctcgaaacc gttggcggcc tgtggtatgc gccgttcggc   8700
acgccgctgc cgaccgacgt cgacgagccg ctcgacgaca agttcaagaa cctgggcttt   8760
atctcggtcg agggcgtaac cgtcaagatc gacgaccaga ccaagccgat cgaggtttgg   8820
ggtggcgacg aaatcggtgc gctgcgcgac aagttcgcga tcgagtacag catgaagctg   8880
ttccaagtgc tgtcgcccga ggtgaacgcc gccatttcg gcgagggcaa cgtgctcacg    8940
tccgaggcca ccgcgatgca cggcgcccgc atgaaggtgc tcatcaacag caagctgccc   9000
aagcgttgct cgctggtgct cgactcggtg tacgaggaca agatgatccg ccaggtcgcg   9060
cagatcgcgc agaaggcggg cctggctgac ctcaagctgg tgcacaacga gccgatggca   9120
ttcgagccga cattcaaggt gctcaagggc actgacggca accacgtcgt gcagtacagc   9180
gacgacggcg tcatttccgt ctagctgaca cctcacagac cggcaccccg cgcgcttttcc  9240 tggtggggc gcggggtgtc tcaccacatt cacaccaggg cacgccagga aacacaccag    9300
gaggttaaaa gctatggaaa tcaacgcgac tgacacggcc cccgaggtcg acgtcgtcga   9360
gcaccaggac gtcgacgagc cggtggcggc cgaggcgacc cccgaggcgg gcaagacgat   9420
cgccgaggag tgggccgacg agtacgacgc gggcgccgag ctgttctgcg ccacgttcga   9480
cgccgacgat ttcgaccccg agtacggcgt caacgagtac cccgacgcca cgaccgtggc   9540
cgtcaagcgg tgcctgcgca agccgccgcc ggggtggatt cgccagcacg cgcacctgtc   9600
cgaccttgag cgcacgttcg cgctgatcga gaagcactgc agcgacaagg ctctcgacat   9660
tctcgacagc ctcgccgaga agccgtggaa tggtttcgtc gaggcgtggg gccgtgacgg   9720
cgggctgatc gagggaaaat ctcgcaggtc tgcgcggcgg taaggcaagt cgaggacgcg   9780
```

```
atccgccggg acatggttct ggcgggtcgc gctttcgacg acgggtcgct cgattgggac   9840
gacctttacg ctttcatttt cgcctcgccg ccgggcaccg cggtgttcca tgcgttcgag   9900
aagggctgga cgacaagcga ttacctgctc gcacacgtga tcgacgccct acggatcaac   9960
aactggcagc gcaccgaggg cgcgcataag aatccgccgc agggcgcacc cgacccgttc  10020
ccgcggccgg gcgacgacga cgacgagccg aagcgcgccg agggcgcggt gtcggccggt  10080
atcacggcgg cgaccaggac gacggtcggc aagttcatgg caatgcgcgc tgagcgcgaa  10140
aagcgttggc gcgaaaagca ccagcgagga gagggggcg taaatgtcag aggccaagta  10200
ttacctgaca atcctccccg agactcgcga gcttgagtcg ggcatccgcg acgcgatgag  10260
ccgcgccgag cgcgggctca aggtcgcccc gaagttcgac acctcgggcg ctcagcgcgc  10320
aggccaggac gcgggcaagg gaatcagccg cggcgtcgat acggccgacc ccggtaaggg  10380
cctgggccgc aagctggccc gcaacctcgg cgacggttcg gcgctcggca agcagtacgg  10440
ctcgcggctg tcggcgggca tcgacagcgc gctgtcggtc gccggtggca tggcgatcgc  10500
caaggttggc agcaagatca gcggggcgct cggctcggcg atgcgggccg ggttcggccg  10560
tctgacgcag atcgactcgg cgcagttcaa gctgaaatcg cttggcaatg aggccagcac  10620
ggtcgcctcg gtcatgcagg acgcgaccgc ggcggtgaag ggtacggcgt tcggcctcga  10680
cgcggctgcg accacggccg cctcggcggt ggccgccggt atcaagccgg gcgagcaact  10740
gaccaagtac ctgtcgctga ccgctgacac ggccgcgatc gccggtacga gcctcgacga  10800
aatgggctcg atcttcaaca aggtgcaggg ctcgggcaag gcgatgacgt tggagcttcg  10860
ccagctcgcc gaccgcggtc tgccgatctt ccaatggctg caggacgagt ttcacgtcag  10920
cggcgacgcg ctgcaggaca tggtcgcgca gggcgcggtc gactctgaga ctttccgccg  10980
ggtgatcgag aagaatatcg gcggcgccgc aaagggtatg gcggcagtt tcgttggctc  11040
gatggcgaac atgaaggccg ctatgtcgcg gttcggcgcc gaggttatgg ggccgatctt  11100
taagggcgtg cagccgctcg cgaccgggct tatgggcgtg ttcgacaagc tgaccgccgc  11160
gatcaaggcg cctatgggca acgtgacgac tgtggtcgag cagtgggcca agggcatgtc  11220
ggacaagatg caggcgtggg ccgacggcga cggcatgaaa aaggtcattg acttttcgg  11280
ccgcgtcggc gactcgatca aggctcttgc gaccggcggc gacagcggca agctcggcga  11340
gattgtccag tcgttcaaaa acattgggcc gtcactgcag acggccgggt cgtcgtttgc  11400
ggcgatcggc gccacgctgg ccgcgatcgg ccccgaggtg ctgtcgtcgg tgctcgtgcc  11460
cgcgctgcag ctcgccgccg gggcgctcaa gttcatggcc gacaatgcct cgtgggcggt  11520
gcctacgatc gtcggcctgc gtgtcgccct gttcgcgcac caggccgtgc tgactgcggt  11580
ggcgatcggc accaaggcgt acggcgtcgc gatggccgtg tggtcgggca tcacgaaggc  11640
cgcgaccgcc gcgcagtggc tattcaacgt cgcgctgacc gctaacccga tcgggctgat  11700
tatcgccgcg gtcgtcgggc tcgctgtcgc gatttgggcg tttttcacga aaaccgaagt  11760
cggccgccaa ctgtggtcga agatttgggg cggcatcaag gccgctgtgc acgtgttcgt  11820
cgagtggttc aagaacacgg ccgtgccgtt catcaaggcc gcctgggaca tgatcgcggc  11880
gggggccatg tggttgtggc acaacgtcat cgagccggtg tgggagggca tcaagacggc  11940
gatcaagttc gccattgatt tcatcaaggc cgagattcaa gcctgggtgg cgatcttcca  12000
tttcatcgag gacgtgtggc gcggcctggt cgacacggcg catgcggtgt ggcagggcat  12060
cgtcgacaag ttcaccggcg tggtgaattt cgtcaaggag ctgcccggca agatcacctc  12120
```

```
ggccgctaag ggcatgtggg acggcatcaa agacgcattc aagtcgatga tcaacagcct    12180
gatcgacatg tggaacgggc tggccgacaa gatgacgttc accgttcccg acattcccgg    12240
cgtgccccgg cgtggcgaga gcgtgcaccc gatcccgaat atcccgcgcc tggcgaccgg    12300
cggccggatc agcgggccgg gcaccggcac gagcgacagc atcctcgcgc gtatcgctaa    12360
cggcgagttc atcaccaacg ccgccgcgac ggcccgcaat ctgccgctgc tgcaggcgat    12420
caactccggt gcgccgctgt gggagctgat tagggcgctg ccgaggttcg ctggcggcgg    12480
cctggccgcg ggcctggcgt ccgagcagaa cctacagccc aacagcatcc tgatttcgcg    12540
gctggtgtcc aagctgttcc gcagatcaa gacgattggc ggctggcggt cgcaggacgc    12600
ttaccccgat cacccgtcgg gccgggcgct cgacattatg atccccaact actcgtcgaa    12660
ggacggtgtt gcgctgggcg acagcgtgat gcagttcctt atgaagaacg ccgacgcgct    12720
cggcgtcgag tacacgatct ggcggcagac ctaccgcaac acctcggggc agtcgaacct    12780
catggaggac cgcggcagcg acacgcagaa ccacatggat cacgtgcacg tgacgtcgaa    12840
gggcggcaag ccgaagggcg gcgtggacac cgcaccggcg ggcctgtctt tgccgtctgg    12900
cgtcaacgtg agcggcctcg acggcgtggg ggtgcctagt ggtggctcgt cggcgctcgg    12960
cagtgccacg tcggcgtctg gcggctcgta ccgggcggcc accgacgacg agcttaaggc    13020
gtcgtcgggc aaggtcgaca gcgcccgcac gtcgctgcgc aacgccgaca aggctatcga    13080
ggacaagcag tacgcgctcg acaaggcgaa gcgtgacctc gaaatcctca agggtaagaa    13140
gcacaccgcg gcgcagcttg aggacgccga gcaccgcgtg cagaaggccg agcgcgacct    13200
ggccgacgcg atcgagaagc gcggcaaggt caacgacaag ctgaccgacg ccgagcaggc    13260
cgacagcgat ctgcgcacca agggcaaggc caccaagggc aagtcgaaag acggcaaggg    13320
cggcggcctc gacggcagcg acctgggcaa gacgttcgtg tcgggcatgc tcgaaagcat    13380
tggcctcgac gggtcgctgt tctcgaatcc gtttgagtgg ccgacggtta agtcggcgct    13440
cgccggtgtg aactacctcg gcaacctgct gtcgggcaag ggccgcgacg gcgaggaggg    13500
caccaccgac agccccggcg ggttcgccgg tggagtcgct gacagcgtcg gcctgggctc    13560
gctgttcaag ggcctgggca gcccgatcga cgggcaggac gtcggctggt cgccgcagtc    13620
tggcagcccc gcgctggcac cgggtgagtt caacccggcc accgtcggcg gcggctcggt    13680
cgccgagggc gccgtcgacg ctatgtcggc gttcgtcccg agcgcggccc aggcggcgca    13740
gggcgatcag cctgcgcagg ttgacaactc gatcaacatt tcggggccgg tcggtatgga    13800
cccggtcgcg ctgcgctcgc agatccacag cgagcagaac gcccgcaccc gctccacggt    13860
tcggcgcgtc tagctaacgg ccggcgagcc gccgattcat gccttgagct gcggcggctc    13920
gtcgagccga ctaacaactt ctatctatgt gaggcggtga agcgcggtca tgtcttggat    13980
gcacgacgat ttctggctcg acccgcccaa gtatccgaat gactggcagg caacccggc    14040
gtaccccgag gagaatccgg cgcacccgca ctttcagcgg atgggcgcct ggcacgacct    14100
cggtaagaac ggcgagtacc tgcggtcgac ggcgaccaag tggtattact gccacccatc    14160
taacggcaag gtgtggcacc tcgccgggcc gggccgcggg cgtgagggcg tcgtgatggc    14220
gcgcgagctt gagggcgtca tgcagcccga tttcgagatc cgttggagtg agggcgctta    14280
cacgatcggc gccaagcccg agcgcgtcga ctataaaaag cggcgcatca acctgggcgt    14340
ggcgattcag cccaacctca acgcggagcg gatcgaggag cctaattcgt tctcgtaccg    14400
catgatcgag gactcgtggt ggtcgtcgtg gtctgagact gtgcccggtt tcctgggctc    14460
gttcacgcgc acgcatgggt tccgttggct gcgtgtgctg ctcggcgagg ccactaaggg    14520
```

```
cgcgctgtcg atcgacccga cgggcaacga caacaactcg gtgattcaca acatggcggt    14580
cgacgccgcc tggccgttct acgccaagcg cccgctcaag cgtgtgtgga aggtcaaccc    14640
ggccgacgtg tacgcgaagg gcaaggccga gggcgttatc gcgatcgcga accgcggcac    14700
gtgggagtcg tggccgaagt tcctggtgcg cgggtctggc gaggtgtgga ttcaggacgg    14760
catcgagggc cggatggtca agctgcccaa gctgtatgac accgacggct cgtacatgat    14820
ggtcgacacc gacccgacgg cgcgcacgat cacgaccgag aaagatccgg tcgacggcca    14880
gctctacaag tacctgcgca acagccaact gctcgacctg ctgctgcacg acgtgacggc    14940
tgcgcggcta ccggcgcagc ggcgcatccc cggtggtatc ggtttcgacg gcaagatccc    15000
gccgcgcacg gtggcgcaca tcaaggtgtc gcacaccaac ccgcagggct caatcacgtg    15060
catcatgccg cagtattacc ggatggcgtg gtcgtgacgg cgacgctgtt ggagccccg    15120 cggatcggcg tcaacggggc gcctgaccct gtgcgcgacc cgattgccgc gtacacctac    15180
ctcgacgcgc gccgcgaggt gatcgacgag gaggcccgcg cccggccgct cattcgcttg    15240
tgggacaagc aaatgcagta cataggcacg gtcgccgccg agaagtcggt cgacgccgag    15300
gagatgttgc acgacaccgg caccggcgac attgtgctgc gcggcgacga ctggctcgtc    15360
gagttcatgc gctcggacgt gcgcaaagac gaggatctgc acatcacgat cgacccgtac    15420
ccgcaccggc gtaactggcg gtggcggtgg aacgcgaagg tcactaacgt gcgcgtgaag    15480
cgcggcgagg atggtctgcg cacggtcacg cttgagtgct cgcacaatcg ggagcattgg    15540
aagcacatct atttcggcgc aacgcctttc agcccgccgg aggtgcagcc gattcgcgcc    15600
tggctgctgc cgggcaacac tcggaccatt atcgcgacaa cgggtttcat caacctggcg    15660
cgtaattaca cccgctgct ggcgttgccc acgcaggtga tgaatcccgg cgcgtggctc    15720
ggcgaggcca gcaatgtgct gaacctcaac ccgttaaatt ggcctgtcca aatgcaattc    15780
gtcaatccgg tgttcgacca gtcgcgcttt agcgtgatca tgtcgcgctg ggctgacgcg    15840
cacagcgtca ccgaggcgat gctgaaagac gcgggctgca acgtgcgcgc gtacatgtgg    15900
ctgcccgagg acgaggacag cccgcacccc gagctggccg cgattatcgg tgagaaggcc    15960
gcccggccga ctcgcgcctg cattgtgctt gcggtggagg acaattcggg ccgcactggc    16020
tggtccggta cggccgccga cggtttcatg cagcttatcg gcgtcactgg cgacgacatg    16080
atccgcgagg tcgtcgggca gatcgacgac aagggccgga ttatcgaccc gataaccaag    16140
gcaacgcttt tcggcaagct gctgggcacc gccccgtcga tcccgagtgt ggtattccgc    16200
gacaccgagc actcgtcgat catcacggcc gagcactcga tgttccgtgc gaaggcccaa    16260
aaaatcctga caggcggaaa atcacccggc tgggttaacc aaactcagac cttcctgatc    16320
cgatatgcgt tgtcgcagtt ggctcaagtg gtgttcgcta ctgagcaacc cggcgccgag    16380
ggcttggaca acctctatca gggccaggcc gacgacacgc tgatggcgtt catcgcgttc    16440
acagatccgt tgcgcgccat gcgttctgga ccgtacggct accttgagca tttcgagcag    16500
ggcagcgggt cggcgtacac ggtcagctcg ggaatgactc tgcggcaagg gcattggaaa    16560
acgcgccctt accaggcgtt caaggtgcag gtgcgcaacg gcggcaacgc cgggacgctt    16620
tactacgatt tcgacctcgg cacgcgcgcc ctgttcgaga ttgaccgcat tatgcacgtc    16680
gaccaggtgt cggcgatcaa gctgcattac gacgagaaca cgcccaagac gttcgacctc    16740
gtgatcggcg acgacgccga gtctgagaat ccgctcgcct caattacccg caccgcgcag    16800
cacttttgga gtgcgctggc gatgctattc ggatcggggg atttgttctg atgcaactgc    16860
```

```
cgaaactcac gccgcgcgag gagatggcgc cgcacgccca ggcgatgcac gacatagccg   16920
acgcgctgca gtaccggcc gacaacatgg ggcgccgcta cgacgttcgg tacctgatcc    16980
cggtgctggc gtttcacctg gcgcgggcgg gctgcgtcat cgaccccgag cgggcgctaa   17040
tcaaaccgcg gcggctgccg ccctcgccgg gcgtcgtcga ggacgcgatc gagtgggtcg   17100
acgtcaacgc ccccaacact atcgacgacg agctggcggg ggcgacgctc gacgacctcg   17160
accggctgtc accggcggcc cgcgctgagc tggtgcgccg cctgggcggc gacggcgcga   17220
aagtggccga ggccgaggca gatacaccgc tcgacgagcg cacgccgtgg cgtgtcgaaa   17280
cgtcgatcca gttcgacgac gaccccgaca gctaacagcc ggcgaatccg ccaatcacac   17340
cgctgacctg cggtggcgct tctgcgtgcc gcaaggtcgg caaacaacga ataggagcga   17400
cctagtcatg gccgaaattc ccgcgaccgg cgacgccgtc aggctgtttc aaacgctgct   17460
gtcggcgacc tggtacggaa tcgtgcgcag caaggacgat cccggcggca tggccgcgac   17520 tatgaaatg atcgacgacg aggcggtcat caccaccgac gtgctgatcg gcccgaaggg    17580
tgacaagggc gacaacgccc cgctggtcga cctgcagtgg ccgccgcttg agcaggccgc   17640
cgacctcgaa ccgttgaagg cgagcctcgg cccgaccgac aagggcaagg cgtggtggat   17700
cgggacgctg gtctatgtct ggacgggcag caagttcgag gcggtgcgcc ccggcccggc   17760
cgggccgcca ggggccacac cgctcatcac ggcgtcggcc gaaacgatcc ccatgtcgga   17820
gcgcacgccc gagagcaaag acgaggtgat cccgtcgggc acttctcttg cgccgcacct   17880
gcatttccgg ctgctctcac cgcaaggccc gcgcgggccg tcgacgaaca ttctcgacgc   17940
ccccgactac gacaacacca aggcgcccga ggacgggcag accccggtgt ggtcgtcggt   18000
caagcaaaag tgggtgccgt cgagtttcgc gcacaagcac ccgcggctgt acagcgtgcc   18060
cgaggcggcg tttcagaact tcaccggcgt tgcccagcgg cacccgatcc tgacgtacat   18120
cgtcgaggcg caggattatg cgtggacgcc gtacgtcacc gggcacctca aggcggttgg   18180
catcgagttc gacgtcgacc cgctgacgat cggctgcgag gtgcgcctcg gcgacgcgac   18240
gaccggcgac ctggtcgccc gcgggtttgg caatatcgcg agctggacga acatttcgcc   18300
gcactactcg accagcgccg acccggccgc ggcggtggcg cccggcaacg gcgtggccgt   18360
cgtgcccgcc ggtcagaccg cgcagatcaa cgtcaacctc tacaacgacg gcatcctcgg   18420
cgcctacctg ttcaaccgga aaggcgcgca actgaccatc ctcaccattc gacaggggga   18480
ataaggctgt ggcataccaa aagtcatacc gcacggtcgt gccgcttgag ccgggcaccg   18540
accgcgacgt ggcgctgtgg cttgtgcgcg agtcgttcga gcgcaaggcc gagggcgacg   18600
ccctggtgct cgtcgagttc gcgcaccgcg acgtcgacgc cgccgatctg ccgccgaagg   18660
ccgagaagca actcggccgc ccgctaaccg atttcgagtt cgtcgagtac accgggggtgg   18720 ggcgccgtgc cgaggcagta tgacagcagg cagctcgtcg tcgaccgcga cccgctgcgg   18780
cagctcatac ccgaccccgg caagctgccg aagctcgacc cgaaagtctt ttacgacggg   18840
ttaattcagg gcatcaagat gctgacgggc atcgacctgt cgtcgcccga ggcgctcgtc   18900
gcgagcatca tcgagctgct taaagacgcc gtcggcggcg cgctcgaccc tacgcagctt   18960
ctcgcgacgt tcgcaagat cctcggtttc gtcggcaccc cggcgagcat cgacgagctg    19020
gcggcgtggg cctcgacgaa cctgttcgga tggatcgacc ccggccgcct gccgatcatc   19080
ccggtgtcgc atatcgggca gatcatcacg agcctgctgc ctaacggcat gttcggaggc   19140
gcgcagtcga tcatcgaccc gaccgggcgg tggctcgtcg acgctgtcga gggcgcggcc   19200
cgcacggtcg ctaacggcac gttcaccgac ctgctgtcaa cggatctgat cagcgtcgcg   19260
```

```
ccgggccagg tgctcaacat cgtcggcaag gtgaagtgga gcggcctgac cgcctcgggc    19320
agcccgatcc agctcggcgt gaccgagtac agcgacgagc gcggcgagaa cctggccggg    19380
cgggctctgg ttgccacgcc tgcgggtcaa accggcacga ccgggtggaa ggacgtcgcg    19440
ggcacttaca ccgtcccaca gggcgttaag gccgtgcggg cgcgtgtcag tgtgggcgcc    19500
gaggccaccg cgggcgacgt gtggttcaag ggcgtggatg ccaaccgggg caactcgctg    19560
ctgccgatcg cgctcgtcga gaacctgtcg agtcggctgg cgagcctgct cggcgtcgac    19620
gtgtggcagt cgttccttga cgccgcgaag ggcgcgacgg gcggctcgat cagcgacatt    19680
atcaaccgca ttgtgcacct gggcgtcgac ggctcgttcg acgcctcgca gctcgtgaac    19740
gtgccgaata tcccaatggt gccgggtacg aaggtcggcg gcctcgccgg aaacatgctg    19800
caggactttg gcagtcacat cgacaacatt gtcaatcggc tgtccggcac ccgcgggtcg    19860
aatcaatctc tcgacgacgc cgacgcggcg ctgggcgccc tgcaagacac cgtgctgggc    19920
ctgagccagg acgtgcaaga cctcaagatc gaccaggctg gcacctcgac gtcgggcaag    19980
aggtaccgcg tcgacttcac aacgctgccc tcggggccgt tctccgcggc gccgttcgac    20040
ctcacgtatt ccggtgctgg ctcagggtat ttagagcttg ccggtagggc tcagtggcac    20100
aaggtgaacg acggcgaccg ctctgtgatc gccaggtaca ccgacggcac caacaccgac    20160
accgaaaccg atttccagtt cattcaggcc accgtcggct cgccaccgga cggcgccgcc    20220
gtgaactacg catgcgctcg gatgaacacc gccaagacga cgtttgtcta cgcgatgggc    20280
tttcgggccg ggttttttcgg gctgcagttc cgagccgagc tgggctgcta cgtcaacggc    20340
gtccggtacg tgtttgtggc gaatgcgcct gcgacgtaca actacaacct cgccttgaag    20400
gcgggcgtgg gcggtaaccc gtaccgtttt caggtgctct cgggcacgac cgtggttatc    20460
gactacaccg acaccagccg cgttagtcag atcggcgcgg cgttccgcgg gtggggtttc    20520
cgctccgaca ccggcaacag cggtagcgat gcgcctgccc ctgcggtgtt cgtcggctgc    20580
gccgataacg ccccggtggg cgtgcagggc accacattc gggcctatcg ttcgctgtcg    20640
agttctgtgt cgaaaccggc gggcaatgtg ccgctcccgg cgaacacgtt cgacaccgtc    20700
gactacatca gctcggactt gaagtggaat cccaccacta cgagataac ggttctcaag    20760 gccggtacct acctgtgctc gatgcgcctg caaggcgcgt cggccctcgg ctttggtaac    20820
ggcaagcggg tttacccgtt ctggttcgtg ggtggcgcag cgaaggcgat gggccacgac    20880
aaatatgcct tgaacctcaa cggtttcggt gccccggcgg cgtcattgga ggatgcgatc    20940
ggcggcgacc cgttcgtcta ttacgttccc gagggcggc tcatccgggc aggggcgggc    21000
aacgccgcga atgccgcgat agctctcgtc ggcgacagcg ccgggctgtc aacatggctg    21060
accgtcgcca gggtgggcta atgccccgac ggctcaacgt atctcagcac atcactactc    21120
actaggagcg cgtaaatatg gcagacgtcg aaaacacggc cgacatggtt caggcggtca    21180
agcagcggct cggcgaggag ctttccgagg agcaggtgca cgccgtgctg gccgcgtgga    21240
acagcgtgcg ggcgcagggc gatccggtcg gcatggtgcg ccgcgacgag gagtcgggca    21300
aggtggcgca ccgcgtcgtc gtcgaggccg tcgagcagtg gcgcgtgagc ggggctgacg    21360
gcgaccagta caacgacctg cagccgacgc tgccctggcc ggtgctgttc gacccgcgct    21420
aatgccttgg acgccaacgc ccccggcggc ccggcgcagc agctacggct ggtcaactaa    21480
cccggccccg ctggcgcagc ccgcgccggt cgggccgggc tggttcgtgt cgctgcacga    21540
gccggccgct gcgctgagta tcagcaccgg cgacgcccgc gtcgtcgtgc agaccgtggc    21600
```

```
ccaggcgcgc ggcatcagcg aggccgacgc ggcgctgctg gtgcacatga tcgggcaggc    21660
gtcgagcgtc agctcgtcga ccgcggcggc ggccgagcac gtgttcgccg acgccctggc    21720
cgcctcggcg agcgcggccc gcgccgacct ggtcgtggaa atcgtcgccg aggcgctcgg    21780
cgtcagcgcc accgacgcgc tgttcgcgct caagttgacc gcggcggcca gctcggcgag    21840
cgacgccgtg gcgaccaacg ctttcccggc gatggccccg ctaccgcaac agttcacggc    21900
cgcgggcaac tacacgtacg cgatcccgta ctggtgccgc ttcatcgaca ttgtggtgct    21960
cggcggcggg ggcggcgggc aggcgtctgc ggcgctgttc aactacggtg cgcccggtga    22020
tcccggccag tatcaggccg tgacgctaga gcgcggcgtc gacattccgt gggcggtggc    22080
ggcgatcacc ggcaccgttg cgacggcgg tagcgcgtgg ggcacgtacg gcgccatccc    22140
cggcggccct ggcggcaata cgacggcgac gttcactggc ggcggcacgc tcagcggccc    22200 aggcggggc ggcggtatcg ggtgggccac ccaagcgggc tctcgcggcc ccggccccgg    22260
caatttcacc tataacgggc agctctacgt cggcggtgga ctggcagacc agggcgccaa    22320
caaacccggc aagccgcctg gtggcgccgg atcaggtaac tctcccggcg ccggtggggc    22380
tggcccaggc gcaccggcg cagtgtggtt ccgcgcctat cagtgaggag tgcaacgaaa    22440
ttgaatcctg acgacgacta cacgttcgcg ctccggtacg agtggctgcc cgaccccggc    22500
gccgaccccg acgacccggc caactggcgc gaatggatca tgcccgccgc gaccctggcc    22560
caggccgagg gctggctcga cgcggtggcg caggcagata cccgcacgc ccgcgggttc    22620 gccatcgtct actcgcccaa ggtcacttgg cggccctggc cgcccgccga cgactgagcg    22680
catgctcgct ggccctgata acggccgagc gggtttcgta gcacgtgcgc ctcgcccgta    22740
gctaaccgcc ggcaaaaact cgagcacccc ctctcacctg cggataccc gcgaaacggc    22800 gcgaggtcgg caaacactgg ataggagcac cgtggcagca acggacgcat tcaagctcgc    22860
gatcgccaac gcgatcggcg cgcaaggcgc actgatcagc ctgcactcgg ctgaccccgg    22920
caagaccgac gcgacggcca acgcgaccga aattagcggc gccggataca cgcgcaagct    22980
gaccgcgtgg ggcgccccgg tcatcgtgtc gggcggcgcc gacgacggca aggcccgcat    23040
caccggctcg acgcagcagt tcaacgtgcc cggcggcgtg ccgatcacgc actacgccgt    23100
gcgcaaggcc gacagcacat tcctgtacgg caagccgctg gcgcccggcg cgaccctcac    23160
cggcaacggt gtcatcgacg tcacgccgac acatacctac gacctgacct agctcgaaat    23220
ggtcggcgtc gagggcattt tcgcagcatt gtctgcggct gtggtgctcg gcgccctcgg    23280
gcactggctc tatgacgtgc tggcgcaccg gcgctacgac aacgacgagg atacgacac    23340 atgagtttca cccggttcct gcaggatgac ccgctgctca cccgcgagca agtgatggcc    23400
gagctgattc gggtcgccga cgagctgaac atgcccgaca agcgcggcgc ctgcgtcatt    23460
gcgggcatga cgatttcgca agaggtcggc gtaaaggaca acgacccgcc gttcgagcgg    23520 cggttctgt gccggccaa ccgcgccgac cccgaatcgt tcaactaccc gcacgactcg    23580
gaatcgaacg acgccgctc ggtcggctac ttccagcagc agaagggcc taacggcgag    23640 ctgtggtgg gcacaacggc atccgagatg aacctgcaca cgccgcgac gcagtttatg    23700 acgcggctca aggcggccgg atacaacgcg agcaacgccc aggcggcgaa cgactcggcg    23760
caggcgatcc agcggtcggg cgtcccgcag gcgtacaagc aatggtggga cgacattaac    23820
cgcctgtacg acaaggtgaa gggctcgggc ggtggcccgg cgcccgcgcc taagccgccg    23880
cagtcggggc cgtggaccgg cgaccgcgtg tggctggccg acgtgctgcg cgccgagggg    23940
ctgaacgtcg tcgagctgcc cggctggctc gaccgcgggc acggcgacat gggccgcttg    24000
```

```
tggggcgtgg tgtgccatca caccggcagc gataacaccc cgtcgagcga gattgcgttt   24060
cacccgtcgc tcggcctgtg ctcgcagatt cacctggcgc gcaacggaac tgtgacgctg   24120
tgcggtgtcg gcatcgcctg gcatgcgggc gtcggcagct atcccggcct gcccgaggac   24180
aacgccaacg cggtcactat cggcatcgag gcccaaaaca gcggcaccta tgacggcgca   24240
ccgcaccgga cgaattggcc tgacgcgcaa tacgacgcct atgtgaagtg ctgcgccgcg   24300
atctgccgcc gcctcggcgt gcgcgccgat cacgtgatca gtcacaagga atgggccggg   24360
cgcaagcaag gcaaatggga tccaggcgcc atcgacatga acatctttcg cgccgacgta   24420
cagcggcgca tcgacgccca tcaaccaaac ggagaggacg atttcatggc cgcactatca   24480
gccgacgagc agcgcgaggt gctgaacctg ctgcgcgtcc tggccgaccg gcggttcgtc   24540
agccgcagcc cgttccgcca ccttggcgag gggccgagcg aaactgtcgc cgggttcggg   24600
ctcaacaccg acggcctcaa tcacgcgcag tacacgattg agcttgcgcg cctgggcgac   24660
ccgacgcacc tcgccctgct gcgcgaggtc gccagcgccg agggtgactc gcgctatccc   24720
gaccggcagt acgacgccaa gctcgccaag cgcgtgctcg ccgaaatcga gggcgccgca   24780
acggcaccgg ccaagccgag cacgccgagc gccccgaccg agcccgcccc cgaggcgccc   24840
acgccgccgg tcaaggccgc gtgtgcgctg tctgcggccg ggtgcgtggt ggctggctcg   24900
acctcgggcg gtggctgcgc cctgtccacc gacggcaccg gcaagtgcgt tgtgaccgcc   24960
gcgaccgacg gcggggccgc ctgatggcct gggtcggttg gcagctcggc atgcagggggg   25020
agcaggtcaa ggtgatacag caaaagctga tcgccaagta ccagtgggtg cgtgaccgtt   25080
acccgcggct gacggccagc ggcgtctatg acgtgaacac gcaggccgcg atcgtcgagt   25140
ttcagttccg cgcagggctt cccgtcaccg gcatagctga ctatgcgacg caggttcggc   25200
tcggcgcggt ggccccggcg ccgccgccgc ggcagcgcat catggtgctg acgtttagcg   25260
gcacctcggc cgacatgtgg accggctatc cggccgacgt cgcgcgtgcg ctcgacccgt   25320
cgatcttcta ctggcagcca gtgtgctacg gccccaacgg catcccggcg atattcccga   25380
tgggttccag cgccaagagc ggcgaggtcg aggggctgcg gctgctcgac gagaaggcgc   25440
gcgatttcga ctacatcgtg cttatcggat actcgcaggg cgcgctgccc gcgtcgcggc   25500
tcatgcggcg catcctgtcg ggcgacctgc agcggttcaa gtccaagctg atcgccggtg   25560
tcacgttcgg caacccgatg cgcgagaagg ggcacacgtt ccccggcggc gccgaccccg   25620
gcgggcacgg cctcgacccg cagtgcctcg tgaatacgcc cgactggtgg cacgactacg   25680
ccgccaaggg cgacatttac accgtcggct cgggcagtaa cgacgagaag gccaacgccg   25740
acatgacgtt catttaccag ctcgtgcagg gcgacattct cggcatgatg ttcggcaccg   25800
gcaacccgct cgacattctc ggcctgctcg gcggcctcgg tggcggcctg ctcggcgcc   25860
tgggcggtgg cctgctcggt ggcggcaagg gtggcctgca gttgccgagc ggcctggtgc   25920
tccccggcgt ccagggcggc gcgctcaccg accaccagcg cggcctcgtc gaggcggtgc   25980
tggcgctgct cgctaacccg ttcgccgagg ttccggcggc ggtcaaggcg attgtgtccg   26040
gtgtcgggtt catcgccacc aacccgccga cggcgccgca catcgagtac cacattcgcg   26100
aggctgcgcc cggcgtgacg tatttccagc acgcgatcga ctacctgcgc caggtcggcg   26160
cgtccgtcgc cgctcgcgcg gcctgacccc gaggagtcaa cccccgatga tgtcgatttt   26220
ggatctgcgc tcgcgcgacg acgtgcggcg cttcattcac agcgtcgccc cggcgatcgc   26280
cgtgctgatg gtcagcatgg gcgtgctcga ccgcaacgtc gcaatgctcg gcgtggctgt   26340
```

```
cgtgctggct gtgttcaacg acaccctggc tcatatcaac tcgtccgatg cgttccgcaa    26400
gtggttctat ccggtgctga cgtcggctac cgcaatgctg atcgggctgg gcatggtgac    26460
cgacgagcag ctcacgccgt ggatcgcgat tatcaccatt ctgatcggcg gcggtgttgc    26520
ggctaagaat gcgctgcccg aggagtgcga ggccgacgac gacgagccgt caggcaagca    26580
cgcgacgaca tgacgccctt gcgggcggtg ccgggcatgc tggctcgtgc tgacaacgcc    26640
tcggcggcga agctggacgg catgcggggg atgccatgac gtaccgctac gtcgagaacc    26700
gggtgctgcg tttcgtgcag ctcgcgctgc tcgtcgacgc cgtcgtgcgc ggcgcgagct    26760
ggatcgcgac cccggcgagc ggcataccccc agcgatcgg cctggccgcc gaaggcaccg    26820
cagccatgtg ggtgtggggc gccgtattcg ccgtgtttgg catcttgggc ctgctcggcg    26880
agctgtggat gcacctcggc gagtctgagc atcgcgcgtg gccgtcattc ctggcgtacg    26940
ccgcgctgct gttcctgttc gccgggctgg ccctgtcggc ggtcaataac gtcatcacaa    27000
cgcacgcaac ggacgggttc agcgcccccat acactttcgc ccttctcgcg ttgctgcatt    27060
gggtgttcgc gaggcggcgg aagcatgtcg gctgagctga tcgagaagct gccgcagcag    27120
tgggtcggca tcgtcgtcct ggtgctgttc gtcgtctacg tggccgggca gctcatcgag    27180
aaatccgagc gcgtcgcgaa gctgctgccc ctcggcgtgt ggtggcgcga gcgcaaccgg    27240
cgcaagtctg cggtcgaccc ggccgagctg acacgcgcgg tcgaggcggc ccggcatgcc    27300
tggtcgcgcg aggagaacgc cgcactggcg gcccttgaga gccgcgtcgc cgtgatcgcc    27360
gcgatttcgg agcaccaggc cctcaacatc aaagagctgc aagactcggt gcgggcgttc    27420
acggcgttct ctgtgtacga cgcgcgctgg caccaccgcg ccgacgtcgc cctggctgac    27480
tgcccgatgt gcgacctgcc cgaccacctc gattacttcg cttcgagcg gctgtggcgc    27540 gaagatccgg ccgccgccgc gaggttgcct gtatgagcct cgctgaccgc ctcgggccgc    27600
tgacacgagc cccgatcggc tgcgcggtgt gccgctggta cgagggcctc gacgacaccg    27660
accggctggg gttcgactcg tgggtcaacg gcggcggcag tatctcgcag ctctggcgcg    27720
agtgctgcgc cgaccccgac aggccgctgc atatcagccg ccccccggttt tccgagtgca    27780 tcaaccaaca ccaccgcgga ggccctcgtg tcgctagctg accggctgag caccccggcg    27840
gtgcccgacg agaagtaccg cccgtcggtc gagttcgaca gccgcggcgc cacgatcgac    27900
accggcgcgg tcgagcagga gcccggccag ccgcccgagt acgccgagct gctgcgccag    27960
gtcggccgcg accccgagcg gttccggctc gtggcgatcg accgcgagaa gcactggcag    28020
gtgccttacc gcccgatcga gggcaccgac gagcgcggca gccgatcct cggcgagctg    28080 acgaccaagt ggctcgcctc gtactcgctg cgcgtcgaac ctatcgacca gggcggcaac    28140
gaccttgagg cgctgatcgc cgaggcccgc aagcgcccca cgatcgagcc cggccagctc    28200
ggctcgccgt attggttcgt ctttcagggc ggcgacctgc agctcggcaa gcgcagccgc    28260
gacggctcga ccgagcagat cgtcgagcgg ttcgtacagt cggtcgaggc cgccaaggct    28320
caactgcacg cctgggcacc cctcggtatc gcggcgtgc agatcagcct gccgggcgac    28380
tgtttggaag gcgtcgtgtc gcagggcggg cgcaactcgt ggctgacgca ggaaacgatc    28440
gccgagcaga cccggctgct gcggcggctc atggtgtaca cgatcgacga gctgcgggcg    28500
gcccccgagg tcaagctcga cgtcgtcggc ggcaaccacg acgacgctaa ccggcagtgg    28560
aacaccaagc ccggcgacaa ttgggcgacc gaggcggcga tcgccgtcga cgacgccctc    28620
aagctcaaca ccgccgcgta cgggcacgtc gaggtgcgca tccctgagtc atggtcggga    28680
cacatgaccg tgccggtcgg cgacaccgtc gtgaccgtga ttcacggcca ccagtggcgc    28740
```

```
aaagggcagg ccctcaagtg gtggagcgag caggcggtgc acaaccagcc gcccggcgct    28800
gcgcacgtgc tgcagcatgg gcactggcac accgcgcgt gggaagcgca cgccaccaag    28860
acgatcgtgt gctcgccgac gttcgactgc gggtcggact ggtaccgcga gcggcacggc    28920
gccgagtccc ggcgcggcgc cctcacgtat ctgctgcgcg gcggcgaggt ttcacgcctg    28980
agtgtcgtgt agctaaccgc cggcaaaaac tcgagcgcac ccgctaagct gcagcaatgc    29040
gctgcgcccg tccgaagtca gcaaacagcg cccctcggct cacgccgggg ggcgtttcgg    29100
cgtttctagg gcctgttgac gcgccaacag ttctgcgcct aagctgttgg ggtatcaaca    29160
ccccagcgga taggagcccg acatgacaac ggcattcgcc gacccgacga tcgaggacgg    29220
tatcgacatg gcccgaggca agcaggtgcg catcgacggc aaggtgcgca cgatcccggc    29280
cgacaaggtc gagcagtacg aggcgatggc aacccgcatc gacgccctgt tccccggcga    29340
ccgcgggcac gagcgccagg ccgcgctgaa agccgccgcg cgcttcatcc tcggcgacct    29400
gaccgtcagc ggcgccggtg acgacctcga tctcgcccgc cgggcgcagg aggaggccgc    29460
cgcagcggcc cgcgcggtcg ctatcctcgc gatcgagaac ggcgccagcg agcagggcac    29520
ggcccgcgag atgggcgtcg accggctgac cgtgcgcaag tggaacggca aggtcgaccg    29580
ggcatgagcg acgaggtgtg ggtgctcgac ttcgaggccg aggggccgga gccgggcgac    29640
tatgtcgggt atcagtcggt gcaccgcacg cgcgacggcg cgagtaaccg gctgctcgaa    29700
cgcctcgccg acgtcgacgt cgacgtggcc gaggtcgagg cgctcggcgg cgcccaggcc    29760
gacgacggca gctacgcggg cgagctggac gccgacggca tgacgatcag ctacggcgtg    29820
caccgcatgc cgatcgagga ctagcgtcac ccgcccggcc cgtagcaatc tgctacacga    29880 ggcgccctg tcgattcgtc ggcgagggcg ctttcgtgtt gacgggtcaa cagcccgcgg    29940
tgtactgttg aggcatcaac agcactacgg gataggagcc caaaatgacc acagcgacat    30000
ggactaaggc cgaggccaag gcgagcgacc gcgagtacgc ccgactggtc ggtatcgccc    30060
aggccgccag cgccgccgtc gacaccgccc acgagcgcgc cctgacggcc gccggggcga    30120
gcatgcagta cctcaacggc gggtaccgcc gcaagggcct gagcttcgac cgtggccgca    30180
ccgaggccac cctcgaccag gcccgcgcga tcgcctcggg caaggagcag tcgccgagcc    30240
ggtacgccga cgtcgagcgc gccgccgagg ccgtcgcccg gtacgacgcc gcggtcgtcg    30300
agtaccgcga ggccaacgcc gcggcccgcg cctgggacga cgcgcattac cagggctggc    30360
ggcgcttttt cctggtgccc ggcggccaca ttcacgagtc gaccgcctgc agctcgctgc    30420
gcatcacgac catgatcgtg tggctgcccg agctgtcggg tgaaaccgag gccgaggcgg    30480
tggccgagca cggcgccctg ctgtgcacca agtgcttccc gtcggcgccg gtcgagtgga    30540
ccgtcggcaa cgtcgacccc gacaagtgca acgggcgccc cgacatggac cgccgccgcg    30600
gccggtacgc gccgtgccgc gagtgcgggt acgtcggcca catcacgacg cacggcaacc    30660
tgcgcaagca caagcgcgag agcgcctgag agccaacgag aaacgccccc gacccggtcg    30720
caccggcggg ggcgttttcg tgcgcctgcg gggcgctcag ccgggcaggt gacccggctc    30780
gtcgggcagc accgtgtcgg gcgtgaccgt gtactgctcg cggtcgttga tcttcatgtc    30840
gacgaaataa ccgccgtacg tggtgcacga gacatagctg cgcccatagc agctcgtgcg    30900
cgtcggcacc tggtgcgccg gtgtccacac gctgcgcttg cgctcccagc tcccgtcggg    30960
ctgcaccggg ccgtcgcaga tcgtgcgccg ctggctgccc aggaatcccc acagcaccgt    31020
gtcgcagttg gggccgaggt caggatcggg ccgagcgtgc gccggggcgg cggccagcac    31080
```

```
ggcaccggcg ccgatggcac cggcgacggc gagtgttgcg gctgttttga atccgatcac    31140
gacgcacccc cgagcgccag gtgggcgccg cccgagaaca tcgagtcgtg caggatcagc    31200
tcggttgcct cggtgccggg cggcacgtcg aacgcgacgc gcgcctgaat cgcgttgcct    31260
gggttaatgt ctccggtcct gcaggtagta ccgcgatttt gacatttgca gcgcctctaa    31320
tatctcgcgc agcttgagcg gtctacccac taagtagcca agcactgcgg caaggctctt    31380
ggcggtgtcg tcgtctggca cctgggtgtc ctgtctatta ggggcgggtc cgaaatcgcc    31440
cgtatggcgt gtcactttag tctaggtttc tggactaaac aataggcttg agcagcgatt    31500
atgagaaacg ctaatcgttc gcgcgtgcaa taagtcgcgc ccaatggtgc agattctgga    31560
caagtgggct atggtgacag ccatgacagc cccgcgacac gagctgcgat ggaatcccgg    31620
caaagtctca aaaacactgg cccgcctcgg tattcgtgac cgcaccgccc tggctaagcg    31680
cgtcagcatg cccaagagca cgatatacgc ggcgttcgac gccgactggt caggcgtagc    31740
aacgaccaac gtgttagcgc aggtcgcagg cgagttaggg gtgtccctgc tcgacctggt    31800
cgccgagccc gcaccgcgcc gaaaccagaa agtgcagaaa actgcaccgc gccggtcggt    31860
gcagaaaact gagcaattcg gcgcgacggt gctgctatga ccggcgcctt gctgacctat    31920
cccgtcgccg acgtcgcgcg acgtatcccc tgctccgagc ggtggctcac cgagcagatc    31980
cgcgccggtc gcatccccgg ccgcaaggtc ggtcgtcact ggcggatgac tgaggccgac    32040
atagaggccg ctctcgaatc gttccgcgtc gcccccgagt cgggtcgcaa gtctgtcgcc    32100
gccgagcgcc cgttcgcgct caccgccacc tcgcaacgcc ggattagggg ctgacgcaat    32160
gcaactcatg cgccacatcg aggagtgccg ccgcctgcag gcacagattg acgagctgac    32220
cgccgagctg cgcgtcgtca ccgacgagcg cgacgccgcg ctgcgcgagc gcgacgagct    32280
ggccgaccgc ctggccgtcg ccgaggccga caaggcgtgg gggcgcgagg agcaccggcg    32340
gctgcacaac ccgatgcccg acatggaccg ctgcggctga tcgccgccta acgacacaa    32400 cccccgcacg aggcggggc tggccgacac aaccaaggga taggagccac ttgttatgcc    32460
gacacagagt ttagcgccag atcggcccgc agtgcctagc gccatgcggg cgtttgcgtc    32520
gaccccggcg ccgtggtgcg acgactgccg ctgcgtgcac gcccggccgt gcgaggcgca    32580
gcagcgcatc aaccgcgccc tcgacgccct cgggttcgcg ctgctcatcc tgacgtcgat    32640
cctgctcggg ctcgccgcgg gggcgctgac cctatgagcc tcaaggacat aacgctcacg    32700
cacgccgagc tgaacctcgc cgcgcacgtc gtcgacaccc acatgacaca gggcttcacg    32760
gcgcacggcg cggtggcctc ggcgattcgg gctgtcaact cgatgcgcaa ccacccggcc    32820
gcgtaccgcc gggtcgacct ggcgcagctc aagcaatctc agcgcagccc gcaccgcggg    32880
gcggggcggt tccgcgtcgc cgactgcgcc gactgccagc tcgacgacaa cacctgcccc    32940
ggccaccgga tttaggagct atcaccgcat gtctgaccta gtgattttcg acgagctgca    33000
gcaaggcgag gagccgcgcg actacgtgcc cgcgttcgag cgggccgtgc tgtacgccat    33060
gcagttcaaa ccgatgtacg agggcaccgt gccgcaccgg gtgcgcgcca agcgccgcga    33120
gcgtaaccgc gtcgcccgcc gttctcgcaa gatcaaccgg aaagccatct agcgcaatga    33180
cttacgaccc aactaaccgc gagcaagaat ccaaggatcg ccgccgcatg cggatcgcgc    33240
agcgcaagcg cgaggcccgc tcggcgatgg ccgtcaagac gtacgtgctc gacgacgtcc    33300
tgcccggcct gccgccgatc cccgacaccg acgacgtgtg caaggccctt ggcatcaagg    33360
cccgcacgac gctgcacaac gtgctttacc gtcaccgtga cgaaatgatc gcgggcggat    33420
gggacgccgc cgcaggcaca ttcacgcgcg aggccgttgt gcggctgtgc ctgctgctgc    33480
```

```
gcgccaccac ctcgcgcaag gcggccgaag tcgccgaggc ggtcggcgcc cgcgatcgcg   33540
tgatcaagtt caacgccagc aaggtgccgc acattcggcg ctgccaggcg ttgatagaca   33600
aggcattcgg ccttgctgag cgcgtgcgcg acgaagatcc cgccgaggtg tggcacgacc   33660
tcaatcagat ggacgcctac acgctgcagg gcatcaccgt ggccctggcg gcgatggtcg   33720
acctcgactc ggcgaccggc ggtgtgacgc agtggcttag ctcgctggcc ccgtctaagc   33780
ggcaccccgg caagggcaac ggcggcgccg cgagcggttt ggcccggctg gtgccgacac   33840
ccgatgaggc gcagggcatc ccgctgggca agatcccgag cctgatcgac cccgagcttg   33900
acgaggtggc gtcgtgatgc acatgcacat gggcggcgac ccgtcggcga tctgcgcgca   33960
aaccgacccc gagctgtggt tcccgacaa agggcagtcg acacgcgacg caaagcgcat   34020
gtgcatgcgc tgcccgctgc tcgacgagtg ccgcgccctg gcgctgcgcg acccgcacct   34080
ggtcggcgtg tggggcggcc taagcgccca ggagcgcagg cggattcgca aggggcgtc   34140 ggcatgacgt acgacgaaac gagcgccacc gaggcgggcg accctgacgc ctgggtcgac   34200
ccgcacctgt gggcacacgc ctgcgtgttc gcgaacgcct gcgtgccacc gcggcggccc   34260
gagagcatgc tgcaggccct cggggcgctc gaccggctga tcgccgagtc gggcgtcacg   34320
gtgcgcgcgt acacgtggct gcccgagcag cccgcgctgc ccgcggccga cccgtcgcag   34380
ccgatcgacg tcgacgtggt cgaggtcggc aaacccaacg cgacaacgg aaacggcgcg   34440 accagcgacg acgcactcgc cggcattcct gcgcagcaaa cgcagccggg cctgccgaag   34500
tggatcgtcg acatggcggc ggatgcggcc tacgagtacg cccgccgctg cggcgccgcg   34560
atcctcgggc tgcccgtcga cccgctcgac gacgtcgtgt atatcgccgg gccgatgacg   34620
ggttacccgc ggtggaacga ggcggcattc accggcatgg ccgcctacct gcgcagcctc   34680
gggcacaccg ttatctcgcc caacgagctg cacgagcccg acgaaaaaca cgccgtgggc   34740
ctggtacatg cggcgcgacc tggccgagct ggtcaagtgc agcaccgtcg tgatgctcag   34800
cggttgggag acagccgcg gggcctcgct tgagcactac gtcgcaaagg cgttggggct   34860
gcgcatcttc tactacccga acattgaggg gctgctgccg tgagcgcaaa cgaaacgatg   34920
aacgtgtcac cgaccggcgg caccaaggcg ggcaatctcg aacggtacga cctgatcccg   34980
gccgtgccgc tgcgcaagct cgcgatttac gcgggcctgg tgcccgtcgg caagccgggt   35040
tcgttctctg agctgaacgc gcacctgtgg cggttctgga tgggcgagga cgtccagccg   35100
acaaccgagt acgagcacct aatcgcggtg gcctggcacg cattccggct cgtcgaggac   35160
aacgtcatgc cgcctaagcc gtggccgcac gacaccagcg agggcgggct gacgcgcgaa   35220
cggtacgacc ggataccggc cgagccgctg cgcatgctgg ccgagcacta cggccgcggc   35280
gcccgcaagt acgccgacga caactggcgc gcgggtacg actggcgcct atcgttcgcc   35340
gcactgaatc ggcacctgtg gcagtggtgg gcgggcgagg agattgacgc cgagacaggc   35400
tcgccgcacc tgatcgccgt cgcctggcat gcgttcacgc tggccgagtt cgtcgagatt   35460
caccccgagt tcgacacccg gctaaagacg ttggacgagc gcgcagtccg cgaggtgacc   35520
gcgtgagtga cagcaagcgg ccgtggtggg ccgacgcaga cgtgttgcgc gacaacctgg   35580
cccgccagga gcacgacgcc gcgatggact acctcgcgc cctggccgag ctggtcgaca   35640
cagcgatcgc ctacggcccc gaggagcccg ccgaggcggc cgggcgggca ctggccgacc   35700
tcgaccgcgg gcggtggctg agcgggcacg tgtggggggcc gtacggcgac gacggcctgc   35760
cgctgaccga gctggacgaa atcgcccgca acatctacgc gcaccccgtt tgcgaacaca   35820
```

```
gcgcatgcag ccccgagctg tgcctcggcg ccgtcggcgc gatgctctcg taccccgcca    35880
acacaaccaa cgaaagggct agcggtgtct gatatttcga gcgtcaaggg gcacgtcgac    35940
ctgctgcggt acgtcaaggc cgaaaaggcg aagctcaagg aaattgagga cgccgcgaag    36000
gccgcggtcg aggaggccct cggcggcgac gacgagggca cgatcgacgg cgaggtcgtg    36060
gtgcgccgca agcggatcaa gagcaaccgc ctcgatcaaa agctgctcaa gagcctgcac    36120
cccgaggcgc acgccgagtg catgagcatg tccgagtcga cgcggttcga ggtcgtcgag    36180
tgagccccga cgaggcggtc ggccggatgc tcaccgcccc gatctgccac ctgtacgcgc    36240
tgctgtggcg cctcggcgta atcgaggtcg tcgcatgaag ggcgctctcg caatggttta    36300
cgccgggctg tggattatgg cggccctgat ctttttcctg acaatctcgg aggtagcact    36360
gtgacaaggc aattggtcgt cgtcgactgc gaaacgacgg gcctgcatga cggcgcagcg    36420
attttggagg tcgccgcggt caacatcgac accggcgccg agctgcattt cgtgccgttc    36480
gtgacgcgcg agcagctcgc ccaggcgcag ccgatggcaa tgcagatgaa ccgctactac    36540
gagcgcggca tatggcagcg caggctgagc cccgacagca ccgacgccgc ctattggaag    36600
ctggcgaaca tgctggcggg caacacattc ggcggcagta acccggcgtt cgactcgcgg    36660
ctgctggccg ccgcgatgcc cgacggcgcc cccgagtggc atcaccggct cgccgacctg    36720
gccgcgttca ccgcgggcaa gctgaatctc gacccggtcg agctgcccgg cctcgacgcc    36780
gtctgcgagc gcctgggcgt caccgtcagc gaccggcact cggcgctggc cgacgcgcac    36840
gccaccgcga cgtgcttcac gatcctgcgt gagatcccgg cggcggcgct gtgaccgccc    36900
tcaagcagca gacgattgtg ctcgccgacg ggcaccgcgt cggcgtcaca accggcggcg    36960
acagcggcac cccgctggtg ctgtttcacg gtttcaccgc caaccgcagg ctgtacgccc    37020
cgatcatgct gcgcgctgatc cggcgcgggt tccgcgtgta cgcaatggat atggccgggc    37080
acggcgacac tgacggcctg gcgagcgggc attcgttcgc cgacatggtc gacctcgccg    37140
tgcgcgccct cgacgtgctc gacgtcggcc gggccgtgat ggttgggcac tcgctgggcg    37200
ggcgcatggt caccgagctg gcggcccggc accccgagcg cgtgcagcag cggtgctca    37260
taaacgccgc cgtgggcgac gatttcgacg agctgaacgt gtcggcccgc gtggcggtca    37320
aggcgcctgg cgcgctcgtc ggcgcggtcg tcgaccgcgc cgacgtgccg tggacgagcc    37380
cccgccgcgg gctgcgctat ctgcggcacc tgtcggcgg cggcgccccg ctgtcggtat    37440
cgggcatttt caacgtcgcg atggcgacca agagccccaa gccgccgacg gttgccatgc    37500
tggcggcgct cgcgccgcca aaggtgccgg tgaccgtcat tcactgcagg gacgaccgga    37560
ttacccgcta ctacaacggc gttcaagccg cgatcgtcgc cgacgggctg ctcatcacgc    37620
tgcccggtca ccacaactgg atcatggtgc acccgcaccg cactgccgag gtaatcgccg    37680
ccgcagtgaa actcgtcgag gagctagccg catgagtgca tcgtcatcgt tcctgggcct    37740
gtcggacgac gccgacccgc gcgacaagcc gagggcggca acattcgacg gcaagctgct    37800
cggcgacctc aagggcgtgc tcaagcgcgc ctggcgcag caccccgcggt cgcagcagcg    37860
cgcgatcggg ccgagcgagg tcgggcaccc ctgcgcccgg cggctcgcct cgacgatgct    37920
tgaacttgac cgcgtcaacc ccgagggcga cccgctgccc gcgtggctcg gcaccgccgg    37980
gcacgccaag ttcgagacag cggtcgagca cgacaacgac cagatcgtcg acgcctggct    38040
gcgcgaccgc agcaagccgt gcaccgcaac ggatcgcggc gacggcgccc cgatcgggcg    38100
gtggctgagc gagcgccgcg tcactgtgcg cggcggcctg acgggcacct gcgaccttta    38160
cgacacgtgg accgacacgg ttatcgacct caagttcccc ggctcgtcga ggtttcagca    38220
```

```
gtacaagcgc aacggcccgg ccgccgagta ccgcacgcag gcgcacctgt atggccgcgg   38280
ctaccgcaat gagggcttcg acgtcaaacg tgttgccata tggttcatcc cgcgcggcgg   38340
cacgctgtcg tcgtcgttcg tgtggtctga gccgtacagc gacaaggtcg tcgacgaggc   38400
cctcgacaag ctcgacaaca tcatcctggt gctgcacgac ctcgacctcg acaaccaccc   38460
cgagcggctg gcgctggtgc ccaagaaggc ccacgactgc gtgttctgcc cgttctttac   38520
cagtcggccc gatcccgagc ggccgtgggc gtgcgagggc ggcaagtgag cgccgacggc   38580
gtcatggtgg cgcagagcaa gcgcaccatg acgtttcgag tcaagctcga caccctgagc   38640
gtgccggtga tcgaggcgct gttcggcccg caggccgcgc tggcgctgca gttccggcgc   38700
atcaatccgc actggtacct cgacggcggt gtcgagtgaa gcgcagcgag gttatcgcca   38760
agatcagcaa ggccgccagg gcgaagggca tgcggttcga gattgcccgc gagggcggca   38820
atcacacgct gtacagcctc ggcggcgtca tggtgccgat cgggcgccac ccgacgtcga   38880
acctgcccgg cggcattgcg ttgcggatct tcaaacagtg tgagccccg ctcggcaagg   38940 gctggtggcg ctgagtttgc cagctatggc gcaacgtggc cgctgatctg cggcgacgcg   39000
aattgccggc gagtagctag ctggcgaaac aacccaaggg ataggagcga acatcatgc   39060 aggacaacga aacaccgtgg tggcggccgg tcgacgactc gtgcttactc acggttgacc   39120
acgtcgcggt cgggccgttc gcgctcgtct acttcatcga ggtgcacgac cgtagcggtc   39180
aaaagcacag gttccgcgcc gagggcgtgt actggtcggt gcgcgacatt cgcgtgcagc   39240
tcgaccaggc ccccgcggtc gggcagtggg agcgggtacc ggcgccgggc gaggccgtcg   39300
agttcgacct cggcgagctg ggcaagctgc tcgacgacgg caagcccccg gccgacaacg   39360
gcgagggcgt gctgtgatca ccgcggcggc caaattcgag aagttccacg ccgataaccc   39420
cgaggtgtac gaggtgctcg tgcgcctggc gcgcgagtgg gtcgaggtga ccgggcgccg   39480
caagctcggt atcgcgaacc tgtacgagcg ggcgcggtgg gaaatcgcca tgcgcacaag   39540
cgaccccgag tacaagctca acaacgatca cagggcgttt tacgcccggc tgatcatggc   39600
acgcgagcct gacctcgacg gcctgttcgc gctgcgcacc agcgaggccg acgagtggat   39660
cgccgaggtg gcggcatgag cctcgacccg gtgtcgcgca tggcgtggga gcagcagctc   39720
gcgatcgcga aggcgacgca gcgcgtgcag cagcggcaga tcgggctgct gacgacgcag   39780
cgcgagatta tcgacgacca gctcgccgac gcggtgcgca agcgcaacga ggccagcggc   39840
ctgattgcgc aggctttggg catgttgaac gctcaacagt gagcactcgg catgaccgtt   39900
atcgctgaat acatctaggc gcatagacat agcagcgtgc ctcaccacaa ctgccccggc   39960
gacgactgcg gtcgttgcga ggcgcgcatt gcggcgatcg agtacgagcg cgaggtcgcg   40020
cacgacgatt acccgcagtt ctacgacggc acctagagcc ccgcgggcgc tcgcgcggga   40080
atccacaacg ggcgcaaatg atcacgaagg aaacacagga acacatgagc aacgattcgt   40140
acggattcct cgcaggcggc ggccggcgt cgggcaagtt caaggccac ggcgacaccg    40200 tcggcggccc gatcgtcgtc gagccctcgc agcagcagca gaccaacatg gacaacaagc   40260
cgctgacctg ggacgacggc agcccccgca tgcagctcgt cgtgaccgtg cagaccgatc   40320
tgcgcgaccc ctcgatcgag gacgacgacg gcaagcgccg cctgttcgtc aagggcgaaa   40380
tgcggaaagc cgtgcagcag gccgtgatcg cggccggggc caagggcctc gacgtcggcg   40440
gcgagctgca cgtgacctac gtcggcgacg gcgaaccgc ccggcccggc ctgacagcgc    40500
cgaagctgta cagcgccaag tacatcaagc cgagcgccgc tgcgctggcg accgccggtg   40560
```

```
gcccggcacc gagcagcgac ctgcccgagg gcgtgacccc cgaggcgttc gaggcgctgc    40620
agaagctcgg catggtcaag tagcacaccg catttcgagg cgggccggtg gcgtggtttt    40680
gggaccgtca ccggcccgtt tcatcaccag ggataggagc cccgagaaca tgatcaccgt    40740
ttacacgacc ggacctgagt gccacaagtg caacctgacc aagcgcgccc tcgacaaggc    40800
gggcgtcgag tacaccgagg tgcgcctcga ccaagatccc gcgctcgcag ccgatttcaa    40860
ggccaaaggg cacaagacgg cgccgatcgt gcgcgacgcg ctcaccgaca caatgtggtc    40920
ggatttccgc ggcgacctaa tcaaggccgc gatcgcggct cgggcggtgg cctgatggac    40980
ggcgagctgg tcgccaaggt gcgcgacgcg atcgaggccg agctgaaagc gcaagcatgg    41040
tgcctgatcg gcgtcgacgg ccgggtcgac tgcgtcgacg gcgacattga cacccacgcg    41100
atcgccgagg ccgctgtcga cgcgatcgag gggcgatcgt gagccgcgag ctgctggcgc    41160
tgcacgaccg gatcaagtgg cagcgcgccg acggccgctg cgagtgtcag ggcgagtgcg    41220
gccggtcgca ccgtttcggc ggcgtgcact accgctgccc gaataagcac ggcaactccg    41280
cggtgcatgg cggcgacaag gtcgtgacgc tgaccgtgcg cccccctcgac ggcgacgagc    41340 gaaacctcga cgagcgcaac ctcatcgcca tgtgccaggc gtgcgtgaag cgccaccgcg    41400
cgaaatgcaa ggccgacgcc gagcgtgagg ccgagcgccg ggcgaccgag gcgcagcacg    41460
agtcgctgtt cgagctaccc gaggtcaccg gcgcggccct gacgccgccc tgactgccccc    41520 cgccccaatg tcgcaccagg cccaacccga tagggacaga atgaatttca cggagctgct    41580
cgactcgctc ggctacatgg agggcgagca cctgtcgctc tgccaccagg tgcccggcca    41640
caacttcatg gcgaacgtga tcgagttcga cgaccgcgcc caagctaagg cgctgcggta    41700
cgtcgacgac tgcgacctgt ggttcggcgt caacccgacc cggcgtcgcg gcgccgacga    41760
aggcggccgg ggcacggccg aggacgtcac ccggctggcc gcgtgtggt gcgacctcga    41820 cgtcaagccg ggcgcgtgcc gcgacctggc gcacgcctgg cagatcatcg acgagctgag    41880
catcctggtc ggccagcggc cgacggcggt cgtgatgagc gggcacggcc tgcagccgta    41940
ttgggagatt gaggacggcc agctcgtgcc gtgtgccgcc gacgccgacg acccgacgat    42000
gcaggccgcc agcgaggagc tgcgcgcgga ggccgccgcg gtgctcaagc ggtggggccg    42060
cctggccgtg atggtcgccg agcgccaggg cgccaagatc gaccgcggcg tgtacgacct    42120
ggcgcgcgtg ctgcgggtgc ccggctcgta caaccgcaag ggtgagccgg tgctcgtcac    42180
gtgtgaacgt ggcggcggtg gcccgctgtc gatcgaggag ctgaccgagc gcctcaacga    42240
ggcgggcgtg cgcgagcagg acggcgaccg gcgcaccgcg atgggcgagg ttgtgtcgaa    42300
acccgacacc tgggaacacg ccgcagctac gtgcgactat ttcgccccga cgatcaaggc    42360
gtggcgcgac gagcagatca ccgagcggca caactggctg gtgacgcagg ccgtgcggat    42420
catgtgcggg ctgcgcaacg gctgcctgac tgaggagcag ttcgagcagg cccgcaaggt    42480
cgtcaccgag cggttcaagg ccgagtgcgc cgcgaccaac cgggcgatcc cgccgtggga    42540
gatccccaac gcattcgcct gggcgaccga tcacgcggcc cgcatgaccg acgccgagct    42600
ggcgagcgag attggcgcgc acctgcacct gtgggagaag gccgagcccc gcccggtgac    42660
cctcgccccc atgcagcccg agcaaaccgc cggcaatacc gcaactgtgc agctcagcga    42720
gataatccgc gagtcgacag ctaacgtcac gccgaccgat accggcaacg ccgacctgct    42780
cgtcagggcg tgctcggatc ggctgcgctg tgccccgag tcgggcaagt ggctggtgtg    42840
gaaaggcacg cggtggcagc cgagcccga cggcggcgag gcgatcatgg cggcgatcga    42900
ggtcgtgcag tcgatcaagg tcgaggacgg cgacaaggcc gggggccagc acaaaatgcg    42960
```

```
cagcctgcag cgccggtcgc tcgacaacat ggtcgcgctc gccaagtgcc gccccggcat   43020
gcgcgtgagc ctggccgacc ttgacgccga cccgtacgcg ctgaacaccc cgagcggtgt   43080
cgtcaacctc aagacgggcg agctgacccc gcaccgcccc gagggctggc acaccagggt   43140
gacgggcgcc gggtacgagc gcgacggcgc ggcgccgcgg tggtgggcgt tcctgcaccg   43200
cacgttcggc ggcgacaagt cgatggtcga gtacgtgcaa cggctggccg gtacgcggc   43260 gatcggcgag gtgacgcacc acgtgttgcc gttcctgttc ggcgccgggt ccaacggcaa   43320
gagcgtgctc atggacgtgc tcagcgcggt gctgggcgac tacgcgatca cagcgccggg   43380
caatttcctg ctcgcgggcc gggagcggca cgaaacggag atagctcgcc tgcacggcgc   43440
ccggctggtc gtgtgctcgg aggtcaacgc cgacagcaag ttcgacgagg ccaaggtcaa   43500
gctgctgacc ggcggcgacg tcctgtcggg gcggttcatg cggcaagact tctttgattt   43560
cgtcccgtcg cacaccttgt tcctaatggg caaccaccag cccgatgtga aggctggcgg   43620
cacctcattc tttcggcggt tccggctgat cccgttcgag cacatagtgc ccgagcgcga   43680
gcgggtcgag ggactggcgc accagctagt cgccgaggag ggcgacgcga tcctggcgtg   43740
gatcgccgac ggcgcccgcc aggtgctcga cggcggcatg cgggagcccg cgagcgtgtt   43800
ggcggctacc gcgcagtacc aggacgacac caggaccggc gtcgcccgct tcctcgacga   43860
gtgctgcacg atcggcgagg gcgaggccga ggtcggggcg gtgcaccagt gctatatcgc   43920
gtgggccatc gcgcacggtg agccgctcgt cgatacggcc aagttcgggc gcgagctgag   43980
cgggaatcag gtcgcccgcc gccgcacggc gaaggcccgc atggcgaagc tgacggttca   44040
cgtcgaccgg ctgccagcaa acggtgacag cacctcaccc taccgtcaca actaccgtca   44100
ccccggtgac agtgcaatga cggatgagtg acggacgtat cgacgtgttt tcgcaggtag   44160
tgacggatat gacggatatg acggactctc gcaacattga aactaacatc aacgcttttg   44220
tgtttggtga cctgcggaaa tgctgcgcgg cagtgctggg tgtaaccgcgt agtgcaaaag   44280 tgccgtcata ccgtcatacc cctggcctgc agcaaacacc gcgccgcgcg gtggctcgcc   44340
gtgtctctcg attacctcgc gcgcaccggc gaggccccga caccgcacgc aactggatag   44400
gagacaggtg cccatgacaa ccgacgaccc ggtggtcgac gaggcgaagc tcgccgcggc   44460
tgacgctgtg ctcgcgatgc tgcccgccga cgcgcacgag gcgctgcgcg aggcgctgca   44520
cgcccgcgtg acgggtgacc gtaacggctc acggcagttg cgtctgttcg tgccgggccg   44580
cccggcgccg cagggctcga aagacttcaa gggcttctct aagacgggca aggcgatcct   44640
caaggagtcg agcgacgccg tcgggccgtg gcgcgagcgt gtggccctgg ccgcggcctc   44700
ggcgatcctg gccgaggggc tgccggtgct cgccaaagag ttctcgatcg ccgcgtcggt   44760
gacgttcgtt atgcctcgcc cggccggggc gccgaagcgc agcacgccgc ccgccgtgaa   44820
gcggcccgac ctcgacaagc tggcccgcgc gatcctcgac gggctgaccg acgtcgtgtg   44880
gatcgacgac agccaggtcg tcgatttgca ctgccgcaag gtgctggccg agctgacgca   44940
gccgccgggc gcgcatatcc gtatcgcgtc gccgggctgg ggcgacgagg cgctcgcgaa   45000
ggctcaggcc gcggctcagg ccgcgatcgc cgctgccgcc gaggcggtgc tgtgaggcac   45060
taccgcatcg agctgctgat caagtcagac ctgaccgagg agcaggtcgc cgagcgcgtc   45120
gagggccgtc ctgggccggt gttcggcggc caggtcgtcg acgccgcggt gtacgaggtg   45180
acgcatttcg aggcgcggcg ctcggaggtg gtcgcgtgag caggcaccgg caagaggatc   45240
gggtgttgcc cggcccgttc gacccgcggc cgatcgtggc gtggtcggag tcgatgggct   45300
```

| | |
|---|---|
| ggacgcggct ggaatggatc gccacgccga ccccgtcggg cgggcatctg tggctttcgg | 45360 |
| acgtttgcca gcaagacccg gccgcggccg atccgtgcag ctcaggcgac gcgctcgagt | 45420 |
| ttttgccggc ggttagctgc gcccggccgc ccgagccgat cgtgacggtt tacgacaagg | 45480 |
| acatgcgcaa gctcgccggg cctgcgccgt ggagccaggt taggagcgtt ttcgaccatg | 45540 |
| cgtgagtgcg cgaactgcaa gggccgcagc gagctgacgg tgtgctggcc gtgcggcaag | 45600 |
| gcgatccgcc gccagctcgt cggcacggcc gaggagccgg gcctcgcgtg gctgatcgac | 45660 |
| cggctgcagg agtcggcgta cggcgaggcg aagatcggcc gcctggcgcc gaaggtgtcc | 45720 |
| ggtcagggcg agcggccggg cctgccgttg aacgcgaaag cggccgagct gctgcgcgac | 45780 |
| attctgcggc gcctgcacaa gtggtccgag ggcgcgctgt ggcgcctgcc cgccgctgcg | 45840 |
| caggccgcga tgatggccga caatgtcccg cggctgatgg cccgcgacga cgccgcggag | 45900 |
| atcctgcgcg agctgctgcg gctgcgcgcc gcggccgagc gggcgatcga cctgccgccc | 45960 |
| gatctgcagt acgtcggcac gtgcccgagc gtgttcgccg acggcccgcg caagggcgag | 46020 |
| gcgtgcgctg tgggcctgta tgtcgagcgg ggcgagtcga cggtgaactg cccgcggtgc | 46080 |
| aagacgccga gcgtcgtcga ggatctgcag cgcaccgcgc ttgagcgggt cgacgacgag | 46140 |
| cccaagacgg ccgccgacat gttccggctg ctgcggtggc tcgggcgtga ggtgccgcgg | 46200 |
| tcgtcgttct atgtgttggt gcgccgtgtc ccggctcgca tgtatctgca gcgcgacggg | 46260 |
| cgtcggaaca tgctgcagca ggagggctct cagccgctct acgcctacag cgacgtcgtg | 46320 |
| tcggccattg acacgtggga ggccgagcag gcggcgcagc gggccgctgg gaagggcaag | 46380 |
| cggggccgcc cacgcaaggc gtcgcccgcg gccgaggcca agcgcgacac ggtgggcgca | 46440 |
| gcgtgttgac agctcaacag tgcgcgggta acgtcgccgg tgttgaccaa tcaacactcg | 46500 |
| ggataggagc ccacgaaatg accgaaatca cagcaggttt gcgagttcag gtgttccgca | 46560 |
| gctcgctcgg cgactgcacc aacggcggcg tgaccagtaa ggccgacgtc gtgacgctga | 46620 |
| tcggctacgc cgaccctcac agtggcgccc tcaagccgct gccgcgcatg tcgcaggtgt | 46680 |
| tcgagcctgc cgacgacgcc ccggcggtcg tcatggtgcg ctcgaacctg cccggcgccc | 46740 |
| tgccgcacct cgtgccgctg gacgccaagc aggcgggcga gtggacgatg cacgcgcgca | 46800 |
| acctggccgg gtcgagcgac tcgcggttcg gcgagctgat cgagaaggtg ttcgacggcc | 46860 |
| cgcgctgcgt tagctcgctg ccggtgcacg atcggatcga gaagtgaagc gcaccaggac | 46920 |
| ggttgcggcg cccccacctg cggcgcagcc cgaggtcgtc gtgcacggcc gcacgcttga | 46980 |
| gccgggcacc gaggtgtcga tccgcggcga gcgcggccgg ttccgctaca tgcgggcgac | 47040 |
| gacgacgagc gcgggccgcc tggtgctcga cttcattggc ggcccggccg gcatgaggc | 47100 |
| gtggcgctcg ttttaccccg agcggattcg cacggttcac cgcatcaaca aaacccgccg | 47160 |
| caacgcggcc tgattcaagc gaggagacac aaacgatgcg caagtggata gcgggcaccg | 47220 |
| cggtggccct ggtggtcgcc ctcggggctc aggtggccgc cggtgtcggc attgtggtgg | 47280 |
| gcctcggcca ggtgccgggc gacttgaacg atctgcccga gctgaccgac gactgaccac | 47340 |
| cacgaaacgc gaaacgccgc aggctgcaac gcttgcggcg ttttcgtgtt gacaggtcaa | 47400 |
| caccacgcat gcttaactgt tgacagctca acaccgacac cgcaagcgcg ggcaaccggg | 47460 |
| ccccgccccg agcccgagga gggcctcatg cacaacaccc acgtttacgg cgagtcggct | 47520 |
| gttgagttcg ccgtcggcca gcgggtcgcg gttcacccga tcaccccgca gttcatgcag | 47580 |
| ggcgaccgtt acgcgaggt cgtgctcgtc ggccgcactc gcgtgtcggt gaagctcgac | 47640 |
| cgatcgggtc gcacgctgcg gttctcgccg cagaacctcg cccacatggc ccgcgactag | 47700 |

```
cgggcctcgg gcaggtaatc gaaacaatcg caacgggata ggagcccacg agatgaccaa  47760
ccacatgaca ccggcgcagg cccgcagaat cgcgaccgac ctgctgcgcg agcacggcct  47820
gaccggctgg tctgtcacgt tcgacaacgc gcgacgccgc gccgggcagt gcagctaccg  47880
cacccggcag atcagcctgt cgaaaccgct tatggcgcag cggtcctacg acgacaccat  47940
gatgacgatt acgcacgagc ttgcgcacgc gctggtcggc ggcaggcatg ggcacgacgc  48000
cgtgtgggcc gcgaagcacc gcgagctggg cggcaacggc aaacggtgct tcgagcactt  48060
cgacgagtcg gcgccgtgga tcggcacgtg cgggcacggc aagcagttca cccgctaccg  48120
cgccccgaag cgcctcgacg ggtggcgctg ccgctgcgcc cgcggtggct cgccgatcac  48180
gtggcagacc cgcgcgcagc gcgccaccga ggcccgcgcg gtcgcgcagg cgcaggcccg  48240
caaggtgccc gcaccggcgg cggcggccga ggtgacccgc acgatcgtgt cgcgcccggt  48300
cggccgcggc cagcagctcg ggctgttctg atgatgaccg acgcagagtt cgccgcccgc  48360
ctcgacgaaa tcgaggcggc gcgcgagcgc gagtatcagg agcacctggc cgccgagcgc  48420
gccaagggca accacattcg caagcgggcc gggcgcagcc tgggcaacca gtggtacagc  48480
caccagcacc gcgtgcagtt catcgagggt tacgtcgacc cgctgtcgca gacgttgtgc  48540
ggcgccgacg caacgatttt cgaccagtcc tgggccgaca cgcggtggcc gaagcaccgc  48600
gccgaggtca cgtgccaggc gtgcatcgac gcccgcctcg ccgacccaaa agcccgccgc  48660
taacccacct cacaaccacc acaacgggat aggagcccct gcaatgtcca accacaccac  48720
cacctcggaa tcgtcgcccc aggaggccgc cacgcggttc ttttgggcct ggctgatcgc  48780
cgccacggcc gcctcaatcc tcgggaacgt cacgcacgcg gtgctcggcg cagccagctc  48840
gccgctgatc gccgcggcgg cggccatcgt cccgccggtc gtgctgctcg gcgcgacgca  48900
cggcgtgcac gccctggtgc gcagccggat cgtcggcgcc gcctaccgcg ccgccctgac  48960
gatcgttgtc gcgcttgcgg tgtgcgcgtt cgtgctcagc ttcgaggcgc tgcgtgagct  49020
ggcgatcgtg cacgcgggca tgcggccgtc gatcgcgtgg ctgtggccgc tggcaatcga  49080
cctgagcatc accggctcga cggttgcgct gctggcgctc accgggcagg ctcgcggcgc  49140
gcaggcgtac gaagtcgagc acctcgacgc gcacccgctg tcacccgtcg cgcctgtaca  49200
cgtgtcggtg cacaccagcg cgcaggcggt cgcgcaggcg gcggccgtcg acgttgctga  49260
gcccgcaacg gatctgccgg tcgaggcggc cgagcggctg ctcgacgccg gggtgacgcg  49320
catcgaccgc gtgaaggtcg cccaggtgct cgccgagcac gccgagggca cggccccgag  49380
catgatcgcg cgcaagctga gcgtcgggta cagcaccgtg gtgcgcatcc ttgagcacca  49440
cactgcgcac gctgcgcagg cggatgcgga ggtgggcgcg tgaacgtcgc cgagcagtac  49500
ccggcacgca cagacggcaa cgggcgcact tggtttcggc cggtgcgccc gccggcgtc   49560 gacgtgtcgc aatggggctg gacgtcgcag cccgagcagg ctcacccga ttacggcctc  49620 gccgaggtgc gcccgctgcc gggcggtggc ctggcagtgc tgccgctggc ggccccgatt  49680
tacgagccgg tcggcgagct tggccccgag tgggtcgacg tcggagcggt cgagcagtgc  49740
tgagcgtgca gccggcatg aacgtgccga agcaacgccg gaagatcgag cagcgcctcg  49800
tcgaggcccc gagcgaggcc catgcgcgtt acctgcggtg gctgctggcg cagttcgacg  49860
agagcctcgc ccgcggcctg ccgcgccgg cgagcgagtt cctgccgatg tacgacgagg  49920
agttcgaccc gtagcaaaat gccggcgagc agccgatttg tgcgctgagc tgcgcgtcgc  49980
cgaaaagtca gcaaacgccc tgaggcccgc gaggactcgg ggcgtttgtg ttgacacctc  50040
```

```
aacaccccgc ggtgtagtgt tgaggtatca acagcacgac gggataggag cccaaaatgt   50100
acaagatgat cgttcaaatg tacggccgca ccgaggttac cgagcacgac acgatcgccg   50160
aggcccgcga gcgcctggtc acgatcgccg ttacgcagaa ctgccgtgtg accggcgaca   50220
acgccaccgg cgagttcatc ctgcgcgacc gggacggcaa cgacacccg cgcgtcacct    50280 ggacttacgg cgcctaccgg atcgaggagg tggccgacgt gcgcaccgag gtgatcgtga   50340
aggccgtcga gaacggctgg gccgtcaacg cgatgcgccc cgacttcatt caggccgccc   50400
gcggcaacgt gaccgcgtac gtggcgctcg acgccgacgg cggcctcgac accgccgagc   50460
tgtacgtcgg gcggcagatc gtcgcctcgg cgtacgccag cgaggacgac gtcgagccga   50520
ccccggcccg cgaggtcgtc ggcaactggc tgacgctggc cgcctgaccg gcgagcacga   50580 ggcaccctg agcccgcggt ggctcggggg gcgctttgtg ttgacacctc aacaggccgc    50640
ggtgtactgt tgaggtatca acagcacgag gggataggag cctacaatgt cgaacttcac   50700
cgccgaggac cgcgtcgcgc agaccattct cgaccagatc ggtgtcggta ccctgatgcg   50760
cctgggcgcg cacaaggtcg agcgttacct cgacgccgtc gcgtttcagg tcaagctggc   50820 gctgccggc cagacccgcg gccggatcat gcgctgcacg atcgacctca ccgcggccga    50880
cctgtacaac gtcaagatcg ggttcctgca gcgcaagacg ctcgattggg tcgcccttga   50940
gaacgtcgag ggcgtcgacg tcgagggcat ggtcacgatc atgcggaagc acgcaaagct   51000
gatctgaacg ccagcgcgaa gcgccccga gccgatagcg gccgggggcg ttttcgtttg    51060
ctgtgcacgc ggcatgcacg caagcgcaga gcgcgtcgcg caatttagac tcccgattgc   51120
agcagcacaa ctgtgcccaa aacagcgcgc aacccgcgcg aggctgccca cacgcgcccg   51180
gccgaacatg ccagggcgcg tctgactttc acgacggggg gcgccggtat gcacgtacgc   51240
ctggcgatcc tcggcaccga ggtgctgagc ctgcacgtcg gccgcggcct ggtgctcgac   51300
gtcgacgccc tggccctcga cgacctcgac gaggacgacg accccgagcc ctgccagctc   51360
gtcggcggcg gcgcctcgca caacttgag cgcgaccccg acccgctgag cgccgacggc     51420
gaggtgccgt ggagcgaggc cgatttcgga ttcggccggt gaccggcgag cgcctgcggc   51480
gccgcctcga actgcgccgg tcgaacgccg cgcagccgca ccgcaaccga caccgcgaac   51540
gccagaccgg gcaggagcag ctcgacgagc catgccccgt cgacggccac ccttgcccct   51600
gcgcccgccg ctaccgctgc cgctaagcac cgcgcatgca cgcaggcgcc gagcacaccg   51660
tgcgccctag cgtcgctcat gtgaccgccg tcgaggccct gacactggca atagtgccgc   51720
taacgattct cgttgcggcc cttgctgcgt ggctggtgac ccgcaaacgc aaggccgcag   51780
cgcatccgac cccggtcgag cgcctcggcg gcggcataca caactacccg cccgactggt   51840
ggctgggcgt cgatcgcccc gagtgggact gagaggagcg acatgctgca gaagatcctg   51900
accggcgtcg ctgccgcggt ggccccggtg atcgcgaagg ccgtcgccga gaagctcgtc   51960
gaggtgctgc ccgagctggc cgacatcatc gtgacccggc tcgctgagaa gctgcccgac   52020
gtcgctgccg cggtggccga ccgcatcctg gcgcacctgc cgacctgtc ggccctcgac    52080 gacgaggcga tcaaggccct gcgtaccctg ccggggctgg gggagcacat cgtgcaggcc   52140
ctactcgacc gcctgcccca ctggcccctc aagttctagg agtaccccg catggctact    52200 cgcaccccgc gtgacgcatt cgacgctgac actgtcgagc aggtcgagca ggacgctgtc   52260
gagcaggccg ctgagcagcc tgctgacgag tcaacagcac cagtcgagac tgacggcaac   52320
gccgcgcccg agcgcgcggt ttacaagccg tttgagtggt gagcgaaggt cgcaacacag   52380
cgcgacgcga tcggttccgt cgcatcattc gccgcgacga gccagactgt cacgtttgcg   52440
```

-continued

```
gcgagccaat cgactaccag gccgaccacc tcgacccgct gtcgttcacg atcgaccaca    52500
taacgcccct tggccttggg tggcactgaca ccctcgacaa cattgggcg gctcaccgca    52560 agtgcaaccg cgacaagagc gacaagccgc cgagctggcg gccgggcgtc actttcgtga    52620
ccgagcgcga gtggtagcaa accgcccggc gagcgagctc agcaaacacg ccctgacctg    52680
cggttatgca ggggagtcga gccagcaaac gcccgcggcg ccgatcgagc gcgtttgtgc    52740
aggtcagcga cccctggggg ggtgccccgc gaacgatcgc ggcgcccctc gcggcat      52797

<210> SEQ ID NO 4
<211> LENGTH: 61147
<212> TYPE: DNA
<213> ORGANISM: Pixie mycopbacteriophage

<400> SEQUENCE: 4
aggcgggttt ctctccccgg catttttcc caaaccgaaa ggtcagcgca ttggacgcct       60
atgagttggc tcaggccaag atcgccgtgc tcggcctcgc cgttcgcacg catgagtcgg      120
gtttcgccga cgaccaggcc accgtcaagg aaaccgccga gcggttctgg gagttcgtcg      180
agggcgacct gtgacgccga ccgtcgggcg catcgtccac tatcagagct acggcacgcc      240
gggcggcgag tacctgcccg agccgcgggc cgcgatcgtc acgcaggtgc acgccgtcga      300
gggcgccgtc ggcctcgcgg tgctgaaccc ctcgggcctg ttcttcaacg agtttgtgga      360
gcacgccgcg ggcgacgtcc cgaccgcggg ctgctggaac tggccgcccc gatgaacgcc      420
gaccagcacc tcgccgccgc ggtggccgcg atcgacaccg agacagtgcc cgacgacata      480
agcgccgtcg tgctgcacgc aatggtcgcc gtcgctatgt acctgcagca gatcgtcaac      540
gattcggccg cgaccgcgaa ggtagcgccg tcgtcgtgat ctggcgcgta ctgctgttcg      600
gcctcgtcga gatcctgcgc gtcgaggtcg tcgacctggt gccgctcgac gacgagccgc      660
ccgtcgaccc gccgcacacg tcggcgctcg gtttcgtgct accgccgcga gactaagcgc      720
agctaacgcc ggcaaaagcg catcgctgca cgtcgtcgcg catatctgcg caaaccagca      780
acacacctgt gcatcgcggt gcacagaagt gaccagacca ccaggagccc accatgcaag      840
caccgagcac agtcgaggtg ccgtgcccgg cctgcgcga gccgatcgtg ctgtcgctgg      900
gcctgacggc cgttgacgcc gagcccggcg acagcgccgc gtacgtcgat gtgtccgttg      960
tcgacgtcga gcagcgcgtg cagtcgcatg gcgaggtgtg cccggttctg gcgggcggtg     1020
gccgctgatg gccgacgaga agctcgaccg ccgcgacctg ttggtgcgca tgcacgacag     1080
ggtcgaggag gcggtatta accccgagac gccgccgcgt gatctcgctg cgttgacgcg     1140
ccgactcatg gagatttcca aggagattga agtgatcgac ctgcagcgcg cgcagcgagg     1200
cgagggcaag caagaggccc cggccgatga ggctttcgat ggcgaggacg tctagccccc     1260
gcctttccga ggtcgcgcgt tacgtcatca agcccgaggg catcgtttcg acgtcctggc     1320
cgtctgtgcg gcatgaggtc acggtcaaca tgggccttgg cttcgatcag tggcaggacg     1380
atctcggaaa gctgatttgc gccaagcgtc ccgacggcct gtacgcggcc gacatgttcg     1440
gcatgtcgat accgcgacag acgggcaaga cgtatttcct tggcgccctc gtctttgcgc     1500
tgtgcaagat gaaccccggc acaacggtga tctggactgc gcaccgtacc cgcaccgcgg     1560
gcgagacgtt ccgcagcatg cagggcctcg ccaagcgtga ggagatcgcc ccgcacatct     1620
tgaacgtgca cacgggcaac ggcaaagagg ccgtgtactt cacgaacggg tcacgcatcc     1680
tgttcggcgc ccgtgagaag ggtttcggcc gtggtttcgc caaggtcgac gtgctgatct     1740
```

```
tcgacgaggc gcagatcctc accgagaacg cgatggacga catggtcccg gcgaccaacg   1800
cctcgcctaa cgcgctgatc ctgctcgccg gtacgccgcc gaagccgaac gatcccggcg   1860
aggtgttcac gaacctgcgc atggacgcga tcaacggcga gtcaaccgac gtcgggtata   1920
tcgagatctc ggccgacgag aacgcgcagc ccgacgacgt cacgcagtac ccgaagatga   1980
acccgagcta cccgcaccgc acctcgctgc gctcgatcct gcgtatgcgt aaggcgttgt   2040
catgggacag ctttcgccgc gaggcaatgg gcatctggga caaggtcact gtgcacgcgc   2100
aggtgatcaa ggctgcgctg tggcgtgagc ttgccgaccc gctcggcccc gagcccggcg   2160
ctaagccgaa cgcgctcggc gtcgacatgt cgcacggccg ggctatctcg atcggcgcct   2220
gctggctcat ggacgacgac gtgcggcacg ttgagcaggt ctgggcgggc accgacaccg   2280
cggcggccgt cgattggatc gtcgagcgtg ccggtcgccg catccctgtg gtgatcgact   2340
cggcgtctcc tgcggcggcc ctcattccag agttgaagcg gcgcagggtg aaagtgatca   2400
ccggcaccgc ggcgatgatg gcgaagggct gcgggctcgt cgagtccagc gcagacaacg   2460
gcacgctgtc gcacggcgac caggtcgacg tcaccgaagc actcaagggc gcccgtaagc   2520
ggcctatccg cgacgcaggc gggtggggct gggaccggcg cgacccaacg tcagtaattc   2580
atccgctagt cgctgtgacg ctggcactgg tcggcgccct cgacgcgccg caacggcgaa   2640
gtggcggcgc cacattcgtg taaagggggc cgcgtgctac cgcagttcat tgagccgacc   2700
gcgcagggcg acggcgatca cgacgacgac gacgtcgagt acgagggccg cctgaccgac   2760
gcgcagatcg tcaagctggt gcaggaaatg tggctgctgc agttgacgga gcgcagccaa   2820
ctggaccgga tctacgagta cacgaagggt cggcgcggcc gtccgaagct gcccgagggc   2880
gcctcggatg aggtgaaaga cattgcggcg ctttcggtca agaacgtgct gcggctggtg   2940
cgcgattcgt tcgcgcagaa cctcagcgtg accgggtacc gcgatctgtc ggcgcaggag   3000
aacagcgcag ggtggcagga ctggcagcgc aaccgtatgg acgcgcggca ggccgaggtg   3060
caccgtcccg cagtgcaata cggctgcgcg tacgtcactg tgacgcctgg gcctgacggc   3120
cccgagtggc gcacaaggtc gccgcggcag ttgctcgcgg tgtacgacga cccggtgctc   3180
gacgcctggc cgcagttcgc gcttgagacg tgggtggcga ccaagaacgc gaagccgcac   3240
cgtcgcgctg tgctgtacga cgacttgtac atgtacgagt tggatctcgg cgaggtgccg   3300
gtcatcgaca agggcgacgg cgagtcgcg agcaagccga tcagcgtgcg cgaggtcgag   3360
gacgtcatac cgcatcacgc gacgttcaac ggcaagccgg tttgcccggt cgtgcggttc   3420
atcaatgacc gcgacgccga cgacatgatc gtgggcgaga tcgagccgct gatcggcatg   3480
cagcaggcca tcaactacgt gaactttgac cgcctggtcg tgtcgaggtt cggcgccaac   3540
ccgcagcggg tcatcaccgg atggtcgggc agcaagaccg aggtgctcaa ggcatctgcg   3600
ttgcgcgtct ggacatttga cgatcccgag gtcaaggcgc aggcgttccc ggcggcctcg   3660
ctgcagccgt acaacgacgt gctcaacgag atgatgcagc acgttgcgat ggaagcgcag   3720
attaacccgt cgacgatcac cagcatttct aacgtctcgg ccgacgccct cgcggcatgc   3780
gagcacaaca tgcagttgaa gctcgccaac aagcgcgaga gtttcggcga gtcctgggag   3840
caggtgctac ggctgtcggc cgcgatgggc gacgacgcca agacggccga cgacgccgcg   3900
gcagaggtca tctggcgcga caccgaggcc cgttcgttcg caacggttgt cgacggaatc   3960
gtcaagctcg ccaccgcggg cgtgccgatc gagttcctgc tgcccctggt gcccggcatg   4020
acgcagcagc agatctcagc cattaagcag gccatgcgcg gcggcggcac gcagtcgctc   4080
gtcgagaagc tgctcagcct gcctcagccc accgagcccg acgccccgcc actcgacgag   4140
```

```
gcgcaggcga gcgccgacaa gagcggaggc acgcagggtg acggaggggc cgcaggcagt    4200
accgcagttt caggggggcgc taacccgcct cagcagtgag gtcggggggcg ccgtcgacag    4260 gctggtgccc cgcctcggcg gcctgacgcg cgccgagggg ctgcggttca tcaccgacgc    4320
atacccgacg ctgatcgacc cgtttctcag tgccgcaggc gatctcaccg cgcagtggta    4380
cggcgagcaa acgccggcaa aagtggtatc tgtgcgggtc agggaccaaa aagccctcgc    4440
tgcagctaat ttcgtcgtcg agcccgcggc gctgcccgac cgcaagcagc ttgctgcctc    4500
gggccgctgg gcgctcatgg agcgcgaccc ggcgctcgcg ctgcggggct cggcgactcg    4560
ttctctgttc tcgcagtctc ggcgcaccgt gcaggacaac gccgaccgcg agggcgtgag    4620
gtacacccgc tacgcctcgg cgaacgcctg cggtttctgc cggatgctcg caacccgcgc    4680
gctgacggtc ggcgagcgcg gcgcaccggg gctgtatcac agcaaggcgt cggccgagcg    4740
caacgcgcac acgtcgaca tgcgcgggca cgatcactgc aagtgcatcg ccgtgccggt    4800
gcgcagcggc acatacgagc cgcccgcgta cgtgcacgac tggctcgacg actacaacgc    4860
cgtttcgcgc gacgccgacg gcgtgctgct gcccgagtgg acgatcgccc ggcgcatgga    4920
gcagcgcgcc gacgagcgcc tcggcaggct caagcgagcc cccggtcgac cccgcaccgc    4980
ggcggccgaa cgtgagcccg tggcggccga tgcgcaggcc ccggccgacg ctgtgcgcgc    5040
acgtgtgcaa gacgtgcagc acctcaccga caagactgcg cagcgcgcag aggcagccgc    5100
acagccgttg cgcgatcgtg tgcagcaggc gcaccagttc gcaacgcgcg ccgacgagat    5160
cgccagcagg gccgccgaga tctcgggtca ggtcaagcag tacaccgacg tggccgaccg    5220
tctgatcggc ggcgccgtgc ccgtggtgcg cgacctcaag ctcgttgtcg acgcgaccga    5280
caaggcgctg cagacggcct cacaggtcac cagcggcgcc gtgcaggtga cgaacctcgc    5340
cacgcagacg atcgaccatg cggtcgacgt tgcgcacggc gtcaagcaga ttgccgacga    5400
ggtcggcggc gtgctcgacg acgcggcggc cgtcgccctc ggcgtgcgca cactgctgac    5460
cgacaccggc aaggcggtgc gcgacaccgc gcagaacgtc aagggcgtgc gcagcgtcga    5520
cgacctcgtc gagcagatcg ccgcgaccgt cgacacggca acgcagatcc aagctgacgg    5580
cctggcgctc gtcgagcagg gccgcgcggt cgtcgagtcg cgcagggca tcgtgcaggg    5640 cgtcaccgag ctacccgcgg tgctgcagaa gccgatcgcc gacgcgcaga agatggcgca    5700
ggccgtccga gacgccgtcg cgacgtcga gcaggcaggc gacgacgcgg cggccgtagc    5760
gcgtgccgtg cagcgcctcg tcgagtcggt cgccgactgg cgacgcgccg agaaggtcgt    5820
cgaggacact cgcccgccgg tattcgtgcc gtccgagcgg atcgacgcac cgaaggcgat    5880
cgaggccggg ccgaaggcga tcgaggcagc cccgcagcgg gctgtcggcg gcgctgacga    5940
ggtaccggcg atcgaggcgg cggccccgct caaggagcta cccgcaccga tcgagccccc    6000
ggcgctgccg cgggtgcctg accgtctggc gatcgaggcc gggccgacgc ccgcacagtt    6060
ggaggatctc gacggcgccc tcgcggagcc gttcggcgag ccccccggcgc cgaagccgaa    6120 gcccgcacgc aagccgcgac ggaccctcga cgaggtcgag gccgagctaa acgccgcaat    6180
cgagatcgac gacggcgagg cgatcgaccg gctcgccgac gaaatggagc ggatcgagaa    6240
gcgcgagagg gccgcagccg cacgcaatga ggcagccaag gccaagcgcg cagcggcccg    6300
cgccgagcgt gaggcggcga aagaggccga gacgcaggcc aagtgggagc gcatgggtca    6360
actcgtcgac gagggatgga gcgaggacga ggccgaggcc gaggcgttcg gcgagtctgt    6420
cgagactgtg cgcaaacgca acttcatgcg gcaggcacag gccgacgggc acagcggcaa    6480
```

```
cacgttcacg aaggtgctca agcagagcta ttactcgctg gtcgacgagg cgtactggaa    6540
ggccgagcag gccacaaacg gcgtgatggt caaacgtcag tttgagggca aggtcagccc    6600
aacgatgttg tggcacatgt ccgaacggga cgcacgcaaa tacatgtccg aggagatggc    6660
cgagtggttc gaccagaacg gccgtctcac gttcatggcg taccggcagt cggtactcga    6720
cgggacaggc aggtggcgca acgcgatgac accggactac ctgcagtgag cgccgacgcc    6780
cccgacaaca aagaggcttg gatcgctgcg cggaatgaag gccgcgcagc gacaccaggc    6840
gacccaaacc cgtactacgg caccgggata cgcgcccgaa tgtggcgcct cggttacaaa    6900
acgatgctgc tcgacaagct caaccgctca cccgcccggc aggcgtacct gtacggcggc    6960
gagtagcaca caccccttt accgcgccga accgctgact gcggatgcct gcgaacgacg    7020
acgcaggcag tttcggccgg gttgatcgtc ggtcaaaact ctacggaggc agcaacaatg    7080
agtgacgcag tcaccggcgg cgacgccgt cccgagggcg gcgaagcgcc gaagcaagac    7140
gaggcgccga agacgttcac gcaggaacag gtcaacagtt tcctcgccaa ccagaagcgc    7200
gaactgacgt cgaagtacgc cgactacgac gacgtcaaga cgaaggcgac gaagttcgac    7260
gagatccaag aggccagcaa ggacgaactg cagcgcgagc gcgaggcccg cgaggcagcc    7320
gaaaagcgcg ctgagaaagc agagttcgct gctttgcgcg accggatcgc caaccgtccc    7380
ggcaaggtcg tgcccgtcgc atcgctgacc ggcaagaccg aggaagaact gactgcgtca    7440
gccgacgcgc tgctcgcgtg gcgcgacgaa acgcccccca gcccgccga aaagcctgcg    7500
cccaagcgca acccggctgg cagcggcggc ggcctcaagt ctggtgccag cggcgccgac    7560
gtcgatccca ccgacaagaa ggagcttgcc gcgaagcgtc tccgacagat gcgcggcggc    7620
gagtaaccgc aacaacttcc gacggggcg acctcggcgg ttgatcacaa cacaactgaa    7680
taaggagtaa cggcacatgg ccgacatttc acgttccgag gtcgcaaccc tcatcgagga    7740
ggcgtacgcc gatacgctgc tcgccgcggc caaggagggc agcaccgtgc tgtccgcatt    7800
ccccaccgtc aacatgggca ccaagaccac gcacctgccg gtgctggcga ccctgcccga    7860
ggccggatgg gtcaccgagt cggcgaccga ccccgcgggc gtcaagccgc agagcaaggt    7920
cacctgggcc gaccggaccc tcgtcgccga ggaaatcgcc gtcatcatcc cggtgcacga    7980
aaacatcatc gacgacgcaa ccgtcgcggt gctgaccgag gtcgccgagt gggcggtca    8040
ggcgatcggc aagaagctcg accaggccgt gctgttcggc acgcagaagc ccgcaagctg    8100
gatcagcccc gcgctgctgc ccgctgcggt ggccgccggt cagtcgatcg ccgtcgtcga    8160
cgggatcgcc aacgagaagg acatcgttgg tgccaccaac aaggtcgccg agcagatcgc    8220
cgtcgccggg tgggcgcccg acacgctgat ctcctcgctg gcgctcaagt tccgtgtcgc    8280
caacctgcgc gacgcgaacg gcaaccccgt gttccgtgac gagagcttcg ccggtttccg    8340
caccttcttc aacaagaacg gtgcatggga cccggccgcg gctgtcgaga tcatcgccga    8400
ctcgtctcgc gtgcgcatcg gcgtgcggca ggacattcag gtgaagttcc tcgatcaggc    8460
gacgctcggc acgggcgaca accagatcaa cctcgccgag cgcgacatgg tcgctctgcg    8520
cctcaaggcc cgctacgcct acgtcctggg caacagcgcg accccgcagg gcgccgacaa    8580
gacgccggtc ggcgtcgtga ccccgacgt cacgccgtag ttcgtgcgtc tgtttcaaca    8640
cgcccacacg ggggcggtca tcggtgcgcc ggaaggcacg ctgttggccg ccctcgtcga    8700
gggtgacgac aactggaccg agtgcgaagg ggtgaccgat gctggccgat ctggacgcgg    8760
taaaggccgc gctaaaagca ctcgggcgaa cggatctcgc ggaaacggta acggccgagg    8820
gcgtcgagcc gctgctgcag gaagcgagcg acctggtgac ggggtatctg tggccgagcc    8880
```

-continued

```
tggcaccgga cccgacaccg gacccgatca aacgggtgac agcgtcgatg gtggcggtgt    8940
gcctgaccag gccgacggag attctgcctg agacgcagca gctttcggct gacgggttcg    9000
gcgtgacgtt cacgccgggc tcgggctcac cggggccgta cctgaccgcg gcgcacaagg    9060
cgcggttgcg gccgttccgc agcggcatga cgtcggtacc gatgagtggt gagagctact    9120
gatgttcccg acaccgttca aggtgctgca cacggcgacg gtcaagaccg gcaccaacag    9180
cgcagggcag gcgatcacgc agccgtggac ggtcgagcgg cgcgtgacca gcttgcgccc    9240
caagcagacc gacacggcga ccgcggcggc cctgcgcgac cggctgatca ccgagtacag    9300
catggtgacg ccggatagcg attggccgca cgggtcgacc gtaaaggact ggcgcggctg    9360
gacgttcacc gttcacggcg acgtcgagga ctacaacggc ggcccgttcg gattccggcc    9420
gggctacatc gtgacactgc ggagggtggt tcaaaatgcc gtaccaaccg cttgacatgc    9480
cgtacggcga acacgacaag atccgcaaca gccccgaggt gacggcggcc gtcgaggcgc    9540
tcgcccgcga gcttgcgggc aaggctgacg ccctggcggg cgaccccggc gggtacaagg    9600
tcaacgtcga gcacggcagc gaccgcgtgc gcgcgacgat tcacgccgag tcgccgaaag    9660
cgatccgagc ggagatcaaa agcagcccgc tgatgacgat tcgggccgag caaggcccgg    9720
cgctggggcc gcggccgtga cgatactgct gccgcccgta gggccgatct cagcggcccg    9780
cacgtacctg ctcgacgaac tggcggcccg caacaacccg ctgccggtcg gcgtcgagcc    9840
gcccgagggg gagccgcagc cgtacgcgct gctgtcgcgg ccgggcacca actccgacgt    9900
gttcctcggg cactttctgc tgcggctgag ggtgttcgat accgacgtcg tgcggttgga    9960
gcgcaacgcc gatctgctgc accggctgat gctgcacgcg acacacaagc gcatcgtcgt   10020
gccgcccacc gagggcggcg acccggcgg cgctgtgtgg atcaccgcgg cggctcatga   10080
gttcggcccg gccgacctcg acgaccccga cgttcccatg ttcggcctgc attcggccgt   10140
gttctggacg atcggactca agccgagcta acgccggcga gcggctcgag caccaccgct   10200
gacctgcggc gacgcgctgt gcgctcgatt ttcagcaaac accaggcaag acgcccgcga   10260
gccaatcccg gccgcgggtt attccgcatg ccctgcgggg ctgtagttag gagcaagtgt   10320
gactcaaccg acgccgcccg cttcgtgggg cgacttcacc aaggtgttcg cggcctcgcc   10380
gtcggacctg gaaaccgttg gcggcctgtg gtacgcgccg ttcggcaccc aactgccgac   10440
cgacgtcgac gagccgctcg acccgctgtt caagaacctg ggtttcatct cggttgcggg   10500
tgtcaccgtc aagttcgacg accagaccaa gcccatcgag gtgtggggcg gcgacgagat   10560
cggcgaactc cgcgacaagt tctcgatcca gtacagcatg tcgctgtttc aggtgctctc   10620
acccgaggtc aacgccgcga tcttcggtag cggcaacgtg tccaccgcgg cggcaaccgc   10680
cgagcacggc gcccgcatga aggtgatgat caacagcaag ctgccgaagc gttgcagcct   10740
ggtgctcgat tccgtgtacg aggacaagat gatccgtcag gttgcgcaga tcgcgcagaa   10800
ggcgggcctc gctgacctca gctggtgca caacgagccg atggcctttg agccgacgtt   10860
caaggtgctc aagggcaccg acggcaacca cgtcatccag tacagcgacg acggcgtcat   10920
cgccgtctag cagacgctag atccgctgcg gcgcaacttg agtcggcccg atgggtcaca   10980
cgcaccgcgc caccctgac cggcacccg cgcgcttaat cctggtgggc gcgcggggtg   11040
cttcccattt ctacacacac caggaacaca ccaggaaaca caccaggagg ttgtatcacc   11100
atgagcgaga acgagaacgt gaccgaggct gacgtcgacc aggtcgagcc cgtcgaggcc   11160
cccgaggacg agcagaccag catcgccgcc gagtgggcgc aggactaccc cgagggcgcg   11220
```

```
cagttgttcg tcggcaagtt cgacgccgag gagttcgacg acgagtacgg cgtcgccgag  11280
ttccccgagg gcgcgacgat cgccgtcaag cgttgcctgc gcaagccccc gcccggctgg  11340
attcgccagc acgcgcacct gtccgacatg cagcgcactt tcgcgctgat cgaaatgcac  11400
gccagcgagc gcgctttgga gatcctcgac agcctgcagc agaagccgtg ggatgacttt  11460
gtcgaggcgt ggggccgcga cggcgggctg atcgagggaa aatcgcgcag gtctgcgcgg  11520
cgttccggtc ggtagagaag ctagaggacg ccttcggcg tgacctactc gtcacgggcc  11580
gcgagttcga cgacggcacg ctttcgtggg atgacctgta cgcctatatt ttcgcagcgc  11640
caccgggcac ggctgtgtac cacgcctttg aaaagggctg gacgacaacc gactatctgc  11700
tcgcgcatct gatcgacggt cagaactggc tcaactggac gaaaaccgag gcggcagaga  11760
agaacccgaa agcgccgccc gagcgattcc cgcggcccgg tgacgaggcc cgagaaaaga  11820
aggacgacgg cacggtatcg gtcggtacca ccgcggcgac caagacgacc gtcggcaatt  11880
tcctcaagat gcgcgccgaa cgcgagaagc gttggcgcga gaaacacggg cagaagggcg  11940
attgatcaat gggcgcaacg tattacctca cagtcctgcc cgagacgaag caactcgtct  12000
ctgggatcaa ggatgcggtg cagggtgcgc agcgcgacat ggtcgtgtcg cccaagttcg  12060
acacgaaggg cgccgcggag gctggccgca aggctggcgc cgacgtgcag gccgggctcg  12120
actcgtcggc ccgtggggc ggtattggcc gtttcctgcg ggccgacggc gcccgttctg  12180
ccggtcaggc cgccggtagc gaggtcaacg ccgggctgca gtctgccaac atcggcggca  12240
gcgtgtcgac ctcgctcggc cgcaacctgc tgaacggcgc agaatcgttg ggccgcaacg  12300
tcggcagcat gatcgcgacg ggcctcaagg taaccgcggc tgtcggcggc acggtcctgg  12360
cgggcggtat cgctggcgcg ctgcacgctg gcctgtctcg cctcacggcg attgacgatg  12420
ccaagttcaa gctgcagggc ctcggcaaca gcaccgagca ggtgcagaac atcatggaca  12480
acgcccttgc ggcggtgaac caaacagctt tcggcctcga cgaggcagcg acgaccgctg  12540
cgtctgcggt ggccgccggt atcaagcccg gcgagcagtt gacgggttac ctcaaggagg  12600
tggccgacac cgcggctatc gcgggcacct cgatggccga catgggctcg atcttcaaca  12660
aggtgcagac gtcgggcaag gcgtttaccg gcgacctcaa catgctgagc gaccgcgggc  12720
tgccgatctt cacgtggctg cagaacgagt acaaggtcag cggcgaggaa ctgtcgaaga  12780
tggtttctga gggcaaggtc gacgccgcga ccttccagcg cgtgattgcc gaaaacatcg  12840
gcggcgcagc gcaaaagatg ggcggcagta ccgcggtca gttgtcgaac ctcaaggcgg  12900
cgtattcgcg tttcggcgcc gagcttgcgg ggccgatctt ctcggccgtc tcgccgctga  12960
cgatcgcgtt taccggcgca ttcgacaaga tcacgaaggc gatcaagccg tacaccgcgc  13020
aactgaccgg gatcatcggc ccgtgggcgc aggacatggc gaacaagatc acggcgtggc  13080
tcgacaacgg cggcgtgcag aaggtcatcg actttatggg ccgcctcgtc gaccgggtgc  13140
aggcgttgcg caccgggcag ggccgcagcg acgcgctcgc gtcgatcacc gagtcggtta  13200
agacgatcgg cccggcgctg cagcagtcag gcccggcgct gcagcagttc ggctcgtcgt  13260
tcgcggcgtt cggtcaggca atcgctgccg tcggcccctc gacgatctca ggcgtgctga  13320
cgcctgcgct gcaggtgctc gccggggcgc tcaagttcgt ggccgacaat gcgtcgtggg  13380
cggtgcccgc gatcggcggc ctggtgctcg cgttcggcgg gttgaagctg ctcgcgtcga  13440
ccgttgcgcc gatcgtggct gcactgaatg gcgcgttcaa gatcatcaac acgcccgtga  13500
tgttggcgca gactgccgcg atccgcgggc aggcaaaggc gatggaggag ttgaccgtcg  13560
cgctgtcgtc ggcgactgtc gcacagggtg ctaacgcggc ctcgactgag gtcaacacgg  13620
```

```
tggcacaggc ggccaaccgc tcgacgtcgc tcggctcggc tatcgcgctg cgtgcgcagg    13680
ccgcggcgac caaggttgtt actgcggcgc agtggctttg gaatgcggca atgagcgcga    13740
acccgatcgg cattgtcatc gtggcgattg ccggtatcgc ggcggccctg tgggcgttct    13800
tcacaaaaac cgagacgggt cgcaagatct ggaacacgct gtggaccggc ataaaggacg    13860
tcgccggtaa ggcgtggcag tggatcaaag acacgttcgg caaggcgtgg gagtcgatac    13920
agcccggtct gcagaagatc ggaaccattg cccgcgaggt gttttcgacg ctcggcaatg    13980
cgatcaagaa cgtgtggacg ttcattcagc ccgcggtcga gtggctcggc aagctgtggc    14040
tcgccgtcgc caagatcgag tttaaggtcg caatcgaggc gttgaagggc ctcggcagcg    14100
tgatcggctg gctgtggcag aacatcgtcg tgcctgcatt caatggcatt gcgaccgtga    14160
tcggcgcctg gtggtctggc acgcaaatcg tctggggcgc agcctcaacc gcgattcagt    14220
gggtcggcga caagatcggg tggctgtggc gcaacgtcgc agtaccggcg ttcgacggca    14280
tcaagctggc cgtgactacc tggtgggacg gcgtcaagtt catttgggat ctgttcaccg    14340
ggcgctcga caagatcggg cagggcgtcg gcgtgttcaa ggacggcatc gttacagcgt    14400
tcaacgctgt gaaggacgtc atcacgacgg tttggaatgc ggtcggcggg atctgggaca    14460
agatcgtgaa cggcatcggc accgtgaccg acgcactcaa gggtgtgggc ggcaaggtgg    14520
cgaacgcgct cggcctgggt ggcggttata ccggcggcta cgttacgggc ggcagcgtgc    14580
tgcctgggta cgcagacggc ggtcagatcc gcgggcctgg caccggcacg tccgactcga    14640
tcctcggttt cccggcgatg gtccgagttg ccaacggcga gtggatcacc aacgcgatgg    14700
cgacggcgca aaacctgccg ctgctgcgga tgatcaacag cggcgtgccc gtgtggcaga    14760
tgctcaaggg gctgctgcct cgtttcgctg cggcggcct ggtgtcggcg caggagcttg    14820
agaagttcgc aagcggcgtc gagggtcagc cgtacaagtg gggcggcgtc gattggggcg    14880
actgctctgg tgcggtgtct gcgatcgcca actacgcgac cggcaagat ccgttcggat    14940
ctcggttcgc cacggcgacc gagggcgacg agttggcgaa gcgcgggttt aagtctggtc    15000
tagggccgtc gggatcgctc aacatcgggt ggtacaacgg cgggcctggc ggcggtcaca    15060
cggccgcgac gctgcccgat gggacgcact ttgagatggg cggcgcccgc ggtaacggtc    15120
agttcggcgg cggcgccgcg ggtgctgagg attcgcagtt tacgaaccac atgcacctgc    15180
cgcccgagtg gtttaccggg ctggacgcg agagtggctc gacgtcggc tctctgagcg    15240
tcggcgccag cacctcggcc gggtcgagcg gtggctcgta tcgggcggcg acgtccgacg    15300
aactgtctgc gtcgtcgagc cgtgtcgact ctgcgcgcac aacggcgaag aacgccgacc    15360
agcgcgtcga cgacgcgacg tacgcacgcg acagggcgca ggaccggctc aacgaggcga    15420
aggcgaaggg caagggcgtc gaggacgctc agcactcgct cgacgtcaag aaccgcgaac    15480
tgcaggacgc gatcgacgcg caggcgaagg cgcaccagaa ggcgaccgac gccgagaaca    15540
aagacaccga actgcgcacc aagggcaagg ccacgaaggg caattcgtca agtgacggaa    15600
agggcctgaa cggtcaggac tttggtaaga cgttcgtgtc tggtgtcttg gagtcgatcg    15660
gcctcgacgg gtcgctgttc tccaatccgc ttgagtggcc gacggtcaag tcggcgatgg    15720
ctggtgtgaa cttcctcggc ggtctgctgt ccggtaaggg gcaggacgac gagcagggg    15780
cgcagcagcc cggcgggttt gcagacggcg tcgccgacag cgtcggcctc ggcgggctgt    15840
tctcggctct gccaaggcg ggcgacgacg agcagcccgg cagcccgaag ctcgcaccgg    15900
gtgatctcaa ccctgcgatg acgccgggcg gtggcttgct gccgtcggcc ggtgacgcgc    15960
```

```
tgtcggcgtt cgtgccgaac gtggcacagc agccgcaagg gcagcaaggt gcgcaggtcg    16020
ataactcgat caacatcaac ggcgacgtgg gcatgaaccc cggcgccgtg atcgacaccg    16080
tgcacgccga gcagaaccag cgcacccgca cgaccgcggt caagtagtac agctaacgcc    16140
ggcaaagcgt cgtatttggt ccctgacctg cggcgctttg tcggcgtagc taactcccac    16200
aactgaatat ggagggctgg cgtgtctgac atttcgacgg gcatccatga cgacttctgg    16260
ctcgacccgc cgaagtacac gcaggacgca tacggaaacg acctttacct gcccgagaac    16320
ccggcgcatc cgtcgtggcg acgcatgtcg aactggcacg acctcgggcc gaacggcgag    16380
cggctgcggt cggtcgcaac caagtgggtg tacgtgcacc cgagcaacaa caagctgtgg    16440
cagttgcgtg gcggcgctga gggccgcgag ggcatcgtgc tggcgcgcga gcttgagggc    16500
gtcgacgacc tcgattacga gatccggtac agcgagggcg cgtacacgat cggcagcaag    16560
ccgcagcgcg tcgactacaa aatgcgcaag atcaacgcgg gcgtgcaggt gcagccccccg   16620
gcgaacccgt ggcggcccga ggagcctaac ccgttctcgt accgcatgat tcactcgtcg    16680
tggaatgcct cgctgagcga gaaggtgccg ggtttcctcg gctgcttcac ccgcgtgcac    16740
ggctggcggt ggctgccggt actcaaggcc gcgggcaaga cgacgtacag cacggacccg    16800
gtcgcgttcg acaacaactc ggtgacgctg ccgctcaacc ttgaggcgcc gtggccgatg    16860
ttcgccaagc gcgccaagac gaagttgtgg cgggcgacgc tcgacgacgt cgaccagcac    16920
ggcattgcgc acggcacgat cgccgtcggc aacgcgggca cgtgggactc atggccgaag    16980
tacctcatca ccgggcacgg cgacgtgcag atcgaggact acggcacggg ccgaatgatc    17040
gacatgccaa cgttttacgc gagcgatggc tcgtacatgt tggtggacac cgacccgaca    17100
aagcgcacga tcacgactga gtctgacccg gtcgacacgc agctctacaa gtacctgcgc    17160
aactcgcagt tgctcgacat tctgctgcac gaccagcttg ccgcgcgcct gcctgcgcag    17220
cgccgcattc ccggcggtat cggtttcgac ggcaaggtgc cgccgcagac gatcgcggcc    17280
gtcaaggtca cgcacagcaa cccgcagggc acggtcacca tgtacatgcc gcaatacttc    17340
cgcggggcgt ggtcttaatg cgtcgctgc tgtggacgcc cccgacgatc ggcgctgacg    17400
gcgtcccaga tcccaccagg gcgcctattt cggcgttccg gtacctcgat gccaagcgaa    17460
tgctgctcga cgaggaggcg cgcgaaaagc cgctcattcg gctgtgggac aagcgattgc    17520
agtacatcgg caccgtcgct aacgaggagt cggtcaacgc cgaggagatg ctgcacgaca    17580
ccggcacggg cgagatcgtg ctgcagcatg acgactggct ggtgcagttc ctccgcgacc    17640
cgaacgaggt tcgcaaagac gaggatctgc atatcacgat cgaccctac cctcaccgcc    17700
gcaactggcg gtggcggtgg aatgcgaaga tcacgaacgt tcgggttaag cgcggcgagg    17760
acgggctgac gaaagtcacg tttgagtgct cgcacaaccg cgagcattgg aagcacattt    17820
accttgccgc aacgcctttc agcgcccccg aggtgcagcc gttgcgcgct tgggtgctgc    17880
cgggcaacac gcgaacgatc atcgcaacga cgggtttcat caacctggca cgcaactact    17940
ggcctgcgct ggcgctgcct gccaacgtga tgaaccccgg cgcgtgggtc ggcgaggcga    18000
gcaacctgct gaacctcaac ccgctgaact ggccggttca aatgcagttc gtgaacccga    18060
ttttcgacca gtcgcgtacg agcgtgctca tgtcgcggtg gtcgagcggg cacgacgtca    18120
cggtcggcat gctcaaggat tcgggctgca atctgcgggc gtacatgtgg ctgcccgagg    18180
acgaggacag cccgcacccc gagcttgcgg cgatcatcgg cgagaaggcg gcgcggccga    18240
cgcgggcgtg cattgtgctt gcagtcgagg acaattcaga ccgcaccggc tggaccggca    18300
cggcctggga cgggtttatg cagcttgctg cggtcaccgg agacaatctg gtcacggaga    18360
```

```
cgatttaccc ggtcgacgag gacggcgacg gcgtcaccga tccggtgatt gcgaagctgc    18420
tcggcgctgc acctgccaag cccaccatcg cgtttcggga taccgagcag tcggcgatca    18480
tctcgtcgga gcatgcgatg tttcgtgcga aggcgggcaa gatctacacg ggcggcaaga    18540
gtcctgggtg ggtcaaccaa acgcagacct ttatgattaa gtatgcgctg agccaacttt    18600
cggcgctgat cgctcaaggt ccgtttgcgg cgcaggcacc gggcaccccc ggtttggagg    18660
agctctatca gtcgcaggcc gacaatattc tgctggccta catgggcgcc accgacccgg    18720
ttcgcgtgga tcgtcaaggg ccgtacgggt atttggagca tttcgagcag ggctcgggct    18780
cggcgtacac gctcagcacg ccgctgacgt tgcgcgaggg ctggtggaaa acccgcccgt    18840
atcaagcgtt caaggtgcag attcgtaacg gcggcaacgg cctttacctt tacaccgact    18900
ttgaccttgc tacgcggtgc ctgtttgaga tcgacggcat tctgtacacc gaccaggtgt    18960
cggccgtccg actcaagtac gacgtgtcga cgcctaagac gttcgacctg tcgatcggtg    19020
acgacgccga gtctgaaaat ccaatggccg cagtgcatcg cacggccgca gcaatgtggt    19080
ctgccctcgg catgctcatg ggaagtgggg atatgttctg atgcaggact acagccagcc    19140
gccgcagttg ccgccgatgc ccgaatgggt cgagtcggat ctcgcaacag cgatggccga    19200
cattgccgac gccctgcact atcccgtcga cagcaagggc cgcgtgtacg acgtgcggta    19260
catgctgccg gtgctcgcgt ttcacctcgc gcgggctggc tgtgtcgtcg accccgaccg    19320
ggctgtcatc aagaagcggc gcctgccgcc gacgcccggc gtggtcgagg acgcggtcga    19380
atgggtcagc cctgacgccc cgaacagcat cgacgacgag cttgccgggg cgacgatcga    19440
cgacattccg cggctgtccg cggcggcccg cgctgagttc atccggcgcc tgggcggcga    19500
cggcacccga gtggagcccg agcccgacga ggtcgacctc gacgagcgtc tcggttggca    19560
tgtgcagacg tcgattcagt tcgacgacga gcccgacagc aaaacgccgg ctcaggtcgg    19620
tttcatggcc tgacctgcgg tagcccgctg ggtcagcaac acacaactga atagaggaga    19680
catggcgcaa gccttgatga cgggcgacgc tacggcgctg ttccaaacgc tgctctcggc    19740
aacgtggatg ggcattgtcg tcgacagtga cacgcccggc ggcatggccg cgacgctgga    19800
aatggtcgac ggcgaggccg tgatcacaac cccggtgctc gtcggtcaga agggcgacaa    19860
gggcgacccg gccccgatcg tcgatctgca gtggccgccg ctcgactcgc ctgccgaact    19920
gaccaagtac atggcgggcg gcagcgaggc gctcggcacg gccgacaagg gcaagggctg    19980
gtggatcggc accgttgtgt acgtctggga cggcgcgcag ttccagcagg tgcgacccgg    20040
cccggcgggg ccgaccggcg cgacgccgca actgacggtt acgtgtgagg tcatcccgat    20100
ggccgagcgc acggcgacga ccaaagatga agtgatccgt acgggtacgg atctgcagcc    20160
gcacctgcac ctgcgcctgc tggcgccgca aggccctgtg gggccgtcga cgaacattct    20220
caacgccccc gactacgaca caccgacgc ccccgaggac gggcagacga tggtgtggtc    20280
ggaggccaag cagaagtggg cgccgtcgga tttcaccgcg aagcacccgc ggctgtactc    20340
gatccccgag gaagcattta cggcgttcac gggtctggca cagcggcaga cgattctgca    20400
gtacacggtc gaggcgcaag acttcgcatg gacgccgcat atcaccgggc acctgaaagc    20460
gtttggcgtc gaactggata ccgacccgct gacgatcggc tgcgaggtgc gcctcggcga    20520
cccgacgtcc ggcacgctgg tggctcgcgg tttcggcaac atcgccaact ggacgaacat    20580
ttcgccgcac tactcgtcga gcagtgacac gacgagcgcc gtctcgcctg acaacggcgt    20640
ggcgacagtt ccggccggtg cgacggcgac gatcaacgtc aacctgtaca acgacggcct    20700
```

```
gctcggcgcg tacgtgttca acaagaccgg cgcgcagttg gcgattctcg ttgtgccgca   20760
gggcgagtaa gggagggcac caggatgccg tacaccaaga tttaccgcac cgttctgccg   20820
cttgaggccg agcacgacgt cgagcaggcg cggtggctca cccgtgaatc gtttgagcgc   20880
aaagctgcgc agcacgggct gcagatcgtc gactacaccg agcgcgttct cgggctcgac   20940
gagatcccgc ccaaggctgc tgatcacctg ccgttgccgt tgtcggcgta cacgtttcac   21000
gagttcgtcg gcacggcgca ggtcaatcaa acgctgctgc agtggtgcca agccgaaagc   21060
gaccacctgc acggaaaggt aaccagtgcc aagggcgcat gaccggcggc cgttgccgat   21120
cgaccgcaac ccgctgtggt cgatcatggg cggcggcgtc ggcaatctcc ccaagctcga   21180
cgcggcgaag ctgtggcagg gctggctcga ctcgttcaag ctgtttacgg gtatcgacct   21240
gtcgtcgccc gtgaagctgg tcagtcgat cgccgacaag atcggcgacg cgctcgatcc   21300
ggcgacgatc atcgcgcaga tcaaggcagc gactcacctc gacctgtcgt cgccgcaggc   21360
gctcgctgcg agcctcggct cgctgatcct cggcggcgac ggcggcggcg tgatcgaccc   21420
gagtcgcctg ccgcagatcc cgctcgccaa catcgtgcag atcgtcacca gcctgctgcc   21480
cggcggcgct atgaccgggc tcgactcggt gctcgacgag ttcggtcact ggtcgtacga   21540
cgactcgtac ggcgagggcg cggcgacggt cacggccgac ggcgccgtgc acgacctgta   21600
ctcgggcgac ctgatcccgg ttaaggcggg cgaggtgctg cacatcaccg gcaaggctcg   21660
gtgggcgggc ctggtcgcta ccggcaaccc ggtcgagatc ggcgtcaccg gctacaccga   21720
caaggcgggc acgtcgtcgg gcgggcgcgc tgcggcggcc tggcctgtga ccccgagcgg   21780
cacgctgccc gactggcaga gcctcgccgg tacctacacc gtgccgaacg gcatcgtggc   21840
cgtacggctg cgtctgacgg tcactgacgg cgccaccgcg ggcacggtca gctttacccc   21900
gcctgacgcg aacaagggcg acaacctgct gccgctcaat ctggtgcagg atctcccgtc   21960
gcggctggcg gcgctgctca gtttcagtac gtggcagcag ttcctcgacg ccgcgaaggg   22020
cagccccggc ggtgcgatct cggatctgat caaccgcatt gtgcacctcg gaaccgatgg   22080
cactttcgac gcctcgcaac tggtgaacgt gccgaacatg cccgcggtgc ccggcgacat   22140
tgtcaccggc atcgagaacg cgcgcgggca gtctgctgca cgacgtcgag gatcacatcga   22200 caacgtcgtg aacaagttttt tcggcatgtt cggcagtggg cactcaaagg acgacgccgc   22260
ggcggcgatg ggcgccattt acaaccaggt gtcagcgacc cgcagaccg tgcagaacat   22320 ggtcaccgcg cagaccggcg acgcgcactc gggtaagtca ttcacggtca agttctctga   22380
ctaccccgac ggcccgtttc cgaacgtgtt caacctgacg tacagcggca gtggcaccgg   22440
ggcgctacag gtcagcggcg gcaaggcgca ctggaataag gtcgccgacg gcgatcgcat   22500
ggtgatcggg ctgtacaacc agggcgacac gctcaccgat tatcagaata tccaaggcac   22560
ggttgccaat ccgatggaca acggcgccgc gaactggctg tttggccgca gcgacgggag   22620
cctgcagaac ttcgtctacg cgaagggcac ccgtaactcg ctgctcgatt tccgggccga   22680
gcttgggtgt ttcgtcgccg ggcatcaagt ggtgtttgcg tcgaacgtcc cggctaatcc   22740
gaacttcaac ctgcaggtgc gaatcggtac gggcaagggg ctgcgcaact ttcaggtgat   22800
ctcgggcaat gacgtgatca tcgactacac cgacgcggcg gcatttcgc aggtcggcgc   22860 cgacaagcgc aaatggggtt tcgtctcggc gacgtcgaac ggcggcaaca cgtgcccgc   22920 ggacgccgcg gtggtcagtt gcgccgacgc cgatccgtcg gcggcgatcg gtcgggcgc   22980 caaaatgtct cgcctgaaca cgggcaacgt caacgtgtca tcgggtaggc gcttggcgcc   23040
gaccaacttc tacgattcat tggagttggc gacgcccgac attaaggctg acgtcgcaaa   23100
```

```
cgcgaaattc actgtgtcgc tggctggttg gtatcgggtt gagatcgcgt tctcgctgaa    23160
cagcttcgcc ggtgcttcgt cgtttcaggt ggcgccggtg ctgtacaaga acggagccgt    23220
gcaccgcgtg ggtacggatg cgtacggctt tcaggcgttc ggcgccggta cggccgcccg    23280
gttcgcgcag acgagtttcg gtgtctacct cgatgctggc gacaacgtgc aggttggtta    23340
cgactctggg gcgtcgatcg tcatcaccat gtcgggtgaa gcagcgcgg tcgaaacgta    23400 tttcggcatt tcactactta acaggagcct cgggtaatgg cagagatcga caacacagac    23460
caggtcgtga aggcgatagc gcagcacctc ggccccgacg tcaccgacga gcaggtcgca    23520
aacgtgctcg ccgcgtggaa caacgtcaag gcaggcgacc cggtcggcat ggtgcggcga    23580
gatcccgaca gcggcagggt cgctcaccgg gtcgaggtcg tcggcgtgca gcagtggcgc    23640
gtgtcggcgc ccgcgcggcga cctgtacagc gacatgcagc ccacgttgcc gtggccggtg    23700
ctgttcgacc cgagcgcagc gtaatgggct gggcggcaac gccctcgcct cgcaagctgg    23760
tcggccgcgg ctggacgacg tcacctcaac cgcaggcggc gtcgcccggc cgtgcttggt    23820
tcgccggtat cgcgcagctt gctgacgcgc tcagcgtgtc ggtgaccgac gctgcgctcg    23880
ccgtcaacgc gacggccgcg gcgctgtcga tcggcaaggc cgaggccctg gtgctgttgc    23940
acgcgacggc ccccgcggtc agcgcgagca ccacggccgc ggcagccgca gagcatgtgt    24000
gggccgacgc cccggcggtg tcggcgggca ccatgcaggc gctcgtcgtc gtcgaggccg    24060
tcgcgcaggc ggtcggcacc tcgtcgtcgg acgcggccct gcacctcgcg gtggcagcgg    24120
cggccggatc gtcgagcacc acgaacgcat cggcgcagga gcgtttctac gttctcgcgc    24180
aggcgttctc ggcgagcgcg acgacgggcg gggcggtatt ccatgcgaac ggcccggcgg    24240
ggctgtcttt cacgacgacg acgtacacct acacgatccc gtggtgggcg aacttcgtcg    24300
acgtgatcct gctcggcgct ggcggcggcg ggcgcagcat gcccgcaatc ggtacctggg    24360
gtcagggcgg ccgggcgggg cagtggttgg tcgtcacgct gcggcgcggc atcgacattg    24420
cttggacgtt gacacagatc accggcacgg taggcgtcgg cggcgcaggc ggcgcagcag    24480 cttttcggcac taaccccggc aagcggggcg gcaacaccac ggcgaccgct gcgggtgtcg    24540
gcacgctcac agcgttgggc ggtgcgggtg gcggcaatga ctttgacccg aacgggcagg    24600
gcgctggcag tcgaaccgtc acagggcagc tttaccaggg cggcgcggag aagagcgcgg    24660
gcggtactgg ctcgaccggc aacggtcctg gcggcggcgg cacggcgtcc gaggtatcgc    24720
tcggtttcac gggcaccgcg ggcggcgctg gcgccaacgg tcaggcgtgg tttttcgcat    24780
accagtagct aacgccggca aaacactcga gaaccccggt tgacctgcgg cgatccgctg    24840
cgggcgccaa accgagcaaa caactgaata ggagttaccc gtggcatcaa cggatgcgtt    24900
caagctcagt gtgcttgcgc agatcctcgc gcagggcaac gtgctcgcgc tgtacagcgc    24960
cgaccccggc acgaccggcg cgaatgagat cagcggcggc agctacgccc gcaagacgtt    25020
cgcgtggcct gccggggcga tcgtcggcgg cgctgcagtg tcgacggccg ctgcgcagca    25080
gatgaatgtg cctggcggcg tgtcggtcac gcattacggc gtgctgaaca gcagcggcgt    25140
tttccagtac ggcaaggccc tcaaccccgg cgcgacgctc aacgcgccgg gcgtcatcga    25200
cgtgacgccg tcgcattcgt acagcggccc tgcgtaacga aaggcggtca gacagttgat    25260
tactcgcgca aatgtcgagg ccgcgaaggc gcttgtcgtc gcccgtctcg gcgaccgcta    25320
cgcctacggc ggcatgttct cgccgacgaa cctcaagcag gcaccgact gctcgggcgt    25380 ctggaatgac gttttgggca tggcggtggg tcgtttccag tggggccgag aggccgaggg    25440
```

```
tgcgacgacc gagtcgtatc gctatatccc ggtcggcggc gtcggccgt  tcggcacggt   25500 gcgggtcgcc agcccggccg acattccggc gaacgccgtc gccaagctcg cgtttcacca   25560
tgagggcaac ggcggcgcct cgtctcacat gtggggcgag ttggacggca tgcggatcga   25620
gtcggcgagc gacccgaagg gcctgtgtac ggcgccgacg gcctgggaga tcaccaaccc   25680
gtacgcgaac gcctgggcgt atctgccggg gccgatcgtc gaggacggca gcacgccgac   25740
gaccgtcgag cccggcgaca cgctgtacgc gacgtcagc  gagtggcagg tgccggtcag   25800
cgacgcctac ctcgacgccg gttaccgggt gatctgcatt cggtcgaacg atggcacgta   25860
ccgagacaag aactggcagc gcaactatcc gtgggcgaag gccgccgcgg acgacgggcg   25920
cctcgcgttc ttcctcgtct atttcgtgtg gcggccgaac tggcaggccg cggtcgacac   25980
gctcaagtct caagtgggcg taccgcatcc gcgcatggcc gtgatgatcg acgtcgagtc   26040
gtggggcggg cagatcacgg gcgaccagtc cgacggcatc aacgccgcgc acgcacagat   26100
cgctgagtgg ctcggcgacg cccgccgggt gatcggttac ggcaacacgg gcgacctcaa   26160
caacctttgg ccgcgtaagc ccgacgggct gcgcctggtg ctcgctgcgt acggatctaa   26220 cccccggctac cccggcaaga tcgcgcacca gtacacgaac ggcggaggtt cggcggtgg   26280 attgcccgag ggcgcaccac ctttcggcaa ttgcgacatg aacagcgccg acggctacac   26340
cgcgacagcg ttcgcggcgg ccctcggaat cgaaacgaac caggaggatg gtcttttgtc   26400
tgcactcaca cctgacgaac agcgcgaagt gctcacgctg ctgcgttggc tggccgccga   26460
gggtaccggc gaactgcgaa agctgttccc gcaccgctcg atgtacgcga caggccccga   26520
gggcgacacg ttcgcgggtc gcgcgatctc ggctcacgca ttcggctggg accagcgggt   26580
cgaggccagc gccatgcgcg gcgagcagtg ggcgatcgac accgtgcggc aggccgccgc   26640
gggcacgatc tggggcgttc ggcagacgcc cgacgcgaag cctgaccgt  tcctcgtcgg   26700 cgtcgcgcag acctacctgc acaagctcgc cgaggcgggc gtgatcgacg acccgtcgcc   26760 gcagccccg  gtcgtcaagc cgcccgtcgt cgagcagccg ccggtcgtca caccgcagcc   26820
gcccgtacag cgggtcactt gcggaatcgg ccccggccct tgcgttctcg tcgccaacgg   26880
cggcgatggc acgtgcgcgc tggccggtaa cgagtgcgtt ctcaagaagg ggtcactgtg   26940
agcaagcctg ttctgctgac ctggtcgggt accggcgccg acatgtggac cggctattgc   27000
gccgaccttg cgcggcgcat ggaggatctg tggtacttcc agccggtcaa ctacggcccg   27060
aacggcatcc cggccgtgtt cccgatgggg ccgtcgtggc tgaccggcgt cgaggagggc   27120
gtgcggctgg tctttcagca cgaaagcgag cccgacccgc caccgttcta cggcgtggcc   27180
gggtactcgc agggcgctat gcctgcggcg caactgcttt gggagttccg gcaggggcgc   27240
ctcaaggcgt ttgagcacaa gctgcaggcg ggcgtcacgt tcggcaaccc gttccgcgag   27300
gcagggcacg acggccccgg cgccggtatc ggcgatcagt tgatcgtcgg tacgcctgac   27360
tggtgggtcg acgaggccga gcccggcgac atttacacct cggtaccggt cggccccggc   27420
ctgcccgacg aggtcgcggc cgacatgcgc gcgatcttca gctggtgca  gttgcgcaac   27480 ctcggtgacg tgctcggcgc tggcgcgctg ctgccgactg tgctcggcat tctgcagtcg   27540
ccgctcaagg cgttcccggc ggtcgtcgag gcgatcatca agggcctgat gttcgtcggc   27600
gccaagcccg cgacggcccc gcatatcgag taccacattc gccagcgcgc gggcaccggg   27660
atgacttact acgagcacgc cgtcgcccat atgcgggctc gcggtgcggt tctacaggca   27720
gcgtgagggg gccgttatga acaaagtcgc tgagacgata cgcagcatgt tcggcaagtt   27780 ctgggcgggcc gtcgtcgcat tcgcaaatga gcgcctcggt attcgcacgt gggaggatct   27840
```

```
gcggctgcag attcacgtgc tgagcccgtt cgccgttacc ggaatggtga cgtgggggat   27900
tgccgataaa gctcacgcgc agttgatcgt cggcctggtg ctcgccgttg cgagcccggc   27960
gctggcggcg tggcacaccc gcgacggttt ccggcgttgg gtgtacggca tcctgccgcc   28020
gctgcaggcg ttgatcgtcg ggtacgggtg ggcgacagac agtgcgttga cgccgatcat   28080
ggcggccgtc gtcgcgctgc tcggcggggc tctcgccgcg gtcaacacgc gcaccagcac   28140
ctcgcccgcc ggtactgaca ccaggcaggc ggcggccgca tgagcctgtc gcccgccgag   28200
tgggtcacga ttgcgtcggg ctcgtcactg ctgacgggcc tcggcgtcaa tctgctgtct   28260
cgcaggcgcg acaacttctc tgctctcacc gaggcatacg gcacgctgat cgagcgtgtg   28320
gcgggccttg agacgcgact cgacaccgtc gagggcaagt acgacgccga gcgtcaagct   28380
cacgaccgtg aacgcgacgc gcacgcgcac acacgcagcc tgctgagtat cgcaatggtg   28440
ttcatccgca acgtgatgaa ttggggcgca ggcgatcgtg tggggccgct gccggtgccg   28500
cccgccgagc ttatggcggg cgagtgagcc tggccgatcg gctcggcgac ccggcgcccg   28560
caccgtcaag cgagtgcgtg gtgtgccgat ggctcgacca ggccgacgag gccgaccggg   28620
tgacgtttga ccgttggatc gccgagggcg ggtcgctctc ggcgctttgg cgttcctgcg   28680
caaccgatcc cgtcaacccg ctgccgatca agcgccccg tttcagcgag ttggtcaacg   28740
atcaccaccg aggaggttcg cgtgtcgctg tctgatcgct tggagacgcc cgcggcgccc   28800
gatgtgcctt accggccgtc ggtcgagttc gacaatcgcg gcgccgtcgt cgagacagga   28860
cacgtcgccg ccgagcccgg tcaaccgatc gagtacgccg agatcctgcg cagcgtagga   28920
aaagaccccg accgctggcg catcgtcgag gtgctgcgcg agtcgcactg gcagacgtat   28980
gacgagcggt ggctcgccgc gtaccggctg cggtgcgagc cggtcgacgt cgacaggacg   29040
accggccttg aggcgctgat cgccgatgcc cgcaaggtgc cgacgatcga ggtcgccacc   29100
gcggcgccgt actggtacgt gtttcaggcg gccgacctgc agatcggtaa acggtcacgt   29160
gacggttcaa ccgaggagat cgtcgagcag ttcgtgcggt cgctggcggc ggcccgtcgg   29220
cagttcgctg cgctggcgcc tctgggcatc gcgggcgtgc agatcagcat gcccggcgac   29280
tgtatcgagg gtgtggctgc gcagaaaggc gcgaacgtct ggctgacgca ggagacgatc   29340
accgaacagt tccgcgtgtt ccgcaggctg ctgcttgagg cggtcgacac gttccgcgcg   29400
gcccccgagg tcaagctcga cgtcgtcaac ggcaatcacg atcaggcgca ccggcagtgg   29460
aatacgaagc ccggcgacgg gtgggcgacc gaggcggcca tcgcggtgcg cgacgccctg   29520
gcgctcaacg agcaggcgta cggacacgtc gaggtgcgag tgcccgaggc gtggtcgggc   29580
tcgatgacgg tacctgtcgg cgacagcgtc gtgaccgtcg tgcacgggca ccagttcacg   29640
cgcggcaagg ccctcgactg gctcgccaag caggcggtgc acaaccagcc cgccggggcg   29700
gcgcaagtgc tgcagcatgg gcactggcac gtcggcaacg tcgagatgca cgcaaccaag   29760
acgattgtgt gcgcgccgac gatggactgc ggcagcgatt ggtaccgcga gcgcaacggc   29820
ggcgaggccc gtcgcggcgc gctcacgtat ctgctgcgcg gcggcgaggt gtcgaacatg   29880
ggcgtgctgt gaagcggcgc ctgcggtaca gcgacaaggg ctggcttgcg atcctcggcc   29940
tggtcgtggc gatcgaggtc tgcgcccgc acggcgaact gctcagcgag ggagtcgatc   30000
gctaccgcag gcggtggccg atcggtacgc ccgcgttcat cttgtacctg gccgttgggc   30060
acctgctgcg cgtgctgcct cgccgggtcg atccgctgac acaggtcgct gatgcgttcg   30120
ggcgctgacg cccggcggca atatccaatc aatctgtagg agacacatgt tccaaaacgg   30180
```

-continued

```
caacggtggc ggcctgctcg gtgggctgct cggcggcctg atcggcaagg tgctcggcgg   30240
cctcggtggg ttgaccccgc cgagtcagcc cggcaatggc ggcggcctcg gtggcggtct   30300
gctcggtggt ctgctcggcg gcctgttcgg cgggcgcaag tagctaacgc cggcaagcag   30360
ctcgagcacc acctctcacc tgcggtaacg ctctaaaacg ccgattctcg gcaaacacgt   30420
taggcccctc gtcgattcgt cggcgggggg cctttcggcg tttctgttga cccgacaaca   30480
ggcgacccgt attgttgagg gtgcaacagc aagccgatcg gataggagcc gacgaaatga   30540
caaccccgac aatggaggtc gcgcacatgg cgcgaggtaa gcaggtcacg attggaggcg   30600
ttcgccgcac cattccggcg atcgacgtcg agcgttacga gcgcatggtc gaccaggtcg   30660
acgcgctgta cagcggcccc gagcacacgc atgagcgggc cgccgcggtc gagcaggtgg   30720
gcctgtacct cgtcgacgac gtcgacgccg aggctgtggg cgcggcgatg cgcgaggccc   30780
gcgaggcgta cgaggcggcg caggccgcta ctcgggtgtt cgtgctgatg gccgtcgagg   30840
acgacgcgag cgaggccggg ctcgcccgcg gcctgggtat cgaccggctg accgtgcgca   30900
agtaccgcgg aaagcaggac cgggcgaagt gagcggcctg cagcgcaagc ccgaggtgct   30960
gccgcggttc gcgttcacgg gcgcggagat cctcgccgag gcgaccgcgg ctgcccggcg   31020
tgagcgtcgg cgcctcgacg atctgcgcac gcccggcacg cccgagtaca acctgcacgt   31080
gtacggctgt gagtgcggcc gtcgctcttg tgatcactga caggttgcag gcgtacagtc   31140
agtctcgttt tcaggacata aggggatagg agccctacag atgagagcaa ccaacggcct   31200
gcacctcacc cgtgcgcagt tgatcgaggc ggcccgcggc gagcgcctcg cgcttgagca   31260
ggacaacctc gcggcccggc gcatgatcac tgatctgcag cgccggatcg acaagaacga   31320
cgagcgcctg cgggcgatcg aggagactct cggtcacctg agctagctcg atcgacgacg   31380 acgcccgtcgg ctacgccggg gggcgttttc gtgtctattc ggccgtctgc gggcagagtt   31440
cgcgctgtgc tgccaacgcg aggccgtcgg cctggtcgcg gtggatgccg ggcaacccgt   31500
tgtacaggtc gtcagcaacg cgctcgcgcg ggcggccgtt ctgcaggtcg acgcagacct   31560
gatacccgag ggcgacgacg gtaccggcgt cgcggacatg aaagccgtaa tcgttcgcca   31620
gcagcgcgag gtaccgtcg ctgctggcgt gcgcggccgg ggcgaatgcg agggccgcgg   31680
ctgcggcggc cgacagggcg agggtgacaa gtttcacgca cgtaagtcta tgcggcgccc   31740
cgtctgagca gggttttggg gccgtgtacc caaactgtgc ggtcggatct gccgtgtggg   31800
tacacctttg ggtacacccc cgtgtacctt atcgctgccc tggaaagtga aaaaccccg    31860 ttgacctggg ggttttcggt ggtgcgccgt cagggtttcg aaccccggac ccgctgatta   31920
agagtctgac tgttacgatt gctcaacagg cgaaatgcct ggtaggacac ggattctcga   31980
ttgctgtcta gcactgtcca gcactgtcta gactgctgtt gggtacacac tttgggtaca   32040
ccactttggg tacacgggta cataggaggt acacggtcag atggttgcga aagctcggcg   32100
agcgcgtggt gagggcggcc tgtttcagcg ggctgacggc aagtgggtcg gccggtgcta   32160
tgtgcccggc cccgacggga cgcgcgagcg taagcagatc gtgcggcgca gtcaggccga   32220
cgcgatcgag gccctggaca agctcaaggc tgacgcccgc gcggggcgtg tggcgccgtc   32280
tggcgcctcg gcgtacacgg tcgagaagtg gctcgcgcat tggatcgacg acattcaccg   32340
ggacaacctc gcgccgggca cgttcgctga ttacaagcgc gtgatccggc tgcacatcgt   32400
gccgcacatc ggccgggtgc gactggacaa gctgacgagt gaggacgtgc tgcgcatgca   32460
gcgggctgtg cagaagtcga cgacgcgcac cgcgcagatt gcacacgtcg tgatcaatcg   32520
tgcactgacc gacgcagtcg cgtgggatgc cgtgcaccgc aacgttgcgg ccgtcgtgcc   32580
```

```
gacaccgaag caccgcacca agaagcgcaa gggtttcaag acggacgtcg cgcggcacat   32640
catcgccacc gcgggcgaga tcgtcgacca ggccgtgacg cccggctatg acacgcgctg   32700
ggccgccgcg tttctgaccg gcgcccggca gggcgaattg ttgggcctga cctgggatcg   32760
agtcgacctc gacgagggca cgatagacct cgcatggcag ttgcagcagt tggagcaggc   32820
gcacggctgc ggagaacagc gcgcagacgg cacctgggaa tgcggccgac agcgccccgg   32880
ctggtgcccc gagcggcatt gggatctgca ccccggtttt gagtacgagg tcgtgcaccg   32940
ttcgctctgt ttcacgcggc ccaagaccga cgagagcacg cgcctggtgc cgctggtgcc   33000
cgaactgtgc accgcactgc gcacgcagcg cgcaactgcg cagcctggtg cgcacaactt   33060
ggtgtggagc tacgcagacg gccgcccgat ctcgccgcgc gacgattaca cgcggtggca   33120
ggcgttgctc gtcgaggcgg gcgtacgcaa ggccaaggag gacggcggcg aggccgtgcc   33180
gctgcaccag gcccgcaaca cgacggcgac gctgttgctt gaggcgggcg tcgacgctca   33240
cgtcatacag tcgatcgtcg ggcacgccga cgtcgtcacg acacgcgggt accagcacgt   33300
cgacctgtct ctgcagcggg cggcgctggc gcacctacgc ggcctgatgg gcgcggcctg   33360
atggacgccg acaacgtcac ggatgattca ccaggcggga aacgtgcaaa gcgcccggca   33420
cgggatataa ctatgcccat gacggcagag gtcgaccgcg agccggtcga ggagagcgtg   33480
cgcaaatggc gctcggcggc ccgcttctac gcgaagcagg cgcaggagtt gtttctagat   33540
tctgccgacg agcagggcaa cgtcgacggc gacgaggccg agcacgttcg acggatgaac   33600
gacgtcgcca cgctggcggc gctggcaacg atgtacttct cgatggcggc cgacgcggag   33660
tgtttcggca agctgccgcc ggttgagcca acagacgacg agtagccaac ccccgaacgg   33720
caacagcccc cggcgatcgc atcgggggct gtttgctgac ttagcgtcga ggcgcaggtc   33780
agtggctata acggtggttt tgccggcctt agctggtcgg gctcgtcggt cggcggctgc   33840
ttttcgacgg cgcccgcggt ggcgagcgtg aggcgttccc ggtgtgactg cagggtgtcg   33900
ccgcgaagct ggcgcctggt cgtgtgcgtg cgcagtagca agcgccggta gtcccacatt   33960
ttgcacagcc atgacagcga agcggtgacg gcgaccagcg ccgagaaggc tgccgcgtg    34020
tagaccggga tcgcgtcgag cgccgggtga ccggcgcgca ccatctcgac gacccgcagc   34080
gcggtggtcg agaggctgag gccgcagcag aacaggtaca gcgtcgtgaa caggcagtaa   34140
cccccggccg cggtacggcg cacggtgcgc agcacgtgta tgagcagcag cgtgaggtac   34200
agcaggcagg cgaggtacag ggtgcgatag gtgagggtcc agaagcccga accgtgcgac   34260
atgacgtcga acgtgggcga cgtcggctcg tcgtgcagcg cggggctcat gtacatggcg   34320
ctgagcatga gcggcaccag gagggtgatc ggccaccgca cgaacgcctc gacgatctcg   34380
cggcgctcgg cgtcgtcggc gagtcggtag agggcgcctt gcagcagcgc gagcgtgccc   34440
gcgacgtagc acagttgccc ggcgaagttg tcgaggtacc cgaaccccgt cgcgtgccat   34500
aggacgtcgc cgacgccgac ggcgtcgatt tcgtcgctgc tgaggaatgt tgcaaccgaa   34560
agcagcagca cggctgcgct tatcgcaatc tcaccgggca ctcgccacgt gcgacgacgg   34620
atgaatagcg acgccgctgc tgtcagaacg gcaaacgtgg tgggggtcac cggcacactg   34680
tacgacgtgt cccagatttg ggacaaatgg cgtaggtcac agtctgctgt gaaatcagag   34740
accggagacg ttcgcgcgca cggatagctc gccgagcttg cggcgcccgc gcttgggtgc   34800
gacgactgag ggcgagacgg cgatcggccg cgcaggtgtg cgcactgccg cggcggccgg   34860
ggcgctgcgc agccggtcgg cgtattcgag cacggcctcg tcgctgatca caccgaagcg   34920
```

```
tgcgagcagg tcaacctcgt ttatgccgag gttctgggcg gcgcgcacca ggttgtcggg   34980
cgtgatgagc ttgccctcgt cgatctgcgc gtaataccgc gatcggctga tctgcagcgc   35040
ctcggtgatc tcgcgcagct tgagcggtct gccgaccagg tacccaagta ccgcggcgag   35100
tgacttgccg ctgtcgtcgt ccatttcgtg tcccttcggt tcccccgact gcgacacgcc   35160
cgtgacagcg tgtccggttg ggagtcaatc tagtccactt tcaggacaa agcaattaca   35220 tagaatttcg taataggtct tagagcagca ttaatctact gaccagtacg tttcgcgcaa   35280
atggtacaag tgtctcggat acggcacagc ccgtaactca caggtaccaa gtgtcctgaa   35340
agcaggacag ttggtgtacc gttcccaacc gtgccagata cgaaacatca actccgttgg   35400
aagccggaaa gcgtcgcccg atgcctcggt gacaacggaa tcagtgaccg tcaccaactt   35460
tcacgaacga ttcacgtagg ccgctcgacc gtgtactcgg cgtttgatga cgcctggtcg   35520
ggcaccgcga cgcatagcgt gctcgccgcc atcgcgggca cgttcggcgt gccgatcggc   35580
gatctcgccg agccggtggc agtcgcgtga cggcccccgc ggtcgtcgtc gaggtcgagc   35640
cgctgttgct cacccgcgag gacgctgccc gcactctcgg cctgtcaacc aaggaggtcg   35700
accggctgcg cgcatccggc gatctgatgc cgcggcggca cggccgcaag gtgctgtttc   35760
ccctcgcaga gctacgtcgg ttcgccgagg gcctgcccgt cgaccagtta ggagcctgaa   35820
acatgcagtt gggcaagcac attgaggtaa cgaacaagct caagcgtgag cgcgacgagg   35880
ccgtcgccga gcgtgacgcc ggtcgtcgtg tgatcgcggc gctgaccgat caactcgccg   35940
cggcgctgcg ggcgcgtgcc gaggacaacg tcgcctcgta cgcccgcatt gaactgctga   36000
ccagcgagcg tgacgccgcg gtcaatgagt acgccgaggc cgacgctgcg caccgggcgg   36060
cgctcgcgga tctcgccgac caggagcgcg aactgtcgac gctgcgcgcg gtcgacgacg   36120
aggagatggg cgttccgacc gtcagggccg atgaggttcg cgtgctgcac gccgagccgg   36180
acatggagcg gtacgggtga ccgcgcaacc acctaaacga cgcaaccccc gcgcgaggcg   36240
ggggctggcc gacacaacca aggggatagg agccacttgt tatgccttgc aggattctac   36300
ggtacgcggg cctcatttca gccgacgacc cgacgattgc gcagcaggtc gagaagctgg   36360
tcggcgaccg gatcgacgag gcgctgaacg accccgaggc gggtctgccg gtcgcgctgt   36420
acggcctgtg gctggaaacg gcactcacga tcgagcacct ggtcgagttg ttcgtcgccc   36480
ggccgatcgt cggcctgctc gcctcggcgg tggcccgatg agcccggcgc catattgctt   36540
gccctgcaac gcacatcacg tacccggcag cacctcgcgg tgcggcgccg agcgtctcgg   36600
tgcgctgctc ggttgggtgc tgctcacgct cgcaatggtg atcgtcggtc tggcgctggg   36660
cgcgctgtcg gtgggcgcct ggtgagcaac gtacgtgagc gcgtcgagga ctgcctcgac   36720
tgccagcgcc ccgacaacac ctgccccggt cacatcacag gaaaggcaaa cgagcagtga   36780
cgtcaattga ggtcgccgag cgccgggctc gcaagcgcga ggagcggggc cgcatcgccg   36840
ccaacacggg cgtgctcgac ctgttccggc cgcgcattgg agaggtcgcc agcgccgagg   36900
aggtgtgccg tctgctggcg atcgagtcgc gcggatctct gcgcaacgtg ctgaaccgtc   36960
acggtgacga attggccgca gacggatggg ataggctgc aaacactttc acccgccggg   37020
cggttatccg cattgcgctg atgctgcggg cgtcgtcgtc gccgcgtgcc gggcgcatcg   37080
caatggccgc caaggctggc agcaaggtga tcagtttcga tcacgccccg ctgtcacgca   37140
tgacgcaggg cgtgctcgac cgcgcgtacg aactggcggc gcaggtgcgc gacgaagatc   37200
ccggcgaggt gtgggcggcg ctcggcaggc tcgaccggca cacgctgcag ggcgtcgctg   37260
tcgcgttggc tgccctgacg ccgatcgagt cgtcgggcgt gacgaggtac ctgcgctcgc   37320
```

```
ttgcgggcgg cggcaacccg gccgcggggc tggctcgtct ggtgccgacc cgcgagacgt    37380
ccgacggcat gcccttgagt ctgctcgacc agatcgaggc agacgacgaa accgaaagcg    37440
agacaacgga atgagcgacg tcgtcgacga gtacatgcag attcccgagc attgggaggc    37500
cgacgcgctg tgccagcagg tcgacccga actgttcttt cctgagcgcg ggcagggcgg     37560
caacgaggct aagcggatct gtgcccgctg cccggtgatc gaggagtgcc gcgagaaggc    37620
gctcagtttc ggcacagaac tgtggggcgt gtggggcggc ctcacgcagc gcgaccgtcg    37680
tctgatcatc cgttccgagc gaaaggccaa cgcagcgtga gtgaatcgac cagtggtgtg    37740
cagtgccacg tgtgcgggct gtacgacgcc cgcgtgttcg acccgagcgg cgcaatgtgg    37800
tgccgggtct gcgacattct cgggctcgga tcaatggccg tcgccgagaa ggtcgccgag    37860
atcgccgagg gcgtcggcaa ggcgttcgac gaggctgcgc tgttcgaccc cgagcatgcc    37920
ctcggcaagc acctcgacaa ggcgctgcgc gaggcgctgg cgacgccgat cgacaccgcg    37980
gtgctgtatg gcggcaaggc aaccgaggcg ggcgaccctg acgcctggga gccgcacgtg    38040
ccggattacg cggcgatcaa cgcgcggtgg cgtgagcaga tgggcgaggc cgccgcgcat    38100
gtcccgaccg cggctgaggc gctcgcagcg tacgaggggc cgctcgtcga cgagatcgcc    38160
gggcgcactg cgcgtatcgg cgaggcgctc gtcgcgggtg tcgacgagat caacgcgcag    38220
ttgcgtgccg gggccgacga cggcgtgcgg ccggatctca tgggcaagct cactgcgctg    38280
ctcgccgaga ctccgctcac ggtcgaggcg cgcacgtggc tgccgggcga cgacgacgac    38340
gaggtgccgt cgccggggcc gctgtacacg atccctgaac cgccgcaggt gttcccgacc    38400
gtgttcgtgc cgggcatcgt cgacagcctc gaccaggccg accgcgggta catctggaaa    38460
gacaccgagg gcgcgcggtg gggctggacg aagccgcacg ggtgggtcgc gtggaatggc    38520
ggcgttgcgc cgtacagccg cggcgccgtc ggcccgttcg tgttcgacgg cccgaacctg    38580
tgcgacgaga acggcaggcc gccaacggat ctgcccgagt ggatcaagcg catgcaggcc    38640
gccgacagca acgacgccgg cgggcctctg accagcgcag acgccgaaac cagcaacgtg    38700
ccgccgcggg tcgattactg ctgcggcggc ggcgccaacc ccggcgggca tgagtggaac    38760
tgcagcaagc tgctaaacct gcagcccgac acggtcgccg acctggccgt cgagacgtcg    38820
ctgcttgtcg agggtgacgc cgtcgagcac ccgtcgcact acacgtcgag caaggcggcg    38880
tgtaagggct gcggccgtcc aatcgagtgc atcgacattg tcgagcacat gggctacagc    38940
ctcggcaacg tcaccaagta cgtgtggcgc tgtgacctca gtgggacgc gatcgaggat     39000 ctgcgaaagg cccgacagta cctcgatttt gagatcgcca agcgcgagcg cgaggcggcg    39060
gccggtgcct gacttgacgg ggccgcaacg cccctggtgg gccgaccgtg acgcggttca    39120
attctggtgc gagcagcagc aatttgaggc aacgctcgcc tactttgacg gcctgaccaa    39180
cgcaatcgag caccagatcg cctatgccgc cgcagatccc gcggtggctg ccagcgacgc    39240
gctgtgcgcg ctcgacatga tctggtaccg gccgcgggtc gtcgtgcagg cgtgggagg    39300 tgaggccgtg cagacgttgc cggttctcaa gcccgagccg ctgccgtttc aactcgacga    39360
cccggcgcac gtcatggtgt gcgcctgcac gcacccgtac accgatcaca gcgacgtggg    39420
ctgcagccat tgcccgcact gcgcaggttt caagtattca cacgacgacg ataggagcga    39480
gtgatggccg ctgacctgag cgaggtcaag ggacacgtcg acctgctgcg gcacgcccgc    39540
ggtgaaaagg cgaagtgggc cgaggtcgag aagatggcta aggccgcgat cgaggaggcc    39600
ctcgacggcg ccgacgaggg cgagatcggc gggcaggttg tggtgcgccg caaggagatc    39660
```

```
aagagcaaca agctcgatca acggctgctc aagtcactgc accccgacgt cgtcgccgag   39720
tgcactgcag tgtcggtcag ttaccgcacg gacctggtcg aaaacaacga gggataggag   39780
cccctgacat ggcaaggcaa ttgatcgtgg tcgacgtcga gacgacggga ctgcatgaca   39840
aggcggcgat tttggaggtc gccgcgatca acgtcgacac gggcgagtcg atggtgttcg   39900
cgccgttcgt cgactgcaag cagttgggtg acgcgcagcc cgaggcaatg gagattaacc   39960
gctactttga gcggggcgtg tggcgcgacg cctacaaccc gcagcagacc gcggcggcgt   40020
ggcgtgatct acaggagtgg ctgcgcggca acacgttcgc cggatcaaac ccgacgttcg   40080
actcgtcgct gatcgcgcag cagatcactg acgccggggc gatcttcaac agctacgtgg   40140
gcaaggtgtg gcatcaccgg ctcgcggatc tcgcggcgta cgcggcgggc aagctcgacg   40200
tcgacccgac cgaacttgag ggcctcgacg gcgtcgccga gcgcctgggc gtgccggtca   40260
ccgagcggca cagcgccctc gccgacgcct gcgcgacggc gatgtgcttc gacatgctgc   40320
gcaacaccaa ggcggcgcac ctgtgacgta caactgggcc gggcaggaca tttcgccggg   40380
cgccgtcgtg tggcggggcg cccgcgacgg caacctgtcg gcgttcaagg tcggcgtcgt   40440
cgaggccgtc ggcgtgcagc ccggcaaggc aacggtgcgg tgggtcgccg agcagggatg   40500
gggcggcgac gcccggctgc tcaactcgac cggccgcccg gccgtcgaca gcctcgcgtt   40560
gatcgacccc tcaaccctca gcgagaagat ccgaaaggcg ttggaactgt gagcagtagc   40620
aatttcgtgc acgtcggcaa ggtcgccgtg cctgagcccg gcaagggtgt cggcgaggtg   40680
atcgtcggcg tgcgcgcgga tctcggccga gtgatcgtgt cgagcaccga ccccgacggc   40740
cgccgcggtg caatgcggcc cctgacgccc gaggaaacgc agaaggtcgc cgggcacatg   40800
atgcgggccg ctggtgtcgc tgcgtcgctc tccgaggcgc acagggtcta tgcggcggcg   40860
ctgcagcagg ccgaggccga cctcgcgcg cgttcgcgc gtgaggtgag cgcatgagcg   40920
gcaacgcagg ttttttcggc ctgaccgacg acgcccccga gcgcgacaag ccccgacac   40980
ctacggccga gttcaacgcg ggcctgctcg gcgatctcaa gggcgtgttt aagcgcgcgt   41040
gggcgacgca cgcccgctcg cagcagcgcg ccctcgggcc gtccgaggtg ggtcacccgt   41100
gcgcgcggcg gctggtcacg gcaatgctgg aaatgccgcg gatcaacccc gagggcgacc   41160
cgctgcccgc atggctcggc acggccgggc acgccaagtt tgaggatgcg gtgctgttcg   41220
acaacgaccg gatcgtcgac gagtggctgc gcgaccgcga gcagcgttgc accgtactgc   41280
gatcggtagc cgagcacggc gacgagccgc agtacgtcgg ccggtggttc tccgagcgtc   41340
gggtgcaggt cgctggcggc ctggccggga cgtgcgacct gttcgacacg tggaccggca   41400
cagtcatcga cctgaaattt cctggcgcga cggcgttctc gacctataag aagcacggcc   41460
cgtcggccga ataccgggtg caggcgcatt gctacggcaa gggctacaga acgagggtt   41520
tcgacgtcaa gcgtgtggcg atctggttca ttccgcgggg cggcacgctg tcgagttcgt   41580
tcgtgtggtc cgaggagtac gacgagcagg tcgtcgccga caccgtcaag cggctgcagg   41640
acatagccct ggtgctgaat gacctcgaca ttgaggagca ccccgagcgg ctggcgatgg   41700
tgcccaagca cccgcataac tgcatgttct gcccgttctt cgtcaccaag cccgaccctg   41760
agcggccgtg ggcctgcgag ggcggggcgt cgtgaggccg tggcgtatcc ggcgcctgac   41820
ggaggacggc cgggtgatcg gttgggtgat cgagcagcac gtgcactacg caggcatgcc   41880
cgagcccgag tacgtggtcg tcgactactt cccgagcggc gtcgcggcga tcgcaacgtt   41940
tgccaatcgg ggcgttttgg cggcctgacg tgcagcgatc cgattttgcc ggcgttagct   42000
cgcgctggct gatccgcaag accggcgggc ggtggcacgt acgccgcccc gtcggcacgt   42060
```

```
tctgggccg  cagcacgcag  cacgacacag  gcgaccaggc  cctcgccgac  ttccgcgcac   42120
agaccgcgca  ccacaagggg  ataggagccc  gcacagcatg  actcaacgat  ccgacgtcgc   42180
cgacaaggcg  gcacggctgc  acctggtcgt  cgcaccgacc  gcggcggccg  acgtcgaccg   42240
ctggctgtgg  cagcagcaga  tcgacacgaa  cacggcgacc  gagcgtgtcg  ccgatcggca   42300
ggtgcggctg  ctgaccgtgc  agcgcgagat  cctcgacagc  cagcttgccg  aggcgaccgc   42360
gaagcgtgac  ggcgcccggc  aggcggtcga  gcttgcccgc  gagatgttgg  cggcctgcga   42420
ggtcgagaag  tgagcgcccg  gtcgacgttc  acggcccgct  atcacggccg  ctgcggcgcc   42480
tgcccgacgt  cggttcaacc  cggcgacgag  gtcgcctata  tgagcgacgg  cgcccttata   42540
catgttgatt  gcgaggacac  ctcgcaggac  tcgaccagcg  cacgacgtca  ccccgtgtgc   42600
tcgacgtgct  ggcttgaaca  cccgaaaggt  gagtgcccct  gatgctcaag  cgaattgccg   42660
ccgctgtggc  ggccgttctg  atcgcttttcg  gcggcaccgc  atgcgatccg  tcgaccggcg   42720
gcggttcggg  cggcagcgtc  gacgacagcg  gcccgcacgg  catcatcccg  atgccgatgc   42780
ccggcggcgg  tacgaacttc  atcgtttttct  gatggctcgc  caccgctgca  gcggcgacgg   42840
gtgcgggtac  tgcgagcgcc  ggatcgccga  gattgagtac  gagcgcgatt  accccgacga   42900
ggttcacgac  ttctacgacg  ggacataagc  cccgcggcgc  cgggcgggcc  gaaaggtgaa   42960
caggcgcaac  aggaaacaca  caactgaaca  aaggaaacac  agaacacatg  agtaacgatt   43020
cgtacgggtt  cctcggcggc  ggcggcccgg  catcggcgaa  gttcaagagc  cacggcgacg   43080
tcgtcggcgg  cgtgatcgcc  gtcgagcccg  agcagcggca  gcagaccgac  ctcaacacca   43140
acgagcccct  gacctggaaa  gacggcagcc  cgcgcatgca  gctggtcgtc  accgtgcaga   43200
ccgacctcaa  cgaccccgag  atcgaggacg  acgacggcat  gcgtcgcctg  ttcgtcaagg   43260
gcgagatgcg  caaggccgtg  cagaaggccg  tcatcgcggc  cggtgcgaag  ggcctcgacg   43320
tcggcggcga  actgttcgtg  acgtacgtcg  gcgacggcga  gaagaagggc  aacctgaccc   43380
cgccgaagct  gtacagcgcg  acctacaaga  agcctgcgcc  cggcgcagcc  ccggctgccg   43440
cggcggcccc  ggctggcgac  gcgctgcccg  agggcgtgac  ccccgaggca  ttcgaggcgc   43500
tgcagcgcat  gggcatgctc  aagtagcagc  ccgacctgta  cggcgagccg  gtggcgcaat   43560
gggacgtcac  cggctcgcct  tgtctctcaa  gcaaattcgt  acaccaggga  taggagcccc   43620
cgatgatcac  gatttacacg  acaggcccgg  cctgcatgaa  gtgcaacctg  acgaaacgcg   43680
cgtttgaggg  caagggtgtc  gagtacaccg  aggtgcgcct  cgacgagtcg  cccgaggcgt   43740
tgacggccga  gttcgtcgcc  gccgggcacc  aggtggcgcc  gatcgtgcac  gactcgctga   43800
ccggcgacct  gtggtcagac  ttccggcgcg  accggatcaa  ggccgcgatc  gaggcccgcg   43860
cctaatgccc  accaacgcag  cactattcga  ccgcatcgcc  atgcgacggg  ctgacatgcg   43920
ctgcgagtgc  gagggcggct  gcggccggtc  gcaccgtttc  ggcattcact  accgctgcgg   43980
caatacgcac  ggccgcccgg  cgctgttcga  cgccgacaag  gtcgtgagcc  tcgccgtcgt   44040
cgcgctcgac  ggcaacgagc  gcaacgaggc  cgacgacaac  gtgatcgcgc  tgtgccaagc   44100
ctgcgtgaag  cgataccgcg  ccaagctcaa  ggccgccgca  gacaaggccg  cggcacgggc   44160
ggcgatcgag  gcgcaacaca  acgggctgtt  tgacgtgccc  gcggtggccg  agggcggcaa   44220
cggcctgacg  ctgtgaccgc  cgcgagatgc  cagcccccac  aactgaatag  aggtttgagt   44280
gaacggcttt  actgacctgc  tggaactgct  cggctacgcc  gacggcgagc  acgtctcaat   44340
caactaccag  gcgcccggcg  gcccgtttca  gtcgaccgtc  atggagtacg  ccgaggacag   44400
```

| | |
|---|---|
| cgacgcgctg cagggcctcg caatggcgct cggcaacggt cggcacctgt ggtttggtgt | 44460 |
| caacccgacg aggccccggc cggtcgacga ggacggcaag cagaagggcc gcggcacggc | 44520 |
| cgaggacgtc acccggctgg cggcgatctg gtgtgacctc gacgtaaagg gcggcgcctg | 44580 |
| cagggatctc gcgcacgcgc accaggtgat cgacgaactg tcggcgatcc tcggcgtgcg | 44640 |
| gccgagcgcc gtcgtgtaca gcggcaacgg gctgcagccg tattggccga tcgacgacgg | 44700 |
| gctgatcgag gccgacggcg ccgaggacat ggccgccgcg agtgctgcct tgcgcgccga | 44760 |
| gtgcgcggcg ctgctcaagc gatggggccg cctcgcgtgc atcgtcgccg agggcctggg | 44820 |
| cgccaagatc gaccgcggcg tgtacgacct cgcccgcgtg ctgcgcgtgc ccggaagctt | 44880 |
| caacctcaag gatgaggccg agccgaagcc cgtcacgatc gaggcagaca cgggcgcccc | 44940 |
| tttgtcactt gacgaattgc gcgaccggct cgacagcac ggcgtcgccg agtacgaggg | 45000 |
| cgaccggcgc acctcgcagg agatcgtcag tcggcccgag gcgtggaagt tcgccgtcgg | 45060 |
| cacgtgcgag tatttcgcgc cgacgatcaa ggcgtgggcc gaggagccga tcactgagcg | 45120 |
| gcacccgtgg ctcgtcaagg tgaccgtgcg actcatggcg gcgctgcgca acggctgcct | 45180 |
| gacggccgac gagttcgcgg cggccgagga catgatcaaa cggcggttca ctgaggagtg | 45240 |
| cgcacgcacc ggccgcgacg tgcccggctt tgagatcccg aacgcattcc gctgggccga | 45300 |
| gatgcaggtc gccgccaagc ccgacgccga gcttgcgacc gagtacggca agcacgtgca | 45360 |
| cctgatcgac cgagtcgcac cgcgcgagat cacgctcgac ctggtgcacg acgagccgca | 45420 |
| gccgcagcaa acgaaacccg agcccgaggc cggcgttagc tcggacggcg cattagcgca | 45480 |
| ggtagtggac ataaacgagc ggcgcaacgc tgttgccccg gccgtgacgc tgaccgagac | 45540 |
| tggcaacgct gacctgctcg tcgaggcgta cggcgaccgg ctgcggtact gccccgacac | 45600 |
| gggtaagtgg ctgacgtggg cgggcgaccg ctggcagcac ggcaccgaca acggcgaggc | 45660 |
| gctggtcgcc gcgcgcaagg tcgtcgaggc aatccgtatc gacgacgaca gcccgcgcga | 45720 |
| tctgatccag caccgcatgc gcagcctgtc ccgcaagggc cttgagaaca tggtcgcgct | 45780 |
| cgccaaggcg cagcccaaga tgcgcgtgcg cctggccgac ctcgacgccg agccgtacga | 45840 |
| gttgaacacg ccgagcggcg tcgtcgacct caagaccggg cacctgctgc agcacagccc | 45900 |
| cgacgggtgg cacacgaaat gcactggcgc cggttacaac ccggccgcgg tggcaccgaa | 45960 |
| gtgggcgaag ttcctcggcg gcacgttcgg cgatgacgta gagctgatca gctatgtgca | 46020 |
| gcgcctcgcc gggctcgccg cgatcggcaa ggtgacgcac cacgtgctgc cgttcctgtt | 46080 |
| cggtggcggg tcgaacggta agagcgtgct catggacgtg ctcagcacag tgctgggcga | 46140 |
| ttacgcgatc acggccccgg cgaacttcct gctggccggg cgtgaccggc acgaaacgga | 46200 |
| gatcgcccgg ctgcacggtg cgcgcatggt cgtgtgctcg gagatcaacg cagagagcaa | 46260 |
| gtttgacgag gccaaggtca aggtgctgac cggcggcgac gttctgtcgg ccgctacat | 46320 |
| gcggcaggac tatttcgact tcatcccgtc gcacacgctg tttctgatgg gcaaccacca | 46380 |
| gccgcaggta tccgctggcg gtacgtcgtt ctggcggcgg ctgcgcctta tcccgttcct | 46440 |
| gcacacggtc ccgccggagc agcgcaatcc caacctcgcc gctgaactgg tcgccgagga | 46500 |
| gggcgccgca atcctcgcct gggtggtggc aggagcccgt cagatcgccg ctgagggcct | 46560 |
| ccgcgagcct gcctcggtgc tggacgccac gaaggaatac agcgagcagg aggacgctct | 46620 |
| cgggcggttt atcgccgagt gctgcgtgtt gacgaccggg gcgccgggcg gggcggggc | 46680 |
| gagtcctgcg ctggtgctca aggcgtatca gcggtgggca atgaccaatg gcgaggacgc | 46740 |
| gatggtttcg caggtgaagc tcggccgcga gttgtcggcg cggttcgggg tgcggtcgat | 46800 |

```
gcctgtgcgc gggtcgcggg tgtattcggg tctggcgctg cagcctggtt gggatctgtc    46860
gaacgagttc ggcgtcgggt tccgctgaca tgcggcggcc ctcgcagcta gctaacggca    46920
cagatctgtg ccaaaagcgt gccaagtgtc tacagatcga acagattggc acagatcgaa    46980
acgccggatc tgttctagcg tttccgcagg taaaagactc ttttaagagc gttgtctaca    47040
gatctacaga tgttttcaag ttgacgactc ttatacaaga ttctcgccgt ttgtcctggt    47100
cgctgtcggt tcggggccgt gtgtgccgct catatggaga gatctgtaga tctgtagaca    47160
cgccccgctg cagcaaacgt cacgggccta gcggggccg cgcggttcga tcgggcgct    47220 gaccggccga aatgagcagc cgagcagcga aaatgctgga cacacaactg aatagggagc    47280
atggagtgac cgaccagact ctcgacctgg ggctgagtgt cgccgggccg atcgggcaag    47340
atccgcaggc gctcgtcgag caggccgacc agtatgcccg cgagcaggcc gccgagcttc    47400
tgctcgacat ggtgcccgcc gagcagtacg acgtgctgta cgcggcgctg agcgcccgtg    47460
tgacgcacga acgtaacggc ggcaggcagt tgcgcatgtt cgtgccgggc aagcctgcac    47520
cgcagggcag taaggatttc aaggggtttg caaaggccgc gccgggtcag tcgcgcggca    47580
aggcgatcct ggtcgagtcg agcgccgagg ttgggccgtg gcgcgctcgt atcgcgctcg    47640
ctgcggctga cgcgatgatg gccgccgggc tgccggtgct cgatcgcaag tacccggtcg    47700
tcacgtcgct gacgttcgtc atgccgcggc cgtcggcac gcccaagagc tacacgccgc    47760
ccgcggtgaa gcgacccgac gccgacaagc tagagcgcgc ggtcaacgac ggcctgactg    47820
acgtctgctg gctggacgat cgcaggtcg tcgagacgca ccgccgcaag gtgttggccg    47880
agatctcgca gcagcctggt gtgcatatcc gtgtgtcgtc gccgggctgg ggtgacgccg    47940
cgatcgaggc gtggcgggcc gagaatgcct gaactgatcg agctttcggt cgacgaggtg    48000
caggtgctcg ccgacacggt gcgctctcgg atcgtgcacc cgtcgcacac gcctgtgcag    48060
gcgatccgcg cgggcctcgc cgcggtcaac gcgatgcgcc tcaaggccgc tgagggtacc    48120
ggcgagttgg cggctgacgc cccggtcgtg atcgtggcgg cgcctgttca ccggcccgg    48180 ccgcgcaagg tgtcgacgct gggcgtgcgc gagcggtcga gcgagtggct cgacgttgac    48240
ggcgaccgtt ggcgctggtg tttcatgcgc aacctgtggc agtaccgccc gtgcgatccg    48300
cagccgtggg agcacagcga cgacgtcgag ggttggatcg actgcccgac gggctcggat    48360
gggtcgccgt cgccgcggta tgcgccgttc accgaggtgc ctcgcgcgtg agtttgccgg    48420
attccgtcag tttcggcgat ccgcgcaggt caccgggggt gctcgaggat tttgccggcg    48480
tttgcccgcg gggcgccggg atctcgtact acggggcgcc tgcgcctgtt catccgaccg    48540
agttcgacgc cgaggagggt gcgcgtggct gagtgccaga actgcaaggg tgcggcgagc    48600
atgacgctgt gctggccgtg cggcaagctg ctgcgcgccg ggctcgccga gttgccttgg    48660
tacctcgcgc gtctcgctga gtcggcgtac ggcgaggcga agctcggccg cgagtcggcg    48720
aaggtgtcga cggggagaa gctgccgagc ctgccgctga tgaacgcgc gagcaagctg    48780 ctgcttgagt gccgcgcgac gctgacccgc tggtacctcg ctgtgattcc gacgtacagc    48840
gagccggtgc cgtcgggtga gggttgcgcc cgcaagctcg ctggcgagat cggcgccctg    48900
atgcgcgctg agaacgccgc cgagatgctc gccgaggtgc ggcgcctgcg cggcgagtgc    48960
gagacggcga tcgacttgcc gccggatctg cagtacgtcg gtttgtgcgc gtcgctgctg    49020
ccgccggtcg acgactacac cgagcccgcc gagtgcgggg cgcgcatgta ctgccgtcag    49080
ggtgacaccg aggtggtgtg ccgtcgctgc aaatcgacgt gggacgtcgc cgagttgcag    49140
```

```
gcgtggatgc tgtcgcgggt cgacgagacg ctgcggtcgc aggctgaaat gtggcggctg    49200
ctcaagtgga ttggccgcga cgtgccccgc tcgacgtttt accggctggt tgcgtgcgag    49260
gtgccttgcc gcgcgtatcg cctcgctgac ggcaagctgg tcgacgatcc ggcaccgtct    49320
gcggtcgcca cgcccgtgta cgcctacagc gacgttgtcg ccgccctgga cgcccgcgac    49380
gccgccgagg ctgagcgcct ggccgccggg cgacgcaagc gcggccgacc ccgcaaggcc    49440
gacacgccgc catctgttga cgaggcaaca gccgcgtgct agcttgctga cgtctcaaca    49500
gttcacggga taggagccca cgaaatgcat tctcagaaaa caggtttacg gcgggcggcg    49560
atgctcgcct cgcttggcgc ggtcgccgcg gcggccgtgc tgcatgcgcc gcaggcacac    49620
gccgacgagt acgaccccgg ctgcaaggtc gacctttggg gtttcctcgg cagcagccgc    49680
cgcgcgatct gcgatggccc gattcggcct gacgggtcgt gggagcgtgc ccgcgagttc    49740
ttcgtgcctg cgcaccgcgt gccgctgcgc acgacgtgct cgggcacgta cagcgtgacg    49800
tgcacgacgt cgggcgggta cttccaagag cgcacctctg acggcgtcga gacgtacgtc    49860
gtcacgcctg acacggttct gcccgacgag cccggtcacc tcgacgaggg cgtgtcgtga    49920
agcgcacaaa ggtgtttcgc gctgagcccg cggcgccgca gcccgaggtc gtcgtcaacg    49980
gccgcgtgtt ggaggttggc accgaggtgt cgatcaaggg tgagcgcggc cggttccggt    50040
tcaagagcgc cgcgcgcacc agcggcggcc ggatcgtgtg cgatttcatc ggcggcccgg    50100
ccgggcatga gcagtggcgc tcgttctacc ccgaacgcat ccgcacggtt caccggctga    50160
atcggacccg cgccaacgcc gcgtgacctc gacgacgagg cgcccctgac ctgcgaggtt    50220
gggggcgcct ctctcatgtg ttgacacctc aacagacatg cattactgtt gagctatcaa    50280
caccgaggga taggagcccc acatgaacat gatcgaccgc agcggcgaca ccgtcacact    50340
gaccgacgag ggtttcgaga tcgccgaccg tatcgacctg tggcttgagg cgcacccccgg    50400 tttccacaat gcgagcaaga tcgcccgcgg cgccaagtgc tcgacgaccg aagcgcacgc    50460
cgtgctcggc tggctgctcg accaggtgat ggtcaaggcc gccggtaacg gctgctggat    50520
caactactcc gcacgctgac ctgcccacgg ggcgcctcac caggggcgc ccctcgtccc    50580 gaaaggggtt gctcatgcac aacactcacg tttacggcga ggccgtcgac gagttcaccg    50640
tcggcgcccg cgtggcgact caccccggca cggtcgcgtt cctgcgcggc gagcggtacg    50700
gcgaggtggt caaggtcggc cgcgacgtcg tgcacgtgcg cctcgatcgc acgcggcggc    50760
ggtcgacgtt cacgccgggc atgctcgccc acatggcgcg cgactagcgc cgttcgggta    50820
acgcctcggt tccgctggca acggaatcgg ggcgtttctc gtttccgtgt tgacacctca    50880
acactgctta gtgttgaata gtcaacagga gccacaacca agggatagga gccccgaatg    50940
agcaagcccc gcacctgcac ctcgcagatc gctttcgacg gctgggcga gcagttgacg    51000 ttttcgcctg cgcctgcagt gatctcgcgg ccggtcgcac gcccggcggc gccggtcacg    51060
cctgcgcaca tgagcatggc cgaggcccgc aagatcgcgc aggcgttgat cgccgagcac    51120
ggcctcgtcg ggtggtcggt gacgttcgac aacgcccgtc gccgcgcggg cgtgtgcaag    51180
tacggcccga agcagatcgg cctgtcaaag ccgctgatgg cgcagcgttc atacgccgac    51240
acgtggcaga cgatcacgca tgagattgcg cacgccctgg tgggtcactc gcacgggcat    51300
gacgccgtgt gggccgccaa gcaccgcagc ctcgcggcca acggtcagcg ttgctttgag    51360
cacctcgacg agacgtcgcc gtgggtcggc cgctgcgggc acggcaagga gttcgcccgg    51420
taccggcagc ccaagaacat gaccggctgg cgttgcaagt gcacgcgcgg cggcagcccg    51480
atcgagtggt cgcggcgctg acctcggcga gacgcccccg agcccacgcg gccggggggg    51540
```

```
tttctcgttt cctgttgaca ctgcaacagg tctagtgttg aatggtcaac agacgccccg   51600
ccggggcgct acgggatagg agcccaacat gattgatctc aacaacctgc cgcacggcct   51660
gcgcctcagc gtgtaccgct cgtcgctcgg cgactgcacc aacggcggcg tgtccgcggc   51720
ggccgatcac ctgacgctcg tcgggtgggt caagcccggc gagaagcacg tgcgtgcgct   51780
gtggcccgag tcgcaggtgt tcccggtgcg cgaggatgcc ccggcggtcg tgatggtcga   51840
gtcgaacctg cacggcgccc tgccgcacct ggtgccgctc gacgctttcc tcgcgggcaa   51900
gtggacgatg cacggcggca acctcgcggg cggcgattcc cgtttcggcg ggctgatcga   51960
gcgcgggtac cgcggcccca agtgcgttgc gacgctgccg gttcacgacc gcatcgagtc   52020
ctgatttcgg gagccccggc gagtcgcttg tcagtgatcg ccggggcgcc ctcgccccct   52080
ccacaatcga acagcagcac aacgggatag gagcccaacc aatgaacacg ttcgacctca   52140
ccggcacgac cgcggcgggt accgcgtggt acgtgcgcgg caaccgtacc gacgtcgcgg   52200
cccggttcgg ccggttcttc gtctccgctt cgttcggccg gggccgcagc ctcgccgaga   52260
tcgccagcac cgtgcgcgtc tcgactgagg tcgtcaagtg accgcgccga gcaggcacgg   52320
cgaccgcacg ccgcgcgagc aggcgacgcg gttcttccgc ggctggctgg ccgctggtgt   52380
cgcggcgtcg atcctcggca acgtcacgca tgcgctgctg aacacgcacg ccggtaaccc   52440
ggtcgtcgcg gcgccctcg cagcggtcgc accgatcgcg ctgctcggcg ctacgcatgg   52500
cgtgcacaag ctggtgcagt cgcgcatcat cggcggcgca tacgctgcgt cgctgtggat   52560
caccgtcgcg gtgccctcgt cggcgttcgc gctgtcgttc gcatcgctgc gcagttggc   52620 gatcgggtgg ggcggcattg cgccggttat cgcgtggctg gtcccggtcg tgatcgacct   52680
ctcgatcacc gggtcgacga tcgccttgct ggcgctgtcg agcagcgagc gcgccgaggt   52740
gcgcgtcgac gagcagcccg ctgcgtacac gctcgacgac ctcgcgcagg agcgcgcgag   52800
cgcgtgggcc gaccgtgcgc acgtgcacac cgaggtgcac gctgctgcgc acgtgcgca   52860 ggagcccgca cagcctgccg cgcgtgctgc gcagccggtg cctacgcagg gcgtgcagtt   52920
ggcggcgatc gacgtcgagc cgtcgactga cccggcgctg ttcggcccgc acgcggtcgc   52980
ggccgagcgg atcgtgtcgg agggtgtgac gcggatcgac cgcggcaagg tcgccgaggt   53040
gctcgccgag cacgccgagg gcaccgcgcc gagcatgatc gcccgcaagc tcggcgtcgg   53100
gtacagcacc gtggtgcgca tccttgagca ccacactgcg caggagcagc ccgcgatcga   53160
ggcgcaggcg gtgggcgcgt gagtgtcgcc gagttgtacc cggcccgagt cggcgccgac   53220
ggccgcgcgt ggtttcgacc cgtgcggcct gcgggcgtcg atctgtcgca gtggggttgg   53280
acgtcgcagg cgagcctcgc tcaccccgac tacgggcaag gcccgcacgt cgtcgtgcac   53340
acgccgtcga gcacggctgt gctgtgcggc ggccccggcg cctgcgtcgc gtgcgacgag   53400
gatcggcaga ccggcggcct gcaccgcgag ggcacgtgcg gcggcgactg cagcggttgc   53460
gtcggcgacg gcgagggcgg gcctacgccc gtcgaggctg cccggctgcg cactgaggcg   53520
tggcggcagg ctgcgggtgt ggctgtcggc ggcccggtcg acgacgttgc ggtcgcgtgg   53580
cgtgacccgc tggcgcggcg catggtggcg ctcgacgacg cccgccgggc gatcgaggcg   53640
acgggggttc tgtggtgatg ggcggctggt atcaccaggg ccgcgcggcg aagctgctcg   53700
gcgtgcgcag gcgtgaggtc ggcaagctga tcggccgcgg gcagttgcgc ggcgagcgga   53760
tctcggacgg caacgcggc accgtgtggg cggtcaacgc gcacgacgtc gacgcgctgc   53820
gccggtcgcc gaactatcaa cacgcccgcg acattccaga tacgcggttc ctcgccgcgg   53880
```

```
tggccgtcgt tacgcatgct cgcggcggcg tgtgggcgaa ccgttgggac gtcgcgcggg    53940
tgctcggcgg tgtggctatc gacggcccgg cgggcgacgt cgtcggcgtg ccgtggcggg    54000
tggtgctcgc caagttccgc agggtcgccg ggcgcgggct ggtgacgggc tgcgactgcg    54060
ggtgtcgcgc cgactttgaa ctgaccgagg cgggctggac gctgctaacc gagcggttcg    54120
cgtgctcacg gtagaccccg gcatgaacgt ggcccggcag cgccgcaaga tcacgacgcg    54180
cgctgtcgac gccgacgacg agtacgaggc ggcgtacctc gtcgccctgc tggcgctgtt    54240
cgacgccgcg gtggccgccg gtacgcctcg ccctgcgcgt gagttcctgc tgatgtggtg    54300
cgaggagttc gacagacccg aacctgcttg acgcgcaagg cgacacgccc tcggctgagt    54360
gatcggtcgg gggcgtttct gcgtgcgacc gttggtgctg ctcgacacaa ctgaataggg    54420
ataggagccc ggtttgaccg accgtaaagg gcactcgatc gccagcgtgg agatcgacgg    54480
cgtgctctac acagacgagt ggccgctgca ggcgcagcgc cgagatccgt tgcaaacgct    54540
gcagttctcg atcgaccggg cgctcgggca gcttgccccg ctgctcggca tcaacctgac    54600
cccggcgcag ccgacgctgc gcgaggccgc cgaggatctg ctcgacgccg cgcgggtgtt    54660
cctgcgcgtg ctgttcctcg ccatcgtggc gtgtttcgac cgcctgggcg ccgctgtggc    54720
gggccgttgg cgggtgctgc gtgcgaggcg ctggggccgc acgcgcgggc cgctgattcg    54780
cctctgggac gccgagtaca acctcgtaca gatcatcccg gccgggcggc ctgagtcgtg    54840
gcgtgcgtgg ctgcggcgta ccgctgcgtt cgtgtgggcg gtggtgcgca atggcgcgtg    54900
aggttgcatt cctcgacggc ccgctgcgcg gccgtgtgca gacgatcgac gacgacgcgg    54960
cccgctggga tcgcctcgac gtgtgttacc tcgccgacga cgtcgagcag cccgccggcc    55020
agacggtcga cgacgcgctg tcgtggcttg agcgcgagca gcggcgccgc acggtcgtca    55080
cgtaccggat ctttccgagc ccgtatctcg cggggccgag gtgggtcgct gcggtcggcg    55140
agaaggtcgg gcagaccgtg atgtgtgtcg tgccgttcac cgattatgcc gcgcgcaatt    55200
tccgcgggtc gatcgacgag attctgagcg agcttgcggc cgagcggctg cggcagttgt    55260
gcgtcgccga gggcctggtc gccgaggaga tccgcgagcg gttccgcggc agcctcgccg    55320
aggcgcaggc ggctgctcac ccgacggccg agggcggccc cgataggtac gcggctgcgg    55380
cggctgcgtt gggcgggtac gtcggcgacc ccgatatgcg tctgtcgttg tggcaggcga    55440
tcgctgcggc cccggccgct gatgtgcagg aggtgcgcga gtgagcgcga gcaaggtcaa    55500
gcccggcgac gagtgcctga cgatcttccc ggttacgcgc gagtacctgt gtcgccagcc    55560
gagcgcggtc gaggtgttga cggccgacgc cgcgcgggtg ctggcgcgca tgtgcgacag    55620
cgagggttac gcggcggccg aggtcacgct cgcatggcgg gggagcctca aggctgctcg    55680
tcgcggcggc ccgaacgtgc acaagggcgc tgtcgacgct gctgcgcagt gggcggcga    55740 ggatgacggc gtgatcctgt tcgtgttcac ggcgaaggct gcgaagcgat gacgggcgtt    55800
gcggtcgtcg ccgcgcggat ggacgccgcc aagacgttgg cgaggcgtct cgggttgccg    55860
gtgtcgcggg cgttctctgc gcgcaacgtg acgacgtcgg tacgcggttg tgtgctcgac    55920
gtggtgctgc tcgacgaggg cgtcgagttg tcgcgcgagg tggccgaggc gctgcagtgc    55980
gcgatgctgg gcagcccgtc gggcggcgag gtgttccggc tgcgcagggt gtcgctgccg    56040
ccaccgttct gagcaaacgc cggcaaagca tgccggcgag cccgtcgtcg ctggcaggcg    56100
ggtttcgctc gaaaagtcag caaacgcccc gcgggcacct caactcgcgg ggcgttctga    56160
cgtgttgaca tctcaacaga caggggttag tgttgagcta tcaacagggg ccgcaagccc    56220
ccggcgattt gaaaactcaa cagtgataac gggataggag cccaacatgt ctgcactcaa    56280
```

```
cgtctcccga ttcggcacca tgcgctcgtc gttcacgtac gaggagcttg cccgagatct  56340
cgccaagctg cagccgcggc tgaacgaact caccgaggca tggctcgacg cgcgcaagct  56400
gtacggcgac gagtcgcccg aggaacacgc aatctggtgg cacctcaaca gcgccgagct  56460
cgcaaagtgc cgcatcctgc gcgaggcggg ccgcctcgac aagatcaacg ggattgcagc  56520
ctgatggccg ccgcggattg caacacctgc ggatggttca agagcaccga ccggcacgac  56580
accgcatgcc agttggccga ccagcacgaa gccaagaccg acaccagga gatcgaggtt  56640 cgatgaccca agcgagacgc cccgccgggc cgccacggcg gggcgttttc gtgtctacgt  56700
gttgacagct caacaggttg tgggttacta ttgacatgtc aacagcacaa cgggatagga  56760
gcccacaatg cagaccacga ccaacatcaa cgaggccgcc accgtcgacg agttcaaggc  56820
gtacgtcgtc gagacggccg acagcgtgca cgtgttcagc gacgaggtcg aggcccgcgc  56880
ctggaaccgg cagaacgtcg gcagcagcat gtggaccgcg tacggcgagg aggcgctgcg  56940
cctctcgtag cccggccgcc gggggcgctg cgacaggccc ccggcacctc gcccgccaac  57000
caacctctga tcttgatagg agcccacaat gcgcgcacag atcctcgaca gcttcgccga  57060
cgtcgacacc ttcgccacgc ccgccgcggt cgaggtcaag gcggccaacc tgcgacccgg  57120
catggtgctg ctcgacccccg agctagggac accggccgcc gggctcgacc acaagctgcg  57180
cgcggcgcgc aacagcggca atgtgtcgtg gttcgtcgcc gatcttgaca acggcgggtg  57240
gcgcgagttg cacctgcggc cgtcgctggt cgtcaaggtc gcggcggcct gacctgccac  57300
gatcaacccg cgagccctg gccgaaattg gtcgggggtt ttcgcgcgta cgtgttgaca  57360
cctcaacagg aatggattag tgttgaggta tcaacagcac gacgggatag gagcccaaaa  57420
tgaccggata caccaaggcc gaggccaagg cagccgacga gatcctcgcc accctgacga  57480
gcgcctggtt tgacgcctac accgcatggg agaaggccgc ggatcgcctg cactacgccg  57540
cagacgacag caagacccgg tacggctgga agatgagcca tgagacggcc ctcgacaagg  57600
cgaccgcccg cgcggccgac gagtcgatcg tcgtctacaa ccgcgaggtg tacgcccgcg  57660
cggttgaggc gtaccccgcc gcggtggccg ccaagcaggc cgcaagcgac gcgatcgacg  57720
ctcacgaagc cgagcactac aagggttggc tgcggttctt cctggtgccc ggcgggcaca  57780
ttcaccgctc gcggcactgc tcgtcgctgc ggatcacgac ccgtattggc tggctgccca  57840
acctgtcggg tgagactgag gccgacgccg tcgccgagca cggcgcgatg ctgtgcacga  57900
agtgcttccc gtcggcgccg gtcgagtgga cgatcggcaa ggcggccccg gccgaccagt  57960
gcgcaggctc gggcacgtgg gactacccgc gcgagacggc ccgcatgggc tactgctcgg  58020
gcaactacgg cgtgtgctcg cactgcggcg accgggtgac gatcagcagc acgggcaaga  58080
tgcgcaagca caaggcgccc aaggcgtagc gccccgcgc agcgaggccc tcgtcgagat  58140
ccggcggggg cctcgctacg tgttgacatc tcaacagacg tcgactagtg ttgaggtatc  58200
aacaacggga tagggagccc aaaatgcaga agccagccag caagattgcc gagacgaccg  58260
ccgaggcgct gctcgccgtg ttcgcaggcg agacggtcac aatggatcaa atcgccgagg  58320
tgctgcagca gcagtacgcc ctcgcccgca agcgtgttgc gttcggcagc tacgtgcagg  58380
tgtaccggct gatcgaggcc gccggggcga cgagccgcta caccggcccc aactacacgg  58440
gcgtgtgcct gtacaccttc ccggccgcct gacgccgct gagacgtcaa ccaaccaaca  58500
ccagggatag gagcccaaca tgaccgcaca gaccaccgag gcccgcaagc aggccgtgct  58560
cgcccgcgcg agcatgcccg tgctgctgca gtcggccgcg acgcttgagg ccctcgcggc  58620
```

```
gccgtcgccc gccgagcgca tgacgcgcgc atgggttttc gacgagatcg agcgccgcgc   58680
gggcaagatc acgcttgacg aggagcccga gtttgagcgc gtgtacgacg acaccggctc   58740
gtacctcgcg gcgctgctgc acatgcgccc gtctctgacg gcctgagcgc cccactgacg   58800
cacgaacgcc ccggcgccgg ataggtagcg ccggggcgtt ctgtagcgcg gcctcaaccc   58860
cccaaagtga gaccgcctca agagcgtaac cgacacgcga aatcaggtgt tgacacctca   58920
acagagtgtg ttagtgttga gctatcaaca cgacgggata ggagcccaa atgagcgtca    58980 aggtcactta ccagggaatg aagttcgacg tcgtcggata cgtcgacccg caccccggca   59040
agctcggcac cgatcggatc gagtggctgg aagattgcgg ccgctgcggt ggctcgggcc   59100
tgtaccgctg ggtgaacagc tttggcgtgt gcgagggcac ctgctacggc tgctttggca   59160
ccggcaaggt tgagcgttcg caggccgtgt cgaccgcccg caaggccgcc cgcgaggccg   59220
ccctgttcgc cgagcacggc gacgcaatcg ccgagtacca cgccaacatt gcccgcgaga   59280
acgcagcgcg cgagctggca gaggcgtggg acgccgcgca cgccgagcag gcccgccgcg   59340
aggcccgcct cgccgcgatg aacaacaaca cggttggcga ggtcggcgag cgcctgcgcg   59400
gcctcgacgc cgaggtcgtc gtgtcggccg gtttcgagcg cgacaagtac gcgggctacg   59460
gcaccgagta cgtcaagatc gtggttttca agctcgccga cggccgcgtg ctcaaggcga   59520
tgggcacctc gcgcgacctg ttcggccttg agcgtggcga catggtcaag gtgaccggca   59580
ctgtcaaggg gtttggcgag tacaagggtc agacgcagac ccttctgcag cgcgtcaagg   59640
tcgaggtggt cgacaccgcg gcggcctgac gaccaggccc tcgacgagcc cccgctacgg   59700
cgggggtttc gtcgtttctg cggccggttc attttcgacg agcagtgaac gcgattgacg   59760
ccgcgcgctt ttagactctc cgacgcaaca gcacaactgt gcccaaaacg gccccggctg   59820
ccccgatcgg gtggcatggg gccgtttcca tagctggccc aacccgtcgc ggagcccagg   59880
cggcacgcgg tcgcagcgcc caggcggcgc gcgaagcggg ttgcgcctag cccgtcgccg   59940
tgatcctgac tctggcgtta cgccatacgc gattaccgtc gcggcctcgc tgcgtggctg   60000
gtcacccgca agcaagccgc aggcgcacgc gagcgaggtc gagcgatccg gcggcgggct   60060
caaacgtcca accaactaga ccgacgagcc gaggagatcc gcacacatga gcccgaaac    60120 gatcggcaag attctcgccc cggccgcggc ggttatcgcc ccggtgctcg ccgacaagct   60180
cgccgagaag ttcgacgaga agctcgacga gatcgtcgac cgcgtgctcg atcggctgct   60240
gcccaagctg ccggatctgt ccaagctcga cgacctggtc gaggccgcca tacggggcgc   60300
tttcaacgcg ctgcccttcc cttttcaagat ctgaggttct gagcaatggt gttggagcgc  60360
aacggaatcg tggaaagcgc cgaggctgca gcagccaaga gcgatgcggc cgtggccgag   60420
gcccttgccc ggctggctgc gcctgctgct cggcggcccc ctgaaacgcc gcagggcgtg   60480
ccgggccgtg ccgggctgcc tgtagacgcg cctgccgaga tcgtcccgca ggagcccgta   60540
caggcccccg tgcagcaggc cccgtacag gcggcgcctg tgcaggcccc cgtgcaggag   60600
gcccctgtgc aggaggcccc tgtgcaggcc cccgtacagc aggcccctgt gcagcacagc   60660
aacctgatgc ctgcccctgc tggtgcaccc gtgcagtatc agcccctcga cgccgaggcc   60720
accgctgcga gcacaccacg caggcgggcc gatgcgagca gcccgttgc atacgaggg     60780 ttctcgttct gacatgagcg agggccgcaa cacagcgagg cgtgatcgct ttcggcgtgt   60840
catcaagcgt cgaggcgacg actgccacct gtgcggcctg cccatcgact acgacctgcc   60900
tcacgatcac gaactgtcat ttcagatcga ccacataacg ccgcttgccc gcggcggcac   60960
ggacacgctc gacaacatcg cggcggccca tcgcaagtgc aaccgcgaca agagcgacac   61020
```

-continued

```
gctgcccgag gtgttctcgg gcggcgtcac cttcgtgacc gagcgagtct ggacgccctg    61080
accgggccga ccaggcaccc cctgggggta tgaccccgac ccccgcgcg cgcctctcg     61140 atggcat                                                             61147
```

<210> SEQ ID NO 5
<211> LENGTH: 60835
<212> TYPE: DNA
<213> ORGANISM: Anaya mycobacteriophage

<400> SEQUENCE: 5

```
aggcaccttt ctctccccag catttttttc caagccgatt cagcgttttt ccacgcccga     60
ccagcacagg agcaaccaat gcacatgacc gaatccgaac cgactgcgcg cgtgtgggcg    120
ttcgaggatc agcgcgaccg cgcggtgcgc gagcaatcaa tgcacatcgc gttgaaggcc    180
gccgacatcg tgggtctcgg cgacgtgacg ctgatcgagg cggccgacaa gatcgccgat    240
ttcatcctcg acggcaaggt cgaccggcgc cccgacgctg agcggagccc cgaatgatga    300
cgcccgccga gcgtctcgcc gcgcagcgcg aggccctcga caagcacgag tggaccgagg    360
tcgagggcga cctcacgccg atcacgctgc actgtctggt cgctattggc gaggtgctcg    420
tcgagctgaa cgcccggcag gcccgccagg aggccgcagc gatgggcgcc ccgtcgtgag    480
cccggtcgtc ggcgtcgtgt cgcgcacgct cgacagcgcg gcccggctcg cccgcgcgct    540
gaacgtggct cgcaccgttc caatgagcgt gccgtcgatc aagcaggggc acggccgcgg    600
gttcagtttc gacgccgtga tcgtcgacga cgaggtgatg ccgctcgatg actgtgtgct    660
cggcacgttg gccccggcga tgcacgctca cggcggaaag atgtacgcgg ttcgggaggt    720
tgagctgtga ccccgactgt cggccgcatc gttcattacc agtcttacgg cacgcccggc    780
ggcgagcacc tgcctgagcc ccgcgccgcg atcgtcacgg ccgtgctcgg cggtggcgtc    840
gtgagcctgt gtgtgctcaa cccgtcgggg ctgttttttca acgagtccgt gcgccaggcc    900
gacgagccga cgccgggccg ctggaattgg ccgccccgca actgatctag cgcgcgtagc    960
ccaaccgacg gatagaggcg gctggtaatt cggcgtcaac gtgccgggcc tcgtcagccc   1020
ggccgcgcgc aaatgggtgt gtagctcaat tggcagagca gcggtctcca aagccgccgg   1080
ttgcacgttc gagtcgtgcc gcgcccgctt ccacaccggc taaccgccgg cgatccgcat   1140
tcccgcacgt caacgccacg aaaggccgtt ttgagctaac acggcacctc aacacaccag   1200
gagatatgac catgcgcgca cccgctaccg ccgaggttcc ttgcccggcc tgcggcgagc   1260
cgatcacgct cgcccttggc tttgagctgg ccgagcctga gcccggcgcc acgactgccc   1320
caatgttcgt gaggccgctc gacattgcag agcgcgcgca ggagcacggc gaggtgtgcc   1380
cggtgtggtc aggcggtggc cgcgatgact gacggcaagc tcgaccggct cggcgagctg   1440
cgacggttgc acgagcgcat ctcgtccgcg gtgttcgacg aggagacgcc gccccgcgac   1500
ctcgcatcgc tgagtcgtcg actcatggag atttccaagg agattgaggc gatcgagctg   1560
cagcgcgctg agacgggcga gggcgccccc gaagttccgg cagatgaacc gttcgatggt   1620
tcagacctgt gagccgcggc tatccgaggt tgctcgccac gtaatcaagc ccgagggcat   1680
cacatcgacg tcgtggccgt ccgttcgcca cgagtgcaac gtcaacatgg ggttgttttt   1740
cgaccaatgg caggacgacc tcggaaagct ggtatgcgcc aagcgatccg acggcctgta   1800
cgcggccgac atgttcgcca tgtcggtgcc gaggcagaca ggcaagacct attttctcgg   1860
cgcgatcgtg tttgcgttct gcaagatgaa tcccggtaca acggtcatct ggactgcgca   1920
```

```
ccggacacgc accgcggctg agacgttcaa gagtatgcag gcgctcgcca agcgcgagca    1980
gatcgcsccg cacatcttga atgtgcacac gggcaacggc aaagaggccg tgctattcac    2040
caacggcagc cgaatcctgt tcggcgcccg tgagaaaggg ttcggccgcg gtttcgccaa    2100
ggtcgacgtc ctgattttcg acgaggctca gatcctcagc gaaaacgcga tggacgacat    2160
gattccggcg accaacgcct cggctaacgg cctgatcctg ttcgcgggca cgccaccgaa    2220
gcccaccgat cccggcgagg tgttcacaaa cctgcgcatg gacgcgatca acggcgaatc    2280
tgacgacgtt gcgtacgtcg agatatcggc cgacgagacc gacgacccag acgaagagtc    2340
gacgtggcgc aagatgaatc cgagctaccc gcaccgacg tctgcgcgag cgatccggcg    2400
tatgcgtaaa gccttgtcct gggacagttt caggcgcgag gcaatgggca tctgggacaa    2460
gatcagcgtg cacgcgcagg tgatcaaggc tggcttgtgg cgcgatatcg ccgacccgct    2520
cggccccgag gacggcgcca aaccggcatc gctcggcgtg gacatgtcac acggcggcgc    2580
tatctccatc ggcggctgct ggctgatcga cgacgagcag cggcacgtcg agcaggtttg    2640
ggctggcacc gacaccgcgg cggccgtcga gttcatcgtc aagcgtgcag ggcgacgcat    2700
cccggttgtg atcgacgacg cgagcccggc gaaatcgctt gtgcctgagc tgaaacgccg    2760
caaggtcaag gtccgcatta cctacgcggg cgacatggcc aaggcgtgcg gcctgttcaa    2820
gaacaacgcc gagggcgaca ccctcacgca cggcgatcag gtcgacgtca ccgaggcgct    2880
caagggcgcc aagcagcggc cgatccgcga cgcgggcggc tggggctggg accggcgaga    2940
cccgacgtgc gtaatccacc cgctagttgc cgtgacgctg gccctgcttg gtgcgctcga    3000
cgccccgaag cgcagcggcg gcgcgatgtt cgtatgagag gggccgtgt gattcccgct    3060 gcctatgacg acgacagcca gctcgacgag cccggcgaaa tcgactggcc cgctgacgcg    3120
ctcgacgcca caagatcgg cgcgctggtg cagcgcatgt acgcgctgca cctcggcgac    3180
cgtcattcgc tcgaccgcat ccacggatac accaagggtg agcgtggcgt gccgagcgtg    3240
cccgacgagg cgagcgagga ggtgaaagaa ctcgccaagc tgtcgattaa gaacgtgctg    3300
cggttgatct gcaactcgtt cgcgcagtcg ctcagcgtgg ttggctaccg ctcgctcacg    3360
gcgcccgaga actctccggc gtggcgcatc tggcaggcga acaagatgga cgcccggcag    3420
gccgaggtgc atcgcccggc cgtcaaatac ggcgcctcgt atgtggttgt gacgccgggc    3480
gtcgacggcc gcaagcctga gatccgttgc cgctcaccgc ggcagctcat cgccgtgtac    3540
gacgacgcgg tgctcgacga ctggccgcag tacgcgcttg aaacgtgggt caccacgaag    3600
gacgccaagc cccggcgcaa gggcgttctg tacgacgagc ggtacatgta cgagcttgac    3660
ctcggcgagc tgccgctcac gtcgaccggc cagcccgagg ttgcgacgaa gcccgtcacg    3720
ctgcgcgacg tcgaggacat catcccgcac tacggcaccg aggacggtaa gcctgtctgt    3780
ccggtcgtgc gtttcgtcaa cgaccgcgac gccgacgaca tgatcgtcgg cgaggttgag    3840
ccgcacatcg gtatgcagaa ggcgatcaac tgtgtgaact tcgaccggct gatcgtgagc    3900
cggttcggcg ccaacccgca gcgcgtgatc agccggatgga ccggcagcaa aaacgaggta    3960
ctcaaggcat cggcgttgcg cgtctggacg tttgacgatc ccgacgtcaa ggcgcaggcg    4020
ttcccgccag cctcggtcga gccgtataac gccgtgctcg acgagatggt gcagcacgtc    4080
gtgatggaag cgcagatcaa cccgtcacag gtcaagctcg tcaatatcag cgccgacgcc    4140
ctggcggcgg ccgagcaccg cgagcagttg aagctcgcca ccaagcgcga gagtttcggc    4200
gagtcctggg agcaggtttt gcgcctgcc gtcgaaatgg acagcgacga gggcacgagc    4260
cccgatatga ccgccgaggt tatttggcgt gacaccgagg cccgttcgtt cggcgccgtc    4320
```

```
gtcgacggga ttgtgaagct ctcgcaggcc ggtgtgccga tcgagtacct gctgccgctc    4380
gtgcccggca tgacgcagca actcattcag gcgatcaaag aagccatgcg cagcggcggc    4440
actcaggcgc tcgtcgacag gctgctcgcc gcccccgagg tgtcgctgcc cgacgcccg    4500 ccagtcgacc aggcgctcgc cagcgccgac agcggagggg gcgagggtga cggagccgaa    4560
ggcggtaccg cagtttcagg gggcgctcgc ccgtctcagt gatgaggcag gcggcgccgt    4620
cgaccggctg atgccacgcc ttggcggcct cacgcgatcc gagggcctcg ccgtgatcag    4680
cgacgtctac ccggcgctgc tcgacccgtt cctgtcggcg tcggggagc tgacgacgca     4740 gtggtacagc gagcaaacgc cggccaaact ggttggcgcg caggtcgcag gcacaaaagc    4800
cctcgccccg gcaaaggact tcctgcctga gcctgccgca ctgccggatc gccgccagct    4860
cgcggcgtcg ggccgctggg cgctgatgca acgcaaccct ggcctggcgc tacgcggcac    4920
tgccacccgg tcagtgttcg actcgtcccg ccgcacggtg cgcgacaacg cgatccgcga    4980
gggcgtcaag tggacgcgct acgcctcggc gaacgcctgc gggttctgcc ggatgctcgc    5040
cacccgcgcc ctgacgaccg aacgccgcgg cgccccggc ctgtacacca gccgggcgac     5100
ggctgagcgc aacgcgcaca cggtcgatat ccgcggccac gatcactgca agtgcctggc    5160
cgtgccggtg cgcagcggtg gctacacgcc gcccgaatac gtgaatgact ggctcgccga    5220
ctacgacgcc gtgagcgtcg gcccgacgg tgccctgcgc agcgagtggc agatcgcccg     5280
gctgatggaa gcccgcgccg acgagcgcct cggcaagccc aaacgcaagc ccggcaggcc    5340
ccgcaaggcc gcgcagccga tcgaggacgt gcgcagcaca ccgcgcgaaa cggtgcgcac    5400
tgcacagcac ctcgtcgaca ccggcaacga ccgcgctgca gcgtacggcg caatcgcgca    5460
cgagcaggtg ctcactgcgc agcaggtgat cacccgagct gacgaggttg tcggcaccgc    5520
ggcgcacatc acgcaacggg tcaagctcgt taccgacgtc gccgacaagg tgctcggcgg    5580
tgccgtgccg gtcgtgcgcg acgtcaagcg tgtggtcgac gctgccgaca aagcgctcgg    5640
cggcgcagcg caggtcaccg gcggtgcgcg tcaggctgcg gacattgccg cacaagccat    5700
cgacagcacg gtgcaggtgg cgcacggcgc gaagcagatc gccgacgagg tgcgcagcgt    5760
gatcgacgag gtgggcctcg tcgccgccgg tgtgcgcacg ctgttcacgg atacgcgcgt    5820
cgctgtgcac gacacggtgc gcgatgcccg caccgtgcgc agcctgtcgg acctgtccga    5880
gcagatcggt gcagcggccg acaccgcacg gcacatcgcc gacgacggcc gcgcgctcgt    5940
cgaccgcgcc aagggtgctg tcgacgcaac gcagggcatc gcacggggcg tccgtgaaat    6000
accggacctg ctgcgcaagc cgatcgccga cgcgcaagag ctggcgcaaa ccatcgccgg    6060
ggctgccggt gacgccagcc aggccgtcga cgaactgcag gacgtcgctc gtgcggtgcg    6120
cggactgatc gacgcggtgg ccggttccgc cggtgaggac gttcgcaagg ctgcccgcca    6180
ggcggccgac gacctcggcc gcatggttgg cgatctgttc aaggtgcccg aggcgcctcg    6240
cgtgccggtg cccgtcatgt ctgaacggct cgacgtgcca ggcgctcgtg tgctcggcgg    6300
tggcgagcca gtcccggcga ttgccgaacg gatcggcctc aagccactgg acggacccgc    6360
ggcccgccag gcgctcgacg gccgcccgcc gatgaaagca cttgaggcgg cacccgaacg    6420
cccgtcagtc gccccgctcg acgtcgaggt cgtcgaggcc ccggcgccag caccgaagcc    6480
gaagcccgcc aagcggacgt tcgacgacgt agaggccgag tttcaggcgg ctgtcgaggc    6540
tggcgacgac gcagcgatcg aggcactgac cgccgaaatg gagaagctcg aagcggccga    6600
aaagaaggcc gccgaacgcg ctgcagcgaa agctgctgcg aagcaagccg aaaccgaggc    6660
```

```
caagaccgac cgactgcttg agctgatcga gcagggttgg gatccggccg aggctgaatc     6720
ggaagcgttc ggcctgtcgg tcgagttcat tcggcgccgc gacttcatgg ctgaggctcg     6780
cgctgccggg catgagggcc gatcgttcga cgagctgctc ggctgggtgt cgaggagcg     6840
catcacggag gcgtatttcg ccgccgagga cgcgacccgc gggcagatgc tcaaacggcg     6900
ctacggcccc gacggcaaga atgtcgatcc gcgaaagctg tggactctca acgagacaac     6960
ggcccgcaag tacatgtcag aggagatggc cgagtggttc gaccagcacg gccgcatcac     7020
tcgcgctgga ctcaaggagg cggtgctttc tggtagcggc aactggcgca acgccatgac     7080
gtcggacttt ctgcaatgac ccgcgacgaa ctggtcgccg cgtaccgagc ggggcgcgcg     7140
gcggccgtcg gcgacgtcaa cccgtacgag ggcaccggcg cccccgcgcg actgtggcgc     7200
aggggttatc gccagatgct cgccgcccgg ctcatgcaat cacccgcgct gcgcgcgtat     7260
ctcgacgcgc aaaagaactg acgcacgacc cacaactgaa taggagaaac accaaatgtc     7320
cgatatcaac ccgaccgaag gcaccgaagg caccgaaggc ggcgaggccc caaggctgc     7380
cgccccggcc gtcgacgatg cccccaaggt cgacgccccc aagacgtaca cgcaggccga     7440
ggtcgacgcg atgatcgccc cgctgcagac tgccgccacc gagctgcaga cgatcaagga     7500
cggcgaaaag accgagctgc agaaggcact cgaccgtgcc gccgaggccg aaaagcgcgc     7560
cgaaaaggcc gagttcacct cgatgcgcga aaaggtcgcc aaccggcccg gcaaggtcgt     7620
gcccgtcgcg tcactgaccg gcaagaccga ggccgagctg atcgcctcgg ctgacgcgct     7680
gatcgcctgg cgcgacgaga acgcccccaa gccgcccgag gccccgaagc agaagcgcaa     7740
cccggccggt agcggcggcg ggttcaagag cggtgccacc ggcgccgacg gcggtacgga     7800
cgatccgaag gtgcgtgccg tagaagcgtt gcggcgcttg cgttccggca agtagcaccc     7860
cacttctcaa cacttccgca cgaggaccga cctcggcggt tgatcaacac aactgaatag     7920
agagagaggc cgtaatggct gacatttccc gcgccgaggt cgcaaccctg atcgaagagg     7980
gttacagcca ctcgctgctg gccgccgcga agcagggcag caccgtgctg tcggcattcc     8040
agaacgtcaa catgggcacc aagaccacgc acctgccggt gctggcgacc ctgcccgagg     8100
ccgattgggt cggcgaatcc gccaccgacc ccgagggcg catcaagacg agcaaggtca     8160
cctgggccaa ccgcacgctg gttgccgaag aggtcgccgt gatcattccg gtgcccgagg     8220
ccgtgatcga cgacgccact gtcgaattgc tgaccgaggt cgccgagacg ggcggccagg     8280
cgatcggcaa gaagctcgac caggccgtca tgttcggcat cgacaagccc gcctcgtggg     8340
tctccccggc gctgctcaag gccgccaccg acgccgggca ggccctcgcc cacgtttccg     8400
gtgtcgccaa cgagtacgac ctcgtgggcg cctccaacaa ggtcgccgag ctggtcgccc     8460
tcgccggttg ggctcccgac accctgctgt cgagcctggc gctgcgctac caggtcgcca     8520
acgtccgcga cgccgacgga aacctcgcgt tccgtgacgg ttcgttcctg ggcttcaata     8580
cccatttcaa ccgcaacggt gcgtggtcgc ctgagtccgc ggtggccttc gtcgccgact     8640
cctcgcgcgt caagatcggt gtgcgccagg acatcaccgt gaagttcctg gatcaggcca     8700
ccctcggcac cggcgacaat cagatcaacc tcgctgagcg cgacatggtg gcgctgcgcc     8760
tcaaggcacg gttcgcgtac gtgctgggtg tgtcggcaac gtcgatgggc gagaacaaga     8820
ctccggttgg cgttgtcacc cctgacgtga cgccgccctc gggcgagtag tgcggtatcg     8880
ccattccctg acgggggcgg tcatcggggt gtctccgggc accctgctgg ccgccgtcgt     8940
cgagggtaac ccgaactgga ccgaatacga ggggtggcc gatgctggca agtctggacg     9000
acgtaaaggc cgccctgcgg gcaatgcgaa agcccgagct ggcggaaagt ctggcggaag     9060
```

-continued

```
cggacgtaac cgacctgctg caggaggcgg ccgacctggt gacggggcac ctgtggccgg   9120
gggaggtgcc gacaccgacg ccgcccacga tcacgagggt gacggcctcg gtggtggcga   9180
cagcactcac gaagccgacg gagctgctac cggagacgga gagcctgcaa gctgacgggt   9240
tcggcgtgaa gttcacaccc ggcgccggtt cgccgggctg ctacctgaca gccgcacaca   9300
agacacgcct gcggccctgg aagtgcagcg ccgtctcggt tcccatgagc agcgagaggt   9360
acccgtgatg ctgccgaccc cgtttgaggt gcagcacacg acgtacgtca aggtcggcga   9420
gaacgccgcg ggccaggcca agacagagcc acgcactcgg ccccgcaggg tgtcgagcct   9480
gcgcaagcgc gtcaacgagc ctggtaccgc ggcggccaac tccgatcagg tcgtcgtcga   9540
gtacaccatg acgacacccg aaagcgattg ggcgcacggc gatctggtca aggactggcg   9600
cggccgtgag ttcaaggtgc acggcgacgt cgacgactac aacagcggcc cgttcgggtt   9660
ccggcccggc tacatcgtga cactgcgaaa ggtggagaaa cgtgccatac cgtccgcttg   9720
atctgccgat cgacgatcac cgcaagatcc gcaacctgcc cgacctcacc aaggcgtgcg   9780
agaagctcgg cgacaagctg cgcggcaagg cagcggccaa ggccaacgcc cacacgcccg   9840
gcgccggtga cgattacgtg accgagaccg tgcacgcccg cgaccgtgtg cgcgtctacg   9900
tccgagctga gggcgcagcg atcggcgtcg agaacgacat agcgccgctc atgcaggtgt   9960
ctgcagaatc ggggccgcgg tgacggtact cgttccgcca gtcggcccgc tgacggccgc  10020
ccgccggtac ctgctcgacg agctggccgc tcgcggcaac ccgctccccg tcgagcagca  10080
gacggtgccc gagggctcgc cgacgtcgta cgcgatcctg tcacggcccg gcacgagtac  10140
cgaggtgttc ctgcagcaca gcctcattcg ggtgcgcgtc tacgacagcg acctcgtgcg  10200
gttggagcgc aacgccgacc tgctgcaccg gctgctgctg cacgccgtgc accgcaaggt  10260
cgttgtgccc gacgagggcg aggtgtggat caccggcgcc acacacgaat acgggcctgc  10320
cgagttcgac gaccggcgcg taccgctgcc cggctaccag tcggcagtgt tctggacgat  10380
cggcctgcgc cccgagcgca gctaacccac cggccgacgc cggccaacct cgagaaccgc  10440
gcttgacgtg cggcgattcg cgctgccgcg attcggcagc aaacacaact gaatagatga  10500
acggagacaa caatgacgca gcccactccc tcggcgctgg gcgacgccac caaggtgttc  10560
gcagcgtcgc cgtcggacct ggaaaccgtt ggcggcctgt ggttcgcacc gttcggcact  10620
gcactgccga ccgacgtcga cgagcccctc gcggacgcat tcaagaacct gggtttcgtg  10680
tcggctgacg gcgttaccgt caagatcgac agccagacca caccgattga ggtatggggc  10740
ggcgacgaaa tcggggcgct gcgagacaag ttctcgatcg agtacagcat gagcctgttt  10800
caggtgctgt cgcccgaggt caatgcggcg atcttcggcg cgggcaacgt gtccactgcc  10860
gcggcgaccg aggcgcacgg cgcccgcatg aaggtgctga tcaactccaa gctgcccaag  10920
cggtgcagcc tggtgctcga ttcggtctac gaggacaaga tcattcggca ggtcgcgcag  10980
atcgcgcagc tttccggcct ggccgacatc aagctcgtgc acaacgcccc gatgcgcttc  11040
gagccgacgt tcaaggtgct taagggcacc gacggcaatc acgtcatcca gtacagcgac  11100
gacgggcagg ttatcgccgc ctagtcgctg accccgatag accagcaccc cgcgcgtttt  11160
cctggtggcg cgcggggtgc tctctcgccc tacccaaaac accagggaca caccaggaaa  11220
cacaccagag aggcaatacc agcatggcaa ccaagaccaa gaccaacgac gacctgaccg  11280
acgtcgacga ggcccccgcg gctgtcgagg ccccgaggga cgagcaggcc agcatcgccg  11340
aggcgtgggc cgaggactac gacgagggca ccgagctgtt cgtcggcaag ttcgacgctg  11400
```

```
acgacttcga cgccgattac ggcgtcgccg agttccccga gggcgcaacg atcgccgtca   11460
agcggtgcct gcgcaagccg cctcccggct ggattcgcca gcacgcgcac ctgtccgacc   11520
ttgagcgcac gttcgctctg atcgaaatgc acgccagcga ccgtgccctc gaaatcctcg   11580
acagcctgca gcagaagccg tgggatgact tcgtggagcg gtggggccgc gatgcgggc    11640 tgatcgaggg aaaatcgcgc aggtctgcgc ggcggcgcgc caggtagagg acgcaatacg   11700
gcgtgacttg atcctcgccg ggcgcgagta cgacgacggc acgctgtcgt gggacgacct   11760
ttacgcattc atctttgcct cgccgccagg gtcggcaata ttccatgcct ttgaaaaggg   11820
ctggaataca accgattacc tgctcgcgca cgtcatcgac gcgctgcggg tcggcctgtg   11880
gcagcgcacc gaggatgcga caaagcccaa cccgcgacac gtgcccgagt tgttcccgcg   11940
ccccggcgat ggcgagaagg acgacgacag cggcgattac gtccaagtgg gctccactgt   12000
ggcgaccaag acaacggtcg gcaagttcct agaaatgcgc gcagaacgcg aaaagcgttg   12060
gcgtgaacga aaaagggca agagcaaggg ggcgtaaatg tccgcaacgt actacctcac    12120
agttctgcct gagacgagca agctcgttcc cggtatccga acggcaatga agggcgccga   12180
gaaggatctg accctgcagc ccaaactcga cacccgcggc gccgctgagg cgggccgccg    12240
ggtcgggcgc gacatgcagg acgggatcga gcagtcggcc cgcggtgctg gcattggccg   12300
gttcctgcgg gccgacggcg ctcgttcggt agggcagcaa gcaggcagcg agattaacgc    12360
gggcctgcag tcggccgacg tcggccgtgg cctcgggtcg cagctcgcgt cgaacctcac   12420
aagcggcgca atgaacctgg ccgcaacgt cggaagcatg attgcgaccg gcctcaaggc    12480
gaccgcggtt gtcggcggca cggtcgccgc cgcgggtatc gctggcgcat tgcacgccgg   12540
tatgagccgg ttgacagcga tcgacgatgc caagttcaag ctgcagggcc tcggcaacga   12600
cacgcaaaag gtccagaaca ttatggacaa cgccctggcc gccgtcgaca agacggcgtt   12660
cgggctcgac gaggccgcca ccacagcagc gtccgcggtg gccgccggta tcgagccggg    12720
cgagcggttg accggctacc tgaaaagcgt cgccgacacc gcggctatcg cgggcacgtc   12780
aatggccgat atgggcgcaa tcttcaacaa ggtgcagacc tccggcaagg cgttcactgg   12840
cgacctgaac atgctttctg accgcggcct gccgatattc acttggctgc aagaggaata   12900
cggcgttacc ggcgaggcgc tctcgaagat ggtcagcgag ggcaaggtcg acgccgcgac   12960
attccagaag gtggttgccg agcgtatcgg cggcgccgct caggaaatgg gcggcagtat   13020
ccgcggccag ttgtccaacc tcaaggcggc ctactcgcgt ttcggcgctg agctggccgg    13080
gccgatcttc gcggccgtgt cgccgttaac taccgctttc acaggagctt caacaagat    13140 aaccgcggcg atcaagccgt acaccgcgca gttgacggcg atcattgggc cgtgggcaac   13200
tgacctcggc aacaagatca cggcgtggct cgacaacggc ggcattcaga acgtcatcga    13260
ctggatgggc cgcttggtcg accgcgtgca ggcgttgcgt acaggcgagg gtcgaggcga   13320
tgcgctgcag tcgatttcgg attctgtcgg caagctcggc ccggcgctgc agcaggctgg    13380 cccgcgctg caaggcgtcg gatcggcatt cgcgcagttc ggccggacga tcgccgagat    13440
tggaccggcg acacttagcg gtgtcctcac gcctgcgctg aacctgctcg ccggtgcgct   13500
gaaattcgtt gcagataacg cctcgtgggc agtgccggtt atcggcggtc tcgctgtggc   13560
gttcctggcg gtgcgcgctg cgacagcggc ggctgcaccg ttcatgcagg cgtacacggc   13620
gacgttcaac ctgattcgca gcccggtcat tctcctgcag gcgcaagcgc agcggcaact   13680
cgccgccgcg atgacgcagc acacggccgc tctggtggcg aacactggcg ctcagagcac   13740
aaacacggtc gcgcagaaca ccaacgccgc gacctcggtt cgctcgcgta tcgcagcgat   13800
```

```
ggcctcggcc gtcgccagtc gcgcagccgc agccgcgcaa tggctttgga atgcggccct   13860
gaccgcaaac ccgatcggcc tcgtgatcgc cgcggtggtc gctatcggcg tcgcattgtg   13920
ggcgttcttc accaagacgg agaccggccg caagctctgg acaagatttt ggaccgggat   13980
taagacgacg gcggtcgtag tttgggactg gctcaaggtc gcgttcgact ggctcggcga   14040
aaagctcacc tggctatggc agaacgtcgc ggtgcccgca ttcgagggca tcaagggcgc   14100
cgtcgaaaca ttctggaagg cgcaaaagt cgtctgggat gcgttcacaa cggtgctcga   14160
cacgatcggc accaaggtag gcgcgttcaa ggacggcatc gtatccgcgt tcaacgccgt   14220
gaaagacgtt gttacgtcgg tgtggtcggc cattggcgga atctgggaca gatcgtgggg   14280
cggcatcggc accgttgcgg acgccctcaa gggtgcgggc ggcacagtgc tgcgggcatt   14340
cggcctggac ggcgctgcca gcggcggcta catcgagggc ggaatggcac ggtacgccaa   14400
cggcggccag atcaacggcc ccggtaccgg cacgagcgac agcattctcg ggttcccggc   14460
aatggtccgc gtggctaacg gcgagttcgt caccaacgcc cgcacgaccg ctcaatacct   14520
cccgctgctg caggcgctca cgccggtat gccgctgagt gacgtactgg gcaagctgct   14580
gccgcggttc gccgacggcg gcctcgtgtc ggccgacgag ctagtcgatt tcgcgcgtgg   14640
cgtcgagggc aagccgtacg tgtggggcgg caccaactgg ggcgactgct ccggtgctgt   14700
ctcggcgatc gccaattacg caactggcct ggccccgttc ggctcgcggt ttgcgactgc   14760
atctgagggt gacgaactgg ctaagcgcgg gttcaagccg ggccttggcc cgtcgggctc   14820
gctgcaaatc ggctggtaca acggcggccc tggcggcggt cacacggcgg caacgctgcc   14880
ggatggcacg aactttgaaa tgggcggcgc acgcggcaac gggcagtttg gtggctcggc   14940
ggcgggagcg gctgattctg agttcacgag ccgtatgcac ttgccacccg aggcgtttac   15000
gggcctcgac ggcggggcgc cgacgatcgg gtcgagcacc tcggctcgcg cgccggtac   15060 ctacaccgcg gcgacaagct cgcagttgag cgcgtcgtcg cgcaaggtcg acactgcccg   15120
cacgtctgcc aagaacgcca atcaggccgt cgacgacgcc acctatcggc gcgacaaggc   15180
gcagacgcgg ctcgacgagg ccaagggcaa gggcaagggc gtcgacgatg ctcagcactc   15240
gctcgacgtc gccaaccgcg agctggccga cgccaaggag cggcaggcca aggcgcacga   15300
caaggtgacc gacgctgaga acgccgacgc cgaactgcgc actaagggca gttcaaaga   15360 gggctcgtcg tcgtcgtcga gtggcgacgg cctgtctggt gctgactttg gcaagacgtt   15420
cgtatcgggg gcgcttgagt cgatcggtct cgacgggtcg ctgttcagca atccgcttga   15480
gtggccgacg gttaagtcgc tcatggcggg ggtgaactac gcgggcggcc tgctcgccaa   15540
cggcaccggc gccgcgacaa gccctggtgg cttcgctgac ggcgtaggcc aggcggtcgg   15600
gctcgatggc ctcatggcgg cgcttccggg cgctgtgggc gatcctgcgg ccggatggac   15660
acctcagagc ggcagccctg cgctggcgcc cggtcagttc aacccggcag tggcaggcgg   15720
cggcccctcg atcgccgagg gcgtcgccaa cgcgatgagc gcattcgcac cggacgcaac   15780
gcagcacggg caaggcgggg gagcagcacc cggcccccgcg ggagacgtga atttcaacgg   15840
ccccgtgggc atggacccgc aagccctgcg aaccgagttc cgtaccgagc tgaacgcgcg   15900
ctcgcgctac agcggcagct caaacgtcaa gtaggtagct aactgccggc gagccgccga   15960
tcgggtctct gacctgcggc ggctcgtcgt gccagctaac gaactttcac aactgaatag   16020
cggggtgagt gagccgtgac tttggcggc atccatgacg atttctatct cgacccgccg   16080
aagtacacgg atgacgccta cgggcgcccg ctgtacggcg ccgagaatcc ggcgcacccg   16140
```

```
agctggcggc gcatgtcgca ctggggcgac ctcgggcgca acggcgagta cctgcggtca   16200
acgcagacga agtgggtcta tatccacccg agcaacaaca aggtttggca cctcgccggg   16260
ccaatgcggg gccgtgaggg cgtcgtgctg gccaaggagc ttgagggcgt tatgcagccc   16320
gagtttgaaa ttctctacag cgagggtgct tacacgatcg gcgccaagcc tgagcggatc   16380
aactacaaga aacggacgat cagcctcggc gtcgtcatcc agcccaacgg caacgccgag   16440
cgggtcgagg agcctaatcc gttctcgtac cggctgattg aggactcgtg gtggtcgtct   16500 cttcggaga cgcagcccgg tttcctcggg tcgttcaccc gcacgcacgg ctggcggtgg   16560
ctggctgtga tcctggccga ggcgtcgaaa acgtctctca agatcgaccc gacggcgcac   16620
gacaacaact ctcagcagta caacatcgtg ctgcacgccc cctggccgtt ctacgccaag   16680
cgcacgctga gcaaggcgtg gctgtccgac ctcgagaatg tcgtagcgaa cgacggtgtg   16740
gcgcagggga ttatccagtg cccgaaccgc ggcacctggg agtcgtggcc gaagtacctc   16800 gttaagggc acgggcaggc gtggattcaa gacggcaacg acgggcaaat gatcaagctg   16860
cccaagttct acgagaccga cggcgagtac atgctcgtcg ataccgatcc gactaagcgc   16920
acgatcacaa ccgagaaaga cccggttgac gggcagctct acaagtatct gcgcgggtcg   16980
cagttgcttg agctgctgct gcacgacgtg acggccgcgc gtctcccggc gcagcgacgc   17040
atccccggcg gcatcgggtt cgacggcaag attccgccgc gcgaggtcgc caatatcaaa   17100
gtgcggcacg acaacccgta cgggtcgatt acgtgcgtca tgccgcagca ctaccggatg   17160
gcgtggtcat agatgtatgt acagaatggc cgcaagctgt gggtgccacc agcgtgcggc   17220
gctaacggcg tccctgatcc cgtcaggaat ccgatcgagg cgtttcggta tctcgacctc   17280
aagcgcgatc tgatcgacgc cgaggcgcgc gagaagcccc tcattcggct gtgggacaag   17340
gcatttaagt acatcggcac cgtggcggct gagaagtcgg tcgacgccga ggaaatgctg   17400
cacgacaccg ggcagggcga cattttgctg cgcggcgacg actggctcgt cgagttcatg   17460
cgtaccgacg tgcgccgcga ggaggatctg cacgtcacga tcgacccgta cccgcaccgg   17520
cgcaactggc ggcggcggtg gcacgccaag gtcaccaacg tgcgggttgc ccgcaacgag   17580
aacgggcagc gcacagtcac attggagtgc gcgcacaacc gcgagcactg aaaacacctg   17640
ctgttcgggg cgacgccttt cagcctcccc gaggtgcagc ctatgcgcgc ctggctgctg   17700
ccgggcaaca cgcgaacgat cgtgagcaca acgggtttca tcaacctggc gcgcaactac   17760
tggcccttgc tggcgctgcc ttcgcaggtg atgaatcccg gcgcgtggat cgggcaggcg   17820
tccaatctcg ccaacctcaa cccgctgaac tggccgcttc aaatgcagtt cgtcaatccg   17880
ctattcgatc ggtcgcgcac aagcgtgctc atgtcgaggt ggtcgaacgc gcacgacgtg   17940
tgcgacgcac tgctcaagta cgccggttgt cacgttcgcg cgtactgctg gctggaagag   18000
gacgaggaca gtccgcaccc cgagctggcg gcgatcgtcg gcgagaagct cgccaggccg   18060
acgcgcaact gcatcgtgct ggcagtcgag gacatgagcg gcacgaccgg agtcaccggc   18120
acggcgctcg acgcgtgct cgacctcatc gcagtgtcgg ccgacaacat tctcagcacg   18180
ctggtgcacg tcgaccgcga cggcgacggc gtagacgatc cgtttatccg caagctgctg   18240
ggagtcgccc cggcgccgcc ggatattaca tttcgagacg tgagtattc gtcgattatc   18300 tcgtctgagc acagcatgtt tcgtgcaaag gcgcagaaaa tactcaccgg cggtcgtagc   18360
cctggctggg taaatcaagt tcagacattt gccattaagt acgcccttc tcaaatttcc   18420 gcaattatcc aagctggccc cgctggtgca tatcagcaac ccggcagctc aggtttagag   18480
gaaatttatc agggccaggc agataatatt ttgctggcct atattcaggt aaccgacccg   18540
```

```
gtgcgtgcga tgcgctccgg tccctatggc tacctggaac atttcgagca aggctcgggc   18600
tcagcataca cggtcagctc ggctatgaca ttagctgagg ggcaccacaa aacgcgcgca   18660
tatcaggcgt tcaaggtgtc cgtgcgtaat ggtgggcaat tccagctgta ctacgatttc   18720
gacctcggat ggcgtgcgaa tttcgagata gatcgcattt tccacaccga ccaggtatca   18780
gccattcggc tgcactacga cgagacgaca ccgaaaactt tcgacttgtc tatcggtagt   18840
gactcggaat cggaaagccc gctagcgcag gtggctcgat cggccgcagc gttctggaat   18900
gccattggca tgttgttcgg atcaggagat atgttctagt ggaaattccc acattgccgc   18960
cgctgcccga cgtgccggaa cacgtaccgg gcgccaactc gacggttgac gcgatgtacg   19020
acattgccga ggccctcaca tatccggtcg acagccgagg tcgacggtac gacgtgcgat   19080
ttctcctgcc ggtgattgcg tttcacctgg cgcgcgctgg ttgtgtcgtc gacccggctc   19140
gggccgtgat caagaagcgg cgcctgccac cgacgggcgg cgtcgtcgag gatgcggtcg   19200
attgggtgcc gctcgacgcc cccgactcga tcgaggacga gctagacggc gcaaccctcg   19260
acgacctccc gcacctgtcc gcggcggccc aagccgaatt tcgacgccgg gcgctcggcg   19320 agccccggc gccgacggcc gtcgacgacc agggcgccga cctcgacgag cgcaacccgt   19380
ggcacgtcga aacgtcgatc acgttcgacg actgagcaac cgccggcaaa acgtcggatt   19440
tataccctga cctgcggtgc agcctcgggt cggcaaacaa ctgaataagg agcaccatat   19500
ggccgagctt gcgccccggc tgacgggcga tgcggtcgcg ctgtttcaga ccctcctgtc   19560
tgccacgtgg tacggcatcg tcggcgacgg aaacacaccc ggcggcatgt cggcaacgct   19620
ggaaatgatc gacggcgagg ccgtgatcac gaccgacgtt ctgatcggcc ccaagggcga   19680
caagggcgac ccggccccgc tggttgatct gcagtggccc gcgctggaat ccccgactga   19740
gctggtcgag ctgcaagacg agctaggcga ggacgataag ggcaagggct ggtggatcgg   19800
cactgttgtc tacgtctgga ccggcaacca attccagatg gtgcggcccg gcccggctgg   19860
gcctcccggc gccacacctc aaatctcgtt tgagttcgag acgatcccga tgtcggagcg   19920 cggcccggc gtcaaagacg aggtgatccg ttccggcact tcacttaacc cgcatatcaa   19980
ggtgcgggca ctgtcgccgc aggggcctgt tggcccgtcg acgaacatca ccggcgcacc   20040
ggactacgac aacagcgagc cgccgaccaa cgggcagacg ctcgtgtgga actcggtaaa   20100
agccaagtgg gagccgtccg atttcactgc caagcacccc cggctgtatt cggttcccga   20160
agcggcgttt acgtccttca ccggcccggc gcagcggcag ccgatcctgc agtaccaagt   20220
tgaggcgcag gacttcgcgt ggaccccgta cgtcaccgga cacatcaagg cgtttggcct   20280
tgagctggac gccgacccgc tgacgatcgg cgtcgaggtg cgcctcggcg acccgctgac   20340
cggcgaactg atcggccgcg ggttcggcaa ctcgtcgatg tggtcgacga tttcgccgca   20400
ctggtcgacc tcgggcgacc ccgcaaccgc ggtggccccc gacaacggcg tcgctaccgt   20460
cgccgccggt caggccgcgc agatcaacgt aaacctttac aacgatggcc tgttcggcgt   20520
ctacgtgttc aacggcaaag gcgctcagct cgcaattctc gttgtgccgc aaggggggata   20580 gcgacacatg gcgtacacca agaattaccg cacgatcgtg ccgcttgagc cgggcgtcga   20640
cctcgacgtc gcgcggtggc tggcccgcga gtcgttcgag cgtgcagcgg gaaacatggg   20700
cctgacgatc gtcgagtacg ccgagcgtga ggtgccgtgg actgatctgc caccgaaggc   20760
cgccgagcac ctggcgcggc acgccgatga gtacacgtgg ttcgagttca ccggcgtggg   20820
ttcgatcccg acggagacga tcgagtggct gaccgcagcg tcggcctggc gtaacacgca   20880
```

| | |
|---|---|
| ggcaggaggt cggtaaatgc ctcccgtgtt tgatcgccgc tcgctcgtca tcgaccgcaa | 20940 |
| cccgctcgtt ggcctgacgc ccgaccccgg caccctgccc aagctcgacc cggcgatgct | 21000 |
| gtggaaacag tggattgacg gattcaagac actgaccgga attgacctat cgtcaccggc | 21060 |
| cgcgctcgtc gccagccttg cgacctgat cggcagcgcc ctcgatcctg caaagctgat | 21120 |
| cgaggcactg acaaaggttt tcggctacgt cggcccgccg ctggcctcac ttgaggcact | 21180 |
| cgcggcgtgg gtcaacgcgc agattttcgg cctgatcgac ccgcggcggc tggcacagat | 21240 |
| cccgctcggc tcgatcgtgc aggagtcgcc aaacctgttg accaacggct cgtttaccga | 21300 |
| cgcaatcgcc atcgacgacg agacgggtcg ctgggtccgc gacaccgcga cgtacaagtc | 21360 |
| ggcgccagcg tcggcacgca ccacggccga cggcacgatc gccgaactgc tgagcattga | 21420 |
| cctgatcccg gtcaagccga aacagaagct cgacattgcg ggattcgtcc gctgggcggg | 21480 |
| cctcattgcc tccgacgggt caatcggtat cggcctgatg gagtacggcg acgctggcga | 21540 |
| gcagcgcgtg ctgatcaagg cgctagatgg cgccagcggc acgcaactga cgtggcagaa | 21600 |
| gatcggcggc cagtacgtcg tacccgacac cggcgtcgac agcgtgcgcg tccgactgat | 21660 |
| cgtcaacgac ggcgcaaccg cgggcaacgt gtggtatgac gagctgagcg cgagcctggg | 21720 |
| cgcaaacctg ctgcccaaga ccgccgtcga gggcctggtc gccgagctga aagcagcgtt | 21780 |
| tgactcggcc gaggccgcgg ctaagcagtt cctcgacttc ctccaaaacc aatggcaggc | 21840 |
| gatgctcaac ggcatcaagg gcggcgtcgg tggcgcaatc gaggacttgt ggaatcggtt | 21900 |
| gctgcacttg acacccgacg gccttttcga tgcctcgcag ctcgtcaacg tcgacaacat | 21960 |
| gccgcagctt cccccggcgg tcgtcgccgg tatcgaggga atcgagaata tcggcgcac | 22020 |
| gattcagcag gcgatcgact acctgtggtc gggcttccgt cgtcaaaccg ggcaaggcaa | 22080 |
| atcgttctcg tcgctggcgc aagccgcgca ggaaacatcg aacgacattc agacggccgt | 22140 |
| gcatctggcg acaatgcacg cgggcattct cagcgagcgg cgcaacaagc ctgcgcactg | 22200 |
| gggcctcgcc gataccgtcg aggtgtcgtt cccgctgtcc gatattgcct acggcacaac | 22260 |
| ggcgccgaca atcccggtca ccgcgacaaa cgcccggctg gcattcattc gctgcggtga | 22320 |
| agcgtccgca aagggattcg tgcagtggct cggctacggc accctgacg ccttctacgt | 22380 |
| gaacgtgtac aagatggacg ccgagggcaa cctcgttcac ctgcacacct cgccgaatat | 22440 |
| cagcaaccag ctacagacca cgatcggctg ggagatgtac gttttcgcgg cgccgatca | 22500 |
| gaccgacgta gagccgggcg acgtgttggc ggtcgagttc gttgtcgagg gatcgacggc | 22560 |
| atacaacatc gccgggtgcg tcaactcgtg ggttccggtt cacccgtcgg cgaacaccaa | 22620 |
| acaccttggt gcggttcgtg gctcgtcgct tagcgggcgg tcaccggcga caattccggc | 22680 |
| tgagctggtc tcatggacgg gcgtcgtgcc gtgggtgtcg atcggaatta gcaacgtgcc | 22740 |
| gccgagctat cggcccccga cggctaccga gttcaaccag gccggacagc agacgtacga | 22800 |
| aattccgctg tgggccaact acattgacgt gatcgcctgc ggtggcggcg gtggcggcgg | 22860 |
| cagctcggcg aacttcctca cggggcaggg cggcgagtgt gggcactgga tcgcggtaac | 22920 |
| gctggtgcgc ggcgtcgact tcgcagagga cgcaacgacg atcaccgtca cattgggcc | 22980 |
| tggcggcgtg ggtggacccc tcaacgccaa cctggcggc aggggatcgc caaccgtcct | 23040 |
| cacctggcgc aagccagacg gttctatcgg aattgctacc gcgcccggcg gcgagtacgg | 23100 |
| cggccccggc ccggcgcaca acggcaacaa cccgaacacg gcatcggctg gcatgggtgc | 23160 |
| gccgaacttc cagtaccgcg cgcaacgta tttcggcggc cccgatgcgt cctacgcacc | 23220 |
| gggcagcgtg ccgggcggcg gcggtgctgg cgggttctcc tacggggcgg gttcggcagg | 23280 |

```
cggccgaggt tccgcgtggc tggtcgcccg gcaatccgag gacgactgag aggggggcgct   23340 atggcgggat ggggtaccga cccgcagccg tcagcgcgtg ccggtagcgg ctgggcaacg   23400
tcgcccgccg caccggcgcc cccgcggccc gactcggtat ggcggccgat cgtgcacgag   23460
ctggcggcgg ccctgagcgt ctcgaccacc gaggcggccc tcgctatccg cgcaacggct   23520
gcagcactga gcgtttcgca cggagacgct gcggccctgc tgcgcatgac ggcctcggcc   23580
gccagcacga gcggatcgtc agcgtcggcg cgagagcact atttcaccgc ggcccccgcg   23640
gacagcacga gcacgaccag ggcatcggcg gtcgtcaagg cggtggctgc agcgctgaac   23700
gtcagctcga cgtcggccgc cgcggtgctg cgggccgtgg cgcccgcggc gtcgacgagc   23760
ggcacgtcgg cctcggcggc gttcccggca atggcgccgg ttgcgcagcg gttcgccact   23820
gtcggcgagt ttgagtttct gatcccgtac tggtgccggt atgtcgacgt gatcctcgtc   23880
ggcgcgggcg cgggcggcaa cggcgggtct gcagccctgg ccgccgggca tggcggcgag   23940
ggcggcaagt gggctgcggt cacgttggag cgtggcgtgc atatcccgct gaccctggcc   24000
tcgatcgtgt gcaccgtgcg ggcaggcggc acgccgggcg gcggtgccgt cgtcggcggt   24060
atcgccacga acggtaaccc caccacagcg caggctgcgg gctgggcagg gctgagcgcc   24120
tcgggtggtg tgcaccgcga gcggatcggg ctgctgcatc aaccgggcga cggccccggc   24180
gatttcactt tcaagggcgt gctgtacgtc ggcggcgccc cgaccaatag cggcaacggc   24240
acagcgggca actcgcctgg cggtgctggc cgcggcggcg acggcggcgc gttcgtcggt   24300
tctcccggcg gtgtcggcgc acccggcgcg cgtggttcc gcgcatacca gtagcaaccg   24360
ccggccaaat gccggattca tagcttgacc tgcggcgctg cctcgggtcg gcaaacacaa   24420
ctgaatagga gcgttctgtg gcttccgcag atcagttcaa gctcgacacc ctcgccgcga   24480
tccttgcgca gggcaacctg ctgagcctgc acagtggcga ccccggcaag acgggcgcca   24540
gcgagattac cggcggcggg tacgccgca agacgttcgc gtggggcgcc ccggcgatcg   24600
tgtcgggcgg cgcagacgac ggcaaggcca aggcgaccgg cgccacacag cagatgaacg   24660
tcgctgcggg cgtggcggtt acgcactacg gcgtacgcaa ggccgacggc acatttctgt   24720
acggcaaggc cctgagcccc ggcgcgactc tcaacgcgaa cggcgtcatt gacgtgaccc   24780
cgacgcacac gtacgacggc ccggtttaga acggagacaa ccgaatatgg aaaaggtact   24840
gccctacgat cggtcgatcg tcccgcagga aacgggttac tggtgcggcc cggccgcaac   24900
gcagatcgtg ctcaattccc gcggcctggt cgtgcccgag gcgaccctcg cccgcgagat   24960
tggcaccacg gtgcgcggca ccgactacgt gggtctgatc gagcggattc tcgacctgcg   25020
ggtgcctgat gcccggtaca cgtcggtgta catcgagaac gacccgccga ccggtgacca   25080
gcgagagacg ttgtggcgca acctcaagag gtcgatcgac gccggttacg gcgtggtgat   25140
gaactgggtt gccccgccga gcaactaccc gcgcggcgtc aagaacagcg tgagcccccg   25200
ctatggcggc ggcactgtgt accactacgt gcgggcgatg ggctacgacg acaacccggc   25260
cgcgcgtgcg gtgtggatcg ctgacagtgg cttcagccg caaggctatt ggatctcgtt   25320
cgaccagtgc gcatcgctga tcccgccgaa gggctacgca ttcgccgacg tcgatcaccc   25380
cgacggcccc gaggcgccgg tcgacgccga cgcgcaggcg gccgacgctc tgctgcggct   25440
gatgggtggc tcgctgccgt tcgctcggta tcaggcgttg ctgcctgcgg tgcgccagtg   25500
cctcaacgag tgcgagtgca cgagcgagcc gcgtatcgct atgtgggggcg cgcaggttgg   25560 gcacgagtcg gtgggcctca aattcatgag tgagctgtgg gggccgacgg ccgcgcagca   25620
```

```
gggttatgag ggccgcgccg acctcggcaa cacgcagccc ggcgacgggt acaggttccg    25680
cggcgccggg ccgattcagg tcaccgggcg gcacaacttc acggtgctgt ctcagtgggc    25740
ctacggcaag gacctcgtgc cgactccgac ctatttcgtc gacaaccccg acgaattgcg    25800
cggcgaccgt tacggattcg tcggcgtcgt ctggtactgg acgacgcaac gcccgatgaa    25860
cgacgcggcc gacgcccgcg atctggtgcg cgcaacgcag tacgtcaacg gcggtcagaa    25920
cggaatcgac gaccgccgca cccgatacaa cggcgccctg gcgatgggtg ccgacctact    25980
caagatcgtt aacggaggcg atgatttcat gtctgcactg accgctgccg agcagcgcga    26040
aatgctcgat ctgctgcgct ggttggcagc accggaaacc ggcgagctgc gcaagaagtt    26100
cccgagccgc agccagttgc gttcggtggg tgagggcctg gtcgacacgt gggctggcat    26160
ggacctcaac caggacgcca acattcacct ggttgccgag tacgtgctcg ccggtatcgg    26220
cgaccccgac gctatcgccc ggctgcgcaa gttggccgcg acgaccgacg ccacccggca    26280
ggggagcgcg gcgctcgcgc agcgcatcct cgaccactac gaccaggcgc acgaggcccc    26340
cgtcgaggtc gacccggccc cggcccgcaa ggtggcgtgt gcgcagggcg gtggcggctg    26400
tgtcctcgtc gccaacggcg gtgacggcac ctgcggcctc gctggcagcg agtgcgtgct    26460
gcgcaagggc ggtgccctgt gagcaagcca atgctgctga ccgccgcggg caccaaggcc    26520
gacgagtgga ccggctaccc ggccgacctc gcgcggcgca tggacgatct gtactacttc    26580
cagccagtgc ggtacggccc caacggaatc ccggcaatgt ggccgatggg cgcctcggct    26640
aagagcggca tcgacgaggg tgtgcgcctg gtgctcgaag ctgaggcgcg gccatcgcgg    26700
gaggtgcccg acgggtacgc cgtgtgtgga tactcgcaag gcggctgggt cgtctccgag    26760
ctgctcggcg agttccgcac cggccgactc aggcacctgc gcgacaagct gatggccggt    26820
gcgacattcg gaaacccgta ccgcgagctg gacggcgacg gcggccgagg aatctccgac    26880
aagcggatcg tcgacacgcc cgatttctgg gtcgacgagt tcgaccgcgg cgacatctac    26940
gcgaacgtgc cgaacaacga cgttggcgag gacatgaccg cgattttcaa gctggtgcgg    27000
ttcaacggca ttggtgacgt gatcgacctc ggcagcgcga tcgacctcgg cagcatcgcg    27060
ggcggcctga tgccgggcgg cggccagctc ggcggcattc tcggcggcct cggcgggctg    27120
ctgggcggcg gcgcgcggca gcaagacaac atcgtcgagc agatcgtcga aatgctcagg    27180
agtccgctgc gcgagttccc ggccgcggtg tcggcgatcc tcaagggcct ggtgttcgtc    27240
ggccagaagc ccgctaccgc gccacacatc gagtaccacc tgcgcgagcg gtcgccgggt    27300
gtcacctact acgagcacgc cgtcgcccac atgcgcgcga tggcggcata aggggggcgag    27360 aatggcaaag gtcgtcgaga caatcctcgg catgttagtg caggtgtgga caggtgtgcg    27420
gcaattcgcc gccgagcgtc tcggcatccg cacgtgggag gatttgcgtc tgcagattca    27480
cgtgctgtcg ccgtacgccg ttacggcaat ggtcacgtgg aacatcgcca gcgaggacaa    27540
ggccaagctg attgtcggcc tcgtgctcgc cgtggcgagc ccggcgctcg cgttcttcaa    27600
cacacgtgac gggttccgac gctgggtgta cggactgctg ccgccgttgc aagcgttcat    27660
tgtcggtttc ggttgggcgc aggattcgac cctgacgccc ctcatggcgg caatcgtcgc    27720
cctgctcggc ggtgcgctgg cggcctccaa caccccggcg tcccgcgggc agaacgatgc    27780
tcgcgcacga catgcggcgg ccgtgaagtg agtgtttctg acctgatgac cggcgagacg    27840
ctcgggatga tcgccgggtc gtcggtcctg tctggctcag ttgtcgcgct gctgtctcgg    27900
cggcgcgaca acttcaaggc actgactgat gcgctgatca aacgggtgac caacctagag    27960
ggccgagtcg atacggtcga gacgaagctc gacgccgagc agaccgcaca cgagcacaca    28020
```

```
cgcaggctgc tggtgcagtc cgaggcgctg ctcgccgcgg cccgtgcgtt catccgcagc   28080
gtgatgcgtt ggggcgcggg cgatcgctcc gaggcgatgc cgacgccgcc cgacgaggtg   28140
atggccgaat gagcctcgct gatcgcctcg gcgacccgca gcccgcaccg tcgagcgagt   28200
gtgccgtgtg ccgctggctc gaccaggccg acgagaccga tcgtgcagcg ttcgaccact   28260
ggctcgcctc tggcgggtcg ctgtcggcgc tgtggcgggc ctgcgccaac gatccgagta   28320
acccgctggc gatcaaacgc ccgcggttct ctgagctgat caacgaccat caccgagggg   28380
gcgcacgtgt cgctgtctga ccggctcgcc acaccggcgg ccacaaacga gaagtaccgg   28440
cccgcggtcg agtttgacaa ccgcggtgcc acgatcgaca cgggcactgt gtaccaggag   28500
ccgggccagc cacccgagta cgccgagatt ctgcgccagg tgggccgcga ccctgagcgg   28560
ttccggctcg tcgagattct gagcgagaag cattggcagg tgccgtatcg gccgtatgtc   28620
cgcgacgacg acggtcagcc gatctttaac gagttcggca agccgcgcct tgaggagcag   28680
gaatttcggt gggcggcgtc gtacaagctg cgcgtcgagc cgatcgaccc tggcggcccc   28740
ggcgaccttg aggcgttgat cgccgacgcc cgcaaggttc gacgatcga accggcgacg   28800 acctcgccgt actggtacgt gtttcaggct ggcgacctgc agctcggcaa gcggtcgcgc   28860
gacgggtcta ccgagcagat cgtcgagcgg ttcgtgcagt cgcttgaggc tgccggtcgg   28920
cagtaccgcg agctggcggc gtccgtcggg atcgccggtg tgcaaatctc gatgccgggc   28980
gactgtatcg agggcgtcgt gtcgcagaag ggcgcgaaca gttggctgac gcaggagacg   29040
atcgccgagc agttccggct gttgcggcgg ctgatggttg aggccgtcga cacgttccgc   29100
gcggccccgg ccgtgtacct cgacgtggtg aacggcaacc acgaccaggc caaccggcag   29160
tggaacacca cccccggcga cgggtgggcg accgaggcgg ccatcgcggt gcgcgacgca   29220
atggtgctca accgcgacgt gtacggacac gtcgaggtgc gggtgcctga gccgtggtcg   29280
ggcagtatga cggtgcccgt cggcgacacc gtggtcactg tgatgcacgg acaccaggcg   29340
accaagggca aggccctcga ctggctcgcc aagcaggcgg tgcacaacca gcccgcgggg   29400
gcctgccaag tgctgcagca cgggcactgg cacgtcggcg ccgtcgaaat gcacgccacc   29460
aagacgatcg tgtgctcgcc gacgttcgac tgtggtagcg attggttccg cgagcgccag   29520
ggcggcgagt cccgccgcgg cgctctcaca tacctgctgc gcagcggtga ggtgtcgagg   29580
ctcagcgtgc tgtagcaact gccggcgaac agctcgagtg cccgccgtga cctgcgccgt   29640
tcaaccgaaa cgccgatttc cggcaaacat tgcgaacgcc cctcgtcgat ccgtcggcgg   29700
ggggcgtttc gtcgtattgt tgacctgcat acaggcggcc cgtattgttg gcatggcaac   29760
aacggcacga cgggatagga gcccgaaatg agcacggacg taatgacagt gcgcaagctg   29820
tccgaacagg aggccgccgc tatggcgcga ggcaagttgg tcagtgtggg aggtaccgc    29880 cgaacgatcc cggcggcgaa cgtgccgcgg tacgaggagc aggtcgcggc gattgaggcc   29940
gagtggcccg cgccgacga ggcgcacatt cggcgcgcgg cgatcgaggc cgtcggccgg   30000
tatctgtgcg acgaggccga cctacccgag gcgatcggcg aggagctggc cgaggcgaaa   30060
gagcagtacg aggccgcgac gtcgcggcc cgcattgttg tgcgcctggc ggtcgaggac   30120
aacgccagcg agctgagcct cgcgcagcgt atgggtatca accggctgac ggtgcgcaag   30180
taccgcggca aggtcgatcg ccgttggcag cgcccgtgag cgccgcgccg gtcgggtctg   30240
aggtgtgggt actcgatctg acgatcgaag gccccgaggg cggcgactat gacgggtggc   30300
agtcggttca cgcgagccgt gagggcgcgt tcaccgtgat gctcggcaag ctcgtcgagc   30360
```

```
acggcgtcga gttcggcgcc gacgttgaga cgctcgccag cgcggcggcc gacaacggca    30420
gcatggcagg cgatttcgct atcgacgagg tggctgtgag ctacggcgtg cacctgatgc    30480
ccgtcgagcc gtgactgcac atgttgacat gcatacagct cgtgagttac tgtatgccta    30540
tcaacaacga cgggatagga gccccaaatg accaccgcaa tcctcacccc caagacccgc    30600
gctcagcttg ccgagattgc caaggctggg ctgacctacg accagcaccg cattgcccgc    30660
gctatcgcta tccgctggga tagcgccgag tttcacacga ccgtggttct agcagtggcc    30720
gaggccctcg acgccaaggg gccacagtgg gcctacagga tcgccagggg gtacttcctg    30780
gacgttgtgc gcgacgagct ggcggcggcc aaggatgcac tggccgggca cccagccatc    30840
acctgatgga caccctcaca acaccccgcc aacacggcgg ggtgttgttg tatgcgggac    30900
gatccgcgcg gttcagcgct atagcacagc tacgatgacc gccatgagtg gggagattag    30960
taccgatact gcaagcctgg acagcgccgc taggggccta tcgacacagg ccgaccagct    31020
acacatcgtg atcgacggga aacctgtcgc cgcggagcac gctagcgtgt tcgccgccgc    31080
gtgtgtgtct gcggacattc agcagttcat gtcagcgcta cgcgggcgga tcaatagtca    31140
agcgacacgc ctgcagcacg cctcggcggc ctacgtcgac accgacgccc gcggcgctga    31200
gcaggtggtc cgatgggtct aacaagaacc ggcatcgacg actatcgcaa cgccgtcaca    31260
gagctgtacg catccgccga cgcttggcgc acggcggccg atcacatcga ccgccgtc     31320 gacggctacg tctcaggtat cactggtacg gattggaccg gagacgccgc cgacgcagca    31380
gaagcctcgg cctatgccga ccgcggagtg gtctacgacg ccgccggtca tctgcgcacc    31440
ttggcacggc acgccgacct cggcgcatcg aatttgaaca cggcacgcgc tcaggtcgcc    31500
gaggttattg ccgccgccga gtctgacggg ttcgccgttg ccgacgattt gcgcatccgc    31560
gacgcgcgcc gctacgacat caacaccata cgggcacgca acgccgcgct ggccgagcat    31620
accgagaacg tgactcgtgc agtggagaag ctagtcgctg aggacgacga ggccgccaac    31680
gcactgactg caaccaatca actagccagc ttcgttccgg cgcgctggcg cgacgattcg    31740
gtagtaaaga ccggtgggca tatcagcgcc gtcgactaca ccaccgacaa tcaggccatc    31800
gggccgtttc cggtaccgcc gtcggtcaag gggcacgaaa agcctttgcc gccagcgccc    31860
ccggcgccac cgccgccgcc gtgggaaggc ccgatcaggg atctgcagaa gcagaacgag    31920
gaacagcaaa agaagattga caagctggaa gccaacggtc acagcccgac gctcgctggc    31980
gcgctcggtg ctgcgggcac gggctgcgcc actggggctg cggcagcagc gatcgccgga    32040
gcgccgaccg gacctggcga aggggtagcg attccgggcg gttgcgtcat cggcggagcg    32100
actggtttag tcgggtactt cgcgggcata tggctcacga acgccgtcga aggggcagc    32160 tagatgcgcg tcacatcctt tgtgctcagc ctggtcggta tttgtctatt cgtactcggt    32220
atgacgacgc tgagtgcagg gcttgaggat tcacaaactc tgctcacatg gatcggtgcg    32280
tctgccttgg cggcaggcat tttgcgtat ggagtcgcca tcaggaaggc gctggtcact    32340
agaaaggccc gccgccgcta atgcgcctcg atggcgacgc cccggcgggg gatttacctg    32400
ccgggggcgt tttcgtgtct gtacggggct actgggccgt ttctgggcac agctcgcgct    32460
gcgccgcgta cgggatgccg tcggcctgct ctcgggtcag ttcctccata ttccaaaaca    32520
acgcctcggc gacgtgctcg cgcggtatcc cgcgcgcag cttgccgcaa atctcatacc    32580
cggctcgcag cgcctcggac tcgttcacga ccggaaagtc gtaatcgacc ccgatccgcg    32640
ccaggtatcc ggcctcactg gcatgggcgg cgccgggcgc caggacgaca gcggcggccc    32700
cgatcacggc cgcggcgagt attcgtttca cccggccgag cctagttggc ggggcctagt    32760
```

```
cagcggcggc acgccgcggt accgtctcgc ctatgcgtca gtttcccggc acaccgtcga    32820
gcggtgtttg ctggcgcagc aaacgaacgg gtggcgtgga tggggcgtgg atggcatcca    32880
cacaacccgc gttgccctgc ggatttcccc gtgttttcgc gtactctcgc gtgtcagttg    32940
gcggcgtttc cgcaggtcag agcccctaga ggggctcggt tcaattcccg gcagctccac    33000
ccttaaacgc cctggtcaga gccacaaaat ctgaccaggg cgttttttgca tccacgcccc    33060
catccacaaa tgtgtacgat ctgcggctat ggcatcgctt cgcaccggca cccgcaaaga    33120
tggctcgaca tatacgcaag tccgctaccg actcaacggc aaagagacgt cgacctcgtt    33180
cgacgacccg gtgcaggccg tcgagttcaa gcggatggtc gagcagctcg gcgcggccaa    33240
ggcccttgag gtgatcgagg cgaccgacgc cgccgaacgg cactacacgc tgagcgcgtg    33300
gctgcgccat tacctcgacc acaagacggg cgtcgagcgg tcgacgatct atgactacga    33360
gaaggtgatc gagaaggata tcgacccggc gctcgggccg atcccgctcg cggcgctgac    33420
cgctgacgac attgcccggt gggtgcaggc cctcgccgag cgcggcctgt cgggcaagac    33480
gattgccaac aagcacgggt tcctgtcgtc ggcgctcaac gccgccgtgc gcgccgggcg    33540
tatccctggc aatccggccg cgggcgctcg actgccgcgc acggagaggg ccgaaatggt    33600
gttcctgtcg cgcgaccagt tcgccaagct gcacgacaac atcacgctgc cgtggcagcc    33660
gctcgtcgag ttcctggtcg ccagcggcgc ccgttggggg gaggttgtcg cgctgcggcc    33720
gtccgacgtc aaccgcgacg agggcacggt gcgcatttcc cgtgcatcga agcgcacata    33780
tgcgcaaggc agctattccg tcggtgcgcc gaaaacgctc aggtcgcggc gcacgatcaa    33840
cgtcgatgcg tcagtgctcg gcaagctcga ctacacaggc gagcacctgt ttacgaacac    33900
cgtcgggaat cccgttcggc acaacaattt tcacgcgaac gtgtggcagc ctgcgctcaa    33960
gcgtgcgggc ctggacgtca agcctcgggt gcacgatctg cggcacacgt gcgcgagctg    34020
gctgattgcc gccggtgtcc cgctgcccgc gatccgcgac cacctcgggc atgagtcgat    34080
caagatcacc gtcgacacgt acgggcacct cgaccgcagc agcggccagg ctgtcgcggc    34140
ggccatcgcg gcgcagctcg accctgcgcg aggctgagca cacgcgag ccccgaggtt     34200
gaatgcctcg gggctcgttt gctgtcttgg ggcgctactg caggtcagcg accaattcgg    34260
gcgttttgcc ggcggtagct aggcggcctc tcgctcagtg ttggggcgca ggcgtcggcg    34320
gtgcgcctcg gcgtgtcgt cacgtagtgc gcggcggctc gtgcgggtgg ctcggatcag    34380
cccgcgatac ggccgaatct tggtgtacca ggaccaggcg aggcacgccg acagcatgat    34440
cgtggtcacg tacccgcaca gcgagacgat cgccgtaacg gcgtgctggg tggccatgaa    34500
ggcgctcgct gtagcgaggg cgcagcacgc gatgcagaac gctagggcaa cgatccagac    34560
caccgccgtg cggccctggt gctcgtcgtg ggctatgtgc cacagacagg agactgccac    34620
cgcgagcaga tgcagtgtcg cgtagtagtg cagcgccgtc gacccgacga tgccaatgtc    34680
ggtcgcaggc atgtcgagca tgttgtgatg cacgctgggc tcgcgcagcg ccgggctgct    34740
catgtgcagc gccagtgtca cgatcggcac gaggtagagc cacggtgcga tccaacgcgc    34800
gaagtacagg cgcacctcgt cgtcgtcgca cacgcggtgc aacatgctga cggcgatagc    34860
cccggcgctg aacaggtaga gcgtgcgacc gagccagtcc tcaaggtgcc agatcccaat    34920
tgcgtgatag atggcgcgcc cgagcgtcat tgacgccacg gtgccgcaca gcgccgcgcc    34980
gaggagctgc agcagcaggg ccgaggtcag cagcccctcg tgcaagatgc gaaaactacg    35040
ccagcgcaac agaactgccg caagagccac aacgcaaacg atccagcgca gcacgataaa    35100
```

```
tgcgacagct attgacatag ccactctctc aagggaaggc gggcggcggc ccgacgatga    35160
aactgccgcc actgtaaacc acgcctcaga gtggtgagaa attacacctc agagacttgg    35220
aatgtcagtc ctcacttgcc ttgtcgtcga ccggcggcgg gtcttttcg gcgcttcctt     35280 cacctcctgc ccaaccatcc gtagcgtctg agggtgggct gtgcctggtg caagactttc    35340
ggcgtaggcg cggatcgagt cgtcgctaat gaggttgtac cgggcaagta ggtcgacctc    35400
gtttatttcg aggttgcggg cggccctgat gaggttgtcg gcggttatca ggcgcccctc    35460
gtcggcttgg ttgtagtagc gggtgcgcga catttgcaga gcttctagca gttcgcgcag    35520
cttgagctgt ctacctacga ggtagctcag cacggcggcg agtgacttgt cagtgtcgtc    35580
gtcggacatg gctcgtgatt cctgtctctc gatcgagctg tttattccct ggcgtgtcac    35640
tttagttcag ttttcgggac tgaacaactc tccgaccagc gtttatgcac ttcttatgta    35700
gtcgttagcg tcccgaaacc acgcaggtgt tcccgatttc gggacttttg gtgatagcgt    35760
ctcacaccgt gcagacaacc acccatcagt tgcgttggcg gcgcgacaac gtggcaaaga    35820
ggatgcgccg caacaacatt caagatcgtg caagtttggc aaaaaggatc aacgtcgggc    35880
gaaccacgat ttactcgact ttccgcgcgg actggtcagg tgtggcaacg cacacggtgc    35940
ttgcgcagat cgttggagag ctgggggggct cgctatctga actcgtctcg gttgaggtgc    36000
gcgcatgacg gcccccggcgc tgacccggcc gcttgctgag gtcgcggcac tgattccgtg    36060
ctccgagcgg tggctcaccg agcaggttcg ggccggtcgc gtccccggcc gcaagatcgg    36120
ccggtcgtgg cgcatgacgc aggccgatat cgacgccgcc cttgagtcct tccgagtcag    36180
ccccgagtcg ggacgcaaga gcgtcgcacc cccggctaat cggccgctcg cactgacccc    36240
cacctcacgc cgccgcacta ggagccgctg acatgacgac gacgacccgt gttcgcaacc    36300
tcgccactgt ggcccggctg cgcatcgagc tgaacgaagc actacgcgag cgtgaccagg    36360
cccgcagtga gcgcaacgcc gcccggcacg tgatcgccga ccaggccgcc gcgctgcaca    36420
gcctcggcga ccacaacggc tacctgctgc aggagcgcga cgagctcgac gcggcacacc    36480
gggcggcgct ggccgacctc gccgaggcgc atcgccagct cgccgcgcac gacgaggcga    36540
ccagcttcct gcagatgcac accgcgacca tcgcggcccc ggcactgcac gaggagcccg    36600
acatggagcg gtacggctga tcttcgaggt ggggcgtcaa acgggttctt acctacttct    36660
tccccgcaag cgtggctcac gacccgttcc ttaccgcgcgaa ggtcactgct gcgccccacc   36720
tccccacaaa cgacgcagcc ccgcactagg cggggctggc cgacacaacc aagggatagg    36780
agccacttgt tatgtcgagc aaaatcctag cgcacaagcg ccgggcggcg cgggatcaac    36840
ggcacggcga gcgcctcggc gcgatcgtcg gcgtgttcct gctcaacctc acaatgaccg    36900
ccgtcggcgc cctcgtcggc gcggcatggg tcggttccta cctgggggcg ccctggtgat    36960
cgccctcacg cacgacgaaa tgcaggccgc tgcccgcgcg atcgacgcca accaggccga    37020
gggcgtgacc accctcggcg cactggccgc cgcggtggcc gctgtcaaca agctgcgcgc    37080 gccccggccgg tcggccgact gcaccgactg ccagcgggtt gacgcaacct gccccggcca    37140
cgtcaaggcg caaggggtgt cacggtgacg gccgcacagc tcggcgaggg cgaggccgcg    37200
gtgcgactgg gcatcactcg caatgcgttg cgctggcgcc gccgcagcgg cacggcgccc    37260
gagcaccggc tcgtcggccg caagatcgtg tacgacgttg cggcacttga cgagtacgcg    37320
accgcggtcg acaacacgca cgtgctcgac atgttcacgc cgcgggttgg cgacacggcg    37380
accgctgacg aggtgtgccg gttgttgcgg atcgaccaaa gcgacgtact gggcaaggtt    37440
ttgaagcgtc acggtgacga attggctgct cacgggtggg atcggttagc gggcactttc    37500
```

```
acccgccggg cgatcattca ggttgcgctg cttgtgcgtt cgtcgacgtc ggcgcgtgcg    37560
gctcggatcg ccaaggccgc caaggcaggc agtcggccga tcagctttgc gcacggcccg    37620
cggtcgcagc agtgcacgca catggttgag cgcgcgttcg acctggcgac cgaggtacac    37680
gacgacgacc ccgcgaggt gtgggcacgg ctgcgcaagc tcgaccgtca cacgctgact     37740
ggcgtcgctg tcgccctggc cgcgatggtc gacgtagagg gcactggcgc cacgaagtac    37800
ctgcgccacc tgtcccgcgg cggcctggcg gccgagggcc tgcagcggtt ggtgccgacc    37860
cgtgagacca ccgacggcgt gccgctgtcg gtgctcgacc agatcgaggc cgacgacgag    37920
gcagaccagc aggacgaggg cgaggtggat cagtgagcga cgcagagcat ttcgacgacg    37980
accccgaggc ttggcgggac agcgccgtgt gcgcgcagac cgaccccgaa atcttctttc    38040
cagagcaggg cggcagcacc cacgaggcga agcgcatttg cggcggctgc caggtggccg    38100
acgagtgcct cacgtgggcg ttgagtcggc cagtcaaccc aacgggcatt tggggcggca    38160
caaccgaacg agcacggcga cggatcaagc gcggacttaa aggggttgcg gcatgagcgg    38220
ttacggcgat ctgtgcggca gcgcgcagtg cgatgtgtgc ggcaagtacg acgcgcaggt    38280
gttcgacccg tgcggcgctg catggtgccg cgtgtgcgac ctgatgggcc tcggcgccct    38340
ggcggtgagc gagcggctcg acgaaatcgc cgagggtatc ggcaaggcgt tcgacgacac    38400
cctgctgttt gggttggacg ccgacagttc ggcgaccgag gcgggcgacc ccgaggcgtg    38460
ggccgacccg acgttcatcc ttcctgagcc ggtgcggcag ctcgccgacc tggcccatca    38520
gttcgccgcc ggtgacgacg gcgtgagggc gcaggcgcag gtgtggctag acgaggcgct    38580
gccgcaggtg ctcggcaaga gcaaggtcga cagcctcgac gacgccgaca aggcgtacgt    38640
gtgggccgac tcgctcggcg cgcactgggg ctggcttgag ggcaccggct gggttgcgtg    38700
gaacaccggc gtagcgccgt ggacgcgggg ggccgtcggc ccgttcgtga tgttctgcag    38760
caacgaggga tttgcggcac gaatcgctct gaccagcgga ggcagcgagg ccggcgaggc    38820
tgtcgagcaa agccccgaca tggtggcgca cccgtcgcac tacacgtcca gccccgccaa    38880
gtgccgggcg tgcggtcacc caatcgagtg catcgacatc acgcagcaca tgggttttg    38940 cctcggcaac gccaccaaat acgtgtggcg ctgcgacctc aagcacgacg caatcgagga    39000
cttgcgcaag gcaattcagt acatcgagtt tgaaatcgac cggcgcgagg cgctggccgc    39060
aaccgaggga taggagccca caacatgatt cgcaagattg ccgtcgtcgc caccgcggca    39120
ctgatcgcag caggcgccac cgcttgcgag ggcggcgcag atggcggcgg cgggcagcag    39180
gatagcgggc ctagcggcgt gatcttcatt ccgcagcccg gcctgcccgg cagccccggt    39240
atcccgatct ttttctgacc gaccaacaac cgaagggaca caaccaatgt caatgatcaa    39300
tcggattgcc gtcggcatga ccgtcggcgc gcttggcgcc gccgcggtgc tgtcaggctg    39360
cgccacgtcc aaccaggaat ggcacacggg ttgcaccgtc aaggccaagg acattgttta    39420
cggcggcagt gatggaaaca ccacgcgcac aaagcgcgtc accacgtcgt gcggatcgtt    39480
caacgtcgag gacgcgatcg aggtcgggca cttcaactcg tgggacgtct gggagtccgt    39540
cgaggttggc aagacgtacg acatgttcac cggcggcccg cggattggct ggctgtcgac    39600
gttcccggtt ctgctggaag tcaagccagc acagtgaccg tcagcaaccg gccgtggtgg    39660
gccgaccgtg aggtcgtcga ggatctggtc gagcaaaagc gtttcgacgc gacgctcgcc    39720
tacctcggcg gcctcgccga cgcaatcgag caccggatcg cctacggcgt cgacgatccc    39780
gcggcggccg ccagctcggc gctgcgcaac ctgcgcgaga ttcaccgctg gccggttgag    39840
```

```
ttcgcggtca tgtggggcgg cgactcgctc acgcggccga tgctcgtcac gccgttggag    39900
cgtcagcgcg aactgaccag cggcctagac gacgtgccga gtgtgcgaga catggccgac    39960
aagatcgacc gccgcgactt tctgcgccgc aggcgacaac tgaaaaggac tggataagtg    40020
gatatttcaa cggtaaaggg tcacgtcgac ctgctcgcgc acgcgcggat cgagaaaaag    40080
aagtgggagg aaatcgagaa gaacgccaag gcggcgatcg acgaggcgct cggcggtgac    40140
gacgagggca cagtcggcgg gcaggtcgtc gtcaagcgca cgcgcaccaa ggtgacccgg    40200
ctcagcggca agctcgtgca atcgctgcac cccgaggttt acgccgagtg cctcgacacc    40260
aacgagcaga cgcgcctgtc ggtggtggcc gacaagtgaa gatcgccgag acgcaccaca    40320
ccacgatcac ggtcgagccc ggcgacaagg tgcgtgacct gcacgctgcg ctcgacgaaa    40380
tgccgaacgg cgccgaaatc agcgtgtacg ccccgccgat gatgtacgac ccgttgctca    40440
gtcaggcggg cgtcgtgatc accgtcaatc acctttcaat cgagggatag gagccccaag    40500
catggcaagg caattgatcg tcgtcgacct ggaaacgacc agcctcgact acgacaccgc    40560
ggccccgttg gaggtcgccc tgctcaacgt cgacaccggc gagtcactgc gctttgtgcc    40620
acacgtgacg tgcgagcagc tcggcgccgc cgacccgaag gcgatggaaa tcaacgggta    40680
ctacgagcgc ggcgtgtggc gcgaggcgct gaccgagcag cagaccgccg tcgcgtgggc    40740
cgaggtgcag gactggctgc gcggcaacac gtttgcgggc agtaacccgg cgttcgactc    40800
gacaatcgtc gcccggcagg tcgccggggg cgtgttcccg acgccgatcg gccgcgtgtg    40860
gcatcaccgg ctcgccgacc tcgcggcgta ctcggcgggc aagctcgacc gcgatccaac    40920
caacctggcg ggcctcgacg acgtggccga gcgcctgggc gtgcaggtcg cacagcggca    40980
caccgcgatt ggcgacgcgg cagccacagg gctgtgcttc gacctgctgc gcaacaccgc    41040
ggcggctcag ctctgatggc gttcaactgg gcagggcagc ggatcgagcc gggcgcgacc    41100
gtgtggcgcg gcggccgtga cggaaacaca agcagtttca aggtcggtcg cgtcgaggcc    41160
gtcgacagga cggcgcgcgt ccggtgggtc gctgagatgg attggcgcgg caacgtccgg    41220
ctgctcggcg agaagtcgat cggacggccg aacgtcgaca gcctggccct gatcgacccg    41280
gcgacattaa gcaacaaggt gcgggaggca ttgcagcagt gagtaacaac aatttcgtgc    41340
acgtcggcaa ggtgacggtc ccggtgagta ggggctcgat cggcaagccg cgggtgcccg    41400
tcgtcgagga cgtcgagatt gtcgtcgcg tgcgcgccga cctcggcgag gtggtcgtct    41460
cgatcgacgg tcagcgcaac ggcaccctgc catcactgac cggcccgcaa gcgtctgccc    41520
tggcggagct gctcgacctg gccgcgggtt ccgccgcctc gctgtccgag catacccaga    41580
cctatcaggc gacgctgcag caggctgagg ccaacctcga gaaagcgttc acgcgggagg    41640
tcggcgcatg aaggtgaccc ttgctctgac cgtattcggt tgccacctgg gcagtctcga    41700
cgtcgaggtc gacggcggcg acgacgacac cacgccccc gcggcgccgg tcaaagcggc    41760
tgcaaagccg gtcaagtgga tgagtcgcat gtgggttaag gggatgatgg cgtgagcacc    41820
aacgcagcgt ttttcgggct gaccgacgac gcccccgagc gggatcggcc gccgaccgac    41880
gagcagcagt tcaacgccga cctgctggcc gacctcaagg gcgtgtttaa acgcgcatgg    41940
gcgcagcacg gccggtcact gcaacgcgcc ctcgggccgt cggagattgg caccgtgc     42000 ccgcggcggc tggcgtcgtc aatgcttgag ctgcctcgga ttaaccccga gggcgacccg    42060
ctgcccgcgt ggctcggcac tgccgggcac acgaaatttg aggatgcggt caacctcgac    42120
aacgagcgga ttatcgacca gtggctcaag gaccggcagc agcgttgcac ggtgctgcgc    42180
ggcgtcactg agagcgatga cccgcagtac gtcggccggt ggttcaccga cgtcgggtt    42240
```

```
acggtgcgcg gcggcctgtc tggcacctgc gacctctacg acacatggac cgacaccgtg   42300
attgacctca agtttccggg ggcgtcgcgg ttcgccgagt acaagaaaga aggcccggcc   42360
cccgagtaca aggtgcaggc acacgcctac ggccgcgggt accgaaacga ggggttcccc   42420
gtcaagcggg tggcgaactg gtatatcccg cgcggcgggt cgctggcgtc gtcgttcgtg   42480
tggtccgagg cgtacagcga cgagattgtc gaccaggcgc tcggcaagct cgacaacatt   42540
cttgtggcgc tcgacgagct gcaggtcgac cagcaccccg aacggatcgc catgctgccg   42600
aaggtgccga gcagttgcat gttctgcccg ttcttctcac cggacggtag gcgccccgag   42660
ccgcacgcct gtgcgggtgg tgcgcagtga ggcgcccggc gccctggcgc attcgccagc   42720
tcgtcgaggg tccggtcgtc gtcgggtggg tcgtcgagca gttgacgctg tacacgttca   42780
cgcccggctc ggttgagggc gagtacgtca ctgtcgacta cttcccgaac ggcccggccg   42840
cgatcgacgc atttgccgga tacggcagtt tggcgatctg acatgcacgg atgcaatttt   42900
gccggcggta gctggcaggg gataggagcc cacaatgagc agtaacccga acgtcgcggc   42960
gatcggcccg acgctggccg cgcaggcaat tggcgccgcg gtcacgatcg ccgacacctc   43020
gcgggcgatg tggcagcagc agctcgccgt cgccgaggct accgagcggg tgcaggagcg   43080
gcagatgcgc ctgctgcacg cacagcgcga cgtgatcaac gcgcaactcg acgaggtgac   43140
gcgcaagcgc gacgacgcaa cccggctcgt cctgcaggcg cagaagatga tcgacgagct   43200
ggccgagccg atggtcgtcg ccaagctcga cccgaccgac cccgctcacc ggacgcgcgc   43260
ctggctcgga caagcgggcg aagtgtggcg ataccacgat gacgactacg ccaagactgg   43320
cgacggcctc ggcacgttcc tgtggacgta cgaccacccg gcagcaatcg cgcgccaggc   43380
cgacacccca atcggccgcc cgttcactga ggtacgggag tgagcgccgg gctgcggtcg   43440
acgttcaccg cgaggtattt cgggcgctgc ggcggctgct cgacccagat ccagcccggc   43500
gacgaggtgg cgtatatggc cgacggcggc cttatacatg ttgattgcga ggacaactcg   43560
cgcgacgaga caaagacccg tcggcacccc gtttgcacgg attgctggct tgagcacccg   43620
aaaggcgagt gtccgtgagc cgtcactact gcacgggtga tgattgctgg cattgcgagc   43680
gccggatcag tcaagccgag tatgagcgcg actgttacgg cgacgacgac tatcccgact   43740
actacgacgg gacatgagcc cccgccgcgc ctggcgggcc gagagggaaa cgggcgcaac   43800
ggaataacaa cacaactgaa caaaggaaca actgaacaat gagcaacgac tcgtacgact   43860
ttctcggcgg cggcgcgtg ccttccggca agttcggcac tcacggcgac gtcgtgggcg   43920
gcgtgatcgc catcgagccc gagcagcggc aacagaccga ctacaagaca ggcgagggcc   43980
tgacctggaa ggacggcagc gcgcgtatgc agctcgtcgt caccgtgcag accgatctgc   44040
gcgaccccga ggtcgaggac gacgacggca agcgtcgcct gttcgtgaag ggtgaaatgc   44100
gcaaggccgt gcagaaggcc gtcattgcgg ccggtgctcg cggcctggac gtcggcggcg   44160
agctgcacgt gacctacgtc ggcgacgcg agaagcgagg caacctcgat ccgccgaagc   44220
tgtacaccgc gacctacaag aagcccgcag cgggagcggc cccggcggcc gccgctcagg   44280
ccgccgaccc gacggcaggc atgacccccg aagcgctggc ggcactcgcc gcactgctgc   44340
cacagcagca gaagtaagcg caccacgcgc tgcgagccgc tgacgttccg caacgggcgt   44400
caccggctcg ctctgtctta caagccattt cgtcaaggga taggagccca cagacaaatg   44460
ctcacgatct acacaaccgg ccccgagtgc tacaagtgca agctgacaaa ggacgcgttc   44520
gacaaggcgg gcatcgacta caccgaggtg cgcctcgacc aggccgacga gtctgtcgcc   44580
```

```
gcgaagttca tcgccgccgg gcacgctcac gccccgtgcg tcgtcgacga cctcgccaat    44640
gcgatgtggt cggacttccg gcgcgacatg atcaaagcct caatcaaggc ccgcgcatga    44700
ggccccgcac tcgacgccgc gcgtatgcac tgttcacgct cgtggcgccg gtggtcgtca    44760
tcctcgcgtt gacgctgacc ggctgcagtg gcaccgatca agagaccggc aacaccgttc    44820
cgagctggat cgccccgcat tccgtcgacc tgcccgacgg ccgccgcgtg ctgtgcgtct    44880
gggagaaaga cggctacggc ggcggcctgt cctgcgattg ggggcgggcg cagtgaacgg    44940
cgcggaattg ttcgaccgca ttgccctgac ccagctgac ggccgctgcg agtgcgaagg    45000
ctcgtgcggc agtagccatc ggttcgccgg tcacacgcgc tgcggcaacg tgcacggccg    45060
cccggcgatt cacggcgccg acaaggtggt cagcctcacc gtggtgcccc gcgacggcga    45120
cggctggaat ctcaccgacg gcaacctgat tgcgtactgc caggcgtgcc ttaagcggca    45180
ccgcgccaag gtcaaagccg ccgcggacaa agcagcagcc cgcgcggcgg ccgaggctgc    45240
cgacggcggc ctgttcgacg tgcccgatac cccggtcgcc gctggcaatg gcgtcacgct    45300
gtgaacgcgc gagcagcgtt gccccacaac tgaatagagg attgagtgaa cggccttact    45360
gatctgctcg aactgctcgg ataccgac ggcgagcatg tgagcctgaa ctaccaggcg     45420
cccggcggcc cgttctcgtc gacggtcgtc gagtaccacg aggacagcga cagcctgcag    45480
ggcctcgcaa tgtcgctcgc caacggccgc aactgctggt ttggcgtcaa cccgacccgg    45540
ccgcggcccg tcgacgagga cggcaagcag aagggccgag gcggcgctga cgacgtgacc    45600
cggctcgccg cgatctggtg cgacctcgac gtaaagcccg gcgcgtgccg cgatatcgag    45660
cacgcacacc aggtgatcga cgagctgagc gcgattctcg gcacccggcc gagcgcggtc    45720
gtgtacagcg gcaacggcct gcaaccgtat tggccgatcg acgacggcac aatcgccccg    45780
atcgacccgg ccgacgggat ggtcgagcag agcgccgagc tgcgcgccga cgcggcggcc    45840
ctgctcaaga ggtgggggccg cctggcgtgc atcgtcgccg acggcctggg cgccaagatc    45900
gaccgaggcg tctacgacct cgcccgcgtg ctgcgcgtgc ccggctcgca caacctcaag    45960
gacaccgaca acccgaagcc cgtcacgatc gacggcgaca ccggcgcacc gctgggcctc    46020
gacgagctgc gcgaccggct cgacgagcac ggcgtcgccg agtatgaggg cgaccggcgc    46080
acctcgcacg aggtgatcag caagcccgac gggtggacgt tcgcgccgag cacctgcgag    46140
tatttcgcgc cgacgatcaa ggcgtggcgc gaggagccga tcaccgagcg gcacccgtgg    46200
ctggtcaagg tcacggtgcg gctgatggcc gcggttcgca acaagtgcct gacggccgac    46260
gagtacgccg aggcccgcaa gatgatcgtc gacaagttca tggtcgagtg cgccgcaacc    46320
ggccgcgacg tgccgagctt cgagattccg aacgcatttt cgtgggccga gcaccacgtc    46380
gccaccaaga cagacgccga gctggcgacc gagttcggtt cgcacctgca cctgtggcag    46440
cgggccgagc cgcggcagat cgagcttgcg ccaatgcccg acaccgacga ccggcagcaa    46500
accgccggca ttggtaccga gggcattagc caagagggat cattggcccc ggtcgtagac    46560
ataaacgcac gtcgcaaccc tgttgctgca gcggtcacgc tgaccgacac cggcaacgcc    46620
gacctgctcg tcgaggcgtg gagcggccga ctgcggtact gccccgacac cggcaagtgg    46680
ttgagctgga agggcaaccg ctgggagcac ggcaccgacc agggcgaggc gatcgtcgcc    46740
gcccgccagg tcgtcgaggc gatccgtatc gacgacgaca gccgaaaga cgttatccag    46800 caccgtatgc gcagcctgtc gcgcaaggga cttgagaaca tggtcgcgct cgccaagtgc    46860
tcgccgcaga tgcgcgtgcg cctggccgac ctcgacgccg agccgtacga gctgaacacg    46920 ccctcggtg tcgtcgacct caagaccggg cacctgctgc cacacacgcc cgacggcggg    46980
```

```
cataccaaga tcaccggcgc cgggtacaac cccgccgcgg tggccccggc ctggcagaag   47040
ttcctcgccg ggacgttcgg cgacgacgtg gaactgatcg ggtacgtgca gcgcctcgcc   47100
gggctcgccg cgatcggcaa ggtgacgcac cacgtgctgc cgttcctgtt tggtggcggg   47160
tcgaacggta agagcgtgct catggacgtg ctcgcaaatg tgttgggcga ctacgcgatc   47220
acggccccgg ccaacttcct gctggctggc cgcgaccggc acgagactga gatcgcccgg   47280
ctgcacggcc cccgcatggt ggtgtgctcg gaaatcaacg ccgaaagcaa gttcgacgag   47340
gccaaggtca aggtgctgac gggtggcgac attctgtctg gccggtacat gaggcaggac   47400
tatttcgact tcaccccgtc gcacacgctg tttctgatgg gaaaccatca accccaagtc   47460
agcgcgggcg gtacatcgtt ctggcggcgg ctacgcctgt tgccgttcct gcatacggtc   47520
ccgccggagc agcgcaaccc gaaccttgcc gctgagctga tccgcgacga gggcgccgcc   47580
atcctggcgt gggtcgtggc gggggcgcgt caaatcgccg ctgacggcct ccgcgagccg   47640
ggctcggtct tggctgccac gaaggagtac agcgagcagg aggacgctct cgggcggttt   47700
atctcggagt gctgcgagct gacgccgggc ggcgccagcg gcggggctaa accggctctg   47760
gtgctcaagg cgtaccagcg ttgggctatg gcgaacggtg aggacgcgat ggtctctcag   47820
atcaagctcg ggcgtgagct gtcggcgcgg ttcggggtgc gctctcaggt gttcaacggg   47880
gcgcggctgt acgtcgggct ggcgctgcaa tcgtcctggg atttgtccca cgagctggcg   47940
ggcgggttcc ggtgatgcac acccggcggt ggccctcgct agcaaccggg gctgatctgt   48000
tctcgaaagt gttctgcgca gaacagatag aacagattca gaacgcattg cgccaccgat   48060
ctgttctgac gttgccgcag gtaaagacag gtaaaagctc ttacagaaca gatagaacag   48120 attttccgg gttgacgtca cgtgtagaaa ttcggggcgt tctccctggt cgggcctctc   48180
ggatcgcctg gtgtaaggct catatgcaga aatctgttct atctgttctg cccctaccgg   48240
cagctaactc tgagacgcgc cccgccgtag cgggggccgg tcgggcgct gaccggcgtc   48300 gttgacgatt ccggccgcca gaatgctgct cgaccacaac tgaatatgga gaaacgagtg   48360
actgaccaca ctctcgacct cgggcttgcc gccgaccagg tggccgccgc cgaggctgcc   48420
gagcgtgccg agctgcacgc caaggctcag gctgccgagc tggtgctcga catgctgccc   48480
gctgagtcgc acgaggccct gtatgcggct ctgagcgccc gcgtgacgca cgagcgcaac   48540
ggaggcaggc agttgcgcct gttcgtgccg ggcaagccag caccgcaggg cagtaaggac   48600
ttcaagggtt ttgcgaagcc gaagccgggc gagacgcgcg gtaaggcgat cctcgtcgag   48660
tcgagcgccg cggttgggcc gtggcgcgaa cgtatcgccc tggccgcggc cgacgcgatg   48720
ctcgccgccg ggctgccggt gctggacaag aaatttccgt gcacggcgtc gttgacgttc   48780
gtcatgcctc gcccgtcggg cacgcccaag agctacacgc cccggctgt gaaacgcccc   48840 gacctcgaca gctggcccg cgccgtgctg gacggcctga ctgatgtttc ctggcttgac   48900
gattcgcagg tcgacgacat gcattgccgc aaggtgctcg ctgcgattgc tcagcagccg   48960
ggcgtgcata tccgcctcac gtcgccgggc tggggcgatg aggctatcgc cgcgtggcag   49020
gccgcgaacg ccgcgggtgg tgtcacgcat gtctgatctg atcgagttgt cggtcgccga   49080
ggtcgacaag atggccgagg ttgtcgctgc gcgtatcgcg cacccgtcgc acacgcctgc   49140
tcgggcgatc cgcgcggggc tgtcggctgt gaacgcgatg cgcctcgacg gtgcgcaggt   49200
gccgcgggtg gagttggtgc aggagcgccg cgcgcctggc acgatgccgc gcccgatcga   49260
ggcacgtcgc ccgttggcgc cggtgcccgt cggtaagcgc cgcgtgcagc acctcgggat   49320
```

```
ggctgagcgc ggcagtgtgt gggaggacgc cgacggcgat caatggcgtt ggtgcttcat   49380
gcaatgcgtg tggcagtaca agcagtttga cgatccgaac ggcccgcagt gggtgaactg   49440
cccgagtaat tacgccgacc gggcgccgaa tccgaactat ggaccgttca cggaggttgg   49500
tcgcgcatga gctacagcga gaatgtcggc gcgtgtacg ggtcggctga ggccctgttg    49560
cgggcgcgga ttgcggcgct cgacactgag attgcttggc gtaaggacac tctggcgcag   49620
cgtgagcgca tggtggccga cgatcgagcg gacatcaacg caatggttgg cgagcgtgcc   49680
tcgctggcgc gggcggtgcg gcagctatga gtttgccgga ttctccgagt ttcggcgatc   49740
ctcgcaggtc accgggcacg ccggtcattt cgccggcggt tagccacggc ctgagttatt   49800
acgggtcgcc gcggccgtct ggaccgtctg agttggacgt gtcgactgcg ccgtcggtgc   49860
ctgagccgtt ggggcgttgc ttgcattgtt cggcgcctgc gcagacgttt ctgtgctggt   49920
cgtgtgtggg catgttgcgc cgccagctcg tcgaggtgcc gtggctgttg catcgtctgc   49980
aggagtcggc gtatggcgag gcgaaggtcg cccgtaaggg tgggccgcgg gtgtcgacgg   50040
gggagcggtt gccgtcgttg ccgttgaaca ctcgcgcggc cgacatgctg cgcgacgctg   50100
cgcgtctggt gtcgtggtgg gagcaggtgg gcggtgtcga ccagggcggc ccgcatgatg   50160
ctgcgcgcgt cgagtctgcg gcccgctggc tggctggcga gccgggcgcg atgatggcgc   50220
acccgtgggc gcctgacgcg cttggttggg tgttgcagtg gcgccaggac gctgagcgtg   50280
tgatcgactt gccgccggat acgcagtacg ccgggccgtg ccagaacgtc gtgcacccgt   50340
cgagcatgtc cgacggcggg attgtgcagc cgcctcgtga gtgcggcacg ccgctatatg   50400
tcgacgccga ggccctggtc gccgagtgct accgctgcgg ctgctcgtgg cgggtcgagg   50460
atttgcagcg gcaggccctc ggtcgtgtcg acgaggccga gcctcgcacg caggccgata   50520
tgtggcggct gctcaagctg attggccgcg acgtgccgcg cagcacgttc tatcggctga   50580
tggttgacgt tgaggcgtgc ggctacaacg ccgacgggtc gcctgtttac acgtacacag   50640
ctgtggttgc tgcgctcgac gcccgagacg ctgccgcgc tgcccgtcgt gctgccggta    50700
agccgaagcg aggcaggccc cgcaagcagg cgagtgttga cacgcataca gaaggtgttg   50760
acgtgcagac agccgaggcg ttaccgtctg cgccgaagca agtcacggga taggagcccc   50820
tgcagatgta tacggaaacg tggtactcac cggccggtac gccggtgacg ccgaaggttc   50880
gcaacgaggt cgacgaggcg cagctcgctg agctgtacga ggccgaggtg tcgcccgata   50940
gcgtgcggtt caacgagctg tacaacgccg ccagcacggc gacgcgctac gcctggcagt   51000
acgggtatcg caacccgcgg gtgccgggcc gtgtcgagga atgcgaggcg ctggtatgaa   51060
gcgcaccaag acggttcggc cgacgccggt cgcacctcag cccgaggttg tggtgcatgg   51120
ccgcgcgttg gagccgggca ccgaggtgtc gatccgcggc gagcgtggcc ggttccgttt   51180
ccgcagtgcg tcgttgacga gcgcgggccg gatcgtgtgc gacttcatcg gcggccctgc   51240
tggtcacgag acttggcggt cgttctatcc cgaccgtatc cgcacggtgc accgtttgaa   51300
ccgcacccgc gcgaacgccg ccgcctagtc gcgtgttgac atgcatacag cgcgaggggt   51360
actgtatgca tatcaacaac accacgggat aggagcccta agtgaccatt tcgaccgcga   51420
cccgcaacat gacgcaggtg gaagctcacc agatcgccgt tggcctgatc cgtgagcacg   51480
gcctgatcgg ctgactgtg agctgggaca acgcgcgccg ccgcgccggt cagtgccgct   51540
acacgtcgcg cacgatcagc ttgtcaaagc gcctgctgcg ccagcgttct tacgacgaca   51600
cgatgatgac cattacgcac gaggttgcgc acgccctggt cggcccgaag cacggacatg   51660
atgccgtgtg ggctgccaag caccggcagc tcggcggcaa cggtcagcgg tgctttgagc   51720
```

```
acctcgacga gtcggcgccg tggatgggta cctgcgacca cggtaagaag ttcgcgcggt    51780
accgcgcacc gaagcgcctc gacggctggc gctgcaagtg cacggcgacg ggtagccccg    51840
tggtgtgggc caagcagcgg tagtgatgac gcccccaatc ttccgaggtt ggggcgtttt    51900
tcgtatctcg tgttgacatg catacagcgc acgggttact gtatgtacat caacaactcc    51960
aagggatagg agcccacaat gtcgaacctc gtcgccgccc ccgccgccgg tcgtttcaac    52020
gccactgccg ccctgaactt gattctcggt atcaacctga ccgacgggca gaagcgtgca    52080
cgcctgctcg cgctggcggt gtcgaatgac gctgcctgcg agttcaacct gcgcgccggt    52140
cgtaaggccg tggctgccgg gcgtctcagc caggcgggcg actacgccga cgctgcggag    52200
ttctacaaca accgcgctgc gcgtctgcgc gccgaggccc gcgctatcta gcgcgccccg    52260
cgctgtgcgg cgcgtcgctg cgcaaaggtc accgcggcgc gtcgcacgcc cccacaatcg    52320
ccattcgagg gataggagcc cacgaacgtg aatcgccacc tgtacaccca acccgaactg    52380
ttcgacgccg acgacgcccg ccagttcgac gtttacgagc ggcccgacgg gtcgcgttac    52440
cgcgttgagc gccccgctgc ggcggtggcc ctgtgagcgc cgttctgacg ccccgcgagt    52500
cggctcagcg gtatttccgt ggctggctgg ccgccggtgt cgtgacgtcg attctgggca    52560
atgctgcgca cgctgtgctc gaccctgacg ccgggtctac ggtgatcgcg gtcgcggtgg    52620
ccgtcctgct gccgctcggc attctcggat cgacgcacgg cgtgcagaag ctcgtcgccg    52680
ccgggatcgt cggccgcgca tacacggcgg cgctgtgcat ttcggtgacc gtcgtcgctg    52740
cggcgttcct gctgtcgttc gcggcgctcg ccgagctggc tgtcgactgg gcagggatct    52800
cgatttggct gtgctggctg gtgccggtgt tcattgatct gagcatcgcc gggtgcaccg    52860
ttgcactgtt cgcgctgtcg ggtgcggagc gggcgaggt gctcgacgct gcggtgcacg    52920
ttgctgcgca ggtgttgcac cctgctgcgc agcctgtgca cgccgttgcg cagcccgctg    52980
acctgcatgt tccttttgccg gccgatttgc agcccgatac gcacctcgtg gcgcgtgagg    53040
ctgacggcct ggtgcacgtg ttcgaggagt cggtgcatga tccggcgccc ggcggtgtca    53100
gcgtcgccga tctgatcgcc cgcgaggccg cgaccagcga cgcgctggct gcgcacttgc    53160
ccgcggctga ggcgatcctc gccgccggtg tgacgcgcat tgatcgcgtc aaggtcgccg    53220
aggtgctcgc cgagcatgag gccgacgtca agccgagcat gatcgcgcgc aaggtgggcg    53280
tcgggtacag caccgtggtg cgcattcttg aacatcacac tgcgcctgat gcgcagcccg    53340
aggctgaggt gatggcgtcg tgagcgtggc tgtgcagtgc ccggcgcgca ccgacacgaa    53400
cggccgcacg tggtggcgcc cggtgcgctc gcccggtacg gatttctcgc agtgggggtg    53460
gacgtcggac ccggcgcagg cgcaccccga ctatgacgcg ctgaacacgt gcacgtgccc    53520
gtacgtcgac ccgtcgctgt ggacgacgca ttacggcgcc gttgagcccg gctcgcagat    53580
ggagcacaac ccgctgtgtc cggtgcatcc cgcgacgctc gtcgacctcg tggtcgctcg    53640
tgatgccccg gtggtcgcgg ccgcggctga cgtgccgag cgttcggcg atgcgtgggc    53700 gcaggtgttc gagctgacgg gcggtggccg tgcgatcgtg ccgattgacc cggcgcccgt    53760
ggagccgctc ggcgagcttg gcgacgagtg ggtgcagctt ggctatgtgg atgagacgca    53820 aggggggtttg tggtgattga cgtatcgagc actgtgccgt tcgcgcacta tcacgcccgc    53880
cgggccgctc gtgtgctcgg cgtcgaccgg gccgtcgtcg acgcgatggc cgacgcgggc    53940
aaggtccgcg cggcgcgtgt gaaggacggg caaggcggct gggtgtgggt tgtcgacgcg    54000
cagcggattg acgagctggc tgccgccaac gagcacacgg ggctgcatcc cgagtgggcg    54060
```

| | |
|---|---|
| tgtggccgtg actgcagtgg ttgtgtcggc gaggggagg gggcgtaatg gctgtgcaca | 54120 |
| atcacggcac cgaggacggc cccggcttgg cgtgccgcga gcggctcgtc gacggcaagc | 54180 |
| tgcgcggcgc ctgcctcgac gaccggccga agatgcacgg gtacgccatg atgcgcagcg | 54240 |
| actcgacggg tacgcattac tggcgccgcg gggccgacgg cgaggctgtc gagatagccc | 54300 |
| gcgacgagtg gctgcggatt acgtgggtgc cgggtgagcc gatttacaac caggtgctcg | 54360 |
| acgccctcgg cgcctgccgt aactgcgggt gtgccgactg tgggtgttgc gttgggtgcg | 54420 |
| ggcaggtcga cgccgacctg ttcggcgcgc atggctatgc gtgtgtggtg tgatgcggcg | 54480 |
| gcctgcgcgg attctcgacg ttgacggcac gctgtgcaac gtcacctcgg tgcgccattt | 54540 |
| cgtgatgcgg cctcgtgagc tgaaagactt cgacagcttc cacgccggta gcgccgactg | 54600 |
| cccgccgaat cagatcgcgc tcgactacgc cgccgagacg gccgcgctcg gcatggtgcc | 54660 |
| ggtcgtggtc acggcccgca tggagcggtg gcggcggtc acgcgcgggt ggctggatcg | 54720 |
| ccacatgcct gttgcgttcg acgggccgtt tcaccggcag gacggcgacc ggcgtagcga | 54780 |
| ccgtgtggtg aagctcgaaa ttctgcgata cctgcgcgc cactacgaca ttcgcggggc | 54840 |
| gatcgacgat aaccccgagg tggtcgcgct gtggcgttcg caaggcatcc cggtcacagt | 54900 |
| ggtgcccggc tgggccgact gacccgacgc gacacgccga cacgacgccc ccgctgaaag | 54960 |
| gtcaagcggg ggcgtcgttg tgtgtttggc tcaatgtgtc tgaccaacaa ctaaatagcg | 55020 |
| ggataggagt acgtgtgtca cctacacgtg tcaatgagcg cctgatcaac tttgcgagcg | 55080 |
| aggtcgacga ccagaccctc gcgcaggcgc agcagatcgc cgatttgcct ttcgtctatc | 55140 |
| cgcatgtggc gctgatgccc gatgcgcatt tcggcaaggg cagcagtgtc ggcacggtga | 55200 |
| tcccaaccga gggcgctgtg atcccggcgg ccgtgggtgt cgatattggt tgcggcatga | 55260 |
| tcgcagcccg caccacgtac acggcgaacg atcttgagtg cctcaagctg tcggatctgc | 55320 |
| gggcgtcgat cgagtccgct atcccgatga gcgccggggg atacaacaag agcctgaacc | 55380 |
| gttttgagtt caccggcgcc cggctggact ggctgcagct cgtcgctacc cggttcgacg | 55440 |
| tcgacctgtc tcactccccg aagtggcgcg agcagctcgg cacactgggc ggcggcaatc | 55500 |
| acttcatcga gctgtgcctc gaccacctcg accgcgtgtg gttgttcctg cactccggtt | 55560 |
| cgcgtggtgt cggtaacaag atcgcgcaga agcacattca ggtcgcgcag ggctattgcc | 55620 |
| aggcgaacgg gctgcacgtg ccgcacaagg atctggcgta cctcgtcgag ggcacggtcg | 55680 |
| agttcgaccg ctacctcgtt gaattgcgat gggcgcagcg gttcgcgtac tacaaccgcg | 55740 |
| ccgaaatgat ggaccgattc gagcaggcgt tcaggcattg ggtcgacgcc gaccagggcc | 55800 |
| ccgagctggt cgtcgagacc atcaacgcgc accacaacta cacgcagaag gagcggcacg | 55860 |
| gcgaccgcga cgtgtggctg acccgtaagg gtgcgatcga cgcgaacgag ggtgtgcggg | 55920 |
| gcctgattcc gggctcgatg ggcacctgtt cgtatgtcgt gaccggcaag ggcaatcccg | 55980 |
| aggcgttgtg ctcggcgccg cacgtgcgg ccgccggtt ctcgcgcacg aaggcgcgca | 56040 |
| agctgttcac agtcgacgac ctcgaggcgc gtatgacggg catcgagtac cgcaagggcg | 56100 |
| aggcgtgggt cgacgagatt cccgacgcat acaagccgat cgacgtcgtg atgcacgacg | 56160 |
| ccgaaacgct ggtgtcggtg gatgccgagc tgcggcagct cttgaacgtc aaggggcagt | 56220 |
| gatgcgcgag gcggtcatcg aattgaaggc cgaccgtcag cacgggctga cgacggcgct | 56280 |
| gctcgacgtg gcgctcgcca acgcccgccg cggcgaccgg gtggtgttct ggtcgccgac | 56340 |
| gtcgggggag tgtgacaacg cattccgtca ggcgcgccac ctgctcgacc cgcaggtgtc | 56400 |
| gagggtcaac gccgccaacg gaaatcagtt cgtggcgtac agcagcggcg gccgtgtcca | 56460 |

-continued

```
gttcgcatgg ggccgcagcc ccgaggacgt gctgtgcgat acgcgcacct gcggcgctgc    56520
ggtctacgtg ttcgacgaca accgcggcag cggtgcacac atcgtgcggc gcaacgcaat    56580
gcgcgacctg cgcgaccggc gagaggtgag gttttcctga tggctgacta ttcgtatgga    56640
gacggcgggg cgcggttcga cgtcgaggcg gtcccgctgg tggagcgcga cgataccgag    56700
ctgccgccgt ggcaggcgca cacaatccgc acgctgcagg agcgtcgaga ggtgtcgttc    56760
tcgctgcagt tcccgcggca gccgcagcct ggccgccgt tgtggctggc gcagttgttc     56820
ggcgtggtcg tgaccccggc gccgccgacg gtgcgcgagg ccgcggtcga cgtgtgggac    56880
gcgctgcgcg tgctgctgcg cgtcgtgtgg gtggcggtgc ggggcgctgc gcaggcggcg    56940
gccgatcgtg tgggcgattg gtggtttgac gtcgtgtacg gcgttctcga ccgctggggc    57000
gtgctgcgcg ggtggggttg gcgtcgccag ctcgtcgggc cgatcgtgcg gctgtgggagc   57060 gcctcgttta tctatcagta cacggtgcct cgtcggcgtg agacgtggcg cgagtggctg    57120
cggcggcagg ctggtctgcc gttggcggtg tggcgtgggg agctcgccgg tgatgttcct    57180
cgacggcccg ctcgccggga ctacgcgcga ggtgcagacg tggccgaatg gcgagctgtc    57240
gccgtacttc aacgtggcga cgccgccgaa gttcgacccg accgaaatgc gcgacctgcg    57300
cgacatgctg cggcccgaaa cgcacacgta tcggatcaag tgcaatcggc tgagctatgg    57360
cccgcagtgg gtcggggcga tcggcgataa ggtcggcgag cagatcgtca cggtgctgcc    57420
gtacgacgag cgagcccgcc agagtgtcgg cgtcgacgag ttcgaggagt acatcactcg    57480
caacgcctac cagagcgcgc agcggcacgc gcagcgcgag ggcctggtcg ccgttgaggt    57540
gcacgaggtt tggcgcggca cgcaagccga ggcccgcgag cagatggtgc gcgagggcaa    57600
gccagtgaag ggcgcccggg cgttcctcga cgccgacggc ccggtgttcc tcgactcgac    57660
cgtgttcgtc gtgcacgagg ccgtggctgt cccgaaagat caggcgcggg aggtgattct    57720
gtgactgaca ccggcacccc gctggacgac ttgacgcccg agcaggccga gcgtctcacg    57780
cggtcgctgc ggcggttcaa cgaggcgatg ggctggcagc tcgaccacgc ccggcaagag    57840
ttggaccgtg accggctgcg gcggctgttc gggaccagct aaggccggcg aggcttgccg    57900
gcgaggccgt cgtcgcaggt agctgcggtg cgggcctgta ggtcagcaaa cgcccctcga    57960
gaatcactcg gggggtgttc tgcattgtgt tgactggcat acagcgagtg tgtttgtata    58020
gcaacacaga aacaccacgg gataggagcc cctgaatgtt caagatgatt gtgcaactgc    58080
atggccgcca agaggttacg gagcacggca cgatcgacga ggcccgcaag cgcctggtcg    58140
atatcgctgt cgcaagcaac tgccgggttg agggcgacaa caccacgggc gagttcatcg    58200
cgttgacccg cgagggtaac gacaacccgc tcgtggactg gacctatggc gcgtaccgga    58260
tcactgagga gcccgccgag ggtgtcgacc aggtgctcgc cgccgctact gcgcggtaca    58320
tgatcgacga gaacctcgac gccgacacgg tgcagatgat ccgcaacagc gaccgcgacg    58380
ggcgcgacct gctggccgcg atcgtggccg agtggctcaa gctgcacccc gagctggccg    58440
accgtgagcg gcacgcggtg gcagcggcgg ccaacggctg gcagcgtttc gaggttgacg    58500
cgacgccgct gcaggtgcgg tatgcccgtg acggtatcga gctggcgatc attgagtacg    58560
acgacgagcg cgcggctcgt agcgccgaga ggtacacgca cggcgtgtgc gacgtggcgc    58620
tgatgcggtg ctgtcccgag gacgacctcg gcgacgtggg cgcgtggctt gcggcggccc    58680
ctgtgccgct ctgagagctt caaacaggtg agggaaaggg ataacatggc gaccatgaca    58740
attacgaggt acacggcggt tgtgacgccc ggcgaggagg tgcacgcgct catccacgtg    58800
```

```
cccgagatcg accagtggac gcaagcccgt agcgaggatg aaatcgaacc aatggcgcgg    58860
gatctgattg cgacgtggct cgacgtgccg gtcgagtcgg tcgaggttga ggtacagcgc    58920
ggctgacgtc gtagcgacaa gagcgcccct gagtcaattg cgactcaggg gcgctttgtt    58980
gttgacatgc atacagcgcg agtgttactg tatgcatgtc aacaactcaa cagggatagg    59040
agcccgcaat gccgaagcgc aacgaggtaa tcaccaagat tcgcaaggcg gccaaggcca    59100
agggactgaa attcaagtcg gttcgcaagg gtgcgaatca cgagattttc gacctcgacg    59160
gcgtaatggt tccgatcggg aatcactcga tcttggacgg ttacctggta ctcaagatct    59220
acaaagagtg cgagccgaag ctaggcaaag gctggtggcg ataaccacag cgacgacgcc    59280
ctcgaccaca tggtcggggg cgttttcgtt tgtgtgttga catgcataca gtgacgggct    59340
attgtatgta tatcaacacc gcgagcggtt gagattgaca actcaagagt gacagtggat    59400
aggagcccac aatgaacgat ttctacattc cgcgtttcct ctcgccgagc tgctcgttta    59460
cctacgacga actcggtaag gccctcgcaa agctgcagcc gcgcctgaac aaagcgactg    59520
aggcatggct cgccgccaag cgcgaccacg gcagcgagag ccccgaggaa cacgccctct    59580
ggcccgagct tgaccggctg gaaatggcta aggcccgcat cctgcgcgag gctaatcgcc    59640
tcgacaagat caacggcctg gccgccgcga tgccgctcta accgacaaaa cccctgctac    59700
ggcgggggtt tttgtcgttg agcacagata gcacagatac gtggcgtgat tggcgcgcgt    59760
cgcttttaga ctgccatccg caacagcaca gctgtaccca aaacggcccc ggcgctccga    59820
aatggagtgt tggggccgtc tccattccag gcgttgaccc gagccgcgcg gcctcctatc    59880
cccgcgcccc ggtcgacgtc tcgcccgccg ccgtgatccc gacacaggcg cacaagcgcc    59940
ccggcgcaag ccgctgcaac agcagggccg cgttggctgg tcaccacgcc gagccacgtt    60000
gcagcgcagc gctgcaaggt cgacgcgatc cggcggcggg cacctacttt cacgagagga    60060
aacgccatgc ccgacaacgc acctgacgcc gcacccgagg cccccacaca ggagaccccc    60120
gcaatggccc ctgctgtccg cgctgaggca ctggcggcca atgcgagggg caaggggaag    60180
gggcggcagg ctacggcgta cgtggccctc gaccggccg aggccaaccg tagggccagg    60240
cgccgacccg ctgccgaggc acgcaagcct gtggcacacg agccgtacga atggtgaggc    60300
tgtcaccacg gcgtgctgag agttggttct gtaccaccag catgaagctg ggcgagctgg    60360
tcgaggcgct ggacctacgc aagcggtacg ccgagcgaca cggtgaacgt gctcgcctgt    60420
tcgtgttctc ggtcggcaag ctgctgatcg tttgggaccg agacagcaag ccatgagcga    60480
gggtcgcaac actgcacggc gcaacaggtt ccggcgctac tggctgcggc ggcgcgagga    60540
ctgcgcagtg tgcggcgagc cgatcgacta cgaggcgcat cacctgcacc ctgactcgtt    60600
tcaggtcgac cacatcacgc cactggatgc aggcggctcg gacacgctcg acaacacgca    60660
accgacgcac cgcaagtgca accgcgacaa gagcaacaag ctgcccgaca gcggcggccc    60720
ggcgcctgcc tcagtgggcg tcacgttcgt gaccgaacgc aactggacac cctgacctca    60780
gcaaaggggt gggggatac tccccgaccc cctccccggt gcacctcgta ggcat          60835

<210> SEQ ID NO 6
<211> LENGTH: 59646
<212> TYPE: DNA
<213> ORGANISM: Mycobacterium phage Adephagia

<400> SEQUENCE: 6 aggcacctttc tctccccag cattttttc caagccattt cagcgttttt ccacacccga       60
ccagcacagg agcaaccaat ggacatgacc gaatccgcac cgactgcgcg cgtgtgggcg     120
```

-continued

```
ttcgaggatc agcgcgaccg cgcggtgcgc gagcaatcaa tgcacatcgc gctgcgccag      180
gccgacagcg tgggtatcgg cgacttgacc gtgatcgagg cggccgacaa gatcgccgct      240
ttcatcctcg acggcaaggt cgaccggcgc cccgacgctg agcggagccc cgaatgatga      300
cgcccgccga gcgtctcgcc gcgcagcgcg aggccctcga caagcacgag tggaccgagg      360
tcgagggcga cctcacgccg atcacactgc actgcctggt cgccattggc gaggtgctcg      420
tcgagctgaa cgcccggcag gcccgccagg aggccgcgac gatgggcgcc ccgtcgtgag      480
cgcggtcgtc ggcgtcgtgt cgcgcactct cgacagcgcg gcccggctcg cccgcgcgct      540
gaacgtggct cgcaccgttc aatgagcgt gccgtcgatc aagcaggggc acggccgcgg       600
gttcagtttc gacgccgtga tcgtcgacga cgaggtgatg ccgctcgatg actgtgtgct      660
cggcacgttg gccccggcga tgcacgctca cggcgcaaag atgtacgcgg ttcgggaggt      720
tgagctgtga ccccgactgt cggccgcatc gttcattacc agtcgtacgg cacgcccggc      780
ggcgagtacc tgcccgagcc gcgcgccgcg atcgtcacgc aagtgcacgc cgtcgagggg      840
gccgtcggcc tcgcggtact caacccgtcg ggcctgttct tcaacgagtt tgtggagcac      900
gccgaggacg acaagccgac tgcgggccgc tggaactggc cgccccgcaa ctgatccagc      960
gccggggcct gttccgcgaa ccgcggtcct cccggcgcgc ctgggtgtgt agctcaatcg     1020
gtagagcagc ggtctccaaa gccgccggtt gcacgttcga gtcgtgccgc gcccgcttcc     1080
acaccggcta accgccggca atttgcattt ctgcacgtca atgccacgaa aggccgtttt     1140
gagctaacac ggcacctcac caaaccagga gatatgacca tgcgcgcacc cgctaccgcc     1200
gaggttcctt gcccggcctg cggcgagccg atcacgctcg cccttggctt tgagctggcc     1260
gagcccgagc ctggcgccac gacggccccca gtgttcgtgc ggcccctcga cgtgaccgag     1320
cgcgcgcagg agcacggcga ggtgtgtccg gtgtggtctg cgggcggtgg ccgtgatgag     1380
tgacgccaag ctcgaccggc tgaacgaatt gcgccggttg cacgagcgaa tctcgggcgc     1440
tgtgttcgat cctgagacac cgccgcgcga cctcgcctca ctgagtcgtc gactcatgga     1500
gatttccaag gaaattgagg cgatcgagct gcagcgcgct gagcagggcg gcggccaggc     1560
cgacgtcccg gccgatgagc cgttcgatgg ttcggacctg tgagccgcgg ctatccgagg     1620
ttgctcgcca cgtaatcaag cccgagggca tcacctcgac gtcgtggccg tccgttcgcc     1680
acgagtgcaa cgtcaacatg gggttgtatt tcgaccaatg gcaggacgac ctcggaaagc     1740
tggtatgcgc caagcgatcc gacggcctgt acgccgccga catgttcgca atgtcgatcc     1800
cgaggcagac aggcaagacc tactttctcg gcgcgatcgt gtttgccctc tgcaagatga     1860
ctcccggtac aacggtcatc tggacggcgc accggacacg tacggccgct gagacgttca     1920
agagtatgca ggcgctcgcc aagcgcgagc agatcgcccc gcacatcttg aacgtgcaca     1980
cgggcaacgg caaagaagcc gtgttgttca ccaacggcag ccgaatcctg ttcggcgctc     2040
gtgagaaagg tttcggccgc ggtttcgcca aggtcgacgt tctgattttc gacgaggctc     2100
agatcctcag tgaaaacgca atggacgaca tggttccggc gaccaacgcc tcgcctaacg     2160
gtctgatcct gttcgcgggc accccgccga agccgacaga tcccggcgag gtgttcacca     2220
acctgcggct ggacgcgatc aacggtgaat ctgacgacgt tgcctacgtc gagatttcgg     2280
ccgacgagaa cgacgaccca gacgaagagt cgacgtggcg caagatgaat ccgagctacc     2340
cgcaccggac gtctgcccgc gctatccgcc gtatgcgtaa agcgttgtcc tgggacagtt     2400
tcaggcgcga ggcaatgggc atctgggaca agatcagcgt gcacgcgcag gtgatcaagc     2460
```

```
cgagcttgtg gcgcgacctg gccgacccgc tcggccccga gcccggcgcc aaaccggcgt  2520
cgctcggcgt ggacatgtca cacggcgcg ctatctcgat cggcggctgt tggctgatcg   2580
acgacgagct gaggcatgtc gagcaggttt gggcgggcac tgacaccgcg cggccgtcg   2640
agttcatcgt cgagcgtgcc aggcgacgta tcccggtcgt gatcgacgac gcgagcccgg  2700
cgaaagcgct tgtgccagag ctgaaacgcc gccgggtcaa ggtccgcatt acctatgcgg  2760
gcgacatggc caaggcgtgc ggcctgttca gaacaacgc tgaggcgag accctcacgc    2820
atggcgatca gctcgacgtc accgaggcac tcaagggcgc caagcaaagg ccgatccgcg  2880
acgcgggcgg ctggggctgg gaccggcgag acccgacgtg cgtaatccat ccgctagttg  2940
ccgtgacgct ggccctgctt ggtgcgctcg acgccccgaa gcgcagcggc ggcgcgatgt  3000
tcgtatgaga gggggccgtg tgattcccgc tgcctatgac gaccgccagc tcgacgagcc  3060
cgacgacgac gaaatcgact ggcccgccga cgcgctcgac gccgaggcga tcggcgagct  3120
ggtgcagcgc atgtacgccc tgcacctcgc cgagcgtgac tcgttcgaca atatccacgc  3180
ctttaccaag ggcgagcgtg gcgtgccgag cgtgcccgac gaggcgagcg acgaggtgaa  3240
ggaactcgcc aagctgtcga taagaatgt gctgcggttg atttgcaact cgttcgcgca   3300
gtcgctcagc gtggttggct accgctcgtt gacggcaccg gagaatgatc cggcttggcg  3360
tatctggcag gcgaacaaga tggacgcccg ccaggccgag gtgcatcgcc cggccgtcaa  3420
gtacggcgcc tcctacgctg tcgtgactcc cggcgtcgac ggccgcaagc tgagattcg   3480
ttgccgctca ccgcggcagc tcatcgccgt gtacgacgac gcggtgctcg acgactggcc  3540
gcagtacgcg ctcgaaacgt gggtcaccac gaaggacgcg aagcctcggc gcaagggcgt  3600
gctgtatgac gagcggtaca tgtatcagct cgacctcggc gagctgccgc tgacgtcgac  3660
cgggcagccc gaggtggcga cgaagcccgt cacgctgcgc gacgtcgagg acatcatccc  3720
gcactacggc accgaggacg gtaagcccgt ctgcccggtt gtccggttcg tcaacgaccg  3780
cgacgccgac gacatgatcg tcggcgaggt cgagccgcac atcggtatgc aaaaggcaat  3840
caactgtgtg aatttcgacc ggctgatcgt gagccggttc ggcgccaatc cacagcgcgt  3900
gatcagcgga tggaccggca gcaaaaacga ggtgctcaag gcatcggcgt tgcgggtctg  3960
gacgtttgac gatcccgacg tcaaggcgca ggcattcccg ccagcctcgg tcgagccgta  4020
taacgccgtg ctcgacgaga tggtgcagca cgtcgtgatg gaagcgcaga ttaatccgtc  4080
acaggtcaag ctcgtgaaca tcagcgcgga cgccctggcg gcggccgagc accgcgagca  4140
gttgaagctc gccaccaagc gcgagagttt cggcgagtcc tgggagcagg ttttgcgcct  4200
ggccgtcgaa atggacagcg acgagacgac gaccccccgac ctgaccgccg aggttatttg  4260
gcgtgacaca gaggcccgct cgttcggcgc gtcgtcgac ggaatcgtga agctctcgca   4320
ggccggtgtg ccgatcgagt acctgctgcc gctcgtgccc ggcatgacgc agcaactcat  4380
tcaggcgatc aaggaagcca tgcgcggcgg cggcactcag gccctcgtcg acaagctgct  4440
cgccgccccc gagctgtcgc tgcccgacgc cccgccgatc gaccaggcgc tcgccagcgc  4500
cgacgacgac gaaggggcg agggtgacgg agccgaaggc ggtaccggag tttcagggggg  4560
cgctcgcccg tctcagtaat gaggtgggcg gcgccgtcga ccggctgatg ccacgccttg  4620
gcggcctgac ccgatccgag ggcctcgctg tgatcagcga cgtgtacccg acgttgctcg  4680
acccgttcct gtcggcgtcg ggggagctga cggcacagtg gtaccgcgag caaacgccgg  4740
ccaaactggt tggcgcgcag gtcgcgggca caaaagccct cgcccggca aaggacttcc    4800
tgcctgagcc cgccgcgctg cccgatcgcc gccagctcgc ggcgtcgggc cgctgggcgc  4860
```

```
tgatgcaacg caaccctggc ctggcgctgc gcggcactgc cacccggtca gtgttcgact    4920
cgtctcgccg cacggtgcgc gacaacgcga tccgcgaggg cgtcaagtgg acgcgatacg    4980
cctcggcgaa cgcctgcggg ttctgccgga tgctcgccac ccgcgccctg acgaccgaac    5040
gccgcggcgc cccggcctg tacaccagca aggcgacggc cgaacgcaac gcgcacaccg     5100
tcgatatccg cggccacgat cactgcaagt gcctggccgt gccggtgcgc agcggtggct    5160
acaccccacc cgaatacgtg aatgactggc tcgccgacta cgacgccgtg agcgtcggcc    5220
ccgacggtgc actccgcaac gagtggcaga tcgcccggct gatggaagcc cgcgccgacg    5280
agcgcctcgg caagcccaaa cgcaagacag gcaggccgcg caaggccgcg cagcccgtcg    5340
aggacgtgcg cagcacaccg cgcgaaacgg tgcgcgctac gcagcacctc gtcgacaccg    5400
gcaacgagcg cgctgcagcg tacgcgcaa tcgcgcacga gcgtgctc actgcgcagc       5460
aggtcatcac ccgcaccgac gaggttgtga gcaccgcggc gcacatcacg cagcgcgtca    5520
agctcgtgac cgacgtcgcc gacaaggtgc tcggcggcgc cgttccggtc gtgcgcgacg    5580
tcaagcgcgt ggtcgacgcg gccgacaagg cactcggcag cgcatcgcag gtcacaggcg    5640
gtgcgcgtca ggccgcggac attgccgcac aggccatcga cagcacggtg caggttgcgc    5700
acggcgccaa gcagattgcc gacgaggtgc gcggcgtgct cgacgaggtg ggcctcgtcg    5760
ctgtcggtct gcgcacgctg ttcacggata cgcgcgtggc tgtgcacgac acggtgcgcg    5820
acgcacgcaa cgtgcgcagc ctgtcggacc tgtccgagca gatcggcgca gcgaccgaca    5880
ccgcgcggca catcgccgac gacggccgtg cactgatgga ccgcgccaag ggcgctgccg    5940
acgcaacgca gggcatcgct cagggcgtcc gcgagatacc ggaactgctg cggcagccga    6000
tcgccgacgc gcaagagctg gcgcaaacca tcgccggggc cgccggtgac gccggtcagg    6060
ttgtcgacga gctgcaggac gtcgcgcgtg cgatgggcaa gctgatcgac gcggtggccg    6120
gttccgccgg tgaggacgtt cgccaggctg cccgtcaggc tgccgacgac ctcgccgca    6180
ttatcggcga cctgttcaag gcacccgagg cgcctcgcgt gccggtgtcc gtcatgtcag    6240
aacgcctcga cgtgccgggc gctcgcgtgc tcggcgggcag tcagccggtc ccggcaatcg    6300
ccgaacgggt cggcctcaag ccgattgacg cacccgaggc ccgccaggcg ctcgacggcc    6360
gcccgccgat gaaagcactt gaggcggcac ccgaacgccc gccggtcgcc ccggtggtcg    6420
acgacgtgct cgacgtcgag gtcgtcgagg ccccggcgcc tgccacgccg aagccgaagc    6480
ccgcaaagcg gacgctcgac gaggtagagg ccgagtttca ggcggccgtc gaggctggcg    6540
acgacgcagc gatcgacgcc ctggtcgccg aaatggagaa gctcgaagcg ccgaaaaga    6600
aggccgccga acgcgccgcg gcgaaagccg ctgcgaagca agcggaaacc gaggccaaga    6660
ccgaccgact gcttgagctg atcgagcaag gttgggatcc ggccgaggct gaatccgagg    6720
cgttcggcct gtccgtcgag ttcattcggc gccgcgactt catggctgag gctcgcgccg    6780
ccgggcacga gggccgatcg ttcgacgagc tgctcggctg ggtgttcgag gagcgcatca    6840
cagaggcgta tttcgccgcc gaggacgcga cacgcgggca gatgctcaag cggcgctacg    6900
gccccgacgg catgaacgtc gatccgcgaa agctgtggac tctcaacgag acaacggccc    6960
gcaagtacat gtccgaggag atggccgagt ggttcgacca gcacgccgc atcactcgcg     7020
ctgcactcaa ggaggcgatt ttggccggtc gcggcaattg gcgtagcgca acgaccgcgg    7080
actttctgca atgacccgcg acgagctggt cgccgcgtac caggccggtc gtgcggcggc    7140
cgtcggcgac accaacccgt acgacggcct cggcgccccg gctcgactgt ggcgccgagg    7200
```

-continued

| | |
|---|---|
| ttaccgccag atgctcgccg cccggctcat gcaatcaccc gcactgcagg cgtatctcaa | 7260 |
| cgcccgcaag gactgagcac gacccctcac aactgaatag gagacacacg aaatgtccga | 7320 |
| aatcaccccg accgacggcg ccgacggcgg cgagggcacc gaggcccccg aaggcggcgc | 7380 |
| cccggccgcc accgacgccc ccaaggtcga caccccgaag gcgtacacgc aggccgaggt | 7440 |
| cgacgccatg ctcgcccccgc tgcagaccgc cgccaacgag ctgcagacga tcaaggacgg | 7500 |
| cgaaaagacc gagctgcaaa aggccctcga ccgagccgcg gcggctgagg cccgcgccga | 7560 |
| gaccgtcgag tttgaacggc tgcgcgacaa ggtcgccaac cgcgagggca agcgcgtgcc | 7620 |
| ggtcgcctcg ctggtcggca agaccgaggc cgaactgatc gcctcggctg acgccctgat | 7680 |
| cgcctggcgc gacgagaacg cccccaagcc gcccgagcag cccaagcagc agaagcgcaa | 7740 |
| cccggctggt agcggcggcg ggttcaagag cggcgcaacc ggctccgacg gcggttcgac | 7800 |
| cgacccgaag gtgcgcgccg tagaagcgtt gcggcgcttg cgttctggca agtagtaccc | 7860 |
| acttcccaac acttccgcac gaggaccgac ctcggcggtt gatcacaact gaatagagag | 7920 |
| agaggccgct atggctgaca tttcccgcgc cgaggtcgca accctgatcg aagagggtta | 7980 |
| cagccactcg ctgctggccg ccgccaagca gggcagcacc gtgctgtcgg cattccagaa | 8040 |
| cgtcaacatg ggcaccaaga ccacgcacct gccggtcctg gcgaccctgc ccgaggccga | 8100 |
| ttgggtcggc gagtctgcca ccgaccccga gggcgtcatc aagacgagca aggtcacctg | 8160 |
| ggcgaaccgc acgctggtcg ccgaagaggt cgccgtgatc attccggtgc ccgaggccgt | 8220 |
| gatcgacgac gccactgtcg aactgctgac cgaggtcgcc gagcagggcg gccaggcgat | 8280 |
| cggcaagaag ctcgaccagg ccgtcatgtt cggcatcgac aagcccgcat cgtgggtctc | 8340 |
| cccggcgctg ctcaaggccg ccaccgacgc cgggcaggcc atcgcccacg tgtccggtgt | 8400 |
| cgccaacgag tacgacctcg tgggcgcctc caacaaggtt gccgagcagg tcgccctcgc | 8460 |
| cggttgggct cccgacaccc tgctgtcgag cctggcgctg cggtaccagg tcgccaacgt | 8520 |
| ccgcgacgcc gacggaaacc tcgcgttccg tgacggttcg ttcctgggct tcaataccca | 8580 |
| tttcaaccgc aacggcgcat ggtcgcccga gtccgcggtg gccttcatcg ccgactcctc | 8640 |
| gcgcgtcaag atcggtgtgc gccaggacat cacggttaag ttcctggatc aggcgaccct | 8700 |
| cggcaccggc gacaatcaga tcaacctcgc cgagcgcgac atggtggcgc tgcgcctcaa | 8760 |
| ggcacggttc gcgtacgtgc tgggtgtctc cgcaaccgcg atgggcgcca acaagactcc | 8820 |
| ggtcggcgtt gtcacccctg acgtgacccc gccgacttcg ggcgagtagt gcggtatcgc | 8880 |
| cacaccctga cgggggcggt catcggggcg ccgaaaggca ccttgctggc cgccctcgtc | 8940 |
| gagggcaacc cgagctggat cgaacacgag ggggtggccg gtgctggcaa gtctggacga | 9000 |
| cgtaaaggca gctctgcggg caatgggaaa gcccgaactg gcggaagctc tcgcagccga | 9060 |
| ggacgtaacc gacctcctgc aggaggcgac cgacctagtg acggggcacc tgtggccggg | 9120 |
| ggaggtgccg agcccgacgc ccccgacgat caccagggtg acggcctcgg tggcagcgac | 9180 |
| agcgctcacg aagccgaagg aactgctgcc ggaaacggag agcctgcaag ctgacgggtt | 9240 |
| cggcgtgaag ttcacacccg gcgcgggatc gccgggctgc tacctgacgg ccgcccaaaa | 9300 |
| gacacgcctg cggccctgga agcgcagcgc tgtctcggtt cccatgagca gcgagaggta | 9360 |
| cccgtgacac tgccgacccc gtgggaagtg caacacacga cgtacgtcaa ggtcggcgaa | 9420 |
| agcgccgcgg gccaggccaa gaccgagccg cgcactcgac cccgcatggt gtcgagcttg | 9480 |
| cgaaagcggg tcaacgagcc tggcgccgcg gcgaccaact ccgatcaggt cgtcgtcgag | 9540 |
| tacacgatgg cgactcccga aagcgattgg gcgcacggcg atctggtcaa ggactggcgc | 9600 |

```
ggccgtgagt tcaaggtgca cggcgacgtc gacgactaca acagcggccc gttcgggttc   9660
cggcccggct acctcgtgac gctgcgaaag gtggagaaac gtgccatacc gaccgcttga   9720
tctgccgttc tctgagcacc gcaagatccg caacctgccc gacctcacca aggcgtgcga   9780
gaagctcggc gacaagctgc gcgacaaggc ggcggccaaa gccaacgccc acacacccgg   9840
cgccggtgac gattacgtga ccgagaccgt gcacggccgc gaccgtgtgc gcgtctacgt   9900
gcgcgctgag ggcgcagcga tcggcgtcga aacgacata gcaccgctga tgcaggtgtc   9960 tgccggaatcg gggccgcggt gacggtactc gttccgccgg tcggcccgct gacggccgca  10020
cgccggtacc tgctcgacga gctggctgcc cgcggtaacc cgctgatcgt cgagcagcag  10080
acggtacccg agggctcgcc gacgtcgtac gcaatcctgt cgcgccccgg cacgagcacc  10140
gaggtgttcc tgcagcacag cctcattcgg gtgcgggtgt acgacaacga cctcgtgcgt  10200
ttggagcgca cgccgatct gctgcaccgg ctgctgctgc acgcggtgca ccgcaaggtc  10260
gtcgtgcccg acgagggcga ggtgtggatc accggcgcca cgcacgaata cgggcctgcc  10320
gagttcgacg accggcgcgt accgctgccc ggctatcagt cggcagtgtt ctggacgatc  10380
ggtctgcgcc ccgagcgcag ctaagtcgcc ggccgatgcc ggccgacctc gagaaccgcg  10440
cttgacgtgc ggcgatgcgc gctgcccgca ttcggcagca aacacaactg aataggagac  10500
aacatgacgc agcccactcc gccctcggcg ctgggcgacg ccaccaaggt gttcgcagcg  10560
tcgccgtcgg acctggaaac cgttggtggc ctttggttcg caccgttcgg caccaagctg  10620
ccgaccgacg tcgacgagcc cctcgaagcg gcattcaaga acctgggttt cgtgtcggct  10680
gacggcgtaa ccgtcaagat cgacagccag accacaccca ttgaggtgtg gggcggcgac  10740
gaaatcgggg cgctgcgaga caagttcagc atcgagtaca gcatgagcct gtttcaggtg  10800
ctgtcgcccg aggtcaacgc ggccattttc ggcgcgggca acgtctcgac tgcggcggct  10860
accgaggcgc acgcgcccg catgaaagtg ctgatcaact ccaagctgcc caagcggtgc  10920
agcctggtgc tcgattcggt gtacgaggac aagatcattc ggcaggtggc gcagatcgcg  10980
cagctttcgg gcctggccga catcaagctc gtgcacaacg ccccgatggc gttcgagccg  11040
acgttcaagg tgctcaaggg caccgacggc aatcacgtca tccagtacag cgacgacggt  11100
cagatcgtgg ccgcctagtc gctcgatagg ccagcacccc gcgcgttttc ctggtggcgc  11160
gcggggtgct ctctcgttct accaaaacac caggggcaca ccaggaaaca caccagagag  11220
gcagtaccag catggcaaaa gagaccaaga ccaacgagac cgacgtcgac gacgccgccg  11280
aggctgtcgt ggctaccgag gatgagcagg ccagcatcgc cgaggagtgg gccgacgact  11340
acgacgaggg caccgagctg ttcgtcggca agttcgacgc tgacgacttc gacaccgact  11400
acggcgtggc cgacttcccc gacggcgcaa cgatcgccgt caagcgctgc ctgcgcaagc  11460
ccccgccggg atggattcgc cagcacgcgc acctgtccga ccttgagcgc acgttcgctc  11520
taatcgaaat gcacgccagc gaccgggctc tcgaaatcct cgacagcctg cagcagaagc  11580
cgtgggacga cttcgtggag cgctggggcc gcgacggcgg gctgatcgag ggaaaatcgc  11640
gcaggtctgc gcggcggcgc gccaggtaga ggacgcaata cggcgtgacc tgatcgtcgc  11700
cgggcgcgag ttcgacgacg gcacaatgtc gtgggacgac ctgtacgcat tcattttgc  11760 ctcgccgcca acgtcggcaa tcttccacgc cttttgaaaag ggctggaata caaccgatta  11820
cctgctcgcg cacgtcattg acgcgctgcg ggtgggcctg tggcagcgca ccgaggatgc  11880
aaccaaaccg aatccgcggc atgtgcccga gctgttcccg cggcccggcg acgacgaaaa  11940
```

```
ggccaccgac ggcggcgagt acgtccaagt tggctcgact gtggcgacca agacaacggt    12000
cggcaagttc ctagaaatgc gcgccgaacg cgaaaagcgt tggcgtgaac ggaaaaaggg    12060
caagagcaag ggggcgtaat gtccgcaacg tactacctca cagttctgcc tgagacgagc    12120
aagctcgttc ccggaatccg aacggcaatg aagggcgccg aaaaggattt aaccctgcag    12180
cccaaactcg acacccgcgg cgccgctgag gcgggccgcc gtgccgggcg cgaaatgcag    12240
gacggtatcg agcagtcggc ccgcggttct ggcattggcc ggttcctgcg ggccgacggc    12300
gctcgttcgg tagggcagca agcaggcagc gagattaacg cggggctgca gtcggccgac    12360
gtcggccgcg gcctcgggtc gcagctcgca tcgaacctga cgagcggcgc aatgaacctg    12420
ggccgcaacg tcggcagcat gattgcgact ggcctcaagg cgacagcggt tgtcggcggc    12480
acggtcgccg ccgcgggtat cgctggcgcg ttgcacgccg gtatgagccg gttgacggcg    12540
atcgacgatg ccaagttcaa gcttcagggc ctcggcaacg acacgcaaaa agtccagaac    12600
attatggaca acgccctggc cgcggttgat aagacggcgt tcgggctcga cgaggccgcc    12660
accactgcag cgtccgcggt ggccgccggt atcgagccgg gcgagcggct gaccggctac    12720
ctgaaaagcg tcgccgacac cgcagctatc gcgggcacgt caatggccga tatgggcgca    12780
atcttcaaca aggtgcagac ctccggcaag gcgttcactg gcgatctcaa catgctttct    12840
gaccgcggcc tgccgatatt cacttggctg caagaggaat acggcgtaac cggcgaggcg    12900
ctctcgaaga tggtcagcga gggcaaggtc gacgccgcga cattccagaa ggttgttgcc    12960
gagcgtatcg gcggtgctgc tcaggaaatg ggcggcagta tccgcggcca gctcgccaac    13020
ctcaaggcgt cctactcgcg tttcggcgct gagctggccg gccgatctt tgcggccgtg    13080 tcgccattaa ccactgcttt cacaggcgct ttcaacaaga tcacggcggc gatcaagccg    13140
tacaccgcgc agttgactgc gatcattggg ccttgggcaa ctgacctcgg caacaagatc    13200
acggcgtggc tcgacaacgg cggcattcag aacgcaatcg actggatggg ccgcttggtc    13260
gaccgcgtgc aggcgttgcg cacgggcgag ggtcgaggcg atgcgctgca gtcgatttcg    13320
gattctgtcg gcaagctcgg cccggcgctg caacaggctg gccggcgct gcaaggcgtc    13380 ggatcggcat tcgcgcagtt cggccggacg atcgccgaga ttggaccggc gacgcttagc    13440
ggtgtcctca ctcccgcgct gaacctgctc gccggtgcgc tgaaattcgt tgcagataac    13500
gcctcgtggg cggttccggt catcggtggt ctcgcggtgg cattcctggc ggtgcgcgct    13560
gcgactgcgg cggctgcacc gttcatgcag gcgtacacgg cgacgttcaa cctgattcgt    13620 agccggtca ttctcctgca ggcgcaagcg cagcggcagc tcgccgccgc gatgacgcag    13680
cacacggccg ccctggtggc gaacactggt gctcagggca caaacacggt cgcgcagaac    13740
accaacgccg cgacctcggt tcgctcgcgt gtcgcagcga tggcctcggc cgtcgccagt    13800
cgcgcagccg cagccgcgca atggctttgg aatgctgccc tgactgcaaa cccgatcggc    13860
ctcgtgatcg ccgcggtggt cgctatcggc gtcgcattgt gggcgttctt caccaagacg    13920
gagaccggcc gcaagctctg ggacaagatt tggaccggga ttaagacgac ggcggtcgta    13980
gtttgggact ggctcaaggt cgcgttcgac tggctcggcg aaaagctcac gtggctatgg    14040
cagaacgtcg cggtgcccgc atttgagggc atcaagggcc ccgtcgaaac attctggaag    14100
ggcgcaaaag tcgtctggga tgcgttcaca acggtgctcg acacgatcgg caccaaggta    14160
ggcgcgttca aggacggcat cgtgaccgcg ttcaacgccg tgaaagacgt tgttacgtcg    14220
gtgtggtcgg ccattggcgg catctgggac aagatcgtgg gcggtatcgg cactgtcgcg    14280
gacgcactca agggtgcggg cggcacagtg ctgcgggcgt tcggcctggg cggcgctgcc    14340
```

```
cgcggtggct acatcgaggg cggaatggca cggtacgcca acggcggcca gatcaacggc    14400
cccggtaccg gcacgagcga cagcattctc gggttccgg cgatggtccg cgtggctaac    14460
ggcgagttcg tcaccaacgc ccgcacgacc gctcagtacc tcccgctgct gcaggcgctc    14520
aacgccggta tgccgctgag tgacgtactg ggcaagctgc tgccgcggtt cgccgacggc    14580
ggcctcgtgt cggccgacga gctggtcgac ttcgcgcgtg gcgtcgaggg caagccgtac    14640
gtgtggggcg gcaccaactg gggcgactgc tccggtgctg tctcggcgat cgccaactac    14700
gcgaccggcc gatcgccgtt cggatctcgt tttgcgacgg cgaccgaggg cgacgagctt    14760
gcggcacgtg ggtttaagcc tggcctcggc ccgacgggct cgctgcaaat cggttggtac    14820
aacggcggtc ctggcggcgg gcacactgcg gcaacgctgc cggatggcac gaactttgaa    14880
atgggcgggg cacgcggcaa cgggcagttt ggtggctcgg ctgcgggcgc ggctgattct    14940
gagttcacca accgtatgca cctgccaccc gaggcgttta cgggcctcga cggcggggcg    15000
ccgacggtcg ggtcgagcac ctcggcccgc ggtgccggta cgtacacccc ggcgacaagc    15060
tcgcagttga gcgcgtcgtc gcgcaaggtc gacactgccc gcacgtctgc caagaacgcc    15120
gaccaggcca tcgacgaccg cacctacgcc cgcgacaagg cacagcagcg gctcgacgag    15180
gccaaggcca agggtaaggg cgtcgacgat gctcagcacc ggctcgacgt cgccaaccgc    15240
gagctggccg acgccaagga gcggcaggcc aaggcgcacg acaaggtgac cgacgcgatg    15300
agcgccgacg aggaactgcg caccaagggc aagttcaaag agggctcgtc gtcgtcgtcg    15360
agtggcgacg gcctgtctgg cgctgatttc ggcaagacgt tcgtatcggg ggcgcttgag    15420
tcgatcggcc tcgacgggtc gctgttcagc aatccgcttg agtggccgac ggttaagtcg    15480
ctcatggctg gcgtgaacta cgcgggcggc ctgctcgcca acggcaccgg cgccgcaaca    15540
agccctggtg gcttcgctga cggcgtgggc caggcggtcg ggctcgatgg cctcatggca    15600
gcgcttccgg gcgctgtggg cgatcctgcg gccggttgga cacctcagag cggcagcccc    15660
gcgctggcgc ccggtcagtt caacccggcg attgcaggcg gcggcccctc gatcgccgag    15720
ggcgtcgcca acgccatgag tgcgttcgca ccggacacca cgcagcacgg gcagggcggg    15780
ggagctgaac ccggcccggc gggagacgtg aatttcaacg gccccgtggg catggacccg    15840
caagcgctgc gaaccgagtt ccgcaccgag ctgaacgcgc gttcgcgcta cagcggcagc    15900
tctaacacga agtaagcagc taacggccgg cgagtcgccg atctggtctc tgacctgcgg    15960
cggctcgtcg cgccagctat cgaactttca caactgaata acggggtgag tgagccgtga    16020
cgcttggcgg catccatgac gatttctatc tcgatccgcc gcggtacaca gatgacgcct    16080
acgggcgacc gctgtacggc cccgagaatc cggcgcaccc gagctggcgg cgcatgtcgc    16140
actggggcga cctcggccgt aacggcgagt acctgcggtc aacgcagacg aagtgggtct    16200
atatccaccc gagcaacaac aaggtgtggc acctcgccgg gcctatgcgc ggccgtgagg    16260
gcgtcgtgct ggccaaggaa cttgagggcg tcatgcagcc cgagtttgaa attctctaca    16320
gcgagggcgc ctatacgatc ggcgccaaac ccgagcggat caactacaag aaacgcacga    16380
tcagcctcgg cgtagtcatc cagcccaacg gcaacgccga gcgggtcgag gagcctaacc    16440
cgttctcgta ccggctgatt gaggactcgt ggtggtcgtc gctgtcggag acgcagcccg    16500
gtttcctggg ctcgttcacc cgcacgcacg gctggcggtg gctggctgtg atcctggccg    16560
aggcgtcgaa aacctccctc aagatcgacc cgacggcgca cgacaacaac tctcagcagt    16620
acaacatcgt gctgcacgcc ccctggccgt tctacgccaa gcgcacgctg agcaaggcgt    16680
```

```
ggctttccga cctcgagaat gtcgtggcga acgacggtgt ggcgcaaggg attatccagt    16740
gcccgaaccg cggcacctgg gagtcgtggc cgaagtacct cgttaagggg cacgggcagg    16800
cgtggattca ggacggcaac gacgggcaga tgatcaagct gcccaagttc tacgagacgg    16860
acggcgagta catgctcgtc gacaccgatc cgactaagcg cacgatcaca accgagaaag    16920
acccggttga cgggcagctc tacaagtatc tgcgcgggtc gcagttgctt gagctgctgc    16980
tgcacgacgt gacggccgcg cgcctcccgg cgcagcgccg catccccggc ggcatcgggt    17040
tcgacggcaa gattccgccg cgcacggtcg ccaatatcaa agtgcggcat gacaacccgt    17100
acgggtcgat tacgtgcgtc atgccgcagc actaccggat ggcgtggtca tagatgtatg    17160
tacagaatgg ccgcaagctg tgggtgccac cagcgtgcgg cgctaacggc gttcccgatc    17220
ccgtcaagaa tccgatcgag gcgtttcggt acctcgacct caagcgcgag ctgatcgacg    17280
ccgaggcccg cgagaagcca ctcattcggc tgtgggacaa ggcgtttaag tacatcggca    17340
ccgtggcggc cgagaagtcg gtcgacgccg aggaaatgct gcacgacacc gggcagggcg    17400
acattgtgct gcgcggcgac gactggctcg tcgagttcat gcgtaccgac gtgcgccgcg    17460
aggaggatct gcacgtcacg atcgacccgt acccgcaccg gcgcaactgg cggcggcggt    17520
ggcacgccaa ggtcaccaac gtgcgggttg cccgcaacga gaacggtcag cgcacagtca    17580
cattggagtg cgcgcacaac cgcgagcact ggaaacacct gctgttcggg gcgacgcctt    17640
tcagcctgcc cgaggtgcag cctatgcgcg cctggctgct gccgggcaac acgcgaacga    17700
tcgtgagcac aacgggtttc atcaacctgg cgcgcaacta ctggcccttg ctggcgctgc    17760
cttcgcaggt gatgaatccc ggcgcgtgga tcgggcaggc gtccaacctc gccaacctca    17820
acccgttgaa ctggccggtt caaatgcagt tcgtcaaccc actattcgat cggtcgcgca    17880
cgagcgtgct catgtcgagg tggtcgaacg cgcacgacgt gtgcgacgcg ctgctcaagt    17940
acgccgggtg tcacgttcgc gcgtactgct ggctggaaga ggacgaggac agcccgcacc    18000
ccgagctggc ggcgatcgtc ggcgagaagc tcgccaggcc gacgcgcaac tgcatcgtgc    18060
tggcagtcga ggacatgagt ggcacgaccg gggtcaccgg cacggcgatc gacggcgtgc    18120
tcgacctcat tgcagtgtcg gccgacaaca ttctcagcac cctggtgcac gtcgaccgtg    18180
acggcgacgg cgtggacgat ccgtttatcc gcaagctgct gggcgtcgcc ccggcgccgc    18240
cggatattac atttcgggat cacgaatatt cgtcgattat ctcgtctgag cacagcatgt    18300
ttcgtgcaaa ggcgcagaaa attctcacgg gcggccgtag tcctggctgg gtaaatcaag    18360
ttcagacatt cgccattaag tacgcgctct ctcaaatttc cgcaattatc caagctggcc    18420
cggctggtgc atatcagcaa cccggcagct cgggtttgga ggaaatttat cagggccagg    18480
ctgacaatat tttgctggcc tatattcagg taaccgaccc ggtgcgcgca atgcgctccg    18540
gaccctacgg ttacctggaa catttcgagc aaggctcggg ttcagcatac acggtcagct    18600
cggcaatgac attagctgag gggcatcaca agacgcgggc atatcaggcg ttcaaggtgt    18660
ccgtacgtaa tggcgggcaa ttccagctgt attacgattt cgatctcggt tggcgcgcga    18720
actttgaaat tgatcgcatt ttccacaccg accaggtgtc agctattcgg ctgcactaca    18780
acgagacgac accgaaaact ttcgacctgt ctatcggtag tgactcggaa tcggaaagcc    18840
cgctagcgca ggtggctcga tcggccgcag cgttctggaa tgccattggc atgttgttcg    18900
gatcaggaga tatgttctag tggaaattcc cacactgccg ccgctgcccg acgtgccaga    18960
acacgtgccg ggcgccaatt cgacggttga cgcgatgtat gacattgccg aggccctcac    19020
atatccggtc gacagccgcg gtcgacggta cgacgtgcga tttctcttgc cggtgattgc    19080
```

```
gtatcacctg gcgcgcgctg gttgtgtcgt cgacccggct cgggccgtga tcaagaagcg  19140
gcgcctgccg ccgacgggcg gcgtcgtcga ggatgcggtc gactgggtgc cgctcgacgc  19200
ccccgactcg atcgaggacg agctagacgg cgcgaccctc gacgacctcc cgcacctgtc  19260
cgcggcggcc caagccgaat ttcgacgccg ggcgctcggc gagccccgg cgccgacggc  19320 cgtcgacgac cagggcgtcg acctcgacga gcgcgccccg tggcacgtcg aaacgtcgat  19380
cacattcgac gactgagcaa ccgccggcaa aacgtcggat tcatacctg acctgcggcg  19440 gagcctcggg tcggcaaaca actgaataag gagcaccata tggccgagct gcgccccgg  19500 ctgacgggcg atgcggtcgc gctatttcag accctcctgt ctgccacgtg gtacggcatc  19560
gtcggcgacg gaaacacacc cggcggcatg tcggcaacgc tggaaatgat cgacggcgag  19620
gccgtgatca ctaccgacgt tctgatcgga cccaagggcg acaagggcga cccggccccg  19680
ctggttgatc tgcaatggcc cgcactggaa tccccgactg aactggtcga gctgcaagac  19740
gagctaggcg aggacgacaa gggcaagggc tggtggatcg gcacggttgt ctacgtctgg  19800
accggcaacc aattccagat ggtgcggccc ggcccggcgg ggcctcccgg cgccacgcct  19860
caaatctcgt ttgagttcga gacgatcccg atgtcggagc gcggcccgg cgtcaaggac  19920 gaggtaatcc gttccggcac ttcgcttaac ccgcacatca aggtgcgggc gctgtcgccg  19980
caggggcctg tcggcccgtc gacgaacatc accggcgcac cggactacga caacagcgag  20040
ccgccgacca acgggcagac gctcgtgtgg aactcggtaa aagccaagtg ggagccgtcc  20100
gacttcactg ccaagcaccc gcggctgtac tcggttcccg aggcagcgtt tacgccgttc  20160
accggcccgg cgcagcggca gccgatcctg cagtaccagg tcgagccgca ggacttcgcg  20220
tggaccccgt acgtcaccgg acacatcaag gcgtttggcc ttgagctgga cgccgacccg  20280
ctgacgatcg gcgtcgaggt gcgcctcggc gacccgctga caggcgagct gatcggccgc  20340
gggttcggca actcgtcgat gtggtcgacg attgcgccgc actggtcgac ctcgggcgac  20400
cccgcgaccg cggtggcccc cgacaacggc gtcgctaccg tcgccgccgg gcaggccgcg  20460
cagatcaacg taaaccttta caacgatggc ctgttcggcg tctacgtgtt caacggcaaa  20520
ggcgcgcagc tcgccattct cgttgtgccg caaggggat agctgcacat gccatacacc  20580
aagaattacc gcacggtcgt gccgcttgag ccgggcgtcg acctcgaact cgcgcggtgg  20640
ctggctcgtg agtcgttcga gcgtgcagcg gaaaacatgg gcctgacgat cgtcgagtac  20700
ggcgagcgtg aggtgccgtg gaccgagctg ccgccgaagg cggccgagca cctggcgctg  20760
cccgctgatg aatacacgtg gttcgagttc accggcgtag gtgcggtttc cgaggttcag  20820
atcgagtggc tgactgcaga gtcggcctgg cgcaaaacgc aggcgggagg tcggtaaatg  20880
cctcccgtct ttgatcgccg ctccctcgtc atcgaccgca accgctcgt tggtctgacg  20940 cccgaccccg gcaccctgcc caagctcgac ccggcgatgc tgtggaaaca gtggattgac  21000
ggtttcaaga cactgaccgg cattgaccta tcgtcaccgg ccgcgctcgt cgccagcctc  21060
ggcgacctga tcggcagcgc cctcgatcct gcaaagctga tcgaggcgct gacaaaggtt  21120
ttcgggtacg tcggcccgcc gctggcctca cttgaggcgc tggcggcatg ggtcaacagt  21180
cagattttcg gcctgatcga cccgcggcgg ctggcacaga tcccgctcgg ctcgatcgtg  21240
caggagtcgc caaacctgtt gaccaacggc tcgtttaccg acgcaatcgc catcgacgac  21300
gagacgggcc gctgggtccg cgacaccgcg acgtacaagt cggcgccagc gtcggcgcgc  21360
acgaccgccg acggcacgat cgccgaactg ctgagcattg atctgatccc ggtcaagccg  21420
```

```
aaacagaagc tcgacattgc gggattcgtc cgctgggcgg gcctggtggc gtctgacggg   21480
tcgatcggta tcgggctgat ggagtacggc gacgctggcg agcagcgggt gctgatcaag   21540
gcgctagacg gcgccagcgg cacgcaactg acgtggcaga aggtcggcgg ccagtacgtc   21600
gtgcccgaca ccggcgtcga cggtgtgcgc gttcggctgg tcgtcaacga cggcgcaacc   21660
gcgggcaacg tgtggtacga cgagctgaac gcgagcctgg gcgcaaacct gctgcccaag   21720
accgccgttg agggcctggt cgccgagctg aaagcagcgt ttgactcggc cgaggccgcg   21780
gctaagcagt tcctcgactt cctccaaaac caatggcagg cgatgctcaa cggcatcaag   21840
ggcggcgtcg gtggagcaat cgaggacttg tggaatcggt tgctgcactt gacacctgac   21900
ggccttttcg acgcctcgca gctcgtcaac gtcgacaaca tgccgcagct tcccccggcg   21960
gtcgtcgcag gtatcgaggg aatcgagaat atcggcgaca cgattcagca ggcgatcgac   22020
tacctgtggt cgggcttccg tcgtcaaacc gggcaaggca atcgttctc gtcgctggca    22080
caagccgcgc aggaaacatc gaacgacatt cagacggccg tgcatctggc gacgatgcac   22140
gcgggcattc tcagcgagcg gcgcaacaag cccgcacact ggggcctcgc cgataccgtc   22200
gaggtgtcgt tcccgttgac cgatattgcc tacggcacaa cggcgccgac aattccggtc   22260
acagcgacaa atgcccggct ggcgttcatc cgctgcggcg aagcgtccac aaagggattc   22320
gtgcagtggc tcggctacgg caccctgac gccttctacg tgaacgtgta caagatggac    22380
gccgagggca acctcgttca cctgcacacc tcgccgaata tcagcaacca actacagacc   22440
acgatcggct gggagatgta cgttttcgcg ggcgccgatc agaccgacgt cgagccgggc   22500
gacgtgctgg cggtcgagtt cgtcgtcgag ggatcgacgg catacaacat cgccgggtgc   22560
gtcaactcgt gggttccggt gcacccgtcg gcgaacacca acaccttgg tgcggtgcgc    22620
ggctcggcgc ttggcgggcg gtcaccggcg acaattccgg ctgagcttgt ctcctggacg   22680
ggcgtagtcc cgtgggtgtc gctcggcatt agcaacgtgc cgccgagcta tcggcccccg   22740
acagcgaccg agttcacgga gactgggcag cagacctacg agattccact gtgggccaac   22800
tacattgacg tgatcgcctg cggtggcggt ggcggcggcg gtagctcggc gaacttcctc   22860
acagggcagg gcggcgagtg tgggcactgg atcgcggtaa cgctggtgcg cggcgtcgac   22920
ttcgcagagg acgcaacgac gatcaccgtc aacattgggc ctggcggcgt tggcggcccc   22980
ctcaacgcca accccggcgg cagggggatcc ccaacggtcc tcacatggcg caagccagac   23040
gggtctatcg gaatggctac cgcacccggc ggcgagtacg gcggccccgg ccccgtgcac   23100
aacggcaaca accccaacac ggcatctgct ggcatgggcg cgccgaactt ccagtaccgc   23160
ggcgcaacgt atttcggcgg ccccgatgcg tcctacgcgc cgggcagcgt gcccggcggc   23220
ggcggtgctg gcgggttctc gtactcgtct ggctgggcgg gcggccgagg ttcggcgtgg   23280
ctggtcgccc ggcaatccga ggacgactga gaggggcgc tatggcggga tggggtaccg    23340
acccgcagcc gtcagcgcgt gccggtagcg gctgggcaac gtcgcccgcc gcaccggcgc   23400
ctccgcggcc cggctcggta tggcggccga tcgtgcacga gctggcggcg gccctgagcg   23460
tctcgaccac cgaggcggcc ctcgctatcc gcgcaacggc cgcagcgctg agcgtttcac   23520
acggagacgt tgcggccctg ctgcgcatga cggcccggc cgccagcacg agcggatcgt    23580
cagcgtcggc acgagagcac tatttcaccg cggccccgc ggacagcacg agcacgaccg    23640
gggcgtcggc ggtcgtcaag gcggtggctg cagcactgaa cgtcagctcg acgtcagccg   23700
ccgcggtgct gcgggccgtg gcgcccgcgg cgtcaacgag cggcacgtcg gcctcggcag   23760
cgttcccggc aatggcgccg gtttcgcagc ggttcgccac tgtcggcgag ttcgagtttc   23820
```

```
tgatcccgta ctggtgccgg tacgtcgacg tgatcctcgt cggcgcgggc gcaggcggca    23880
acggcgggtc tgcagcactg gccgccgggc atggtggcga gggtggcaag tgggccgcgg    23940
tcacgttgga gcgtggcgtg catatcccgc tgaccctcgc ctcgatcgtg tgcaccgtgc    24000
gtgcgggtgg cacgccgggc ggcggcgccg tcgtcggcgg tatcgccacg gacggcaacc    24060
ccaccacggc gcaggcggcg ggctgggcag ggctgagtgc tgcgggcggt gtgcaccgcg    24120
agcggatcgg gctgctgcat cagccgggcg acggcccggg cgatttcact ttcaagggcg    24180
tgctgtacgt cggcggcgcg ccgaccaata gcggcaacgg cacagcgggc aactcgcctg    24240
gcggtgctgg ccgcggcggc gacggcgcg cgttcgtcgg ttctcccggc ggtgtcggcg    24300
cacccggagc ggcgtggttc cgcgcatacc agtagcaacc gccggccaaa tgccggactc    24360
atagcttgac ctgcggcgct gcctcgggtc ggcaaacaca actgaatagg agcgttctgt    24420
ggcttccgca gatcagttca agctcgacac cctcgctgca atcctcgcgc agggcaacct    24480
gctgagcctg cacagtggcg accccggcaa gacgggcgcc agcgagatta ccggcggcgg    24540
gtacggccgc aagacgttcg cgtggggcgc cccggcgatc gtgtcgggcg cgccgacga    24600 cggcaaggcc aaggcgaccg cgccactca gcagatgaac gtcgctgcgg gcgtggcggt    24660
tacgcactac ggcgtacgca aggccgacgg cacatttctg tacggcaagg ccctgagccc    24720
cggcgcgact ctcaacgcga acggcgtcat tgacgtgacc ccgacgcaca cgtacgacgg    24780
cccggtttag aacggagaca accgaatatg gaaaaggtac tgccctacga tcgggtgatc    24840
gtcccacagg aaacgggcta ctggtgcggc ccggccgcaa cgcagatcgt gctcaattcc    24900 ccgcggcctgg tcgtgcccga ggcgaccctc gcccgcgaga ttggcaccac ggtgcgcggc    24960
accgactacg tgggtctgat tgagcggatt ctcgacctgc gggtgcctga tgcccggtac    25020
acgtcggtgt acatcgagaa cgacccgccg accgctgtcc agcgggagac gttgtggcgc    25080
aacctcaagc ggtcgatcga cgccggttac ggcgtggtga tgaactgggt tgccccgccg    25140
agcaactacc cgcgcggcgt caagggcagc gtgagccccc ggtatggcgg cggcaccgtg    25200
taccactacg tcgcggcgat gggctacgac gacaacccgg ccgcgcgtgc ggtgtggatc    25260
gctgacagtg gctttcagcc gcaaggctat tggatctcgt tcgaccagtg cgcgtcgctg    25320
atcccgccga agggctacgc attcgccgac gtcgatcacc ccgacggccc cgaggcgccg    25380
gtcgacgccg acgcgcaggc ggccgacgcg ctgctgcggc tgatgggcgg ctcgctgccg    25440
ttcgctcggt atcaggcgct actgcccgcg gtgcgccagt gcctcaatga gtgcgagtgc    25500
acgaccgagc cccgcatcgc tatgtggggc gcgcaggttg ggcacgagtc ggtgggcctc    25560
aaattcatga gcgagctgtg ggggccgacg gccgcgcagc agggctatga aggccgcgca    25620
gacctcggca acacgcagcc cggcgacggg taccggttcc gcggcgccgg gcctatccag    25680
gtcaccggac ggcataactt cacggtgctg tcgcagtggg cctacggcaa gggcctcgtg    25740
ccgacaccga cctatttcgt cgacaacccc gacgaattgc gcggcgaccg ttacggattc    25800
gtcggcgtcg tctggtactg gacgacgcaa cgcccgatga cgacgcggc agacgcccgc    25860 gatctggtgc gcgcaacgca gtacgtcaac ggcggtcaga acggaatcga cgaccgccgc    25920
acccgataca acgcgcccct ggcgatgggt gccgacctac tcaagatcgt taacggaggc    25980
gatgatttca tgtctgcact gaccgctgcc gagcagcgcg aaatgctcga tctgctgcgc    26040
tggttggcag caccggaaac cggcgagctg cgcaagaagt tcccgagccg cagccagttg    26100
cgcgccgtcg gcgagggcct ggtcgacacg tgggcgggta tggacctcaa ccaggacgcc    26160
```

```
aacattcacc tggtcgccga gtacgtgctc gccggtatcg gcgatcccga cgcaatcgcc    26220
cggctgcgca agctggccgc gacgaccgac gccacccgtc gggggagcgc ggcgctcgcg    26280
cagcgcatcc tcgaccacta cgaccaggcg cacgaggccc ccgccgaggt cgacccggcc    26340
ccggcgcgca aggtggcgtg tgcgcagggc ggtggcggtg tgtcctcgt cgccaacggc     26400
ggtgacggca cctgcggcct cgctggcagc gagtgcgtgc tgcgcaaggg cggtgccctg    26460
tgagcaagcc aatgctgctg accgccgcgg gcaccaaggc cgacgagtgg accggctacc    26520
cggccgacct cgcgcggcgc atggaggatc tgtactactt ccagccagtg cggtacggcc    26580
ccaacggaat cccggcaatg tggccgatgg gtgcctcggc taagaccggc atcgacgagg    26640
gtgtgcgcct ggtgctcgaa gccgaggcgc ggccatcgcg ggaggtgccc gacgggtacg    26700
ccgtgtgtgg atactcgcaa ggcggctggg tcgtgtccga gctgctcgac gagttccgca    26760
ccggccgact caagcacctg cgcggcaagt tgatggccgg tgcgacattc ggcaacccgt    26820
accgcgagct ggacagcgac ggcggccgag gaatctccga caagcggatc gtcaacacgc    26880
ccgatttctg ggtcgacgag ttcgaccgcg gcgacatcta cgcgaacgtg ccgaacaacg    26940
acgttggcga ggacatgacc gcgattttca agctggtgcg gttcaacggc attggtgacg    27000
tgatcgacct cggcagcgcg atcgacctcg gcagtatcgc gggcggcctg gtgccggggcg   27060
gcggccacct cggcggcatt ctcggcggcc tcggcgggct gctgggtggc ggcgcgcggc    27120
agcaagacaa catcgtcgag cagatcgtcg aaatgctcag gagtccgctg cgcgagttcc    27180
cggccgcggt gtcggcgatc ctcaagggcc tggtgttcgt cggccagaag cccgcgaccg    27240
cgccacacat cgagtaccac ctgcgcgagc ggtcgccggg tgtcacctac tacgagcacg    27300
ccgtcgccca catgcgcgcg atggcggcat aagggggcga gaatggcaaa ggtcgtcgag    27360
acaatcctcg gcatgttagt gcaggtgtgg acaggtgtgc ggcaattcgc cgccgagtgt    27420
ctcggcatcc gcacgtggga ggatttgcgt ctgcagattc acgtgctgtc gccgtacgca    27480
gttacggcaa tggtcacgtg gaacatcgcc agcgaggaca aggccaagct gattgttggc    27540
ctcgtgctcg ccgttgcgag cccggcgctc gcgttcttca acacacgtga cgggttccgg    27600
cgtttggtgt acggactgct gccgccgttg caggcgttca ttgtcggttt cggttgggcg    27660
caggattcga ccctgacgcc tctcatggcg gcgatcgtcg cgctgctcgg cggcgcaatg    27720
gctgccgcta acacgccgtc gagccgcggg ccgaaagaca cgcggacggc ggcagtgccg    27780
tgagcatgtc tgacctgatg accggcgaga cagtcggaat gatcgccggg tcgtcggtcc    27840
tgtctggcgc cgtcggggca ctactgtccc ggcggcgcga caacttcaag acgctgactg    27900
atgcactgat caagcgcgtt accgaccttg aggggcgcgt cgatacggtc gagtcgaaac    27960
tcgacgccga gcagaccgcg cacgagcaca cacgcaggct gctcgtgcag tccgaggcac    28020
tgctcgccgc ggcccgtgcg ttcatccgca ctgtgatgcg ttggagcgca ggcgatcgtg    28080
ccgagccgat gccaacgcca cccgacgagg tgatggccga atgagcctcg ccgaacgtct    28140
cggcgacccg cagcccgcac cgtcgagcga gtgcgccgtg tgccgctggc tcgaccaggc    28200
cgacgagacc gatcgtgcag cgttcgacaa ctggctcgct tccggcgggt cgctgtcggc    28260
gctgtgcgg gcctgcgcca acgatccgag taacccgctg gcgatcaagc gcccgcggtt     28320
ctctgagctg atcaacgacc atcaccgagg aggcgcacgt gtcgctgtct gacaggctcg    28380
ccacaccggc ggtcacaaac gagaaatacc ggcccacggt cgagttcgac aaccgcggcg    28440
ccacgatcga cacgggcacc gtgtaccagg agccgggcca gccacccgag tacgcggaaa    28500
ttctgcgcca ggtcgggcgc gaccccgaac ggttccggct cgtcgagatt ctgagcgaga    28560
```

```
agcattggca ggtgccgtat cggccgtacg tccgcgacga cgacggtcag ccgatcttta    28620
acgagttcgg caagccacgc cttgaggagc aagagtttcg gtgggcggcg tcctacaagc    28680
tgcgcgtcga gccgatcgac cgcggcggcc cgagcgacct tgaggcgctg atcgccgacg    28740
cccgcaaggt gccgacgatc gccccggcga cgacctcgcc gtactggtac gtgtttcagg    28800
cgggcgacct gcagctcggc aagcggtcac gcgacgggtc taccgagcag atcgtcgagc    28860
ggttcgtgca gtcgcttgag gccgccggtc ggcagtaccg cgagctggcg cgtccgtcg    28920
ggatcgccgg tgtgcaaatc tcgatgccgg gcgactgtat cgagggcgtc gtgtcgcaga    28980
agggcgcgaa tagctggctg acacaggaga cgatcgccga gcagttccgg ctgctgcggc    29040
ggctgatggt tgaggccgtc gacacgttcc gcgcggcccc ggccgtgtac ctcgacgtcg    29100
tgaacggcaa ccacgaccag gccaatcggc agtggaacac caaccccgga gacgggtggg    29160
cgaccgaggc agccatcgcg gtgcgcgacg cgatggtgct caaccgcgac gtgtacggac    29220
acgtcgaggt gcgggtgcct gaaccgtggt cgggcagcat gacggtgccc gtcggcgaca    29280
ccgtggtcac tgtgatgcac ggacaccagt cgcccaaggg caaggccctc gactggctcg    29340
ccaagcaggc ggtgcacaac cagcccgcgg gggcctgcca ggtgttgcaa cacggacact    29400
ggcacgtcgg cgccgtcgaa atgcacgcca caaagacgat cgtgtgctcg ccgacattcg    29460
actgcggcag cgattggttc cgcgagcgcc agggcggcga gtcccgccgc ggcgctctca    29520
cctacctgct gcgcagcggc gaggtgtcga acctgggcgt gctgtagcaa ccgccggcaa    29580
aaacctcgag cgcctgccgt gacctgcgcc gatcaatcga aacgccgatt tccggcaaac    29640
attgcgaacg ccccctcgtcg atccgtcggc gggggcgtt tcgtcgtatt gttgacctgc    29700
atacaggtgg cccgtattgt tggcatggca acaacggcac aacgggatag gagcccgaaa    29760
tgagcacgga cgtaatgaca gtgcgcaagc tgtccgaaca ggaggccgcc gctatggcac    29820
gaggcaagtt ggtcagtgtg ggaggcaccc gccgaacgat cccggcggcg aacgtgccgc    29880
ggtacgagga gcaggtcgcg gcgattgagg ccgagtggcc cggcgccgac gaggcgcaca    29940
ttcggcgcgc ggcgattgag gccgtcggcc ggtacctgtg cgacgaggcc gacctgcccg    30000
agacgatcgg cgaggagctg gccgaggcga aagagcagta cgaggccgcg acgtcggcgg    30060
cccgcatggt cgtgcgcctg gcggtcgagg acaacgccag cgagctgagc ctcgcgcagc    30120
gtatgggtat caaccggctg actgtgcgca agtaccgcgg caaggtcgat cgccgttggc    30180
agcgcccgtg agcgccgcgc cggtcgggtc tgaggtgtgg gtactcgatc tgacgatcga    30240
aggccccgag ggcggcgact atgacgggtg gcagtcggtg cacgcgagcc gcgagggcgc    30300
actcggggcg atgctcgaca agctcggcga gcatggcgtg agcctcggcg ccgacgtcga    30360
cacgatcgcc agcgcggcgg ccgacaatgg cagcctggcg ggcgattttg cgatcgacga    30420
gctggctgtg agctacggcg tgcacctgat gccggtcgag ccctaaccca cgtgttgaca    30480
tgcatacagt tcgcgggtta ctgtatgcat accaacaacg cacacgggat aggagcccac    30540
gatgagcgag tacaccaagg ccgaggccaa ggcagccgat gcgatcctcg ccaagctgac    30600
cgatgagttt ttcgaggcgt atgccgcctg ggagcgggcc gccgaccggc tgcacggcgc    30660
cgcgggcgac gacaagaccc gatacggctg gaagatgagc cacgacgagg ccctcgccaa    30720
ggcgaccgag cgcgcggccg acgagcggat cgtcaaattc aaccgcgacg ggtacgcccg    30780
cgccgtcgag gcgtaccccg cggcagtggc cgccaagagc gccgcgacaa aggcgatcga    30840
cgaccacgag gccgccaact acaagggatg gctgcggttc ttcctggtgc cgggtgggca    30900
```

```
cattcaccgc tcgcgcggct gcgcgtcgct gcggatcaca accaagatcg gttggctgcc   30960
caacctgtcg ggcgagaccg aggccgaggc cgtcgcggag cacggcgcca tgctgtgcac   31020
aaagtgcttt ccgtcggcgc cggtcgagtg gacgatcggc aagcccgccg accccgacgc   31080
ctgccctggt agcggcgagc gcccggtcga gggcacgatc gtgcgtcggt accgcagcgc   31140
ttacgccgag tgcaccggct gcggcgtgcg gcacgtctac accatgtcgg gcgtgatcaa   31200
gaagcacaag cgccccaagg tcaagtagcc ccggcccggc gaggcccccg tcgacacggc   31260
gggggcctcc ttggtgttga catacataca ctcgacgggt tactgtatgt acatcaacaa   31320
cgcacacggg ataggagccc acaatgtcga tcaacaccgc taccccttc acctgcaacc    31380
ctggcacgat caacggccgc gaggttgccc gcggctacat ggccgaggcc gacgacgcac   31440
gcgagctggc ggcgttcgac gaccgtctca ctgaggcgca gtaccgcacc ctgcaggctg   31500
cgatcaacag cggcctgccg gtcgtgctga cgatccgtga gcaaggcgag cgcccggccg   31560
cccgcaaggt gacggcgatc gtcgagtacg caacgatttt cccgcgcaag gccgacgacc   31620
ccaccgcggg ctcgggcaac ctgattcgcg cgcgctactg gggattcggt cacaacgtct   31680
ggctgcagga cattatcgac ctcgacaccc ccgaggttga gttcatcgac ctgcccgagt   31740
agctcggcct gagcacctcg acgacgacgc ccccggcggg attacctgcc gggggcgttt   31800
tcgtgtctat gcgggctact cggcggtgtc tgggcacagc tcacgctgcg cgctgtacgc   31860
gatcccgtcg gcatggtcgc gtgtcatgtc gagcaccttc aagaacatgc gatcggcgac   31920
gacctcgcgg ggcttgcccg tccgcagctc gtcgcacacg gcgtaaccga gcgcgagcgc   31980
ctctcgctct tcgagtatgt cgagcccgta gtcgacactg atcctcgcca ggtatccggc   32040
ctcaccggcg tgtgcggcgc cgggcgccag gacgacagag gcggccccga tcgtggccgc   32100
gacgagtatt cgtttcaccc ggctaagcct agttggcggg gcctggtctg tggcggcacg   32160
ccgcggtacc gtctgccgta tgcgtcagtt cccggcaca ccggcgagcg gcgtttgctg     32220
gcgcggcaaa cgaacggggg gcgtggatgg ggcgtggatg gcatccacac agcccgcgtt   32280
gccctgcgga ttgccccgtg ttttcgcgta ctctcgcgtg tcagttagcg gcgtttccgc   32340
aggtcagagc ccctagaggg gctcggttca attcccggca gctccacccg taaacgccct   32400
ggtcagagcc aaaaatctga ccggggcgtt ttttacatcc acacccacat ccacaaatgt   32460
gtacgatctg cggctatggc atccctccgc accggcaccc gcaaagatgg ctcgacatac   32520
acgcaggtgc gttaccggct gaacggcaaa gagacgtcga cctcgttcga cgaccgggtg   32580
caggccgttg agttcaagcg gatggttgat caactcggcg cggccaaggc ccttgaggtg   32640
atcgaggcga ccgacgccgc gcaccggcac tacacgctga gcgagtggct gcggcactac   32700
ctcgaccaca agacgggcgt cgagcggtcg acgatctacg actacgagaa agttgtcgcc   32760
aaggacattg acccggtgct cggcccgatc ccgctcgccg cgctgacggg tgacgacatt   32820
gccaagtggg tgcaggccct cgctgaccgc gggctcaagg gcaaaacgat ttccaacaag   32880
cacgggtttc tgtcgtcggc gctgaacgcc gcagtgcgcg ccgggcgtat ccccggcaac   32940
ccggccgcgg gcgcgcggct gccgcgcacc gaaaaggccg aaatggtgtt cctgacgcgc   33000
gagcagtacg ccaagctgca cgacaacatc acgctgccgt ggcagccgct cgttgagttc   33060
ctggtcgcca gcggcgcccg ctggggcgag gtcgtcgcgc tgcggccgtc cgacgttaac   33120
cgtgacgcca gcacggtgcg catttcccgt gcatcgaagc gcacatatgc gcaaggcagc   33180
tattcggttg gtgcgccgaa aacgaacaag tcggtgcgca cgatcaacgt cgacgcatcg   33240
gtgctcgaca agctcgacta cacgcgcgag tacctgttta cgaacacggt cggcaacccg   33300
```

```
gttcggcaca acaactttca cgcgaacgtg tggcagcctg cgctcaagcg tgcgggcctc   33360
gacgtcaagc ctcgggtgca cgatctgcgg cacacgtgcg cgagctggct gatcgccgcc   33420
gggctcccac tgctcgcggt ccgtgaccac ctggggcatg agtcgatcaa gatcactgtc   33480
gacacgtacg ggcacctcga ccgcaccaac gggcaggcgg tcgcggcggc catcgctgcg   33540
cagctcgacc cggcgcgcgg ctgagcgcaa cacgcacgag ccccgaagct gaacgcctcg   33600
gggctcgttt gctgtatctg gggcctactg caggtcagcg ggcaattcga gtgctttgcc   33660
ggcggtagct aggcggcctc ccgctcgatg tcggggcgca gacgtcggcg atgcgcctcg   33720
gcggtgtcat cgcgcagtgc acggcgactg gtgcgggtcg cccgaatcag cccgcgatac   33780
ggccgaatct tcgtccacca cgaccaggcc aggcacgccg acagcatgac cgtggtcacg   33840
tatccacaga ccgagatcat tgccgtaatg cgtgctggg tggccatgaa ggcgctcgcc   33900
acggcgaggg cgcagcacgc gatgcagaac gccagggcga cgatccagac caccgcaata   33960
cggccctggt gctcgtcgtg ggcgatgtgc cagaggcagg cgacggccac cgcgagcagg   34020
tgcatggtcg cgtagtagtg cagcgccgtc gccccgacga tgccaatgtc agtggcgggc   34080
atgtcgagca tgttgtggtg cacggcgggc tcgcgcagcg ccgggctgct cacctgcagc   34140
gccagcgtca caaccggcgt gaggtagagc cacggtgcga cccaacgtgc gaagaacacg   34200
cgcacctcgt cgtcgtcgca cacgcggtgc aacatgctga cggcgatagc cccggcgctg   34260
aacaggtaga gcgtgcggcc gagccagtcc tcaagatgcc agacgccaat tgcttggtag   34320
atggtgcggc cgagcgtcat tgacgccacg gtgccgcaca cgccgcacc aagaagctgc   34380 agcagcaggg ccgaggtcag cagtccctcg tgcaggatgc gaaagctacg ccagcgcaac   34440
agaactgccg caagagctac cacacaaaca atccagcgca gcacgataaa tgcgacagct   34500
attgacatag ccactctctc agggaaggcg ggcggcggcc cgacgatcaa actgccgcca   34560
ctgtaaacca cgcctcagag tggtgagaaa ttacacatca aagactcgga atgtcaggcc   34620
tcacttgcct tgtcgtcgac cggcggcggg tcttcttcgg cgcttccttc acctcccgtc   34680
caaccgtccg gagcgcctga gggtggggtg gactcggcgc caggccctcg gcgtaggcgc   34740
ggatcgagtc gtcgctgatg aggttgtacc gggcaagtag gtcgacctcg tttatttcga   34800
ggttgcgggc ggctctgatg aggttatcgg cggttatcag gcgcccctcc tcggcttggt   34860
tgtagtagcg ggtgcgcgac atttgcagcg cttctagcat ttcgcgcagc ttgagctgcc   34920
taccgacaag gtagctcagc acggcggcga gtgacttgtc ggtgtcgtcc tcaggcatgg   34980
ctcgtgattc ctgtctgttg ttcgagctgt tcattccctc ggcgtgtcac tttagttcag   35040
ttttcgggac tgaacaactc tcttaccagc gtttatgcac ttcttatgca gtcgttagcg   35100
tcccgaaaca acgcagatgt tcctgatttc gggactttg gtgctactgt ctcacaccgt   35160
gcagacaacc actcatcagt tgcgttggcg gcgcgacaac gtggcaaaga ggatgcgccg   35220
caacaacatt caagatcgtg caactttggc aaaaaggatc aacgtcgggc gaaccacgat   35280
ttactccacc ttccgcgcgg actggtcagg tgtggcaacg cacacggtgc tggcgcagat   35340
cgtcggagaa ctgggggggct cgctatctga actcgtgtca gttgaggccc gcgcatgacg   35400
gcccccgcgc tgacccgtcc gcttgctgag gtcgcggcac tgattccgtg ctcagagcga   35460
tggctgaccg agcaggttcg agccgggcgc gttcccggcc gcaagatcgg ccgccactgg   35520
cgcatgacgc aggccgacgt cgacgccgcc cttgagtcct tccgagtcag ccccgagtcg   35580
ggccgcaagt cggtcgcacc tcccgccgac cggccgatcg cacttacccc cacctcacgc   35640
```

```
cgtcggacta ggagccgctg acatgacgat gaccacccgc acccgcaacc tcgccgccgc   35700
ggcccggctg cgcatcgaac tgaacgaggc cctacgcgag cgcaaccagg cccgcagcga   35760
gcgcgacgcc gggcgccagg taatcgccga ccaggccgcc gcgctgcaca gcctcggcga   35820
tcagaacgcc tacctgctgc aggagcgcga cgagctggac acggcgcacc gcgcggcgct   35880
ggccgacctc ggcgaggcgc atcgccagct cgctgagcgc gacaacctcg acaacctgat   35940
gcaactcgcc actgcgaccg tcgcggcccc ggcgccactg cacgacgagc cggatatgga   36000
gcggttcggc tgagcttgga ggtggggcgt caaacgggtt tctttcgctg ttttcttccc   36060
ccgcaagcgt ggcccacgac ccgctgacta cttccggcga ggtcactgct gcgccccacc   36120
tccccacaaa cgacgcagcc ccgcactagg cggggctggc cgacacaacc aagggatagg   36180
agccacttgt tatgtcgagc aaaatcctag cgcacaagcg ccaggcggcg cgggatcaac   36240
ggcacggcga gcgcctcggc gcgatcgtcg gcgtgttcct gctccacgcc acgatgggcg   36300
ccgttggcgg ccttgtcggg gcggcatggg tcggcctcta cctgggggcg ccctggtgat   36360
cacgctcaac cacgacgaaa tgcaggccgc tgcccgcgcc atcgacgcca accaggccga   36420
gggcgtgact accctcggcg cactggccgc cgcggtggcc gctgtcaaca agctgcgcag   36480
ccccggccgg tcgtccgact gcaccgactg ccagcggtgt gacgccacct gccccggtca   36540
cgtcaaggcg caggcggtgt cacggtgacg gccgcgcagc tcggcgaggg cgaggccgct   36600
gtgcgccttg ggattacgcg caatgcactg cgctggcgcc ccgcagcgg cacggcaccc   36660 gagcaccagc tcgtcggccg caaaatcatg tacgacgttg cggcacttga cgagtacgcg   36720
accgcggtcg acaacacgca cgtgctcgac atgttcacgc cgcggttgg cgacacggcg   36780 accgctgacg aggtgtgccg gttgctgcgg attgaccaaa gcgacgtact gggcaaggtt   36840
ttgaagcgtc acggtgacga attggctgct cacggctggg atcgtgaaag tggcacgttc   36900
acccgccggg cgatcattca ggttgcgttg ctggtgcgtt cgtcgacctc ggcgcgtgca   36960
ggtcgcatcg ccaaggccgc caaggcaggc agtcggccga tcagtttcga ccacagcccg   37020
cggtcgcagc agtgcactca catgcttgag cgcgcattcg atctggcgac cgaggtacac   37080
gacgacgacc ccggcgaggt gtgggcacgg ctgcgcaagc tcgaccgtca cgcactgacc   37140
ggcgtcgctg tcgccctggc cgcgatggtc gacgttgagg gcaccggcgc cacgaagtac   37200
ctgcgccacc tgtcccgcgg cggcctggcg gccgagggcc tgcagcggtt agtgccgact   37260
cgtgagacga ccgacggcgt gccgctgtca gtgctcgacc agatcgaggc cgacgacgag   37320
gccgaccagc aagacgaggg cgaggtggat cagtgagcga cgcagagcat tcgacgacg   37380 accccgaggc ttggcgggat aacgccgtat gcgcgcagac cgaccccgaa atcttctttc   37440
cagagcaggg cggcagcacc cgcgaggcca gcgcatttg cggcggctgc caggtggccg   37500
acgagtgcct cgcgtgggcg ctgagtcagc cagtcaaccc aacgggcatt tggggcggca   37560
caaccgaacg agcacggcga cgaatcaagc gcggacttaa aggggttgca gcatgagcga   37620
ttacaacgac gcgaccggcg cccggtgcga tgtgtgcggc aagtacgagg cgcgggtgtt   37680
cgacccgtgc ggggcgatgt ggtgccgggt gtgcgacctg atgggcctcg cgcccctggc   37740
ggtgagcgag cagctcgccg aggtcgccga gttcgtcggc aagacgttcg acgagacgcc   37800
gctgttcggc atggacaccg acagctcggc gaccgaggcg ggcgaccccg aggcatgggc   37860
cgacccgacg ttcatccttc ccgagccggt gcagcagatc gccgacctgg cccaccagtt   37920
cgccgccggt gacgacggcg tgagggcgca agcgcaggtc tggctcgacg aggcgctgcc   37980
gcaagtgctc ggcgagagca aggtcgacag cctcgacgac gccgacccgg cgcacgtgtg   38040
```

```
gcaggacgcg ctcggcgcgc actggggctg gctgcatggc agcggttggg ttgcatggaa   38100
tagcggcgtc tacgtgcatg gccgcggcgc ggttggcccg ttcaaggtcg catatcggcg   38160
gccggtcggc gagttcaccc cgatgctgct cgaactcggc ggcggcctcg cgttcggctg   38220
cgacatggcc cacggcccta gcaacgacac cggcgtcacg gaaaactcca cgaccagcgc   38280
agacagcttg gccggcgagc ctgccgagca aacgcccgac atggtggcgc acccgtcgca   38340
ctacacgtcc agccccgcca agtgccgggc gtgtggtcac ccaatcgagt gcatcgacat   38400
caccgagcac atggggtttt gcctcggcaa cgccaccaaa tacgtctggc gctgcgacct   38460
caagcacgac gcaatcgagg acttacgcaa ggcaattcag tacatcgagt ttgaaatcgc   38520
ccggcgcgaa gcgctgagca caaccgaggg ataggagccc acaacatgat tcgcaagatt   38580
gccgtcgtcg ccaccgcggc actgatcgca gcaggcgcca ccgcgtgcga gggcggcgca   38640
gatggcggcg gcgggcagca ggatagcggg cctagcggcg tgatcttcat gccgatgccg   38700
ggcgttcccg cgccggtat gccgatcttc ttctgaccaa cgaccaacca ccaaaggggc   38760
acaaccaatg tcaatgatca accgtattgc cgtcggcatg accgtcggcg cgatcggcgc   38820
cgccgcggtg ctgtcgggct cgccacgtc caaccaggaa tggcacacgg ttgcaccgt   38880 caaggccaag gacattgttt acggcggcag cgacggaaac accacgcgca caaagcgcgt   38940
caccacgtcg tgcggatcgt tcaacgtcga ggacgcgatc gaggtcgggc acttcaactc   39000
gtgggacgtc tgggagtccg tcgaggtcgg caagacgtac gacatgttca ccggcggccc   39060
gcggatcggc tggctgtcga cgttcccggt tctgctggaa gtcaagccag cacagtgacc   39120
gtcagcaacc ggccgtggtg ggccgaccgt gaggtcgtcg aggatctggt cgagcagaag   39180
cgtttcgacg cgacgctcgc ctacctcggc ggcctcgccg acgccatcga gcaccggatc   39240
gcctacggcg tcgacgatcc cgcgatggcc gccagctcgg cgctgcgaaa cctgcgcgag   39300
attcaccgct ggccggttga gttcgcggtc acgtggggcg cgacacgct cacgcggccg   39360 atgctcgtca ccccgttgga gcgacaacgc gaactgacca gcggcctaga cgacgtgccg   39420
agcgtgcgcg acctgggcga caagatcgac cgccgcgact ttctgcgccg caggcggcaa   39480
ctgaaaaggg ataggtaagt ggatatttca gcggtaaagg gtcacgtcga cctgctcgcg   39540
cacgcgcgga tcgagaaaaa gaagtgggag gaaatcgaga agaacgccaa ggcggcgatc   39600
gacgaggcgc tcggcggtga cgacgagggc acggtcggcg gcgaggttgt cgtcaagcgt   39660
tcgcgcacca aggtgacccg gctcagcggc aagttggtgc aatcgctgca ccccgaggtt   39720
tacgccgagt gcctcgacac caacgagcag actcgcctat cggtggtggg caagtgaagg   39780
tttcagagac gcaccacacc acgatcacgg tcgagccggg cgacaaggtg cgcgacctgt   39840
gcgcggtgct cgacgaaatg ccgaacgcg ccgaaatcag cgtgtacgca ccgcttccga   39900
tgttcaacac cgacccgacc gtcaaccagt acgccggggt gatcagcgtc gatcacctct   39960
caatcgaggg ataggagccc caagcatggc aaggcaattg atcgtggtcg acctggaaac   40020
gaccagcctc gactacgaca ccgcggcccc gttggaggtc gcactgctca cgtcgacac   40080 cggcgagtcg ctgcggttcg tgccgcacgt gacgtgcgag cagctcggcg cggccgaccc   40140
gaaggcgatg gaaatcaacg ggtactacga gcgcggcgtg tggcgtgagg cgctgaccga   40200
gcagcagacc gccgtcgcgt ggtccgaggt gaaggattgg ctgcgcggca acacgtttgc   40260
gggcagtaac ccggcgttcg actcggcgat cgtcgcccgg caggccgccg gtggcatgtt   40320
cccggcgccg atcggccgcg tgtggcatca ccggctcgct gacctggcgg cgtactccgc   40380
```

```
gggcaagctc gaccgcgatc caaccgagct ggcgggcctc gacgacgtgg ccgagcgcct   40440
gggcgtgcag gtggcgcagc ggcacaccgc aattggcgac gcggcagcga cggggctgtg   40500
cttcgacctg ctgcgcaaca ccaaggcggc ggcactctga tggcgttcaa ctgggcaggg   40560
cagcggatcg agccgggcgc gaccgtgtgg cgcggcggcc gtgacggaaa acaagcagt   40620 ttcaaggtcg gtcgcgtcga ggccgtcgac aggacggcgc gcgtccggtg ggtcgctgag   40680
atggattggc gcggcaacgt gcgtctgctc ggcgagaagt cggtcgggcg gccgaacgtc   40740
gacagcctgg cgttgatcaa cccggcgaca ttgagcgaca gggtgcggga ggcattgcag   40800
cagtgagtaa caacaatttc gtgcacgtcg gcaaggtgac ggtcccggtg ggtaagggct   40860
cgatcggcaa gccgcgggtg cccgtcgtcg aggacgtcga gattgtcgtc ggcgtgcgcg   40920
ccgacctcgg cgaggtggtc gtcgcgatcg acggtcagcg caacggcgcc ctgccatcgc   40980
tgaccggacc gcaagcgtct cgcgctggcg gagctgctcga cctggccgcg ggttccgccg   41040
cctcgctgtc cgaggcatac cagacctatc aggcgacgct gcagcgggcc gaggctgacc   41100
tagagcaggc gttcgcgcag ggggcgagcg catgagggtg agttttgctc tgaccgtgct   41160
cggttgccac ctgggcacgc tcgacgtcga ggtcgacggc gacgacgaga ccacggcccc   41220
cgcggcgcca gtgaaggcgg caacgaagcc ggtcaagtgg gcgagtcgcc tgtgggttaa   41280
ggggatgatg gcgtgagcac caatgcagcg ttttcgggc tgaccgacga cgcccccgag   41340
cgggatcggc cgccgaccga cgagcagcag ttcaacgccg atctgctggc cgacctcaag   41400
ggcgtgttta aacgcgcctg ggcgcagcat ggccggtcac tgcagcgcgc tctcgggccg   41460
tctgagattg ggcacccgtg cccgcggcgg ctggcgtcgt cgatgcttga gctgcctcgg   41520
attaaccccg agggcgaccc gctgcccgcg tggctcggca ctgccgggca cacgaagttc   41580
gaggatgcgg tcaacctcga caacgagcgg attatcgacc agtggctcaa ggaccgcgag   41640
cagcgttgca cggtcctgcg cggcgtcact ggcggcgatg acccgcagta tgtcggccgg   41700
tggttcactg agcggcgggt tacgggtgcgc ggcggcctgt ctggcacgtg cgacctgtac   41760
gacacgtgga ctgacaccgt gattgacctc aagtttcctg gggcgtcgcg gttcgccgag   41820
tacaagaaag aaggccccggc gcccgagtac aaggtgcagg cgcacgccta cggccgcggg   41880
taccgaaatg aggggttccc cgtcaagcgg gtggcgaact ggtatatccc gcgcggcggg   41940
tcgctggcgt cgtcgttcgt gtggtccgag gcgtacagcg acgagattgt cgacgagacg   42000
ctcggcaagc tcgacaacat tctcgtggcg ctcgacgagc tgcaggtcga ccagcacccc   42060
gaacggatcg ccatgctgcc gaaggtgcct agcagttgca tgttctgccc gttcttctca   42120
ccggacggta ggcgccccga ccgcacgcc tgcacgggcg gtgcgcagtg aagcccccccg   42180 cgccctggcg tatccgccag ctcgtcgagc aggtgcccgt cggcgacttc gatagcaccg   42240
cgacgcggca gacggtcgtc gtcgggtggg tcgtcgagca gttgaccctg tacacgttca   42300 cgccggctc ggttgagggc gagtacgtca ctgtcgacta cttcccgaac ggcccggccg   42360
cgatcgacgc atttgccgga tacggcagtt tggcgatctg acatgcacgg atgcaatttt   42420
gccggcggta gctggcaggg gataggagcc cacaccatga gcggcgaggc aggtcagtga   42480
gcgcgggcct gcggtcgacg ttcaccgcga agtatttcgg ccggtgcggc ggctgcccga   42540
gccagatccg acctggcgag gaggtggcgt ttatggctga tggcggcctt atacatgttg   42600
attgcgagga caactcgcat gagcccgtaa acgcccgcaa gcggccgaca tgtccgcact   42660
gctggcttga gcacgcagga gattgcccgt aatgagttcg caccgttgcg taggtgacga   42720
ctgcgggatc tgtgcgcaac ggatcgaaca ggccgagtat gaccgcgact gcccggccga   42780
```

```
cgactatccc gactactacg acggaacata gccacccgcc gcgcctggcg ggccgagagg    42840
gaaacgggcg caacgcaata acggaacaac tgaacaaagg aacaactgaa caatgagcaa    42900
cgactcgtac gacttcctcg gcggcggcgg cgtcccatct ggcaagttcg gcagccccgg    42960
cgacgtcgtg ggcggcgtaa tcgccatcga gcccgagcaa cggcagatga ccgactacaa    43020
gaccggcgac ctgctgacct ggaaggacgg cagcccgcgt atgcagctcg tcgtcaccct    43080
gcagaccgat ctgcgcgacc ccgaggtcga ggacgacgac ggcaagcgtc gcctattcgt    43140
gaagggcgaa atgcgcaagg ccgttcagaa ggccgtcatt tcggccggtg cccgcggcct    43200
ggacgtcggc ggcgagctgc acgtcaccta caccggcgac ggcgacaaga agggcaacct    43260
ggacccgccg aagctgtaca gcgccaccta caagaagccc gcaccgggcg cagccgcggc    43320
agcccccgcg caggccgacc cgacggcggg catgacgccc gaggcgctgg ccgcactcgc    43380
tgcactgctg ccacagaagt aagcgcacaa cgcgctgcga gccggtgacg ttccgcaacg    43440
gggcgttacc ggctcgctct gtctaacaag ccatttcgac gagggatagg agcccaccga    43500
aaaatgctga cgatctacac cacaggcccc gagtgctaca agtgcaacct gacaaaggac    43560
aggttcgaca aggcgggcgt tgcctacacc gaggtgcgcc tcgaccaggc cgacgaggct    43620
gtcactgcga agttcgtcgc cgccgggcac gctcacgccc cggtcgtcgt cgacgagctg    43680
accaatgtca tgtggtcgga cttccggcac gacatgatca aggccgcgat caaggcccgc    43740
gcatgaagcc ccgcaatcgc cgccgcgcgt acgccctgtt cactgtcctg gcgccgtcgg    43800
cgttcatcct cgccatgatg ctgaccggct gctctggcac cgatcaagag accggcaacg    43860
acattccgag ctggatcgcc ccgcatacgg tcaacctgcc cgacggccga aaggtcttgt    43920
gcgtgtggga gaaagacggg tacgcgcgcg gcctgtcctg cgattggagc cgggcacagt    43980
gaacggcgca gaactgttcg accgcatcgc cctgacccga gccgacggcc gctgcgagtg    44040
cgaaggcgct tgcggcagta gccatccgtg cgccggtcac acccgctgcg ccaacgtgca    44100
cggccgcccg gcgattcacg gcgccgacaa ggtggtcagc ctcaccgtgg tgccacgcaa    44160
cggcgacggc cggaatctcg ccgacggcaa cctgattgcg ttctgtcagg cgtgccttaa    44220
gcggcaccgc gccaagctca aggctgccgc ggacaaggat gcagcccgag cggcggccga    44280
ggctgccgac ggcgggctgt tcgacgtgcc cgacgtcccg gtcgctacag gcaacggcgt    44340
cacgctgtga acgcgcgagc agccttgccc cacaactgaa tagaggaatg agtgaacggc    44400
ctaactgatc tgctcgaact gctcggctac gccgacggcg agcacgtgag cctcaactac    44460
caggcgcccg gcgccccgtt ctcgtcgacg gtcgtcgagt accaagagga cagcgacagc    44520
ctgcagggcc tcgcaatgtc gctcgccaac ggccgcaact gctggtttgg tgtcaacccg    44580
acgctaccgc ggccggtcga cgctgacggc aagcagaagg gccgcggcgg tgccgacgac    44640
gtgacccggc tcgctgcgat ctggtgcgac ctcgacgtca gccgggcgc ctgccgcgac    44700
attgagcacg cccaccaggt gatcgacgag ctgagcgcaa ttctcggcac ccggccgagc    44760
gcagtcgtgt acagcggcaa cggcctgcag ccgtattggc cgatcgacga cggcacgatc    44820
gccccgccg agccggtcgg cgacctcgac gagcagacga tcgccgcgag cgctgagctg    44880
cgcgccgacg ccgcggccct actcaagcgg tgggccgcc tggcgtgcat cgtcgccgac    44940
ggcctgggcg ccaagatcga ccgaggcgtc tacgacctcg cccgcgtgct gcgcgtgccc    45000
ggctcacaca acctcaagga caccgacaac ccgaagcccg tcacgatcga cggcgacacc    45060
ggcgccccgc tgggcctcga cgagctgcgc gagcgcctcg acgagcacgg cgtcgccgag    45120
```

```
tacgagggcg accgacgcac ctcgcacgag gtgatcagca agcccgacgg ctggacgttc    45180
gcgccgagca cctgcgacta tttcgcgccg acgatcaggg cgtggcgcga ggagccgatc    45240
accgaacggc acccgtggct ggtcaaggtc accgtgcggc tgatggcagc ggttcgcaac    45300
aagtgcctga cggccgacga gtacgccgag gcccgcaaga tgatcgtcga caagttcatg    45360
gccgagtgcg cggcgactgg ccgcgacgtg ccgagtttcg agattccgaa cgcattttcg    45420
tgggccgagc accacgtcgc caccaagaca gacgccgagc tggcgaccga gttcggctcg    45480
cacctgcacc tgtggcagcg ggccgagccc cggcagatcg agcttgcgcc tatgcccggc    45540
gtcgacgacc ggcagcaaac cgccggcatt ggtgccgagg gtgttagctc agagggatca    45600
ttagccccgg tcgtggacat taacgcccgg cgcaatccgg ttgccccggc ggtcacgctg    45660
accgacaccg gcaacgccga tctgctcgtc gaggcgtggg gcgcccggct gcggtactgc    45720
cccgacacgg gtaagtggct gagctggaag ggcacccgct gggagcacgg caccgaccag    45780
ggcgaggcga tcgtcgccgc gcgccaggtg gtcgaggcga tcaagctcga cgacgacagc    45840
ccgaaagacg ttatccagca ccgtatgcgc agcctgtcgc gcaagggact tgagaacatg    45900
gtcgcgctcg ccaagtgctc gcccgacatg cgcgtgcgcc tggccgacct cgacgccgag    45960
ccgtacgagc tgaacacgcc gagcggcgtc gtcgacctgc gcaccgggca cctgctgcca    46020
cacagccccg acgggtggca tacgaagatc accggcgccg ggtacaaccc tgccgcggtg    46080
gccccggcct ggcagaagtt ccttgctggc acgttcggcg acgacgtgga actgatcggg    46140
tatgtgcagc gcctcgccgg gctcgccgcg atcggcaagg tgacgcacca cgtgctgccg    46200
ttcctgttcg gcggcgggtc gaacggtaaa agcgtgctca tggacgtgct cgcaaacgtg    46260
ttgggcgact atgcgattac agccccggcc aacttcctgc tggcgggccg cgatcggcac    46320
gagacgagga tcgcccggct gcacggcgcc cgcatggtcg tgtgctcgga aatcaacgct    46380
gagagcaagt tcgacgaggc caaggtcaag gtgctgacgg gtggcgacat tctgtctggc    46440
cggtacatga ggcaggacta tttcgacttc accccgtcgc acacgctgtt tctgatggga    46500
aaccatcaac cccaagtcag cgcgggcggt acatcgttct ggcggcggct gcgcctgttg    46560
ccgttcctgc atacggtccc gccggagcag cgtaaccccc acctcgccgc tgagctgatc    46620
cgcgacgagg gcgccgccat cctggcttgg gtcgtggcgg gggcgcgtca aatcgccgct    46680 gacgcctcc gcgagcctgg ctcggtcttg gcagccacca aggagtacag cgagcaggag    46740
gacgctctgg ggcggtttat ctcggagtgc tgcgagctga cgccgggcgc cagcggcggg    46800
gctaaaccgg ccctggtgtt gaaggcgtat cagcgctggg ccatgtccaa cggcgaggac    46860
gcgatggtgt ctcagatcaa gctcgggcgt gagctgtcgg ctcggttcgg ggtgcgcagc    46920
gtggcgactc acgggcagcg ggtctatgcg ggccttgccc tgcaagcttc ctgggacttg    46980
tcgcacgagc tggcgggcgg gttccgctga tgctgcggtg gccctcgcaa tcgacggcgg    47040
cagctaacgg cacggattca cgccaaaacc cgtgcccggc ggcacagatg gcacagattg    47100
gcacagattc aaaaaacgaa cttgtgcccg cgttgccgca ggtaaatacc cctaacgggg    47160
ctttgggcac agatggcaca gattttacg ggttgacttc acgtgtagag attcggggcg    47220
ttttccctgg tcgagtcgcg ccgagtgcgt ggtgtgaggc tcatatgcaa aaaagtgtgc    47280
catctgtgcc cgacccgtgc cgagcaaact ccgagacgcg ccccgccgta gcggggcct    47340 ggcggggcgc tgacaggcgt cgttgacggt ttctgccgcc agaatgctgc tcgaccacaa    47400
ctgaatatga agaaacgagt gactgaccac actctcgacc tcgggcttgc cgccgaccag    47460
gtggccgccg ccgaggctgc cgagcgggcc gagctgcacg ccaaggctga ggctgccgag    47520
```

```
ctggtgctcg acatgctgcc cgccgagtcg cacgaggccc tgtatgcggc cctgagtgcc    47580
cgtgtgacgc acgagcgcaa cggcggcagg cagttgcgcc tgttcgtgcc gggcaagcct    47640
gcgccgcagg gatcgaagga cttcaagggg tttgcgaagc cgaagccggg cgagacgcgc    47700
ggtaaggcga tcctcgtcga gtcgagcgcc gcggttgggc cgtggcgcga acgtatcgcc    47760
ctggctgcgg ccgacgcgat gctcgccgcc gggctgccgg tgctcggcaa gaaattcccg    47820
tgcacggcgt cgctgacgtt cgtcatgcct cgcccgtcgg gcacgcccaa gagctacacg    47880
cccgcggctg tgaagcgccc cgacctcgac aagctggccc gcgccgtgtt ggacggcctg    47940
actgatgttg cctggcttga cgattcgcag gtcgatgaca tgcattgccg caaggtgctg    48000
gctgcgatcg ctcagcagcc gggtgtgcat atccgcctcg cgtcgccggg ctggggcgat    48060
gaggctatcg ccgagtggat ggctgcgaac gctgcgggtg tgtcacgca tgtctgatct    48120 gatcgagttg tcggtcgccg aggtcgacaa gatggccgag gttgtcgctg cgcgtatcgc    48180
gcacccgtcg catacgcctg ctcgggcgat ccgcgcgggg ctgtcggcgg tgaacgcgat    48240
gcgcctcgat ggtgcgcagg tgccgcgggt ggagttggtg caggagcgcc gcgcgcctgg    48300
cacgatgccg cgcccgatcg aggcacgtcg cccgttggcg ccggtgcccg ccggtaagcg    48360
ccgcgtgtcg catctgggga tggctgagcg cggcagcgtg tgggaggacg ccgacggcga    48420
tcaatggcgc tggtgcttca tgcaatcggt gtggcagtac aagcagttcg acgatccgaa    48480
cggcccgcag tgggtgaact gcccgagtaa ttacgccgac caggcgccga atccgaacta    48540
tggaccgttc acggaggttg gccgcgcatg agtttgccgg attctccgag tttcggcgat    48600
ccgcgcaggt caccgggcac gccgacgatt tcgccggccg ttagccacgg cctgagttat    48660
tacgggtcgc cgcggccgtc tggaccgtct gagttggacg tggcgactgc gccgtcggtg    48720
cctgagccgc tggggcgttg cttgcattgt tcggcgcctg cgcagacgtt tctgtgctgg    48780
tcgtgtgtgg gcatgttgcg ccgccagctc gtcgaggtgc cttggctgtt gcgtcgtctg    48840
caggagtcgg cgtacggcga ggcgaaggtc gcccgtaagg gtgggcctcg ggtgtcgacg    48900 gggagcggc tgccgtcgtt gccgttgaac actcgcgcgg ccgacatgct gcgcgacgct    48960
gcgcgtctgg tgtcgtggtg ggagcaggtg ggtggcgtcg accagggcgg cccgcatgat    49020
gctgcgcgcg tcgagtccgc ggcccgctgg ctggccgccg agccgggcgc gatgatggcg    49080
cacccgtggg cacctgacgc gctgggttgg gtgttgcagt ggcgccagga cgctgagcgt    49140
gtgatcgact tgccgccgga tacgcagtac gccgggccgt gccagaacgt cgtgcagccg    49200
ccgagtgcat ccgacgccgg tacgccgctg ccgcctcgtg agtgcggcac gccgctgtat    49260
gtcgacgccg aggccctggt cgccgagtgc taccgctgcg gctgctcgtg gcgggtcgag    49320
gatttgcagc ggcaggccct cgatcgcatc gacgaggccg cgccccgcac ggccgccgat    49380
atgtggcggc tgctcaagtt cgcgggccgc gacgttaagc ggtcgacgtt ttacaagctg    49440
atgacgaccg ttgaggcgca cagctatgac gctgacgggt cgccggtgta catgtaccgc    49500
aaggtggttg acgcgctcga tgctgccgat cggaaggccg ccgagcgcca agctgccgct    49560
gcagcccggc aggccgccgt gctcgatgcc cacgattcag gtatggcgcc gtcgacgatc    49620
gcccgcacat tgcgcatggg acacgctgca gtgaaacgca ttttgatcag tgcgggtgtt    49680
gacgcgcata cagaatgtgt tgacgtgcag acagccgagg cgttaccgtc tgcgccgaag    49740
caagtcacgg gataggagcc cctgcagatg tacacagaaa cgtggtactc accggctggt    49800
acgccggtga cgccgaaggt tcgcaacgag gtcgacgagc cacagctcgc cgcgttgtac    49860
```

```
gaggctgagg tgtcgcccga ggttgggcgg ttcaacgagc tgtacaacgc cgccagcacg    49920
gcgacgcgct acgcctggca gtacgggtat cgcaacccgc gggtgccggg ccgtgtcgcc    49980
gaatgcgagg cgctggtatg aagcgcacca agacagttcg gccgtcgccg gtcgccccgc    50040
agcccgacgt tgtggtgcat ggccgcacgt tggagccggg caccgaggtg tcgatccgcg    50100
gcgagcgtgg ccggttccgg ttccgcagtg cgtcgttgac gagcgcgggc aggatcgtgt    50160
gcgacttcat cggcggccct gctggtcacg agacctggcg gtcgttctat cccgaccgta    50220
tccgcacggt gcaccgtttg aaccgcaccc gcgcgaacgc tgccgcatag tcacgtgttg    50280
acatgcatac agcgtgaggg gtactgtatg catgtcaaca cacaccggga taggagccca    50340
cagtgacgat ttcgaccgcg acccgcaaca tgacgcagat ggaagctcac cagatcgccg    50400
ttggcctgat ccgcgagcat ggtctgatcg gctggactgt gagctgggac aacgcccgtc    50460
gtcgcgccgg tcagtgccgc tacacgtcgc gcacgatcag cttgtcaaag ccgctgctgc    50520
gccagcgttc ctacgacgac acgatgatga ccattacgca cgagattgcg cacgccctgg    50580
tcggcccgaa gcacgggcat gacgccgtgt gggcggccaa gcaccgacag ctcggcggca    50640
acggtcagcg ctgctttgag cacctcgacg agtcggcgcc gtggatgggc acgtgcgacc    50700
acggtaagaa gttcgcgcgg taccgggcac cgaagcgcct cgacgggtgg cgctgcaagt    50760
gcacggccgc cggtagcccc gtggtgtggg tcaaccagcg atagcgtcga cgcccccaat    50820
cttccgaggt tgggggcgtt ttcgtctctc atgttgacat gcatacagcc cacgggttac    50880
tgtatgcata ccaacaacgc actgaccacc taccgatagg agcccacaat gtcgaacatc    50940
gtcgccgccg cccccgccgc cggtcgtttc aacgccgctg ccgcgctgaa catgattctc    51000
ggtatcaacc tgtcggacgg gcagaagcgt gcgcgcctgc tcgcgctggc ggtgtcgaat    51060
gacgctgcct ctgagttcaa cttgcgcgcc gctcgcaagg cgctggccgc cggtcgcctg    51120
gccgaggctg atcgttgcgt cgacgctgcg gagttctaca caaccgcgc caagcgcctg    51180 cgcgacgagg cccgcgctat ctagcgcgcc cggcgcgtcg ccgcgcaaag gtcaccctgg    51240
cgcccggtgc gcccccagaa tcgccgatcg agggatagga gcccacgaac gtgaatcgcc    51300
acctgtacac gcaacccgag ctgttcgacg ccgacgacgc ccgccagttc gacgtctacg    51360
agcgccccga cggctcgcgc taccgcgttg agcgccccgc tgcggcggtg gccctgtgag    51420
cgccgccctg acgccgcgag agtcggcgca aaggtatttc gcggctggc ttgccgccgg    51480 tgtcgtgacg tcgattctgg gcaacgctgc gcacgctgtg ctcgaccctg acgccgggtc    51540
tgtggtgatc gcggtcgcgg tggccgtcct gctgccgctg ggcatcctcg ggtcgacgca    51600
cggcgtgcac aagctcgtcg ccgccgggat cgtcggccgc gcatacacgg cggcgctgag    51660
catttcggtg accgtcgtcg ctgcggcgtt cctgctgtcg ttcgcggcgc tcgccgagct    51720
ggcggtcgac tgggcgggta tctcgatctg gttgtgctgg ctggtgccgg tgttcattga    51780
tctgagcatc gccgggtgca ccgttgcact gttcgcgctg tcgggtgcgg agcgcggcga    51840
ggtgctcgac gctgcggtgc acgtcgctgc gcaggtggtg caccctgctg cgcagtctgt    51900
gcacgccgtt gcgcagcccg ctgacctgca tgttcctttg ccggccgaat tgcagcccga    51960
tacgcacctc gtggcgcgtg aggctgacgg cctggtgcac gtgttcgagg agtcggtgca    52020
cgatccggtg cccggcggtg tcagtgtcgc cgatctgatc gcccgcgagg ctgcgaccag    52080
cgacgcgctg gctgcgcact tgcccgcggc cgaggcgatc ctcgccgccg gtgtgacgcg    52140
cattgatcgc gtcaaggtcg ccgaggtgct cgccgagcat gaggccgacg tcaagccgag    52200
catgatcgcg cgcaagctgg gcgtcgggta cagcaccgtg gtgcgcattc tcgaccatca    52260
```

```
cactgcgcag gacgatgcac aggccgaggt gctcgacgcg gaggtgctcg cgtcgtgagc    52320
atcgcagcgc agtacccggc gcgcactgac acgctcggcc gcacgtggtg gcgcccggtg    52380
cgcccggcgg gcactgatct gtcgcagtgg ggttggacgt cggacccggc gcaggcgcac    52440
cccgactatg acgcgctgaa cacgtgcacg tgcccgtacg tcgacccgtc gctgtggacg    52500
acgcattacg gcgccgtgga gccggcagc gcgcaggagc ataacccgct gtgtccggtg    52560
cacccggcga cgctcgtcga cctcatggtc gcccgtgagg ccccggtggt cgccgccgcg    52620
gctgagcgtg ccgaggtgtt cggcgatgcg tgggcgcagg tgttcgagct ggcgggcggt    52680
ggccgtgcga tcgtgccgcg cgacccgctg ccggttgagg cgctcggcga gcttggcgac    52740
gagtgggtgc agcttggcta tgtggatgag acgcaagggg cttttgtggtg agtatcgagg    52800 tgtatcgagt cgcgccgttc ccgcactatc acgcccgccg ggctgctcgg gtgctcggcg    52860
tcggcctggc tgtcgtcgag gcgatggccg ccgcgggcaa ggtccgcgct gtgcgtgtgc    52920
agaacggtgc cggtggttcg gtgtgggcgc tcgacgcgct gcgcgtcgac gagctggtcg    52980
ccgccaacga gaacacgggg ctgcaccctg agtgggcgtg tggccgcgac tgcagcggtt    53040
gcgtcggcga gggtgagggg gcgtgatggg cgactgtctc gtcgacccgc tgccgcgccg    53100
tgtgtcgacg acgatgcgca ttgactcgac gggcacgcac tactggcggc gcgacgccga    53160
cggcaacctg agcgtgataa cccgcgacga gtggcgacgt ctgacgttct ggccgtcgac    53220
gccgatctac gaccaggtgc tcgacgacct cggcgcgtgc ctcaactgcc ggtgtgctga    53280
ctgcggctgc tgctacggct gcgggcagcc cgacgctgac ctgttcggct cgcatgggta    53340
cggcgccgag tatggcgggt gcgtgtaatg ctcagcgtct caccgggtat ggacgtggcc    53400
cggcagcgcc gcaagttcat tggccgaata ctcgccgagg acgacgacca cgctgccgcg    53460
tatctggtct ggctgctgag cctgttcgat gccgcggtgg ccgccggtac gccgaggccc    53520
gcgagcgagt ttctgccgat gttccaagag gagtttgacc gatgaccgaa accgaaaagc    53580
tcgccctgat cgaggcgtgg atgcaccccg gcctgtggtc ggccctcgac ggccgacgca    53640
acgcaatcct gcggattctc aagggcgaga gtgtgacccc gccggattgg gcggtaacca    53700
acccgctgcc ctgaccggcg cgacacgccg acacgacgcc cccgctgaaa ggtcaagcgg    53760
ggccgtcgtt gtgtgtttgg ctcaatgtgt ctgaccaaca actaaatagc gggataggag    53820
aacgtgtgtc acctacacgt gtcaatgagc gcctgatcaa ctttgcgagc gaggtcgacg    53880
accagaccct cgcgcaggcg cagcagatcg ccgatctgcc tttcgtttat ccacatgtgg    53940
cgctgatgcc cgatgcgcat ttcggtaagg gcagcagtgt cggcacggtg atcccgaccg    54000
agggcgctgt gatcccggcg gctgtcggcg tcgatattgg ctgcggcatg atcgcagccc    54060
gcaccacgta cacggcgaac gatcttgagg gcctcaagct gtcggatctg cgggagtcga    54120
tcgagtcggc tatcccgatg agcgccgggg gatacaacaa gagcctgaac cgttttgagt    54180
tcaccggcgc ccggttggac tggctgcagc tcgtcgctac ccggttcgac gtcgacctgt    54240
ctcactcccc gaagtggcgg gagcagctcg gcacgttggg cggcggcaat cacttcatcg    54300
agctgtgcct cgaccacctc gaccgcgtgt ggttgttcct gcactccggt tcgcgtggtg    54360
tcggtaacaa gatcgcgcag aagcacattc aggccgcgca gggctattgc caggccaacg    54420
ggctgcacgt gccgcacaag gatctggcgt acctcgtcga gggcacggtc gagttcgacc    54480
gctacctcgt tgaattgcgt tgggcgcagc ggtttgcgta ctacaaccgc gccgaaatga    54540
tggaccgatt tatacaggcg ttcgcgcatt ggattccgga caatcaccag agtcacggcg    54600
```

```
atttcgtcgt cgagaccatc aacgcgcacc acaactacac gcagaaggag cggcacggcg   54660
accgtgacgt gtggctgacc cgtaagggtg cgatcgacgc gaacgagggt gtgcggggcc   54720
tgattccggg ctcgatgggc acctgttcgt atgtcgtgac cggcaagggc aatcccgagg   54780
cgttgtgctc ggcgccgcac ggtgcgggcc gccggttctc acgcacgaag gcgcgcaagc   54840
tgttcacggt cgacgacctc gaggcgcgta tggcgggcat cgagtaccgc aagggcgagg   54900
cgtgggtcga cgagattccc gacgcataca agccgatcga cgttgtgatg cacgacgccg   54960
aaacgctggt gtcggtggat gctgagctgc ggcagctctt gaacgtcaag gggcagtgat   55020
gttggacgat cgcaacgcgc acagcttgct gttgtcgtca cgctggcggc agggcggcaa   55080
gaccacggca ctgctcgacg tcgcgctcgc caacgctcgc cgcgggcttg aggtggtgtt   55140
ctggtcgggc tcggcccgcc agtgcactga ggcgtttcgg atgggtcggt cgctcgctga   55200
gcgtgaccgg gtgccgttct cgtggtcgcc cgccaatggc aatgagtgga ttcgctacga   55260
cggcggcggc cgtgtgcggt tcatctgggg gcaccagggc agccgggtcg acgctcacgt   55320
cgacatggca attcaagaca gcaacgggct cacgggcctg atcgagcggc gcagcgagcg   55380
ccgaggaatg ggcgtgatct gatggccgac tactcatacg cgccaggcgg ccggttcgag   55440
gtctcacctg tcccgatcgc cgaggggag gacgaggcgc tgcacccgtg gcaggcgcag   55500
acggttcgca cgctgcagga gcgtcgagag gtgtcgttct cgctgcagtt cccgcggcag   55560
ccgcagacgg gtatgccgtt gtggctggcg cagttgttcg gcgtggtcgt gaccccggcg   55620
ccgccgacgg tgcgcgaggc cgcggtcgac gtatgggacg cgctgcgcgt gctgctgcgc   55680
gtcgtgtggg tggctgtgcg gggcgctgtg acagcggcgg ccgatcgtgt gggcgattgg   55740
tggtttgacg tcgtttacgg cgctttcgac cgctgggacg tgctgcgcgg gtggggttgg   55800
cgtcgccagc tcgtcggccc gacagtgacg ctgtggagcg cctcgtttat ctaccagtac   55860
acggtgcctc gtcggcgtga cgggcgc gagtggctgc ggcggcaggc tggtctgccg   55920
ttggcggtgt ggcgtgggta gctcgccggt gatgttcctc gacggcccgc tcgccgggac   55980
tacgcgcgag gtgcagacgt ggccgaatgg cgaactcgcg ccgtacttca atgtggcgac   56040
gccgccgaag ttcgacccgt ccgaaatgcg cgagccgccg cggacgctgc tgcctgagac   56100
gcacacgtat cggatcaagt gcaatcggct gagctacggc ccgcagtggg tcggggcgat   56160
cggcgataag gtcggcgagc agatcgtcac ggtgctgccg tacgacgagc gagcccgcca   56220
gagcgtcggc gtcgacgagt tcgaggagta catcacccgc aacgcctacc agagcgcgca   56280
gcggcacgcg ggcggcgagg gcctggtcgc cgttgaggtg cacgagggttt ggcgtggcac   56340 gcaagccgag gcccgcgagc agatggtgcg cgagggtaag ccggtgaagg gcgccccggc   56400
gttcctcgcc gccgacggcc cggtgttcct cgactcgacc gtgttcgtcg tgcatgaggc   56460
cgtggctgtc ccgaaagatc aggcgcggga ggtgattctg tgactgacac cggcaccccg   56520
ctggacgact tgacgcccga gcaggccgag cgtctcacgc ggtcgctgcg gcggttcaac   56580
gaggcgatgg gctggcagct cgaccacgcc cggcaagagt tggaccgtga ccggctgcgg   56640
cggctgttcg gcaccagcta acgccggcaa aggtcgccgg cctggctgtc gccgcaggta   56700
gttgcggtgc gggtctggaa gttggcaaac gcccctcggg taatcctcgg ggggcgttct   56760
gctttccgtg ttgacgcaca taaaccaat gtgtttgcat atcaacacac accacgggat   56820
aggagccccc tgaatgttca agatgattgt gcaactgcat ggccgccaag aggttacgga   56880
gcacgacacg atcgacgagg cccgcaagcg cctggtcgat attgctgtcg caagcaactg   56940
ccggggttga g ggcgacaacg ccacgggcgt gttcatcgcg ctgacccgcg agggtcggga   57000
```

```
caatccgctg gtggactgga cctatggcgc gtaccgcatc acggaggagc ccgccggggg   57060
cgtcgaccag gcgctcgccg ccgctactgc gcggtacatg atcgacgaga acctcgacgc   57120
cgacacggtg cagatgatcc gcaacagcga ccgcgacggg cgcgacctgc tggccgcgat   57180
cgtggccgag tggctcaagc tgcaccctga gctgtccgac cgggatcggc acgctgtggc   57240
tgcggcggcc aatggctggc agcgtttcga ctacgccctc gtgccgtcgc aggtgcgtta   57300
cgtccgtgat ggcggcgagc tggcgatcgt cgagtacgac gacgagcgcg cggcccgcag   57360
cgccgagctg tacgtgcacg gcgtgtgcga cgcggcgctg atgcagtgct gcgacctcgg   57420
cgacgtcgac aggtggctcg tagcggcccc tgtgccgctc tgagagcttc aaacagatga   57480
gggaaaggga taacatggca accatgacaa ttacgaggta cacggcggtt gtgacgcccg   57540
gcgagcagta cacgctgatt cacgtgcctg agatcgacca gtggacgcaa gcccgtagcg   57600
aggatgaaat cgagccgatg gcgcgggatc tgattgcgac gtggctcgac gtgccggtcg   57660
agtcggtcga ggtcgaggtg cagcgcggct gacgtcacag cgacaagagc gcccctgagt   57720
caatgcaact cgggggcgct ttgttgttga catgcataca gcgcgggtgt tactgtatgc   57780
atgtcaacaa ctcaacaggg ataggagccc acaatgccga agcgcaacga ggtaatcacc   57840
aagatccgca aggcggccaa ggccaagggg ctgaaattca gtcggttcg caagggtgcg   57900 aatcacgaga ttttcgacct cgacggcgta atggttccga tcgggaatca ctcgatcttg   57960
gacggttacc tggtactcaa gatttacaaa gagtgcgagc cgaagctagg caaaggctgg   58020
tggcgataac cacagcggcg acgccctcga ccacatggtc gggggcgttt tcgtttctgt   58080
gttgacatgc atacagccac gggctattgt atgtatatca cagcgcgag cggttgagat   58140 tgacaactca agagtgacag tggataggag cccacgatga acgatttcta cattccgcgt   58200
ttcctctcgc cgagctgctc gtttacctac gacgaactcg gtaaggccct cgcaaagctg   58260
cagccgcgcc tgaacaaagc gactgaggca tggctcgccg ccaagcgcga ccacggcagc   58320
gagagccccg aggaacacgc cctctggccc gagctcgacc ggctggaagt ggctaaggcc   58380
cgcatcctgc gcgaggctaa tcgcctcgac aagatcaacg gcctggccgc cgcgatgccc   58440
ctctaaccga ctacgccccg ccgggccgac cacaccggcg gggcgttttc gttttcgtcg   58500
atgcccgccg acgcccgccg acgcccgccg aagcccgccg acgttcgcat acgtggcgtg   58560
attggcgcgc gtcgctttta gactgccgat cgcaacagca cagctgtacc caaaacggcc   58620
ccggcgctcc gaaatggagt gttggggccg ttcccattcc aggcgtcgac cagcgttgcg   58680
cggcctccta tccccgcgcc ctggtcgacg tctaagcccg tcgccgtgat cccgacactg   58740
gcgctacgcg cgcctcggcg cgatccgctg cagcccctcg ccgcgttggc tggtcaccac   58800
gcgagcaccg gcgcagcgca gcgctacaga ggtcgacgcg atccggcggc gggcacttac   58860
ttcacgagag gaaacgccat gtccgacacc gcacctgacg ccgccaccga ggcccccgca   58920
caggaggccc ccgcaatggc ccctactgcc gcgctgagg cactggcggc caatgccagg   58980
ggtaagggga aagggcggca ggctacggcg tacgtggccc tcgacccggc cgaggccaac   59040
cgtagggcca ggcggcggcc cgctgccgag gcgcgcaagc ctgtggcaca cgagccgtac   59100
gaatggtgag gctctcacca cggcgcgctg agagctggtt ctgtaccacc agcatgaagc   59160
tgggcgagct ggtcgaggcg ctggacctac gcaagcggta cgccgagcga cacggtgaac   59220
gcgctcgcct gttcgtgttc tcggtcggca agctgctgat cgtttgggac cgagacagca   59280
agccatgagc gagggccgca acactgcacg gcgcaacagg ttccggcgct actggctgcg   59340
```

-continued

| | |
|---|---|
| gcggcgcgag gactgcgcag tgtgcggcga gccgatcgac tacgaggcgc atcacctgca | 59400 |
| ccctgactcg tttcaggttg accacatcac gccactggac gcaggcggct cggacacgct | 59460 |
| cgacaacacg caaccgacgc accgcaagtg caaccgcgac aagagcaaca agctgcccga | 59520 |
| cagcggcggc ccggcgcctg cctcggtggg cgtcacgttc gtgaccgaac ggcactggcg | 59580 |
| accctgacct cagcaaaggg gtgggggagt actccccgac ccctcccgg tgcacctcgt | 59640 |
| aggcat | 59646 |

<210> SEQ ID NO 7
<211> LENGTH: 59598
<212> TYPE: DNA
<213> ORGANISM: Mycobacterium phage Angelica

<400> SEQUENCE: 7

| | |
|---|---|
| aggcaccttt ctctccccgg catttttttc caagccattt tggcgttttg tcacgtctga | 60 |
| ccagcacagg agcaaccaat ggacatgacc gaatccgcac cgactgcccg cgtgtgggcg | 120 |
| ttcgaggatc agcgcgaccg cgcggtgcgc gagcaatcaa tgcacatcgc gctgcgccag | 180 |
| gccgacagcg tgggaatcgg cgacttgacg gtgatcgagg cggccgacaa gatcgccgct | 240 |
| ttcatcctcg acggcaaggt cgaccggccc gccgagattg aacggccgc cgaatgatga | 300 |
| cgcccaccga gcgcctcgcc gcacagcgcg aggccctcga caagcacgag tggaccgagg | 360 |
| tagagggcga ccctcacgcc gatcacgctg cactgcctggt cgccattggc gaggtgctcg | 420 |
| tcgagctgaa cgcccggcag gcccgccagg aggccgcagc gatgggcggt ggctcgtgag | 480 |
| cgcggtcgtc ggcgtcgtgt cgcgcacgct cgacagcgcg gcccggctcg cccgcgctct | 540 |
| gaacgtggct cgcaccgttc caatgagcgt gccgtcgatc aagcaagggc acggccgcgg | 600 |
| gttcagtttc gacgccgtga tcgtcgacga cgaggtgatg ccgctcgacg actgtgtgct | 660 |
| cggcacgttg gccccggcga tgcacgctca cggcggaaag atgtacgcgg ttcgggagat | 720 |
| tgagctgtga ccccgactgt cggccgcatc gttcattacc agtcgtacgg cacgcctggc | 780 |
| ggcgagtacc tgcctgagcc gcgcgccgcg atcgtcacgg ccgtgctcgg cggtggcgtc | 840 |
| gtcagcctgt gcgtgctcaa cccgacgggg ctgttttttca acgagtccgt gcgccaggcc | 900 |
| gacgagccga cgccgggccg ttggaactgg ccgccccgca actgatccag cgccgggcct | 960 |
| cgttccgcca accgcggtcc tcccggcgcg cctgggtgtg tagctcaatt ggcagagcag | 1020 |
| cggtctccaa agccgccggt tgcacgttcg agtcgtgccg cgcccgcttc cacaccggct | 1080 |
| aaccgccggc aatttgcatt cccgcacgtc aatgccacga aggccgttt tgagctaaca | 1140 |
| cggcacctca ccacaccagg agatatgacc atgcgcgcac ccgctaccgc tgaggttcct | 1200 |
| tgccccggcct gcggcgagcc gatcacgctc gcccttggct tcgagctggc cgagcccgag | 1260 |
| cccggcgcca cgactgcccc aatgttcgtg aagccgctcg acattgccga gcgcgcgcag | 1320 |
| gagcacggcg aggtgtgccc ggtctggtcg ggcggtggcc gcgatgactg accgcaagct | 1380 |
| cgaccggctc gacgaactac gccggttgca cgagcgcatt tcagatgccg tgttcgacga | 1440 |
| ggagacgccg ccccgcgacc tcgcctcgct gagtcgacga ctcatggaga tttccaagga | 1500 |
| aattgaggcg atcgagctgc agcgcgccga gcagggcgag ggcgccccg aagttcccgc | 1560 |
| agatgaaccg ttcgatggtt cggacctgtg agccgcggct atccgaggtt gctcgccacg | 1620 |
| taatcaagcc cgagggcatc acatcgacgt cgtggccgtc cgtacgccac gagtgcaacg | 1680 |
| tcaacatggg gttgttttc gaccaatggc aggacgacct cggaaagctg gtatgcgcca | 1740 |
| agcgatccga cggcctgtac gcggccgaca tgttcgccat gtcgattccg cggcagacag | 1800 |

```
gcaagaccta tttctcggc gcgatcgtgt tcgcgttctg caagatgaat cccggcacaa    1860
cggtcatctg gacagcgcac cggacacgca ccgcagctga cgttcaag agtatgcagg    1920 cgctcgccaa gcgtgagcag atcgccccgc acatcttgaa cgtgcacacg ggcaacggca    1980
aagaggccgt tctgttcacc aacggcagtc gaatcctgtt cggcgcacgc gagaaagggt    2040
tcggccgtgg tttcgccaag gtcgacgtcc tgatcttcga cgaggcgcag attctcagcg    2100
aaaacgcgat ggacgacatg atcccggcga ccaacgcatc gcctaacggt ctgatcctgt    2160
tcgcgggcac gccgccgaag cccaccgatc ccggcgaggt attcaccaac ctgcgcatgg    2220
atgcgctcaa cggcgaatct gacgacgttg cttacgtcga gatatcggcc gacgaaaacg    2280
acgacccaga cgaagagtcg acctggcgca agatgaatcc gagctacccg catcggacgt    2340
ccgcgcgagc gattcgccgt atgcgtaaag ccttgtcctg ggacagtttc aggcgcgagg    2400
caatgggcat ctgggacaag atcagcgtgc acgcacaggt gatcaaggct ggcttgtggc    2460
gcgacctggc cgaccgctc ggccccgagc ccggcgccaa accggcgtca ctcggcgtag    2520
acatgtcgca tggcggcgct atctcgatcg gcggctgttg gctgatcgac gacgagctga    2580
ggcatgtcga gcaggtttgg gcgggcactg acaccgcggc ggccgtcgag ttcatcgtcg    2640
agcgtgccgg gcgacgtatc ccggtcgtga tcgacgacgc gagcccggcg aaagctcttg    2700
taccagagct gaaacgtcga aaggtcaagg tccgcattac gtacgcgggc gacatggcca    2760
aggcgtgcgg cctgttcaag aacaacgccg agggcgactc gctcactcac ggcgatcagc    2820
tcgacctcac cgaggcaatc aagggcgcca agcaaaggcc gatccgcgac gcgggcggtt    2880
ggggctggga ccggcgagac ccgacgtgcg caattcaccc gctagttgcc gtgacgctgg    2940
ccctgcttgg ggcgctggat gctccgaagc gcagcggcgg cgcgatgttc gtatgagagg    3000
gggccgtgtg attcccgctg cctatgacga cagccagctc gacgagcccg ccgacggcga    3060
aatcgactgg cccgctgacg cactcgacgc tgagaagatc ggcgagctgg tgcagcgtat    3120
gtatcggttg cacctcggcg accgtgattc gctcgaccgc atttacgagt atgccaaggg    3180
cgagcgtggc aggccgaacg tgcccgacga ggcgagcgaa gaggtcaagg aactcgccag    3240
gctgtcgatc aagaatgtgc tgcggttgat ttgcaactcg ttcgcgcaat cgctcagcgt    3300
ggtggggtac cgctcactgt cggcgccgga caacgatccc gcgtggcgga tctggcaggc    3360
gaacaagatg gacgcccgcc aagccgaggt gcatcgcccg gccgtcaagt acggcgcagc    3420
gtatgcggtc gtgacgcccg gccccgacgg aacgcctgag atccgttgcc gctcaccgcg    3480
gcagctcatc gccgtctacg acgacgcggt gctcgacgat tggccgcagt acgcgcttga    3540
aacgtggatc accacgaagg acgctaagcc gcgccgcaag ggcgtgctgt acgacgagcg    3600
gtacatgtac ctgctcgacc tcggcgagct gcctttgacg tcgaccggca agcccgaagt    3660
tgccacgaag ccaatcacgc tgagcgacgt cgaggacatc atcccgcatt acggcaccga    3720
ggacggcaag ccggtgtgcc cggttgtgcg gttcgtcaac gaccgcgacg ccgacgacat    3780
gatcgtcggc gaggttgagc cgcacatcgg tatgcagaag gcgatcaact gtgtgaactt    3840
cgaccggctg atcgtgtcgc ggttcggcgc caacccgcag cgcgtgatca gcggatggac    3900
cggcagcaaa aacgaggtgc tcaaggcatc ggcgttgcgg gtctggacgt ttgacgaccc    3960
cgacgtcaag gcgcaggcgt tcccgccagc gtcgatcgag ccgtataacg ccgtgctcga    4020
cgagatggtg cagcacgtcg tgatggaagc gcagatcaat ccgtcgcagg tcaagctggt    4080
gaatatcagc gccgacgccc tggcggcggc cgagcaccgc gagcagttga agctcgccac    4140
```

```
caagcgcgag agtttcggcg agtcctggga gcaggttttg cggctggctg tcgaaatgga   4200
cagcgacgag ggcacgagcc ccgacctgac cgccgaggtt atttggcgag acaccgaggc   4260
ccgatcattc ggcgccgtcg tcgacgggat tgtgaagctc tcgcaggccg gtgtgccgat   4320
tgagtacctg ctgccactcg tgcccggcat gacgcagcaa ctcattcagg cgatcaagga   4380
agccatgcgc ggcggcggca ctcaggcgct cgtcgacaag ctgctcgccg ctcccgaggt   4440
atcgctgccc gacgcccac cgatcgacca ggcgctcgcc agcgccgaca acgaaggggg   4500
cgagggtgac ggagccgaag gcggtaccgg agtttcaggg ggcgctcgcc cgtctcagta   4560
atgaggtggg cggcgccgtc gaccggctaa tgccccgcct cggcggcctc acgcgctccg   4620
agggcctcgc tgtgatcagc gacgtttacc cggcgatgct cgacccgttc ctgtcggcgt   4680
cgggggagct gacggcgcag tggtacagcg agcaaacgcc ggcaaagttg gttggcgcgc   4740
aggtcgcggg cacaaaagcc ctcgccccgg caaaggattt cctgcctgag cctgccgcgc   4800
tgccggatcg ccgccagctc gcggcgtcgg gccgctgggc gctgatgcaa cgcaaccctg   4860
gcctggcgct gcgcggcact gccacccggt cagtgttcga ctcgtctcgc cgcacggtgc   4920
gcgacaacgc gatccgcgag ggcgtcaagt ggacgcgata cgcctcggcg aacgcttgcg   4980
ggttctgccg gatgctcgcc acccgcgccc tgacgaccga gcgccgcggc gccccggcc   5040 tgtacacgag caaggcgacg gccgaacgca acgcgcacac cgtcgatatt cgcggccacg   5100
atcactgcaa gtgcctggct gtgccggtgc gcagcggtgg ctacaccccg cccgaatacg   5160
tgaatgactg gctcgccgac tacgacgccg tgagcgtcgg cccgacggt gcactccgcg   5220 gcgagtggca gatcgcccag ctgatggaag cccgcgccga cgagcgccta ggcaagccca   5280
agcgcaagcc cggcaggccc cgcaaggccg cgcagcccgt cgaggacgtg cgcagcgcac   5340
cgcgcgaaac ggtgcgcgct acgcagcacc tcgtcgacac cggcagcgag cgcgctgcag   5400
cgtacggcgc aatcgcgcac gagcacgtgc tcactgcgca gcaggtcatc acccgcaccg   5460
acgaggttgt gagcaccgcg gcgcacatca cgcagcgcgt caagctcgtg accgacgtcg   5520
ccgacaaggt gctcggcggc gccgttccgg tcgtgcgcga cgtcaagcgc gtggtcgacg   5580
cggccgacaa ggcactcggc agcgcatcgc aggtcacagg cggtgcgcgt caggccgcgg   5640
acattgccgc acaggccatc gacagcacgg tgcaggttgc gcacggcgcc aagcagattg   5700
ccgacgaggt gcgcggcgtg ctcgacgagg tgggcctcgt cgctgctggt ctgcgcacgc   5760
tgttcacgga cacgcgcgtg gctatgcacg acacggtgcg cgacgcacgc aacgtgcgca   5820
gcctgtcgga cctgtccgag cagatcgcg cagcgaccga caccgcgcgg cacgtcgccg   5880
acgacggccg tgcactgatc gaccgcgcca agggcgccgc cgacgcaacg cagggcatcg   5940
cgcagggcgt ccgcgagata ccggaactgc tgccggcagcc gatcgccgac gcgcaagagt   6000
tggcgcaaac catcgtcggg gccgccggtg acgcgagcca ggcagttggc gagctgcagg   6060
acgtggcgcg tgcgatgggc aagctgatcg acgcggtggc cggttctgcc ggtgaggacg   6120
ttcgcaaggc tgcccgtcag gctgccgacg acctcggccg cattatcggc gacctgttca   6180
aggcacccga ggcgcctcgc gtgccggtgc ccgtcatgtc agaacgcctc gacgtgcccg   6240
gcgctcgtgt gctcggcggc ggtgagccgg tcccggcgat cgctgaacgg atcggcctca   6300
agccaattga ggcacccgag gccgccagg cgctcaacgg tcgcccgccg atgaaagcac   6360
ttgagacgga acccgaacgc ccgccggtcg ccccggtggt cgacgacgtg ctcgacgtcg   6420
aggtcgtcga ggccccggcg tcaacgccga agccgaagcc cgcaaaacgg acgctcgacg   6480
aggtagaggc cgagtttcag gcggctgtcg aggctggtga cgacgcagcg atcgacgcac   6540
```

-continued

```
tggtcgccga aatggagaag ctcgaagcgg ccgaaaagaa ggccgccgaa cgcgccgcgg   6600
cgaaagctgc tgcgaagcaa gccgaaaccg aggccaatac cgaccggatg cttgagctga   6660
tcgagcaggg ttgggatccg gccgaggcgg aatcggaggc gttcggcatg tcggtcgagt   6720
tcattcggcg ccgcgacttc atggcggagg ctcgcgctgc cgggcatgag ggccgagggt   6780
tcgacgagct gctcggcggg gtgttcgagg aacgggtcac ggaggcctat ttcgctgccg   6840
aggactcgac ccacgggtac atgctcaaga cgcgttacgg ccccggcggc atgaatatcg   6900
acccgcgaaa gctgtggacg ctcaacgaga taacggctcg caagtacatg tcagacgaga   6960
tggccgagtg gttcgaccag aacggccgta tcactcgcgc tggactcaag gaggcgattt   7020
tggccggtcg cggcaactgg cgcagcgcaa cgaccgcgga cttcctgcaa tgacccgcga   7080
cgagctggtc gccgcgtacc aggccggggc gcgggcggcc gtcggcgaca ccaacccgta   7140
cgacggcctc ggcgccccag cgcgtatgtg gcgccggggc tatcgccaga tgctcgccga   7200
gcggctcatg caatcacccg cactgcaggc gtatctcaac gcccgcaaga actgagcacg   7260
accccctcac aactgaatag gagatacacc agatggaccc gaaaacgaa ggcaacgagg   7320
cccccgaggg aaccgagccc accgacggtg gcgccccgcc tgccgacgac gccccgaagg   7380
ccgacgcgcc aaagacgttc acgcaggccg aggttgacgc gatgatcgcc ccgctgcaga   7440
ctgccgccca agagctgcag acgatcaagg acggcgaaaa gaccgagctg caaaaggctc   7500
tcgatcgcgc cgcggcggct gaggcccgcg ccagagaccgt cgaatttgag cggctgcgcg   7560
acaaggtcgc caaccgcgag ggcaagcggg taccgtcgc gtcgctggtc ggcaagaccg   7620
aggcagagct gatcgcctcg gctgacgcgc tgatcgcctg gcgcgacgag aacgccccca   7680
agccgcccga gcccaagcag cagaagcgca accggctgg cagtggcggc gggttcaaga   7740
gcggtgccac cggcgccgac ggaggttcta ccgacgcgaa ggtcaaggcc gtagaagcgt   7800
tgcggcgctt gcgttccggc aagtagcacc tacctttcaa cacttccgca cgagggccga   7860
cctcggcggt tgatcacaac tgaatagaga gagaggccgt aatggctgac atttcccgcg   7920
ccgaggtcgc aaccctgatc gaagagggct acagccactc gctgctggcc gccgcgaagc   7980
agggcagcac cgtgctgtcg gcattccaga acgtcaacat gggcaccaag acctcgcacc   8040
tgccggtcct ggcgaccctg cccgaggctg attgggtcgg cgaatccgcc accgaccccg   8100
cgggcgtcat caagacgagc aaggtcacct gggccaaccg cacgctggtt gccgaagagg   8160
tcgccgtgat cattccggtg cccgaggccg tgatcgacga cgccactgtc gaactgctga   8220
ccgaagtcgc tgagcagggc ggccaggcga tcggcaagaa gctcgaccag gccgtcatgt   8280
tcggcatcga caagcccgct tcgtgggtct ccccggcgct gctcaaggcc gccaccgacg   8340
ccgggcaggc cattgcccac gtgtccggtg tcgccaacga gtacgacctc gtgggcgcct   8400
ccaacaaggt cgccgagcag gtcgcgctcg ccggttgggc tcccgacacc ctgctgtcga   8460
gcctggcgct gcgtaccag gtcgccaacg tccgtgacgc cgacggaaac ctcgcgttcc   8520
gtgacggttc gttcctgggc ttcaataccc atttcaaccg caacggcgca tggtcgcctg   8580
agtccgcggt ggccttcatc gccgactcct cgcgcgtcaa gatcggtgtg cgccaggaca   8640
tcacggtcaa gttcctggat caggcgaccc tcggcaccgg cgagaatcag atcaacctcg   8700
ccgagcgcga catggtggcg ctgcggctca aggcacggtt cgcgtacgtg ctgggtgtct   8760
ccgcaaccgc gatgggctcc gacaagagact cggtcggtgt tgtcaccccct gacgtgaccc   8820
cgccgacttc gggcgagtag tgcggtatcg ccacaccctg acggggtgg tcatcggggc   8880
```

```
accgaaaggc accctgctgg ccgccctcgt cgagggcaac ccgaactgga tcgaacacga   8940
gggggtggcc ggtgctggca agtctggacg acgtaaaggc agcgctgcgg gcaatgggaa   9000
agcccgaact ggcggaagcg ctcgcggccg aggacgtagc cgacctcctg caggaggcga   9060
ccgacctagt gacggggcac ctgtggccgg ggaggtgcc gagcccgacg cccccgacga    9120
tcaccaggt gacggcctcg gtggcagcga cagcgctcac gaagccgaag gaactgctgc    9180
cggaaacgga gagcctgcaa gctgacgggt tcggcgtgaa gttcacaccc ggcgccggat   9240
cgccgggctg ctacctgacg gccgcacaaa agacacgcct gcggccctgg aagcgcagcg   9300
ctgtctcggt tcccatgagc agcgagaggt acccgtgaca ctgccgaccc cgtgggaagt   9360
gcaacacacg acgtacgtca aggtcggcga aaacgccgcg ggccaggcca agaccgagcc   9420
acgcactcga ccccgcaacg tgtcgagctt gcgaaagcgg gtcaacgagc ctggcgccgc   9480
ggcggccaac tccgatcagg tcgtcgtcga gtacacgatg gcgacacccg aaagcgattg   9540
gacgcacggc gatctggtca aggactggcg cggccgtgag ttcaaggtgc acggcgacgt   9600
cgacgactac aacagcggcc cgttcgggtt ccggcccggc tacctcgtga cgctgcgaaa   9660
ggtggagaaa cgtgccatac cgtccgcttg atctgccgtt ctccgagcac cgcaagatcc   9720
gcaatctgcc cgacctcacc aaggcgtgcg agaagctcgg cgacaagctg cgcgacaagg   9780
cggcggccaa agccaacgcc cacactcccg gcgccggtga cgattacgtg accgagaccg   9840
tgcacgccg cgaccgtgtg cgcgtctacg tgcgcgctga gggcgcagcg atcggcgtcg    9900
agaacgacat agcgccactg atgcaggtat ctgcggaatc ggggccgcgg tgacggtact   9960
cgttccgccg gtcggcccgc tgacggccgc acgtcggtac ctgctcgacg agctggctgc   10020
ccgcggcaac ccgctgatcg tcgagcagca gactgtgccc gagggctcgc cgacgtcgta   10080
cgcgatcctg tcgcgtcccg gcacgagcac cgaggtgttc ctacagcaca gcctcattcg   10140
ggtgcgtgtg tatgacgacg acctcgtgcg tttggaacgc aacgccgatc tgctgcaccg   10200
gctgctactg cacgccgtgc accgcaaggt cgtcgtgccc gacgagggcg aggtgtggat   10260
caccggcgcc acgcatgaat acgggcctgc cgagttcgac gaccggcgtg taccgctgcc   10320
cggctatcag tcgcggtgt tctggacgat cggcctgcgc cccgagcgta gttaactccc    10380
cggccgacgc cggccgacct cgagaaccgc acttgacgtg cggcgatgcg tgctgcccgc   10440
attcggcagc aaaacacaact gaataggaga caacatgcct gagactcccg cggtcacggc   10500
gctgggcgac gccaccaagg tgttcgcagc gtcgccgtcg gacctggaaa ccgttggcgg   10560
cctgtggttt gcgccgtttg gcaccaagct gccgaccgac gtcgacgagc cgctcgaagc   10620
ggcgttcaag aacctgggtt tcgtgtcggc tgacggcgtt accgtcaaga tcgacagtca   10680
gaccacaccc attgaggtgt ggggcggcga cgaaatcggg gcgctgcgag acaagttcag   10740
catcgagtac agcatgagcc tgtttcaggt gctgtcgccc gaggtcaacg cggccatttt   10800
cggcgcgggc aacgtctcga ctgcggcggc caccgaggcg cacggcgccc gcatgaaagt   10860
gctgatcaac tccaagctgc ccaagcggtg cagcctggtc ctcgattcgg tgtacgagga   10920
caagatcatt cggcaggtgg cgcagatcgc gcagctttcg ggcctggctg acatcaagct   10980
cgtgcacaac gccccgatgg cgttcgagcc gacgttcaag gtgctcaagg gcaccgacgg   11040
caatcacgtc atccagtaca gcgacgacgg tcagatcgtg gccgcctagt cgctcgatag   11100
gccagcaccc cgcgcgtttt cctggtggcg gcgcggggtgc tctctcgttc taccaaaaca   11160
ccaggggcac accaggaaac acaccagaga ggcagtacca gcatggcaaa agagaccaag   11220
accaacgaga ccgacgtcga cgacaccgcc gaggctgtcg tggctaccga ggatgagcag   11280
```

```
gccagcatcg ccgaggagtg ggccgacgac tacgacgagg gcaccgagct gttcgtcggc   11340
aagttcgacg ctgacgactt cgacaccgac tacggggtcg ccgacttccc cgacggcgca   11400
acgatcgccg tcaagcgctg cctgcgcaag cccccgccgg gatggattcg ccagcacgcg   11460
cacctgtccg accttgagcg cacgttcgct ctgatcgaaa tgcacgccag cgaccgggct   11520
ctcgaaatcc tcgacagcct gcagcagaag ccgtgggacg acttcgtgga gcgctggggc   11580
cgcgacggcg ggctgatcga gggaaaatcg cgcaggtctg cgcggcggcg cgccaggtag   11640
aggacgcaat acggcgtgac ctgatcgtcg ccgggcgcga gttcgacgac ggcacaatgt   11700
cgtgggacga cctgtacgca ttcgtctttg cctcgccgcc aacgtcggca atcttccacg   11760
cctttgaaaa aggctggaat acaaccgatt acctactcgc gcacgtcatt gacgcgctgc   11820
gggtgggcct gtggcagcgc accgaggatg caaccaaacc gaatccgcgg catgtgcccg   11880
agctgttccc gcggcctggc gacgacgaaa aggccaccga cggcggcgag tacgtccaag   11940
ttggctcgac tgtggcgacc aagacaacg tcggcaagtt cctagaaatg cgcgccgaac   12000
gcgaaaagcg ttggcgtgaa cggaaaaagg gcaagagcaa gggggcgtaa tgtccgcaac   12060
gtactacctc acagttctgc ctgagacgag caagctcgtt cccggtatcc gaacggcaat   12120
gaagggcgcc gaaaaggatt taaccctgca gcccaaactc gacacccgcg cgccgctga   12180 ggcgggccga cgtgccgggc gcgaaatgca ggacggtatc gagcagtcgg cccgcggttc   12240
tggcattggc cggttcctgc gggccgacgg cgctcgttcg gtagggcagc aagcaggcag   12300
cgagattaac gcggggctgc agtcggccga cgtcggccgc ggcctcgggt cgcagctcgc   12360
atcgaacctg acgagcggcg caatgaacct gggccgcaac gtcggcagca tgattgcgac   12420
cggcctcaag gcgacagcgg ttgtcggcgc cacggtcgcc gccgcgggta tcgctggcgc   12480
gctgcacgcc ggtatgagcc ggttgacggc gatcgacgac gccaagttca agctgcaggg   12540
cctcggcaac gacacgcaaa aagtccagaa catcatggac aacgccctgg ccgcggttga   12600
caagacggcg ttcgggctcg acgaggccgc caccacagcg gcgtccgcgg tggccgccgg   12660
tatcgagccg ggcgagcggc tgaccggcta cctgaaaagc gtcgccgaca ccgcggctat   12720
cgcgggcacg tcaatggccg atatgggcgc aatcttcaac aaggtgcaga cctccggcaa   12780
ggcgttcact ggcgatctca acatgctttc tgaccgcggc ctgccgatat tcacttggct   12840
gcaggaggaa tacggcgtaa ccggcgaggc cctctcgaag atggtcagcg agggcaaggt   12900
cgacgccgcg acattccaga aggttgttgc cgagcgcatc ggcggcgccg ctcaggaaat   12960
gggcggcagt atccgcggcc agctcgccaa cctcaaggcg tcctactcgc gtttcggcgc   13020
tgagctggcc gggccgatct tcgcggccgt gtcgccgtta accactgctt tcacaggcgc   13080
tttcaacaag atcacggcgg cgatcaagcc gtacaccgcg cagttgacgg cgatcattgg   13140
gccgtgggca actgacctcg gcaacaagat cacggcgtgg ctcgacaacg gcggcattca   13200
gaacgcaatc gactggatgg gccgcttagt cgaccgcgtg caggcgttgc gcacgggcga   13260
gggtcgaggc gatgcgctgc agtcgatttc ggattctgtc ggcaagctcg gcccggcgct   13320
gcagcaggct ggcccggcgc tgcaaggcgt cggatcggca ttcgcgcagt tcggccggac   13380
gatcgccgag attggaccgt cgacgcttag cggtgtcctc acgcccgcgc tgaacctgct   13440
cgccggtgcg ctgaaatttg ttgcagataa cgcctcgtgg gcggtgccgg ttatcggcgg   13500
gctcgctgcg gcgttcctgg cggtgcgcgc tgcaactgcg gcggctgcac cgttcatgca   13560
ggcgtacacg gcgacgttca acctgattcg tagcccggtc attctcctgc aggcgcaagc   13620
```

```
gcagcggcag ctcgccgccg cgatgacgca gcacacggcc gccctggtgg cgaacactgg    13680
cgctcagagc acaaacacgg tcgcgcagaa caccaacgcc gcgacctcgg ttcgctcgcg    13740
tgtcgcagcg atggcctcgg ccgtcgccag tcgcgcagcc gcagccgcgc aatggctttg    13800
gaatgctgcc ctgactgcaa acccgatcgg cctcgtgatc gccgcggtgg tcgctattgg    13860
cgtcgcattg tgggcgttct tcaccaagac ggagaccggc cgcaagctct gggacaagat    13920
ctggaccggg attaagacga cggcggtcgt tgtttgggac tggctcaagg tcgcgttcga    13980
ctggctcggc gaaaagctca cgtggctatg cagaacgtc gcggtgcccg cattcgaggg     14040
catcaagggc gccgtcgaaa cattctggaa gggcgcaaaa gtcgtctggg atgcgttcac    14100
aacggtgctc gacacgatcg gcaccaaggt aggcgcgttc aaggacggca tcgtgaccgc    14160
gttcaacgcc gtgaaagacg ttgttacgtc ggtgtggtcg gccatcggcg gcatctggga    14220
caagatcgtg ggcggtatcg gtactgtcgc ggatgcactc aagggtgcgg gcggcacggt    14280
gctgcgggcg ttcggcctgg gcggcgctgc ccgcggtggc tacatcgagg gcggaatggc    14340
acggtacgcc aacggcggcc agatcaacgg ccctggtacc ggcacgagcg acagcattct    14400
cggtttcccg gcgatggtcc gcgtggctaa cggtgagttc gtcaccaacg cccgcacgac    14460
cgctcagtac ctcccgctgc tgcaggcgct caacgccggt atgccgctga gtgacgtgct    14520
gggcaagctg ctgccgcggt tcgccgacgg cggcctcgtg tcggccgacg agctggtcga    14580
cttcgcgcgt ggcgtcgagg gcaagccgta cgtgtggggc ggcaccaact ggggcgactg    14640
ctccggtgct gtctcggcga tcgccaacta cgcgaccggc cgatcgccgt tcggatctcg    14700
ttttgcgacg gcgaccgagg gcgacgagct tgcggcgcgt gggtttaagc ctggcctcgg    14760
cccgacgggc tcgctgcaaa tcggttggta caacggcggc cctggcggcg gcacactgc     14820
ggcaacgctg ccggatggca cgaactttga aatgggcggt gcacgcggca cgggcagtt     14880
tggtggctcg gctgcgggtg cggccgattc tgagttcacc aaccgtatgc acctgccacc    14940
cgaggcgttt acgggcctcg acggcggggc gccaacggtc gggtcgagca cctcggcccg    15000
cggtgccggt acgtacaccc cggcgacaag ctcgcagttg agtgcgtcgt cgcgcaaggt    15060
tgacactgcc cgtacgtctg caaagaacgc cgaccaggcc gtcgacgacg ccacctatcg    15120
gcgcgacaag gcgcagacgc ggctcgacga ggccaagagc aagggcaagg cgtcgacga    15180
tgctcagcac tcgctcgacg tcgccaaccg cgagctggcc gacgcaagg agcggcaggc    15240
caaggcgcac gacaaggtga ccgacgcaat gagcgccgac gaggaactgc gcactaaggg    15300
caagttcaaa gagggctcgt cgtcgtcgag tggcgacgg ctgtctggtg cggactttgg    15360
caagacgttc gtatcggggg cgcttgagtc gatcggcctc gacgggtcgc tgttcagcaa    15420
tccgcttgag tggccgacgg ttaagtcgct catggcgggc gtgaactacg cgggcggcct    15480
gctcgccaac ggcaccggcg ccgcaacgag ccccggtggc ttcgctgacg gcgcgggcca    15540
ggcggtcggg ctcgatggcc tcatggcagc gcttccgggc gctgtgggcg atcctgcggc    15600
cggttggaca cctcagagcg gcagccctgc gctggcgccc ggtcagttca acccggcgat    15660
tgcaggcggc ggccctcga tcgccgaggg cgtcgccaac gccatgagtg cgttcgcacc     15720
ggacaccacg cagcacgggc agggcggggg agctgaacct ggcccggcgg agacgtgaa     15780
tttcaacggc cccgtgggca tggacccgca agcgctgcga accgagttcc gcaccgagct    15840
gaacgcgcgt tcgcgctaca gcggcagctc caacacgaag taagcagcta acggccggcg    15900
agccgccgat ctggtctctg acctgcgcg gctcgtcgcg ccagctatcg aactttcaca    15960
actgaataac ggggtgagtg agccgtgacg cttggcggca tccatgacga tttctatctc    16020
```

```
gatccgccgc ggtacacaga tgacgcctac gggcgaccgc tgtacggccc cgagaatccg     16080
gcgcacccga gctggcggcg catgtcgcac tggggcgacc tcggccgtaa cggcgagtac     16140
ctgcggtcaa cgcagacgaa gtgggtctat atccacccga gcaacaacaa ggtgtggcac     16200
ctcgccgggc ctatgcgcgg ccgtgagggc gtcgtgctgg ccaaggaact tgagggcgtc     16260
atgcagcccg agtttgaaat tctctacagc gagggcgcct atacgatcgg cgccaaaccc     16320
gagcggatca actacaagaa acgcacgatc agcctcggcg tagtcatcca gcccaacggc     16380
aacgccgagc gggtcgagga gcctaacccg ttctcgtacc ggctgattga ggactcgtgg     16440
tggtcgtcgc tgtcggagac gcagcccggt ttcctgggct cgttcacccg cacgcacggc     16500
tggcggtggc tggctgtgat cctggccgag gcgtcgaaaa cctccctcaa gatcgacccg     16560
acggcgcacg acaacaactc tcagcagtac aacatcgtgc tgcacgcccc ctggccgttc     16620
tacgccaagc gcacgctgag taaggcgtgg ctgtccgacc tcgagaatgt cgtggcgaac     16680
gacggtgtgg cgcaggggat tatccagtgc ccgaaccgcg gcacctggga gtcgtggccg     16740
aagtacctcg ttaaggggca cgggcaggcg tggattcagg acggcaacga cgggcagatg     16800
atcaagctgc ccaagttcta cgagacggac ggcgagtaca tgctcgtcga caccgatccg     16860
actaagcgca cgatcacaac cgagaaagac ccggttgacg gcagctcta caagtatctg     16920 cgcgggtcgc agttgcttga gctgctgctg cacgacgtga cggccgcgcg cctcccggcg     16980
cagcgccgca ttcccggcgg catcgggttc gacggcaaga ttccgccgcg cacggtcgcc     17040
aatatcaaag tgcggcatga caacccgtac gggtcgatta cgtgcgtcat gccgcagcac     17100
taccggatgg cgtggtcata gatgtatgta cagaatggcc gcaagctgtg ggtgccacca     17160
gcgtgcggcg ctaacggcgt tcccgatccc gtcaagaatc cgatcgaggc gtttcggtac     17220
ctcgacctca gcgtgagct gatcgacgcc gaggcccgcg agaagccact cattcggctg     17280
tgggacaagg cgtttaagta catcggcacc gtggcggctg agaagtcggt cgacgccgag     17340
gaaatgctgc acgacaccgg gcagggcgac attgtgctgc gcggcgacga ctggctcgtc     17400
gagttcatgc gcactgacgt gcgccgcgag gaggatctgc acgtcacgat cgacccgtac     17460
ccgcaccggc gcaactggcg gcggcggtgg cacgccaagg tcaccaacgt gcgggttgcc     17520
cgcaacgaga acgtcagcg cacagtcaca ttggagtgcg cgcacaaccg cgagcactgg     17580
aaacacctgc tgttcggggc gacgcctttc agcctgcccg aggtgcagcc tatgcgtgcc     17640
tggctgctgc cgggcaacac gcgaacgatc gtgagcacaa cgggtttcat caacctggcg     17700
cgcaactact ggcccttgct ggcgctgcct tcgcaggtga tgaatcccgg cgcgtggatc     17760
gggcaggcgt ccaacctcgc caacctcaac ccgttgaact ggccggttca aatgcagttc     17820
gtcaatccgc tattcgatcg gtcgcgcacg agcgtgctca tgtcgaggtg gtcgaacgcg     17880
cacgacgtgt gcgacgcgct gctcaagtac gccgggtgtc acgttcgggc gtactgctgg     17940
ctggaagagg acgaggacag cccgcacccc gagctggcgg cgatcgtcgg cgagaagctc     18000
gccaggccga cgcgcaactg catcgtgctg gcagtcgagg acatgagcgg cacgaccggg     18060
gtcaccggca cggcgatcga cggcgtgctc gacctgattg cagtgtcggc cgacaacatt     18120
ctcagcaccc tggtgcatgt cgaccgtgac ggcgacggtg tggacgatcc gtttatccga     18180
aagctgctgg gcgtcgcccc ggcgccgccg gatattacat ttcgggatca cgaatattcg     18240
tcgattattt cgtctgagca cagcatgttt cgtgcaaagg cgcagaaaat tctcacgggc     18300
ggccgtagtc ctggctgggt aaatcaagtt cagacattcg ccattaagta cgccctctct     18360
```

-continued

```
caaatttccg caattatcca agctggcccg gctggtgcat atcagcaacc tggcagctcg    18420
ggtttggagg aaatttatca gggccaggct gacaatattt tgctggccta tattcaggta    18480
accgacccgg tgcgtgcaat gcgctccgga ccatatggtt acctggaaca tttcgagcag    18540
ggctcgggtt cagcatacac ggtcagctcg gcaatgacat tagctgaggg gcaccacaag    18600
acgcgggcat atcaggcgtt caaggtgtca gttcgtaatg gcgggcaatt ccagctgtat    18660
tacgatttcg atctcggttg gcgcgcgaac tttgaaatag atcgcatttt tcacaccgac    18720
caggtatcag ccattcggct gcactacaac gagacgacac cgaaaacttt cgacctgtct    18780
atcggtagtg attcggaatc ggaaagcccg ctagcgcagg tggctcgatc ggccgcagcg    18840
ttctggaatg ccattggcat gttgttcgga tcaggagata tgttctagtg gaaattccca    18900
cactgccgcc gctgcccgac gtgccagaac acgtgcgggc cgccaactcg acggttgacg    18960
cgatgtacga cattgccgag gccctcacat atccggtcga cagccgcggt cgacggtacg    19020
acgtgcgatt tctcttgccg gtgattgcgt atcacctggc gcgcgctggt tgtgtcgtcg    19080
acccggctcg ggccgtgatc aagaagcggc gcctgccgcc gacgggtggc gtcgtcgagg    19140
atgcggtcga ctgggtgccg ctcgacgccc ccgactcgat cgaggacgag ctagacggcg    19200
cgaccctcga cgacctcccg cacttgtccg cggcggccca agccgaattt cgacgccggg    19260
cgctcggcga gccccggcg ccgacggccg tcgacgacca gggcgtcgac ctcgacgggc    19320
gcgcccgtg gcacgtcgaa acgtcgatca cgttcgacga ctgagcaacc gccggcaaaa    19380
cgtcggattc ataccctgac ctgcggcgca gcctcgggtc ggcaaacaac tgaataagga    19440
gcaccatatg gccgagcttg cgccccggct gacgggcgat gcggtcgcgc tatttcagac    19500
cctcctgtct gccacgtggt acggcatcgt cggcgacgga acacacccg gcggcatgtc    19560
ggcaacgctg gaaatgatcg acggcgaggc tgtgatcact accgacgttc tgatcggacc    19620
caagggcgac aagggcgacc cggcccgct ggtcgatctg caatggcccg cactggaatc    19680
cccgactgag ctggtcgagc tgcaagacga gctaggcgag gacgacaagg gcaagggctg    19740
gtggatcggc acggttgtct acgtctggac cggcaaccaa ttccagatgg tgcggcccgg    19800
ccccggcggg cctcccggcg ccacgcctca aatctcgttt gagttcgaga cgatcccgat    19860
gtcggagcgc ggccctggcg tcaaggacga ggtaatccgt tccggcactt cgcttaatcc    19920
gcacatcaag gtgcgggcgc tgtcgccgca ggggcctgtc ggcccgtcga cgaacatcac    19980
cggcgcgccg gactacgaca acagcgtgcc gccgaccaac gggcagacgc tcgtgtggaa    20040
ctcggtaaaa gccaagtggg agccgtccga cttcactgcc aagcacccgc ggctgtactc    20100
ggttcccgag gcggcgttta cgccgttcac cggcccggcg cagcggcagc cgatcctgca    20160
gtaccaggtc gagccgcagg acttcgcgtg gaccccgtac gtcaccgggc acatcaaggc    20220
gtttggcctt gagttggacg ccgacccgct gacgatcggc gtcgaggtgc gcctcggcga    20280
cccgctgacg ggcgagctga tcggccgcgg gttcggcaac tcgtcgatgt ggtcgacgat    20340
ttcgccgcat tggtcgacct cgggcgaccc cgcaaccgcg gtggccccg ataacggcgt    20400
cgccacgatc gccgccggtc aggccgcgca gatcaacgta aacctttaca acgatggcct    20460
gttcggcgtc tacgtgttca acggcaaagg cgcgcagctc gccattctcg ttgtgccgca    20520
agggggatag ctgcatatgc catacaccaa gaattaccgc acggtcgtgc cgcttgagcc    20580
gggcgtcgac ctcgaactcg cgcggtggct ggctcgtgag tcgttcgagc gtgcagcgga    20640
aaacatgggc ctgacgatcg tcgagtacgg cgagcgtgag gtgccgtgga ctgacctgcc    20700
gccgaaggct gccgagcacc tggcgctgcc cgccgatgaa tacacgtggt tcgagttcac    20760
```

```
cggcgtaggt gcggtttccg aggttcagat cgagtggctg actgcagagt cggcctggcg    20820
caacacgcag gcgggaggtc ggtaagtgcc tcccgtcttt gatcgccggt ccctcgtcat    20880
cgaccgcaac ccgctcgttg ggctgacgcc cgaccccggc actctgccca agctcgaccc    20940
ggcgatgctg tggaaacagt ggattgacgg tttcaagaca ctgaccggaa ttgacctatc    21000
gtcaccggcc gcgctcgtcg ccagcctcgg cgatctgatc ggcagcgccc tcgatcctgc    21060
aaagctgatt gaggcgctga caaaggtttt cgggtacgtc ggccctccgc tggcctcgct    21120
tgaggccctc gctgcgtggg tcaacagtca gattttcggc ctgatcgacc cgcggcggct    21180
ggctcagatc ccgctcggct cgatcgtgca ggagtcgcca aacctgttga ccaacggctc    21240
gtttaccgac gcaattgcca tcgacgacga gacgggccgc tgggtccgcg ataccgcgac    21300
gtacaagtcg gcgccagcgt cggcacgcac gaccgccgac ggcacgatcg ccgaactgct    21360
gagcattgac ctgatcccgg tcaagccgaa acagaagctc gacattgcgg gtttcgtccg    21420
ctgggcgggc ctggtggcgt ccgacgggtc gatcggtatc gggctgatgg agtacggcga    21480
cgctggcgag cagcgtgtgc tgatcaaggc gctagacggc gccagcggca cgcaactgac    21540
gtggcagaag gtcggcggcc agtacgtcgt gcccgacacc ggcgtcgaca gtgtgcgcgt    21600
ccgactggtc gtcaacgacg gcgcgaccgc gggcaatgtc tggtacgacg agctgaacgc    21660
gagcctgggc gcaaacctgc tgcccaagac ggccgtcgag ggcctggtcg ccagctgaa    21720
agcagcgttt gactcggccg aggccgcggc taagcagttc ctcgacttcc tgcaaaacca    21780
atggcaggcg atgctcaacg gcatcaaggg cggcgtcggc ggcgcaatcg aggacttgtg    21840
gaatcggttg ctgcacttga cgcctgacgg cctgtttgac gcctcgcagc tcgtcaacgt    21900
cgacaacatg ccgcagcttc ccccggcggt cgtcgcgggt atcgagggca tcgagaatat    21960
cggcgacacg attcagcagg cgattgatta cctgtggtcg ggcttccggc gccaaaccgg    22020
gcaaggcaaa tcgttttcgg cactggcgca agccgcacag gaaacgtcaa acgacattca    22080
gaccgccgtg cacctggcgg cgatgcacgc gggcattctg agcgaacggc gcaacaaacc    22140
ggcgcattgg ggcctcgccg ataccgtcga ggtgtcgttc ccgttgtccg atattgccag    22200
tggcacaacg gcgccaacga tcccgatcac ggcgacaagc gcccgcatgg cgctcattcg    22260
ttgcggcgaa tctgctacca agggctttgt gcagtggctc ggctacggca cccctgatgc    22320
cttctacgtg aacgtgtaca agatggacgc cgagggcaac ctcgtgcacc tgcacacctc    22380
gccgaatctg agcaaccagt tacaggccac gatcggttgg gagatgtacg ttttcgcggg    22440
catcaaccag accgaggtgg accctggcga cgtgttggcg gtcgagttcg tcgccgaggg    22500
ttcgggcacg tacaacatcg ccgggtgcgt gacgtcgtgg gtgccggttc acccgtcggc    22560
gaacaccaag cacctcggcg cggcgcgaag cccggcgctg ggtgggcggg caccggcgac    22620
tatcccggct gagcttgtct cgtggtcggg cacggtgccg tgggtgtcga tcggcattag    22680
caacgtgccg ccgagctacc agccccgac cgcgactgag ttcaaccagg ttgggcaaca    22740
gacctacgaa attccgttgt gggccaatta cgttgacgtg atcgcctgcg ggggcggcgg    22800
tggtggtggc agctcggcga acttccttac cgggcagggc ggcgagtgtg gcactggat    22860
cgctgcaacg ctggtgcgtg gcgtcgactt cgcagacgac gcaacgacga tcaccgtcaa    22920
cattggcact ggcggcgcag gcggcccct caacgccaac tctggcggcg acggtgcgcc    22980
gacggtaatc acctggcgca agccagacgg gtctatcggc tcgatcgccg caaccggcgg    23040
acagcacggc ggccccggcc cgattcataa cggcaacaac cccaatacgg ccactgcagg    23100
```

```
catggggcg ccgaacttcc cataccgcgg cgcaacgtat ttcggtggtc ccgatgcgtc    23160
caccgcgccg ggcagcgcgc ccggcggagg tggttctggc gggttctcat acggggcggg    23220
ctgggttggt ggtcgtggcg cggcgtggtt ggtcgcgcgg caatccgagg atgactgaga    23280
gggggcgcta tggcgggatg gggcactgac ccgcagccgt cagcgcgtgc cggtagcggc    23340
tgggcaacgt cgcccgccgc accggcgccc ccgcggcccg gctcggtatg gcggccgatc    23400
gtgcacgagc tggcggcggc cctgagcgtc tcgaccaccg aggcgaccct cgcaatccgc    23460
gcaacggccg cagcgctgag cgtttcacac ggagacgctg cagccctgct gcgcatgacg    23520 gccccgccg ccagcacgag cggatcgtca gcgtcggcgc gagagcacta tttcaccgcg    23580 gccccgcgg acagcacgag cacgaccggg gcgtcggcgg tcgtcaaggc ggtggctgca    23640
gcgctgaacg tcagctcgac gtcggccgcc gcgctgctgc gggccgtggc gcccgcggcg    23700
tcgatgagcg gcacgtcggc ctcggcagcg ttcccggcaa tggcgccggt tgcgcagcgg    23760
ttcgccactg tcggcgagtt cgagtttctg atcccgtact ggtgccggta cgtcgacgtg    23820
atcctcgtcg gcgcgggcgc gggcggcaac ggcggatctg cggccctggc cgccgggcat    23880
ggcggcgagg gcggcaagtg ggccgcggtc acgttggagc gtggcgtgca catcccgctg    23940
accctggcct cgatcgtgtg caccgtgcgt gcggcgga cgccgggcgg cggcgccgtc    24000
gtcggcggta tcgccacgga cggcaaccca accacagcgc aggctgcggg ctgggcaggg    24060
ctgagtgccg cgggcggtgt gcaccgcgac cggatcgggc tgctgcatca accgggcgac    24120
ggccccggcg atttcacttt caagggcgtg ctgtacgtcg gcggcgcccc gaccaatagc    24180
ggcaacggca cagcgggcaa ctcgcccggc ggcgctggcc gcggcggcga cggcggcgcg    24240
ttcgtcggtt ctcccggcgg tgtcggcgca cccggcgcgg cgtggttccg cgcataccag    24300
tagcaaccgc cggccaaatg ccggattcat agcctgacct gcggcgctgc ctcgggtcgg    24360
caaacacaac tgaataggag cgttctgtgg cttccgcaga tcagttcaag ctcgacaccc    24420
tcgccgcgat cctcgcgcag ggcaacctgc tgagcctgca cagtggcgac cccggcaaga    24480
cgggcgccag cgagattacc ggcggcggct acggccgcaa gacgttcacg tggggcgccc    24540
cggcgatcgt gtcgggcggc gccgacgacg gcaaggccaa ggcgaccggc gccacacagc    24600
agatgaacgt cgctgcgggc gtgtcggtta cgcactacgg cgtacgcaag gccgacggca    24660
catttctgta cggcaaggca ctgagccccg gcgcgactct caacgcgaac ggcgtcattg    24720
acgtgacccc gacccacacg tacgacggcc cggtttagaa cggagacaac cgaatatgga    24780
aaaggtactg ccctacgacc gggcgatcgt cccgcaggaa acggggtact ggtgcggccc    24840
ggccgcaacg cagatcgtgc tcaactcccg cggcctggtc gtgcccgagg cgaccctcgc    24900
ccgcgagatt ggcaccacgg tgcgcggcac cgactacgtg ggtctgatcg agcggattct    24960
cgacctgcgg gtacccgatg cccggtacac gtcggtgtac atcgaaaacg acccgccaac    25020
catcgaccag cgagagacat tgtggcgcaa cctcaagcag tcgatcgacg ccggttacgg    25080
cgtggtgatg aactgggttg ccccgccgag caactacccg cgcggcgtca agaacagcgt    25140 gagccccgc tatggcggcg gcaccgtgta ccactacgtc gcggcgatgg gctacgacga    25200
taacccgacc gcgcgtgcgg tgtggatcgc tgacagtggc tttcagccgc aaggctattg    25260
gatctcgttc gaccagtgcg cgtcgctgat cccgccgaag ggatacgcat tcgccgacgt    25320
cgaccacccc gacggccccg aggcgccggt cgacgccgac gcgcaggcgg ccgacgcgct    25380 gctgcgcctat atgggcggct cgctgccgtt cgctcggtat caggcattgc tgcccgcggt    25440
gcgccagtgc ctcaacgagt gcgagtgcac gaccgagccc cgtatcgcta tgtgggcgc    25500
```

```
gcaggttggg cacgagtcgg tgggcctcaa attcatgagc gagctgtggg ggccgacggc   25560
cgcacagcag ggctatgagg gccgcgcaga cctcggcaac acgcagcccg cgacgggta    25620 caggttccgc ggcgccgggc cgatccaggt caccggacgg cacaacttca cggtgctgtc   25680
ccaatgggcc tacggcaagg gcctcgtgcc gaccccgacc tatttcgtcg acaacccga   25740 cgaattgcgc ggcgaccgtt acggattcgt cggcgtcgtc tggtactgga cgacgcaacg   25800
cccgatgaac gacgcggcag acgcccgcga tctggtgcgc gcaacgcagt acgtcaacgg   25860
cggtcagaac ggaatcgacg accgccgcac ccgatacaac ggcgccctgg cgatgggtgc   25920
cgacctactc aagatcgtta acggaggcga tgatttcatg tctgcactga ccgctgccga   25980
gcagcgcgaa atgctcgatc tgctgcgctg gttggcagca ccggaaaccg gcgagctgcg   26040
caagaagttc ccgagccgca gccagttgcg cgccgtcggc gagggcctgg tcgacacgtg   26100
ggcaggcatg gacctcaacc aggacgccaa cattcacctg gtcgccgagt acgtgctcgc   26160
cggtatcggc gatcccgacg caatcgcccg gctgcgcaag ctggccgcaa cgaccgacgc   26220
aacccggcgg gggagcgcgg cgctcgcgca gcgcatcctc gaccactacg accaggcgca   26280
cgaggccccc gccgaggtcg acccggcccc ggcccgcaag gtggcttgtg cgcagggcgg   26340
tggcggctgt gtcctcgtcg ccaacggcgg cgacggcacc tgcggcctcg ctggcagcga   26400
gtgcgtgctg cgcaagggcg gtgccctgtg agcaagccaa tgctgctgac cgccgcgggc   26460
accaaggccg acgagtggac cggctacccg gccgacctcg cgcggcgcat ggaggatctg   26520
tactacttcc agccagtgcg ctacggcccc aacggaatcc cggcaatgtg gccgatgggc   26580
gcctcggcta agagcggcat cgacgagggt gtgcgcctgg tgctcgaagc cgaggcgctg   26640
ccatcgcggg aggtgcccga cgggtacgcc gtgtgtggat actcgcaagg cggctggtt    26700 gtgtccgagc tgctcggcga gttccgcacc ggccgactca agcacctgcg cggcaagctg   26760
atggccggtg cgacattcgg caacccgtac cgcgagctgg acagcgacgg cggccgagga   26820
atctccgaca agcggatcgt caacacgccc gatttctggg tcgacgagtt cgaccccggc   26880
gacatctacg cgaacgtgcc gaacaacgac gttggcgagg acatgaccgc gattttcaag   26940
ctggtgcggt tcaacggcat tggtgacgtg atcgacctcg gcagcatcgc gggcggcctg   27000
gtgccgggcg gcggccagct cggcggcatt ctcggcggcc tcggcgggct actgggcggc   27060
ggcgcccggc agcaagacaa catcgtcgag cagatcgtcg aaatgctcag gagtccgctg   27120
cgcgagttcc cggccgcggt gtcggcgatc ctcaagggcc tggtgttcgt cggccagaag   27180
cccgcgaccg cgccacacat cgagtaccac ctgcgcgagc ggtcgccggg tgtcacctac   27240
tacgagcacg ccgtcgccca catgcgcgcg atggcggcat aaggggcga gaatggcaaa    27300 ggtcgtcgag acaatcctcg gcatgttagt gcaggtgtgg acaggtgtgc ggcaattcgc   27360
cgccgagcgt ctcggcatcc gcacgtggga ggatttgcgt ctgcagattc acgtgctgtc   27420
gccgtacgcc gttacggcaa tggtcacgtg aacatcgcc agcgaggaca aggccaagct   27480
gattgttggc ctcgtgctcg ccgtggcgag cccggcgctc gcgttcttca acacacgtga   27540
cgggttccgg cgctgggtgt acggactgct gccgccgttg caagcgttca ttgtcggttt   27600
cggttgggcg caggattcga ccctgacgcc tctcatggcg gcgatcgtcg cgctgctcgg   27660
cggcgcaatg gctgccgcta acacgccgtc gagccgcggg ccgaaagaca cgcggacggc   27720
ggcagtgccg tgagcatgtc tgacctgatg accggcgaga cagtcggaat gatcgccggg   27780
tcgtcggtcc tgtctggcgc cgtcggggca ctactgtccc ggcggcgcga caacttcaag   27840
```

```
acgctgactg atgcgctgat caagcgcgtt accgaccttg aggggcgcgt cgatacggtc    27900
gagtcgaaac tcgacgccga gcagaccgcg cacgagcaca cacgcaggct gctcgtgcag    27960
tccgaggcgc tgctcgccgc ggcgcgtgcg ttcatccgca ctgtgatgcg ttgggcgca     28020
ggcgatcgtg ccgagccgat gccaacgccg cccgacgagg tgatggccga atgagcctcg    28080
ccgaacgcct cggcgacccg cagcccgcac cgtcgagcga gtgcgccgtg tgccgctggc    28140
tcgacaacgc caacgagacc gaccgcgcag cgttcgacaa ctggctcgcc tctgcgggt     28200
cgctgtcggc actgtggcgg gcctgcgcca acgatccgag taacccgctg gcgatcaaac    28260
gcccgcggtt ctctgagctg atcaacgacc atcaccgagg aggcgcacat gtcgctgtct    28320
gacaggctcg ccacaccggc ggccgtaaac gagaaatacc ggcctaccgt cgagttcgac    28380
aaccgcggcg ccacgatcga caccggcacc gtgtaccaag agccgggcca gccacccgag    28440
tacgccgaga ttctgcgcca ggtgggccgc gaccccgagc ggttccggct cgtcgagatt    28500
ctgagcgaga agcattggca ggtgccttac cggccgtacg tccgcgacga cgacggtcag    28560
ccgatcttta acgagttcgg caagccgcgc cttgaggagc aagagtttcg gtgggcggcg    28620
tcctacaagc tgcgcgtcga gccgatcggc cgcggcggcc cgagcgacct tgaggcgctg    28680
atcgccgacg cccgcaaggt gccgacgatc gccccggcga ccacctcgcc gtactggtac    28740
gtgtttcagg cgggcgacct gcagctcggc aagcggtcac gcgacgggtc taccgagcag    28800
atcgtcgagc ggttcgtgca gtcgcttgag gccgccggtc ggcagtaccg cgagctggcg    28860
gcgtccgtcg gtatcgctgg ggtgcaaatc tcgatgccgg gcgactgtat cgagggcgtc    28920
gtgtcacaga agggcgcgaa tagctggctg acacaggaga cgatcgccga gcagttccgg    28980
ctgctgcggc ggctgatggt tgaggccgtc gacacgttcc gcgcggcccc ggccgtgtac    29040
ctcgacgtcg tgaacggcaa ccacgaccag gccaacggc agtggaacac caaccctggc    29100
gacgggtggg cgaccgaggc ggccatcgcg gtgcgcgacg caatggtgct caaccgcgac    29160
gtgtacggac acgtcgaggt gcgggtgcct gaaccgtggt cgggcagcat gacggtgccc    29220
gttggcgaca ctgtggtcac tgtgatgcac ggacaccagt cgcccaaggg caaggccctc    29280
gattggctcg ccaagcaggc ggtacacaac cagcccgcgg gggcctgcca ggtgctgcaa    29340
catgggcact ggcatgtcgg cgccgtcgaa atgcacgcca ccaagacgat cgtgtgctcg    29400
ccgacgttcg actgtggcag cgattggttc cgcgagcgcc agggcggcga gtcccgccgc    29460
ggcgctctca cctacctgct gcgcagcggc gaagtgtcga acctgggcgt gctgtagcaa    29520
ccgccggcaa aagcctcgag cgcctgccgt gacctgcgcc gatcaaccga atgccgatt    29580
tccggcaaac attgcgaacg cccctcgtcg atccgtcggc gggggcgtt tcgtcgtatt    29640
gttgacctgc atacaggcgg cccgtattgt tggcatggca acaacggcac aacgggatag    29700
gagcccgaaa tgagcacgga cgtaatgaca gtgcgcaagc tgtccgaaca ggaggccgcc    29760
gctatggcgc gaggcaagtt ggtcagtgtg ggaggcaccc gccgaacgat cccgcggcg    29820
aacgtgccgc ggtacgagga gcaggtcgcg gcgattgagg ccgagtggcc cggcgctgac    29880
gaggcgcaca ttcggcgggc ggcgattgag gccgtcggtc ggtatctgtg cgacgaggcc    29940
gacctgcccg aggcggtcgg cgaggagctg gccgaggcga aagagcagta cgaggctgcg    30000
acgtcggcgg cccgcatggt cgtgcgcctg gcggtcgagg acaacgccag cgagctgagc    30060
ctcgcgcagc gtatgggtat caaccggctg actgtgcgca agtaccgcgg caaggttgat    30120
cgccgttggc agcgcccgtg acggccgcgc cggtcgggtc tcaggtgtgg gtgctcgatc    30180
tgacgatcga aggccccgag gcggcgact atgacgggtg gcagtcggtg cacgcgagcc    30240
```

```
gcgagggcgc actcggggttg atgctcgaca agctcggcga gcatggcgtg agcctcggcg    30300
ccgacgttgg cacgatcgcc agcgcggcgg ccgacaatgg cagcctggcg ggcgattttg    30360
cgatcgacga gctggctgtg agctacggcg tgcacctgat gccggtcgag ccctaactcg    30420
cgtgttgaca tgcatacagt tcgcgggtta ctgtatgcat accaacaacg cacacgggat    30480
aggagcccac gatgactgaa tacaccaagg ccgaggccaa ggccgccgac cgcgtgctcg    30540
ccaagctgac cagtgcgtac ttcgacgcgc aggacgcttg ggagcgtgcg gccgatcgcc    30600
tgcacggcgc ggcggccgac aacaagaccg catacggctg aagatgacg cacgagactg    30660
cgctcgccga ggcgcagaag cgggccgccg atgagagcat tgtgcgcttc aaccgcgagg    30720
gtatcgagcg cgccgtcgcc gcgtacagcc cggcgctcga cgcctaccgt gccgcaaatg    30780
ctgcgatcga cgagcacgag gccgccaact acaagggctg gcagcggttt tcctcgtgc     30840
ccgacgggca cattcacgcc tcgcgcgcct gtgggtcgct gcgcatcacg accaagatcg    30900
gttggctgcc tgagctttcc ggcgagaccg aggccgaggc cgtcgctgcg cacggcgcaa    30960
tgctgtgcac tcggtgtttc ccgacggcgc cggtcgagta cacccgtggc aaggacgccc    31020
ccgccgacca gtgccccggc agcggcaagc ggtacgtcga gggcactaag accgaccccgc   31080
ggcggcgcac cgtgtacggc gagtgccagc actgccacgt tccgcaggtc atcaccatgt    31140
acggcgtgac gcgcaagcat aagctgccca aggtcaagta gcgccgaccc cgcgaggcct    31200
ccgtcaacac ggcgggggcc tcatttgtgt tgacatacat acagccgacg ggttactgta    31260
tgcatagcaa caatgcgagg ggataggagc ccgaaatgac cgccaccaca gtgacttatc    31320
agggcatgaa attcgtcgtc gagtcctatg tcgacccgtg ccccggcctc ggtgcccgcg    31380
atcgggtcga gtggatggac gagtgccctc gctgcggcgg cacgggtgtg taccgctggg    31440
tcaatgcgat gggcaactgc gagggctcat gctttggctg ctggggcacc ggcaaggttg    31500
agcgctcgca ggccgcgcag acgctccgca agatcgcccg cgacgaggcg ctgcaccgcg    31560
agcatggcga ggctatcgcc gagtaccacg ccaacatcgc ccgcgagaac gaggcccgcg    31620
agctggcgac cgcatgggac gaggcgcacg ccgagcaggc ccgccgcgag ccccggctcg    31680
ccgcgatgaa caacaacacc gttggcgagg tcggcgagcg gctgcgcaac ctcgacgccg    31740
aggtcgttgt gtcggccgga ttcgagcgcg acgcctaccg cggctatggc accgagtacg    31800
tcaagatcgt ggttttcgcg ctcgccgacg gccgccagct caaggcgatg ggcaccggca    31860
acgccctgta cggcctcgac cgcggcgaca aggtgcgcgt gaccggcact gtcaagggca    31920
ccggcgagta ccgcgggcag gtgcagacca tcctgcagcg cgtcaaggtt gaggtcgtcg    31980
agtagccgtc gacgacagcg cccccggctg gattgcctgc cggggcgtt ttcgtgtccg     32040
tgcggcgcta ctgggccgtt tctgggcaca gctcgcgctg cgcgctgaac gcgatgccgt    32100
cggcgtgcgt gcgtgtcatg tcgagaactt tcagaaacat tcgatcggcg accacctcgc    32160
gcggtttgcc tgcccgtagc tcgtcgcaca cggcgtaacc gagggcgagc gcctcacgct    32220
cgtcgaatat gtcgagcccg tagtcgacgc tgatcctcgc caggtatccg gcctcaccgg    32280
cgtgtgcggc gccgggcgcc aggacgacag aggcggcccc gatcgtggcc gcgacgagta    32340
ttcgtttcac ccggctgagc ctagttggcg gggcctggtc tgcggcggca cgccgcgtta    32400
ccgtctcgcc tatgcgtcag tttcccggca caccgtcgag cggtgtttgc tggcgcggca    32460
aacaaagtgg gggcgttgat ggggtgttga tgccatcaac acaaccccg ttgccctgcg     32520
ggtttggccg tattttcgcg tactcccgcg tgtcgaacgg gggcgtttcg ccaggtcagc    32580
```

```
ggcactaaat ggtgcaggtt caattcccgg cagctccacg agtaaaggcc ctggtcagag    32640
acatattttc tgaccggggc cttttacat caacgctcac atcaacacat ctgtaatatc    32700
ggccgctatg gcctccctcc gcaccagctc ccgcaaagat ggcagcacct acacgtcggt    32760
tctgtaccga ctcaatggca agcagacctc aacgtcgttc gatgacccgg tgcaggccgt    32820
ggagttcaag cggatggtcg agcagctcgg cgcggccaag gcccttgagg tgatcgagac    32880
gaccgacgcc gccgcccggc actacaccct gagcgagtgg ctgcggcact acctcgatca    32940
caagaccggc gtcgaaaagt cgacgatcta cgactacgag aaagttgtcg ccaaggacat    33000
tgacccggcg ctcggcccga tcccgctcgc gcgctgacg ggtgacgaca ttgccaagtg    33060
ggtgcaggcc ctcgccgacc gcggcctcaa gggcaagacg atttccaaca agcacgggtt    33120
tctgtcgtcg gcgctgaacg ccgcagtgcg cgccgggcgc atccccggca acccggccgc    33180
gggcgctcgg ctgccgcgca ccgaaaaggc cgaaatggtg ttcctgacgc gcgagcagta    33240
cgcgaagctg cacgacaaca tcacgctgcc gtggcagccg ctcgtcgagt tcctggtcgc    33300
cagcggcgcc cgttggggcg aagtcgtcgc gctgcgccc tccgacgtca accgcgacgc    33360
cagcacggtg cgcatttccc gtgcatcaaa gcgcacatac gaaaagggca gctacgcgct    33420
cggtgcgccc aaaacgctca agtcgcgccg cacgatcaac gtcgatgcat cggtgctcgg    33480
caagctcgac tattccggcg agtacctgtt tacgaacacg gtcggcaatc cggttcggca    33540
caacaatttc cacgcgaacg tgtggcagcc tgcgctcaag cgcgcgggcc tcgacgtcaa    33600
gcctcgggtg cacgatctgc ggcacacgtg cgcgagctgg ctgattgccg ccggtgttcc    33660
gctgcccgcg atccgcgacc acctgggggca cgagtcgatc aagatcaccg tcgacacgta    33720
cgggcacctc gaccgcagca gcggccagat cgtggcggcg gccatcgctg cgcagctcga    33780
cccggcgcgc ggctgagcgc acacaagcga gccccgaggt gatcgactcg ggctcgttt    33840 gctgcatctg gggcctgctg caggtcagcg gccaattcgt gcgttttgcc ggcggtagct    33900
aggcagcctc tcgctcggcg tcggggcgca ggcgtcggcg atgcgcctcg gcggtgtcct    33960
cccgcagtgc acggcggctg gtgcgggtcg cccgaatcag cccgcgatac ggccgaatct    34020
tcgtccacca cgaccaggcc aggcacgccg aaagcatgac cgtggtcacg tatccacaga    34080
ccgagatcat tgccgtaatg gcgtgctggg tggccatgaa ggcgctcgct agagcgaggg    34140
cgcagcacgc gatgcagaac gccagggcga cgatccagac caccgcaatg cggccctggt    34200
gctcgtcgtg ggcgatgtgc cacaggcagg cgactgccac cgcgagcagg tgcagtgttg    34260
tgtagtagtg cagcgccgtc gctccgacga cgccaatgtc agtggcgggc atgtcgagca    34320
tgttgtggtg cacgctgggc tcgcgcagcg cggggctgct catctgcagc gccagcgtca    34380
caaccggcgt gaggtagagc cacggtgcga cccagcgcgc gaagtacagg cgcacctcgt    34440
cgtcgtcgca cacgcggtgc aacatgctga cggcgatcgc cccggcgctg aataggtaga    34500
gcgtgcggcc gagccagtcc tcaaggtgcc agatcccaat tgcttggtag atggtgcggc    34560
cgagcgtcat tgacgctacg gtgccgcaca gcgccgcgcc gatgagctgc agcagcaggg    34620
ctgaggtgag cagcccctcg tgcaggatgc gaaagctacg ccagcgcaac agaactgccg    34680
caagagctac tacacaaaca atccagcgca gcacgataaa ggcgacagct attgacatag    34740
ccactctttc aagggaaggc gggcggcggc ccgacgatga aactgccgcc actgtaaacc    34800
acccctcgga gtggtgagaa attacaccct agagacttgg aatgtcagtc ctcacttgcc    34860
ttgtcgtcgc ccggcggcgg ggcttcttcg gcgcttcttt cacctcctgc caaccaccc    34920 gtagcgtctg agggtggccg gggcctggcg ccagcccctc ggcgtaggca cggatcgagt    34980
```

```
cgtcactgat gaggttgtac cgggcgagta ggtcgacctc gttgatttcg aggttgcggg   35040
cggctctgat caggttgtcg gccgttatca ggcgccccctc ctcggcttgg ttgtagtagc   35100
gggtgcgtga catttgcagc gcttctagca gttcgcgcag cttgagctgt ctacctacga   35160
ggtagctcag cacggcggcg agtgacttgt cggtgtcgtc gtcggacatg gctcgtggtt   35220
cctgtctctc gatcgagcgg tttgttccct ggcgtgtcac tttagttcag atttcgggac   35280
tgaacaagtc tgtgacctgc ctttatgcac tccttatgca gtcgttagcg tcccgaaacg   35340
tggcagatgt tcccgatttc gggacttttg gtgataccgt ctcacaccgt gcagacaacc   35400
actcatgagc tgaggtggcg gcgcgacaag gtggctaaca ggatgcgccg caacaacatt   35460
caagatcgtg caactttggc aaaaaggatc aacgtcgggc gaacgacgat ttactccact   35520
ttccgcgcgg actggtctgg tgtggcaacg cacacagtgc tggcgcagat cgtcggagaa   35580
ctgggggggct cgctatctga actcgtgtca gttgaggccc gcgcatgacg gccccggcgc   35640
tgacccgtcc gcttgctgag gtcgcggcac tgattccgtg ctctgagcga tggctgaccg   35700
agcaggttcg agccggtcgc gttcccggcc gcaagatcgg ccgccactgg cgcatgacgc   35760
aggccgacgt cgacgccgcc cttgagtcct tccgagtcag ccccgagtcg ggccgcaagt   35820
cggtcgcacc ttccgccgac cggccgatcg cacttacccc tacctcacgc cgtcggacta   35880
ggagccgctg acatgacgat gaccacccgc acccgcaacc tcgccgccgt ggcccggctg   35940
cgcatcgagc tgaacgaggc actgcgcgag cgcaaccagg cccgcagcga gcgcgacgcc   36000
gggcgtcagg tgatcgcaga ccaggccgcc gcgctgcaca gcctcggcga tcagaacgcc   36060
tacctgctgc aggagcgcga cgagctggac acggcgcacc gggcggcgct ggccgacctc   36120
ggcgaggcgc atcgccagct cgctgagcgc gacagcctcg acaacctgat gcaactcgcc   36180
actgcgaccg tcgcggcccc ggcaccactg cacgacgagc cggatatgga gcggttcggc   36240
tgagcttgga ggtggggcgt caaacgggtt tctttcgctg ttttcttccc ccgcaagcgt   36300
ggcccacgac ccgctgacta ctcccggcaa ggtcactgct gcgccccacc tccccacaaa   36360
cgacgcagcc ccgcactagg cggggctggc cgacacaacc aagggatagg agccacttgt   36420
tatgtcgagc aaaatcctag cgcacaagcg ccaggcggcg cgggatcaac ggcacggcga   36480
gcgcctcggc gcgatcgtcg gcgtattcct gctccacgcc acgatgggcg ccgttggcgg   36540
cctcgtcggg gcggcatggg tcggcctcta cctgggggcg ccctggtgat cacgctcaac   36600
cacgacgaaa tgcaggccgc tgcccgcgcc atcgacgcca accaggccga gggcgtgacc   36660
accctcggcg cactggccgc cgcggtggcc gctgtcaaca agctgcgcgc gccggtccgg   36720
tcggccgact gcaccgactg ccagcggtgt gacgccacct gccccggtca cgtcaagacg   36780
caggcggtgt cacggtgacg gccgcgcagc tcggcgaggg cgaggccgct gtgcgccttg   36840
ggattacgcg caatgcactg cgctggcgcc gccgcagcgg cacggcgccc gagcaccagc   36900
tcgtcggccg caaaatcatg tacgacgttg cggcacttga cgagtacgcg accgcggtcg   36960
acaacacgca cgtactcgac atgttcaccc cgcgggttgg cgacacggcg accgctgacg   37020
aggtgtgccg gttgctgcgg attgaccaaa gcgacgtact cggcaaggtt ttgaagcgtc   37080
acggtgacga attggctgct cacggctggg atcgtgaaag tggcacgttc acccgccggg   37140
cgatcattca ggttgcgttg ctggtgcgtt cgtcgacctc ggcgcgtgca ggtcgcatcg   37200
ccaaggccgc caaggcgggc agtcggccga tcagtttcga ccacagcccg cggtcgcagc   37260
agtgcactca cgtgcttgag cgcgcattcg atctggcgac cgaggtacac gacgacgacc   37320
```

| | |
|---|---|
| ccggcgaggt gtgggcacgg ctgcgcaagc tcgaccgtca cgcactgacc ggcgtcgctg | 37380 |
| tcgccctggc cgcgatggtc gacgttgagg gcaccggcgc cacgaagtac ctgcgccacc | 37440 |
| tctcccgcgg cggcctggcg gccgagggtc tgcagcggtt ggtgccgact cgcgagacga | 37500 |
| ccgacggcgt gccgctgtca gtgctcgacc agatcgaggc cgacgacgag gccgaccagc | 37560 |
| aagacgaggg cgaggtggat cagtgagcga cgcagagcat ttcgacgacg accccgaggc | 37620 |
| ttggcgggat aacgccgtat gcgcgcagac cgaccccgaa atcttctttc cagagcaggg | 37680 |
| cggcagcacc cgcgaggcca agcgcatttg cggcggctgc caggtggccg acgagtgtct | 37740 |
| cacgtgggcg ctgagtcagc cggtcaaccc aacgggcatt tggggcggca aaccgaacg | 37800 |
| agcacggcga cgaatcaagc gcggacttaa aggggttgcg gcatgagcgg ttacggcgat | 37860 |
| atgtgcggca gcgcgcagtg cgatgtgtgc ggcaagtacg acgcgcaggt gttcgacccg | 37920 |
| tgcggcgccg cgtggtgccg agtgtgcgac ctgatgggcc tcggcgagct ggcggtgagc | 37980 |
| gagcggctcg acgaaatcgc cgagggtatc ggcaaggcgt tcgacgacac cctgctattc | 38040 |
| ggaatgggca ccgacagttc ggcgaccgag gcgggcgacg ccgaggcatg ggtgccggat | 38100 |
| tacgccggga tcaaccgcaa ttggcgcgag cagtcgggtg agcccaacga cgccgagacc | 38160 |
| ctcgacggcg ccgaccccgc gtacgtgtgg caggacattc tcggcgcgca ctggggctgg | 38220 |
| ctgaatggca gcggttgggt tgcgtggaat agcggcctgt acgtgcaggg ccgcggcgcg | 38280 |
| gttggcccgt tcgggtcgc ataccggcgg ccggtcggcg agttcacccc gatgctgctc | 38340 |
| gacctcggcg gcggcctcgc gttcggctgc gacatggccc gcggccctag caacgacacc | 38400 |
| ggcgtcacgg ataacgcccc gaccagcgca gacagcttgg ccggcaagcc ggtcgagcaa | 38460 |
| acgcccgaca tggtggcgca cccgtcgcac tacacgtcca gccccgccaa gtgccgggcg | 38520 |
| tgtggtcacc caatcgagtg catcgacatc accgagcaca tggggttttg cctcggcaac | 38580 |
| gccaccaaat acgtctggcg ttgcgacctc aagcacgacg caatcgagga cttacgtaag | 38640 |
| gcaattcagt acatcgagtt tgaaatcgcc cggcgcgaag cgctgagcac aaccgaggga | 38700 |
| taggagccca caacatgatt cgcaagattg ccgtcgtcgc caccgcggcg ctgatcgcag | 38760 |
| caggcgctac cgcgtgcgag ggcggcgcgg atggcggcgg cgggcagcag gatagcgggc | 38820 |
| ctagcggcgt gatcttcatg ccgatgccgg gcgttcccgg cgccggtatg ccgatcttct | 38880 |
| tctgaccaac gaccaaccac caaaggggca caaccaaatg tcaatgatca accgtattgc | 38940 |
| cgtcggcatg accgtcggcg cgatcggcgc cgccgcggtg ctgtcgggct gcgccacgac | 39000 |
| caaccaggaa tggcacacgg gttgcaccgt caaggccaag gacattgttt acggcggcag | 39060 |
| cgacggaaac accacgcgca caaagcgcgt cactacgtcg tgcggatcgt tcaacgtcga | 39120 |
| ggacgcgatc gaggtcgggc acttcaactc gtgggacgtc tgggagtccg tcgaggtcgg | 39180 |
| caagacgtac gacatgttca ccggcggccc gcggatcggc tggctgtcga cgttcccggc | 39240 |
| tctgctggaa gtcaagccag cacagtgacc gtcagcaacc ggccgtggtg ggccgaccgc | 39300 |
| gaggtcgtcg aggatctggt cgagcagaag cgtttcgacg cgacgctcgc ctacctcggc | 39360 |
| ggcctcgccg acgcaatcga gcaccggatc gcctacggcg ttgacgatcc ggcggcggcc | 39420 |
| gccagctcgg cgctgcgcaa cctgcgcgag attcaccgct ggccggttga gttcgcggtc | 39480 |
| acgtggggcg gcgactcgct cacgcggccg atgctcgtca ccccgttgga gcgtcagcgc | 39540 |
| gaactgacca gcggcctaga caacgtgccg agggttcggg acatggccgc caagatcgac | 39600 |
| cgccgcgaaa ttctgcgccg caggcggcag taactgaaag gggataggta agtggatatt | 39660 |
| tcagcggtaa agggtcacgt cgacctgctc gcgcacgcgc ggatcgagaa aaagaagtgg | 39720 |

```
gaggaaatcg aaaagaacgc caaggcggcg atcgacgagg cgctcggcag tgacgacgag   39780
ggcaccgtcg gcggcgaggt tgtcgtcaag cgttcgcgca ccaaggtgac ccggctcagc   39840
ggcaagttgg tgcaatcgct gcaccccgag gtttacgccg agtgcctcga caccaacgag   39900
cagacgcgcc tgtcggtggt gagcaagtga agatcgccga gacgcaccac accacgatca   39960
ctgtcgagcc cggcgacaag gtgcgcgatc tgtgcgaggc gctcaacaag ctgccgaacg   40020
gcgccgaaat cagcgtgtac gcaccgctgc cgatgttcaa caccgacccg accgcaaacc   40080
agtacgccgg gttgatcagc gtcgatcacc tgagcacaac caagggatag gagcccaagc   40140
atggcaaggc aattgatcgt ggtcgacctg gaaacaacca gcctcgacta cgacaccgcg   40200
gccccgttgg aggtcgccct gctcaacgtc gacaccggcg agtcgctgcg gttcgtgccg   40260
cacgtgacgt gcgagcagct cggcgcggcc gacccgaagg cgatggaaat caacgggtac   40320
tacgagcgcg gcgtgtggcg tgaggcgctg accgaacatc agacggccgt cgcgtggtcc   40380
gaggtgaagg actggctgcg cgacaacacg tttgcgggca gtaacccggc gttcgactcg   40440
gcgatcgtcg cccggcaggc cgccggtggc atgttcccgg cgccgatcgg ccgcgtgtgg   40500
catcaccggc tcgctgacct ggcggcgtac tcggcgggca agctcgaccg cgatccggcc   40560
gagctggtgg gcctcgacga cgtggccgag cgcctgggcg tgcaggtcgc gcagcggcac   40620
accgcaattg gcgacgcggc agcgacgggg ctgtgcttcg acctgctgcg taacaccagg   40680
gcggcggcac tctgatggcg ttcaactggg cagggcagcg gatcgagccg ggcgcgatcg   40740
tgtggcgcgg cggccgtgac ggaaacacaa gcagtttcaa ggttggtcgc gtcgaggccg   40800
tcgacaggac ggcgcgcgtc cggtgggtcg ctgagatgga ttggcgcggc aacgtgcgtc   40860
tgctcggcga gaagtcgatc gggcggccga acatcgacag cctggcgttg atcgacctgg   40920
cgacattgag caacaaggtg cgggaggcat tgcagcagtg agtaacaaca atttcgtgca   40980
cgtaggcaag gtgaccgtgc cgaccagggc ctcgtggcgt gtgaaggccg tcgaggatgt   41040
cgagattgtc gtcggcgtgc gcgccgacct cggcgaggtg gtcgtttcga tcgacggtca   41100
gcgcaacggc gccctgccgt cactgaccgg cccgcaggcg tctgcgctgg ccagctgct   41160
cgacctggcc gcgggttccg ctgcctcgct gtctgaggcg taccagacct atcaggcgac   41220
gctgcagcag gccgaggcca acctcgaaaa ggcgttcact cgggaggcga gcgcatgaag   41280
gtgagtcttg cgctgaccgt gctcggctgc cacctgggca cgctcgacgt cgaggtcgac   41340
ggcgacgacg acgccacggc ccccgcggcg ccggtgaagg cggcagcgaa gccggtcaag   41400
tggatgagtc gactgtggtt taaggggatg acggcgtgag cggcaatgca gcgttttcg   41460
ggctgaccga cgacgccccc gagcgggatc ggccgccgac cgacgagcag cagttcaacg   41520
ccgacctgct ggccgacctc aagggcgtgt ttaaacgcgc gtgggcgcag cacggccggt   41580
cgctgcagcg tgcgctcggg ccgtcggaga ttgggcaccc gtgcccgcgg cggctggcgt   41640
cgtcgatgct tgagctgcct cggattaacc ccgaggcga cccgctgccc gcgtggctcg   41700
gcactgccgg gcatacgaag tttgaggatg cggtcaacct cgacaacgag cggattatcg   41760
accagtggct caaggaccgc gagcagcgtt gtacggtgct gcgcggcgtc gctgggggcg   41820
atgacccgca gtatgtcggc cggtggttca ctgagcggcg ggttacggtg cgcggcggcc   41880
tgtctggcac gtgcgacctc tacgacacgt ggactgacac cgtgattgac ctcaagtttc   41940
cgggggcgtc gcggttcgct gagtacaaga aattcggccc ggtcgaaaag gcccccgagt   42000
atcgagtgca ggcgcacgcc tacggccgcg ggtaccaaaa cgagggggttc ccggtcaagc   42060
```

```
gggtggcgat ctggtttatc ccccgcggcg gcaccctgtc ggcgtcgttc gtgtggtccg    42120
agccgtacaa caacggaatc attgacgggg cgctcgtcaa cctcgacaac attctcgtgg    42180
cgctcgacga gctgcaggtc gacaagtacc ccgagcggat cgccctcgtg ccgaaggtgc    42240
cgagtaactg catgttctgc ccgttcttct caccggacgg caggcgcccc gaggtgcacg    42300
cctgcgcggg tggtgcgcag tgaagccccc cgcgccctgg cgtatccgcc agctcgtcga    42360
gcaggtgccc gtcggcgact tcgatagcac agtgacgcgg cagacggtcg tcgtcgggtg    42420
ggtcgtcgag cagttgaccc tgtacacgtt cacgcccggc tcggttgagg gcgagtacgt    42480
cactgtcgac tacttcccga acggcccggc cgcgatcgac gcatttgccg gatacggcag    42540
tttggcgatc tgacatgcac ggatgcgatt ttgccggcgg tagctggcag gggataggag    42600
cccacaccat gagcagcgag gcaggtcagt gagcgcgggt ctgcggtcga cattcaccgc    42660
gaagtatttc ggccgatgcg gcggctgccc gagccagatc cgacccggcg aggaggtggc    42720
gtttatggct gacggcggcc ttatacatgt tgattgcgag gcaactcgc acgagcccgt    42780 aaacgcccgc aagcggccga catgcccgca ctgctggctt gaacacgcag gagattgccc    42840
gtaatgagtt cgcaccgttg cacaggtgac gactgcggga tctgtgcgca acggatcgaa    42900
caggccgagt atgaccgcga ctgcccggcc gacgactatc ccgactacta cgacgggaca    42960
tgagcccccc gccgcgcctg gcgggccgag agggaaacgg gcgcaacgca ataacggaac    43020
aactgaacaa aggaacaact gaacaatgag caacgactcg tacgacttcc tcggcggcgg    43080
cggcgtccca tccggcaagt tcggcagccc cggcgacacc gtgggcggcg taatcgccat    43140
cgagcccgag caacggcaga tgaccgacta caagaccggc gacctgctga cctggaagga    43200
cggcagcccg cgtatgcagc tcgtcgtcac cctgcagacc gatctgcgcg accccgaggt    43260
cgaggacgac gacggcaagc gtcgcctgtt cgtcaagggc gaaatgcgca aggccgttca    43320
gaaggccgtc atttcggccg gtgcccgcgg cctggacgtc ggcggcgagc tgcacgtcac    43380
ctacaccggc gacggcgaca agaagggcaa cctggacccg ccgaagctgt acagcgccac    43440
ctacaagaag cccgcaccgg gcgcagcccc ggcggccccc gcgcaggccg acccgacagc    43500
gggcatgacg cccgaggcgc tggccgcact cgctgcactg ctgccacaga gtaagcgcca    43560
caacgcgctg cgagccggtg acgttccgca acggggcgtt accggctcgc tctgtctaac    43620
aagccatttc gacgagggat aggagcccac cgaaaaatgc tgacgatcta caccacaggc    43680
cccgagtgct acaagtgcaa cctgacaaag gacaggttcg acagggcggg cgttgcctac    43740
accgaggtgc gcctcgacca ggccgacgag gctgtcactg cgaaattcgt cgccgccggg    43800
cacgctcacg ccccggtcgt cgtcgacgag ctgaccaatg tcatgtggtc ggacttccgg    43860
cacgacatga tcaaggccgc gatcaaggcc cgcgcgtagt gaacggcgca gaactgttcg    43920
accgcatcgc cctgacccga gccgacggcc gctgtgagtg cgaaggcgct tgcggcagta    43980
accatcggtt cgccggtcac acccgctgcg gcaacgtgca cggccgcccg gcgattcatg    44040
gcgccgacaa ggtggtcagc ctcactgtgg tgccacgcaa cggcgacggc cggaatctcg    44100
ccgacggcaa cctgattgcg ttctgccagg cgtgccttaa gcggcaccgc gccaagctca    44160
aggccgccgc ggacaaggct gcagcccgcg cggcggccga ggctgcagac ggcgggctgt    44220
tcgacgtgcc cgacgtcccg gtcattgcag gcaatggcgt cacgctgtga acgcgcgagc    44280
agccttgtcc cacaactgaa tagaggaatg agtgaacggc ctaactgatc tgctcgaact    44340
gctcggctac gccgacggcg agcacgtgag cctcaactac caggcgcccg gcggcccgtt    44400
ctcgtcgacg gtcgtcgagt accaagagga cagcgacagc ctgcagggcc tcgcaatgtc    44460
```

```
gctcgccaac ggccgcaact gctggtttgg cgtcaacccg acgctaccgc ggccggtcga   44520
cgccgacggc aagcagaagg gccgcggcgg ggccgacgag gtgacccggc tcgctgcgat   44580
ctggtgcgac ctcgacgtca agccgggcgc ctgccgcgac attgcgcacg cccaccaggt   44640
gatcgacgag ctgagcgcaa ttctcggcac ccggccgagc gcagtcgtgt acagcggcaa   44700
cggcctacag ccgtattggc cgatcgacga cggcacgatc gccccggccg agccggtcgg   44760
cgacctcgac gagcagacga tcgccgcgag cgccgagctg cgccgccgacg cggcggccct   44820 actcaagcgg tggggccgcc tggcgtgcat cgtcgccgac ggcctgggcg ccaagatcga   44880
ccgaggcgtc tacgacctcg cccgcgtgct gcgcgtgccc ggctcgcaca acctcaagga   44940
caccgacaac ccgaagcccg tcacgatcga cggcgacacc ggcgccccgc tgggcctcga   45000
cgagctacgc gagcgcctcg acgagcacgg cgtcgccgaa tacgagggcg accgacgcac   45060
ctcgcacgag gtgatcagca agcccgacgg ctggacgttc gcgccgagca cctgcgagta   45120
tttcgcgccg acgatcaggg cgtggcgcga ggagccgatc accgagcggc acccgtggct   45180
ggtcaaggtc accgtgcggc tgatggcagc ggttcgcaac aagtgcctga cggccgacga   45240
gtacgccgag gcccgcaaga tgatcgtcga caagttcatg gccgagtgcg cggcgactgg   45300
ccgcgacgtg ccgagtttcg agattccgaa cgcattttcg tgggccgagc accacgtcgc   45360
caccaagaca gacgccgagc tggcgaccga gttcggctcg cacctgcacc tgtggcagcg   45420
cgccgagccc cggcagatcg agcttgcgcc tatgcccggc gtcgacgacc gacagcaaac   45480
cgccggcatt ggtgccgagg gtgttagctc agagggatca ttggccccgg tcgtggatat   45540
taacgcccgg cgcaatccgg ttgccccggc ggtcacgctg accgacaccg gcaacgccga   45600
tctgctcgtc gaggcgtggg gcgcccggct gcggtactgc cccgacacgg gcaagtggct   45660
gagctggaag ggcacccgct gggagcacgg caccgaccag ggcgaggcga tcgtcgccgc   45720
gcgccaggtg gtcgaggcga tcaagctcga cgacgacagc ccgaaagacg ttatccagca   45780
ccgtatgcgc agcctgtcgc gcaagggact tgagaacatg gtcgcgctcg ccaagtgctc   45840
gcccgacatg cgggtgcgcc tggccgacct cgacgccgag ccgtacgagc tgaacacgcc   45900
gagcggcgtc gtcgacctgc gcaccgggca cctgctgcca cacagcccg acgggtggca   45960 tacgaagatc accggcgccg ggtataaccc tgccgcggtg gccccggcct ggcagaagtt   46020
ccttgctggc acgttcggcg acgacgtgga actgatcggg tatgtgcagc gcctcgccgg   46080
gctcgccgcg atcggcaagg tgacgcacca cgtgctgccg ttcctgttcg gcggcgggtc   46140
gaacggtaag agcgtgctca tggacgtgct cgcaaacgtg ttgggcgact atgcgatcac   46200
ggccccggcc aacttcctgc tggctggccg cgatcggcac gagacggaga tcgcccggct   46260
gcacggcgcc gcatggtcg tgtgctcgga aatcaacgct gagagcaagt tcgacgaggc   46320
caaggtcaag gtgctgacgg gtggcgacat tctatctggc cgctacatga ggcaggacta   46380
tttcgacttc accccatcgc acacgctgtt tctgatggga aaccatcagc ccaagtcag   46440 cgcgggcggt acatcgttct ggcggcggct gcgcctgttg ccgttcctgc atacggtccc   46500
gccggagcag cgtaacccca acctcgccgc tgagctgatc cgcgacgagg cgccgccat   46560 cctggcttgg gtcgtggcgg gggcgcgtca aatcgccgct gacggcctcc gcgagccggg   46620
ctcggtgttg gctgccacca aggagtacag cgagcaggag gacgctctgg ggcggtttat   46680
ctcggagtgc tgcgagctga cgccgggcgc cagcggcggg gctaaaccgg ccctggtgtt   46740
gaaggcgtat cagcgctggg ccatgtccaa cggcgaggac gcgatggtgt ctcagatcaa   46800
```

```
gctcgggcgc gagctgtcgg ctcggttcgg ggtccgcagc gtggcgatca atggggcgcg   46860
cgtgtatgcg ggccttgccc tgcaagcttc ctgggacttg gcgcacgagc tggcgggcgg   46920
gttccgctga tgctgcggtg gccctcgcaa gcgacggcgc tagctaacgg tttcaaatct   46980
gtgctgaaag cgtgctgcgc agcacagata gcacagatca gcacagatcg tttttttcaaa  47040
agtgtgctga tgtttgcgca ggtaaaagct gttaagtacg tgtacagcac agatagcaca   47100
gattttacg  ggttgacgtc acgtgtagag aatcggggcg ttttttcctgg tcgactctcg   47160
ccgggcgctc ggtgtgagcc ttatatggga aaaagtgtgc tatctgtgct gaccctgccc   47220
gcagctaact tggaaacgcg ccccgccgta gcggggggcct ggccgggcgc tgacaggcgt   47280
cgttgacggt ttctgccgtg agaatgctgc tcgaccacaa ctgaatatgg agaaacgagt   47340
gactgaccac actctcgacc tcgggcttgc cgccgaccag gtggccgccg ccgaggctgc   47400
cgagcgggcc gagctgcacg ccaaggctga ggctgccgag ctggtgctcg acatgctgcc   47460
cgccgagtcg cacgaggccc tgtatgcggc cctgagtgcc cgtgtgacgc acgagcgcaa   47520
cggaggcagg cagttgcgcc tgttcgtgcc gggcaagcct gcgccgcagg gatcgaagga   47580
cttcaagggg tttgcgaagc cgaggccggg cgagacgcgc ggtaaggcga tcctcgtcga   47640
gtcgagcgca gcggttgggc cgtggcgcga gcgtatcgcc ctggctgcgg ccgacgcgat   47700
gctcgccgct gggttgccgg tgctcggcaa gaaattcccg tgcacggcgt cgctgacgtt   47760
cgtcatgcct cgcccgtcgg gcacgcccaa gagctacacg cccgcggctg tgaagcgccc   47820
cgacctcgac aagctggctc gcgccgtgct ggacggcctg actgatgttg cctggcttga   47880
cgattcgcag gtcgatgaca tgcattgccg caaggtgttg gctgcgatcg ctcagcagcc   47940
gggtgtgcat atccggctgg cgtcgccggg ttggggcgat gcggctatcg ctgagtggat   48000
ggctgcgaac gctgcgggtg gtgtcgagca tgtctgatct gatcgagttg tcggtcgccg   48060
aggtcgacaa gatggccgag gttgtcgctg cacgcatttc gcatccgtcg catacgcctg   48120
ctcgggcgat ccgcgcgggg ctgtcggctg tgaacgcgat gcgtctggat ggtgcgcagg   48180
tgccgcgggt ggagttggtg caggagcgcc gggcgcctgg cacgatgccg cgcccgatcg   48240
aggcacgtcg cccgttggcg ccggtgcccg ccggtaagcg ccgtgtgtcg catctgggga   48300
tggctgagcg gccgtttgtg tgggaggacg ccgacggcga tcaatggcgt tggtgcttca   48360
tgcaatcggt gtggcagtac aagcagttcg acgatccgaa cggcccgcag tgggtgaact   48420
gcccgagtaa ttacgccgac caggcgccga atccaaacta tggaccgttc acggaggttg   48480
gccgcgcatg aggtacagcg agaacgtcgg ccgcgtgtac gggtcggctg aggccctgtt   48540
gcgggcgcgg attgcggccc tcgacactga gattgcttgg cgtaaggaca ctctggcgca   48600
gcgtgagcgc atggtggccg acgatcgggc agacatcaac gcaatggttg gcgagcgtgc   48660
ctcgctggcg cgggcggtgc ggcagctatg agtttgccgg attctccgag tttcggcgat   48720
ccgcgcaggt caaccggcac gccggtgatt tcgccggccg ttagccacgg cctgagttat   48780
tacgggtcgc cgcggccgtc tggtccgtct gagttggacg tggagactgc gccgtcggtg   48840
cctgagtcgc tggggcgttg cttgcattgt tcggcgcctg cgcagacgtt tctgtgttgg   48900
tcgtgtgtgg gcatgttgcg ccgccagctc gtcgaggtgc cttggctgtt gcgtcgtctg   48960
caggagtcgg cgtatggcga ggcgaaggtc gcccgtaagg gtgggcctcg ggtgtcgacg   49020
ggggagcggt tgccgtcgtt gccgttgaac actcgcgcgg ccgacatgct gcgcgacgct   49080
gcgcgtctgt tgtcgtggcg ggagcaggtg agtggcgtcg atcagggcgg cccgcatgat   49140
gctgcgcgtg tcgagtccgc ggcccgctgg ctgtcggccg agccgggcgc gatgatggcg   49200
```

```
cacccgtggg cgcccgacgc gctgggttgg gtgttgcagt ggcgccagga tgctgagcgt   49260
gtgatcgact tgccgccgga tacgcagtac gccgggccgt gtcagaacgt cgtgcagccg   49320
ccgagtgcat ccgacgccgg tacgccgctg ccaccgcggg agtgcggcac gccgctgtat   49380
gtcgacgctg aggccctggt cgccgagtgc taccgctgcg gctgctcgtg gcgggttgag   49440
gatctgcagc gccaggccct cgatcgcatc gacgaggccg cgccccgcac ggccgccgat   49500
atgtggcggc tgctcaagtt cgcgggccga gacgtcaagc ggtcgacgtt ttacaagctg   49560
atgacgaccg ttgaggcgca cagctatgac gccgacgggt cgccggtgta catgtaccgc   49620
aaggtggttg acgcgctcga cgctgccgat cggaaggtcg ccgagcgcca agctgccgcc   49680
gcagcccggc aggccgccgt gctcgatgcc cacgattcag gtatggcgcc gtcgacgatc   49740
gcccgcacgt tgcgcatggg acacgctgca gtgaaacgca ttttgaccag tgcgggtgtt   49800
gacgcgcata cagaaggtgt tgacgtgcag acagtcgagg cgttaccgtc tgcgccgaag   49860
caagtcacgg gataggagcc cttgcagatg tacacagaaa cgtggttctc accgccggt   49920
acgccggtga cgccgaaggt tcgcaacgag gtcgacgagg cgcagctcgc tgagctgtat   49980
gccgccgagg tgtcgccgga tagcgtgcgg ttcaacgagc tgtacaacgc cgccagcacg   50040
gcgacgctgt acgcctggcg ttacgggtac cgcaatccgc gcgtggcggg tcgcgtcgag   50100
gaatgcgagg cgctggcgtg aagcaggtca aggcggttcg ccgcccggcg ccggtcgccc   50160
cgcagcccga cgttgtggtg catggccgca cgttggagcc gggcacagag gtgtcgatcc   50220
gcggcgagcg tggccggttc cgtttccgca gtgcgtcgtt gacgagtacc ggccggatcg   50280
tgtgcgactt catcggcggc cctgctgggc acgagacttg gcggtcgttc tatcccgacc   50340
gtatccgcac ggtgcaccgt ttgaaccgca cccgcgcgaa cgccgcctag cggcattgac   50400
gccctcgaca ctggtcgggg gcgtttctgc tttcatgttg acatgcatac agcacgcggg   50460
ttactgtatg cataccaaca acgcgctgac cacctaccga taggagccca caatgtcgaa   50520
catcatcgcc gccgccccg ccgccggtcg tttcaacgcc actgccgccc tgaatctgat   50580
tctcggtatc aacctgaccg acgggcagaa gcgtgcacgc ctgctcgcgc tggcggtgtc   50640
gaatgacgct gcctgcgagt tcaacctgcg cgccggtcgc aaggccgtgg ccgccgggcg   50700
tctcagccag gcgagcgact acgccgacgc tgcggagttc tacaacaacc gcgctgcacg   50760
cctgcgcgcc gaggcccgcg ctatctagcg cgcccggcgc gtcgccgcgc aaaggtcacc   50820
ccggcgcctc gtgcgccccc agaatcgccg atcgagggat aggagcccac gaacgtgaat   50880
cgtcacctgt acacgcaacc tgaactgttc gacgccgacg ccgacgcccg gcagttcgac   50940
gtttacgagc gccctgacgg ctcgcgctac cgcgttgagc gccccgctgc ggcggtggcc   51000
ctgtgagcgc cgctctgacg ccgcgagagt cggcgcaaag gtatttccgc ggctggctgg   51060
ccgccggtgt cgtgacgtcg attctgggca acgctgcgca cgcgctgctc gaccctgacg   51120
ccgggtctaa gttcatcgct gccgcggtgg ccgtcctgct gccgctcggc attctcgggt   51180
cgacgcacgg cgtgcataag ctcgtcgcgg ccgggatcgt tggccgcgca tacaccgcgg   51240
cgctgagcat ttcggtgacc gtcgtcgctg cggcgttcct gctgtcgttc gcggcgctcg   51300
ccgagctggc tgtcgactgg gctggtatct cggtgtggct gtgctggctg gtgccggtgt   51360
tcattgatct gagcatcgcc gggtgcaccg tagcactgtt cgcgctgtcg ggtgcggagc   51420
gtggcgaggt gctcgacgct gcggtgcacg tcgctgcgca ggtggtgcac cctgctcgcg   51480
agcctgtgca cgctgttgcg cagcccgctg acctgcatgt tcctttgccg gccgaattgc   51540
```

```
agcccgatac gcacctcgtg gcgcgtgagg ccgacggcct ggtgcacgtg ttcgaggagt    51600
cggtgcacga tccggcgccc ggcggtgtca gtgtcgccga tctgatcgcc cgcgaggctg    51660
cgaccagcaa cgcgctggct gcgcacttgt ccgcggccga ggcgatcctc gacgccggtg    51720
tgacgcgcat tgatcgcgtc aaggtcgccg aggtgctcgc cgagcatgac gccgacgtta    51780
agccgagcat gatcgcgcgc aagctgggcg tcgggtacag caccgtggtg cgcattctcg    51840
accatcacac tgcgcaggac gatgcacagg ccgaggtcga tgcggaggtg ctcgcgtcgt    51900
gagcgtcgca gcgcagtacc cggcgcgcac cgatacgaac ggccgcacgt ggtggcgccc    51960
ggtgcgcccg gcgggcactg atctgtcgca gtggggttgg acgtcggacc cggcgcaggc    52020
gcaccccgac tatgacgcgc tgagcacgtg cacgtgcccg tacgtcgacc cgtcgctgtg    52080
gacgacgcat tacggcgccg tggagcccgg cagcgcgcag gagcacaacc cgttgtgtcc    52140
ggtgcatacc gcgacgctcg tcgacctcgt ggtcgcgcgt gaggcccgg tggtcgccgc    52200
cgcggtcgag cgtgccgagg tgttcggcga tgcgtgggcg gccgtgttcg agttgtcggg    52260
cggtggccgt gcgatcgtgc cgattgaccc gccgccggtt gagccgctcg gcgagcttgg    52320
ccccgagtgg gtcgagttgg ggtatgtgga tgagacgcaa gggggtttgt ggtgatgggg    52380
cacgagcatg agggctggca gattcagccg agcgcctcgg gtggttggta ctgcgcggcg    52440
tgcggcgagg ctgtctcggg gccgccggtg ttgcgtacgg cgccgttccc gcactatcac    52500
gccccggcggg ctgctcgggt gctcggccgtc ggcctggccg tcgtcgaggc gatggccgcc    52560
gcgggcaagg tccgtgcggt gcgcgtggaa gacgggcaag gcggctgggt gtgggcggtc    52620
gacgcgctgc gggtcgacga gctggtcgag gccaatgcac gcacgggcct gcatccgtac    52680
tgggcgtgtg gctttgccca cggctgcaac ggttgtgtca gcgagggtga gggcgcctga    52740
tgttgagcgt gtcgccgggt atggacgtgg cccggcagcg ccgcaagttc attggtcgaa    52800
tactcgccga ggacgacgac cacgccgccg cgtacctcgt ctggctgctg tctctgtttg    52860
acgccgcggt ggccgccggt acgccgcgcc ctgcgagcga gtttctgccg atgtttcaag    52920
aggagtttga ccgatgaggc tttgcactgt gtgcgctcga ccgtcgttga ccgattgccg    52980
ctgtggcggt gagctgacgc cgggcgacaa gctcgcccctg atcgagtcgt ggatgcaccc    53040
cggcctatgg tcggcactcg acggccgccg caacgcaatc ctgcggattc tcaacggcga    53100
gagcgtgacc ccgccggatt gggcggtaac tgaccgctg ccctgaccgg cgcgacacgc    53160
cgacacgacg cccccgctga aaggtcaagc gggggcgttg ttgtgtgttt ggctcaatgt    53220
gtctgaccaa caactaaata gcgggatagg agtacgtgtg tcacctacac gtgtcaatga    53280
gcgcctgatc aactttgcga gcgaggtcga cgaccagacg cttgcgcagg cgcagcagat    53340
cgccgatctg cctttcgttt atccgcatgt ggcgctgatg cctgatgcgc atttcggtaa    53400
gggcagcagt gtcggcacgg tgatcccgac cgagggcgct gtgatcccgg cggccgtcgg    53460
cgtcgatatt ggctgcggca tgatcgcagc ccgcaccacg tacacggcga acgatcttga    53520
gggcctcaag ctgtcggatc tgcgggagtc gatcgagtcc gctatcccga tgagcgccgg    53580
gggatacaac aagagcctga accgttttga gttcaccggc gcccggctgg actggctgca    53640
gctcgtcgct acccggttcg acgtcgacct gtctcactcc ccgaagtggc gggagcagct    53700
cggcacgctg ggcggcggca atcacttcat cgagctgtgc ctcgaccacc tcgaccgcgt    53760
gtggttgttc ctgcactccg gttcgcgtgg cgtcggtaac aagatcgcgc agaagcacat    53820
tcaggccgcg cagggctatt gcctcgccaa tgggctgcac gtgccacaca aggatctggc    53880
gtacctcgtc gagggcacgg tcgagttcga ccgctacctc gttgaattac gttgggcgca    53940
```

```
gcggtttgcg tactacaacc gcgccgaaat gatggaccga ttcgagcagg cgttccgcca    54000
ttgggtcggc gccgaccagg gcgccgagct ggtcgtcgag accatcaacg cgcaccacaa    54060
ctacacgcag aaggagcggc acggcgaccg tgacgtgtgg ttgacccgta agggtgcgat    54120
cgacgcgaac gagggtgtgc ggggcctgat tccgggctcg atgggcacct gttcgtatgt    54180
cgtgaccggc aagggcaatc ccgaggcgtt gtgctcggcg ccgcacggtg cgggccgccg    54240
gttctcgcgc acgaaggcac gcaagctgtt cacggtcgac gacctcgaag cgcgtatgac    54300
gggcatcgag taccgcaagg gcgaggcgtg ggtcgatgag attcccgacg cttacaagcc    54360
gatcgacgtt gtgatgcacg acgccgaaac gctggtgtcg gtggatgccg agctgcgcca    54420
gctcttgaac gtcaaggggc agtgatgtcg gacgatcgca acgcgcacag cttgctgttg    54480
ttgtcacgct ggcggcaggg cggcaagacc acggccctgc tcgacctcgc gctcgccaac    54540
gctcgccgtg ggcttgaggt ggtgttctgg tcgggctcgg cccgccagtg cacggaggcg    54600
tttcggatgg gccggtcgct cgctgagcgt gaccgtgtgc cgttctcgtg gtcgcccgcc    54660
aatggcaatg agtggattcg ctacgacggc ggcggccgtg tgcggttcat ctgggggcac    54720
cagggcagcc gggtcgacgc tcacgtcgac atggcaattc aagacgacaa cgggctcacg    54780
ggcctgatcg agcggcgcag cgagcgccga ggaatgagcg tgacctgatg gctgactact    54840
catacgcgcc gggcggttac gtgacggccg acgagccgat cgccagcttt accgccgagg    54900
gtgaggacaa ggcgctgcac ccgtggcagg tgcagtcgat tcacacgctg cggcaggggc    54960
gtcgagaggt gtcgttctcg ctgcagttcc cgcggcagcc gcagaccgga atgccgttgt    55020
ggctggcgca gttgttcggc gtgacgctgg ccccggcgcc gccgacggtg cgcgaggctg    55080
cggtcgacgt gtgggacgcg ctgcgcgtgc tgctgggcct cgtgtgggcg accgtgcggg    55140
gcgctgtgac cgcggcggcc gatcgtgtgg gcgatcggtg gtttggcgtc gtgtacggcg    55200
ttctcgaccg ctgggacgtg ctgcgcgggt ggggttggcg tcgccagctc gtcgggccga    55260
tcgtgcggct gtggagcgcg tcgtttgtgt accagtacac gatgcctcgt cggcgtgaga    55320
cgtggcgtga gtggctgcgg cggcaggctg gtctgccgtt ggcggtgtgg cgtgggtagt    55380
acgccggtga tgttcctcga cgggccgctc gctggtcgca cccgcgaagc gtgggcgcac    55440
cccgacggtt cgccggggcc tgtgtactgc gcgcttgagt cggtcagctt cgactcaccc    55500
gactggcctg cccgcagggt cacgtatcag atcaagcgca accggctgag ctacggcccg    55560
caatgggtcg gggcgatcgg cgataaggtc ggcgagcaga tcgtcacggt gctgccgtac    55620
gacgagcgag cccggcacgc cgtcggcgtc gacgagttcg aggagtacat cacccgcaac    55680
gcctaccaga gcgcgcagcg gcacgcccag ggcgagggcc tggtcgccgt tgaggtgcac    55740
gaggtttggc gcggcacgca agccgaggcc cgcgagcaga tggtgcgcga gggtaagcca    55800
gtgaagggcg ccccggcgtt cctcgacgcc gacggcccgg tgttcctcga ctcgaccgtg    55860
ttcgtcgtgc acgaggctgt ggcggtcccg aaagatcagg cgcgggaggt gattctgtga    55920
ctgacaccgg caccccgctg gacgacttga cgcccgagca ggccgagcgt ctcacgcggt    55980
cgctgcggcg gttcaacgag gcgatggggc ggcagctcga ccacgcccgg caagagttgg    56040
accgtgaccg gctgcggcgg ctgttcggca ccagctaacg ccggcaaagg tcgccggcct    56100
ggccgttgtc gcaggtagtt gcggtgcggg tctggaagtt ggcaaacgcc cttcgggtaa    56160
tcctcggggg gcgttctgct ttccatgttg acgcacatac aaccgatgtg tttgcatatc    56220
aacacacacc acgggatagg agccccaaat gttcacgatg attgtgcaga tgcatggccg    56280
```

```
ccaagaggtc accgagcacg ccacgatcgc cgaggcacgc aagcgcctgg tcgacattgc    56340
cgtcgccagc cactcgcgta tcgagggcga cgacaccacg ggcgagttca tcgcgctgac    56400
ccgcgagggc agcgacaacc cgctcgtgga ctggacgtat ggcgcctacc ggatcacaga    56460
ggagcctgcc actttcgtgc cgctgtccgg cggcgaggtc gaggcgttgt tccccggtaa    56520
cgccgagtac gtcgctgtgc tcatcgcgca cgccgtgcgc aacgacggcg agccgcaggt    56580
gcggggctgc gagctgtgcc gcgagtcgct gcggttgtgg ctggccgccg aaactgactg    56640
gcgcaccgtg cgggccgccc acgaggccga gcgcgcactc gcggcggcta cggcgcggta    56700
catgatcgac gagaacctcg acgccgacac ggtgcagatg atccgcaaca gcgaccgcga    56760
cgggcgcggc ctgctcgccg tgattgtggc cgagtggctc aagctgcacc ccgagctgtc    56820
cgaccgggat cggcacgcgg tgactgcggc ggcccacggg tggcagcgtt tcgacacggg    56880
cgacggggcg ccggtgcggt acgcccgtga gggcgaggaa gctgtgatta tcgactatcg    56940
aggtggggcg ctgcgcatcg ctgagcgttg gatctgccgg gtggtcgacg cggtggttat    57000
tgcgggcgac cccgacgacg accaggccga cgttgacagg tggctcgcgg cggcccctgt    57060
gccgctctga gagcttcaaa caggtgaagg aaagggataa catggcgacc atgacaatta    57120
cgaggtacac ggcggttgtg acgcccggcg agcagtacgc gctgattcac gtgcctgaga    57180
tcgaccagtg gacgcaggcc cgcagcgacg acgagatcgt gccgatggcg cgggatctga    57240
tcgcaacgtg gcttgatgtg ccggtcgagt cgatcgaggt tgtggtgcag cgaggctgac    57300
gccgtagcga cggggcgccc ctgagtcatt gcgactcggg ggcgctttgt tgttgacatg    57360
catacagcgc tggtgttact gtatgcatgt caacaactca acaggatag gagccccaaa    57420 atgccgaagc gcaacgaggt catcaccaag atccgcaagg cggccaaggc caagggactg    57480
aaattcaagt cggttcgcaa gggtgcgaat cacgagattt tcgacctcga cggcgtaatg    57540
gttccgatcg ggaatcactc gatcttggac ggttacctgg tactcaagat ttacaaagag    57600
tgcgagccga agctaggcaa aggctggtgg cgataaccac agcgacgacg ccctcgacca    57660
catggtcggg ggcgttttcg ttcctgtgtt gacatgcata cagtcacgag gctattgtat    57720
gtacatcaac agcgcgagcg gttgagattg acaactcaag agtgacagtg gataggagcc    57780
cacgatgaac gatttctaca ttccgcgttt cctctcgccg agctgctcgt ttacctacga    57840
cgaactcggt aaggccctcg ccaagctgca gccgcgcctg aacgaagcga ctgaggcatg    57900
gctcgccgcc aagcgagacc acggcagcga gagccccgaa gaacacgccc tctggcccga    57960
gcttgaccgg ctggaaatgg ctaaggcccg catcctgcgc gaggctaatc gcctcgacaa    58020
gatcaacggc ctggccgccg cgatgccgct ctaaccgact gcgccccgcc gggccgacca    58080
caccggcggg gcgttttgta tgtacgcata cagtcgtgct actgtatgta tagcaacaac    58140
gcgaacggga taggagccca aaatgagcaa gtcaatcgca gaccgcaagg ccgccctgct    58200
cgcccgcacg agcacgccag tgctgctgca gtcggccgag acgctggaag cgatcgaggc    58260
gccgaccgcc gagcagcgca tggttcgcgc ctggacgctc gacgagcttg agcgccgagt    58320
tggcccgatc acgctcgacg aggaacccga gtttgagcgg gtctatgacg aaacgggcaa    58380
ctacttgacc gcgctcaagg cgctgcgccc ggcgctcggc gagtagctgc ctcactcgac    58440 aaaaccctg ctacggcggg ggttttcctc gttcttccgc gatcttccgc atattgccgc    58500
atatgtggcg agattggcgc gcgtcgcttt tagactgcca tccgcaacag cacagctgta    58560
cccaaaacgg ccccggcgct ccgaaatgga gtgttgggcg cgttcccatt ccaggcgttg    58620
accagcgttg cgcggcctcc tatccccgcg ccctggtcga cgtctacgcc cgtcgccgtg    58680
```

```
atcccgacac tggcgctatg cgcgcctcgg cgcgatccgc tgcagcccct cgccgcgttg    58740
gctggtcacc acgcgagcac cggcgcagcg cagcgctaca gaggtcgacg cgatccggcg    58800
gcgggcactt acttcacgag aggaaacgcc atgtccgaca acgcacctga cgccaccacc    58860
gaggcccccg cgcaggaggc ccccgcaatg gcccctgctg cccgcgctga ggcactggcg    58920
gccaatgcca ggggtaaggg gaaggggcgg caggctacgg cgtacgtggc cctcgacccg    58980
gccgaggcta accgtagggc caggcggcgg cccgctgccg aggctcgcaa gcctgtggca    59040
cacgagccgt acgaatggtg aggctttcac cacggcgtgc tgagagctgg ttctgtacca    59100
ccagcatgaa gctgggcgag ctggtcgagg cgctggacct acgcaagcgg tacgccgagc    59160
gacacggtga acgtgctcgc ctgttcgtgt tctcggtcgg caagctgctg atcgtttggg    59220
atcgagacag caagccatga gcgagggtcg caacactgca cggcgcaaca ggttccggcg    59280
ctactggctg cggcggcgtg aggattgcgc agtgtgcggc gagccgatcg actacgaggc    59340
gcatcacctg caccctgact cgtttcaggt tgaccacatc acgccactgg acgcaggcgg    59400
ctcggacacg ctcgacaaca cgcagccgac gcaccgcaag tgcaaccgcg acaagagcaa    59460
caagctgccc gacagcggcg gcccggcgcc tgcctcggtg ggcgtcacgt tcgtgaccga    59520
acggcactgg cgaccctgac ctcagcaaag gggtgggggg atactccccg accccctcccc   59580 ggtgcacctc gtaggcat                                                 59598

<210> SEQ ID NO 8
<211> LENGTH: 59798
<212> TYPE: DNA
<213> ORGANISM: Mycobacterium phage CrimD

<400> SEQUENCE: 8
ggcacctttc tctccccagc atttttttcc aagccgattt ggcgttttc cacacccgac      60 cagcgcagga gcaaccaatg cacgtgaacg aatccgacct gactaagcgc gtgtggtcgt     120
tcgagactgt cgagtcgcgc gacatgccgc agctacgcct cggctgcgct gacctcgcgt     180
acaagatgca cctcgacggc ctgaacgacg acggcgcgac ggtgcttgag acggcccgcc     240
agctcgccgg gttcgtcgag ggctccgaat gatgacgccc accgagcggc tcgctgcgca     300
gcgcgaggcc ctcgacaagc acgagtggac cgaggtcgag ggcgacctca cgccgatcac     360
gctgcactgt ctggtcgcca ttggcgaggt gctcgtcgag ctgaacgccc ggcaggcccg     420
ccaggaggcc gcggcgatgg gcgcgccgtc gtgagcgccg tcgtcgccgt cgtgtcgcgc     480
acgctcgaca cgcgcggccg gctcgcccgc gcgctgaacg tcgctcgtgc cgagcctatg     540
agcgtgccgt cgatcaagca ggggcatggc cgcgggctga gcctcgacct ggtgatcgtc     600
gacgacgagg tgatgccgct cgacgactgt gtgctcggca cgctggcccc gtcgatgcac     660
gcccacggcg caaaggtgta cgcggttcgg gaggtcaagc tgtgaccccg actgtcggcc     720
gcatcgttca ttaccagtcg tacggcacgc cggcggcga gtacctgccc gagccacgcg     780
ccgcgatcgt cacgcaagtg cacgccgtcg agggcgctgt cggcctcgct gtgctcaacc     840
cgtcgggcct gttcttcaac gagtttgtgg agcacgccga ggacgacaaa ccgactgcgg     900
gccgctggaa ctggccgccc cgcaactgat ccagcgccgg ggcctgttcc gcgaaccgcg     960
gtcctcccgg cgcgcctggg tgcgtagctc aatcggtaga gcagcggtct ccaaagccgc    1020
cggttgcacg ttcgagtcgt gccgcgcccg ctcccacacc ggctaaccgc ggcaatttg     1080 cattcctgca cgtcaaccgc acgaaaggcc gttctgagct aacacggcac ctcacacacc    1140
```

| | |
|---|---|
| aggagatatg accatgcgcg cacccgctac cgccgaggta ccttgcccgg cctgcggcga | 1200 |
| gccgatcacg ctcgcccttg gctttgagct ggccgagccc gagcctggcg ccacgacggc | 1260 |
| ccccgtgttc gtgcggcccc tcgacgtgac cgagcgcgtg caggagcacg gcgaggtgtg | 1320 |
| cccggtgtgg tctgcgggcg gtggccgcga tgagtgacgc caagctcgac cggctcgccg | 1380 |
| agctgcgccg gttgcatgag cgcatttcgg ccgcggtgtt cgacgacgag accccgccgc | 1440 |
| gcgacctcgc ctcactgagt cgccgactca tggagatttc caaggaaatt gaggcgatcg | 1500 |
| agctgcagcg cgccgagcag ggcgtcggcc aggccgacgt cccggccgat gagccgttcg | 1560 |
| atggttcgga cctgtgagcc gcggctatcc gaggttgctc gccacgtaat caagcccgag | 1620 |
| ggcatcacct cgacgtcgtg gccgtccgtt cgccacgagt gcaacgtcaa catggggttg | 1680 |
| tatttcgacc aatggcagga cgacctcgga aagctggtat gcgccaagcg atccgacggc | 1740 |
| ctgtacgccg ccgacatgtt cgcaatgtcg atcccgaggc agacaggcaa gacctacttt | 1800 |
| ctcggcgcga tcgtgttcgc gctctgcaag atgactcccg gtacaacggt catctggacg | 1860 |
| gcgcaccgga cacgtacggc ggctgagacg ttcaagagta tgcaggcgct cgccaagcgc | 1920 |
| gagcagatcg ccccgcacat cttgaacgtg cacaccggca acggcaaaga ggccgtgttg | 1980 |
| ttcaccaacg gcagccgaat cctgttcggc gcccgtgaga aagggttcgg ccgcggtttc | 2040 |
| gccaaggtcg acgttctgat tttcgacgag gctcagatcc tcagcgaaaa cgcaatggac | 2100 |
| gacatggttc cggcgaccaa cgcctcacct aacggtctga tcctgttcgc gggcacccg | 2160 |
| ccgaagccga cagaccccgg cgaggtgttc accaacctgc ggctggacgc gatcaacggc | 2220 |
| gaatctgacg acgttgcgta cgtagagatt cggccgacg agaacgacga cccagacgaa | 2280 |
| gagtcgacgt ggcgcaagat gaatccgagc tacccgcacc ggacgtctgc gcgcgctatc | 2340 |
| cgccgtatgc gtaaagcgtt gtcctgggac agtttcaggc gcgaggcaat gggcatctgg | 2400 |
| gacaagatca gcgtgcacgc gcaggtgatc aagccgagcc tgtggcgcga cctggccgac | 2460 |
| ccgctcggcc ccgagcccgg cgccaaaccg gcgtccctcg gcgtggacat gtcacacggc | 2520 |
| ggcgctatct cgatcggcgg ttgctggctg atcgacgacg agctgaggca cgtcgagcag | 2580 |
| gtctgggctg gcacggacac cgcggcggcc gtcgagttca tcgtcgagcg tgccgggcga | 2640 |
| cgtatcccgg tcgtgatcga cgacgcgagc ccggcgaaat cgcttgtgcc agagctgaaa | 2700 |
| cgccgaaagg tcaaggtccg cattacctat gcggtgacaa tggctaaggc gtgcggcctg | 2760 |
| ttcaagaaca acgctgaggg cgagaccctc acgcacggcg atcagctcga cgtcaccgag | 2820 |
| gcgctcaagg gcgccaagca gcggccgatc cgcgacgcgg gcggttgggg ctgggaccgg | 2880 |
| cgagacccga cgtgcgtaat ccatccgcta gttgccgtga cgctggccct gcttggtgcg | 2940 |
| ctcgacgccc ccaagcgcag cggcggcgcg atgttcgtat gagagggggc cgtgtgattc | 3000 |
| ccgctgccta tgacgaccgc cagctcgacg agcccgacga cgaaatcgac tggcccgccg | 3060 |
| acgccctcga cgccgaggcg atcggcgagc tggtgcagcg catgtatgcc ctgcaccttg | 3120 |
| ccgagcgcga ctcgttcgac aatatccacg cctttaccaa gggcgagcgt ggcgtgccga | 3180 |
| gcgtgcccga cgaggcgagc gacgaggtga aggaactcgc caagctgtcg ataaagaatg | 3240 |
| tgctgcgcct gatctgcaac tcgttcgcgc agtcgctcag tgtggttggc taccgctcgc | 3300 |
| tgacggcgcc cgagaatgat ccggcgtggc gcatctggca ggcgaacaag atggacgccc | 3360 |
| gccaggccga ggtgcatcgc ccggccgtca agtacggccg ctcctacgct gtggtaacgc | 3420 |
| ccggcgtcga cggccgcaag cccgagattc gttgccgctc accgcggcag ctcatcgccg | 3480 |
| tgtacgacga cgcggtgctc gacgactggc cgcagtacgc gctcgaaacg tgggtcacca | 3540 |

```
cgaaggacgc gaagccgcgg cgcaagggcg tgctgtatga cgagcggtac atgtatcagc    3600
tcgacctcgg cgagctgccg ctgacgtcga ccgggcggcc cgaggtggcg acgaagcccg    3660
tcacgctgcg cgacgtcgag gacatcatcc cgcattacgg caccgaggac ggcaagcccg    3720
tctgcccggt tgtccggttc gtcaacgacc gcgacgccga cgacatgatc gtcggcgagg    3780
tcgagccgca catcggtatg cagaaggcaa tcaactgtgt gaatttcgac cggctgatcg    3840
tgagccggtt cggcgccaac ccgcagcgcg tgatcagcgg atggaccggc agcaaaaacg    3900
aggtgctcaa ggcatcggcg ttgcgggtct ggacgtttga cgatcccgac gtcaaggcgc    3960
aggcattccc gccagcctcg gtcgagccgt ataacgccgt gctcgacgag atggtgcagc    4020
acgtcgtgat ggaagcgcag attaacccgt cacaggtcaa gctcgtgaac atcagcgcgg    4080
acgccctggc ggcggccgag caccgcgagc agttgaagct cgccaccaag cgcgagagtt    4140
tcggcgagtc ctgggagcag gttctgcgcc tggccgtcga aatggacagc gacgaggcga    4200
cgagccccga cctgaccgcc gaggttattt ggcgtgacac cgaggcccgc tcgttcggtg    4260
ccgtcgtcga cggaatcgtg aagctcgcac agcagggcgt gccgatcgag tacctgctgc    4320
cgctcgtgcc cggcatgacg cagcaactca ttcaggcgat caaagaagcc atgcgcggcg    4380
gcggcgttca ggcgctcgtc gacaagctgc tcgccgctcc cgaggtgtcg ctgcccgacg    4440
ccccgccgat cgaccaggcg ctcgccagcc ccgacggggg aggggcgac ggtgacggag    4500
ccgaaagcgg taccggagtt tcaggggcg ctcgcccgtc tcagtgatga ggtgggcggc    4560
gccgtcgacc ggatgatgcc gcggctcggc ggcctgaccc gatctgaggg cctgccgtg    4620
atcaccgacg tctacccgac gttgctcgac ccgttcctgt cggcgtcggg agaaatgacg    4680
gcgcagtggt accgggagca aacgccggcc aagttggttg gcgcgcaggt cgcgggcaca    4740
aaagcactcg ccccggcaaa ggacttcctg cctgagcctg ccgcgctgcc cgatcgccgc    4800
cagctcgcgg cgtctggccg ctgggcgctg ctgcagcgca accctggcgt tgcgttgcgc    4860
ggtacggcaa cccgatcggt gttcgactcg tcccggcgca cggtgcgtga caacgcgatc    4920
cgcgagggcg tcaagtggac gcgctacgcc tcggccaacg cctgcgggtt ctgccggatg    4980
ctcgccaccc gtgcgctcac caccgagcgc cagggcgcgc ccggcctgta cggcagcaag    5040
gcgacggccg aacgcaaccc gcactcattc gacctgatcc gcgggcacga tcactgcaag    5100
tgcctggccg tgccggtgcg cagcggtggc tacaccccgc cggaatacgt gcacgactgg    5160
ctcgccgact acgacgccgt gagcgtcggc cccgacggcg ccctgcgcaa cccgtgggaa    5220
atcgcgcggc tgatggaggc ccgcggcgac gagcggatcg gcaagcccaa cgcaagcccc    5280
ggcaggcccc gcaaggccgc tgagccggtc gaggacgtgc gcagcacacc gcgcgaaacg    5340
gtgcgcgcta cgcagcacct cgtcgacacc ggcaacgagc gcgctgcagc gtacggcgca    5400
atcgcgcacg agcacgtgct cactgcgcag caggtcatca cccgcaccga cgaggttgtg    5460
agcaccgcgg cgcacatcac gcagcgcgtc aagctcgtga ccgacgtcgc cgacaaggtg    5520
ctcggcggcg ccgttccggt cgtgcgcgac gtcaagcgcg tggtcgacgc ggccgacaag    5580
gcactcggca gcgcatcgca ggtcacaggc ggtgcgcgtc aggccgcgga cattgccgca    5640
caggccatcg acagcacggt gcaggttgcg cacggcgcca agcagattgc cgacgaggtg    5700
cgcggcgtgc tcgacgaggt gggcctcgtc gctgccggtc tgcgcacgct gttcacggat    5760
acgcgcgtgg ctgtgcacga cacggtgcgc gacgcacgca acgtgcgcag cctgtcggac    5820
ctgtccgagc agatcggcgc agcgaccgac accgcgcggc acatcgccga cgacggccgt    5880
```

```
gcactgatcg accgcgccaa gggcgctgcc gacgcaacgc agggcatcgc tcagggcgtc    5940
cgcgaaatac cggatctgct gcggcagccg atcgccgacg cacaagagct ggcgcaaacc    6000
atcgtcgggg ccgccggtga cgccggtcag gctgtcgacg agctgcagga cgtcgcgcgt    6060
gcgatgggca agctgatcga cgcggtggcc ggttccgccg gtgaggacgt tcgccaggcc    6120
gcccgccagg ccgccgacga cctcggccgc attatcggcg acctgttcaa ggcccccgag    6180
gcgcctcgcg tgccggtgtc cgtcatgtca gaacgcctcg acgtgccggg cgcccgtgtg    6240
ctcggcggca gtcagccagt cccggcgatc gctgaacggg tcggcctcaa gccgattgac    6300
gcacccgagg cacgccaggc gctcgacggc cgcccgccga tgaaagcact tgaggcggca    6360
cccgaacgcc cgccggtcgc cccggtggtc gacgacgtgc tcgacgtcga ggtcgtcgag    6420
gcccccgcgg ctgccacgcc gaagccgaag cccgcaaagc ggacgctcga cgaggtagag    6480
gccgagtttc aggcggccgt cgaggctggc gacgacgcgg cgatcgacgc actggtcgcc    6540
gaaatggaga agctcgaagc ggccgaaaag aaggccgccg aacgcgccgc ggcgaaagcc    6600
gctgcgaagc aagcggaaac cgaggccaat accgaccgga tgcttgagct gatcgagcag    6660
ggttgggatc cagcagaggc ggaatccgag gcgttcggcc tgacggtcga gttcattcgg    6720
cgccgcgact tcatggccga ggctcgcgct gctgggcatg agggccgatc gttcgacgag    6780
ctgctcggct gggtgttcga ggagcgcgtc acagaggcgt atttcgctgc cgaggacgcc    6840
accaacgggc agatgctcaa gcgggcctac ggggtggacg gccgcaacgt cgacccgcga    6900
aagctgtgga ctctcaacga acaacggcc cgcaagtaca tgtccgagga aatggccgag    6960
tggttcgacc agcacggccg catcactcgc gctggactca aggaggcggt gctttctggt    7020
agcggcaact ggcgcaacgc catgacgtcg gactttctgc aatgaccgc gacgagctgg    7080 tcgccgcgta ccaggccggt cgcgcggcgg ccgtcggaga caccaacccg tacgaaggca    7140
ccggcgcccc ggctcgactg tggcgccgag gctaccgcca gatgctcgcc gaccgactca    7200
tgcaatcacc cgcgctgcag gcatatctca acgcccgcaa gaactgagca cgacccctca    7260
caactgaata ggagacacac gaaatgtccg aaatcacccc gaccgacggc gccgacggcg    7320
gcgagggcac agaggccccc gaaggcggcg ccccggccgc caccgacgcc cgaaggtcg    7380 acaccccgaa ggcgtacaca caggccgagg tcgacgccat gctcgccccg ctgcagtctg    7440
ctgccgacga gctgcagacg atcaaggacg gcgaaaagac cgagctgcaa aaggctctcg    7500
accgcgccgc ggctgccgag gcccgcgccg agaccgtcga gtttgagcgg ctgcgcgaca    7560
aggtggccaa ccgcgagggc aagcgcgtgc cggtcgcctc gctggtcggc aagaccgagg    7620
ccgaactgat cgcctcggct gacgcgctga tcgcctggcg cgacgagaac gcccccaagc    7680
cgcccgagca gcccaagcag cagaagcgca acccggccgg tagcggcggc gggttcaaga    7740
gcggcgcaac cggctccgac ggcggttcga ccgacccgaa ggtgcgcgcc gtagaagcgt    7800
tgcggcgctt gcgttctggc aagtagtacc cacttcccaa cacttccgca cgaggaccga    7860
cctcggcggt tgatcacaac tgaatagaga gagaggccgt aatggctgac atttcccgcg    7920
ccgaggtcgc aaccctgatc gaagagggtt acagccactc gctgctggcc gccgccaagc    7980
agggcagcac cgtgctgtcg gcattccaga acgtcaacat gggcaccaag accacgcacc    8040
tgccggtcct ggcgaccctg cccgaggccg attgggtcgg cgaatccgcc accgaccccg    8100
agggcgtcat caagacgagc aaggtcacct gggcgaaccg cactctggtc gccgaagagg    8160
tcgccgtgat cattccggtg cccgaggccg tgatcgacga cgccactgtc gaactgctga    8220
ccgaggtcgc cgagcagggc ggccaggcga tcggcaagaa gctcgaccag gccgtcatgt    8280
```

```
tcggcatcga caagcccgca tcgtgggtct ccccggcgct gctcaaggcc gccaccgacg   8340
ccgggcaggc catcgcccac gtctccggtg tcgccaacga gtacgacctc gtgggcgcct   8400
cgaacaaggt cgccgagcag gtcgccctcg ccggttgggc tcccgacacc ctgctgtcga   8460
gcctggcgct gcggtaccag gtcgccaacg tccgcgacgc cgacgaaat ctcgcgttcc    8520
gtgacggttc gttcctgggc ttcaataccc acttcaaccg caacggcgcg tggtcgcccg   8580
agtccgcggt ggccttcatc gccgactcct cgcgcgtcaa gatcggtgtg cgccaggaca   8640
tcaccgtgaa gttcctggat caggcgaccc tcggcaccgg cgagaatcag atcaacctcg   8700
ccgagcgca catggtggcg ctgcgcctca aggcacggtt cgcgtacgtg ctgggcgtct    8760
ccgcaaccgc gatgggctcc aacaagactc cggtcggtgt tgtcaccct gacgtgacgc    8820
cgcccgcggg cgagtagtgc ggtatcgcca caccctgacg ggggcggtca tcggggcgcc   8880
gaaaggcacc ttgctggccg ccctcgtcga gggcaacccg aactggatcg aacacgaggg   8940
ggtggccggt gctggcaagt ctggacgacg taaaggcagc tctgcgggca atgggaaagc   9000
ccgagctggc ggaagctctc gcggccgagg acgtaaccga cctcctgcag gaggcgaccg   9060
acctagtgac ggggcacctg tggccggggg aggtgccgag cccgacgcct ccgacgatca   9120
ccagggtgac ggcctcggtg gcagcgacag cgctcacgaa gccgaaggaa ctgctgccgg   9180
agacggagag cctgcaagct gacgggttcg gcgtgaagtt cacacccggc gccggatcgc   9240
cgggctgcta cctgacggcc gcgcaaaaga cacgcctgcg gccctggaag cgcagcgctg   9300
tctcggttcc catgagcagc gagaggtacc cgtgagcctg ccgaccccgt gggaagtgca   9360
acacgacg tacgtcaagg tcggcgagaa cgccgcgggc caggccaaga ccgagccacg     9420
cactcgacgc cgcatggtgt cgagcctgcg caagcgggtc aacgagcctg gcaccgcggc   9480
ggccaactcc gatcaggtcg tcgtcgagta cacgatggcg cacccgaaa gcgattgggc    9540
gcacggcgat ctggtcaagg actggcgcgg ccgtgagttc aaggtgcatg gcgacgtcga   9600
cgactacaac agcggcccgt tcgggttccg gcccggctac ctcgtgacgc tgcgaaaggt   9660
ggagaaacgt gccttaccgt ccgcttgatc tgccgttctc tgagcaccgc aagatccgca   9720
acctgcccga cctcaccaag gcgtgcgaga agcttggcgg caagctgcgc gacaaggcgg   9780
cggccaaggc caacgcccac actcccggcg ccggtgacga ttacgtgacc gagaccgtgc   9840
acggccgcga ccgtgtgcgc gtgtacgtgc gtgctgaggg cgcagcgatc ggcgtcgaga   9900
acgacatagc gccgctgatg caggtgtctg cggaatcggg gccgcggtga cggtactcgt   9960
tccgccggtc ggcccgctga cggccgcacg ccggtacctg ctcgacgagc tggctgcccg   10020
caacaatccg ctgatcgtcg agcagcagac ggtgcccgag ggctcgccaa cgtcgtacgc   10080
gatcctgtcg cggcccggca cgagcaccga ggtgttcctg caacacagcc tcattcgggt   10140
gcgggtgtac gacaacgacc tcgtgcgctt ggagcgcaac gccgatctgc tgcacaggct   10200
gctgctgcac gccgtgcacc gcaaggtcgt cgtgcccgac gagggcgagg tgtggatcac   10260
cggcgccaca cacgaatacg ggcctgccga gttcgacgac cggcgcgtac cgctgcccgg   10320
ctatcagtcg gcagtgttct ggacgatcgg cctgcgcccc gagcgcagct aagtcgccgg   10380
ccgttgccgg ccgacctcga gaaccgcgct tgacgtgcgg cgatgcgcgc tgcccgcatt   10440
cggcagcaaa cacaactgaa taggagacaa catgacgcag cccactccgc cctcggcgct   10500
gggcgacgcc accaaggtgt tcgcagcgtc gccgtcggac ctggaaaccg ttggcggcct   10560
ttggttcgca ccgttcggca ccaagctgcc gaccgacgtc gacgagcccc tcgaagcagc   10620
```

```
attcaagaac ctgggtttcg tgtcggctga cggcgttacc gtcaagatcg acagccagac   10680
cacacccatt gaggtgtggg gcggcgacga aatcggggcg ctgcgagaca agttcagcat   10740
cgagtacagc atgagcctgt ttcaggtgct gtcgcccgag gtcaacgcgg ccattttcgg   10800
cgcgggcaac gtctcgaccg cggcggccac cgaggcgcac ggcgcccgca tgaaagtgct   10860
gatcaactcc aagctgccca agcggtgcag cctggtgctc gattcggtgt acgaggacaa   10920
gatcattcgg caggtggcgc agatcgcgca gctttcgggc ctggccgaca tcaagctcgt   10980
gcacaacgcc ccgatggcgt tcgagccgac gttcaaggtg ctcaagggca ccgacggcaa   11040
tcacgtcatc cagtacagcg acgacggtca gatcgtggcc gcctagtcgc tcgataggcc   11100
agcaccccgc gcgttttcct ggtggcgcgc ggggtgctct ctcgtctacc aaaacaccag   11160
gggcacacca ggaaacacac cagagaggca gtaccagcat ggcaaaagag accaggacca   11220
acgacctgac cgacgtcgac gaggcccccg tggctgtcga cgcccccgag gacgaggccg   11280
ccagcattcg ggaggaatgg gccgacgact acgacgaggg caccgagctg ttcgtcggca   11340
agttcgacgc cgacgacttc gacgccgact acggcgtcgc cgagttcccc gagggcgcaa   11400
cgatcgccgt caagcgctgc ctgcgcaagc cccgccgggg gtggattcgc cagcacgcgc   11460
acctgtccga ccttgagcgc acgttcgctc tgatcgaaat gcacgccagc gaccgcgctc   11520
tcgaaattct cgacagcctg cagcagaagc cgtgggatga cttcgtggag cgctggggcc   11580
gcgacgcgg gctgatcgag ggaaaatctc gcaggtctgc gcggcggcgc gccaggtaga   11640
ggacgcaata cggcgtgacc tgatcgttgc cgggcgcgag ttcgacgacg cactatgtc   11700
gtgggacgac ctgtacgcat tcattttcgc gtcgccgcca acgtcggcaa ttttccacgc   11760
ttttgaaaag ggctggaata caaccgatta cctgctcgcg cacgtcattg acgcgctgcg   11820
ggtgggcctg tggcagcgca ccgaggatgc aaccaagccg aatccgcgac atgtgcccga   11880
gctgttcccg cggcctggcg acgacgaaaa ggccacggac ggcggcgagt acgtccaagt   11940
tggctcgact gtggcgacca agacaacggt cggcaagttc ctagaaatgc gcgccgaacg   12000
cgaaaagcgt tggcgtgagc gaaaaaggg caagagcaag ggggcgtaaa tgtccgcaac   12060
gtattacctc accgttctac ccgagacgag caagctcgtt cccggtatcc gctcggccat   12120
gaagggcgcc gaaaaggatc tgacactgca gcccaagctc gacacccgcg cgccgctga   12180
ggcgggccgc cgggtcgggc gcgacatgca ggacggaatc gagcagtcgg cccgcggcgg   12240
cactggcatt ggccggttcc tgcgggccga cggcgctcgc tcggtagggc agcaggcagg   12300
cagcgagatt aacgcgggcc tgcagtcgg cgacgtcggc cgtggcctcg ggtcgcagct   12360
cgcatcgaac ctcacgagcg gcgcaatgaa cctgggccgc aacgtcggca gcatgattgc   12420
gacgggcctc aaggcgacag ccgtcgtcgg cggcacggtc gccgccgcgg gcatcgctgg   12480
cgccctgcac gccggtatga gccggttgac ggcgatcgac gatgccaagt tcaagctgca   12540
gggcctcggc aatagcaccg aaaaagtgca gtcgattatg gacaacgccc tggcggccgt   12600
cgacaagacg gcgttcgggc tcgacgaggc tgccaccaca gcggcgtccg cggtggccgc   12660
cgggcttgag ccgggcgagc agctcactgg ctacttgaaa accgtcgcag acacggccgc   12720
tatcgccggt acctcaatgg ccgacatggg cgcaatcttc aacaaggtgc agacgtcagg   12780
caaggcgttt accggcgatc tcaacatgct ctctgatcgc ggcctgccga tattcaagtg   12840
gctgcaagag gaatacggcg taaccggcga ggcgctctcg aagatggtca gcgagggcaa   12900
ggtcgacgct gcgacattcc agaaggttgt tgccgagcgc atcggcggtg ccgctcagga   12960
tatgggcggc agcatccgcg gccagctctc caacctcaag gcgtcctact cgcgtttcgg   13020
```

```
cgccgagctg gcggggccga tcttcgcggc cgtctcgccg ctgacgctcg cgttcaccaa   13080
tgcgtttaac aagatcaccg cggcgatcaa gccgtacacc gcagagttga cagcgattat   13140
cgggccgtgg gcaactgacc tcggcaacaa gatcacagca tggctcgaca acggcggcat   13200
tcagaacgtc atcgactgga tgggccgctt ggtcgaccgc gtgcaggcgt tgcgcaccgg   13260
cgagggtcga ggcgatgcgc tgcagtcgat ttcggattct gtcggcaagc tcggcccggc   13320
gctgcagcag gctggcccgg cgctggaagg tgtcggatcg gcattcgcgc agttcggtcg   13380
gacgatcgcc gagattggtc cggcgacgct tagcggtgtc ctcacgcccg cgctgaacct   13440
gctcgccggt gcgctgaaat tcgttgcgga taacgcctcg tgggcggtgc cggttatcgg   13500
cggtctcgct gtggcgttcc tggcggtgcg cgctgcgacc gcggcggctg cacctttcat   13560
gcaggcgtat acgcgacgt tcaacctgat tcgtagcccg gtcattctcc tgcaggcgca   13620
agcgcagcgg cagctcgccg ccgcgatgac gcagcacacg gccgctctgg tggcgaacac   13680
tggcgctcag ggcacaaaca cggtcgcgca gaacgcgaac gccgcaacct cggtccgctc   13740
gcgtgtcgcc gcgatggcct cggcggtcgc cagtcgcgca gccgcagcgg cgcaatggct   13800
ttggaatgcg gcactgactg caaacccgat tggcctcgtg atccgcgcgg tggtcgctat   13860
cggcgtcgcg ttgtgggcgt tcttcaccaa gacggagacc ggccgcaagc tctgggacaa   13920
gatttggacc gggattaaga cgacggccgt cgtggtctgg gactggctca aggtcgcgtt   13980
cgactggctc ggcgaaaagc tcacgtggtt gtggcagaac gtcgcggtgc ctgccttga   14040 gggcatcaag ggcgccgtcg aaacattctg gaagggcgca aaagtcgtct gggatgcgtt   14100
cacaacggtg ctcgacacga tcggcaccaa ggtaggcgcg ttcaaggatg cgtcgtggc   14160 ggcgttcaac gccgtgaaag acgttgtgac gtcggtgtgg tcggctattg gcggcatctg   14220
ggacaagatc gtgggtggca ttggaactgt cgcggacgca ctcaagggtg cggcggcac   14280 agtgctgcgg gcgttcggcc tgggcggcgc tgcccgtggt ggctacatcg agggcggaat   14340
ggcacggtac gccaacggcg gtcagatcaa cggcccggt accggcacga gcgacagcat   14400
tctcgggttc ccggcgatgg tccgcgttgc taacggtgag ttcgtcacca acgcccgcac   14460
gaccgctcag tacctcccgc tgctgcaggc gctcaacgcc ggtatgccgc tgagtgatgt   14520
gctgggcaag ctgctgcctc ggttcgccga cggcggcctc gtgtcggctg acgagctggt   14580
cgatttcgcg cgtggcgtcg agggcaagcc gtacgtgtgg ggcggcacca actggggcga   14640
ctgctccggt gctgtctcgg cgatcgccaa ctacgcgacc ggccggtcgc cgttcggatc   14700
tcgttttgcg acggcgaccg agggcgacga gctggcggcg cgtgggttta gcctggcct   14760 cggcccggcg ggctcgctgc aaatcggttg gtacaacggc ggccctggcg gcgggcacac   14820
cgcggcaacg ctgccggatg gcacgaactt tgaaatgggc ggtgcgcgcg caacgggca   14880 gtttggtggc tcggctgcgg gtgcggctga ttctgagttc accaaccgta tgcacctgcc   14940
acccgaggcg tttacgggcc tcgacggcgg ggcgccgacg atcgggtcga gcacctcggc   15000
ccgcggtgcc ggtacgtaca ccccggcgac aagctcgcag ttgagcgcgt cgtcacgcaa   15060
ggtcgacacc gctcgcacgt ctgccaagaa cgccgaccag gccgtcgacg acgccaccta   15120
tcggcgcgac aaggcgcagg cacggctcga cgaggccaag gcaagggca agggcgtcga   15180 cgatgctcag cactcgctcg acgtcgccaa ccgcgagctg gccgacgcca aggagcggca   15240
ggccaaggcg cacgacaagg tgaccgacgc aatgagcgcc gacgaggaac tgcgcacaaa   15300
gggcaagttc aaagagggcg cgtcgtcgtc gagtggcgac ggcctgtctg gcgcggactt   15360
```

```
tggcaagacg ttcgtgtcgg gggcgcttga gtcgatcggc ctcgacgggt cgctgttcag   15420
caatccgctt gagtggccga cggttaagtc gctcatggcg ggggtgaact acgcgggcgg   15480
cctgctcgcc aacggcaccg gcgccgcgac aagccctggt ggcttcgctg acggcgtggg   15540
ccaggcggtc gggctcgatg gcctcatggc agcgcttccg ggcgctgtgg gcgatcctgc   15600
ggccggttgg acacctcaga gcggcagccc cgcgctggcg cccggtcagt tcaacccggc   15660
gattgcaggc ggcggcccct cgatcgccga gggcgtcgcc aacgccatga gtgcgttcgc   15720
accggacacc acgcagcacg ggcagggcgg gggagctgca cccggcccgg cgggagacgt   15780
gaatttcaac ggccccgtgg gcatggaccc gcaagcgctg cgaaccgagt tccgcaccga   15840
gctgaatgcg cgttcgcgct acagcggcag ctccaacacg aagtaagcag ctaacggccg   15900
gcgagccgcc gatctggtct ctgacctgcg gcggctcgtc gcgccagcta tcgaactttc   15960
acaactgaat aacggggtga gtgagccgtg acgcttggcg gcatccatga cgatttctat   16020
ctcgatccgc cgcggtacac agatgacgcc tacgggcgac cgctgtacgg ccccgagaat   16080
ccggcgcacc cgagctggcg gcgcatgtcg cactgggggca acctcggccg taacggcgag   16140
tacctgcggt caacgcagac gaagtgggtc tatatccacc cgagcaacaa caaggtgtgg   16200
cacctcgccg ggcctatgcg cggccgtgag ggcgtcgtgc tggccaagga acttgagggc   16260
gtcatgcagc ccgagtttga aattctctac agcgagggcg cttatacgat cggcgccaag   16320
cctgagcgga tcaactacaa gaaacgcacg atcagcctcg gcgtagtcat ccaacccaac   16380
ggcaacgccg agcgggtcga ggagcctaac ccgttctcgt acaggctgat tgaggactcg   16440
tggtggtcgt cgctgtcgga gacgcagccc ggtttcctgg gctcgttcac ccgcacgcac   16500
ggctggcggt ggctggccgt gatcctggcc gaggcgtcga aaacctccct caagatcgac   16560
ccggtagcgc acgacaacaa ctctcagcag tacaacatcg tgctgcacgc ccctggccg   16620 ttctacgcca agcgcacgct gagcaaggcg tggctgtccg acctcgagaa tgtcgtggcg   16680
aacgacggtg tggcgcaagg gattatccag tgcccgaacc gcggcacctg ggagtcgtgg   16740
ccgaagtacc tcgttaaggg gcacgggcag gcgtggattc aggacggcaa cgacgggcag   16800
atgatcaagc tgcccaagtt ctacgagacg acggcgagtc acatgctcgt cgacaccgat   16860
ccgactaagc gcacgatcac aaccgagaaa gacccggttg acgggcagct ctacaagtat   16920
ctgcgcgggt cgcagttgct tgagctgctg ctgcacgacg tgacggccgc gcgcctcccg   16980
gcgcagcgcc gcattcccgg cggcatcggg ttcgacggca agattccgcc gcgcacggtc   17040
gccaatatca aagtgcggca cgacaacccg aaagggtcga ttacgtgcgt catgccgcag   17100
cactaccgga tggcgtggtc atagatgtat gtacagaatg gccgcaagct gtgggtgcca   17160
ccagcgtgcg gcgctaacgg cgttcccgat cccgtcaaga atccgatcga ggcgtttcgg   17220
tacctcgacc tcaagcgcga gctgatcgac gccgaggccc gcgagaagcc actcattcgg   17280
ctgtgggaca aggcgtttaa gtacatcggc accgtggccg ccgagaagtc ggtcgacgcc   17340
gaggaaatgc tgcacgacac cgggcagggc gacattgtgc tgcgcggcga cgactggctc   17400
gtcgagttca tgcgtaccga cgtgcgccgc gaggaggatc tgcacgtcac gatcgacccg   17460
tacccgcacc ggcgcaactg gcggcggcgg tggcacgcca aggtcaccaa cgtgcgggtt   17520
gcccgcaacg agaacggtca gcgcacagtc acattggagt gcgcgcacaa ccgcgagcac   17580
tggaaacacc tgctgttcgg ggcgacgccg ttcagcttgc ctgaggtgca gcctatgcgc   17640
gcctggctgt tgccgggcaa cacccgaacg atcgtgagca caacgggttt catcaacctg   17700
gcgcgcaact actggcccct tgctggccctg ccgtcgcagg tgatgaatcc cggcgcgtgg   17760
```

```
atcgggcagg cgtccaacct cgccaacctc aacccgctga actggccggt tcaaatgcag   17820
ttcgtcaatc cactattcga tcggtcgcgc acaagcgtgc tcatgtcgag gtggtcgaac   17880
gcgcacgacg tgtgcgacgc actgctcaag tacgccgggt gtcacgttcg cgcgtactgc   17940
tggctggaag aggacgagga cagcccgcac cccgagctgg cggcgatcgt cggcgagaag   18000
ctcgccaggc cgacgcgcaa ctgcatcgtg ctggcagtcg aggacatgag cggcacgacc   18060
ggggtcaccg gcacgcgat cgacggcgtg ctcgacctca ttgcagtgtc ggccgacaac   18120
attctcagca ccctggtgca cgtcgaccgt gacggcgacg tgtggacga tccgtttatc   18180 cgcaagctgc tgggcgtcgc cccggcgccg ccggatatta catttcggga tcacgaatat   18240
tcgtcgatta tctcgtctga gcacagcatg tttcgtgcaa aggcgcagaa aattctcacg   18300
ggcggccgta gtcctggctg ggtaaatcaa gttcagacat ttgccattaa gtacgccctt   18360
tctcaaattt ccgcaattat ccaagctggc ccggctggtg catatcagca acccggcagc   18420
tcgggtttgg aggaaattta tcaggggcag gctgacaata ttttgctggc ctatatccag   18480
gtaaccgatc cagtgcgcgc aatgcgctcc ggtccctatg ctacctgga acatttcgag   18540 caaggctcgg gctcagcata cacggtcagc tcggcaatga cattagctga ggggcaccat   18600
aaaacgcggg cgtatcaggc gttcaaggtg tccgtacgta acggcgggca attccagctg   18660
tattacgatt tcgacctcgg ttggcgcgcg aactttgaaa tagatcgcat tttccacacc   18720
gaccaggtat cagccattcg gctgcactac aacgagacga caccgaaaac tttcgacctg   18780
tctatcggta gtgactcgga atcggagagc ccgctagcgc aggtggctcg ctcggccgca   18840
gcgttctgga atgccattgg catgttgttc ggatcaggag atatgttcta gtggaaattc   18900
ccacactgcc gccgctgccc gacgtgccag aacacgtgcc gggcgccaac tcgacggttg   18960
acgcgatgta cgacattgcc gaggccctca catatccggt cgacagccgc ggtcgacggt   19020
acgacgtgcg atttctcttg ccggtgattg cgtatcacct ggcgcgcgct ggttgtgtcg   19080
tcgacccggc tcgggccgtg atcaagaagc ggcgcctgcc accgacgggc ggcgttgtcg   19140
aggatgcggt cgactgggtg ccgctcgatg ccccgactc gatcgaggac gagctagacg   19200
gcgcgaccct cgacgacctc ccgcacctgt ccgcggcggc ccaagccgaa tttcgacgcc   19260
gggcgctcgg cgagccccg cgccgacgg gcgtcgacga ccagggcgtc gacctcgacg   19320
agcgcgcccc gtggcacgtc gaaacgtcga tcacgttcga cgactgagca accgccggca   19380
aaacgtcgga ttcatacccct gacctgcggc gcagcctcgg gtcggcaaac aactgaataa   19440
ggagcaccat atggccgagc ttgcgccccg gctgacgggc gatgcggtcg cgctatttca   19500
gaccctcctg tctgccacgt ggtacggcat cgtcggcgac ggaaacacac ccggcggcat   19560
gtcggcgacg ctgaaaatga tcgacggcga ggccgtgatc actaccgacg ttctgatcgg   19620
acccaagggc gacaagggcg acccggcccc gctggttgat ctgcaatggc ccgcgctgga   19680
atccccgacg gaactggtcg agctgcaaga cgagctaggc gaggacgaca agggcaaggg   19740
ctggtggatc ggcacggttg tctacgtctg gaccggcacg caattccaaa tggtgcggcc   19800
cggcccggcg gggcctcccg gcgccacacc tcaaatctcg ttcgagttcg agacgatccc   19860
aatgtcggag cgcggcccg gcgtcaagga cgaggtaatt cgttccggca cttcacttaa   19920
cccgcacatc aaggtgcgtg cgctgtcgcc acaggggcct gtcggcccgt cgacgaacat   19980
caccggcgca ccggactacg acaacagcga gccgccgacc aacgggcaga cgctcgtgtg   20040
gaactcggta aaagccaagt gggagccgtc cgacttcact gccaagcacc cgcggctgta   20100
```

```
ctcggttccc gaggcagcgt ttacgccgtt caccggccca gcgcagcggc agccgatcct   20160
gcagtaccag gtcgagccgc aggacttcgc gtggaccccg tacgtcaccg acacacatcaa  20220
ggcgtttggc cttgagctgg acgccgaccc gctgacgatc ggcgtcgagg tgcgcctcgg   20280
cgacccgctg acaggcgagc tgatcggccg cgggttcggc aactcgtcga tgtggtcgac   20340
gatttcgccg cactggtcga cctcgggcga ccccgcaacc gcggtggccc ccgacaacgg   20400
cgtcgctacc gtcgccgccg gtcaggccgc gcagatcaac gtcaacctt acaacgatgg    20460
cctgttcggc gtctacgtgt tcaacggcaa gggcgcacag ctcgccattc tcgttgtgcc   20520
gcaaggggga tagctgcaca tgccatacac caagaactac cgcacggtcg tgccgcttga   20580
gccgggcgtc gacctcgacc tcgcgcggtg gcttgctcgt gagtcgttcg agcgtgcagc   20640
ggaaaacatg ggcctgacga tcgtcgagta cggcgagcgt gaggtgccgt ggaccgagct   20700
gccgccgaag gctgccgagc acctggcgct gcccgccgat gcgtacacgt ggttcgagtt   20760
caccggcgta ggtgcggttt ccgaggttca gatcgaatgg ctgactgcag agtcggcctg   20820
gcgcaacacg caggcgggag gtcggtaagt gcctcccgtc tttgatcgcc gttccctcgt   20880
catcgaccgc aacccgctcg ttggcctgac gcccgacccc ggcaccctgc ccaagctcga   20940
cccggcgatg ctgtggaaac agtggattga cggtttcaag acactgaccg gaattgacct   21000
gtcgtcaccg gccgcactcg tcgccagcct cggcgacctg atcggcagcg ccctcgatcc   21060
tgcaaagctg atcgaggcgc tgacaaaggt tttcggctac gtcggcccgc cgctggcctc   21120
acttgaggcg ctcgcggcgt gggtcaacag ccagattttc ggcctgatcg accgcggcg    21180
gctggctcag atcccgctcg gctcgatcgt gcaggagtcg ccaaacctgc tgaccaacgg   21240
ctcgtttacc gacgcaatcg ccatcgacga cgagacgggc cgctgggtcc gcgataccgc   21300
gacgtacaag tcgcgccag cgtcggcacg cacgaccgcc gacggcacga tcgccgaact    21360
gctgagcatt gacctgatcc cggtcaagcc gaaacagaag ctcgacattt cgggatttgt   21420
ccgctgggcg ggcctcgtgg cgtccgacgg gtcggtcggt atcgggctga tggagtacgg   21480
cgacgctggc gagcagcgcg tgctgatcaa ggcgctagac ggcgccagcg gcacgcaact   21540
gacgtggcag aagatcggcg gccagtacgt cgtgcccgac accggcgtcg acagtgtgcg   21600
cgtccgtctg gtcgtcaacg acggcgctac cgctggcaat gtgtggtacg acgagctgaa   21660
cgcgagcctg ggcgcaaacc tgctgccaaa gaccgccgtc gagggcctgg tcgctgagct   21720
gaaagcagcg tttgactcgg ccgaggccgc ggctaagcag ttcctcgact tcctgcaaaa   21780
ccaatggcag gcgatgctca acggcatcaa gggcggcgtc ggtggggcaa tcgaggactt   21840
gtggaatcgg ttgctgcact tgacacctga cggccttttc gacgcctcgc agctcgtgaa   21900
cgtcgacaac atgccgcagc ttccccggc ggtcgtcgcc ggtattgagg gaatcgagaa    21960
tatcggcgac acgattcagc aggcgatcga ctacctgtgg tcgggcttcc ggcgccaaac   22020
cgggcagaac aaatcgttct cgtcgctggc gcaggcggcg caggaaacat cgaacgacat   22080
tcagaccgcc gtgcacctgg cgacgatgca cgcgggcatc tcagtgagc gccgcaacaa    22140
accggcacat tggggcctcg ccgataccgt cgaggtgtcg ttcccgttga ctgacattgc   22200
ctacggcaca gcgcgccga cgatcccaat aacggcgcag aacgcccgca tggcgttcat    22260
tcgctgcggc gagtcggcca caaagggctt tgtgcagtgg ctcggctacg caccccctga   22320
cgccttctac gtgaacgtgt acaagatgga cgccgagggc aacctcgtgc acctgcatac   22380
ctcgccgaat ctgagcaacc agctacaggc cacgatcggc tgggagatgt acgttttcgc   22440
gggcaccgac caaaccaagg tcgaccccgg cgacgtcctg gcggtcgagt tcgtcgtcga   22500
```

```
gggctccaac gcatacaaca ttgccgggtg cgtcacgtcg tgggtgccgg ttcacccgtc   22560
ggcgaacacc aaacaccttg gcgcagtgcg cggtgccgcg ctgggcggac gggcaccggc   22620
gactatcccg gccgagcttg tctcttggac gggcacggtc ccgtgggtgt cgatcggcat   22680
aagcaacgtg ccgccggaat atcagccccc gactgctacc gagttcgacc aggttggaca   22740
gcacacctac gaaattccac tgtgggccaa ctacattgac gtgatcgcct gcggggggcgg   22800 cggtggtggt ggcagctcgg cgaacttcct cacggggcag ggcggcgagt gcgggcactg   22860
gatcgccgta acgcttgtgc ggggcgtcga cttcgcagag gacgcaacga caatcaccgt   22920
caacattggt gagggtggcg cgggcggccc gcttaacgcc aacgctggcc gcgacggctc   22980
gccgacggtc ctcacctggc gcaagccaga cgggtctatc ggcatcgcct cggcgactgg   23040
cggccagcat ggcggccccg gcccggttca acagcagcaat aacccaaca cggcctcggc   23100 gggtatgggc gcaccgaacc accagtaccg cggcgcaacg tatttcggcg ccccgatgc    23160 gtcctacgca ccgggcagca cgccgggcgg cggcggtgct ggcgggttct cctactcgtc   23220
gggctcagca ggtggccgag gcgcggcgtg gctggtcgcg cggcagtccg aggatgactg   23280
agagggggcg ctatgcgggg atggggtacc gaccccgcagc cgtcagcgcg tgccggtagc   23340
ggttgggcaa cgtcgcccgc cgcaccggcg ccccccgcgcc ccggctcggt atggcggccg   23400
atcgtgcacg agctggcggc ggccctgagt gtctcgacca ccgaggcggc cctcgctatc   23460
cgcgcaacgg ctgcggcgct gagcgtttca cacagcgacg ctgcggccgc actgcggatg   23520 acggcccccgg ccgccagtgc gagcagctcg tcagcgtcgg cgcgagagca ctacttcgcc   23580
gcggcccccg cggagagcac gagcacgagc agggcgtcgg cagttgtcaa ggccgtggcc   23640
tcagcgctga acgtcagcac gacgtcggcc gccgcggtgc tgcggaccgt ggcgcctgca   23700
gcgtcgacga gcggcacgtc ggcctcggcg gcgttccccgg caatgtcgcc ggtttcgcaa   23760
cagttcgcaa cggtcggaac tttcgagttc ccgatcccgt attggtgccg gtatgtcgac   23820
gtgatcctcg tcggcgcagg cgcaggcggc aacggcggat ctgcagcact ggctgccggg   23880
catggcggcg agggtggcaa gtgggtggcg gtcacgttgg agcgtggcgt gcatatcccg   23940
ctgaccctgg ccgcgatcgt ctgcaccgtg cgagctggcg gcacgccggg cggtggcgcc   24000
gtcgtcggcg gtatcgccac ggacggcaac ccaacaacgg cgcaggccga gggctgggca   24060
ggtctgagcg ccgcgggcgg cctgcaccgc gagcggatcg gcctgctgca ccaacctggc   24120
gacagccccg gcaatttcac cttcaacggc ctgctgtacg tcggcggcgc cgcaacgaac   24180
agcggaaacg gcacaccggg taactcgccc ggcggcggtg gccgaggcgg tgacggcggc   24240
gcgttcgtgg gttctcccgg cggcgtcggc gcgccaggcg ccgcgtggtt ccgcgcatac   24300
cagtagcaac cgccggccaa acgccggatt cacactctga cctgcggtgc agcctcgggt   24360
cggcaaacaa ctgaatagga gcattctgtg gctgccgcag atcaattcaa gctcgacacc   24420
ctggctgcga tcctcgcgca gggcagcctg ctgagcctgc acagcggcga ccccggcaag   24480
acgggcgcca acgaaattac cggcggcggg tacgccgcca agacgttcgc gtggggcgcc   24540
ccggcgatcg tgtccggcgg cgccgacgac ggcaaggcca aggcgaccgg ctccacgcag   24600
cagatgaacg tcgctgcggg cgtggcggtt acgcactacg gcgtacgcaa ggccgacggc   24660
acatttctgt acggcaaggc cctgagcccc ggcgcgaccc tcaacgcgaa cggcgtcatt   24720
gacgtgaccc cgacgcacac ctacggcgac ccggtttaag aacggagaca accgaatatg   24780
gaaaaggtac tgccctacga tcggtcgatc gtcccgcagg aaacgggggta ctggtgcggc   24840
```

```
cccgccgcaa cgcagatcgt gctcaactcc cgcggcctgg tcgtgcccga ggcgaccctc    24900
gcccgcgaga ttggcaccac ggtgcgcggc accgattacg tcggactgat cgagcgcatt    24960
ctcgacctgc gggtgcctga cgcccggtac acgtcggtgt acatcgagaa cgacccgccg    25020
accggcgacc agcgagagac gttgtggcgc aacctcaagc gctcgatcga cgccggttac    25080
ggcgtggttc tgaactgggt cgccccgccg agcaactacc cgcgcggcgt caagggcagc    25140
gtgagccccc ggtatggcgg cggcacggtg taccactacg tcgcggcgat gggctacgac    25200
gacaacccgg ccgcgcgcgc ggtgtggatc gctgacagcg gctttcagcc gcaaggctat    25260
tggatctcgt tcgatcaatg cgcgtcgctg atcccgccca agggctacgc cttcgcagac    25320
gtcgaccacc ccgacggccc cgaggccccg atcgacaccg acgcgcaggc ggccgacgct    25380
ctcatgcgcc tgatgggcgg ctcgctgcca ttcgcgcggt atcaggcgct actgcccgca    25440
gtgcagcagt gcctcgccga gtgcgagtgc acgaccgagc ccgtatcgc catgtggggc     25500 gcgcaggttg ggcacgagtc ggtcggcctc aagttcatga gtgagctgtg ggggccgacg    25560
gccgcacagc agggctacga gggccgcatc gacctcggca acacgcagcc cggcgacggg    25620
tacaggttcc gcggcgccgg gcctatccag gtgaccgggc ggcacaactt cacggtgctg    25680
tcgcggtggg cctacgacaa gggcctcgtg ccgacaccga cctatttcgc cgacaacccc    25740
gacgaattgc gcggcgaccg ttacggattc gtcggcgtcg tctggtactg gacgacgcaa    25800
cgcccgatga cgacgcggc cgacgcccgc gacctggtgc gcgcaacgca gtacgtcaac    25860
ggcggtcaga acggaatcga cgaccgccgc acccgataca acggcgccct ggcgatgggt    25920
gccgacctac tcaagatcct taacggaggc gatgatttca tgtctgcact gaccgctgcc    25980
gagcagcgag aaatgctcga tatgctgcgg tggctggcag caccgggcac cggcgagctg    26040
cgcaagaagt tcccgagccg cagccaattg cgcgcggtgg gcgaggggct cgtcgacacc    26100
tgggcgggca tggacctcaa ccaggacgcc aacattcacc tggtcgccga gtacgtgctc    26160
gccggtatcg gcgaccccga cgctatcgcg cgactgcgga agctggccgc gacgaccgac    26220
gccgaccgga aggggagcgc ggcgctggcg cagcgcatcc tcgaccacta cgacgagtcg    26280
cacgaggccc ccgccgagcc cgacccggct ccggcccgca aggtgtcgtg tgcgcagggc    26340
ggtggcggct gtgtcctcgt cgccaacggc ggtgacggca cctgcggcct cgccggtacc    26400
gagtgcgtgc tgcgcaaggg cggtgccctg tgagcaagcc aatgctgctg accgcagcgg    26460
gcaccaaggc cgacgagtgg accggctacc cggccgacct cgcgcggcgc atggaggatc    26520
tgtactactt ccagccagtg cgctacggcc caacggaat cccggcaatg tggccgatgg     26580
gcgcctcggc caagaccgga atcgacgagg cgtgcgcct ggtgctcgaa gccgaggccc     26640
ggccgtcgcg ggaggtgccc gacgggtacg ccgtgtgtgg atactcgcaa ggcggctggg    26700
tcgtttccga gctgctcggc gagttccgca ccggccgact caagcacctg cgcggcaagc    26760
tgatggccgg tgcgacgttc ggcaacccgt accgcgagct ggacgacgac ggcggccgag    26820
gcatctccga caagcggatc gtcgacacgc ctgatttctg ggtcgacgag ttcgaccccg    26880
gcgacattta cgcgaacgtg ccgaacaacg acgttggcga ggacatgacc gcgatttta    26940 agctggtgcg gttcaacggc attggcgacg tgatcgacct cggcagtgcg atcgacctcg    27000
gcagcatcgc gggcggcctg gtgccggcg gcgccagct cggcggcatc ctcggcggcc     27060
tcggcgggct gctgggtggc ggcgggcggc agcaggacaa catcaccgag cagatcgtcg    27120
aaatgctgcg cagcccgctg cgcgagttcc cggccgcggt gtcggcgatc ctcaagggcc    27180
tggtgttcgt cggccagaag cctgcgaccg caccgcacat cgaataccac ctacgcgagc    27240
```

```
ggtcgccggg tgtcacctac tacgagcacg ccgtcgccca catgcgcgcg atggcggcat   27300 gaggggggcga gaatgacgaa ggtcgtcgag acaatcctcg gcatgttagt gcaggtgtgg   27360
gcaggtgtgc ggcgtttcgc cgccgagcgt ctcggcatcc gcacgtggga ggacttgcgc   27420
ctgcagattc acgtgctgtc gccgtacgcc gttacggcaa tggtcacgtg gaatatcgcc   27480
agcgaggaca aggccaagct gattgttggc ctggtgctcg cggtggcgag cccggcgctg   27540
gctttcttca acacacgtga cgggttccgg cgctgggtgt acggactgct gccgccgctg   27600
caggcgttca tcgttggttt cggctgggcg caggattcga ccctgacgcc gctcatggcg   27660
gcgatcgtcg ctctacttgg cggggcaatg gccgccgcta acacgccgtc gagccgcggg   27720
ccgaaagaca cgcggacggc ggccgtgcgg tgagcgatgg aatcacagcg tttgaagctg   27780
tcgcggcctt cgctgggtcg tcggtcctgt cggtgtccgt cggggcgctg atggcccggc   27840
gccgcgacaa cttcaaggcg ctgaccgacg ttctgatgga tcgggttacc aagctcgaaa   27900
cgcgagtcga cacggtagag acgaagctcg acgccgagca gatcgcgcac gagaaaactc   27960
gaatggtgct ggcggcccgc gaaatgacgt tggccgccgc ccgcgcattc atccgcaccg   28020
ttcagcgctg ggcagccggt gaccgcgtag acccgatccc gacgccgccc gacgaggtga   28080
tggccgaatg agcctcgctg agcgcctggg cgacccgcag cccgcgccgt cgagtgagtg   28140
cgccgtgtgc cgctggctcg acaacgccga cgagaccgac cgcgcagcgt tcgacaactg   28200
gctcgcttcc ggcgggtcac tgtcggcgct gtggcgggcc tgcgccaccg atcccggcaa   28260
cccgctggcg atcaagcgcc cgcggttctc tgagctgatc aacgaccatc accgaggggg   28320
cgcacatgtc gctgtctgac aggctcgcca caccggcagc cgcaaacgag aaataccggc   28380
ccacggtcga gttcgacaac cgcggcgcca cgatcgacac gggcaccgtg taccaagagc   28440
cgggccagcc acccgagtac gccgagattc tgcgccaggt cggccgcgac cccgaacggt   28500
tccggctcgt cgagattctg agcgagaagc attggcaggt gccatatcgg ccgtacgtgc   28560
gcgacgacga cggtcagccg atctttaacg agttcggcaa gccgcgcctt gaggagcaag   28620
agtttcgctg ggcggcgtcc tacaagctgc gcgtcgagcc gatcgaccgc ggcggcccga   28680
gtgaccttga ggcgttgatc gccgacgccc gcaaagtgcc gatgatcgaa ccggcgacca   28740
cctcgccgta ctggtacgtg tttcaagctg gcgacttgca gctcggcaag cggtcgcgtg   28800
acggctctac cgagcagatc gtcgagcggt tcgtgcagtc ccttgaggcc gccgggcggc   28860
agtaccgcga gctggcggcg tccgtcggcg tcgccggtgt gcaaatctcg atgccgggcg   28920
actgtatcga gggcgtcgtg tcgcagaagg gcgcgaacag ttggctgacg caggagcgac   28980
tcgccgagca gttccggctg ctgcggcggc tgatggtcga ggccgtcgac acgttccgcg   29040
cggccccggc cgtgtatctc gacgtggtga acggcaacca cgaccaggcc aacggcagt   29100 ggaacaccaa ccccggcgac gggtgggcga ccgaggcggc catcgcggtg cgcgacgcaa   29160
tggtgctcaa ccgcgacgtg tacgacacg tcgaggtgcg ggtgcctgag ccgtggtcgg   29220
gcagcatgac ggtgcccgtt ggcgacaccg tggtcactgt gatgcacgga caccaggcgc   29280
ccaagggcaa ggccctcgac tggctcgcca agcaggcggt gcacaaccag cccgcggggg   29340
cctgccaagt gctgcagcac gggcactggc atgtcggcgc cgtcgaaatg cacgccacca   29400
agacgatcgt gtgctcgccg acgttcgact gcggcagcga ttggttccgc gagcgccagg   29460
gcggcgagtc ccgccgcggc gctctcacct acctgctgcg cagcggcgag gtgtcgaggc   29520
tcagcgtgct gtagcaaccg ccggcaaaaa cctcgagcgc ctgccgtgac ctgcgccgat   29580
```

```
caaccgaaac gccgatttcc ggcaaacact gcgaacgccc ctcgtcgatc cgtcggcggg    29640
gggcgtttcg tcgtattgtt gacctgcata caggcggccc gtattgttgg catggcaaca    29700
acggcacgac gggataggag ccccgaaatg agcacggacg taatgacagt gcgcaagctg    29760
tccgaacagg aggccgccgc tatggcgcga ggcaagttgg tcagtgtggg aggcacccgc    29820
cgaacgatcc cggcggcgaa cgtgccgcgg tacgaggaga aggtcgcggc gatcgaggcc    29880
gagtggcccg cgccgacga ggcgcacatt cggcggcgg caatcgaggc tgtcggccgg     29940
tacctgtgcg acgaggccga cctacccgag gcggtcggcg aggagctggc cgaggcgaaa    30000
gagcagtacg aggccgcgac gtcggcggct cgcatggtcg tgcgcctggc ggtcgaggac    30060
aacgccagcg agctgagcct cgcgcagcgt atgggtatca accggctgac ggtgcgcaag    30120
taccgcggca aggttgatcg ccgttggcag cgcccgtgac cgccgcgccg gtcgggtctg    30180
aggtctgggt gctcgacgtg tcgatcgagg ggccggaggc tggcgactat gacggctggc    30240
agtcggtgca cgcgagccgc gagggcgccc tcgggcgct gctcgacaag ctcggcgagc     30300
atggcgtggg cctcggcgcc gacgtcgaca cgatcgccag cgcggcggcc gacaatggca    30360
gcctggcggg cgactttgcg atcgacgagc tggcggtgag ctacggcgtg cacctgatgc    30420
cggtcgagcc ctgaccgcac gtgttgacat gcatacagtt cgcgggttac tgtatgcaca    30480
tcaacaacgc acacgggata ggagcccacg atgagcgagt acaccaaggc tgaggccaag    30540
gccgccgatg cgatcctcgc caagctgacc gatgagtttt tcgaggcgta tgccgcctgg    30600
gagcgggccg cggatcgcct gcacagcgcc gcgggcgacg acaaaacccg gtacggctgg    30660
aagatgagca cgacgaggc cctcgccaag gcgaccgagc gggcggccga cgagcggatc     30720
gtcaagtgga atcgggacgg gtacgcccgc ccgtcgagg cgtaccccgc cgcggtggcc     30780
gccaagagcc ccgccgacaa ggcgatcgac gaccacgagg ccgccaacta caagggctgg    30840
ctgcggttct tcctggtgcc gggcgggcac attcaccgct cgcgcggctg ctcgtcgctg    30900
cggatcacga cccgtatcgg ctggctgccc aacctgtcgg gcgagaccga ggccgaggcc    30960
gtcgccgcac acggcgcgat gctgtgcacc aagtgttttc cgtcggcgcc ggtcgagtgg    31020
acgatgggca agcctgccga tcccaacgcc tgccccggta gcggcgagcg gccggtcgag    31080
ggcacgatct cgcgccggta ccgcagcgcg tacgccgagt gcaccggctg cggtgtgcgg    31140
caggtctaca ccatgtcggg cgtgatcaag aagcacaagc gccccaaggc caagtagcac    31200
cggccccgcg aggcccccgt cgacacggcg ggggcctctt tggtgttgac atgcatacag    31260
cagtgtggtt attgtatgta catcaacaac gccacgggat aggagcccac aatgaccagc    31320
acgaccgtca cctaccaggg aatgaaattc gtcgtcgagt cctacgtcga cccgtgcccc    31380
ggcctcggcg cccgcgatcg tgtcgagtgg gtcgagaact gcgggcgctg cggcggcacc    31440
ggcgttttcc gctgggtcaa cgcgatgggc aactgcgagg gctcgtgctt tggctgctgg    31500
ggtaccggca aggttgagcg ttcgcaggcc gcgcagaccc tccgcaagat cgcccgcgac    31560
gaggccctgc accgcgagca cggcgacgca atcgccgagt accacgccaa cattgcccgc    31620
gagaacatgg cgcgcgagct ggcgaccgcg tgggatgagg cgcacgccga gcaggctcgc    31680
cgcgaggccc ggctcgccgc gatgaacaac aacacggttg gcgaggtcgg cgagcgactg    31740
cgcaacctcg acgccgaggt gatcgtgtcg gccggatttg agcgcgacgc ctaccgcggc    31800
tacggcaccg agtacgtcaa gatcgtggtt ttcgcgctcg ccgacggccg tcagctcaag    31860
gcgatgggca ccgcagcag cctgtacggc ctcgaccgcg cgacaaggt gcgcgttacc     31920
ggcacagtca agggcaccgg cgagtaccgc ggccaggtgc agaccatcct gcagcgcgtc    31980
```

```
aaggtcgagg cggcctgagt gccctcgacg acgacgcccc ggcgggatta cctgccgggg   32040
cgttttcgtg tccgtacggg gctactcggc cgtttctggg cacagctcgc gctgcgcgct   32100
gaaagcgatg ccgtcggcgt gctcgcgcgt catgtcgaga accttcagaa acagtcgatc   32160
ggcgatcacc tcgcgcggct tgcctgcccg cagctcgtcg cacacggcgt agccgagggc   32220
gagcgcctcg cgctcgtcga gtatgtcgag cccgtagtcg acgctgatcc tcgctaggta   32280
tccggcgtca ccggcgtggg cggcgccggg cgccaggacg acagcggcgg ccccgatcac   32340
ggccgcggcg agtattcgtt tcacggggcc gagcctaatc ggcggggcct ggtctgcggc   32400
ggcactccgc ggtaccgtct ggcctatgcg tcagtttccc ggcacaccgt cgagcggtgt   32460
ttgctggcgc ggcaaacaaa gtggggcgt tgatggggtg ttgatgccat caacacagcc   32520
cccgttgtcc tgcgggtttg gccgtatttt cgcgtactct ggcgtgtcga actggtgcat   32580
ttcgccaggt cggcggcact aaatggtgca ggttcaattc ccggcagctc cacccgtaaa   32640
ggccctggtc agagacatat tttctgaccg gggccttttt acatcaacgc tcacatcaac   32700
acatctgtaa tatctgcggc tatggcctcc ctccgcacca gctcccgcaa agatggcagc   32760
acctacacat cggttctgta ccggctcaac ggcaagcaga cctcaacgtc gttcgacgac   32820
ccggtgcagg ccgtcgagtt caagcggatg gtcgagcagc tcggcgcggc caaggccctt   32880
gaggtgatcg agacgaccga cgccgccgcc cggcactaca ccctgagcga gtggctgagg   32940
cactacctcg accacaagac cggcgtcgaa aagtcgacga tctacgacta cgagaaagtt   33000
gtcgccaagg acattgaccc ggtgctcggg ccgatcccgc tcgccgcact gaccggagac   33060
gacattgcca agtgggtgca ggccctcgcc gagcgcggcc tcaagggcaa gacgatttcc   33120
aacaagcacg ggtttctgtc gtcggcgctg aatgccgcgg tgcgcgccgg gcgcatccct   33180
ggcaaccccg ccgcgggcgc tcgcctgccg cgcactgaga agccgaaaat ggtgttcctg   33240
acgcgcgagc agtacgccaa gctgcacgac aacatcacgc tgccgtggca gccgctcgtc   33300
gagttcctgg tcgccagcgg cgcccgctgg ggcgaggtcg tcgcgctgcg gccgtccgac   33360
gtcaaccgtg acgccagcac ggtgcgcatt tcccgcgcgt caaagcgcac atatgaaaag   33420
ggcagctact ccgtcggtgc accgaaaacg cacaagtcgg tgcgcacgat caacgtcgac   33480
gcatcggtgc tcgacaagct cgactattcc ggtgagcacc tgttcacgaa caacgtcggc   33540
aacccggttc ggcacaacaa ctttcatgcg aacgtctggc agcctgcgct caagcgcgcg   33600
ggcctcgacg tcaagcctcg ggtgcacgat ctgcggcaca cgtgcgcgag ctggctgatc   33660
gccgccggtg tcccgctgcc cgcgatccgc gaccacctcg ggcacgagtc gatcaagatc   33720
acggtcgaca cgtacgggca cctcgaccgc agcagcgggc aggccgtggc ggcggccatc   33780
gcggcgcagc tcgacccggc gcgcggctga gtgcacacaa tcgagcccg aggttggtcg   33840 cctcggggct cgtttgctgt atctggggtc tgctgcaggt cagcggccaa ttcgggagtt   33900
ttgccggcgg tagctaggcg gcctctcgct cggtgtcggg gtgcaggcgt cggcggtgcg   33960
cctcggcggt gtcgtcgcgc agttcgcggc ggctcgtgcg ggtggctcga atcagcccgc   34020
gatacgggcg aatcttggtc caccacgacc aggcgaggca cgccgacagc atgaccgtgg   34080
tcacgtaccc gcagaccgag atcattgccg taatggcgtg ctgggtggcc atgaaggcgc   34140
tcgccacggc gagggcgcag cacgcgatgc agaacgccag ggcgatgatc cagaccaccg   34200
caatgcggcc ctggtgctcg tcgtgggcga tgtgccacag gcaggcgact gccacggcga   34260
gcagatgcag tgtcgcgtag tagtgcagcg ccgtcgcccc gacgatgcca atgtcagtgg   34320
```

```
cgggcatgtc gagcatgttg tggtgcacgc tgggctcgcg tagcgccggg ctgctcatct   34380
gcagcgccag tgtcacaacc ggcgtgaggt agagccacgg agcgacccaa cgcgcgaagt   34440
acaggcgcac ctcgtcgtcg tcgcacactc ggtgcaacat gctgacggcg atagcgccgg   34500
cgctgaacag atagagcgtg cggccgagcc agtcctcaag gtgccagaca ccaactacgt   34560
ggtagatggt gcggccgatc gtcattgacg ccacggtgcc gctcagcgca gccccgacga   34620
gctgcagcag cagggccgag gtcagcagcc cctcgtgcaa gatccgaaag ctgcgccagc   34680
gcaacagaac tgccgcaaga gctaccacac aaacaatcca gcgcagcacg ataaatgcga   34740
cagctattga catagccact ctctcaggga aggcgggcgg cggcccgacg atcaaactgc   34800
cgcaactgta aaccacgcct cagagtggtg agaaattgca catcaaagac tcggaatgtc   34860
aggcctcact tgccttgtcg tcgagcgcg gcgggtcttc ttcggcgctt ccttcacctc   34920
ctgcccgacc gtccgtagcg tctgagggtt ggcgcttggc gccagctcct cggcataggc   34980
gaggattgcg tcgtcactga tcaggttgta ccgggcaagc aggtcgacct cgtttattcc   35040
gagattgcgg gcggcccgaa tgaggttgtc ggcggttatc aggcgcccct cctcctgctg   35100
gctgtagtag cgggagcgcg acatttgcag cgcttccagc agttcgcgca gcttgagctg   35160
tctacccacg aggtagctca gcacggatgc gagcgacttg tcggtgtcgt cgtcggacat   35220
ggctcgtgat tcctgtctct cgatcgagcg gtttgttccc tggcgtgtca ctttagttca   35280
gttttcggga ctgaacaagt ctgtgacctg cctttatgca ctccttatgc gctcgttagc   35340
ttcccgaaat ttggcagatg ttccgatttt cgggactttt cgtgtagcgt cccacaccgt   35400
gcagacaacc actcatgagc tgaggtggcg gcgcgacaag gtggcaaaca ggatgcgccg   35460
caacaacatt caggatcgtg caactttggc aaaaaggatc aacgtcgggc gaaccacgat   35520
ttactccact ttccgcgcgg actggtcagg tgtggcaacg cacacggtgc tggcgcagat   35580
cgtcggagag ctgggggggct cgctatctga actcgtgtca gttgaggccc gcgcatgacg   35640
gccccgcgc tgacccgtcc gcttgctgag gtcgcgcac tgattccgtg ttctgagcga   35700
tggctgaccg agcaggttcg agccggtcgc atccccggcc gcaagatcgg ccgccattgg   35760
cgcatgacgc aggccgacgt tgacgccgcc cttgagtcct tccgagtcag ccccgagacg   35820
ggccgcaagt cggtcgcatt gcctgccgac cggccgctcg cacttacccc cacctcacgc   35880
cgtcggacta ggagccgctg acatgccgat gaccacccgc acccgcaacc tgccgccgc   35940
ggcccggctg cgcatcgagc tgaacgaggc cctgcgcgag cgcaaccagg cccgcagcga   36000
gcgcgacgcc gggcgccagg tgatcgccga ccaggccgcc gcgctgcaca gcctcggcga   36060
tcagaacgcc tacctgctgc aggagcgcga cgagctggac gcggcgcacc gggcagcgct   36120
ggccgacctc ggcgaggcgc atcgccagct cgctgagcgc gactcgctgg cctcgcacct   36180
cgccacgatc gcggccccgg cgccgctgca tgacgagccg gatatggagc ggttcggctg   36240
agcttggggg tggggcgtca aacgggttct tacttcttct gtcccgcaag cgtggcccac   36300
gacccgctga ctactcccgg cgaggtcact gctgcgcccc acctcccac aaacgacgca   36360
gccccgcgct aggcggggct ggccgacaca accaagggat aggagccact tgttatgtcg   36420
aacaggatct taacgcacaa ccgcgtgtt tcacccgatc ggcggccgg cgagcgcctc   36480
ggcgcgatcg tcggcgtgtt cctgctcaac gccgcaatga ccgtcgtcgg cggtctcgtc   36540
ggtgccgcgt gggtcggtct gtacctgggg gcgccgtggt gatcacgctc tcgcacgaag   36600
agatgaaggc agccgccgcg gtgctcgaca cctaccgggc cgaggggctg accagcctcg   36660
gcgcggtggc cgccgcagtg aacgccgtca acaagctgcg cacgcccggc cggtcggccg   36720
```

-continued

```
actgcaccga ctgccagcgg tgtgacgcca cctgccccgg tcacgtcaag gcgcaggcgg    36780
tggcacagtg acggccgcgc agctcggcga gggcgaggcc gctgtgcgcc ttgggattac    36840
gcgcaacgca ctgcgctggc gccgccgcag cggcacggca cccgagcacc agctcgtcgg    36900
ccgcaaaatt atgtacgacg ttgcggcact tgacgaatac gccactgcgg ttgacaacac    36960
gcacgtgctc gacatgttca ccccgcgggt tggcgacacg gcgaccgctg acgaggtgtg    37020
ccggttgctg cgcatcgacc aaagcgacgt cctgggcaag gttttgaagc gtcacgtga     37080
cgaattggct gctcacggct gggatcgtga aagtggcacg ttcacccgcc gggcgatcat    37140
tcaggttgcg ttgctggtgc gttcgtcgac ctcggcgcgt gcaggtcgca tcgccaaggc    37200
cgccaaggca ggcagtcggc cgatcagctt cgaccacagc ccgcggtcgc agcagtgcac    37260
tcacatgctt gagcgcgcat tcgatctggc gaccgaggta cacgacgacg accccggcga    37320
ggtgtgggca cggctgcgca agctcgaccg tcacaccctg accggcgtcg ctgtcgccct    37380
ggccgcgatg gtcgacgttg agggcaccgg cgccacgaag tacctgcgcc acctgtcccg    37440
cggcggcctg gcggccgagg gcctgcagcg gttggtgccg actcgtgaga cgaccgacgg    37500
cgtgccgctg tcggtgctcg accagatcga ggccgacgac gaggccgacc agcacgacga    37560
gggcgaggtg gatcagtgag cgacgcaggg catttcgacg acgaccccga agcttggcgg    37620
gacaaggccg tgtgtgcgca gaccgacccc gaaatcttct ttccagagca gggcggcagc    37680
acccgcgagg ccaagcgcat ttgcggcggc tgccaggtgt ccgacgagtg ccttacgtgg    37740
gcgctgagtc agcccgtcaa cccgacgggc atttggggcg gcactaccga acgagcacgg    37800
cgacggatca agcgcggact taaaggggtt gcggcatgag cggttacggc gatctgtgcg    37860
gcagcgcgca gtcgatgtg tgcggcaagt acgacgcgca ggtgttcgac ccgtgcggcg    37920
ctatgtggtg ccgggtgtgc gacctgatgg gcctcggcgc cctggcggtg agcgagcggg    37980
ccgacgaggt tgccgaggcg gtcggccgtc ggttcgacga gacgctgcta ttcggagtgg    38040
atgccgacac tgaggcgttg cgcgaggcgc tcggcgacgc gctgcgcgag gcgatggcga    38100
cgccgatcga ccatgcggcg ctgctcggcc aggtcgacag cccggcaacc gaggcaggcg    38160
accccgaggc atgggtgccg gattacgcgg cgataaaccg caattggcgc gagctggcgg    38220
gcgagcccaa cgccgccgag gccctcgacg acgccgacaa ggcgtacgtg tggcaggaca    38280
ttctcggcgc gcactgggc tggctggatg gcagcggttg ggttgcgtgg aatagcggcg    38340
tgtacgtgca tggccgcggt gcggttggcc cgttcaaggt cgcataccgg cggcccgtcg    38400
gcgagttcac cccgatgctg ctcgaactcg gcggcggcct cgtgttcggt tgcgacatgg    38460
cccacggccc tagcaacgac accggcggcg cagaaaactc cccgaccagc gcagacagct    38520
tggcggcga gctggacgag caaacggcg acatggtggc gcacccgtcg cactacacat    38580
caagcccggc caagtgcaag gcgtgcggtc acccaatcga gtgcatcgac attacgcagc    38640
acatggggtt ttgcctcggc aacgccacca agtacgtgtg gcgctgcgac ctcaagcacg    38700
acgcaatcga ggacttacgc aaggcaattc agtgcatcga gtttgaaatc gcccggcgcg    38760
aagcgctgag cacaaccgag ggataggagc ccacaacatg attcgcaaga ttgccgtcgt    38820
cgccaccgcg gcactgatcg cagcaggcgc caccgcgtgc gagggcggcg cagatggcgg    38880
cggcgggcac caggataacg ggcctagcgg cgtgatcttc attccgcagc cgggcctgcc    38940
tggcagcccc ggtatcccga tcttcttctg accaacgacc aaccaccgaa gggacacaac    39000
gcaaatgcag atgatcaacc ggattgccgt cggcatgacc gtcggcgcga tcggcgccgc    39060
```

```
cgcggtgctg tcgggctgcg ccacaaccaa ccaggaatgg cacacgggtt gcaccgtcaa    39120
ggccaaggac attgtttacg gcggcagcga cggaaacacc acgcggacaa agcgcgtcac    39180
cacgtcgtgc ggatcgttca acgccgagga cgcgatcgag gtcgggcact tcaactcgtg    39240
ggacgtctgg gagtccgtcg aggtcggcaa gacgtacgac atgttcaccg gcggcccgcg    39300
gatcggctgg ctgtcgacgt tcccggttct gctggaagtc aagccagcac agtgaccgtc    39360
agcaaccggc cgtggtgggc cgaccgtgag gtcgtcgagg atctggtcga gcagaagcgt    39420
ttcgacgcga cgctcgccta cctcggcggc ctcgccgacg ccatcgagca ccggatcgcc    39480
tacggcgttg acgacccggc ggcggccgcc agctcgtcat tgcgcaacct gcgcgagatt    39540
caccgctggc cggttgagtt cgcggtcgcg tggggcggcg actcgctcac gcggccgatg    39600
ctcgtcaccc cgttggagcg tcagcgcgaa ctgaccagcg gcctagacga cgtgccgagc    39660
gtgcgggaca tggccgccag gatcgaccgc cgcgagtttc tgcgcaggcg acaactgaaa    39720
agggataggt aagtggatat ttcagcggta aagggtcacg tcgacctgct cgcgcacgcg    39780
cggatcgaga aaagaagtg gaggaaatc gagaagaacc caaggcggc gatcgacgag    39840 gcgctcggcg gcgacgacga gggcacggtc ggcggcgagg ttgtcgtcaa gcgcagccgt    39900
acgaaggtga cccggctcag cggcaagttg gtgcaatcgc tgcaccccga ggtttacgcc    39960
gagtgcctcg acaccaacga gcagacgcgc ctgtcggtgg tgagcaagtg aaggtttccg    40020
agacgcacca cacgacgatc acggttgagc ctggcgacaa ggtgcgcgat ctgtacgcgg    40080
tgctcgacga gatgccgaac ggcgccgaaa tcagcgtgta cgcaccgctt ccgatgttca    40140
acaccaaccc gaccgtcaac cagtacgccg gggtgatcag cgtcgatcac ctctcaatcg    40200
agggatagga gcccaagcat ggcaaggaaa ttgatcgtgg tcgacctgga aacgaccagc    40260
ctcgactacg acaccgcggc cccgttggag gtcgcactgc tcaacgtcga caccggcgcg    40320
tcgctgcggt tcgtgccgca cgtgacgtgc gagcagctcg gcgcggccga cccgaaggct    40380
atggaaatca cgggtacta cgagcgcggc gtgtggcgtg aggcgttgga cgagcggcag    40440
accgccgtcg cgtggtccga ggtgcaggac tggctgcgcg gcaacacgtt gcgggcagt    40500 aacccggcgt tcgactcgac gatcgtcgcc cggcagcgcg ccgggtgcat gttcacatcg    40560
ccggtcggtc gggtgtggca tcaccggctc gctgacctgg cggcgtactc agcgggcaag    40620
ctcgaccgcg atcctgccga gctggtgggc ctcgacgacg tggccgagcg cctgggcgtg    40680
caggtcgcgc agcggcacac cgcaattggc gacgcggcag cgacgggcct gtgctttgac    40740
gtgctgcgca acaccgcggc ggcgcacctg tgagcgagaa tgtgaccgtc ggccgcgtgt    40800
acgtcggcga gaagcccaag cccggcggta ggacaaggga ttacgtcgac gttcgcgtgt    40860
cgccgaagga cggcaacgtg tgggtctcgc cctcgtctca gcattcgatc aacgtcgacg    40920
aggaccaatc gcgccggatc gccgacctga tggcacgggc acatgccgcg gccccgtcga    40980
tcgttgcggc ctaccagacc cgcgagcggg cacgggagac ggcgaacgcg acgtaccagc    41040
ggatcgtgcg gcgcgctatc gaggtggggc gctgatggcg ttcaactggg cagggcagcg    41100
gatcgagccg ggcgcggtcg tgtggcgcgg cggccgtgat ggaaacacaa gcagtttcaa    41160
ggtcggtcgc gtcgaggccg tcgacaggac ggcgcgcgtc cggtgggtcg ctgagatgga    41220
ttggcgcggc aacgtccggc tgctcggcga caagtcggtc gggcggccga atgtcgacag    41280
cctggcgttg atcgacccgg cgacattgag caacaaggtg cgggaggcat tgcagcggtg    41340
agtaatccaa atttcgtgca tgtggggcgc gttgtggtgc ggcccgccgg gcgtggtggg    41400
ccgttcgacg atccggcggt cgaggtggtc gtcggcgtcc gagctgacct cgggcatgtg    41460
```

```
gtcgtcaata ccagcgggca aagggcggc gttgcgccgc cgctgacgcc cgagcaggcg    41520
gcggcgctgg ccctgctcgt cgaccgggcg gccggtgtgg cgcgcgagct ggcggctgcc    41580
tatcgcacgt accaggaggc ggtgcgggcg gccgaggaga agctcgccgc cgcggtgaat    41640
cgtgaggtcg gcgcatgaag gtgagtcttg ctctgaccgt gctcggttgc cacctgggca    41700
cgctcgacgt cgaggtcgac ggcgacgacg acaccacggc ccccgcggcg ccggtgaagg    41760
cggcagcgaa gccggtcaag tgggcgagtc gcctgtgggt taaggggatg atggcgtgag    41820
cggcaatgca gcgttttcg ggctgaccga cgacgcccc gagcgggatc ggccgccgac    41880
cgacgagcag cagttcaacg ccgatctgct ggccgacctc aagggcgtgt ttaaacgcgc    41940
ctgggcgcag cacggccggt cactgcagcg tgctctcggg ccgtcggaga ttgggcaccc    42000
gtgcccgcgg cggctggcct cgtcgatgct tgagctgcca cggattaacc ccagggcga    42060 cccgctgccc gcgtggctcg gcactgccgg tcacacgaaa ttcgaggatg cggtcaacct    42120
cgacaacgag cggattatcg accagtggct caaggaccgc gagcagcgtt gcacggttct    42180
gcgcggcgtc actggcggcg atgacccgca gtatgtcggc cggtggttca ccgagcgtcg    42240
ggttacggtg cgcggcggcc tgactggcac gtgcgacctg tacgacacgt ggaccgacac    42300
cgtgatcgac ctcaagtttc ctgggcgtc gcggttcgcc gagtacaaga agaaggccc    42360 ggcgcccgag tacaaggtgc aggcgcacgc ttacggccgc gggtaccgaa cgagggggtt    42420
ccccgtcaag cgggtggcga actggtatat cccacggggc gggtcgctcg cgtcgtcgtt    42480
cgtgtggtcc gaggcgtaca acgacgagat tgtcgaccag gcgctcggca agctcgacaa    42540
cattctcgtg ctgctcgacg agctgcaggt cgaccagcac cccgaacgga tcgccatgct    42600
gccgaaggtg ccgagcagtt gcatgttctg cccgttcttc tcaccggcgg ccggtcgccc    42660
cgagccgcac gcctgcacgg gtggtgcgca gtgaagcccc cggcgccctg gcgcattcgc    42720
cagctcgtcg aggggccggt cgtcgtcggg tgggtcgtcg agcagttgac cctgtacacg    42780
ttcacgcccg gctcagttga gggcgagtac gtcactgtcg actacttccc gaacggcccg    42840
gcggcgatcg acgcatttgc cggatacgg agtttggcga tctgacatgc accgatgcaa    42900
ttttgccggc ggtagctggc aggggatagg agcccaccat gagcagtaac ccgaacgtcg    42960
cggcgattgg cccggcgctc gcagcgcagg cgatcggcgc cgcggtcacg atcgccgaca    43020
cctcgcgggc aatgtggctg cagcagcttg ccgtcgctga ggctaccgag cgggtgcagg    43080
atcggcagtt gcgcctgctg ttcgcacagc gcgcggtgat cgacgaccag atcgaagctg    43140
cgacgagtaa gcgtgacgag gcaacccggc tcgtgctgca ggcgcagaaa gcgctcgacg    43200
tgccgatgat cgtcgacaag ctcgatccgg ccaaccccgc tcaccgggcg cgcgtctggc    43260
gcggccaggc gggcgaggtg tggcgatacc acgatgacga gtacgccaag atcggcgacg    43320
gcctcggcac gttcctgtgg acgtacgaac accggcagc gattccacgc caggccgatg    43380
ccccgacggg cggcccgttc accgaggtgc gggagtgagc gcgggcctgc ggtcgacgtt    43440
caccgcgaag tatttcggcc gctgcggcgg ctgcccgagc cagatccgac ccggcgagga    43500
ggtggcgttt atggctgatg gcggccttat acatgttgat tgcgaggaca actcgcatga    43560
gcccgtaaac gcccgcaagc ggccgacatg cccgcactgc tggcttgagc acgcaggaga    43620
ttgcccgtaa tgagttcgca ccgttgcgca ggtgacgact gcgggttttg cgcgcaacgg    43680
atcgaacagg ctgagtatga ccgcgactgc ccggccgacg actatcccga ctactacgac    43740
gggacatgag ccacccgccg cgcctggcgg gccgagaggg aaacgggcgc aacgcaataa    43800
```

```
cggaacaact gaacaaagga acaactgaac aatgagcaac gactcgtacg acttcctcgg   43860
cggcggcggc gtcccatctg gcaagttcgg cagccccggc gacaccgtgg gcggcgtaat   43920
cgccatcgag cccgagcagc ggcagatgac cgattacaag accggcgacc tgctgacctg   43980
gaaggacggc agtccgcgta tgcagctcgt cgtcaccctg cagaccgatc tgcgcgaccc   44040
cgaggtcgag gacgacgacg gcaagcgtcg cctgttcgtg aagggcgaaa tgcgcaaggc   44100
tgttcagaag gcagtcattt cggccggtgc ccgcggcctg gacgtcggcg gcgagctgca   44160
cgtcacctac accggcgacg gcgacaagaa gggcaacctg gacccgccga agctgtacag   44220
cgccacctac aagaagcccg caccgggcgc agccgcggcg gccccgcgc aggccgaccc   44280
gacggcgggc atgacgcccg aggcgctggc cgcactcgct gccctgctgc cacagaagta   44340
agcgcacaac gcgctgcgag ccggtgacgt tccgcaacgg ggcgttaccg gctcgctctg   44400
tctaacaagc catttcgacg agggatagga gcccaccgaa aaatgctgac gatctacaca   44460
accggccccg agtgctacaa gtgcaagctg acaaaggatg cgttcgacaa ggcgggcatc   44520
gactacaccg aggtgaatct cgccgaggtc gacgaggctg tcaccgcgaa gttcgttgcc   44580
gccggtcacg cgcacgcccc ggttgtcgtc gacgagctga ccaacgccat gtggtcggac   44640
ttccggcgcg atctgatcaa ggccgcgatt aaggcccgcg catgaggcgc cgcgcggtaa   44700
tcgccctggc cgccgcgggc gcaatcctgc tggctggctg cgctggcact gacccggcga   44760
ccggcaacga cattcccgac tggatcgccc cgcacaccgt cgacctgccc gacggccgaa   44820
aggtgttgtg cgtgtgggaa aagttcgact acgccggggg cctgtcgtgc gattggagcc   44880
gggcacagtg aacggcgccg aactgttcga ccgcatcgcc ctgacccgag ctgacggccg   44940
ctgcgagtgc gaaggtgctt gcggcagtag ccatcggttc gccggtcaca cccgctgcgc   45000
caacgtgcac ggccgcccgg cgattcacgg cgccgacaag gtggtcagcc tcaccgtggt   45060
gccgcgcaac ggcgacggcc ggaatctcgc tgacggcaac ctgattgcgt tctgtcaggc   45120
gtgcctcaag cggcaccgcg ccaagctcaa agccgccgcg gacaaggccg cagcccgcgc   45180
ggcggccgag gctgccgacg gcgggctgtt cgacgtgccc gacgtcccgg tcactgcagg   45240
caacggcgtc acgctgtgaa cgcgcgagca gccttgcccc acaactgaat agaggaatga   45300
gtgaacggcc taactgatct gctcgaactg ctcggctacg ccgacggcga gcacgtgagc   45360
ctcaactacc aggcgcccgg cggcccgttc tcgtcgacgg tcgtcgagta ccaagaggac   45420
agcgacagcc tgcagggcct tgcaatgtcg ctcgccaacg gccgcaactg ctggtttggt   45480
gtcaacccga cgctaccgcg gccggtcgac gctgacggca agcagaaggg ccgcggcggt   45540
gccgacgacg tgacccggct cgctgcgatc tggtgcgacc tcgacgtcaa gcccggcgcc   45600
tgccgcgaca ttgcgcacgc gcaccaggtg atcgacgagc tgagcgcaat tctcggcacc   45660
cggccgagcg cggtcgtgta cagcggcaac ggcctgcagc cgtattggcc gatcgacgac   45720
ggcacgatcg ccccggccga gccgctcggc gacctcgacg agcagacgat cgcagcgagc   45780
gctgagctgc gcgccgacgc ggcggccctg ctcaagaggt ggggccgcct ggcgtgcatc   45840
gtcgctgacg gcctgggcgc caagatcgac cgaggcgtct acgacctggc ccgcgtgctg   45900
cgcgtgcccg gctcgcacaa cctcaaggac accgacaacc gaagccagt cacgatcgac   45960
ggcgacaccg gcgccccgct gggcctcgac gagctgcgcg accggctcga cgagcacggc   46020
gtcgctgagt atgagggcga ccggcgcacc tcgcacgagg tgatcagcaa gcccgacggc   46080
tggacgttcg cgccgagcac ctgcgagtat ttcgcgccga cgatcagggc gtggcgcgag   46140
gagccgatca ccgagcggca cccgtggctg gtcaaggtca ccgtgcggct gatggcagcg   46200
```

```
gttcgcaaca agtgcctgac ggccgacgag tacgccgagg cccgcaagat gatcgtcgac    46260
aagttcatgg ccgagtgcgc ggcgactggc cgcgacgtgc cgagtttcga gattccgaac    46320
gcattttcgt gggccgagca ccacgtcgcc accaagacag acgccgagct ggcgaccgag    46380
ttcggctcgc acctgcacct gtggcagcgg gccgagcccc ggcagatcga gcttgcgcct    46440
atgcccggcc tcgacgaccg gcagcaaacc gccggcattg tgtcgaggg tgttagctca    46500
gagggatcat tagccccggt cgtggacatt aacgcccggc gcaatccagt tgccccggcg    46560
gtcacgctga ccgacaccgg caacgccgat ctgctcgtcg aggcgtgggg cgccaagctg    46620
cggtactgcc ccgacacggg caagtggctg agctggaagg gcacccgctg ggagcacggc    46680
accgaccagg gcgaggcgat cgtcgccgcg cgccaggtgg tcgaggcgat caagctcgac    46740
gacgacagcc cgaaagacgt tatccagcac cgtatgcgca gcctgtcacg caagggactt    46800
gagaacatgg tcgcgctcgc caagtgctcg cccgacatgc gcgtgcgcct ggccgacctc    46860
gacgccgagc cgtacgagct gaacacgccg agcggcgtcg tcgacctgcg caccgggcac    46920
ctgctgccac acagccccga cgggtggcat acgaagatca ccggcgccgg gtacaaccct    46980
gccgcggtgg ccccggcctg gcagaagttc cttgctggca cgttcggcga cgacgtggaa    47040
ctgatcgggt atgtgcagcg cctcgccggg ctcgccgcga tcggcaaggt gacgcaccac    47100
gtgctgccgt tcctatttgg tggcgggtcg aacggtaaga gcgtgctcat ggacgtgctc    47160
gcaaacgtgc tgggcgacta cgcgattaca gccccggcca acttcctgct ggcgggccgc    47220
gatcggcacg agacggagat cgcccggctg cacggcgccc gcatggtcgt gtgttcggaa    47280
atcaacgctg agagcaagtt cgacgaggcc aaggtcaagg tgctgacggg tggcgacatt    47340
ctgtctggcc ggtacatgag gcaggactat ttcgacttca ccccgtcgca cacgctgttt    47400
ctgatgggaa accatcagcc ccaagtcagc gcgggcggta catcgttctg gcggcggctg    47460
cgcctgttgc cgttcctgca tacggtcccg ccggagcagc gtaacccaa tctcgccgct    47520
gagctgatcc gcgacgaggg cgccgccatc ctggcttggg tcgtggcggg ggcgcgtcaa    47580
atcgccgctg acggcctccg cgagccgggc tcggtgttgg cggccacgaa ggagtacagc    47640
gagcaggagg acgctctcgg gcggtttatc tcggagtgct gcgagctgac gccgggcgcc    47700
agcggcgggg ctaaaccggc actggtgttg aaggcgtatc agcgctgggc catgtccaac    47760
ggcgaggacg cgatggtgtc tcagatcaag ctcgggcgtg agctgtcggc tcggttcggg    47820
gtgcgcagcg tggcgactca tgggcagcgg gtctatgcgg gcctggccct gcaagcttcc    47880
tgggacttgt cgcacgagct ggcgggcggg ttccgctgat gctgcggtgg ccctcgcaag    47940
cgacggcggc agctaacggc acagattcgt gcccgaagcc gtgcccggcg gcacagatgg    48000
cacagattgg cacagattca aaagcgaac ttgtgccgc gttgccgcag gtaaatcccc    48060
ttaaagggc tttgggcaca gatggcacag attttacgg gttgacatca cgtgtagaga    48120
ttcggggcgt tttccctggt cgagtctcgc tgagtgcgtg gtgtgggct catatgcgaa    48180
aaagtgtgcc atctgtgccc gacccgtgcc gagcaaactc cgagacgcgc cccgcgtagc    48240
gggggcctgg cggggcgctg accggcgtcg ttgacggttt ccgccgcgag aatgcagctc    48300
gaccacaact gaatatggag aaatgagtga ctgaccacac tctcgacctc gggcttgccg    48360
ccgaccaggt gggcgctgcc gaggctgccg agcgtgccga gctgcacgcc aaggctcaag    48420
ctgccgagct ggtgctcgac atgctgcccg ctgaatcgca tgaggccctg tatgcggccc    48480
tgagcgcccg tgtgacgcac gagcgcaacg ggggcaggca gttgcgcctg ttcgtgccgg    48540
```

```
gcaagcctgc accgcaggga tcgaaggact tcaagggggtt tgcgaagccg aagccggggg   48600
agacgcgagg taaggcgatc ctcgtcgagt cgagcgccgc ggtcgggccg tggcgcgaac   48660
gcatcgccct ggccgccgcc gacgcgatgc tcgccgccgg gctgccggtg ctggacaaga   48720
aatttccggt cacggcgtcg ctgacgttcg ttatgcctcg cccgtcgggc acgcctaaga   48780
gctacacgcc cgcggctgtc aagcgtcccg acctcgacaa gctggcccgc gccgtgttgg   48840
acggcttgac tgatgttgcc tggcttgatg attcgcaggt cgacgatatg cattgccgca   48900
aggtgctcgc tgcgatcgct cagcagccgg gttgccatat ccggttggcg tcgccgggtt   48960
ggggcgatga ggctatcgcc gcgtggatgg ctgcgaacgc gaacggagcc gagcatgttt   49020
gagctgccac ctgccgcccg tgaggctgcg cagcacgcca tcgctggcac gatcgccgac   49080
attgctctgc atcggtgcgc gccgtctgcc gagctggtcg gcgcgattgt cgacgccgtg   49140
gccgtgcaca cgactgtgct gccgccgcgg cctgaccgct acgagctgag cgccgacgag   49200
cgccgcgccg cggtgctggt gctcgttact cgccgccatg acgccgggtt tcgcagcacc   49260
gaggtgctcg acgaactgct cgctgcgatc aacgggctc gggggttcgg gcatgtctga   49320
gctgatcgag ttgtcggtcg ccgaggtcga gaagatggcc gaggttgtcg ccgcacgcat   49380
ttcgcacccg tcgcacacgc ccgctcgggc gatccgcgcg gggctgtcgg ctgtgaactc   49440
gatgcgcctc gacgatgcgc aggtgccgcg ggtggagctg gcgcaggatc gccgcgcgcc   49500
cggcacgatg ccgcgcccga tcgaggcccg tcgcccgttg gcgccggtgc ctgccggtaa   49560
gcgtcgtgtg gcgcatctgg ggatggctga gcggccgttt gtgtgggagg acgccgacgg   49620
cgatcactgg cgttggtgct tcatgcaatc ggtgtggcag tacaagcagt cgacgatcc   49680 gaacggcccg cagtgggtga actgcccgag tcagtacgcc gaccaggcgc cgaatccgaa   49740
ctatggaccg ttcacggagg ttggtcgggc atgagtttgc cggttctcc gagtttcggc   49800 gatccgcgca ggtcgccggg cacgccggtt gcgtcgccgg cggttagcta ctacgggtcg   49860
ccgcggccga ctgcgccgtc tgagttggac gtcgccacac cgcgcgttga cgtgccgcca   49920
gcgcatgagg gtaagtgccg ccattgtggc gccgaggcgc tcacgccgtt gtgctggtcg   49980
tgcacgcgca tgttcgcccg ccagctcgtc gaggtgcctt ggctgttgcg ccgtctgcat   50040
gagtcggcgt atggcgaggc gaaggtcgcc cgtaagggtg ggccgcgggt gtcgacgggg   50100
gagcgtctgc cgtcgttgcc gttgaacacg cgggcggccg acttgctgcg cgacgctgcg   50160
cgtttggtgg cgtggtggga gcaggtgcgt ggcgtcgatc agggcggcct gtgggacgcc   50220
tcgcgtgtcg agttcgctgc ccgctggctg gcgggtgagc cgggcgcgat gatgcgcac   50280 ccgtgggcgc ccgaggcgct gggctgggtg ttgcagtggc gtgatgacgc cgagcgtgtg   50340
atcgacttgc cgccggatct gcagtacgcc gggccgtgcc agaacgtcgt gcagccgccg   50400
agtgcgtcgg acgccggtac gccgttgccg ccacgggagt gcggcacgcc gctgtatgtc   50460
gacgctgagg ccctggtggt cgagtgctat cagtgccggt gttcgtggcg ggtcgaggat   50520
ttgcagcggc aggccctcga tcgggtcgac gagacggagc cccgcacggc cgccgatatg   50580
tggcgtctgt tcaagctgat tggccgcgac gtgccgcgca gcacgttcta ccggctgatg   50640
accgggattg aggctcacgg ctacaacgcc gacgggttgc ctgtttacac gtacacagct   50700
gtggttgctg cgctcgatgc ccgcgacgct gccgcggctg agcgtcgcgc tgccggtaaa   50760
ccgaagcgag gcaggccccg caaaaaggcg agtgttgaca cgcatacaga aggtgttgac   50820
gtgcagacag ccggggcgtt accgtctgcg ccgaagcaag tcacgggata ggagcccttg   50880
caatgttcac tgaaacgtgg ttttcacccg ctggtacgcc ggtgacgccg aaggttcgca   50940
```

```
acgaggtcga cgaggcgcag ctcgctgagc tgtatgccgc cgagtcgtcg ccggatagcg   51000
tgcggttcaa cgagctctac aacgccgcca gcacggcgac gttgtacgcc tggcgttacg   51060
ggtaccgcaa tccgcgggtg gcgggtcgcg tcgaggaatg cgaggcgctc gcgtgaagca   51120
ggtcaaggcg gttcgccgcc cggcgccggt cgccccgcag cccgacgttg tggtgcatgg   51180
ccgcatgttg gagccgggca ccgaggtgtc gatccgcggc gagcgtggcc ggttccgttt   51240
ccgcagtgcg tcgttgacga gtaccggccg gatcgtgtgc gacttcatcg gcggccctgc   51300
gggtcacgag acctggcggt cgttctatcc cgaccgtatc cgcacggtgc accgtttgaa   51360
ccgcactcgc gcgaacgctg cttagcgcgc aacgccctcg acgctggtcg ggggcgtttc   51420
tgctttcgtg ttgacatgca tacagcacac gggttactgt atgcatgtca acaacgcaca   51480
cgggatagga gcccacaatg tcgaacatca tcgccgccgc cgcccccgcc gcccgcaagt   51540
tcaacgccac tgccgcgctg aacatgattc tcggtatcaa cctgtcggac gggcagaagc   51600
gtgcccgtct gctcgccctg gcggtgtcga atgacgctgc ggccgagttc aatctcgccg   51660
ctgcccgcaa ggcgctggcc gccggtcgcc tcgccgaggc tgatcgttgc gtcgacgctg   51720
cggagttcta caacaaccgc gccaagcgcc tgcgcgacga ggcccgcgct atctagcgcg   51780
ccccggcgcg tcgccgcgca aaggtcaccc tggcgcccgg tgcgccccca gaatcgccga   51840
tcgagggata ggagcccacg aacgtgaatc gccacctgta cacgcaaccc gaactgttcg   51900
ccgacgtcga cgacggccgc cagttcgacg tctacgagcg ccccgacggg tcgcgctaca   51960
gcgtcgagcg ccccgctgcg gcggtggccc tgtgagcgcc gctgtgtcgc cgcgtgagtc   52020
ggcgcagacg tatttccgtg gctggctggc cgccggtgtc gtgacgtcga ttctgggcaa   52080
cgctgcgcac gctgcgctcg accctgacgc cgggtctaag gcgatcgcgg tcgcggtggc   52140
cgtcctgctg ccgctgggca tcctcgggtc gacgcacggc gtgcacaagc tcgtcgccgc   52200
tgggatcgtc ggccgcgcgt acacggcggc gctgagcatt tcggtgaccg tcgtcgccgc   52260
ggcgttcctg ctgtcgttct tctcgctcgc cgagctggcg gtcgactggg cagggatctc   52320
ggtttggctg tgctggctgg tgccggtgtt catcgacctg agcatcgccg ggtgcaccgt   52380
tgcactgttc gcgctgtcgg gtgcggagcg tagcgaggtg ctcgacgctg cggtgcacgt   52440
cgctgcgcag gtggtgcacc ctgctgtgca cgctgttgcg cagcccgctg accagcatgt   52500
tcctttgccg gccgattcgc agcccgatac gcacctcgtg gcgcgtgagg ccgacggcct   52560
ggtgcacgtg ttcgaggagt cagtgcacga tccggtgccc ggcggtgtca gtgtcgccga   52620
tctaatcgcc cgcgaggctg cgaccagcga gcgcgctggct gcgcacttgc ccgcggccga   52680
ggcgatcctc gccgccggtg tgacgcgcat tgatcgcgtc aaggtcgccg aggtgctcgc   52740
cgagcatgag gccgacgtca agccgagcat gatcgcgcgc aagctcggcg tcgggtacag   52800
caccgtggtg cgcattctcg accatcacac tgcgcaggac gatgcacagg ccgaggtgct   52860
cgatgcggag gtgctcgcgt cgtgagcatc gcagcgcagt accggcgcg caccgacacg   52920 aacgggcgca cgtggtggcg gccggtgcgc cccgcgggca ccgatctgtc gcagtggggt   52980
tggacgtcgg accgggcgca ggcgcacccc gactacgacg cgctgaacac gtgcacgtgc   53040
ccgtgggtcg accgtcgct gtggacgacg cattacggcg ccgtcgagcc cggcagcacg   53100
cgggagcaca accgctatg tccggtgcac ccggcgacgc tcgtcgagct ggccgtcgcg   53160
cgtgaggccc cggcggtcgc cgctgcggct gagcgtgccg aggcatacgg cgatgcgtgg   53220
gcgcaggtgt tcgagctggc gcaggaccgg ctgccgctgt cacgtagttg gaactgcgac   53280
```

| | |
|---|---|
| gagcagggcc gcacgctgtg cggtgcgtcc gtctgcggca cgtgcgacgg gggaggctgc | 53340 |
| tttgactgca ccgactgagg gcgtcgagct gccacgcgcg cacgacctcg acccgcggcg | 53400 |
| ctggcggctg ccgagcggcg aaatcgtctt tgagacggtc aaccgcgatg cgatcgaact | 53460 |
| gctgaaagct gaccctgacg agtatttccg gcgcacccgg cgggcgtcgt gctgagcgtg | 53520 |
| tcgccgggca tggacgtggc ccggcagcgc cgcaagttcg tcggccgaat actcgccgag | 53580 |
| gacgacgacc acgctgccgc gtatctggtc tggctgctga gcctgttcga tgccgcggtg | 53640 |
| gccgccggta cgccgaggcc cgcgagcgag tttctgccga tgtttcaaga ggagtttgac | 53700 |
| cgatgacgag tgatgaaaag ctggcgctga tcgaggcgtg gatgcacccc ggcctgtggt | 53760 |
| ctgccctcga cgggcgccgc aacgcaatcc tgcggattct caagggcgag agtgtgagcc | 53820 |
| cgccggattg ggcggtaacc aacccgctgc cctgactggc gcgacacgcc gacacgacgc | 53880 |
| ccccgctgaa aggtcaagcg ggggcgttgt tgtgtgtttg gctcaatgtg tctgaccaac | 53940 |
| aaccgaataa caactgaata ggggccattg tgtcgccaac ggtaatcaac gaccgactga | 54000 |
| tcaactttgc gagcgaggtc gacgaccaga ccctcgcgca ggcgcagcag atcgccgatc | 54060 |
| tgcctttcgt ttatccgcat gtggcgctga tgcccgatgc gcatttcggt aagggcagca | 54120 |
| gtgtcggcac ggtgatcccg accgagggcg ctgtgatccc ggccgcggtg ggcgtcgata | 54180 |
| ttggctgcgg catgatcgcg gcccgcacca cgtacacggc gaacgatctt gagggcctca | 54240 |
| agctgtcgga tctgcgggag tcgatcgagt ccgctatccc gatgagcgcc ggggatacaa | 54300 |
| acaagagcct gaaccgttttt gagttcaccg gcgcccggct ggactggcta cagctcgtcg | 54360 |
| ctacccggtt cgacgtcgac ctgtcgcact ccccgaagtg gcgggagcag ctcggcacgc | 54420 |
| tgggcggcgg caatcacttc atcgagctgt gcctcgacca cctcgaccgg gtgtggttgt | 54480 |
| tcctgcactc cggttctcgt ggtgtcggta acaagatcgc gcagaagcac attcaggccg | 54540 |
| cgcagggcta ttgcctcgcc aacgggctgc acgtgccgca caaggatctg gcgtacctcg | 54600 |
| tcgagggcac ggtcgagttc gaccgctacc tcgtcgaact gcgctgggcg cagcggttcg | 54660 |
| cgtactacaa ccgcgccgaa atgatggacc gattcgagca ggcgttcagg cattgggtcg | 54720 |
| gcgccgacca gggcgccgag ctggtcgtcg agaccatcaa cgcgcaccac aactacacgc | 54780 |
| aaaaggagcg gcacggcgac cgtgatgtgt ggctgacccg taagggggcg atcgacgcga | 54840 |
| acgccggtgt gcgggccctg attccgggct cgatgggcac ctgttcgtat gtcgtgaccg | 54900 |
| gcaagggtaa tcccgaggcg ttgtgctcgg cgccgcacgg tgcgggccgc cggttctcgc | 54960 |
| gcacgaaggc gcgcaagctg ttcacggtcg acgacctcga ggcgcgtatg gcgggcatcg | 55020 |
| agtaccgcaa gggcgaggcg tgggtcgacg agattcccga cgcatacaag ccgatcgacg | 55080 |
| tcgtgatgca cgacgccgaa acgctggtgt cggtggatgc cgagctgcgg cagctcttga | 55140 |
| acgtcaaggg gcagtgatgc gcgaggccgt catcgaattg aaggccgacc gtcagcacgg | 55200 |
| gctgacgacg gcgctgctcg acgtggcgct cgccaacgcc cgccgaggcg accgggtgat | 55260 |
| gttctggtcg ccgacgtcgg gggagtgtga caacgcattc cgtcaggcgc gccacctgct | 55320 |
| cgacccgcag gtgtcaaggg tcaacgccgc caacggaaat cagtacgtga cgtacggcag | 55380 |
| cggcggccga gtccagttcg tatgggccg cagccccgag gacgtgctgt gcgatacgcg | 55440 |
| cacctgcggc gctgcgctct acgtgttcga cgacaaccgc ggcagcggtg cacacatcgt | 55500 |
| gcggcgcaac gcaatgcgcg acctgcgcaa ccgacgagag gtgaggtttt tctgatggcc | 55560 |
| gactattcgc acactgacca tctgctcggc gagcctgcgg agccgatcgc agggctgacc | 55620 |
| gagcgggagg gcgacgacaa ggcgctgtac ccgtggcagg cgcaagcggt ccgcacgctg | 55680 |

```
caggagcgtc gagaggtgtc gttctcgctg cagttcccgc ggcagccgca gccccgcccg   55740
ccgttgtggc tggcgcagtt gttcggcgtg gtcgtgaccc cggcgccgcc gacggtgcgc   55800
gaggccgccg tcgacgtgtg ggacgcgctg cgcgtgctgc tgcgcgtcgt gtgggtggcc   55860
atgcggggcg ctgcgcaggc ggcggccgac agcgtgctcg actggtggtt tgacgtcgtg   55920
tacggcgctt tcgaccgctg ggacgtgctg cgcgggtggg gttggcgtcg ccagctcgtc   55980
gggccgacgg tgcggctgtg gagcgcctca ttcatctatc agtacacagt gcctcgtcgg   56040
cgtgaggcat ggcgcgagtg gctgcggcgg caggctggtc tgccgttggc ggtgtggcgt   56100
gggtagcgcc ccggtgatgt tcctcgacgg cccgctcgcc gggactaccc gcgaggtgcc   56160
gacgtggcca atggtgaac tgtcgccgta cttcaacgtg gcgacgccgc cgaagttcga   56220
cccgtccgaa tggcgcgacc cgccgcgcac gctcttgccc gagacgcata cgtaccggat   56280
caagtgcaac cggctgagct acggcccgca gtgggtcggt gcgatcggcg ataaggtcgg   56340
cgagcagatc gtcaccgtgc tgccgtacga cgagcgagcc cggcagagcg tcggcgtcga   56400
ccagttcgag gactacatca cccaaaacgc ctaccagagc gcgcagcggc acgcgcaggg   56460
cgagggcctg gtcgccgttg aggtgcacga ggtttggcgc ggcacgcaag ccgaggcccg   56520
cgagcagatg gtgcgcgagg gcaagccagt gaagggcgcc ccggcgttcc tcggcgccga   56580
cggcccggtg ttcctcgact cgaccgtgtt cgtcgtgcac gaggccgtgg cagtgcccaa   56640
agatcaggcg cgggaggtga ttctgtgact gacaccggca ccccgctgga cgacttgacg   56700
cccgagcagg ccgagcgtct cacgcggtcg ctgcggcggt tcaacgaggc gatgggctgg   56760
cagctcgacc acgcccggca agagttggac cgtgaccggc tgcggcggct gttcggcacc   56820
agctaacgcc ggcaaaggtc gccggcctgg ctgtcgtcgc aggtagttgc ggtgcgggtc   56880
tggaagttgg caaacgcccc tcgggtaatc ctcgggggc gttctgcttt ccatgttgac   56940
gcacatacaa ccgatgtgtt tgcatatcaa cacacaccac gggataggag ccctgaatg   57000 ttcaagatga ttgtgcaact gcatggccgc caagaggtta cggagcacga cacgatcgac   57060
gaggcccgca agcgcctggt cgatattgct gtcgcaagca actgccgggt tgagggcgac   57120
aacgccacgg gtgtgttcat cgcgctgacc cgcgagggtc gggacaatcc gctggtggac   57180
tggacctatg gcgcgtaccg gatcacggag gagcccgccg ggggcgtcga ccaggcgctc   57240
gccgccgcta ctgcgcggta catgatcgac gagaacctcg acgccgacac ggtgcagatg   57300
atccgcaata gcgaccgcga cgggcgcgac ctcctggcgg cgatcgtggc cgagtggctc   57360
aagctgcacc ccgagctgtc cgaccgggat cggcacgctg tgactgcggc ggcccacggc   57420
tggcagcgtt tcgacacggg cgacggggcg ccggtgcggt acgcccgcga cggcgagggc   57480
gtgattatcg actaccgcga cggggcgcta cgcatcgctg agcgttggat ctgccggtg   57540 atcgacgcaa tggtcgaggt gggcgtcgag ggtgacgacc cggccgacgt cgacaggtgg   57600
ctcgtagcgg cccctgtgcc gctctgagag cttcaaacag atgagggaaa gggataacat   57660
ggcaaccatg acaattacga ggtacacggc ggttgtgacg cccggcgagc agtacacgct   57720
gatccacgtg cctgagatcg accagtggac gcaggcccgc agcgacgacg aaatcgagcc   57780
gatggcgcgg gatctgatcg caacgtggct cgacgtgccg gtcgagtcgg tcgaggttgt   57840
ggtgcagcga ggctgacgcc gccagcgacg gggcgcccct gagtctttcg actcgggggc   57900
gttttgttgt tgcatgcat acagcgccgg tgttactgta tgcatgtcaa caactcaaca   57960
gggataggag cccacgatgc cgaagcgcag cgagattgtt accaagatcc gcaaggcggc   58020
```

```
caaggccaag ggtctgaaat tcaagtcggt tcgcaagggt gcgaatcacg agattttcga    58080
cctcgacggc gtaatggtgc cgatcggcaa ccacacggtg ctggatggct acctcatgct    58140
caagatttac aaagagtgtg agccgaagct cggtaaaggc tggtggcgat aaccaccacg    58200
gcgacgccct cgaccacatg gtcgggggcg ttttcgtttc tgtgttgaca tgcatacagc    58260
gacaggctat tgtatgtata tcaacagcgc gagcggttga gattgacaac tcaagagtga    58320
cagtggatag gagcccacaa tgaccgatct gtacattccg cgtttcctct cgccgagctg    58380
ctcgtttacc tacgacgaac tcggcaaggc ccttgcaaag ctgcagccgc gcctgaacaa    58440
agcgactgag gcatggctcg ccgccaagcg cgaccacggc agcgagagcc ccgaggaaca    58500
cgccctctgg cccgagcttg accggctgga aatggctaag gcccgcatcc tgcgcgaggc    58560
gaatcgcctc gacaagatca acggcctggc cgccgcgatg ccgctctaac cgatacgccc    58620
cgccgggccg accacaccgg cggggcgttt tcgttttcgc cgacgcccgc cgacgcccgc    58680
cgacgcccgc cgaggttcgc atacgtggcg tgattggcgc gcgtcgcttt tagactgcca    58740
tccgcaacag cacagctgta cccaaaacgg ccctggcgcc ccgaaacggg gtgttggggc    58800
cgttcccatt ccaggcgttg accagcgttg cgcggcctcc tatccccgcg ccctggtcga    58860
cgtctacgcc cgccgccgtg atcccgacac tggcgctatg tgcgcctcgg cgcgatccgc    58920
tgcagccccc tcgccgcgtt ggctggtcac cacgcgagca ccggcgcagc gcagcgctac    58980
agaggtcgac gcgatccggc ggcgggcact tacttcacga gaggaaacgc catgcccgac    59040
aacgcacctg acgccgccac tgaggccccc gcacaggaga cccccgcaat ggcccctgcc    59100
gcccgcgctg aggccctggc ggccaatgcg aggggtaagg gcaaggggcg gcaggctacg    59160
gcgtacgtgg ccctcgaccc ggccgaggcc aaccgtaggg ccaggcggcg gcccgctgcc    59220
gaggcgagca agcctgtggc acacgagccg tacgagtggt gaggctttca ccacggcgtg    59280
ctgagagttg gttctgtgcc accagcatga agctgggcga gctggccgag gcgctggacc    59340
tacgcacgcg gtacgccgag cgtcacggtg agcgtgctcg tctgttcgtg ttctcggtcg    59400
gcaagctgct gatcgtttgg gaccgagaca gcacgccatg agcgagggtc gcaacactgc    59460
gcggcgcaac aggttccggc gctactggct gcggcgccgt gaggtttgcg ccgtgtgcgg    59520
tgaggcgatc gactacgagg cgcatcacct gcaccctgac tcgtttcagg ttgaccacat    59580
cacgccgctg gatgcaggcg gttcggacac gctcgacaac acgcagccga cgcaccgcaa    59640
gtgcaaccgc gacaagagca acaagctgcc cgacagcggc ggcccggcgc ccgtctcggt    59700
gggcgtcacg ttcgtgaccg aacggcactg gcgaccctga ccagcaaagg ggtgggggggg   59760 tactccccga cccgcaaaag gtgcacctcg taggcata                            59798
```